(12) United States Patent
Parris et al.

(10) Patent No.: US 6,957,150 B2
(45) Date of Patent: Oct. 18, 2005

(54) METHODS FOR IDENTIFYING AN AGENT THAT INTERACTS WITH AN ACTIVE SITE OF ACYL CARRIER PROTEIN SYNTHASE OR ACYL CARRIER PROTEIN SYNTHASE COMPLEX

(75) Inventors: Kevin Delos Parris, Auburndale, MA (US); William Stuart Somers, Cambridge, MA (US); Amy Szepui Tam, Medford, MA (US); Laura Long Lin, Weston, MA (US); Mark Lloyd Stahl, Lexington, MA (US)

(73) Assignees: Wyeth, Madison, NJ (US); Millennium Pharmaceuticals, Inc., Cambridge, MA (US)

( * ) Notice: Subject to any disclaimer, the term of this patent is extended or adjusted under 35 U.S.C. 154(b) by 232 days.

(21) Appl. No.: 09/771,383

(22) Filed: Jan. 25, 2001

(65) Prior Publication Data

US 2002/0094562 A1 Jul. 18, 2002

Related U.S. Application Data

(60) Provisional application No. 60/178,639, filed on Jan. 28, 2000.

(51) Int. Cl.[7] .......................... G06F 19/00; G01N 33/48; G01N 31/00
(52) U.S. Cl. ............................... 702/27; 702/19; 702/22
(58) Field of Search ............................... 702/19, 22, 27

(56) References Cited

U.S. PATENT DOCUMENTS 5,096,676 A   3/1992   McPherson et al.
5,221,410 A   6/1993   Kushner et al.

OTHER PUBLICATIONS

Jan Drenth, Principles of Protein X-ray Crystallography, 1995, Springer–Verlag, p. 16).*
Rosowsky et al., 1999, J. Med. Chem., 42, 4853–4860.*
Ahern, Holly, May 13, 196, The Scientist 10[10], May 13, 1996, pp. 1–4.*
Tripos Inc., Sybyl Product Sheet.*
Jan Drenth, Principles of Protein X–ray Crystallography, 1994, Springer–Verlag, pp. 93–95.*
News Focus, Science, Nov. 1, 2002, vol. 298, pp. 948–950.*
Knegtel et al., Molecular docking to ensembles of protein structures. J. Mol. Biol., 266:424–40, Feb. 2, 1997.
Lambalot et al., A new enzyme superfamily—the phosphopantetheinyl transferases. Chemistry & Biology, 3(11):923–36, Nov. 1996.
Makino and Kuntz, Automated flexible ligand docking method and its application for database search. Journal of Computational Chemistry, 18(14):1812–25, Nov. 15, 1997.
Parris et al., Crystal structures of substrate binding to *Bacillus subtilis* holo–(acyl carrier protein) synthase reveal a novel trimeric arrangement of molecules resulting in three active sites. Structure, 8:883–95, Jul. 27, 2000.
Qui et al., Crystal structure of β–ketoacyl–acyl carrier protein synthase III. The Journal of Biological Chemistry, 274(51):36,465–471, Dec. 17, 1999.
Reuter et al., Crystal structure of the surfactin synthetase – activating enzyme Sfp: a prototype of the 4'–phosphopantetheinyl transferase superfamily. EMBO J., 18(23):6823–31, 1999.

* cited by examiner

Primary Examiner—Aroin H. Marschel
Assistant Examiner—Cheyne D Ly
(74) Attorney, Agent, or Firm—Fish & Richardson P.C.

(57) ABSTRACT

This invention is directed to Acyl Carrier Protein Synthase (ACPS) crystals and crystals of Acyl Carrier Protein Synthase–Coenzyme A (ACPS-CoA) complex, and to the use of these crystals to determine the three dimensional structure of ACPS. This invention is further directed to the use of rational drug design methods to identify agents that may interact with active sites of ACPS and ACPS-CoA complex, and to the testing of these agents to identify agents that may inhibit ACPS and/or ACPS-CoA complex activity.

56 Claims, 137 Drawing Sheets

FIG. 1

| | | Atom Type | Res. | | X | Y | Z | OCC | B | MOL |
|---|---|---|---|---|---|---|---|---|---|---|
| ATOM | 1 | C | GLY | 1 | 69.326 | 51.394 | 17.320 | 1.00 | 31.75 | CPS1 |
| ATOM | 2 | O | GLY | 1 | 69.833 | 51.813 | 16.277 | 1.00 | 31.77 | CPS1 |
| ATOM | 3 | N | GLY | 1 | 70.959 | 52.760 | 18.620 | 1.00 | 35.87 | CPS1 |
| ATOM | 4 | CA | GLY | 1 | 70.031 | 51.571 | 18.653 | 1.00 | 32.48 | CPS1 |
| ATOM | 5 | N | ILE | 2 | 68.153 | 50.776 | 17.347 | 1.00 | 28.47 | CPS1 |
| ATOM | 6 | CA | ILE | 2 | 67.404 | 50.567 | 16.121 | 1.00 | 26.25 | CPS1 |
| ATOM | 7 | CB | ILE | 2 | 66.717 | 49.195 | 16.134 | 1.00 | 25.90 | CPS1 |
| ATOM | 8 | CG2 | ILE | 2 | 65.743 | 49.071 | 14.958 | 1.00 | 25.20 | CPS1 |
| ATOM | 9 | CG1 | ILE | 2 | 67.788 | 48.104 | 16.055 | 1.00 | 28.68 | CPS1 |
| ATOM | 10 | CD1 | ILE | 2 | 67.235 | 46.714 | 16.136 | 1.00 | 29.70 | CPS1 |
| ATOM | 11 | C | ILE | 2 | 66.379 | 51.671 | 15.959 | 1.00 | 24.77 | CPS1 |
| ATOM | 12 | O | ILE | 2 | 65.635 | 51.988 | 16.893 | 1.00 | 24.24 | CPS1 |
| ATOM | 13 | N | TYR | 3 | 66.358 | 52.282 | 14.781 | 1.00 | 23.49 | CPS1 |
| ATOM | 14 | CA | TYR | 3 | 65.407 | 53.355 | 14.515 | 1.00 | 23.75 | CPS1 |
| ATOM | 15 | CB | TYR | 3 | 65.923 | 54.291 | 13.420 | 1.00 | 25.80 | CPS1 |
| ATOM | 16 | CG | TYR | 3 | 64.952 | 55.408 | 13.087 | 1.00 | 28.36 | CPS1 |
| ATOM | 17 | CD1 | TYR | 3 | 64.870 | 56.552 | 13.887 | 1.00 | 30.78 | CPS1 |
| ATOM | 18 | CE1 | TYR | 3 | 63.950 | 57.569 | 13.608 | 1.00 | 33.13 | CPS1 |
| ATOM | 19 | CD2 | TYR | 3 | 64.090 | 55.307 | 11.999 | 1.00 | 29.71 | CPS1 |
| ATOM | 20 | CE2 | TYR | 3 | 63.166 | 56.313 | 11.709 | 1.00 | 32.64 | CPS1 |
| ATOM | 21 | CZ | TYR | 3 | 63.102 | 57.444 | 12.517 | 1.00 | 34.23 | CPS1 |
| ATOM | 22 | OH | TYR | 3 | 62.204 | 58.454 | 12.225 | 1.00 | 36.12 | CPS1 |
| ATOM | 23 | C | TYR | 3 | 64.075 | 52.766 | 14.068 | 1.00 | 23.33 | CPS1 |
| ATOM | 24 | O | TYR | 3 | 63.022 | 53.193 | 14.517 | 1.00 | 24.16 | CPS1 |
| ATOM | 25 | N | GLY | 4 | 64.130 | 51.792 | 13.166 | 1.00 | 21.11 | CPS1 |
| ATOM | 26 | CA | GLY | 4 | 62.909 | 51.182 | 12.672 | 1.00 | 20.13 | CPS1 |
| ATOM | 27 | C | GLY | 4 | 63.216 | 49.984 | 11.799 | 1.00 | 19.67 | CPS1 |
| ATOM | 28 | O | GLY | 4 | 64.354 | 49.800 | 11.371 | 1.00 | 18.21 | CPS1 |
| ATOM | 29 | N | ILE | 5 | 62.211 | 49.145 | 11.562 | 1.00 | 18.70 | CPS1 |
| ATOM | 30 | CA | ILE | 5 | 62.402 | 47.985 | 10.704 | 1.00 | 17.69 | CPS1 |
| ATOM | 31 | CB | ILE | 5 | 62.470 | 46.666 | 11.510 | 1.00 | 18.45 | CPS1 |
| ATOM | 32 | CG2 | ILE | 5 | 63.538 | 46.799 | 12.610 | 1.00 | 17.74 | CPS1 |
| ATOM | 33 | CG1 | ILE | 5 | 61.103 | 46.329 | 12.127 | 1.00 | 17.47 | CPS1 |
| ATOM | 34 | CD1 | ILE | 5 | 61.097 | 44.956 | 12.830 | 1.00 | 18.74 | CPS1 |
| ATOM | 35 | C | ILE | 5 | 61.225 | 47.936 | 9.736 | 1.00 | 17.16 | CPS1 |
| ATOM | 36 | O | ILE | 5 | 60.170 | 48.525 | 10.001 | 1.00 | 16.88 | CPS1 |
| ATOM | 37 | N | GLY | 6 | 61.414 | 47.248 | 8.616 | 1.00 | 16.81 | CPS1 |
| ATOM | 38 | CA | GLY | 6 | 60.353 | 47.163 | 7.632 | 1.00 | 16.27 | CPS1 |
| ATOM | 39 | C | GLY | 6 | 60.398 | 45.846 | 6.893 | 1.00 | 17.21 | CPS1 |
| ATOM | 40 | O | GLY | 6 | 61.468 | 45.303 | 6.623 | 1.00 | 17.76 | CPS1 |
| ATOM | 41 | N | LEU | 7 | 59.220 | 45.345 | 6.555 | 1.00 | 17.08 | CPS1 |
| ATOM | 42 | CA | LEU | 7 | 59.085 | 44.080 | 5.858 | 1.00 | 18.22 | CPS1 |
| ATOM | 43 | CB | LEU | 7 | 58.631 | 43.006 | 6.857 | 1.00 | 18.52 | CPS1 |
| ATOM | 44 | CG | LEU | 7 | 58.266 | 41.643 | 6.270 | 1.00 | 18.46 | CPS1 |
| ATOM | 45 | CD1 | LEU | 7 | 59.552 | 40.921 | 5.800 | 1.00 | 18.60 | CPS1 |
| ATOM | 46 | CD2 | LEU | 7 | 57.546 | 40.825 | 7.342 | 1.00 | 19.42 | CPS1 |
| ATOM | 47 | C | LEU | 7 | 58.025 | 44.246 | 4.780 | 1.00 | 18.80 | CPS1 |
| ATOM | 48 | O | LEU | 7 | 57.036 | 44.935 | 4.988 | 1.00 | 19.60 | CPS1 |
| ATOM | 49 | N | ASP | 8 | 58.240 | 43.632 | 3.623 | 1.00 | 18.18 | CPS1 |
| ATOM | 50 | CA | ASP | 8 | 57.256 | 43.693 | 2.558 | 1.00 | 18.85 | CPS1 |
| ATOM | 51 | CB | ASP | 8 | 57.514 | 44.898 | 1.629 | 1.00 | 20.11 | CPS1 |
| ATOM | 52 | CG | ASP | 8 | 56.550 | 44.927 | 0.447 | 1.00 | 21.89 | CPS1 |
| ATOM | 53 | OD1 | ASP | 8 | 56.853 | 44.324 | -0.600 | 1.00 | 24.47 | CPS1 |
| ATOM | 54 | OD2 | ASP | 8 | 55.471 | 45.524 | 0.585 | 1.00 | 25.95 | CPS1 |
| ATOM | 55 | C | ASP | 8 | 57.293 | 42.422 | 1.723 | 1.00 | 18.97 | CPS1 |
| ATOM | 56 | O | ASP | 8 | 58.353 | 41.856 | 1.486 | 1.00 | 19.21 | CPS1 |

FIG. 1A-1

| | | | | | | | | | | |
|---|---|---|---|---|---|---|---|---|---|---|
| ATOM | 57 | N | ILE | 9 | 56.124 | 41.944 | 1.328 | 1.00 | 19.03 | CPS1 |
| ATOM | 58 | CA | ILE | 9 | 56.051 | 40.795 | 0.444 | 1.00 | 19.29 | CPS1 |
| ATOM | 59 | CB | ILE | 9 | 55.393 | 39.567 | 1.093 | 1.00 | 21.16 | CPS1 |
| ATOM | 60 | CG2 | ILE | 9 | 55.354 | 38.416 | 0.080 | 1.00 | 20.76 | CPS1 |
| ATOM | 61 | CG1 | ILE | 9 | 56.198 | 39.115 | 2.308 | 1.00 | 19.57 | CPS1 |
| ATOM | 62 | CD1 | ILE | 9 | 55.560 | 37.946 | 3.081 | 1.00 | 21.48 | CPS1 |
| ATOM | 63 | C | ILE | 9 | 55.161 | 41.304 | -0.683 | 1.00 | 20.60 | CPS1 |
| ATOM | 64 | O | ILE | 9 | 54.102 | 41.904 | -0.431 | 1.00 | 18.57 | CPS1 |
| ATOM | 65 | N | THR | 10 | 55.601 | 41.100 | -1.916 | 1.00 | 20.85 | CPS1 |
| ATOM | 66 | CA | THR | 10 | 54.828 | 41.556 | -3.064 | 1.00 | 22.77 | CPS1 |
| ATOM | 67 | CB | THR | 10 | 55.555 | 42.710 | -3.789 | 1.00 | 25.32 | CPS1 |
| ATOM | 68 | OG1 | THR | 10 | 55.699 | 43.816 | -2.889 | 1.00 | 26.50 | CPS1 |
| ATOM | 69 | CG2 | THR | 10 | 54.758 | 43.168 | -5.014 | 1.00 | 26.33 | CPS1 |
| ATOM | 70 | C | THR | 10 | 54.598 | 40.400 | -4.028 | 1.00 | 22.74 | CPS1 |
| ATOM | 71 | O | THR | 10 | 55.506 | 39.633 | -4.314 | 1.00 | 21.67 | CPS1 |
| ATOM | 72 | N | GLU | 11 | 53.359 | 40.270 | -4.495 | 1.00 | 24.96 | CPS1 |
| ATOM | 73 | CA | GLU | 11 | 52.993 | 39.223 | -5.445 | 1.00 | 25.76 | CPS1 |
| ATOM | 74 | CB | GLU | 11 | 51.475 | 38.995 | -5.394 | 1.00 | 28.49 | CPS1 |
| ATOM | 75 | CG | GLU | 11 | 50.969 | 37.968 | -6.383 | 1.00 | 31.23 | CPS1 |
| ATOM | 76 | CD | GLU | 11 | 49.445 | 37.895 | -6.440 | 1.00 | 34.90 | CPS1 |
| ATOM | 77 | OE1 | GLU | 11 | 48.773 | 38.865 | -6.019 | 1.00 | 33.91 | CPS1 |
| ATOM | 78 | OE2 | GLU | 11 | 48.923 | 36.867 | -6.926 | 1.00 | 35.55 | CPS1 |
| ATOM | 79 | C | GLU | 11 | 53.420 | 39.693 | -6.842 | 1.00 | 25.44 | CPS1 |
| ATOM | 80 | O | GLU | 11 | 53.000 | 40.761 | -7.293 | 1.00 | 24.85 | CPS1 |
| ATOM | 81 | N | LEU | 12 | 54.252 | 38.912 | -7.525 | 1.00 | 26.00 | CPS1 |
| ATOM | 82 | CA | LEU | 12 | 54.715 | 39.316 | -8.857 | 1.00 | 27.71 | CPS1 |
| ATOM | 83 | CB | LEU | 12 | 55.599 | 38.242 | -9.488 | 1.00 | 28.64 | CPS1 |
| ATOM | 84 | CG | LEU | 12 | 56.860 | 37.729 | -8.793 | 1.00 | 31.06 | CPS1 |
| ATOM | 85 | CD1 | LEU | 12 | 57.721 | 37.022 | -9.836 | 1.00 | 31.75 | CPS1 |
| ATOM | 86 | CD2 | LEU | 12 | 57.643 | 38.862 | -8.157 | 1.00 | 31.13 | CPS1 |
| ATOM | 87 | C | LEU | 12 | 53.557 | 39.608 | -9.810 | 1.00 | 28.75 | CPS1 |
| ATOM | 88 | O | LEU | 12 | 53.630 | 40.526 | -10.631 | 1.00 | 28.32 | CPS1 |
| ATOM | 89 | N | ALA | 13 | 52.498 | 38.813 | -9.708 | 1.00 | 29.63 | CPS1 |
| ATOM | 90 | CA | ALA | 13 | 51.330 | 38.987 | -10.565 | 1.00 | 32.09 | CPS1 |
| ATOM | 91 | CB | ALA | 13 | 50.281 | 37.918 | -10.238 | 1.00 | 32.02 | CPS1 |
| ATOM | 92 | C | ALA | 13 | 50.732 | 40.379 | -10.397 | 1.00 | 33.63 | CPS1 |
| ATOM | 93 | O | ALA | 13 | 50.280 | 41.000 | -11.369 | 1.00 | 33.79 | CPS1 |
| ATOM | 94 | N | ARG | 14 | 50.732 | 40.864 | -9.160 | 1.00 | 34.46 | CPS1 |
| ATOM | 95 | CA | ARG | 14 | 50.188 | 42.178 | -8.846 | 1.00 | 35.63 | CPS1 |
| ATOM | 96 | CB | ARG | 14 | 50.170 | 42.380 | -7.330 | 1.00 | 38.10 | CPS1 |
| ATOM | 97 | CG | ARG | 14 | 48.818 | 42.770 | -6.772 | 1.00 | 41.02 | CPS1 |
| ATOM | 98 | CD | ARG | 14 | 48.815 | 44.197 | -6.276 | 1.00 | 42.88 | CPS1 |
| ATOM | 99 | NE | ARG | 14 | 49.762 | 44.395 | -5.183 | 1.00 | 43.99 | CPS1 |
| ATOM | 100 | CZ | ARG | 14 | 50.030 | 45.575 | -4.628 | 1.00 | 45.35 | CPS1 |
| ATOM | 101 | NH1 | ARG | 14 | 49.420 | 46.670 | -5.063 | 1.00 | 46.27 | CPS1 |
| ATOM | 102 | NH2 | ARG | 14 | 50.915 | 45.664 | -3.642 | 1.00 | 44.46 | CPS1 |
| ATOM | 103 | C | ARG | 14 | 51.022 | 43.264 | -9.508 | 1.00 | 36.31 | CPS1 |
| ATOM | 104 | O | ARG | 14 | 50.484 | 44.232 | -10.055 | 1.00 | 36.04 | CPS1 |
| ATOM | 105 | N | ILE | 15 | 52.340 | 43.095 | -9.457 | 1.00 | 35.62 | CPS1 |
| ATOM | 106 | CA | ILE | 15 | 53.258 | 44.046 | -10.062 | 1.00 | 36.49 | CPS1 |
| ATOM | 107 | CB | ILE | 15 | 54.720 | 43.639 | -9.788 | 1.00 | 34.84 | CPS1 |
| ATOM | 108 | CG2 | ILE | 15 | 55.666 | 44.453 | -10.646 | 1.00 | 34.69 | CPS1 |
| ATOM | 109 | CG1 | ILE | 15 | 55.037 | 43.835 | -8.298 | 1.00 | 32.18 | CPS1 |
| ATOM | 110 | CD1 | ILE | 15 | 54.936 | 45.275 | -7.834 | 1.00 | 33.49 | CPS1 |
| ATOM | 111 | C | ILE | 15 | 52.995 | 44.093 | -11.566 | 1.00 | 39.03 | CPS1 |
| ATOM | 112 | O | ILE | 15 | 53.103 | 45.147 | -12.195 | 1.00 | 38.89 | CPS1 |
| ATOM | 113 | N | ALA | 16 | 52.651 | 42.946 | -12.141 | 1.00 | 41.54 | CPS1 |

FIG. 1A-2

| ATOM | 114 | CA | ALA | 16 | 52.336 | 42.887 | -13.564 | 1.00 | 44.64 | CPS1 |
|---|---|---|---|---|---|---|---|---|---|---|
| ATOM | 115 | CB | ALA | 16 | 52.211 | 41.436 | -14.018 | 1.00 | 44.42 | CPS1 |
| ATOM | 116 | C | ALA | 16 | 51.016 | 43.629 | -13.784 | 1.00 | 46.09 | CPS1 |
| ATOM | 117 | O | ALA | 16 | 50.869 | 44.377 | -14.746 | 1.00 | 47.05 | CPS1 |
| ATOM | 118 | N | SER | 17 | 50.064 | 43.425 | -12.877 | 1.00 | 49.05 | CPS1 |
| ATOM | 119 | CA | SER | 17 | 48.752 | 44.076 | -12.959 | 1.00 | 51.73 | CPS1 |
| ATOM | 120 | CB | SER | 17 | 47.823 | 43.567 | -11.851 | 1.00 | 51.91 | CPS1 |
| ATOM | 121 | OG | SER | 17 | 47.472 | 42.208 | -12.048 | 1.00 | 53.45 | CPS1 |
| ATOM | 122 | C | SER | 17 | 48.851 | 45.594 | -12.854 | 1.00 | 53.68 | CPS1 |
| ATOM | 123 | O | SER | 17 | 48.310 | 46.316 | -13.691 | 1.00 | 54.03 | CPS1 |
| ATOM | 124 | N | MET | 18 | 49.530 | 46.075 | -11.816 | 1.00 | 55.71 | CPS1 |
| ATOM | 125 | CA | MET | 18 | 49.697 | 47.511 | -11.611 | 1.00 | 57.69 | CPS1 |
| ATOM | 126 | CB | MET | 18 | 50.429 | 47.787 | -10.293 | 1.00 | 58.63 | CPS1 |
| ATOM | 127 | CG | MET | 18 | 49.679 | 47.357 | -9.046 | 1.00 | 60.86 | CPS1 |
| ATOM | 128 | SD | MET | 18 | 50.678 | 47.547 | -7.546 | 1.00 | 64.39 | CPS1 |
| ATOM | 129 | CE | MET | 18 | 50.115 | 49.133 | -6.944 | 1.00 | 63.23 | CPS1 |
| ATOM | 130 | C | MET | 18 | 50.489 | 48.126 | -12.758 | 1.00 | 58.14 | CPS1 |
| ATOM | 131 | O | MET | 18 | 50.147 | 49.200 | -13.253 | 1.00 | 58.47 | CPS1 |
| ATOM | 132 | N | ALA | 19 | 51.545 | 47.440 | -13.178 | 1.00 | 58.63 | CPS1 |
| ATOM | 133 | CA | ALA | 19 | 52.393 | 47.930 | -14.257 | 1.00 | 59.73 | CPS1 |
| ATOM | 134 | CB | ALA | 19 | 53.432 | 46.881 | -14.626 | 1.00 | 58.94 | CPS1 |
| ATOM | 135 | C | ALA | 19 | 51.593 | 48.320 | -15.490 | 1.00 | 61.14 | CPS1 |
| ATOM | 136 | O | ALA | 19 | 51.267 | 49.491 | -15.679 | 1.00 | 61.35 | CPS1 |
| ATOM | 137 | N | GLY | 20 | 51.282 | 47.329 | -16.322 | 1.00 | 62.81 | CPS1 |
| ATOM | 138 | CA | GLY | 20 | 50.537 | 47.568 | -17.549 | 1.00 | 64.34 | CPS1 |
| ATOM | 139 | C | GLY | 20 | 49.331 | 48.486 | -17.438 | 1.00 | 65.24 | CPS1 |
| ATOM | 140 | O | GLY | 20 | 49.010 | 49.210 | -18.382 | 1.00 | 65.67 | CPS1 |
| ATOM | 141 | N | ARG | 21 | 48.660 | 48.459 | -16.292 | 1.00 | 65.86 | CPS1 |
| ATOM | 142 | CA | ARG | 21 | 47.485 | 49.295 | -16.081 | 1.00 | 66.76 | CPS1 |
| ATOM | 143 | CB | ARG | 21 | 46.595 | 48.672 | -14.996 | 1.00 | 68.01 | CPS1 |
| ATOM | 144 | CG | ARG | 21 | 45.294 | 49.417 | -14.698 | 1.00 | 70.30 | CPS1 |
| ATOM | 145 | CD | ARG | 21 | 44.482 | 49.731 | -15.959 | 1.00 | 72.22 | CPS1 |
| ATOM | 146 | NE | ARG | 21 | 44.987 | 50.908 | -16.671 | 1.00 | 73.68 | CPS1 |
| ATOM | 147 | CZ | ARG | 21 | 44.415 | 51.435 | -17.750 | 1.00 | 74.14 | CPS1 |
| ATOM | 148 | NH1 | ARG | 21 | 43.314 | 50.891 | -18.253 | 1.00 | 74.30 | CPS1 |
| ATOM | 149 | NH2 | ARG | 21 | 44.941 | 52.510 | -18.324 | 1.00 | 74.39 | CPS1 |
| ATOM | 150 | C | ARG | 21 | 47.862 | 50.728 | -15.703 | 1.00 | 66.35 | CPS1 |
| ATOM | 151 | O | ARG | 21 | 47.312 | 51.296 | -14.759 | 1.00 | 66.83 | CPS1 |
| ATOM | 152 | N | GLN | 22 | 48.803 | 51.304 | -16.450 | 1.00 | 65.49 | CPS1 |
| ATOM | 153 | CA | GLN | 22 | 49.263 | 52.676 | -16.219 | 1.00 | 64.27 | CPS1 |
| ATOM | 154 | CB | GLN | 22 | 50.068 | 52.755 | -14.913 | 1.00 | 64.78 | CPS1 |
| ATOM | 155 | CG | GLN | 22 | 49.187 | 52.941 | -13.675 | 1.00 | 66.23 | CPS1 |
| ATOM | 156 | CD | GLN | 22 | 49.924 | 52.717 | -12.368 | 1.00 | 67.13 | CPS1 |
| ATOM | 157 | OE1 | GLN | 22 | 50.946 | 53.353 | -12.097 | 1.00 | 67.87 | CPS1 |
| ATOM | 158 | NE2 | GLN | 22 | 49.401 | 51.812 | -11.544 | 1.00 | 67.13 | CPS1 |
| ATOM | 159 | C | GLN | 22 | 50.086 | 53.230 | -17.393 | 1.00 | 62.83 | CPS1 |
| ATOM | 160 | O | GLN | 22 | 49.559 | 53.962 | -18.239 | 1.00 | 63.71 | CPS1 |
| ATOM | 161 | N | GLY | 23 | 51.368 | 52.878 | -17.452 | 1.00 | 59.93 | CPS1 |
| ATOM | 162 | CA | GLY | 23 | 52.215 | 53.360 | -18.532 | 1.00 | 54.65 | CPS1 |
| ATOM | 163 | C | GLY | 23 | 53.259 | 54.325 | -18.006 | 1.00 | 51.39 | CPS1 |
| ATOM | 164 | O | GLY | 23 | 53.852 | 55.099 | -18.765 | 1.00 | 50.70 | CPS1 |
| ATOM | 165 | N | ARG | 24 | 53.474 | 54.268 | -16.694 | 1.00 | 47.29 | CPS1 |
| ATOM | 166 | CA | ARG | 24 | 54.433 | 55.121 | -16.007 | 1.00 | 42.63 | CPS1 |
| ATOM | 167 | CB | ARG | 24 | 53.798 | 56.490 | -15.771 | 1.00 | 45.51 | CPS1 |
| ATOM | 168 | CG | ARG | 24 | 54.684 | 57.512 | -15.095 | 1.00 | 48.36 | CPS1 |
| ATOM | 169 | CD | ARG | 24 | 54.194 | 58.925 | -15.397 | 1.00 | 50.96 | CPS1 |
| ATOM | 170 | NE | ARG | 24 | 52.773 | 59.092 | -15.108 | 1.00 | 53.61 | CPS1 |

FIG. 1A-3

| ATOM | 171 | CZ | ARG | 24 | 52.092 | 60.215 | -15.320 | 1.00 | 54.82 | CPS1 |
|---|---|---|---|---|---|---|---|---|---|---|
| ATOM | 172 | NH1 | ARG | 24 | 52.704 | 61.281 | -15.824 | 1.00 | 55.59 | CPS1 |
| ATOM | 173 | NH2 | ARG | 24 | 50.796 | 60.270 | -15.039 | 1.00 | 55.48 | CPS1 |
| ATOM | 174 | C | ARG | 24 | 54.842 | 54.480 | -14.673 | 1.00 | 38.31 | CPS1 |
| ATOM | 175 | O | ARG | 24 | 55.617 | 55.045 | -13.906 | 1.00 | 35.06 | CPS1 |
| ATOM | 176 | N | PHE | 25 | 54.338 | 53.279 | -14.420 | 1.00 | 34.51 | CPS1 |
| ATOM | 177 | CA | PHE | 25 | 54.630 | 52.585 | -13.166 | 1.00 | 32.21 | CPS1 |
| ATOM | 178 | CB | PHE | 25 | 53.805 | 51.298 | -13.074 | 1.00 | 33.02 | CPS1 |
| ATOM | 179 | CG | PHE | 25 | 54.016 | 50.536 | -11.797 | 1.00 | 33.13 | CPS1 |
| ATOM | 180 | CD1 | PHE | 25 | 54.917 | 49.482 | -11.741 | 1.00 | 33.65 | CPS1 |
| ATOM | 181 | CD2 | PHE | 25 | 53.323 | 50.889 | -10.642 | 1.00 | 34.84 | CPS1 |
| ATOM | 182 | CE1 | PHE | 25 | 55.129 | 48.784 | -10.553 | 1.00 | 33.64 | CPS1 |
| ATOM | 183 | CE2 | PHE | 25 | 53.527 | 50.201 | -9.450 | 1.00 | 34.46 | CPS1 |
| ATOM | 184 | CZ | PHE | 25 | 54.432 | 49.146 | -9.405 | 1.00 | 34.16 | CPS1 |
| ATOM | 185 | C | PHE | 25 | 56.103 | 52.273 | -12.902 | 1.00 | 29.41 | CPS1 |
| ATOM | 186 | O | PHE | 25 | 56.632 | 52.657 | -11.862 | 1.00 | 29.18 | CPS1 |
| ATOM | 187 | N | ALA | 26 | 56.771 | 51.585 | -13.826 | 1.00 | 26.94 | CPS1 |
| ATOM | 188 | CA | ALA | 26 | 58.177 | 51.245 | -13.621 | 1.00 | 25.77 | CPS1 |
| ATOM | 189 | CB | ALA | 26 | 58.702 | 50.403 | -14.785 | 1.00 | 25.23 | CPS1 |
| ATOM | 190 | C | ALA | 26 | 59.043 | 52.480 | -13.459 | 1.00 | 25.39 | CPS1 |
| ATOM | 191 | O | ALA | 26 | 59.955 | 52.511 | -12.632 | 1.00 | 22.61 | CPS1 |
| ATOM | 192 | N | GLU | 27 | 58.757 | 53.502 | -14.260 | 1.00 | 24.05 | CPS1 |
| ATOM | 193 | CA | GLU | 27 | 59.537 | 54.726 | -14.210 | 1.00 | 25.73 | CPS1 |
| ATOM | 194 | CB | GLU | 27 | 59.225 | 55.589 | -15.436 | 1.00 | 25.99 | CPS1 |
| ATOM | 195 | CG | GLU | 27 | 59.695 | 54.987 | -16.750 | 1.00 | 26.79 | CPS1 |
| ATOM | 196 | CD | GLU | 27 | 58.896 | 53.770 | -17.202 | 1.00 | 28.20 | CPS1 |
| ATOM | 197 | OE1 | GLU | 27 | 57.680 | 53.695 | -16.908 | 1.00 | 30.98 | CPS1 |
| ATOM | 198 | OE2 | GLU | 27 | 59.481 | 52.894 | -17.877 | 1.00 | 29.45 | CPS1 |
| ATOM | 199 | C | GLU | 27 | 59.315 | 55.519 | -12.924 | 1.00 | 26.62 | CPS1 |
| ATOM | 200 | O | GLU | 27 | 60.158 | 56.322 | -12.532 | 1.00 | 27.44 | CPS1 |
| ATOM | 201 | N | ARG | 28 | 58.179 | 55.312 | -12.272 | 1.00 | 26.83 | CPS1 |
| ATOM | 202 | CA | ARG | 28 | 57.924 | 56.002 | -11.014 | 1.00 | 28.43 | CPS1 |
| ATOM | 203 | CB | ARG | 28 | 56.422 | 56.062 | -10.727 | 1.00 | 31.75 | CPS1 |
| ATOM | 204 | CG | ARG | 28 | 55.736 | 57.322 | -11.243 | 1.00 | 38.22 | CPS1 |
| ATOM | 205 | CD | ARG | 28 | 54.229 | 57.195 | -11.093 | 1.00 | 41.94 | CPS1 |
| ATOM | 206 | NE | ARG | 28 | 53.891 | 56.446 | -9.885 | 1.00 | 46.44 | CPS1 |
| ATOM | 207 | CZ | ARG | 28 | 53.088 | 55.387 | -9.869 | 1.00 | 47.55 | CPS1 |
| ATOM | 208 | NH1 | ARG | 28 | 52.534 | 54.953 | -11.000 | 1.00 | 48.25 | CPS1 |
| ATOM | 209 | NH2 | ARG | 28 | 52.855 | 54.751 | -8.726 | 1.00 | 49.13 | CPS1 |
| ATOM | 210 | C | ARG | 28 | 58.629 | 55.267 | -9.877 | 1.00 | 27.14 | CPS1 |
| ATOM | 211 | O | ARG | 28 | 59.086 | 55.885 | -8.928 | 1.00 | 27.28 | CPS1 |
| ATOM | 212 | N | ILE | 29 | 58.729 | 53.944 | -9.985 | 1.00 | 26.44 | CPS1 |
| ATOM | 213 | CA | ILE | 29 | 59.363 | 53.137 | -8.938 | 1.00 | 26.04 | CPS1 |
| ATOM | 214 | CB | ILE | 29 | 58.901 | 51.657 | -9.004 | 1.00 | 26.47 | CPS1 |
| ATOM | 215 | CG2 | ILE | 29 | 59.520 | 50.865 | -7.858 | 1.00 | 28.14 | CPS1 |
| ATOM | 216 | CG1 | ILE | 29 | 57.374 | 51.565 | -8.976 | 1.00 | 27.67 | CPS1 |
| ATOM | 217 | CD1 | ILE | 29 | 56.722 | 52.214 | -7.796 | 1.00 | 28.72 | CPS1 |
| ATOM | 218 | C | ILE | 29 | 60.888 | 53.122 | -8.980 | 1.00 | 25.23 | CPS1 |
| ATOM | 219 | O | ILE | 29 | 61.549 | 53.123 | -7.934 | 1.00 | 25.57 | CPS1 |
| ATOM | 220 | N | LEU | 30 | 61.445 | 53.119 | -10.188 | 1.00 | 23.44 | CPS1 |
| ATOM | 221 | CA | LEU | 30 | 62.885 | 53.031 | -10.371 | 1.00 | 22.74 | CPS1 |
| ATOM | 222 | CB | LEU | 30 | 63.185 | 52.029 | -11.487 | 1.00 | 22.73 | CPS1 |
| ATOM | 223 | CG | LEU | 30 | 62.509 | 50.656 | -11.381 | 1.00 | 22.89 | CPS1 |
| ATOM | 224 | CD1 | LEU | 30 | 62.817 | 49.861 | -12.635 | 1.00 | 22.68 | CPS1 |
| ATOM | 225 | CD2 | LEU | 30 | 63.004 | 49.922 | -10.126 | 1.00 | 22.78 | CPS1 |
| ATOM | 226 | C | LEU | 30 | 63.590 | 54.344 | -10.686 | 1.00 | 23.94 | CPS1 |
| ATOM | 227 | O | LEU | 30 | 63.027 | 55.228 | -11.336 | 1.00 | 23.90 | CPS1 |

FIG. 1A-4

| ATOM | 228 | N   | THR | 31 | 64.830 | 54.451 | -10.224 | 1.00 | 24.75 | CPS1 |
|------|-----|-----|-----|----|--------|--------|---------|------|-------|------|
| ATOM | 229 | CA  | THR | 31 | 65.643 | 55.636 | -10.461 | 1.00 | 25.03 | CPS1 |
| ATOM | 230 | CB  | THR | 31 | 66.787 | 55.749 | -9.457  | 1.00 | 26.35 | CPS1 |
| ATOM | 231 | OG1 | THR | 31 | 67.725 | 54.692 | -9.695  | 1.00 | 26.00 | CPS1 |
| ATOM | 232 | CG2 | THR | 31 | 66.261 | 55.671 | -8.031  | 1.00 | 26.75 | CPS1 |
| ATOM | 233 | C   | THR | 31 | 66.271 | 55.469 | -11.832 | 1.00 | 24.44 | CPS1 |
| ATOM | 234 | O   | THR | 31 | 66.163 | 54.416 | -12.441 | 1.00 | 22.68 | CPS1 |
| ATOM | 235 | N   | ARG | 32 | 66.963 | 56.503 | -12.293 | 1.00 | 25.91 | CPS1 |
| ATOM | 236 | CA  | ARG | 32 | 67.607 | 56.458 | -13.603 | 1.00 | 26.68 | CPS1 |
| ATOM | 237 | CB  | ARG | 32 | 68.342 | 57.780 | -13.848 | 1.00 | 26.75 | CPS1 |
| ATOM | 238 | CG  | ARG | 32 | 68.970 | 57.939 | -15.236 | 1.00 | 29.21 | CPS1 |
| ATOM | 239 | CD  | ARG | 32 | 69.551 | 59.348 | -15.344 | 1.00 | 29.81 | CPS1 |
| ATOM | 240 | NE  | ARG | 32 | 70.015 | 59.707 | -16.684 | 1.00 | 32.75 | CPS1 |
| ATOM | 241 | CZ  | ARG | 32 | 71.129 | 59.256 | -17.254 | 1.00 | 34.02 | CPS1 |
| ATOM | 242 | NH1 | ARG | 32 | 71.916 | 58.404 | -16.606 | 1.00 | 33.55 | CPS1 |
| ATOM | 243 | NH2 | ARG | 32 | 71.476 | 59.692 | -18.464 | 1.00 | 31.94 | CPS1 |
| ATOM | 244 | C   | ARG | 32 | 68.572 | 55.276 | -13.728 | 1.00 | 26.02 | CPS1 |
| ATOM | 245 | O   | ARG | 32 | 68.539 | 54.542 | -14.721 | 1.00 | 25.46 | CPS1 |
| ATOM | 246 | N   | SER | 33 | 69.422 | 55.088 | -12.721 | 1.00 | 26.77 | CPS1 |
| ATOM | 247 | CA  | SER | 33 | 70.390 | 53.990 | -12.725 | 1.00 | 28.08 | CPS1 |
| ATOM | 248 | CB  | SER | 33 | 71.277 | 54.037 | -11.473 | 1.00 | 31.22 | CPS1 |
| ATOM | 249 | OG  | SER | 33 | 72.112 | 55.182 | -11.481 | 1.00 | 38.13 | CPS1 |
| ATOM | 250 | C   | SER | 33 | 69.686 | 52.645 | -12.772 | 1.00 | 27.50 | CPS1 |
| ATOM | 251 | O   | SER | 33 | 70.113 | 51.738 | -13.487 | 1.00 | 28.27 | CPS1 |
| ATOM | 252 | N   | GLU | 34 | 68.613 | 52.510 | -11.998 | 1.00 | 25.55 | CPS1 |
| ATOM | 253 | CA  | GLU | 34 | 67.857 | 51.262 | -11.970 | 1.00 | 25.24 | CPS1 |
| ATOM | 254 | CB  | GLU | 34 | 66.842 | 51.298 | -10.822 | 1.00 | 25.04 | CPS1 |
| ATOM | 255 | CG  | GLU | 34 | 67.531 | 51.247 | -9.455  | 1.00 | 24.32 | CPS1 |
| ATOM | 256 | CD  | GLU | 34 | 66.575 | 51.424 | -8.280  | 1.00 | 26.32 | CPS1 |
| ATOM | 257 | OE1 | GLU | 34 | 66.860 | 50.849 | -7.202  | 1.00 | 24.86 | CPS1 |
| ATOM | 258 | OE2 | GLU | 34 | 65.557 | 52.145 | -8.423  | 1.00 | 25.42 | CPS1 |
| ATOM | 259 | C   | GLU | 34 | 67.167 | 50.997 | -13.302 | 1.00 | 25.57 | CPS1 |
| ATOM | 260 | O   | GLU | 34 | 67.113 | 49.852 | -13.767 | 1.00 | 26.12 | CPS1 |
| ATOM | 261 | N   | LEU | 35 | 66.649 | 52.056 | -13.919 | 1.00 | 25.65 | CPS1 |
| ATOM | 262 | CA  | LEU | 35 | 65.978 | 51.931 | -15.209 | 1.00 | 25.43 | CPS1 |
| ATOM | 263 | CB  | LEU | 35 | 65.362 | 53.269 | -15.626 | 1.00 | 24.81 | CPS1 |
| ATOM | 264 | CG  | LEU | 35 | 64.044 | 53.625 | -14.936 | 1.00 | 25.80 | CPS1 |
| ATOM | 265 | CD1 | LEU | 35 | 63.598 | 55.028 | -15.354 | 1.00 | 24.72 | CPS1 |
| ATOM | 266 | CD2 | LEU | 35 | 62.980 | 52.592 | -15.320 | 1.00 | 24.55 | CPS1 |
| ATOM | 267 | C   | LEU | 35 | 66.961 | 51.465 | -16.278 | 1.00 | 25.60 | CPS1 |
| ATOM | 268 | O   | LEU | 35 | 66.608 | 50.663 | -17.139 | 1.00 | 25.96 | CPS1 |
| ATOM | 269 | N   | ASP | 36 | 68.189 | 51.968 | -16.213 | 1.00 | 26.39 | CPS1 |
| ATOM | 270 | CA  | ASP | 36 | 69.221 | 51.586 | -17.176 | 1.00 | 28.65 | CPS1 |
| ATOM | 271 | CB  | ASP | 36 | 70.549 | 52.267 | -16.814 | 1.00 | 30.67 | CPS1 |
| ATOM | 272 | CG  | ASP | 36 | 71.653 | 51.992 | -17.834 | 1.00 | 34.97 | CPS1 |
| ATOM | 273 | OD1 | ASP | 36 | 71.397 | 52.122 | -19.045 | 1.00 | 36.35 | CPS1 |
| ATOM | 274 | OD2 | ASP | 36 | 72.780 | 51.653 | -17.421 | 1.00 | 38.35 | CPS1 |
| ATOM | 275 | C   | ASP | 36 | 69.374 | 50.061 | -17.176 | 1.00 | 29.59 | CPS1 |
| ATOM | 276 | O   | ASP | 36 | 69.510 | 49.429 | -18.229 | 1.00 | 29.62 | CPS1 |
| ATOM | 277 | N   | GLN | 37 | 69.331 | 49.466 | -15.987 | 1.00 | 29.16 | CPS1 |
| ATOM | 278 | CA  | GLN | 37 | 69.446 | 48.019 | -15.860 | 1.00 | 27.84 | CPS1 |
| ATOM | 279 | CB  | GLN | 37 | 69.737 | 47.648 | -14.404 | 1.00 | 29.01 | CPS1 |
| ATOM | 280 | CG  | GLN | 37 | 70.983 | 48.305 | -13.850 | 1.00 | 32.00 | CPS1 |
| ATOM | 281 | CD  | GLN | 37 | 71.075 | 48.186 | -12.348 | 1.00 | 34.39 | CPS1 |
| ATOM | 282 | OE1 | GLN | 37 | 71.087 | 47.079 | -11.805 | 1.00 | 34.90 | CPS1 |
| ATOM | 283 | NE2 | GLN | 37 | 71.142 | 49.329 | -11.662 | 1.00 | 34.48 | CPS1 |
| ATOM | 284 | C   | GLN | 37 | 68.156 | 47.335 | -16.301 | 1.00 | 27.75 | CPS1 |

FIG. 1A-5

| ATOM | 285 | O | GLN | 37 | 68.183 | 46.328 | -17.012 | 1.00 | 27.75 | CPS1 |
| ATOM | 286 | N | TYR | 38 | 67.031 | 47.885 | -15.858 | 1.00 | 26.28 | CPS1 |
| ATOM | 287 | CA | TYR | 38 | 65.705 | 47.352 | -16.167 | 1.00 | 25.28 | CPS1 |
| ATOM | 288 | CB | TYR | 38 | 64.657 | 48.251 | -15.500 | 1.00 | 25.99 | CPS1 |
| ATOM | 289 | CG | TYR | 38 | 63.213 | 47.908 | -15.772 | 1.00 | 26.20 | CPS1 |
| ATOM | 290 | CD1 | TYR | 38 | 62.468 | 48.648 | -16.688 | 1.00 | 26.19 | CPS1 |
| ATOM | 291 | CE1 | TYR | 38 | 61.121 | 48.385 | -16.903 | 1.00 | 26.29 | CPS1 |
| ATOM | 292 | CD2 | TYR | 38 | 62.567 | 46.881 | -15.074 | 1.00 | 26.31 | CPS1 |
| ATOM | 293 | CE2 | TYR | 38 | 61.219 | 46.611 | -15.280 | 1.00 | 25.67 | CPS1 |
| ATOM | 294 | CZ | TYR | 38 | 60.501 | 47.370 | -16.200 | 1.00 | 28.03 | CPS1 |
| ATOM | 295 | OH | TYR | 38 | 59.166 | 47.120 | -16.428 | 1.00 | 27.03 | CPS1 |
| ATOM | 296 | C | TYR | 38 | 65.420 | 47.208 | -17.668 | 1.00 | 26.52 | CPS1 |
| ATOM | 297 | O | TYR | 38 | 64.912 | 46.175 | -18.122 | 1.00 | 23.95 | CPS1 |
| ATOM | 298 | N | TYR | 39 | 65.756 | 48.235 | -18.440 | 1.00 | 26.98 | CPS1 |
| ATOM | 299 | CA | TYR | 39 | 65.502 | 48.193 | -19.880 | 1.00 | 29.18 | CPS1 |
| ATOM | 300 | CB | TYR | 39 | 65.757 | 49.579 | -20.488 | 1.00 | 28.06 | CPS1 |
| ATOM | 301 | CG | TYR | 39 | 64.725 | 50.615 | -20.060 | 1.00 | 27.09 | CPS1 |
| ATOM | 302 | CD1 | TYR | 39 | 63.365 | 50.313 | -20.080 | 1.00 | 26.88 | CPS1 |
| ATOM | 303 | CE1 | TYR | 39 | 62.402 | 51.252 | -19.691 | 1.00 | 26.96 | CPS1 |
| ATOM | 304 | CD2 | TYR | 39 | 65.109 | 51.890 | -19.641 | 1.00 | 26.42 | CPS1 |
| ATOM | 305 | CE2 | TYR | 39 | 64.154 | 52.841 | -19.245 | 1.00 | 27.05 | CPS1 |
| ATOM | 306 | CZ | TYR | 39 | 62.806 | 52.510 | -19.274 | 1.00 | 26.67 | CPS1 |
| ATOM | 307 | OH | TYR | 39 | 61.856 | 53.426 | -18.876 | 1.00 | 27.91 | CPS1 |
| ATOM | 308 | C | TYR | 39 | 66.279 | 47.108 | -20.641 | 1.00 | 31.26 | CPS1 |
| ATOM | 309 | O | TYR | 39 | 65.899 | 46.727 | -21.750 | 1.00 | 32.43 | CPS1 |
| ATOM | 310 | N | GLU | 40 | 67.351 | 46.597 | -20.046 | 1.00 | 32.52 | CPS1 |
| ATOM | 311 | CA | GLU | 40 | 68.150 | 45.555 | -20.690 | 1.00 | 33.92 | CPS1 |
| ATOM | 312 | CB | GLU | 40 | 69.602 | 45.621 | -20.207 | 1.00 | 35.68 | CPS1 |
| ATOM | 313 | CG | GLU | 40 | 70.340 | 46.890 | -20.579 | 1.00 | 38.76 | CPS1 |
| ATOM | 314 | CD | GLU | 40 | 70.370 | 47.130 | -22.079 | 1.00 | 41.13 | CPS1 |
| ATOM | 315 | OE1 | GLU | 40 | 70.557 | 46.153 | -22.835 | 1.00 | 43.88 | CPS1 |
| ATOM | 316 | OE2 | GLU | 40 | 70.220 | 48.297 | -22.501 | 1.00 | 41.69 | CPS1 |
| ATOM | 317 | C | GLU | 40 | 67.616 | 44.147 | -20.419 | 1.00 | 34.35 | CPS1 |
| ATOM | 318 | O | GLU | 40 | 68.089 | 43.177 | -21.008 | 1.00 | 33.76 | CPS1 |
| ATOM | 319 | N | LEU | 41 | 66.626 | 44.036 | -19.541 | 1.00 | 33.60 | CPS1 |
| ATOM | 320 | CA | LEU | 41 | 66.080 | 42.733 | -19.176 | 1.00 | 34.81 | CPS1 |
| ATOM | 321 | CB | LEU | 41 | 65.658 | 42.757 | -17.702 | 1.00 | 33.78 | CPS1 |
| ATOM | 322 | CG | LEU | 41 | 66.725 | 43.183 | -16.690 | 1.00 | 33.47 | CPS1 |
| ATOM | 323 | CD1 | LEU | 41 | 66.084 | 43.291 | -15.309 | 1.00 | 33.49 | CPS1 |
| ATOM | 324 | CD2 | LEU | 41 | 67.879 | 42.188 | -16.678 | 1.00 | 33.26 | CPS1 |
| ATOM | 325 | C | LEU | 41 | 64.910 | 42.221 | -20.013 | 1.00 | 35.00 | CPS1 |
| ATOM | 326 | O | LEU | 41 | 64.199 | 42.992 | -20.654 | 1.00 | 34.86 | CPS1 |
| ATOM | 327 | N | SER | 42 | 64.713 | 40.904 | -19.984 | 1.00 | 36.21 | CPS1 |
| ATOM | 328 | CA | SER | 42 | 63.615 | 40.271 | -20.709 | 1.00 | 37.02 | CPS1 |
| ATOM | 329 | CB | SER | 42 | 63.788 | 38.752 | -20.716 | 1.00 | 37.19 | CPS1 |
| ATOM | 330 | OG | SER | 42 | 63.601 | 38.228 | -19.413 | 1.00 | 37.95 | CPS1 |
| ATOM | 331 | C | SER | 42 | 62.321 | 40.628 | -19.986 | 1.00 | 37.67 | CPS1 |
| ATOM | 332 | O | SER | 42 | 62.355 | 41.124 | -18.856 | 1.00 | 37.09 | CPS1 |
| ATOM | 333 | N | GLU | 43 | 61.180 | 40.378 | -20.618 | 1.00 | 37.74 | CPS1 |
| ATOM | 334 | CA | GLU | 43 | 59.917 | 40.705 | -19.970 | 1.00 | 39.67 | CPS1 |
| ATOM | 335 | CB | GLU | 43 | 58.716 | 40.282 | -20.829 | 1.00 | 42.30 | CPS1 |
| ATOM | 336 | CG | GLU | 43 | 57.421 | 40.990 | -20.417 | 1.00 | 46.74 | CPS1 |
| ATOM | 337 | CD | GLU | 43 | 56.177 | 40.466 | -21.122 | 1.00 | 49.57 | CPS1 |
| ATOM | 338 | OE1 | GLU | 43 | 56.253 | 40.155 | -22.333 | 1.00 | 51.74 | CPS1 |
| ATOM | 339 | OE2 | GLU | 43 | 55.116 | 40.384 | -20.465 | 1.00 | 50.82 | CPS1 |
| ATOM | 340 | C | GLU | 43 | 59.833 | 40.012 | -18.611 | 1.00 | 38.42 | CPS1 |
| ATOM | 341 | O | GLU | 43 | 59.425 | 40.619 | -17.623 | 1.00 | 37.06 | CPS1 |

FIG. 1A-6

| ATOM | 342 | N | LYS | 44 | 60.223 | 38.743 | -18.567 | 1.00 | 37.89 | CPS1 |
|---|---|---|---|---|---|---|---|---|---|---|
| ATOM | 343 | CA | LYS | 44 | 60.176 | 37.985 | -17.318 | 1.00 | 38.86 | CPS1 |
| ATOM | 344 | CB | LYS | 44 | 60.566 | 36.525 | -17.562 | 1.00 | 40.32 | CPS1 |
| ATOM | 345 | CG | LYS | 44 | 60.777 | 35.706 | -16.292 | 1.00 | 43.45 | CPS1 |
| ATOM | 346 | CD | LYS | 44 | 60.766 | 34.214 | -16.594 | 1.00 | 46.17 | CPS1 |
| ATOM | 347 | CE | LYS | 44 | 61.613 | 33.425 | -15.603 | 1.00 | 47.94 | CPS1 |
| ATOM | 348 | NZ | LYS | 44 | 63.073 | 33.691 | -15.805 | 1.00 | 50.56 | CPS1 |
| ATOM | 349 | C | LYS | 44 | 61.086 | 38.587 | -16.257 | 1.00 | 37.33 | CPS1 |
| ATOM | 350 | O | LYS | 44 | 60.661 | 38.823 | -15.127 | 1.00 | 36.33 | CPS1 |
| ATOM | 351 | N | ARG | 45 | 62.338 | 38.835 | -16.625 | 1.00 | 36.56 | CPS1 |
| ATOM | 352 | CA | ARG | 45 | 63.310 | 39.403 | -15.695 | 1.00 | 35.88 | CPS1 |
| ATOM | 353 | CB | ARG | 45 | 64.700 | 39.412 | -16.333 | 1.00 | 37.23 | CPS1 |
| ATOM | 354 | CG | ARG | 45 | 65.356 | 38.041 | -16.385 | 1.00 | 39.66 | CPS1 |
| ATOM | 355 | CD | ARG | 45 | 65.840 | 37.633 | -15.008 | 1.00 | 42.70 | CPS1 |
| ATOM | 356 | NE | ARG | 45 | 66.842 | 38.569 | -14.498 | 1.00 | 45.11 | CPS1 |
| ATOM | 357 | CZ | ARG | 45 | 66.700 | 39.307 | -13.399 | 1.00 | 46.10 | CPS1 |
| ATOM | 358 | NH1 | ARG | 45 | 65.593 | 39.226 | -12.672 | 1.00 | 45.56 | CPS1 |
| ATOM | 359 | NH2 | ARG | 45 | 67.666 | 40.140 | -13.033 | 1.00 | 47.39 | CPS1 |
| ATOM | 360 | C | ARG | 45 | 62.920 | 40.807 | -15.254 | 1.00 | 34.51 | CPS1 |
| ATOM | 361 | O | ARG | 45 | 63.182 | 41.200 | -14.120 | 1.00 | 33.99 | CPS1 |
| ATOM | 362 | N | LYS | 46 | 62.294 | 41.565 | -16.148 | 1.00 | 32.94 | CPS1 |
| ATOM | 363 | CA | LYS | 46 | 61.857 | 42.911 | -15.802 | 1.00 | 32.28 | CPS1 |
| ATOM | 364 | CB | LYS | 46 | 61.165 | 43.580 | -16.990 | 1.00 | 32.34 | CPS1 |
| ATOM | 365 | CG | LYS | 46 | 62.109 | 44.110 | -18.051 | 1.00 | 32.52 | CPS1 |
| ATOM | 366 | CD | LYS | 46 | 61.327 | 44.905 | -19.113 | 1.00 | 33.61 | CPS1 |
| ATOM | 367 | CE | LYS | 46 | 62.262 | 45.515 | -20.151 | 1.00 | 34.98 | CPS1 |
| ATOM | 368 | NZ | LYS | 46 | 61.505 | 46.250 | -21.211 | 1.00 | 36.94 | CPS1 |
| ATOM | 369 | C | LYS | 46 | 60.888 | 42.868 | -14.621 | 1.00 | 31.45 | CPS1 |
| ATOM | 370 | O | LYS | 46 | 61.002 | 43.655 | -13.684 | 1.00 | 30.01 | CPS1 |
| ATOM | 371 | N | ASN | 47 | 59.937 | 41.942 | -14.672 | 1.00 | 30.18 | CPS1 |
| ATOM | 372 | CA | ASN | 47 | 58.951 | 41.806 | -13.606 | 1.00 | 30.39 | CPS1 |
| ATOM | 373 | CB | ASN | 47 | 57.886 | 40.773 | -14.012 | 1.00 | 32.50 | CPS1 |
| ATOM | 374 | CG | ASN | 47 | 56.914 | 40.449 | -12.885 | 1.00 | 35.59 | CPS1 |
| ATOM | 375 | OD1 | ASN | 47 | 57.020 | 39.401 | -12.246 | 1.00 | 39.44 | CPS1 |
| ATOM | 376 | ND2 | ASN | 47 | 55.969 | 41.346 | -12.635 | 1.00 | 35.35 | CPS1 |
| ATOM | 377 | C | ASN | 47 | 59.608 | 41.424 | -12.273 | 1.00 | 28.81 | CPS1 |
| ATOM | 378 | O | ASN | 47 | 59.252 | 41.971 | -11.230 | 1.00 | 27.56 | CPS1 |
| ATOM | 379 | N | GLU | 48 | 60.568 | 40.503 | -12.308 | 1.00 | 27.77 | CPS1 |
| ATOM | 380 | CA | GLU | 48 | 61.265 | 40.064 | -11.093 | 1.00 | 26.38 | CPS1 |
| ATOM | 381 | CB | GLU | 48 | 62.172 | 38.870 | -11.417 | 1.00 | 30.74 | CPS1 |
| ATOM | 382 | CG | GLU | 48 | 61.417 | 37.675 | -12.004 | 1.00 | 34.10 | CPS1 |
| ATOM | 383 | CD | GLU | 48 | 62.338 | 36.589 | -12.553 | 1.00 | 37.43 | CPS1 |
| ATOM | 384 | OE1 | GLU | 48 | 61.815 | 35.595 | -13.106 | 1.00 | 38.39 | CPS1 |
| ATOM | 385 | OE2 | GLU | 48 | 63.577 | 36.727 | -12.434 | 1.00 | 38.18 | CPS1 |
| ATOM | 386 | C | GLU | 48 | 62.101 | 41.201 | -10.498 | 1.00 | 26.11 | CPS1 |
| ATOM | 387 | O | GLU | 48 | 62.132 | 41.416 | -9.271 | 1.00 | 22.48 | CPS1 |
| ATOM | 388 | N | PHE | 49 | 62.792 | 41.919 | -11.377 | 1.00 | 23.64 | CPS1 |
| ATOM | 389 | CA | PHE | 49 | 63.628 | 43.042 | -10.976 | 1.00 | 24.48 | CPS1 |
| ATOM | 390 | CB | PHE | 49 | 64.356 | 43.591 | -12.197 | 1.00 | 24.05 | CPS1 |
| ATOM | 391 | CG | PHE | 49 | 65.252 | 44.754 | -11.903 | 1.00 | 24.66 | CPS1 |
| ATOM | 392 | CD1 | PHE | 49 | 66.591 | 44.552 | -11.572 | 1.00 | 26.69 | CPS1 |
| ATOM | 393 | CD2 | PHE | 49 | 64.771 | 46.052 | -11.982 | 1.00 | 23.63 | CPS1 |
| ATOM | 394 | CE1 | PHE | 49 | 67.438 | 45.632 | -11.329 | 1.00 | 27.13 | CPS1 |
| ATOM | 395 | CE2 | PHE | 49 | 65.601 | 47.137 | -11.743 | 1.00 | 25.03 | CPS1 |
| ATOM | 396 | CZ | PHE | 49 | 66.938 | 46.933 | -11.416 | 1.00 | 26.71 | CPS1 |
| ATOM | 397 | C | PHE | 49 | 62.777 | 44.152 | -10.364 | 1.00 | 23.89 | CPS1 |
| ATOM | 398 | O | PHE | 49 | 63.124 | 44.721 | -9.323 | 1.00 | 24.30 | CPS1 |

FIG. 1A-7

| ATOM | 399 | N   | LEU | 50 | 61.672 | 44.476 | -11.029 | 1.00 | 22.90 | CPS1 |
| ATOM | 400 | CA  | LEU | 50 | 60.795 | 45.534 | -10.557 | 1.00 | 23.71 | CPS1 |
| ATOM | 401 | CB  | LEU | 50 | 59.732 | 45.836 | -11.617 | 1.00 | 24.35 | CPS1 |
| ATOM | 402 | CG  | LEU | 50 | 58.714 | 46.928 | -11.325 | 1.00 | 25.33 | CPS1 |
| ATOM | 403 | CD1 | LEU | 50 | 59.403 | 48.253 | -11.010 | 1.00 | 24.88 | CPS1 |
| ATOM | 404 | CD2 | LEU | 50 | 57.805 | 47.055 | -12.536 | 1.00 | 25.38 | CPS1 |
| ATOM | 405 | C   | LEU | 50 | 60.132 | 45.138 | -9.236  | 1.00 | 23.44 | CPS1 |
| ATOM | 406 | O   | LEU | 50 | 60.011 | 45.957 | -8.322  | 1.00 | 22.54 | CPS1 |
| ATOM | 407 | N   | ALA | 51 | 59.698 | 43.884 | -9.148  | 1.00 | 22.99 | CPS1 |
| ATOM | 408 | CA  | ALA | 51 | 59.056 | 43.399 | -7.929  | 1.00 | 23.20 | CPS1 |
| ATOM | 409 | CB  | ALA | 51 | 58.581 | 41.959 | -8.123  | 1.00 | 23.60 | CPS1 |
| ATOM | 410 | C   | ALA | 51 | 60.034 | 43.476 | -6.754  | 1.00 | 21.98 | CPS1 |
| ATOM | 411 | O   | ALA | 51 | 59.655 | 43.884 | -5.653  | 1.00 | 23.47 | CPS1 |
| ATOM | 412 | N   | GLY | 52 | 61.284 | 43.089 | -6.998  | 1.00 | 21.48 | CPS1 |
| ATOM | 413 | CA  | GLY | 52 | 62.297 | 43.120 | -5.951  | 1.00 | 22.37 | CPS1 |
| ATOM | 414 | C   | GLY | 52 | 62.585 | 44.523 | -5.460  | 1.00 | 22.17 | CPS1 |
| ATOM | 415 | O   | GLY | 52 | 62.715 | 44.764 | -4.256  | 1.00 | 21.91 | CPS1 |
| ATOM | 416 | N   | ARG | 53 | 62.675 | 45.461 | -6.402  | 1.00 | 23.24 | CPS1 |
| ATOM | 417 | CA  | ARG | 53 | 62.933 | 46.862 | -6.076  | 1.00 | 23.63 | CPS1 |
| ATOM | 418 | CB  | ARG | 53 | 63.169 | 47.654 | -7.364  | 1.00 | 25.69 | CPS1 |
| ATOM | 419 | CG  | ARG | 53 | 64.546 | 48.242 | -7.490  | 1.00 | 29.63 | CPS1 |
| ATOM | 420 | CD  | ARG | 53 | 65.618 | 47.212 | -7.338  | 1.00 | 28.33 | CPS1 |
| ATOM | 421 | NE  | ARG | 53 | 66.937 | 47.751 | -7.675  | 1.00 | 29.58 | CPS1 |
| ATOM | 422 | CZ  | ARG | 53 | 67.976 | 46.986 | -7.980  | 1.00 | 29.37 | CPS1 |
| ATOM | 423 | NH1 | ARG | 53 | 67.821 | 45.670 | -7.978  | 1.00 | 29.23 | CPS1 |
| ATOM | 424 | NH2 | ARG | 53 | 69.153 | 47.525 | -8.299  | 1.00 | 26.48 | CPS1 |
| ATOM | 425 | C   | ARG | 53 | 61.752 | 47.468 | -5.336  | 1.00 | 23.34 | CPS1 |
| ATOM | 426 | O   | ARG | 53 | 61.921 | 48.237 | -4.389  | 1.00 | 22.79 | CPS1 |
| ATOM | 427 | N   | PHE | 54 | 60.551 | 47.146 | -5.801  | 1.00 | 22.67 | CPS1 |
| ATOM | 428 | CA  | PHE | 54 | 59.335 | 47.638 | -5.181  | 1.00 | 22.96 | CPS1 |
| ATOM | 429 | CB  | PHE | 54 | 58.114 | 47.106 | -5.947  | 1.00 | 22.72 | CPS1 |
| ATOM | 430 | CG  | PHE | 54 | 56.807 | 47.619 | -5.429  | 1.00 | 24.49 | CPS1 |
| ATOM | 431 | CD1 | PHE | 54 | 56.074 | 46.882 | -4.506  | 1.00 | 24.85 | CPS1 |
| ATOM | 432 | CD2 | PHE | 54 | 56.329 | 48.865 | -5.828  | 1.00 | 24.29 | CPS1 |
| ATOM | 433 | CE1 | PHE | 54 | 54.883 | 47.376 | -3.983  | 1.00 | 25.96 | CPS1 |
| ATOM | 434 | CE2 | PHE | 54 | 55.143 | 49.370 | -5.316  | 1.00 | 25.86 | CPS1 |
| ATOM | 435 | CZ  | PHE | 54 | 54.414 | 48.624 | -4.387  | 1.00 | 26.67 | CPS1 |
| ATOM | 436 | C   | PHE | 54 | 59.285 | 47.177 | -3.724  | 1.00 | 22.66 | CPS1 |
| ATOM | 437 | O   | PHE | 54 | 59.018 | 47.970 | -2.808  | 1.00 | 21.27 | CPS1 |
| ATOM | 438 | N   | ALA | 55 | 59.556 | 45.896 | -3.508  | 1.00 | 20.95 | CPS1 |
| ATOM | 439 | CA  | ALA | 55 | 59.524 | 45.349 | -2.147  | 1.00 | 20.91 | CPS1 |
| ATOM | 440 | CB  | ALA | 55 | 59.733 | 43.846 | -2.191  | 1.00 | 20.44 | CPS1 |
| ATOM | 441 | C   | ALA | 55 | 60.568 | 45.990 | -1.234  | 1.00 | 20.32 | CPS1 |
| ATOM | 442 | O   | ALA | 55 | 60.288 | 46.295 | -0.075  | 1.00 | 18.66 | CPS1 |
| ATOM | 443 | N   | ALA | 56 | 61.779 | 46.172 | -1.751  | 1.00 | 18.74 | CPS1 |
| ATOM | 444 | CA  | ALA | 56 | 62.861 | 46.761 | -0.971  | 1.00 | 19.35 | CPS1 |
| ATOM | 445 | CB  | ALA | 56 | 64.180 | 46.698 | -1.762  | 1.00 | 19.52 | CPS1 |
| ATOM | 446 | C   | ALA | 56 | 62.543 | 48.201 | -0.593  | 1.00 | 20.45 | CPS1 |
| ATOM | 447 | O   | ALA | 56 | 62.773 | 48.617 | 0.543   | 1.00 | 18.52 | CPS1 |
| ATOM | 448 | N   | LYS | 57 | 62.015 | 48.969 | -1.545  | 1.00 | 18.95 | CPS1 |
| ATOM | 449 | CA  | LYS | 57 | 61.677 | 50.352 | -1.270  | 1.00 | 19.87 | CPS1 |
| ATOM | 450 | CB  | LYS | 57 | 61.427 | 51.107 | -2.583  | 1.00 | 19.77 | CPS1 |
| ATOM | 451 | CG  | LYS | 57 | 62.707 | 51.225 | -3.393  | 1.00 | 20.64 | CPS1 |
| ATOM | 452 | CD  | LYS | 57 | 62.533 | 52.055 | -4.679  | 1.00 | 21.45 | CPS1 |
| ATOM | 453 | CE  | LYS | 57 | 63.801 | 51.995 | -5.512  | 1.00 | 22.31 | CPS1 |
| ATOM | 454 | NZ  | LYS | 57 | 63.888 | 53.112 | -6.510  | 1.00 | 22.70 | CPS1 |
| ATOM | 455 | C   | LYS | 57 | 60.487 | 50.461 | -0.329  | 1.00 | 19.95 | CPS1 |

FIG. 1A-8

| ATOM | 456 | O   | LYS | 57 | 60.458 | 51.352 | 0.515  | 1.00 | 20.79 | CPS1 |
|------|-----|-----|-----|----|--------|--------|--------|------|-------|------|
| ATOM | 457 | N   | GLU | 58 | 59.513 | 49.561 | -0.463 | 1.00 | 19.28 | CPS1 |
| ATOM | 458 | CA  | GLU | 58 | 58.358 | 49.567 | 0.436  | 1.00 | 21.04 | CPS1 |
| ATOM | 459 | CB  | GLU | 58 | 57.324 | 48.516 | 0.013  | 1.00 | 22.82 | CPS1 |
| ATOM | 460 | CG  | GLU | 58 | 56.428 | 48.907 | -1.170 | 1.00 | 28.45 | CPS1 |
| ATOM | 461 | CD  | GLU | 58 | 55.586 | 50.145 | -0.886 | 1.00 | 31.31 | CPS1 |
| ATOM | 462 | OE1 | GLU | 58 | 55.244 | 50.371 | 0.295  | 1.00 | 33.36 | CPS1 |
| ATOM | 463 | OE2 | GLU | 58 | 55.253 | 50.886 | -1.840 | 1.00 | 34.15 | CPS1 |
| ATOM | 464 | C   | GLU | 58 | 58.851 | 49.242 | 1.856  | 1.00 | 19.94 | CPS1 |
| ATOM | 465 | O   | GLU | 58 | 58.456 | 49.899 | 2.818  | 1.00 | 19.84 | CPS1 |
| ATOM | 466 | N   | ALA | 59 | 59.717 | 48.234 | 1.979  | 1.00 | 18.95 | CPS1 |
| ATOM | 467 | CA  | ALA | 59 | 60.251 | 47.861 | 3.300  | 1.00 | 19.85 | CPS1 |
| ATOM | 468 | CB  | ALA | 59 | 61.155 | 46.618 | 3.185  | 1.00 | 18.19 | CPS1 |
| ATOM | 469 | C   | ALA | 59 | 61.044 | 49.037 | 3.881  | 1.00 | 20.46 | CPS1 |
| ATOM | 470 | O   | ALA | 59 | 60.954 | 49.359 | 5.076  | 1.00 | 20.70 | CPS1 |
| ATOM | 471 | N   | PHE | 60 | 61.831 | 49.691 | 3.042  | 1.00 | 19.23 | CPS1 |
| ATOM | 472 | CA  | PHE | 60 | 62.606 | 50.824 | 3.538  | 1.00 | 19.91 | CPS1 |
| ATOM | 473 | CB  | PHE | 60 | 63.500 | 51.407 | 2.440  | 1.00 | 20.97 | CPS1 |
| ATOM | 474 | CG  | PHE | 60 | 64.280 | 52.613 | 2.893  | 1.00 | 21.48 | CPS1 |
| ATOM | 475 | CD1 | PHE | 60 | 65.503 | 52.463 | 3.530  | 1.00 | 21.47 | CPS1 |
| ATOM | 476 | CD2 | PHE | 60 | 63.737 | 53.891 | 2.768  | 1.00 | 23.08 | CPS1 |
| ATOM | 477 | CE1 | PHE | 60 | 66.183 | 53.576 | 4.053  | 1.00 | 22.10 | CPS1 |
| ATOM | 478 | CE2 | PHE | 60 | 64.403 | 55.017 | 3.286  | 1.00 | 23.29 | CPS1 |
| ATOM | 479 | CZ  | PHE | 60 | 65.628 | 54.852 | 3.930  | 1.00 | 23.90 | CPS1 |
| ATOM | 480 | C   | PHE | 60 | 61.673 | 51.919 | 4.047  | 1.00 | 20.74 | CPS1 |
| ATOM | 481 | O   | PHE | 60 | 61.916 | 52.515 | 5.098  | 1.00 | 21.03 | CPS1 |
| ATOM | 482 | N   | SER | 61 | 60.604 | 52.191 | 3.302  | 1.00 | 20.69 | CPS1 |
| ATOM | 483 | CA  | SER | 61 | 59.669 | 53.237 | 3.702  | 1.00 | 21.92 | CPS1 |
| ATOM | 484 | CB  | SER | 61 | 58.625 | 53.488 | 2.607  | 1.00 | 22.10 | CPS1 |
| ATOM | 485 | OG  | SER | 61 | 57.716 | 52.406 | 2.499  | 1.00 | 23.85 | CPS1 |
| ATOM | 486 | C   | SER | 61 | 58.967 | 52.917 | 5.020  | 1.00 | 22.52 | CPS1 |
| ATOM | 487 | O   | SER | 61 | 58.574 | 53.824 | 5.760  | 1.00 | 23.57 | CPS1 |
| ATOM | 488 | N   | LYS | 62 | 58.811 | 51.633 | 5.314  | 1.00 | 21.64 | CPS1 |
| ATOM | 489 | CA  | LYS | 62 | 58.170 | 51.220 | 6.563  | 1.00 | 22.44 | CPS1 |
| ATOM | 490 | CB  | LYS | 62 | 57.705 | 49.767 | 6.463  | 1.00 | 22.20 | CPS1 |
| ATOM | 491 | CG  | LYS | 62 | 56.539 | 49.575 | 5.483  | 1.00 | 25.33 | CPS1 |
| ATOM | 492 | CD  | LYS | 62 | 56.149 | 48.113 | 5.354  | 1.00 | 29.01 | CPS1 |
| ATOM | 493 | CE  | LYS | 62 | 54.862 | 47.975 | 4.560  | 1.00 | 32.68 | CPS1 |
| ATOM | 494 | NZ  | LYS | 62 | 54.355 | 46.585 | 4.526  | 1.00 | 36.07 | CPS1 |
| ATOM | 495 | C   | LYS | 62 | 59.155 | 51.392 | 7.719  | 1.00 | 22.39 | CPS1 |
| ATOM | 496 | O   | LYS | 62 | 58.782 | 51.841 | 8.806  | 1.00 | 21.87 | CPS1 |
| ATOM | 497 | N   | ALA | 63 | 60.413 | 51.040 | 7.479  | 1.00 | 20.82 | CPS1 |
| ATOM | 498 | CA  | ALA | 63 | 61.444 | 51.194 | 8.502  | 1.00 | 21.70 | CPS1 |
| ATOM | 499 | CB  | ALA | 63 | 62.755 | 50.574 | 8.022  | 1.00 | 22.55 | CPS1 |
| ATOM | 500 | C   | ALA | 63 | 61.633 | 52.688 | 8.786  | 1.00 | 23.41 | CPS1 |
| ATOM | 501 | O   | ALA | 63 | 61.886 | 53.092 | 9.928  | 1.00 | 22.35 | CPS1 |
| ATOM | 502 | N   | PHE | 64 | 61.498 | 53.498 | 7.737  | 1.00 | 23.23 | CPS1 |
| ATOM | 503 | CA  | PHE | 64 | 61.638 | 54.946 | 7.838  | 1.00 | 25.59 | CPS1 |
| ATOM | 504 | CB  | PHE | 64 | 61.638 | 55.559 | 6.430  | 1.00 | 27.30 | CPS1 |
| ATOM | 505 | CG  | PHE | 64 | 62.121 | 56.979 | 6.381  | 1.00 | 30.46 | CPS1 |
| ATOM | 506 | CD1 | PHE | 64 | 63.464 | 57.279 | 6.593  | 1.00 | 31.49 | CPS1 |
| ATOM | 507 | CD2 | PHE | 64 | 61.237 | 58.015 | 6.107  | 1.00 | 29.70 | CPS1 |
| ATOM | 508 | CE1 | PHE | 64 | 63.920 | 58.596 | 6.528  | 1.00 | 33.53 | CPS1 |
| ATOM | 509 | CE2 | PHE | 64 | 61.681 | 59.333 | 6.039  | 1.00 | 31.57 | CPS1 |
| ATOM | 510 | CZ  | PHE | 64 | 63.021 | 59.624 | 6.249  | 1.00 | 32.65 | CPS1 |
| ATOM | 511 | C   | PHE | 64 | 60.477 | 55.504 | 8.667  | 1.00 | 26.41 | CPS1 |
| ATOM | 512 | O   | PHE | 64 | 60.564 | 56.613 | 9.193  | 1.00 | 27.04 | CPS1 |

FIG. 1A-9

| | | | | | | | | | | |
|---|---|---|---|---|---|---|---|---|---|---|
| ATOM | 513 | N | GLY | 65 | 59.388 | 54.735 | 8.751 | 1.00 | 27.22 | CPS1 |
| ATOM | 514 | CA | GLY | 65 | 58.229 | 55.102 | 9.554 | 1.00 | 28.06 | CPS1 |
| ATOM | 515 | C | GLY | 65 | 57.135 | 55.940 | 8.923 | 1.00 | 29.26 | CPS1 |
| ATOM | 516 | O | GLY | 65 | 56.143 | 56.260 | 9.577 | 1.00 | 29.04 | CPS1 |
| ATOM | 517 | N | THR | 66 | 57.299 | 56.279 | 7.650 | 1.00 | 29.45 | CPS1 |
| ATOM | 518 | CA | THR | 66 | 56.333 | 57.119 | 6.951 | 1.00 | 30.32 | CPS1 |
| ATOM | 519 | CB | THR | 66 | 57.033 | 58.351 | 6.391 | 1.00 | 30.19 | CPS1 |
| ATOM | 520 | OG1 | THR | 66 | 57.997 | 57.922 | 5.424 | 1.00 | 31.68 | CPS1 |
| ATOM | 521 | CG2 | THR | 66 | 57.751 | 59.114 | 7.489 | 1.00 | 31.63 | CPS1 |
| ATOM | 522 | C | THR | 66 | 55.640 | 56.453 | 5.764 | 1.00 | 30.61 | CPS1 |
| ATOM | 523 | O | THR | 66 | 54.548 | 56.862 | 5.365 | 1.00 | 30.50 | CPS1 |
| ATOM | 524 | N | GLY | 67 | 56.280 | 55.443 | 5.188 | 1.00 | 30.12 | CPS1 |
| ATOM | 525 | CA | GLY | 67 | 55.713 | 54.809 | 4.011 | 1.00 | 30.43 | CPS1 |
| ATOM | 526 | C | GLY | 67 | 56.020 | 55.750 | 2.852 | 1.00 | 31.44 | CPS1 |
| ATOM | 527 | O | GLY | 67 | 56.622 | 56.806 | 3.058 | 1.00 | 30.31 | CPS1 |
| ATOM | 528 | N | ILE | 68 | 55.626 | 55.383 | 1.639 | 1.00 | 31.40 | CPS1 |
| ATOM | 529 | CA | ILE | 68 | 55.886 | 56.239 | 0.486 | 1.00 | 32.28 | CPS1 |
| ATOM | 530 | CB | ILE | 68 | 55.869 | 55.429 | -0.844 | 1.00 | 31.80 | CPS1 |
| ATOM | 531 | CG2 | ILE | 68 | 56.083 | 56.375 | -2.048 | 1.00 | 32.06 | CPS1 |
| ATOM | 532 | CG1 | ILE | 68 | 56.975 | 54.364 | -0.826 | 1.00 | 29.99 | CPS1 |
| ATOM | 533 | CD1 | ILE | 68 | 58.391 | 54.924 | -0.821 | 1.00 | 29.70 | CPS1 |
| ATOM | 534 | C | ILE | 68 | 54.812 | 57.315 | 0.429 | 1.00 | 33.69 | CPS1 |
| ATOM | 535 | O | ILE | 68 | 53.623 | 57.028 | 0.556 | 1.00 | 34.51 | CPS1 |
| ATOM | 536 | N | GLY | 69 | 55.233 | 58.558 | 0.248 | 1.00 | 35.19 | CPS1 |
| ATOM | 537 | CA | GLY | 69 | 54.281 | 59.649 | 0.187 | 1.00 | 36.88 | CPS1 |
| ATOM | 538 | C | GLY | 69 | 54.989 | 60.985 | 0.167 | 1.00 | 37.34 | CPS1 |
| ATOM | 539 | O | GLY | 69 | 56.065 | 61.115 | -0.413 | 1.00 | 37.87 | CPS1 |
| ATOM | 540 | N | ALA | 70 | 54.394 | 61.977 | 0.821 | 1.00 | 38.19 | CPS1 |
| ATOM | 541 | CA | ALA | 70 | 54.964 | 63.314 | 0.866 | 1.00 | 38.33 | CPS1 |
| ATOM | 542 | CB | ALA | 70 | 54.010 | 64.252 | 1.609 | 1.00 | 39.53 | CPS1 |
| ATOM | 543 | C | ALA | 70 | 56.352 | 63.383 | 1.493 | 1.00 | 38.24 | CPS1 |
| ATOM | 544 | O | ALA | 70 | 57.188 | 64.171 | 1.067 | 1.00 | 39.11 | CPS1 |
| ATOM | 545 | N | GLN | 71 | 56.612 | 62.547 | 2.494 | 1.00 | 38.21 | CPS1 |
| ATOM | 546 | CA | GLN | 71 | 57.901 | 62.578 | 3.177 | 1.00 | 37.58 | CPS1 |
| ATOM | 547 | CB | GLN | 71 | 57.704 | 62.177 | 4.642 | 1.00 | 40.14 | CPS1 |
| ATOM | 548 | CG | GLN | 71 | 56.511 | 62.867 | 5.297 | 1.00 | 44.12 | CPS1 |
| ATOM | 549 | CD | GLN | 71 | 56.276 | 62.410 | 6.724 | 1.00 | 45.82 | CPS1 |
| ATOM | 550 | OE1 | GLN | 71 | 57.140 | 62.570 | 7.587 | 1.00 | 46.65 | CPS1 |
| ATOM | 551 | NE2 | GLN | 71 | 55.101 | 61.838 | 6.980 | 1.00 | 46.84 | CPS1 |
| ATOM | 552 | C | GLN | 71 | 58.997 | 61.706 | 2.557 | 1.00 | 35.81 | CPS1 |
| ATOM | 553 | O | GLN | 71 | 60.175 | 61.854 | 2.885 | 1.00 | 35.04 | CPS1 |
| ATOM | 554 | N | LEU | 72 | 58.619 | 60.805 | 1.662 | 1.00 | 33.50 | CPS1 |
| ATOM | 555 | CA | LEU | 72 | 59.602 | 59.917 | 1.053 | 1.00 | 31.98 | CPS1 |
| ATOM | 556 | CB | LEU | 72 | 59.899 | 58.762 | 2.010 | 1.00 | 30.93 | CPS1 |
| ATOM | 557 | CG | LEU | 72 | 60.905 | 57.699 | 1.561 | 1.00 | 30.26 | CPS1 |
| ATOM | 558 | CD1 | LEU | 72 | 62.311 | 58.276 | 1.592 | 1.00 | 31.32 | CPS1 |
| ATOM | 559 | CD2 | LEU | 72 | 60.801 | 56.483 | 2.490 | 1.00 | 29.64 | CPS1 |
| ATOM | 560 | C | LEU | 72 | 59.104 | 59.364 | -0.269 | 1.00 | 30.33 | CPS1 |
| ATOM | 561 | O | LEU | 72 | 58.025 | 58.794 | -0.333 | 1.00 | 30.73 | CPS1 |
| ATOM | 562 | N | SER | 73 | 59.907 | 59.526 | -1.315 | 1.00 | 30.09 | CPS1 |
| ATOM | 563 | CA | SER | 73 | 59.550 | 59.051 | -2.649 | 1.00 | 30.01 | CPS1 |
| ATOM | 564 | CB | SER | 73 | 59.795 | 60.161 | -3.679 | 1.00 | 30.79 | CPS1 |
| ATOM | 565 | OG | SER | 73 | 59.700 | 59.659 | -5.007 | 1.00 | 33.48 | CPS1 |
| ATOM | 566 | C | SER | 73 | 60.348 | 57.824 | -3.070 | 1.00 | 28.08 | CPS1 |
| ATOM | 567 | O | SER | 73 | 61.447 | 57.596 | -2.574 | 1.00 | 28.49 | CPS1 |
| ATOM | 568 | N | PHE | 74 | 59.792 | 57.032 | -3.985 | 1.00 | 28.86 | CPS1 |
| ATOM | 569 | CA | PHE | 74 | 60.512 | 55.869 | -4.502 | 1.00 | 28.18 | CPS1 |

FIG. 1A-10

| ATOM | 570 | CB | PHE | 74 | 59.712 | 55.173 | -5.608 | 1.00 | 28.46 | CPS1 |
|---|---|---|---|---|---|---|---|---|---|---|
| ATOM | 571 | CG | PHE | 74 | 58.581 | 54.331 | -5.106 | 1.00 | 28.51 | CPS1 |
| ATOM | 572 | CD1 | PHE | 74 | 58.833 | 53.164 | -4.398 | 1.00 | 29.22 | CPS1 |
| ATOM | 573 | CD2 | PHE | 74 | 57.264 | 54.695 | -5.358 | 1.00 | 28.56 | CPS1 |
| ATOM | 574 | CE1 | PHE | 74 | 57.789 | 52.364 | -3.951 | 1.00 | 29.35 | CPS1 |
| ATOM | 575 | CE2 | PHE | 74 | 56.213 | 53.907 | -4.914 | 1.00 | 30.56 | CPS1 |
| ATOM | 576 | CZ | PHE | 74 | 56.479 | 52.734 | -4.209 | 1.00 | 28.99 | CPS1 |
| ATOM | 577 | C | PHE | 74 | 61.818 | 56.377 | -5.107 | 1.00 | 29.02 | CPS1 |
| ATOM | 578 | O | PHE | 74 | 62.846 | 55.697 | -5.076 | 1.00 | 28.52 | CPS1 |
| ATOM | 579 | N | GLN | 75 | 61.776 | 57.586 | -5.660 | 1.00 | 29.54 | CPS1 |
| ATOM | 580 | CA | GLN | 75 | 62.959 | 58.168 | -6.289 | 1.00 | 30.04 | CPS1 |
| ATOM | 581 | CB | GLN | 75 | 62.555 | 59.395 | -7.117 | 1.00 | 31.75 | CPS1 |
| ATOM | 582 | CG | GLN | 75 | 61.636 | 59.056 | -8.284 | 1.00 | 31.66 | CPS1 |
| ATOM | 583 | CD | GLN | 75 | 62.300 | 58.137 | -9.295 | 1.00 | 32.50 | CPS1 |
| ATOM | 584 | OE1 | GLN | 75 | 61.673 | 57.207 | -9.816 | 1.00 | 34.26 | CPS1 |
| ATOM | 585 | NE2 | GLN | 75 | 63.571 | 58.393 | -9.584 | 1.00 | 30.64 | CPS1 |
| ATOM | 586 | C | GLN | 75 | 64.052 | 58.543 | -5.294 | 1.00 | 30.56 | CPS1 |
| ATOM | 587 | O | GLN | 75 | 65.205 | 58.768 | -5.681 | 1.00 | 29.97 | CPS1 |
| ATOM | 588 | N | ASP | 76 | 63.697 | 58.605 | -4.011 | 1.00 | 30.64 | CPS1 |
| ATOM | 589 | CA | ASP | 76 | 64.669 | 58.943 | -2.972 | 1.00 | 29.57 | CPS1 |
| ATOM | 590 | CB | ASP | 76 | 63.975 | 59.494 | -1.718 | 1.00 | 30.95 | CPS1 |
| ATOM | 591 | CG | ASP | 76 | 63.293 | 60.824 | -1.955 | 1.00 | 32.86 | CPS1 |
| ATOM | 592 | OD1 | ASP | 76 | 63.804 | 61.614 | -2.771 | 1.00 | 33.98 | CPS1 |
| ATOM | 593 | OD2 | ASP | 76 | 62.254 | 61.083 | -1.313 | 1.00 | 32.57 | CPS1 |
| ATOM | 594 | C | ASP | 76 | 65.472 | 57.720 | -2.546 | 1.00 | 28.65 | CPS1 |
| ATOM | 595 | O | ASP | 76 | 66.430 | 57.835 | -1.788 | 1.00 | 28.90 | CPS1 |
| ATOM | 596 | N | ILE | 77 | 65.085 | 56.551 | -3.038 | 1.00 | 27.41 | CPS1 |
| ATOM | 597 | CA | ILE | 77 | 65.752 | 55.318 | -2.644 | 1.00 | 26.26 | CPS1 |
| ATOM | 598 | CB | ILE | 77 | 64.750 | 54.372 | -1.947 | 1.00 | 25.85 | CPS1 |
| ATOM | 599 | CG2 | ILE | 77 | 65.494 | 53.213 | -1.295 | 1.00 | 26.27 | CPS1 |
| ATOM | 600 | CG1 | ILE | 77 | 63.927 | 55.145 | -0.912 | 1.00 | 25.55 | CPS1 |
| ATOM | 601 | CD1 | ILE | 77 | 62.613 | 54.455 | -0.547 | 1.00 | 25.71 | CPS1 |
| ATOM | 602 | C | ILE | 77 | 66.323 | 54.562 | -3.830 | 1.00 | 26.41 | CPS1 |
| ATOM | 603 | O | ILE | 77 | 65.633 | 54.355 | -4.819 | 1.00 | 28.03 | CPS1 |
| ATOM | 604 | N | GLU | 78 | 67.573 | 54.134 | -3.726 | 1.00 | 26.24 | CPS1 |
| ATOM | 605 | CA | GLU | 78 | 68.179 | 53.359 | -4.800 | 1.00 | 26.41 | CPS1 |
| ATOM | 606 | CB | GLU | 78 | 69.198 | 54.197 | -5.586 | 1.00 | 27.49 | CPS1 |
| ATOM | 607 | CG | GLU | 78 | 69.942 | 53.392 | -6.661 | 1.00 | 31.00 | CPS1 |
| ATOM | 608 | CD | GLU | 78 | 70.711 | 54.265 | -7.657 | 1.00 | 34.35 | CPS1 |
| ATOM | 609 | OE1 | GLU | 78 | 70.059 | 54.887 | -8.526 | 1.00 | 35.58 | CPS1 |
| ATOM | 610 | OE2 | GLU | 78 | 71.959 | 54.328 | -7.568 | 1.00 | 34.83 | CPS1 |
| ATOM | 611 | C | GLU | 78 | 68.856 | 52.116 | -4.235 | 1.00 | 26.51 | CPS1 |
| ATOM | 612 | O | GLU | 78 | 69.581 | 52.183 | -3.244 | 1.00 | 26.47 | CPS1 |
| ATOM | 613 | N | ILE | 79 | 68.595 | 50.976 | -4.863 | 1.00 | 26.08 | CPS1 |
| ATOM | 614 | CA | ILE | 79 | 69.205 | 49.731 | -4.445 | 1.00 | 25.84 | CPS1 |
| ATOM | 615 | CB | ILE | 79 | 68.192 | 48.545 | -4.459 | 1.00 | 25.79 | CPS1 |
| ATOM | 616 | CG2 | ILE | 79 | 68.942 | 47.221 | -4.467 | 1.00 | 25.99 | CPS1 |
| ATOM | 617 | CG1 | ILE | 79 | 67.282 | 48.595 | -3.224 | 1.00 | 28.30 | CPS1 |
| ATOM | 618 | CD1 | ILE | 79 | 66.246 | 49.685 | -3.247 | 1.00 | 25.92 | CPS1 |
| ATOM | 619 | C | ILE | 79 | 70.329 | 49.419 | -5.420 | 1.00 | 26.11 | CPS1 |
| ATOM | 620 | O | ILE | 79 | 70.186 | 49.598 | -6.633 | 1.00 | 24.92 | CPS1 |
| ATOM | 621 | N | ARG | 80 | 71.455 | 48.974 | -4.876 | 1.00 | 26.85 | CPS1 |
| ATOM | 622 | CA | ARG | 80 | 72.604 | 48.582 | -5.675 | 1.00 | 26.89 | CPS1 |
| ATOM | 623 | CB | ARG | 80 | 73.708 | 49.616 | -5.587 | 1.00 | 29.63 | CPS1 |
| ATOM | 624 | CG | ARG | 80 | 73.353 | 50.965 | -6.123 | 1.00 | 31.02 | CPS1 |
| ATOM | 625 | CD | ARG | 80 | 74.524 | 51.844 | -5.838 | 1.00 | 35.09 | CPS1 |
| ATOM | 626 | NE | ARG | 80 | 74.282 | 53.237 | -6.147 | 1.00 | 35.47 | CPS1 |

FIG. 1A-11

| ATOM | 627 | CZ | ARG | 80 | 75.084 | 54.205 | -5.736 | 1.00 | 33.96 | CPS1 |
|---|---|---|---|---|---|---|---|---|---|---|
| ATOM | 628 | NH1 | ARG | 80 | 76.149 | 53.896 | -5.009 | 1.00 | 32.40 | CPS1 |
| ATOM | 629 | NH2 | ARG | 80 | 74.824 | 55.460 | -6.053 | 1.00 | 34.37 | CPS1 |
| ATOM | 630 | C | ARG | 80 | 73.130 | 47.294 | -5.090 | 1.00 | 27.91 | CPS1 |
| ATOM | 631 | O | ARG | 80 | 72.704 | 46.877 | -4.017 | 1.00 | 26.72 | CPS1 |
| ATOM | 632 | N | LYS | 81 | 74.061 | 46.662 | -5.794 | 1.00 | 28.40 | CPS1 |
| ATOM | 633 | CA | LYS | 81 | 74.671 | 45.436 | -5.301 | 1.00 | 29.29 | CPS1 |
| ATOM | 634 | CB | LYS | 81 | 74.395 | 44.275 | -6.260 | 1.00 | 31.32 | CPS1 |
| ATOM | 635 | CG | LYS | 81 | 72.962 | 43.773 | -6.177 | 1.00 | 34.37 | CPS1 |
| ATOM | 636 | CD | LYS | 81 | 72.745 | 42.490 | -6.965 | 1.00 | 38.80 | CPS1 |
| ATOM | 637 | CE | LYS | 81 | 71.388 | 41.887 | -6.623 | 1.00 | 41.39 | CPS1 |
| ATOM | 638 | NZ | LYS | 81 | 71.175 | 40.558 | -7.270 | 1.00 | 45.04 | CPS1 |
| ATOM | 639 | C | LYS | 81 | 76.159 | 45.688 | -5.173 | 1.00 | 29.85 | CPS1 |
| ATOM | 640 | O | LYS | 81 | 76.754 | 46.332 | -6.039 | 1.00 | 29.65 | CPS1 |
| ATOM | 641 | N | ASP | 82 | 76.768 | 45.225 | -4.088 | 1.00 | 28.96 | CPS1 |
| ATOM | 642 | CA | ASP | 82 | 78.194 | 45.443 | -3.952 | 1.00 | 29.85 | CPS1 |
| ATOM | 643 | CB | ASP | 82 | 78.642 | 45.423 | -2.480 | 1.00 | 29.47 | CPS1 |
| ATOM | 644 | CG | ASP | 82 | 78.413 | 44.095 | -1.796 | 1.00 | 28.92 | CPS1 |
| ATOM | 645 | OD1 | ASP | 82 | 78.331 | 43.051 | -2.471 | 1.00 | 29.25 | CPS1 |
| ATOM | 646 | OD2 | ASP | 82 | 78.346 | 44.105 | -0.552 | 1.00 | 30.21 | CPS1 |
| ATOM | 647 | C | ASP | 82 | 78.918 | 44.388 | -4.773 | 1.00 | 30.66 | CPS1 |
| ATOM | 648 | O | ASP | 82 | 78.281 | 43.626 | -5.496 | 1.00 | 29.93 | CPS1 |
| ATOM | 649 | N | GLN | 83 | 80.239 | 44.342 | -4.667 | 1.00 | 32.99 | CPS1 |
| ATOM | 650 | CA | GLN | 83 | 81.023 | 43.394 | -5.450 | 1.00 | 34.77 | CPS1 |
| ATOM | 651 | CB | GLN | 83 | 82.512 | 43.700 | -5.287 | 1.00 | 37.08 | CPS1 |
| ATOM | 652 | CG | GLN | 83 | 82.860 | 45.145 | -5.635 | 1.00 | 38.94 | CPS1 |
| ATOM | 653 | CD | GLN | 83 | 84.352 | 45.399 | -5.653 | 1.00 | 40.99 | CPS1 |
| ATOM | 654 | OE1 | GLN | 83 | 85.032 | 45.115 | -6.643 | 1.00 | 42.58 | CPS1 |
| ATOM | 655 | NE2 | GLN | 83 | 84.874 | 45.925 | -4.549 | 1.00 | 41.73 | CPS1 |
| ATOM | 656 | C | GLN | 83 | 80.746 | 41.924 | -5.151 | 1.00 | 35.50 | CPS1 |
| ATOM | 657 | O | GLN | 83 | 81.123 | 41.056 | -5.930 | 1.00 | 35.54 | CPS1 |
| ATOM | 658 | N | ASN | 84 | 80.094 | 41.640 | -4.027 | 1.00 | 36.07 | CPS1 |
| ATOM | 659 | CA | ASN | 84 | 79.757 | 40.258 | -3.684 | 1.00 | 35.57 | CPS1 |
| ATOM | 660 | CB | ASN | 84 | 79.863 | 40.014 | -2.178 | 1.00 | 37.57 | CPS1 |
| ATOM | 661 | CG | ASN | 84 | 81.284 | 39.960 | -1.700 | 1.00 | 39.82 | CPS1 |
| ATOM | 662 | OD1 | ASN | 84 | 82.116 | 39.250 | -2.270 | 1.00 | 41.25 | CPS1 |
| ATOM | 663 | ND2 | ASN | 84 | 81.577 | 40.702 | -0.639 | 1.00 | 40.86 | CPS1 |
| ATOM | 664 | C | ASN | 84 | 78.335 | 39.937 | -4.113 | 1.00 | 34.27 | CPS1 |
| ATOM | 665 | O | ASN | 84 | 77.856 | 38.824 | -3.899 | 1.00 | 34.98 | CPS1 |
| ATOM | 666 | N | GLY | 85 | 77.659 | 40.914 | -4.706 | 1.00 | 31.13 | CPS1 |
| ATOM | 667 | CA | GLY | 85 | 76.289 | 40.703 | -5.137 | 1.00 | 29.50 | CPS1 |
| ATOM | 668 | C | GLY | 85 | 75.274 | 41.002 | -4.040 | 1.00 | 27.83 | CPS1 |
| ATOM | 669 | O | GLY | 85 | 74.089 | 40.743 | -4.209 | 1.00 | 27.44 | CPS1 |
| ATOM | 670 | N | LYS | 86 | 75.737 | 41.548 | -2.919 | 1.00 | 26.25 | CPS1 |
| ATOM | 671 | CA | LYS | 86 | 74.858 | 41.888 | -1.797 | 1.00 | 25.96 | CPS1 |
| ATOM | 672 | CB | LYS | 86 | 75.664 | 41.946 | -0.500 | 1.00 | 26.50 | CPS1 |
| ATOM | 673 | CG | LYS | 86 | 74.905 | 42.542 | 0.680 | 1.00 | 26.15 | CPS1 |
| ATOM | 674 | CD | LYS | 86 | 73.833 | 41.595 | 1.234 | 1.00 | 24.85 | CPS1 |
| ATOM | 675 | CE | LYS | 86 | 73.002 | 42.312 | 2.322 | 1.00 | 24.53 | CPS1 |
| ATOM | 676 | NZ | LYS | 86 | 72.000 | 41.403 | 2.973 | 1.00 | 23.95 | CPS1 |
| ATOM | 677 | C | LYS | 86 | 74.164 | 43.232 | -2.002 | 1.00 | 24.92 | CPS1 |
| ATOM | 678 | O | LYS | 86 | 74.812 | 44.253 | -2.223 | 1.00 | 25.51 | CPS1 |
| ATOM | 679 | N | PRO | 87 | 72.830 | 43.256 | -1.938 | 1.00 | 24.79 | CPS1 |
| ATOM | 680 | CD | PRO | 87 | 71.858 | 42.148 | -1.905 | 1.00 | 26.28 | CPS1 |
| ATOM | 681 | CA | PRO | 87 | 72.157 | 44.538 | -2.123 | 1.00 | 23.90 | CPS1 |
| ATOM | 682 | CB | PRO | 87 | 70.702 | 44.136 | -2.356 | 1.00 | 25.37 | CPS1 |
| ATOM | 683 | CG | PRO | 87 | 70.571 | 42.868 | -1.581 | 1.00 | 26.57 | CPS1 |

FIG. 1A-12

| ATOM | 684 | C   | PRO | 87 | 72.300 | 45.486 | -0.933 | 1.00 | 24.14 | CPS1 |
|------|-----|-----|-----|----|--------|--------|--------|------|-------|------|
| ATOM | 685 | O   | PRO | 87 | 72.355 | 45.061 | 0.222  | 1.00 | 23.36 | CPS1 |
| ATOM | 686 | N   | TYR | 88 | 72.383 | 46.775 | -1.223 | 1.00 | 23.09 | CPS1 |
| ATOM | 687 | CA  | TYR | 88 | 72.456 | 47.775 | -0.170 | 1.00 | 22.80 | CPS1 |
| ATOM | 688 | CB  | TYR | 88 | 73.903 | 48.132 | 0.169  | 1.00 | 23.97 | CPS1 |
| ATOM | 689 | CG  | TYR | 88 | 74.662 | 48.796 | -0.948 | 1.00 | 23.15 | CPS1 |
| ATOM | 690 | CD1 | TYR | 88 | 74.617 | 50.176 | -1.121 | 1.00 | 23.81 | CPS1 |
| ATOM | 691 | CE1 | TYR | 88 | 75.334 | 50.803 | -2.148 | 1.00 | 24.04 | CPS1 |
| ATOM | 692 | CD2 | TYR | 88 | 75.438 | 48.042 | -1.823 | 1.00 | 23.00 | CPS1 |
| ATOM | 693 | CE2 | TYR | 88 | 76.163 | 48.653 | -2.853 | 1.00 | 23.00 | CPS1 |
| ATOM | 694 | CZ  | TYR | 88 | 76.106 | 50.031 | -3.007 | 1.00 | 24.59 | CPS1 |
| ATOM | 695 | OH  | TYR | 88 | 76.807 | 50.635 | -4.029 | 1.00 | 23.69 | CPS1 |
| ATOM | 696 | C   | TYR | 88 | 71.697 | 48.978 | -0.676 | 1.00 | 24.07 | CPS1 |
| ATOM | 697 | O   | TYR | 88 | 71.492 | 49.131 | -1.882 | 1.00 | 24.63 | CPS1 |
| ATOM | 698 | N   | ILE | 89 | 71.265 | 49.821 | 0.247  | 1.00 | 23.90 | CPS1 |
| ATOM | 699 | CA  | ILE | 89 | 70.486 | 50.992 | -0.096 | 1.00 | 24.96 | CPS1 |
| ATOM | 700 | CB  | ILE | 89 | 69.183 | 51.038 | 0.763  | 1.00 | 25.43 | CPS1 |
| ATOM | 701 | CG2 | ILE | 89 | 68.580 | 52.445 | 0.773  | 1.00 | 23.76 | CPS1 |
| ATOM | 702 | CG1 | ILE | 89 | 68.179 | 50.007 | 0.237  | 1.00 | 25.76 | CPS1 |
| ATOM | 703 | CD1 | ILE | 89 | 66.920 | 49.857 | 1.102  | 1.00 | 25.48 | CPS1 |
| ATOM | 704 | C   | ILE | 89 | 71.230 | 52.304 | 0.086  | 1.00 | 26.98 | CPS1 |
| ATOM | 705 | O   | ILE | 89 | 72.018 | 52.470 | 1.020  | 1.00 | 27.02 | CPS1 |
| ATOM | 706 | N   | ILE | 90 | 70.984 | 53.227 | -0.840 | 1.00 | 28.88 | CPS1 |
| ATOM | 707 | CA  | ILE | 90 | 71.543 | 54.567 | -0.750 | 1.00 | 31.89 | CPS1 |
| ATOM | 708 | CB  | ILE | 90 | 72.383 | 54.968 | -1.983 | 1.00 | 34.52 | CPS1 |
| ATOM | 709 | CG2 | ILE | 90 | 72.685 | 56.465 | -1.930 | 1.00 | 35.39 | CPS1 |
| ATOM | 710 | CG1 | ILE | 90 | 73.692 | 54.176 | -2.020 | 1.00 | 34.95 | CPS1 |
| ATOM | 711 | CD1 | ILE | 90 | 74.585 | 54.381 | -0.812 | 1.00 | 36.25 | CPS1 |
| ATOM | 712 | C   | ILE | 90 | 70.299 | 55.433 | -0.715 | 1.00 | 32.42 | CPS1 |
| ATOM | 713 | O   | ILE | 90 | 69.450 | 55.342 | -1.599 | 1.00 | 32.97 | CPS1 |
| ATOM | 714 | N   | CYS | 91 | 70.165 | 56.246 | 0.320  | 1.00 | 32.73 | CPS1 |
| ATOM | 715 | CA  | CYS | 91 | 69.002 | 57.106 | 0.433  | 1.00 | 34.96 | CPS1 |
| ATOM | 716 | CB  | CYS | 91 | 68.008 | 56.543 | 1.463  | 1.00 | 32.49 | CPS1 |
| ATOM | 717 | SG  | CYS | 91 | 66.523 | 57.557 | 1.657  | 1.00 | 29.59 | CPS1 |
| ATOM | 718 | C   | CYS | 91 | 69.452 | 58.494 | 0.848  | 1.00 | 38.10 | CPS1 |
| ATOM | 719 | O   | CYS | 91 | 70.079 | 58.666 | 1.893  | 1.00 | 40.46 | CPS1 |
| ATOM | 720 | N   | THR | 92 | 69.124 | 59.476 | 0.014  | 1.00 | 42.14 | CPS1 |
| ATOM | 721 | CA  | THR | 92 | 69.489 | 60.870 | 0.246  | 1.00 | 45.56 | CPS1 |
| ATOM | 722 | CB  | THR | 92 | 68.964 | 61.772 | -0.898 | 1.00 | 46.93 | CPS1 |
| ATOM | 723 | OG1 | THR | 92 | 67.552 | 61.562 | -1.069 | 1.00 | 48.39 | CPS1 |
| ATOM | 724 | CG2 | THR | 92 | 69.686 | 61.454 | -2.205 | 1.00 | 47.93 | CPS1 |
| ATOM | 725 | C   | THR | 92 | 69.001 | 61.457 | 1.571  | 1.00 | 46.35 | CPS1 |
| ATOM | 726 | O   | THR | 92 | 69.345 | 62.592 | 1.901  | 1.00 | 47.51 | CPS1 |
| ATOM | 727 | N   | LYS | 93 | 68.211 | 60.703 | 2.332  | 1.00 | 46.09 | CPS1 |
| ATOM | 728 | CA  | LYS | 93 | 67.714 | 61.218 | 3.602  | 1.00 | 46.14 | CPS1 |
| ATOM | 729 | CB  | LYS | 93 | 66.214 | 60.944 | 3.725  | 1.00 | 46.87 | CPS1 |
| ATOM | 730 | CG  | LYS | 93 | 65.395 | 61.870 | 2.837  | 1.00 | 48.42 | CPS1 |
| ATOM | 731 | CD  | LYS | 93 | 63.903 | 61.704 | 3.034  | 1.00 | 49.49 | CPS1 |
| ATOM | 732 | CE  | LYS | 93 | 63.148 | 62.908 | 2.482  | 1.00 | 50.63 | CPS1 |
| ATOM | 733 | NZ  | LYS | 93 | 63.471 | 63.177 | 1.054  | 1.00 | 52.22 | CPS1 |
| ATOM | 734 | C   | LYS | 93 | 68.452 | 60.733 | 4.844  | 1.00 | 45.50 | CPS1 |
| ATOM | 735 | O   | LYS | 93 | 68.167 | 61.182 | 5.954  | 1.00 | 45.52 | CPS1 |
| ATOM | 736 | N   | LEU | 94 | 69.408 | 59.829 | 4.657  | 1.00 | 44.83 | CPS1 |
| ATOM | 737 | CA  | LEU | 94 | 70.200 | 59.313 | 5.770  | 1.00 | 44.48 | CPS1 |
| ATOM | 738 | CB  | LEU | 94 | 69.376 | 58.330 | 6.611  | 1.00 | 44.44 | CPS1 |
| ATOM | 739 | CG  | LEU | 94 | 68.488 | 57.283 | 5.928  | 1.00 | 44.15 | CPS1 |
| ATOM | 740 | CD1 | LEU | 94 | 69.258 | 56.498 | 4.886  | 1.00 | 42.30 | CPS1 |

FIG. 1A-13

| | | | | | | | | | |
|---|---|---|---|---|---|---|---|---|---|
| ATOM | 741 | CD2 | LEU | 94 | 67.934 | 56.361 | 6.997 | 1.00 43.28 | CPS1 |
| ATOM | 742 | C | LEU | 94 | 71.486 | 58.641 | 5.307 | 1.00 44.30 | CPS1 |
| ATOM | 743 | O | LEU | 94 | 71.692 | 58.432 | 4.111 | 1.00 44.84 | CPS1 |
| ATOM | 744 | N | SER | 95 | 72.353 | 58.308 | 6.257 | 1.00 43.56 | CPS1 |
| ATOM | 745 | CA | SER | 95 | 73.612 | 57.655 | 5.934 | 1.00 44.17 | CPS1 |
| ATOM | 746 | CB | SER | 95 | 74.583 | 57.748 | 7.107 | 1.00 44.85 | CPS1 |
| ATOM | 747 | OG | SER | 95 | 75.803 | 57.098 | 6.784 | 1.00 47.82 | CPS1 |
| ATOM | 748 | C | SER | 95 | 73.408 | 56.184 | 5.577 | 1.00 43.59 | CPS1 |
| ATOM | 749 | O | SER | 95 | 72.676 | 55.462 | 6.258 | 1.00 43.06 | CPS1 |
| ATOM | 750 | N | PRO | 96 | 74.065 | 55.720 | 4.503 | 1.00 42.46 | CPS1 |
| ATOM | 751 | CD | PRO | 96 | 75.025 | 56.444 | 3.650 | 1.00 42.90 | CPS1 |
| ATOM | 752 | CA | PRO | 96 | 73.939 | 54.325 | 4.079 | 1.00 41.30 | CPS1 |
| ATOM | 753 | CB | PRO | 96 | 74.757 | 54.286 | 2.788 | 1.00 42.08 | CPS1 |
| ATOM | 754 | CG | PRO | 96 | 75.821 | 55.316 | 3.045 | 1.00 42.41 | CPS1 |
| ATOM | 755 | C | PRO | 96 | 74.473 | 53.379 | 5.153 | 1.00 39.30 | CPS1 |
| ATOM | 756 | O | PRO | 96 | 74.098 | 52.210 | 5.206 | 1.00 38.17 | CPS1 |
| ATOM | 757 | N | ALA | 97 | 75.348 | 53.901 | 6.008 | 1.00 37.86 | CPS1 |
| ATOM | 758 | CA | ALA | 97 | 75.929 | 53.117 | 7.095 | 1.00 36.05 | CPS1 |
| ATOM | 759 | CB | ALA | 97 | 76.982 | 53.940 | 7.819 | 1.00 37.73 | CPS1 |
| ATOM | 760 | C | ALA | 97 | 74.857 | 52.681 | 8.090 | 1.00 35.10 | CPS1 |
| ATOM | 761 | O | ALA | 97 | 74.992 | 51.662 | 8.770 | 1.00 35.38 | CPS1 |
| ATOM | 762 | N | ALA | 98 | 73.789 | 53.460 | 8.173 | 1.00 33.38 | CPS1 |
| ATOM | 763 | CA | ALA | 98 | 72.717 | 53.160 | 9.107 | 1.00 31.76 | CPS1 |
| ATOM | 764 | CB | ALA | 98 | 72.057 | 54.454 | 9.546 | 1.00 33.83 | CPS1 |
| ATOM | 765 | C | ALA | 98 | 71.657 | 52.220 | 8.537 | 1.00 30.24 | CPS1 |
| ATOM | 766 | O | ALA | 98 | 70.734 | 51.849 | 9.255 | 1.00 31.14 | CPS1 |
| ATOM | 767 | N | VAL | 99 | 71.796 | 51.831 | 7.269 | 1.00 26.77 | CPS1 |
| ATOM | 768 | CA | VAL | 99 | 70.803 | 50.980 | 6.607 | 1.00 25.25 | CPS1 |
| ATOM | 769 | CB | VAL | 99 | 70.258 | 51.695 | 5.331 | 1.00 24.54 | CPS1 |
| ATOM | 770 | CG1 | VAL | 99 | 69.091 | 50.920 | 4.731 | 1.00 24.61 | CPS1 |
| ATOM | 771 | CG2 | VAL | 99 | 69.829 | 53.107 | 5.676 | 1.00 26.14 | CPS1 |
| ATOM | 772 | C | VAL | 99 | 71.272 | 49.576 | 6.207 | 1.00 23.74 | CPS1 |
| ATOM | 773 | O | VAL | 99 | 72.390 | 49.393 | 5.720 | 1.00 23.55 | CPS1 |
| ATOM | 774 | N | HIS | 100 | 70.395 | 48.595 | 6.422 | 1.00 22.48 | CPS1 |
| ATOM | 775 | CA | HIS | 100 | 70.640 | 47.195 | 6.075 | 1.00 21.75 | CPS1 |
| ATOM | 776 | CB | HIS | 100 | 70.873 | 46.360 | 7.334 | 1.00 23.99 | CPS1 |
| ATOM | 777 | CG | HIS | 100 | 72.020 | 46.846 | 8.160 | 1.00 27.42 | CPS1 |
| ATOM | 778 | CD2 | HIS | 100 | 72.060 | 47.696 | 9.212 | 1.00 28.79 | CPS1 |
| ATOM | 779 | ND1 | HIS | 100 | 73.329 | 46.542 | 7.859 | 1.00 28.14 | CPS1 |
| ATOM | 780 | CE1 | HIS | 100 | 74.128 | 47.190 | 8.689 | 1.00 30.71 | CPS1 |
| ATOM | 781 | NE2 | HIS | 100 | 73.383 | 47.898 | 9.519 | 1.00 30.58 | CPS1 |
| ATOM | 782 | C | HIS | 100 | 69.394 | 46.686 | 5.357 | 1.00 20.99 | CPS1 |
| ATOM | 783 | O | HIS | 100 | 68.270 | 47.007 | 5.752 | 1.00 20.00 | CPS1 |
| ATOM | 784 | N | VAL | 101 | 69.593 | 45.893 | 4.312 | 1.00 20.41 | CPS1 |
| ATOM | 785 | CA | VAL | 101 | 68.473 | 45.357 | 3.551 | 1.00 20.21 | CPS1 |
| ATOM | 786 | CB | VAL | 101 | 68.181 | 46.244 | 2.290 | 1.00 20.23 | CPS1 |
| ATOM | 787 | CG1 | VAL | 101 | 69.391 | 46.245 | 1.344 | 1.00 22.43 | CPS1 |
| ATOM | 788 | CG2 | VAL | 101 | 66.958 | 45.723 | 1.553 | 1.00 21.20 | CPS1 |
| ATOM | 789 | C | VAL | 101 | 68.761 | 43.939 | 3.084 | 1.00 20.38 | CPS1 |
| ATOM | 790 | O | VAL | 101 | 69.920 | 43.527 | 2.986 | 1.00 19.26 | CPS1 |
| ATOM | 791 | N | SER | 102 | 67.702 | 43.167 | 2.835 | 1.00 19.19 | CPS1 |
| ATOM | 792 | CA | SER | 102 | 67.867 | 41.833 | 2.280 | 1.00 19.46 | CPS1 |
| ATOM | 793 | CB | SER | 102 | 67.884 | 40.742 | 3.345 | 1.00 18.79 | CPS1 |
| ATOM | 794 | OG | SER | 102 | 68.068 | 39.478 | 2.720 | 1.00 18.64 | CPS1 |
| ATOM | 795 | C | SER | 102 | 66.677 | 41.638 | 1.358 | 1.00 20.37 | CPS1 |
| ATOM | 796 | O | SER | 102 | 65.581 | 42.095 | 1.658 | 1.00 20.10 | CPS1 |
| ATOM | 797 | N | ILE | 103 | 66.902 | 40.964 | 0.236 | 1.00 19.92 | CPS1 |

FIG. 1A-14

| ATOM | 798 | CA  | ILE | 103 | 65.847 | 40.737 | -0.744 | 1.00 | 19.71 | CPS1 |
|------|-----|-----|-----|-----|--------|--------|--------|------|-------|------|
| ATOM | 799 | CB  | ILE | 103 | 66.122 | 41.550 | -2.033 | 1.00 | 19.02 | CPS1 |
| ATOM | 800 | CG2 | ILE | 103 | 64.988 | 41.337 | -3.054 | 1.00 | 19.50 | CPS1 |
| ATOM | 801 | CG1 | ILE | 103 | 66.234 | 43.031 | -1.682 | 1.00 | 18.90 | CPS1 |
| ATOM | 802 | CD1 | ILE | 103 | 66.767 | 43.904 | -2.828 | 1.00 | 19.01 | CPS1 |
| ATOM | 803 | C   | ILE | 103 | 65.804 | 39.265 | -1.090 | 1.00 | 20.30 | CPS1 |
| ATOM | 804 | O   | ILE | 103 | 66.847 | 38.620 | -1.164 | 1.00 | 20.97 | CPS1 |
| ATOM | 805 | N   | THR | 104 | 64.603 | 38.729 | -1.287 | 1.00 | 20.48 | CPS1 |
| ATOM | 806 | CA  | THR | 104 | 64.468 | 37.316 | -1.623 | 1.00 | 20.34 | CPS1 |
| ATOM | 807 | CB  | THR | 104 | 64.172 | 36.462 | -0.350 | 1.00 | 21.86 | CPS1 |
| ATOM | 808 | OG1 | THR | 104 | 64.222 | 35.065 | -0.671 | 1.00 | 21.77 | CPS1 |
| ATOM | 809 | CG2 | THR | 104 | 62.804 | 36.795 |  0.213 | 1.00 | 20.65 | CPS1 |
| ATOM | 810 | C   | THR | 104 | 63.346 | 37.139 | -2.642 | 1.00 | 21.68 | CPS1 |
| ATOM | 811 | O   | THR | 104 | 62.501 | 38.018 | -2.813 | 1.00 | 20.50 | CPS1 |
| ATOM | 812 | N   | HIS | 105 | 63.345 | 36.003 | -3.325 | 1.00 | 22.11 | CPS1 |
| ATOM | 813 | CA  | HIS | 105 | 62.323 | 35.728 | -4.331 | 1.00 | 24.82 | CPS1 |
| ATOM | 814 | CB  | HIS | 105 | 62.884 | 35.948 | -5.747 | 1.00 | 27.53 | CPS1 |
| ATOM | 815 | CG  | HIS | 105 | 63.383 | 37.335 | -6.020 | 1.00 | 32.22 | CPS1 |
| ATOM | 816 | CD2 | HIS | 105 | 64.585 | 37.915 | -5.782 | 1.00 | 34.13 | CPS1 |
| ATOM | 817 | ND1 | HIS | 105 | 62.615 | 38.292 | -6.648 | 1.00 | 36.59 | CPS1 |
| ATOM | 818 | CE1 | HIS | 105 | 63.322 | 39.402 | -6.786 | 1.00 | 35.80 | CPS1 |
| ATOM | 819 | NE2 | HIS | 105 | 64.521 | 39.199 | -6.271 | 1.00 | 35.22 | CPS1 |
| ATOM | 820 | C   | HIS | 105 | 61.863 | 34.268 | -4.280 | 1.00 | 24.66 | CPS1 |
| ATOM | 821 | O   | HIS | 105 | 62.570 | 33.400 | -3.766 | 1.00 | 23.89 | CPS1 |
| ATOM | 822 | N   | THR | 106 | 60.667 | 34.027 | -4.811 | 1.00 | 24.24 | CPS1 |
| ATOM | 823 | CA  | THR | 106 | 60.127 | 32.677 | -5.003 | 1.00 | 24.46 | CPS1 |
| ATOM | 824 | CB  | THR | 106 | 59.008 | 32.271 | -4.019 | 1.00 | 25.81 | CPS1 |
| ATOM | 825 | OG1 | THR | 106 | 57.840 | 33.073 | -4.253 | 1.00 | 25.01 | CPS1 |
| ATOM | 826 | CG2 | THR | 106 | 59.483 | 32.419 | -2.570 | 1.00 | 24.51 | CPS1 |
| ATOM | 827 | C   | THR | 106 | 59.500 | 32.820 | -6.388 | 1.00 | 25.67 | CPS1 |
| ATOM | 828 | O   | THR | 106 | 59.496 | 33.915 | -6.953 | 1.00 | 25.60 | CPS1 |
| ATOM | 829 | N   | ALA | 107 | 58.962 | 31.740 | -6.939 | 1.00 | 25.39 | CPS1 |
| ATOM | 830 | CA  | ALA | 107 | 58.355 | 31.824 | -8.262 | 1.00 | 25.43 | CPS1 |
| ATOM | 831 | CB  | ALA | 107 | 57.743 | 30.463 | -8.637 | 1.00 | 25.15 | CPS1 |
| ATOM | 832 | C   | ALA | 107 | 57.288 | 32.918 | -8.363 | 1.00 | 25.95 | CPS1 |
| ATOM | 833 | O   | ALA | 107 | 57.233 | 33.660 | -9.353 | 1.00 | 25.81 | CPS1 |
| ATOM | 834 | N   | GLU | 108 | 56.452 | 33.035 | -7.335 | 1.00 | 24.82 | CPS1 |
| ATOM | 835 | CA  | GLU | 108 | 55.356 | 34.007 | -7.367 | 1.00 | 25.17 | CPS1 |
| ATOM | 836 | CB  | GLU | 108 | 54.043 | 33.295 | -7.008 | 1.00 | 27.79 | CPS1 |
| ATOM | 837 | CG  | GLU | 108 | 53.688 | 32.198 | -8.005 | 1.00 | 34.77 | CPS1 |
| ATOM | 838 | CD  | GLU | 108 | 52.404 | 31.450 | -7.675 | 1.00 | 39.77 | CPS1 |
| ATOM | 839 | OE1 | GLU | 108 | 52.146 | 30.431 | -8.355 | 1.00 | 43.18 | CPS1 |
| ATOM | 840 | OE2 | GLU | 108 | 51.652 | 31.864 | -6.758 | 1.00 | 42.25 | CPS1 |
| ATOM | 841 | C   | GLU | 108 | 55.486 | 35.267 | -6.507 | 1.00 | 24.23 | CPS1 |
| ATOM | 842 | O   | GLU | 108 | 54.654 | 36.178 | -6.615 | 1.00 | 22.93 | CPS1 |
| ATOM | 843 | N   | TYR | 109 | 56.518 | 35.330 | -5.669 | 1.00 | 21.86 | CPS1 |
| ATOM | 844 | CA  | TYR | 109 | 56.678 | 36.480 | -4.788 | 1.00 | 21.64 | CPS1 |
| ATOM | 845 | CB  | TYR | 109 | 56.320 | 36.077 | -3.352 | 1.00 | 22.31 | CPS1 |
| ATOM | 846 | CG  | TYR | 109 | 54.889 | 35.632 | -3.180 | 1.00 | 23.87 | CPS1 |
| ATOM | 847 | CD1 | TYR | 109 | 53.868 | 36.562 | -2.999 | 1.00 | 23.05 | CPS1 |
| ATOM | 848 | CE1 | TYR | 109 | 52.546 | 36.164 | -2.894 | 1.00 | 24.80 | CPS1 |
| ATOM | 849 | CD2 | TYR | 109 | 54.550 | 34.283 | -3.253 | 1.00 | 24.86 | CPS1 |
| ATOM | 850 | CE2 | TYR | 109 | 53.226 | 33.872 | -3.154 | 1.00 | 27.10 | CPS1 |
| ATOM | 851 | CZ  | TYR | 109 | 52.233 | 34.818 | -2.977 | 1.00 | 24.92 | CPS1 |
| ATOM | 852 | OH  | TYR | 109 | 50.924 | 34.420 | -2.916 | 1.00 | 25.87 | CPS1 |
| ATOM | 853 | C   | TYR | 109 | 58.066 | 37.100 | -4.741 | 1.00 | 21.01 | CPS1 |
| ATOM | 854 | O   | TYR | 109 | 59.063 | 36.476 | -5.091 | 1.00 | 21.94 | CPS1 |

FIG. 1A-15

| ATOM | 855 | N | ALA | 110 | 58.097 | 38.347 | -4.292 | 1.00 | 20.81 | CPS1 |
|------|-----|-----|-----|-----|--------|--------|--------|------|-------|------|
| ATOM | 856 | CA | ALA | 110 | 59.344 | 39.074 | -4.057 | 1.00 | 20.89 | CPS1 |
| ATOM | 857 | CB | ALA | 110 | 59.483 | 40.256 | -5.013 | 1.00 | 21.11 | CPS1 |
| ATOM | 858 | C | ALA | 110 | 59.155 | 39.574 | -2.617 | 1.00 | 19.96 | CPS1 |
| ATOM | 859 | O | ALA | 110 | 58.043 | 39.941 | -2.238 | 1.00 | 21.37 | CPS1 |
| ATOM | 860 | N | ALA | 111 | 60.209 | 39.576 | -1.805 | 1.00 | 18.57 | CPS1 |
| ATOM | 861 | CA | ALA | 111 | 60.074 | 40.062 | -0.435 | 1.00 | 17.40 | CPS1 |
| ATOM | 862 | CB | ALA | 111 | 59.780 | 38.896 | 0.509 | 1.00 | 16.67 | CPS1 |
| ATOM | 863 | C | ALA | 111 | 61.362 | 40.756 | -0.023 | 1.00 | 17.97 | CPS1 |
| ATOM | 864 | O | ALA | 111 | 62.411 | 40.476 | -0.580 | 1.00 | 17.28 | CPS1 |
| ATOM | 865 | N | ALA | 112 | 61.275 | 41.676 | 0.931 | 1.00 | 16.46 | CPS1 |
| ATOM | 866 | CA | ALA | 112 | 62.458 | 42.374 | 1.394 | 1.00 | 17.56 | CPS1 |
| ATOM | 867 | CB | ALA | 112 | 62.786 | 43.553 | 0.444 | 1.00 | 17.14 | CPS1 |
| ATOM | 868 | C | ALA | 112 | 62.263 | 42.880 | 2.809 | 1.00 | 16.81 | CPS1 |
| ATOM | 869 | O | ALA | 112 | 61.143 | 43.042 | 3.270 | 1.00 | 17.67 | CPS1 |
| ATOM | 870 | N | GLN | 113 | 63.361 | 43.106 | 3.514 | 1.00 | 17.77 | CPS1 |
| ATOM | 871 | CA | GLN | 113 | 63.267 | 43.639 | 4.863 | 1.00 | 17.30 | CPS1 |
| ATOM | 872 | CB | GLN | 113 | 63.469 | 42.554 | 5.929 | 1.00 | 18.78 | CPS1 |
| ATOM | 873 | CG | GLN | 113 | 64.842 | 41.925 | 5.912 | 1.00 | 22.22 | CPS1 |
| ATOM | 874 | CD | GLN | 113 | 65.029 | 40.878 | 6.990 | 1.00 | 26.02 | CPS1 |
| ATOM | 875 | OE1 | GLN | 113 | 66.130 | 40.366 | 7.182 | 1.00 | 29.00 | CPS1 |
| ATOM | 876 | NE2 | GLN | 113 | 63.950 | 40.541 | 7.688 | 1.00 | 28.62 | CPS1 |
| ATOM | 877 | C | GLN | 113 | 64.370 | 44.658 | 4.985 | 1.00 | 18.39 | CPS1 |
| ATOM | 878 | O | GLN | 113 | 65.410 | 44.550 | 4.338 | 1.00 | 19.07 | CPS1 |
| ATOM | 879 | N | VAL | 114 | 64.142 | 45.639 | 5.836 | 1.00 | 18.02 | CPS1 |
| ATOM | 880 | CA | VAL | 114 | 65.128 | 46.675 | 6.042 | 1.00 | 17.24 | CPS1 |
| ATOM | 881 | CB | VAL | 114 | 64.702 | 47.987 | 5.317 | 1.00 | 17.08 | CPS1 |
| ATOM | 882 | CG1 | VAL | 114 | 65.511 | 49.194 | 5.863 | 1.00 | 16.82 | CPS1 |
| ATOM | 883 | CG2 | VAL | 114 | 64.897 | 47.837 | 3.810 | 1.00 | 15.69 | CPS1 |
| ATOM | 884 | C | VAL | 114 | 65.223 | 46.962 | 7.526 | 1.00 | 18.35 | CPS1 |
| ATOM | 885 | O | VAL | 114 | 64.228 | 46.862 | 8.260 | 1.00 | 17.93 | CPS1 |
| ATOM | 886 | N | VAL | 115 | 66.429 | 47.280 | 7.973 | 1.00 | 19.07 | CPS1 |
| ATOM | 887 | CA | VAL | 115 | 66.622 | 47.702 | 9.351 | 1.00 | 20.05 | CPS1 |
| ATOM | 888 | CB | VAL | 115 | 67.435 | 46.698 | 10.193 | 1.00 | 21.79 | CPS1 |
| ATOM | 889 | CG1 | VAL | 115 | 67.695 | 47.297 | 11.582 | 1.00 | 24.02 | CPS1 |
| ATOM | 890 | CG2 | VAL | 115 | 66.680 | 45.387 | 10.322 | 1.00 | 21.49 | CPS1 |
| ATOM | 891 | C | VAL | 115 | 67.411 | 49.003 | 9.266 | 1.00 | 20.53 | CPS1 |
| ATOM | 892 | O | VAL | 115 | 68.416 | 49.077 | 8.552 | 1.00 | 19.46 | CPS1 |
| ATOM | 893 | N | ILE | 116 | 66.921 | 50.038 | 9.943 | 1.00 | 22.12 | CPS1 |
| ATOM | 894 | CA | ILE | 116 | 67.620 | 51.321 | 9.987 | 1.00 | 22.75 | CPS1 |
| ATOM | 895 | CB | ILE | 116 | 66.694 | 52.492 | 9.629 | 1.00 | 22.88 | CPS1 |
| ATOM | 896 | CG2 | ILE | 116 | 67.430 | 53.825 | 9.850 | 1.00 | 23.51 | CPS1 |
| ATOM | 897 | CG1 | ILE | 116 | 66.232 | 52.353 | 8.172 | 1.00 | 22.44 | CPS1 |
| ATOM | 898 | CD1 | ILE | 116 | 65.208 | 53.382 | 7.742 | 1.00 | 20.81 | CPS1 |
| ATOM | 899 | C | ILE | 116 | 68.090 | 51.495 | 11.430 | 1.00 | 25.25 | CPS1 |
| ATOM | 900 | O | ILE | 116 | 67.312 | 51.296 | 12.363 | 1.00 | 22.08 | CPS1 |
| ATOM | 901 | N | GLU | 117 | 69.362 | 51.845 | 11.610 | 1.00 | 28.24 | CPS1 |
| ATOM | 902 | CA | GLU | 117 | 69.923 | 52.041 | 12.944 | 1.00 | 33.38 | CPS1 |
| ATOM | 903 | CB | GLU | 117 | 71.297 | 51.384 | 13.074 | 1.00 | 34.32 | CPS1 |
| ATOM | 904 | CG | GLU | 117 | 71.376 | 49.888 | 12.878 | 1.00 | 36.79 | CPS1 |
| ATOM | 905 | CD | GLU | 117 | 72.808 | 49.388 | 13.006 | 1.00 | 38.57 | CPS1 |
| ATOM | 906 | OE1 | GLU | 117 | 73.266 | 49.163 | 14.144 | 1.00 | 40.54 | CPS1 |
| ATOM | 907 | OE2 | GLU | 117 | 73.489 | 49.243 | 11.971 | 1.00 | 40.35 | CPS1 |
| ATOM | 908 | C | GLU | 117 | 70.119 | 53.524 | 13.216 | 1.00 | 36.51 | CPS1 |
| ATOM | 909 | O | GLU | 117 | 70.269 | 54.317 | 12.289 | 1.00 | 36.14 | CPS1 |
| ATOM | 910 | N | ARG | 118 | 70.120 | 53.890 | 14.493 | 1.00 | 40.58 | CPS1 |
| ATOM | 911 | CA | ARG | 118 | 70.358 | 55.275 | 14.884 | 1.00 | 45.79 | CPS1 |

FIG. 1A-16

| ATOM | 912 | CB | ARG | 118 | 69.712 | 55.600 | 16.235 | 1.00 | 46.59 | CPS1 |
|---|---|---|---|---|---|---|---|---|---|---|
| ATOM | 913 | CG | ARG | 118 | 68.229 | 55.336 | 16.356 | 1.00 | 49.65 | CPS1 |
| ATOM | 914 | CD | ARG | 118 | 67.792 | 55.527 | 17.809 | 1.00 | 52.26 | CPS1 |
| ATOM | 915 | NE | ARG | 118 | 66.418 | 55.092 | 18.046 | 1.00 | 54.79 | CPS1 |
| ATOM | 916 | CZ | ARG | 118 | 65.337 | 55.786 | 17.702 | 1.00 | 55.39 | CPS1 |
| ATOM | 917 | NH1 | ARG | 118 | 64.131 | 55.299 | 17.956 | 1.00 | 56.47 | CPS1 |
| ATOM | 918 | NH2 | ARG | 118 | 65.458 | 56.972 | 17.120 | 1.00 | 56.32 | CPS1 |
| ATOM | 919 | C | ARG | 118 | 71.868 | 55.331 | 15.069 | 1.00 | 48.09 | CPS1 |
| ATOM | 920 | O | ARG | 118 | 72.435 | 54.481 | 15.755 | 1.00 | 49.38 | CPS1 |
| ATOM | 921 | N | LEU | 119 | 72.529 | 56.308 | 14.462 | 1.00 | 50.93 | CPS1 |
| ATOM | 922 | CA | LEU | 119 | 73.973 | 56.418 | 14.631 | 1.00 | 53.26 | CPS1 |
| ATOM | 923 | CB | LEU | 119 | 74.651 | 56.655 | 13.277 | 1.00 | 53.81 | CPS1 |
| ATOM | 924 | CG | LEU | 119 | 74.474 | 55.541 | 12.239 | 1.00 | 54.33 | CPS1 |
| ATOM | 925 | CD1 | LEU | 119 | 75.203 | 55.906 | 10.953 | 1.00 | 54.92 | CPS1 |
| ATOM | 926 | CD2 | LEU | 119 | 75.006 | 54.234 | 12.801 | 1.00 | 54.83 | CPS1 |
| ATOM | 927 | C | LEU | 119 | 74.286 | 57.568 | 15.591 | 1.00 | 54.40 | CPS1 |
| ATOM | 928 | OT1 | LEU | 119 | 74.613 | 57.278 | 16.765 | 1.00 | 55.09 | CPS1 |
| ATOM | 929 | OT2 | LEU | 119 | 74.177 | 58.740 | 15.166 | 1.00 | 55.10 | CPS1 |
| ATOM | 930 | C | GLY | 0 | 77.740 | 47.623 | 17.259 | 1.00 | 45.52 | CPS2 |
| ATOM | 931 | O | GLY | 0 | 78.476 | 48.184 | 16.444 | 1.00 | 47.54 | CPS2 |
| ATOM | 932 | N | GLY | 0 | 79.569 | 47.872 | 18.959 | 1.00 | 47.48 | CPS2 |
| ATOM | 933 | CA | GLY | 0 | 78.237 | 47.280 | 18.650 | 1.00 | 46.63 | CPS2 |
| ATOM | 934 | N | GLY | 1 | 76.484 | 47.284 | 16.983 | 1.00 | 43.42 | CPS2 |
| ATOM | 935 | CA | GLY | 1 | 75.916 | 47.570 | 15.679 | 1.00 | 38.90 | CPS2 |
| ATOM | 936 | C | GLY | 1 | 75.631 | 46.308 | 14.888 | 1.00 | 35.36 | CPS2 |
| ATOM | 937 | O | GLY | 1 | 76.138 | 45.233 | 15.198 | 1.00 | 35.52 | CPS2 |
| ATOM | 938 | N | ILE | 2 | 74.818 | 46.451 | 13.853 | 1.00 | 32.81 | CPS2 |
| ATOM | 939 | CA | ILE | 2 | 74.444 | 45.331 | 12.997 | 1.00 | 30.92 | CPS2 |
| ATOM | 940 | CB | ILE | 2 | 73.034 | 45.554 | 12.419 | 1.00 | 30.17 | CPS2 |
| ATOM | 941 | CG2 | ILE | 2 | 72.715 | 44.495 | 11.369 | 1.00 | 28.15 | CPS2 |
| ATOM | 942 | CG1 | ILE | 2 | 72.019 | 45.547 | 13.564 | 1.00 | 30.04 | CPS2 |
| ATOM | 943 | CD1 | ILE | 2 | 70.624 | 45.977 | 13.162 | 1.00 | 29.29 | CPS2 |
| ATOM | 944 | C | ILE | 2 | 75.427 | 45.143 | 11.851 | 1.00 | 30.22 | CPS2 |
| ATOM | 945 | O | ILE | 2 | 75.785 | 46.098 | 11.157 | 1.00 | 29.17 | CPS2 |
| ATOM | 946 | N | TYR | 3 | 75.866 | 43.906 | 11.657 | 1.00 | 29.82 | CPS2 |
| ATOM | 947 | CA | TYR | 3 | 76.797 | 43.596 | 10.577 | 1.00 | 29.72 | CPS2 |
| ATOM | 948 | CB | TYR | 3 | 77.594 | 42.334 | 10.900 | 1.00 | 32.80 | CPS2 |
| ATOM | 949 | CG | TYR | 3 | 78.536 | 41.959 | 9.782 | 1.00 | 37.46 | CPS2 |
| ATOM | 950 | CD1 | TYR | 3 | 79.553 | 42.827 | 9.394 | 1.00 | 39.59 | CPS2 |
| ATOM | 951 | CE1 | TYR | 3 | 80.382 | 42.538 | 8.314 | 1.00 | 42.43 | CPS2 |
| ATOM | 952 | CD2 | TYR | 3 | 78.370 | 40.775 | 9.064 | 1.00 | 39.81 | CPS2 |
| ATOM | 953 | CE2 | TYR | 3 | 79.196 | 40.470 | 7.974 | 1.00 | 42.42 | CPS2 |
| ATOM | 954 | CZ | TYR | 3 | 80.201 | 41.364 | 7.607 | 1.00 | 44.04 | CPS2 |
| ATOM | 955 | OH | TYR | 3 | 81.024 | 41.099 | 6.531 | 1.00 | 46.34 | CPS2 |
| ATOM | 956 | C | TYR | 3 | 76.032 | 43.379 | 9.275 | 1.00 | 28.30 | CPS2 |
| ATOM | 957 | O | TYR | 3 | 76.420 | 43.872 | 8.211 | 1.00 | 28.24 | CPS2 |
| ATOM | 958 | N | GLY | 4 | 74.944 | 42.619 | 9.363 | 1.00 | 25.87 | CPS2 |
| ATOM | 959 | CA | GLY | 4 | 74.141 | 42.355 | 8.182 | 1.00 | 22.75 | CPS2 |
| ATOM | 960 | C | GLY | 4 | 72.849 | 41.652 | 8.547 | 1.00 | 21.62 | CPS2 |
| ATOM | 961 | O | GLY | 4 | 72.724 | 41.085 | 9.639 | 1.00 | 21.41 | CPS2 |
| ATOM | 962 | N | ILE | 5 | 71.877 | 41.703 | 7.640 | 1.00 | 20.89 | CPS2 |
| ATOM | 963 | CA | ILE | 5 | 70.593 | 41.042 | 7.859 | 1.00 | 19.45 | CPS2 |
| ATOM | 964 | CB | ILE | 5 | 69.453 | 42.057 | 8.118 | 1.00 | 18.65 | CPS2 |
| ATOM | 965 | CG2 | ILE | 5 | 69.846 | 43.011 | 9.259 | 1.00 | 19.69 | CPS2 |
| ATOM | 966 | CG1 | ILE | 5 | 69.129 | 42.843 | 6.842 | 1.00 | 19.64 | CPS2 |
| ATOM | 967 | CD1 | ILE | 5 | 67.947 | 43.809 | 7.020 | 1.00 | 20.64 | CPS2 |
| ATOM | 968 | C | ILE | 5 | 70.272 | 40.216 | 6.618 | 1.00 | 18.82 | CPS2 |

FIG. 1A-17

| ATOM | 969 | O | ILE | 5 | 70.778 | 40.498 | 5.524 | 1.00 | 18.88 | CPS2 |
| ATOM | 970 | N | GLY | 6 | 69.456 | 39.184 | 6.794 | 1.00 | 19.17 | CPS2 |
| ATOM | 971 | CA | GLY | 6 | 69.108 | 38.325 | 5.679 | 1.00 | 19.31 | CPS2 |
| ATOM | 972 | C | GLY | 6 | 67.687 | 37.815 | 5.794 | 1.00 | 19.36 | CPS2 |
| ATOM | 973 | O | GLY | 6 | 67.176 | 37.614 | 6.887 | 1.00 | 18.63 | CPS2 |
| ATOM | 974 | N | LEU | 7 | 67.053 | 37.606 | 4.649 | 1.00 | 19.78 | CPS2 |
| ATOM | 975 | CA | LEU | 7 | 65.680 | 37.141 | 4.617 | 1.00 | 19.08 | CPS2 |
| ATOM | 976 | CB | LEU | 7 | 64.733 | 38.328 | 4.366 | 1.00 | 19.19 | CPS2 |
| ATOM | 977 | CG | LEU | 7 | 63.238 | 38.018 | 4.161 | 1.00 | 18.29 | CPS2 |
| ATOM | 978 | CD1 | LEU | 7 | 62.658 | 37.539 | 5.491 | 1.00 | 18.90 | CPS2 |
| ATOM | 979 | CD2 | LEU | 7 | 62.472 | 39.269 | 3.651 | 1.00 | 17.44 | CPS2 |
| ATOM | 980 | C | LEU | 7 | 65.552 | 36.139 | 3.487 | 1.00 | 18.38 | CPS2 |
| ATOM | 981 | O | LEU | 7 | 66.113 | 36.338 | 2.417 | 1.00 | 19.54 | CPS2 |
| ATOM | 982 | N | ASP | 8 | 64.845 | 35.042 | 3.724 | 1.00 | 18.51 | CPS2 |
| ATOM | 983 | CA | ASP | 8 | 64.651 | 34.091 | 2.647 | 1.00 | 20.25 | CPS2 |
| ATOM | 984 | CB | ASP | 8 | 65.727 | 32.998 | 2.657 | 1.00 | 21.81 | CPS2 |
| ATOM | 985 | CG | ASP | 8 | 65.487 | 31.943 | 1.580 | 1.00 | 25.13 | CPS2 |
| ATOM | 986 | OD1 | ASP | 8 | 64.777 | 30.949 | 1.851 | 1.00 | 25.80 | CPS2 |
| ATOM | 987 | OD2 | ASP | 8 | 65.989 | 32.124 | 0.454 | 1.00 | 28.14 | CPS2 |
| ATOM | 988 | C | ASP | 8 | 63.297 | 33.433 | 2.740 | 1.00 | 20.84 | CPS2 |
| ATOM | 989 | O | ASP | 8 | 62.826 | 33.137 | 3.834 | 1.00 | 19.86 | CPS2 |
| ATOM | 990 | N | ILE | 9 | 62.669 | 33.223 | 1.584 | 1.00 | 19.61 | CPS2 |
| ATOM | 991 | CA | ILE | 9 | 61.391 | 32.520 | 1.533 | 1.00 | 20.19 | CPS2 |
| ATOM | 992 | CB | ILE | 9 | 60.222 | 33.393 | 1.015 | 1.00 | 21.26 | CPS2 |
| ATOM | 993 | CG2 | ILE | 9 | 58.950 | 32.526 | 0.904 | 1.00 | 20.13 | CPS2 |
| ATOM | 994 | CG1 | ILE | 9 | 59.959 | 34.555 | 1.973 | 1.00 | 21.42 | CPS2 |
| ATOM | 995 | CD1 | ILE | 9 | 58.878 | 35.500 | 1.490 | 1.00 | 21.37 | CPS2 |
| ATOM | 996 | C | ILE | 9 | 61.641 | 31.415 | 0.519 | 1.00 | 20.37 | CPS2 |
| ATOM | 997 | O | ILE | 9 | 62.132 | 31.685 | -0.572 | 1.00 | 20.53 | CPS2 |
| ATOM | 998 | N | THR | 10 | 61.313 | 30.182 | 0.892 | 1.00 | 20.80 | CPS2 |
| ATOM | 999 | CA | THR | 10 | 61.519 | 29.032 | 0.022 | 1.00 | 22.14 | CPS2 |
| ATOM | 1000 | CB | THR | 10 | 62.584 | 28.076 | 0.630 | 1.00 | 23.02 | CPS2 |
| ATOM | 1001 | OG1 | THR | 10 | 63.837 | 28.770 | 0.746 | 1.00 | 25.04 | CPS2 |
| ATOM | 1002 | CG2 | THR | 10 | 62.785 | 26.859 | -0.253 | 1.00 | 25.37 | CPS2 |
| ATOM | 1003 | C | THR | 10 | 60.211 | 28.275 | -0.184 | 1.00 | 21.99 | CPS2 |
| ATOM | 1004 | O | THR | 10 | 59.471 | 28.038 | 0.761 | 1.00 | 21.01 | CPS2 |
| ATOM | 1005 | N | GLU | 11 | 59.938 | 27.912 | -1.435 | 1.00 | 23.31 | CPS2 |
| ATOM | 1006 | CA | GLU | 11 | 58.723 | 27.177 | -1.794 | 1.00 | 24.42 | CPS2 |
| ATOM | 1007 | CB | GLU | 11 | 58.438 | 27.355 | -3.296 | 1.00 | 26.52 | CPS2 |
| ATOM | 1008 | CG | GLU | 11 | 57.052 | 26.900 | -3.721 | 1.00 | 28.30 | CPS2 |
| ATOM | 1009 | CD | GLU | 11 | 56.897 | 26.756 | -5.231 | 1.00 | 32.57 | CPS2 |
| ATOM | 1010 | OE1 | GLU | 11 | 57.820 | 27.134 | -5.991 | 1.00 | 32.18 | CPS2 |
| ATOM | 1011 | OE2 | GLU | 11 | 55.833 | 26.256 | -5.654 | 1.00 | 33.69 | CPS2 |
| ATOM | 1012 | C | GLU | 11 | 58.941 | 25.692 | -1.480 | 1.00 | 23.56 | CPS2 |
| ATOM | 1013 | O | GLU | 11 | 59.853 | 25.070 | -2.026 | 1.00 | 22.90 | CPS2 |
| ATOM | 1014 | N | LEU | 12 | 58.110 | 25.124 | -0.612 | 1.00 | 23.91 | CPS2 |
| ATOM | 1015 | CA | LEU | 12 | 58.260 | 23.715 | -0.249 | 1.00 | 26.06 | CPS2 |
| ATOM | 1016 | CB | LEU | 12 | 57.147 | 23.269 | 0.705 | 1.00 | 28.23 | CPS2 |
| ATOM | 1017 | CG | LEU | 12 | 57.554 | 23.114 | 2.176 | 1.00 | 31.10 | CPS2 |
| ATOM | 1018 | CD1 | LEU | 12 | 58.046 | 24.448 | 2.710 | 1.00 | 30.63 | CPS2 |
| ATOM | 1019 | CD2 | LEU | 12 | 56.360 | 22.605 | 3.005 | 1.00 | 32.22 | CPS2 |
| ATOM | 1020 | C | LEU | 12 | 58.271 | 22.795 | -1.461 | 1.00 | 27.56 | CPS2 |
| ATOM | 1021 | O | LEU | 12 | 59.054 | 21.846 | -1.519 | 1.00 | 27.33 | CPS2 |
| ATOM | 1022 | N | ALA | 13 | 57.401 | 23.077 | -2.427 | 1.00 | 27.64 | CPS2 |
| ATOM | 1023 | CA | ALA | 13 | 57.321 | 22.255 | -3.628 | 1.00 | 28.06 | CPS2 |
| ATOM | 1024 | CB | ALA | 13 | 56.163 | 22.714 | -4.506 | 1.00 | 28.61 | CPS2 |
| ATOM | 1025 | C | ALA | 13 | 58.622 | 22.279 | -4.413 | 1.00 | 29.21 | CPS2 |

FIG. 1A-18

| ATOM | 1026 | O | ALA | 13 | 58.982 | 21.281 | -5.048 | 1.00 | 28.52 | CPS2 |
| ATOM | 1027 | N | ARG | 14 | 59.335 | 23.404 | -4.375 | 1.00 | 29.11 | CPS2 |
| ATOM | 1028 | CA | ARG | 14 | 60.599 | 23.495 | -5.098 | 1.00 | 30.50 | CPS2 |
| ATOM | 1029 | CB | ARG | 14 | 61.065 | 24.951 | -5.221 | 1.00 | 32.06 | CPS2 |
| ATOM | 1030 | CG | ARG | 14 | 62.248 | 25.118 | -6.171 | 1.00 | 34.92 | CPS2 |
| ATOM | 1031 | CD | ARG | 14 | 62.528 | 26.576 | -6.477 | 1.00 | 36.22 | CPS2 |
| ATOM | 1032 | NE | ARG | 14 | 63.217 | 27.245 | -5.381 | 1.00 | 38.47 | CPS2 |
| ATOM | 1033 | CZ | ARG | 14 | 64.522 | 27.137 | -5.142 | 1.00 | 39.99 | CPS2 |
| ATOM | 1034 | NH1 | ARG | 14 | 65.284 | 26.385 | -5.926 | 1.00 | 39.47 | CPS2 |
| ATOM | 1035 | NH2 | ARG | 14 | 65.066 | 27.787 | -4.119 | 1.00 | 39.80 | CPS2 |
| ATOM | 1036 | C | ARG | 14 | 61.670 | 22.655 | -4.411 | 1.00 | 30.84 | CPS2 |
| ATOM | 1037 | O | ARG | 14 | 62.488 | 22.021 | -5.077 | 1.00 | 31.28 | CPS2 |
| ATOM | 1038 | N | ILE | 15 | 61.672 | 22.650 | -3.078 | 1.00 | 31.04 | CPS2 |
| ATOM | 1039 | CA | ILE | 15 | 62.637 | 21.845 | -2.332 | 1.00 | 31.02 | CPS2 |
| ATOM | 1040 | CB | ILE | 15 | 62.480 | 22.037 | -0.803 | 1.00 | 30.76 | CPS2 |
| ATOM | 1041 | CG2 | ILE | 15 | 63.314 | 21.002 | -0.056 | 1.00 | 29.83 | CPS2 |
| ATOM | 1042 | CG1 | ILE | 15 | 62.940 | 23.441 | -0.407 | 1.00 | 29.97 | CPS2 |
| ATOM | 1043 | CD1 | ILE | 15 | 64.431 | 23.685 | -0.657 | 1.00 | 30.60 | CPS2 |
| ATOM | 1044 | C | ILE | 15 | 62.397 | 20.369 | -2.673 | 1.00 | 33.28 | CPS2 |
| ATOM | 1045 | O | ILE | 15 | 63.338 | 19.604 | -2.900 | 1.00 | 33.51 | CPS2 |
| ATOM | 1046 | N | ALA | 16 | 61.133 | 19.974 | -2.712 | 1.00 | 34.78 | CPS2 |
| ATOM | 1047 | CA | ALA | 16 | 60.789 | 18.597 | -3.039 | 1.00 | 37.29 | CPS2 |
| ATOM | 1048 | CB | ALA | 16 | 59.285 | 18.395 | -2.921 | 1.00 | 36.48 | CPS2 |
| ATOM | 1049 | C | ALA | 16 | 61.264 | 18.286 | -4.459 | 1.00 | 39.28 | CPS2 |
| ATOM | 1050 | O | ALA | 16 | 61.839 | 17.230 | -4.716 | 1.00 | 40.75 | CPS2 |
| ATOM | 1051 | N | SER | 17 | 61.034 | 19.219 | -5.375 | 1.00 | 40.88 | CPS2 |
| ATOM | 1052 | CA | SER | 17 | 61.439 | 19.046 | -6.763 | 1.00 | 43.46 | CPS2 |
| ATOM | 1053 | CB | SER | 17 | 61.012 | 20.261 | -7.588 | 1.00 | 44.13 | CPS2 |
| ATOM | 1054 | OG | SER | 17 | 61.450 | 20.150 | -8.930 | 1.00 | 46.75 | CPS2 |
| ATOM | 1055 | C | SER | 17 | 62.949 | 18.857 | -6.866 | 1.00 | 44.93 | CPS2 |
| ATOM | 1056 | O | SER | 17 | 63.432 | 18.058 | -7.672 | 1.00 | 44.94 | CPS2 |
| ATOM | 1057 | N | MET | 18 | 63.694 | 19.597 | -6.052 | 1.00 | 45.72 | CPS2 |
| ATOM | 1058 | CA | MET | 18 | 65.148 | 19.499 | -6.060 | 1.00 | 47.01 | CPS2 |
| ATOM | 1059 | CB | MET | 18 | 65.780 | 20.713 | -5.374 | 1.00 | 47.40 | CPS2 |
| ATOM | 1060 | CG | MET | 18 | 65.783 | 21.978 | -6.201 | 1.00 | 48.61 | CPS2 |
| ATOM | 1061 | SD | MET | 18 | 66.874 | 23.231 | -5.488 | 1.00 | 51.56 | CPS2 |
| ATOM | 1062 | CE | MET | 18 | 65.856 | 23.843 | -4.148 | 1.00 | 49.70 | CPS2 |
| ATOM | 1063 | C | MET | 18 | 65.637 | 18.233 | -5.369 | 1.00 | 47.60 | CPS2 |
| ATOM | 1064 | O | MET | 18 | 66.589 | 17.605 | -5.822 | 1.00 | 48.05 | CPS2 |
| ATOM | 1065 | N | ALA | 19 | 64.982 | 17.863 | -4.275 | 1.00 | 48.91 | CPS2 |
| ATOM | 1066 | CA | ALA | 19 | 65.365 | 16.682 | -3.512 | 1.00 | 50.86 | CPS2 |
| ATOM | 1067 | CB | ALA | 19 | 64.590 | 16.637 | -2.209 | 1.00 | 50.39 | CPS2 |
| ATOM | 1068 | C | ALA | 19 | 65.135 | 15.396 | -4.296 | 1.00 | 53.04 | CPS2 |
| ATOM | 1069 | O | ALA' | 19 | 65.897 | 14.433 | -4.171 | 1.00 | 52.81 | CPS2 |
| ATOM | 1070 | N | GLY | 20 | 64.084 | 15.384 | -5.108 | 1.00 | 54.91 | CPS2 |
| ATOM | 1071 | CA | GLY | 20 | 63.773 | 14.201 | -5.888 | 1.00 | 56.86 | CPS2 |
| ATOM | 1072 | C | GLY | 20 | 64.693 | 13.980 | -7.072 | 1.00 | 58.24 | CPS2 |
| ATOM | 1073 | O | GLY | 20 | 65.285 | 12.909 | -7.217 | 1.00 | 58.99 | CPS2 |
| ATOM | 1074 | N | ARG | 21 | 64.827 | 14.996 | -7.916 | 1.00 | 59.32 | CPS2 |
| ATOM | 1075 | CA | ARG | 21 | 65.652 | 14.882 | -9.107 | 1.00 | 60.71 | CPS2 |
| ATOM | 1076 | CB | ARG | 21 | 65.279 | 15.975 | -10.112 | 1.00 | 61.88 | CPS2 |
| ATOM | 1077 | CG | ARG | 21 | 65.739 | 17.362 | -9.716 | 1.00 | 63.83 | CPS2 |
| ATOM | 1078 | CD | ARG | 21 | 65.818 | 18.274 | -10.930 | 1.00 | 65.39 | CPS2 |
| ATOM | 1079 | NE | ARG | 21 | 66.617 | 19.471 | -10.669 | 1.00 | 67.17 | CPS2 |
| ATOM | 1080 | CZ | ARG | 21 | 66.250 | 20.467 | -9.867 | 1.00 | 67.54 | CPS2 |
| ATOM | 1081 | NH1 | ARG | 21 | 65.082 | 20.423 | -9.237 | 1.00 | 68.19 | CPS2 |
| ATOM | 1082 | NH2 | ARG | 21 | 67.057 | 21.507 | -9.693 | 1.00 | 67.30 | CPS2 |

FIG. 1A-19

| ATOM | 1083 | C | ARG | 21 | 67.153 | 14.932 | -8.857 | 1.00 | 61.11 | CPS2 |
| ATOM | 1084 | O | ARG | 21 | 67.942 | 14.571 | -9.735 | 1.00 | 61.28 | CPS2 |
| ATOM | 1085 | N | GLN | 22 | 67.564 | 15.375 | -7.674 | 1.00 | 61.25 | CPS2 |
| ATOM | 1086 | CA | GLN | 22 | 68.994 | 15.461 | -7.402 | 1.00 | 60.88 | CPS2 |
| ATOM | 1087 | CB | GLN | 22 | 69.340 | 16.826 | -6.795 | 1.00 | 61.70 | CPS2 |
| ATOM | 1088 | CG | GLN | 22 | 69.033 | 17.998 | -7.722 | 1.00 | 62.47 | CPS2 |
| ATOM | 1089 | CD | GLN | 22 | 69.522 | 19.331 | -7.180 | 1.00 | 63.25 | CPS2 |
| ATOM | 1090 | OE1 | GLN | 22 | 69.279 | 20.381 | -7.779 | 1.00 | 63.34 | CPS2 |
| ATOM | 1091 | NE2 | GLN | 22 | 70.218 | 19.297 | -6.047 | 1.00 | 63.02 | CPS2 |
| ATOM | 1092 | C | GLN | 22 | 69.563 | 14.351 | -6.530 | 1.00 | 60.08 | CPS2 |
| ATOM | 1093 | O | GLN | 22 | 68.836 | 13.608 | -5.867 | 1.00 | 60.33 | CPS2 |
| ATOM | 1094 | N | LYS | 23 | 70.886 | 14.253 | -6.569 | 1.00 | 59.12 | CPS2 |
| ATOM | 1095 | CA | LYS | 23 | 71.665 | 13.273 | -5.823 | 1.00 | 57.97 | CPS2 |
| ATOM | 1096 | CB | LYS | 23 | 73.137 | 13.684 | -5.890 | 1.00 | 59.44 | CPS2 |
| ATOM | 1097 | CG | LYS | 23 | 73.362 | 15.214 | -5.851 | 1.00 | 60.21 | CPS2 |
| ATOM | 1098 | CD | LYS | 23 | 73.057 | 15.850 | -4.501 | 1.00 | 59.91 | CPS2 |
| ATOM | 1099 | CE | LYS | 23 | 73.391 | 17.340 | -4.455 | 1.00 | 60.70 | CPS2 |
| ATOM | 1100 | NZ | LYS | 23 | 72.466 | 18.181 | -5.268 | 1.00 | 59.44 | CPS2 |
| ATOM | 1101 | C | LYS | 23 | 71.253 | 13.118 | -4.360 | 1.00 | 56.31 | CPS2 |
| ATOM | 1102 | O | LYS | 23 | 70.226 | 12.517 | -4.027 | 1.00 | 57.13 | CPS2 |
| ATOM | 1103 | N | ARG | 24 | 72.112 | 13.635 | -3.496 | 1.00 | 53.19 | CPS2 |
| ATOM | 1104 | CA | ARG | 24 | 71.909 | 13.629 | -2.062 | 1.00 | 50.41 | CPS2 |
| ATOM | 1105 | CB | ARG | 24 | 73.117 | 12.987 | -1.365 | 1.00 | 51.60 | CPS2 |
| ATOM | 1106 | CG | ARG | 24 | 74.311 | 12.739 | -2.286 | 1.00 | 51.97 | CPS2 |
| ATOM | 1107 | CD | ARG | 24 | 75.442 | 12.014 | -1.565 | 1.00 | 52.64 | CPS2 |
| ATOM | 1108 | NE | ARG | 24 | 75.105 | 10.634 | -1.218 | 1.00 | 51.83 | CPS2 |
| ATOM | 1109 | CZ | ARG | 24 | 75.534 | 9.570 | -1.892 | 1.00 | 51.87 | CPS2 |
| ATOM | 1110 | NH1 | ARG | 24 | 76.318 | 9.728 | -2.950 | 1.00 | 51.30 | CPS2 |
| ATOM | 1111 | NH2 | ARG | 24 | 75.187 | 8.347 | -1.505 | 1.00 | 51.09 | CPS2 |
| ATOM | 1112 | C | ARG | 24 | 71.787 | 15.110 | -1.717 | 1.00 | 47.01 | CPS2 |
| ATOM | 1113 | O | ARG | 24 | 72.640 | 15.690 | -1.043 | 1.00 | 46.57 | CPS2 |
| ATOM | 1114 | N | PHE | 25 | 70.725 | 15.721 | -2.238 | 1.00 | 42.31 | CPS2 |
| ATOM | 1115 | CA | PHE | 25 | 70.450 | 17.134 | -2.019 | 1.00 | 38.57 | CPS2 |
| ATOM | 1116 | CB | PHE | 25 | 69.115 | 17.508 | -2.679 | 1.00 | 37.72 | CPS2 |
| ATOM | 1117 | CG | PHE | 25 | 68.680 | 18.926 | -2.416 | 1.00 | 36.40 | CPS2 |
| ATOM | 1118 | CD1 | PHE | 25 | 67.682 | 19.202 | -1.485 | 1.00 | 36.71 | CPS2 |
| ATOM | 1119 | CD2 | PHE | 25 | 69.285 | 19.986 | -3.080 | 1.00 | 37.10 | CPS2 |
| ATOM | 1120 | CE1 | PHE | 25 | 67.297 | 20.518 | -1.220 | 1.00 | 36.02 | CPS2 |
| ATOM | 1121 | CE2 | PHE | 25 | 68.910 | 21.305 | -2.824 | 1.00 | 35.88 | CPS2 |
| ATOM | 1122 | CZ | PHE | 25 | 67.914 | 21.572 | -1.891 | 1.00 | 36.06 | CPS2 |
| ATOM | 1123 | C | PHE | 25 | 70.415 | 17.465 | -0.528 | 1.00 | 36.15 | CPS2 |
| ATOM | 1124 | O | PHE | 25 | 71.053 | 18.423 | -0.079 | 1.00 | 35.69 | CPS2 |
| ATOM | 1125 | N | ALA | 26 | 69.671 | 16.664 | 0.228 | 1.00 | 33.10 | CPS2 |
| ATOM | 1126 | CA | ALA | 26 | 69.548 | 16.865 | 1.667 | 1.00 | 32.04 | CPS2 |
| ATOM | 1127 | CB | ALA | 26 | 68.663 | 15.780 | 2.270 | 1.00 | 30.86 | CPS2 |
| ATOM | 1128 | C | ALA | 26 | 70.931 | 16.835 | 2.312 | 1.00 | 31.57 | CPS2 |
| ATOM | 1129 | O | ALA | 26 | 71.249 | 17.655 | 3.180 | 1.00 | 28.07 | CPS2 |
| ATOM | 1130 | N | GLU | 27 | 71.747 | 15.881 | 1.868 | 1.00 | 29.98 | CPS2 |
| ATOM | 1131 | CA | GLU | 27 | 73.102 | 15.717 | 2.382 | 1.00 | 30.25 | CPS2 |
| ATOM | 1132 | CB | GLU | 27 | 73.745 | 14.457 | 1.794 | 1.00 | 31.17 | CPS2 |
| ATOM | 1133 | CG | GLU | 27 | 73.219 | 13.134 | 2.356 | 1.00 | 35.24 | CPS2 |
| ATOM | 1134 | CD | GLU | 27 | 71.772 | 12.823 | 1.978 | 1.00 | 37.65 | CPS2 |
| ATOM | 1135 | OE1 | GLU | 27 | 71.300 | 13.296 | 0.918 | 1.00 | 38.95 | CPS2 |
| ATOM | 1136 | OE2 | GLU | 27 | 71.113 | 12.076 | 2.742 | 1.00 | 40.73 | CPS2 |
| ATOM | 1137 | C | GLU | 27 | 73.974 | 16.925 | 2.063 | 1.00 | 28.88 | CPS2 |
| ATOM | 1138 | O | GLU | 27 | 74.879 | 17.254 | 2.823 | 1.00 | 28.66 | CPS2 |
| ATOM | 1139 | N | ARG | 28 | 73.705 | 17.578 | 0.935 | 1.00 | 27.77 | CPS2 |

FIG. 1A-20

| ATOM | 1140 | CA | ARG | 28 | 74.470 | 18.754 | 0.532 | 1.00 | 29.47 | CPS2 |
| ATOM | 1141 | CB | ARG | 28 | 74.201 | 19.076 | -0.948 | 1.00 | 30.98 | CPS2 |
| ATOM | 1142 | CG | ARG | 28 | 74.785 | 20.407 | -1.424 | 1.00 | 35.00 | CPS2 |
| ATOM | 1143 | CD | ARG | 28 | 74.806 | 20.528 | -2.953 | 1.00 | 38.43 | CPS2 |
| ATOM | 1144 | NE | ARG | 28 | 73.480 | 20.654 | -3.557 | 1.00 | 40.71 | CPS2 |
| ATOM | 1145 | CZ | ARG | 28 | 72.809 | 21.797 | -3.683 | 1.00 | 42.27 | CPS2 |
| ATOM | 1146 | NH1 | ARG | 28 | 73.327 | 22.940 | -3.248 | 1.00 | 42.45 | CPS2 |
| ATOM | 1147 | NH2 | ARG | 28 | 71.613 | 21.798 | -4.259 | 1.00 | 44.17 | CPS2 |
| ATOM | 1148 | C | ARG | 28 | 74.137 | 19.987 | 1.387 | 1.00 | 28.50 | CPS2 |
| ATOM | 1149 | O | ARG | 28 | 75.003 | 20.811 | 1.669 | 1.00 | 29.58 | CPS2 |
| ATOM | 1150 | N | ILE | 29 | 72.879 | 20.105 | 1.788 | 1.00 | 26.47 | CPS2 |
| ATOM | 1151 | CA | ILE | 29 | 72.426 | 21.256 | 2.570 | 1.00 | 26.32 | CPS2 |
| ATOM | 1152 | CB | ILE | 29 | 70.908 | 21.475 | 2.389 | 1.00 | 25.79 | CPS2 |
| ATOM | 1153 | CG2 | ILE | 29 | 70.467 | 22.729 | 3.147 | 1.00 | 24.32 | CPS2 |
| ATOM | 1154 | CG1 | ILE | 29 | 70.559 | 21.566 | 0.902 | 1.00 | 23.95 | CPS2 |
| ATOM | 1155 | CD1 | ILE | 29 | 71.283 | 22.665 | 0.158 | 1.00 | 26.12 | CPS2 |
| ATOM | 1156 | C | ILE | 29 | 72.681 | 21.128 | 4.064 | 1.00 | 26.65 | CPS2 |
| ATOM | 1157 | O | ILE | 29 | 73.024 | 22.110 | 4.739 | 1.00 | 26.47 | CPS2 |
| ATOM | 1158 | N | LEU | 30 | 72.516 | 19.908 | 4.566 | 1.00 | 26.29 | CPS2 |
| ATOM | 1159 | CA | LEU | 30 | 72.638 | 19.616 | 5.981 | 1.00 | 26.30 | CPS2 |
| ATOM | 1160 | CB | LEU | 30 | 71.518 | 18.645 | 6.371 | 1.00 | 26.05 | CPS2 |
| ATOM | 1161 | CG | LEU | 30 | 70.095 | 19.059 | 5.957 | 1.00 | 26.30 | CPS2 |
| ATOM | 1162 | CD1 | LEU | 30 | 69.081 | 18.002 | 6.387 | 1.00 | 26.56 | CPS2 |
| ATOM | 1163 | CD2 | LEU | 30 | 69.762 | 20.400 | 6.602 | 1.00 | 24.24 | CPS2 |
| ATOM | 1164 | C | LEU | 30 | 73.972 | 19.075 | 6.497 | 1.00 | 27.26 | CPS2 |
| ATOM | 1165 | O | LEU | 30 | 74.731 | 18.419 | 5.771 | 1.00 | 28.28 | CPS2 |
| ATOM | 1166 | N | THR | 31 | 74.246 | 19.372 | 7.765 | 1.00 | 26.23 | CPS2 |
| ATOM | 1167 | CA | THR | 31 | 75.451 | 18.898 | 8.434 | 1.00 | 26.09 | CPS2 |
| ATOM | 1168 | CB | THR | 31 | 75.844 | 19.806 | 9.627 | 1.00 | 24.78 | CPS2 |
| ATOM | 1169 | OG1 | THR | 31 | 74.834 | 19.723 | 10.638 | 1.00 | 25.44 | CPS2 |
| ATOM | 1170 | CG2 | THR | 31 | 75.998 | 21.253 | 9.172 | 1.00 | 25.52 | CPS2 |
| ATOM | 1171 | C | THR | 31 | 75.106 | 17.516 | 8.978 | 1.00 | 26.34 | CPS2 |
| ATOM | 1172 | O | THR | 31 | 73.945 | 17.106 | 8.956 | 1.00 | 25.24 | CPS2 |
| ATOM | 1173 | N | ARG | 32 | 76.108 | 16.791 | 9.463 | 1.00 | 28.14 | CPS2 |
| ATOM | 1174 | CA | ARG | 32 | 75.872 | 15.456 | 10.005 | 1.00 | 30.16 | CPS2 |
| ATOM | 1175 | CB | ARG | 32 | 77.195 | 14.862 | 10.519 | 1.00 | 32.90 | CPS2 |
| ATOM | 1176 | CG | ARG | 32 | 77.070 | 13.518 | 11.243 | 1.00 | 37.77 | CPS2 |
| ATOM | 1177 | CD | ARG | 32 | 78.452 | 13.018 | 11.667 | 1.00 | 42.29 | CPS2 |
| ATOM | 1178 | NE | ARG | 32 | 78.428 | 12.082 | 12.796 | 1.00 | 46.64 | CPS2 |
| ATOM | 1179 | CZ | ARG | 32 | 78.020 | 10.817 | 12.728 | 1.00 | 48.51 | CPS2 |
| ATOM | 1180 | NH1 | ARG | 32 | 77.588 | 10.314 | 11.581 | 1.00 | 50.24 | CPS2 |
| ATOM | 1181 | NH2 | ARG | 32 | 78.058 | 10.045 | 13.809 | 1.00 | 49.25 | CPS2 |
| ATOM | 1182 | C | ARG | 32 | 74.812 | 15.450 | 11.116 | 1.00 | 29.69 | CPS2 |
| ATOM | 1183 | O | ARG | 32 | 73.946 | 14.577 | 11.149 | 1.00 | 29.33 | CPS2 |
| ATOM | 1184 | N | SER | 33 | 74.858 | 16.428 | 12.019 | 1.00 | 29.98 | CPS2 |
| ATOM | 1185 | CA | SER | 33 | 73.886 | 16.473 | 13.112 | 1.00 | 29.46 | CPS2 |
| ATOM | 1186 | CB | SER | 33 | 74.338 | 17.475 | 14.180 | 1.00 | 32.61 | CPS2 |
| ATOM | 1187 | OG | SER | 33 | 74.402 | 18.784 | 13.645 | 1.00 | 37.61 | CPS2 |
| ATOM | 1188 | C | SER | 33 | 72.464 | 16.813 | 12.652 | 1.00 | 28.59 | CPS2 |
| ATOM | 1189 | O | SER | 33 | 71.488 | 16.317 | 13.211 | 1.00 | 27.50 | CPS2 |
| ATOM | 1190 | N | GLU | 34 | 72.345 | 17.682 | 11.654 | 1.00 | 27.39 | CPS2 |
| ATOM | 1191 | CA | GLU | 34 | 71.036 | 18.051 | 11.131 | 1.00 | 27.27 | CPS2 |
| ATOM | 1192 | CB | GLU | 34 | 71.178 | 19.215 | 10.140 | 1.00 | 26.09 | CPS2 |
| ATOM | 1193 | CG | GLU | 34 | 71.493 | 20.554 | 10.824 | 1.00 | 27.08 | CPS2 |
| ATOM | 1194 | CD | GLU | 34 | 71.939 | 21.642 | 9.860 | 1.00 | 27.39 | CPS2 |
| ATOM | 1195 | OE1 | GLU | 34 | 71.813 | 22.838 | 10.220 | 1.00 | 26.38 | CPS2 |
| ATOM | 1196 | OE2 | GLU | 34 | 72.427 | 21.310 | 8.755 | 1.00 | 25.66 | CPS2 |

FIG. 1A-21

| ATOM | 1197 | C | GLU | 34 | 70.443 | 16.828 | 10.437 | 1.00 | 27.36 | CPS2 |
|---|---|---|---|---|---|---|---|---|---|---|
| ATOM | 1198 | O | GLU | 34 | 69.239 | 16.562 | 10..532 | 1.00 | 26.33 | CPS2 |
| ATOM | 1199 | N | LEU | 35 | 71.302 | 16.077 | 9.750 | 1.00 | 28.28 | CPS2 |
| ATOM | 1200 | CA | LEU | 35 | 70.862 | 14.877 | 9.045 | 1.00 | 29.11 | CPS2 |
| ATOM | 1201 | CB | LEU | 35 | 72.021 | 14.251 | 8.270 | 1.00 | 28.46 | CPS2 |
| ATOM | 1202 | CG | LEU | 35 | 72.336 | 14.922 | 6.940 | 1.00 | 27.65 | CPS2 |
| ATOM | 1203 | CD1 | LEU | 35 | 73.659 | 14.380 | 6.379 | 1.00 | 29.47 | CPS2 |
| ATOM | 1204 | CD2 | LEU | 35 | 71.182 | 14.664 | 5.965 | 1.00 | 28.02 | CPS2 |
| ATOM | 1205 | C | LEU | 35 | 70.281 | 13.851 | 9.998 | 1.00 | 30.80 | CPS2 |
| ATOM | 1206 | O | LEU | 35 | 69.303 | 13.191 | 9.668 | 1.00 | 31.95 | CPS2 |
| ATOM | 1207 | N | ASP | 36 | 70.883 | 13.709 | 11.175 | 1.00 | 32.92 | CPS2 |
| ATOM | 1208 | CA | ASP | 36 | 70.380 | 12.756 | 12.161 | 1.00 | 35.31 | CPS2 |
| ATOM | 1209 | CB | ASP | 36 | 71.247 | 12.759 | 13.416 | 1.00 | 38.59 | CPS2 |
| ATOM | 1210 | CG | ASP | 36 | 72.527 | 11.974 | 13.236 | 1.00 | 43.41 | CPS2 |
| ATOM | 1211 | OD1 | ASP | 36 | 72.449 | 10.838 | 12.713 | 1.00 | 47.13 | CPS2 |
| ATOM | 1212 | OD2 | ASP | 36 | 73.606 | 12.480 | 13.618 | 1.00 | 45.83 | CPS2 |
| ATOM | 1213 | C | ASP | 36 | 68.948 | 13.107 | 12.531 | 1.00 | 35.32 | CPS2 |
| ATOM | 1214 | O | ASP | 36 | 68.108 | 12.228 | 12.733 | 1.00 | 35.28 | CPS2 |
| ATOM | 1215 | N | GLN | 37 | 68.675 | 14.404 | 12.621 | 1.00 | 34.28 | CPS2 |
| ATOM | 1216 | CA | GLN | 37 | 67.338 | 14.881 | 12.945 | 1.00 | 32.79 | CPS2 |
| ATOM | 1217 | CB | GLN | 37 | 67.401 | 16.378 | 13.297 | 1.00 | 33.92 | CPS2 |
| ATOM | 1218 | CG | GLN | 37 | 68.022 | 16.651 | 14.662 | 1.00 | 35.15 | CPS2 |
| ATOM | 1219 | CD | GLN | 37 | 68.443 | 18.110 | 14.876 | 1.00 | 36.52 | CPS2 |
| ATOM | 1220 | OE1 | GLN | 37 | 68.733 | 18.517 | 16.001 | 1.00 | 37.53 | CPS2 |
| ATOM | 1221 | NE2 | GLN | 37 | 68.495 | 18.887 | 13.799 | 1.00 | 34.94 | CPS2 |
| ATOM | 1222 | C | GLN | 37 | 66.431 | 14.645 | 11.733 | 1.00 | 32.14 | CPS2 |
| ATOM | 1223 | O | GLN | 37 | 65.284 | 14.214 | 11.863 | 1.00 | 31.52 | CPS2 |
| ATOM | 1224 | N | TYR | 38 | 66.971 | 14.914 | 10.552 | 1.00 | 30.64 | CPS2 |
| ATOM | 1225 | CA | TYR | 38 | 66.239 | 14.753 | 9.307 | 1.00 | 30.51 | CPS2 |
| ATOM | 1226 | CB | TYR | 38 | 67.112 | 15.245 | 8.148 | 1.00 | 29.87 | CPS2 |
| ATOM | 1227 | CG | TYR | 38 | 66.544 | 15.040 | 6.762 | 1.00 | 30.29 | CPS2 |
| ATOM | 1228 | CD1 | TYR | 38 | 66.975 | 13.983 | 5.957 | 1.00 | 31.01 | CPS2 |
| ATOM | 1229 | CE1 | TYR | 38 | 66.500 | 13.829 | 4.653 | 1.00 | 31.49 | CPS2 |
| ATOM | 1230 | CD2 | TYR | 38 | 65.614 | 15.935 | 6.231 | 1.00 | 30.83 | CPS2 |
| ATOM | 1231 | CE2 | TYR | 38 | 65.135 | 15.792 | 4.938 | 1.00 | 31.82 | CPS2 |
| ATOM | 1232 | CZ | TYR | 38 | 65.582 | 14.742 | 4.153 | 1.00 | 32.74 | CPS2 |
| ATOM | 1233 | OH | TYR | 38 | 65.116 | 14.623 | 2.868 | 1.00 | 33.33 | CPS2 |
| ATOM | 1234 | C | TYR | 38 | 65.802 | 13.308 | 9.064 | 1.00 | 31.79 | CPS2 |
| ATOM | 1235 | O | TYR | 38 | 64.631 | 13.048 | 8.773 | 1.00 | 30.55 | CPS2 |
| ATOM | 1236 | N | TYR | 39 | 66.739 | 12.372 | 9.190 | 1.00 | 31.62 | CPS2 |
| ATOM | 1237 | CA | TYR | 39 | 66.423 | 10.965 | 8.946 | 1.00 | 33.46 | CPS2 |
| ATOM | 1238 | CB | TYR | 39 | 67.675 | 10.096 | 9.077 | 1.00 | 31.46 | CPS2 |
| ATOM | 1239 | CG | TYR | 39 | 68.760 | 10.350 | 8.045 | 1.00 | 30.99 | CPS2 |
| ATOM | 1240 | CD1 | TYR | 39 | 68.449 | 10.548 | 6.702 | 1.00 | 31.00 | CPS2 |
| ATOM | 1241 | CE1 | TYR | 39 | 69.458 | 10.707 | 5.744 | 1.00 | 31.73 | CPS2 |
| ATOM | 1242 | CD2 | TYR | 39 | 70.108 | 10.321 | 8.413 | 1.00 | 32.22 | CPS2 |
| ATOM | 1243 | CE2 | TYR | 39 | 71.125 | 10.474 | 7.468 | 1.00 | 32.57 | CPS2 |
| ATOM | 1244 | CZ | TYR | 39 | 70.795 | 10.665 | 6.137 | 1.00 | 32.96 | CPS2 |
| ATOM | 1245 | OH | TYR | 39 | 71.813 | 10.784 | 5.211 | 1.00 | 33.59 | CPS2 |
| ATOM | 1246 | C | TYR | 39 | 65.331 | 10.411 | 9.862 | 1.00 | 34.30 | CPS2 |
| ATOM | 1247 | O | TYR | 39 | 64.653 | 9.451 | 9.506 | 1.00 | 35.26 | CPS2 |
| ATOM | 1248 | N | GLU | 40 | 65.155 | 11.015 | 11.030 | 1.00 | 36.00 | CPS2 |
| ATOM | 1249 | CA | GLU | 40 | 64.144 | 10.555 | 11.980 | 1.00 | 38.47 | CPS2 |
| ATOM | 1250 | CB | GLU | 40 | 64.468 | 11.069 | 13.387 | 1.00 | 41.11 | CPS2 |
| ATOM | 1251 | CG | GLU | 40 | 65.650 | 10.394 | 14.052 | 1.00 | 46.35 | CPS2 |
| ATOM | 1252 | CD | GLU | 40 | 65.427 | 8.903 | 14.247 | 1.00 | 49.30 | CPS2 |
| ATOM | 1253 | OE1 | GLU | 40 | 64.505 | 8.527 | 15.006 | 1.00 | 50.90 | CPS2 |

FIG. 1A-22

| ATOM | 1254 | OE2 | GLU | 40 | 66.174 | 8.108 | 13.632 | 1.00 | 51.72 | CPS2 |
|------|------|-----|-----|----|--------|-------|--------|------|-------|------|
| ATOM | 1255 | C | GLU | 40 | 62.720 | 10.980 | 11.631 | 1.00 | 38.59 | CPS2 |
| ATOM | 1256 | O | GLU | 40 | 61.761 | 10.472 | 12.210 | 1.00 | 38.70 | CPS2 |
| ATOM | 1257 | N | LEU | 41 | 62.579 | 11.905 | 10.688 | 1.00 | 37.33 | CPS2 |
| ATOM | 1258 | CA | LEU | 41 | 61.262 | 12.409 | 10.318 | 1.00 | 37.21 | CPS2 |
| ATOM | 1259 | CB | LEU | 41 | 61.371 | 13.881 | 9.908 | 1.00 | 36.12 | CPS2 |
| ATOM | 1260 | CG | LEU | 41 | 61.978 | 14.843 | 10.928 | 1.00 | 35.44 | CPS2 |
| ATOM | 1261 | CD1 | LEU | 41 | 62.095 | 16.224 | 10.296 | 1.00 | 35.33 | CPS2 |
| ATOM | 1262 | CD2 | LEU | 41 | 61.110 | 14.897 | 12.175 | 1.00 | 36.15 | CPS2 |
| ATOM | 1263 | C | LEU | 41 | 60.540 | 11.653 | 9.210 | 1.00 | 37.79 | CPS2 |
| ATOM | 1264 | O | LEU | 41 | 61.147 | 10.905 | 8.441 | 1.00 | 37.84 | CPS2 |
| ATOM | 1265 | N | SER | 42 | 59.231 | 11.882 | 9.130 | 1.00 | 38.99 | CPS2 |
| ATOM | 1266 | CA | SER | 42 | 58.394 | 11.272 | 8.105 | 1.00 | 39.66 | CPS2 |
| ATOM | 1267 | CB | SER | 42 | 56.916 | 11.461 | 8.451 | 1.00 | 40.41 | CPS2 |
| ATOM | 1268 | OG | SER | 42 | 56.529 | 12.813 | 8.277 | 1.00 | 40.55 | CPS2 |
| ATOM | 1269 | C | SER | 42 | 58.688 | 11.947 | 6.769 | 1.00 | 40.88 | CPS2 |
| ATOM | 1270 | O | SER | 42 | 59.404 | 12.948 | 6.716 | 1.00 | 40.22 | CPS2 |
| ATOM | 1271 | N | GLU | 43 | 58.118 | 11.405 | 5.698 | 1.00 | 41.38 | CPS2 |
| ATOM | 1272 | CA | GLU | 43 | 58.310 | 11.948 | 4.358 | 1.00 | 41.99 | CPS2 |
| ATOM | 1273 | CB | GLU | 43 | 57.466 | 11.173 | 3.340 | 1.00 | 44.33 | CPS2 |
| ATOM | 1274 | CG | GLU | 43 | 56.922 | 9.822 | 3.821 | 1.00 | 47.83 | CPS2 |
| ATOM | 1275 | CD | GLU | 43 | 55.963 | 9.946 | 5.005 | 1.00 | 50.30 | CPS2 |
| ATOM | 1276 | OE1 | GLU | 43 | 55.186 | 10.935 | 5.055 | 1.00 | 50.62 | CPS2 |
| ATOM | 1277 | OE2 | GLU | 43 | 55.982 | 9.045 | 5.877 | 1.00 | 48.97 | CPS2 |
| ATOM | 1278 | C | GLU | 43 | 57.921 | 13.425 | 4.294 | 1.00 | 40.64 | CPS2 |
| ATOM | 1279 | O | GLU | 43 | 58.662 | 14.259 | 3.767 | 1.00 | 40.30 | CPS2 |
| ATOM | 1280 | N | LYS | 44 | 56.747 | 13.739 | 4.825 | 1.00 | 39.19 | CPS2 |
| ATOM | 1281 | CA | LYS | 44 | 56.249 | 15.112 | 4.821 | 1.00 | 39.31 | CPS2 |
| ATOM | 1282 | CB | LYS | 44 | 54.787 | 15.140 | 5.269 | 1.00 | 40.00 | CPS2 |
| ATOM | 1283 | CG | LYS | 44 | 54.112 | 16.491 | 5.107 | 1.00 | 42.53 | CPS2 |
| ATOM | 1284 | CD | LYS | 44 | 52.721 | 16.472 | 5.719 | 1.00 | 44.55 | CPS2 |
| ATOM | 1285 | CE | LYS | 44 | 52.031 | 17.817 | 5.592 | 1.00 | 45.48 | CPS2 |
| ATOM | 1286 | NZ | LYS | 44 | 50.783 | 17.861 | 6.406 | 1.00 | 47.64 | CPS2 |
| ATOM | 1287 | C | LYS | 44 | 57.075 | 16.023 | 5.732 | 1.00 | 38.50 | CPS2 |
| ATOM | 1288 | O | LYS | 44 | 57.446 | 17.136 | 5.345 | 1.00 | 38.08 | CPS2 |
| ATOM | 1289 | N | ARG | 45 | 57.345 | 15.554 | 6.947 | 1.00 | 36.81 | CPS2 |
| ATOM | 1290 | CA | ARG | 45 | 58.125 | 16.335 | 7.898 | 1.00 | 36.28 | CPS2 |
| ATOM | 1291 | CB | ARG | 45 | 58.162 | 15.624 | 9.254 | 1.00 | 37.98 | CPS2 |
| ATOM | 1292 | CG | ARG | 45 | 56.911 | 15.843 | 10.106 | 1.00 | 41.93 | CPS2 |
| ATOM | 1293 | CD | ARG | 45 | 57.135 | 16.960 | 11.117 | 1.00 | 45.38 | CPS2 |
| ATOM | 1294 | NE | ARG | 45 | 57.655 | 18.160 | 10.468 | 1.00 | 49.29 | CPS2 |
| ATOM | 1295 | CZ | ARG | 45 | 58.565 | 18.968 | 11.002 | 1.00 | 49.81 | CPS2 |
| ATOM | 1296 | NH1 | ARG | 45 | 59.064 | 18.714 | 12.206 | 1.00 | 51.08 | CPS2 |
| ATOM | 1297 | NH2 | ARG | 45 | 58.993 | 20.022 | 10.323 | 1.00 | 50.35 | CPS2 |
| ATOM | 1298 | C | ARG | 45 | 59.537 | 16.595 | 7.382 | 1.00 | 34.46 | CPS2 |
| ATOM | 1299 | O | ARG | 45 | 60.105 | 17.657 | 7.629 | 1.00 | 33.18 | CPS2 |
| ATOM | 1300 | N | LYS | 46 | 60.107 | 15.630 | 6.662 | 1.00 | 32.44 | CPS2 |
| ATOM | 1301 | CA | LYS | 46 | 61.444 | 15.814 | 6.110 | 1.00 | 32.32 | CPS2 |
| ATOM | 1302 | CB | LYS | 46 | 61.891 | 14.589 | 5.295 | 1.00 | 32.49 | CPS2 |
| ATOM | 1303 | CG | LYS | 46 | 62.375 | 13.419 | 6.133 | 1.00 | 33.28 | CPS2 |
| ATOM | 1304 | CD | LYS | 46 | 62.872 | 12.296 | 5.245 | 1.00 | 34.31 | CPS2 |
| ATOM | 1305 | CE | LYS | 46 | 63.389 | 11.131 | 6.065 | 1.00 | 35.44 | CPS2 |
| ATOM | 1306 | NZ | LYS | 46 | 63.700 | 9.994 | 5.169 | 1.00 | 36.69 | CPS2 |
| ATOM | 1307 | C | LYS | 46 | 61.479 | 17.039 | 5.206 | 1.00 | 31.46 | CPS2 |
| ATOM | 1308 | O | LYS | 46 | 62.393 | 17.856 | 5.290 | 1.00 | 31.48 | CPS2 |
| ATOM | 1309 | N | ASN | 47 | 60.481 | 17.163 | 4.336 | 1.00 | 30.42 | CPS2 |
| ATOM | 1310 | CA | ASN | 47 | 60.417 | 18.286 | 3.407 | 1.00 | 31.16 | CPS2 |

FIG. 1A-23

| ATOM | 1311 | CB  | ASN | 47 | 59.240 | 18.101 | 2.437  | 1.00 | 32.45 | CPS2 |
|------|------|-----|-----|----|--------|--------|--------|------|-------|------|
| ATOM | 1312 | CG  | ASN | 47 | 59.080 | 19.269 | 1.470  | 1.00 | 34.97 | CPS2 |
| ATOM | 1313 | OD1 | ASN | 47 | 59.977 | 19.575 | 0.684  | 1.00 | 37.44 | CPS2 |
| ATOM | 1314 | ND2 | ASN | 47 | 57.928 | 19.923 | 1.525  | 1.00 | 35.87 | CPS2 |
| ATOM | 1315 | C   | ASN | 47 | 60.290 | 19.612 | 4.157  | 1.00 | 29.73 | CPS2 |
| ATOM | 1316 | O   | ASN | 47 | 60.946 | 20.587 | 3.803  | 1.00 | 28.79 | CPS2 |
| ATOM | 1317 | N   | GLU | 48 | 59.462 | 19.637 | 5.195  | 1.00 | 28.89 | CPS2 |
| ATOM | 1318 | CA  | GLU | 48 | 59.265 | 20.853 | 5.984  | 1.00 | 29.80 | CPS2 |
| ATOM | 1319 | CB  | GLU | 48 | 58.162 | 20.642 | 7.019  | 1.00 | 32.74 | CPS2 |
| ATOM | 1320 | CG  | GLU | 48 | 56.837 | 20.225 | 6.424  | 1.00 | 37.62 | CPS2 |
| ATOM | 1321 | CD  | GLU | 48 | 55.785 | 19.953 | 7.482  | 1.00 | 40.29 | CPS2 |
| ATOM | 1322 | OE1 | GLU | 48 | 54.683 | 19.506 | 7.113  | 1.00 | 41.90 | CPS2 |
| ATOM | 1323 | OE2 | GLU | 48 | 56.059 | 20.193 | 8.679  | 1.00 | 42.74 | CPS2 |
| ATOM | 1324 | C   | GLU | 48 | 60.554 | 21.231 | 6.700  | 1.00 | 28.72 | CPS2 |
| ATOM | 1325 | O   | GLU | 48 | 60.956 | 22.396 | 6.720  | 1.00 | 27.50 | CPS2 |
| ATOM | 1326 | N   | PHE | 49 | 61.192 | 20.230 | 7.296  | 1.00 | 26.72 | CPS2 |
| ATOM | 1327 | CA  | PHE | 49 | 62.432 | 20.433 | 8.023  | 1.00 | 26.17 | CPS2 |
| ATOM | 1328 | CB  | PHE | 49 | 62.877 | 19.116 | 8.665  | 1.00 | 27.12 | CPS2 |
| ATOM | 1329 | CG  | PHE | 49 | 64.186 | 19.205 | 9.397  | 1.00 | 26.24 | CPS2 |
| ATOM | 1330 | CD1 | PHE | 49 | 64.219 | 19.514 | 10.750 | 1.00 | 27.02 | CPS2 |
| ATOM | 1331 | CD2 | PHE | 49 | 65.385 | 18.967 | 8.734  | 1.00 | 28.35 | CPS2 |
| ATOM | 1332 | CE1 | PHE | 49 | 65.429 | 19.578 | 11.436 | 1.00 | 27.13 | CPS2 |
| ATOM | 1333 | CE2 | PHE | 49 | 66.603 | 19.030 | 9.411  | 1.00 | 27.87 | CPS2 |
| ATOM | 1334 | CZ  | PHE | 49 | 66.615 | 19.336 | 10.770 | 1.00 | 27.13 | CPS2 |
| ATOM | 1335 | C   | PHE | 49 | 63.522 | 20.935 | 7.091  | 1.00 | 24.61 | CPS2 |
| ATOM | 1336 | O   | PHE | 49 | 64.208 | 21.907 | 7.390  | 1.00 | 24.60 | CPS2 |
| ATOM | 1337 | N   | LEU | 50 | 63.685 | 20.266 | 5.957  | 1.00 | 23.67 | CPS2 |
| ATOM | 1338 | CA  | LEU | 50 | 64.710 | 20.650 | 5.000  | 1.00 | 23.23 | CPS2 |
| ATOM | 1339 | CB  | LEU | 50 | 64.763 | 19.626 | 3.862  | 1.00 | 24.17 | CPS2 |
| ATOM | 1340 | CG  | LEU | 50 | 65.810 | 19.767 | 2.758  | 1.00 | 26.00 | CPS2 |
| ATOM | 1341 | CD1 | LEU | 50 | 67.217 | 19.817 | 3.351  | 1.00 | 25.89 | CPS2 |
| ATOM | 1342 | CD2 | LEU | 50 | 65.685 | 18.570 | 1.810  | 1.00 | 26.96 | CPS2 |
| ATOM | 1343 | C   | LEU | 50 | 64.465 | 22.053 | 4.448  | 1.00 | 23.30 | CPS2 |
| ATOM | 1344 | O   | LEU | 50 | 65.391 | 22.849 | 4.317  | 1.00 | 22.85 | CPS2 |
| ATOM | 1345 | N   | ALA | 51 | 63.218 | 22.366 | 4.127  | 1.00 | 21.99 | CPS2 |
| ATOM | 1346 | CA  | ALA | 51 | 62.914 | 23.684 | 3.586  | 1.00 | 21.37 | CPS2 |
| ATOM | 1347 | CB  | ALA | 51 | 61.438 | 23.766 | 3.206  | 1.00 | 19.49 | CPS2 |
| ATOM | 1348 | C   | ALA | 51 | 63.262 | 24.772 | 4.610  | 1.00 | 19.95 | CPS2 |
| ATOM | 1349 | O   | ALA | 51 | 63.812 | 25.815 | 4.252  | 1.00 | 19.91 | CPS2 |
| ATOM | 1350 | N   | GLY | 52 | 62.943 | 24.508 | 5.871  | 1.00 | 20.32 | CPS2 |
| ATOM | 1351 | CA  | GLY | 52 | 63.207 | 25.466 | 6.939  | 1.00 | 20.53 | CPS2 |
| ATOM | 1352 | C   | GLY | 52 | 64.690 | 25.678 | 7.161  | 1.00 | 21.59 | CPS2 |
| ATOM | 1353 | O   | GLY | 52 | 65.140 | 26.823 | 7.292  | 1.00 | 20.12 | CPS2 |
| ATOM | 1354 | N   | ARG | 53 | 65.452 | 24.581 | 7.211  | 1.00 | 20.75 | CPS2 |
| ATOM | 1355 | CA  | ARG | 53 | 66.900 | 24.681 | 7.405  | 1.00 | 21.49 | CPS2 |
| ATOM | 1356 | CB  | ARG | 53 | 67.511 | 23.289 | 7.639  | 1.00 | 20.94 | CPS2 |
| ATOM | 1357 | CG  | ARG | 53 | 67.662 | 22.904 | 9.121  | 1.00 | 21.90 | CPS2 |
| ATOM | 1358 | CD  | ARG | 53 | 66.357 | 23.082 | 9.905  | 1.00 | 23.39 | CPS2 |
| ATOM | 1359 | NE  | ARG | 53 | 66.538 | 22.829 | 11.335 | 1.00 | 24.30 | CPS2 |
| ATOM | 1360 | CZ  | ARG | 53 | 65.666 | 23.195 | 12.272 | 1.00 | 25.08 | CPS2 |
| ATOM | 1361 | NH1 | ARG | 53 | 64.548 | 23.827 | 11.934 | 1.00 | 25.43 | CPS2 |
| ATOM | 1362 | NH2 | ARG | 53 | 65.921 | 22.959 | 13.551 | 1.00 | 26.80 | CPS2 |
| ATOM | 1363 | C   | ARG | 53 | 67.541 | 25.359 | 6.201  | 1.00 | 20.90 | CPS2 |
| ATOM | 1364 | O   | ARG | 53 | 68.447 | 26.176 | 6.353  | 1.00 | 20.27 | CPS2 |
| ATOM | 1365 | N   | PHE | 54 | 67.069 | 25.021 | 5.002  | 1.00 | 20.29 | CPS2 |
| ATOM | 1366 | CA  | PHE | 54 | 67.583 | 25.631 | 3.779  | 1.00 | 21.05 | CPS2 |
| ATOM | 1367 | CB  | PHE | 54 | 66.889 | 24.996 | 2.550  | 1.00 | 21.38 | CPS2 |

FIG. 1A-24

| ATOM | 1368 | CG | PHE | 54 | 67.310 | 25.573 | 1.218 | 1.00 | 22.85 | CPS2 |
|---|---|---|---|---|---|---|---|---|---|---|
| ATOM | 1369 | CD1 | PHE | 54 | 66.623 | 26.646 | 0.660 | 1.00 | 23.51 | CPS2 |
| ATOM | 1370 | CD2 | PHE | 54 | 68.363 | 25.008 | 0.495 | 1.00 | 23.11 | CPS2 |
| ATOM | 1371 | CE1 | PHE | 54 | 66.970 | 27.148 | -0.600 | 1.00 | 23.62 | CPS2 |
| ATOM | 1372 | CE2 | PHE | 54 | 68.716 | 25.499 | -0.761 | 1.00 | 24.74 | CPS2 |
| ATOM | 1373 | CZ | PHE | 54 | 68.015 | 26.575 | -1.313 | 1.00 | 24.84 | CPS2 |
| ATOM | 1374 | C | PHE | 54 | 67.334 | 27.144 | 3.823 | 1.00 | 20.71 | CPS2 |
| ATOM | 1375 | O | PHE | 54 | 68.225 | 27.939 | 3.523 | 1.00 | 20.44 | CPS2 |
| ATOM | 1376 | N | ALA | 55 | 66.118 | 27.542 | 4.191 | 1.00 | 20.38 | CPS2 |
| ATOM | 1377 | CA | ALA | 55 | 65.772 | 28.967 | 4.268 | 1.00 | 20.18 | CPS2 |
| ATOM | 1378 | CB | ALA | 55 | 64.299 | 29.138 | 4.665 | 1.00 | 19.50 | CPS2 |
| ATOM | 1379 | C | ALA | 55 | 66.654 | 29.701 | 5.276 | 1.00 | 20.15 | CPS2 |
| ATOM | 1380 | O | ALA | 55 | 67.111 | 30.822 | 5.021 | 1.00 | 19.68 | CPS2 |
| ATOM | 1381 | N | ALA | 56 | 66.872 | 29.071 | 6.428 | 1.00 | 20.22 | CPS2 |
| ATOM | 1382 | CA | ALA | 56 | 67.706 | 29.657 | 7.476 | 1.00 | 19.63 | CPS2 |
| ATOM | 1383 | CB | ALA | 56 | 67.670 | 28.772 | 8.737 | 1.00 | 20.93 | CPS2 |
| ATOM | 1384 | C | ALA | 56 | 69.152 | 29.841 | 7.014 | 1.00 | 20.43 | CPS2 |
| ATOM | 1385 | O | ALA | 56 | 69.780 | 30.869 | 7.307 | 1.00 | 19.00 | CPS2 |
| ATOM | 1386 | N | LYS | 57 | 69.702 | 28.840 | 6.322 | 1.00 | 19.36 | CPS2 |
| ATOM | 1387 | CA | LYS | 57 | 71.084 | 28.955 | 5.858 | 1.00 | 19.89 | CPS2 |
| ATOM | 1388 | CB | LYS | 57 | 71.622 | 27.598 | 5.388 | 1.00 | 19.91 | CPS2 |
| ATOM | 1389 | CG | LYS | 57 | 71.595 | 26.550 | 6.501 | 1.00 | 20.56 | CPS2 |
| ATOM | 1390 | CD | LYS | 57 | 72.389 | 25.285 | 6.150 | 1.00 | 21.63 | CPS2 |
| ATOM | 1391 | CE | LYS | 57 | 72.426 | 24.334 | 7.358 | 1.00 | 20.15 | CPS2 |
| ATOM | 1392 | NZ | LYS | 57 | 73.457 | 23.262 | 7.208 | 1.00 | 19.99 | CPS2 |
| ATOM | 1393 | C | LYS | 57 | 71.176 | 29.993 | 4.754 | 1.00 | 19.82 | CPS2 |
| ATOM | 1394 | O | LYS | 57 | 72.136 | 30.755 | 4.698 | 1.00 | 20.57 | CPS2 |
| ATOM | 1395 | N | GLU | 58 | 70.179 | 30.036 | 3.871 | 1.00 | 18.71 | CPS2 |
| ATOM | 1396 | CA | GLU | 58 | 70.187 | 31.045 | 2.822 | 1.00 | 20.25 | CPS2 |
| ATOM | 1397 | CB | GLU | 58 | 68.993 | 30.868 | 1.870 | 1.00 | 23.44 | CPS2 |
| ATOM | 1398 | CG | GLU | 58 | 69.120 | 29.710 | 0.871 | 1.00 | 28.15 | CPS2 |
| ATOM | 1399 | CD | GLU | 58 | 70.261 | 29.896 | -0.124 | 1.00 | 31.42 | CPS2 |
| ATOM | 1400 | OE1 | GLU | 58 | 70.713 | 31.042 | -0.335 | 1.00 | 33.78 | CPS2 |
| ATOM | 1401 | OE2 | GLU | 58 | 70.701 | 28.891 | -0.713 | 1.00 | 35.13 | CPS2 |
| ATOM | 1402 | C | GLU | 58 | 70.116 | 32.436 | 3.477 | 1.00 | 20.06 | CPS2 |
| ATOM | 1403 | O | GLU | 58 | 70.878 | 33.335 | 3.117 | 1.00 | 20.02 | CPS2 |
| ATOM | 1404 | N | ALA | 59 | 69.203 | 32.611 | 4.433 | 1.00 | 18.56 | CPS2 |
| ATOM | 1405 | CA | ALA | 59 | 69.066 | 33.901 | 5.107 | 1.00 | 19.36 | CPS2 |
| ATOM | 1406 | CB | ALA | 59 | 67.919 | 33.853 | 6.142 | 1.00 | 18.28 | CPS2 |
| ATOM | 1407 | C | ALA | 59 | 70.388 | 34.280 | 5.789 | 1.00 | 19.60 | CPS2 |
| ATOM | 1408 | O | ALA | 59 | 70.833 | 35.429 | 5.712 | 1.00 | 20.42 | CPS2 |
| ATOM | 1409 | N | PHE | 60 | 71.016 | 33.314 | 6.452 | 1.00 | 18.99 | CPS2 |
| ATOM | 1410 | CA | PHE | 60 | 72.284 | 33.591 | 7.119 | 1.00 | 19.29 | CPS2 |
| ATOM | 1411 | CB | PHE | 60 | 72.790 | 32.350 | 7.862 | 1.00 | 20.46 | CPS2 |
| ATOM | 1412 | CG | PHE | 60 | 74.128 | 32.555 | 8.501 | 1.00 | 21.05 | CPS2 |
| ATOM | 1413 | CD1 | PHE | 60 | 74.225 | 33.085 | 9.785 | 1.00 | 21.57 | CPS2 |
| ATOM | 1414 | CD2 | PHE | 60 | 75.297 | 32.313 | 7.783 | 1.00 | 23.12 | CPS2 |
| ATOM | 1415 | CE1 | PHE | 60 | 75.476 | 33.377 | 10.343 | 1.00 | 22.68 | CPS2 |
| ATOM | 1416 | CE2 | PHE | 60 | 76.554 | 32.605 | 8.332 | 1.00 | 22.55 | CPS2 |
| ATOM | 1417 | CZ | PHE | 60 | 76.638 | 33.136 | 9.610 | 1.00 | 22.82 | CPS2 |
| ATOM | 1418 | C | PHE | 60 | 73.338 | 34.020 | 6.092 | 1.00 | 20.21 | CPS2 |
| ATOM | 1419 | O | PHE | 60 | 74.089 | 34.965 | 6.320 | 1.00 | 19.97 | CPS2 |
| ATOM | 1420 | N | SER | 61 | 73.396 | 33.318 | 4.960 | 1.00 | 20.80 | CPS2 |
| ATOM | 1421 | CA | SER | 61 | 74.372 | 33.641 | 3.920 | 1.00 | 20.87 | CPS2 |
| ATOM | 1422 | CB | SER | 61 | 74.287 | 32.633 | 2.762 | 1.00 | 21.27 | CPS2 |
| ATOM | 1423 | OG | SER | 61 | 73.161 | 32.874 | 1.942 | 1.00 | 22.46 | CPS2 |
| ATOM | 1424 | C | SER | 61 | 74.190 | 35.058 | 3.389 | 1.00 | 21.75 | CPS2 |

FIG. 1A-25

| ATOM | 1425 | O | SER | 61 | 75.161 | 35.709 | 2.981 | 1.00 | 22.83 | CPS2 |
|---|---|---|---|---|---|---|---|---|---|---|
| ATOM | 1426 | N | LYS | 62 | 72.949 | 35.541 | 3.396 | 1.00 | 20.78 | CPS2 |
| ATOM | 1427 | CA | LYS | 62 | 72.657 | 36.890 | 2.934 | 1.00 | 21.54 | CPS2 |
| ATOM | 1428 | CB | LYS | 62 | 71.158 | 37.027 | 2.627 | 1.00 | 22.99 | CPS2 |
| ATOM | 1429 | CG | LYS | 62 | 70.696 | 36.164 | 1.444 | 1.00 | 27.37 | CPS2 |
| ATOM | 1430 | CD | LYS | 62 | 69.195 | 35.912 | 1.505 | 1.00 | 30.44 | CPS2 |
| ATOM | 1431 | CE | LYS | 62 | 68.439 | 36.617 | 0.401 | 1.00 | 33.74 | CPS2 |
| ATOM | 1432 | NZ | LYS | 62 | 68.581 | 35.960 | -0.917 | 1.00 | 35.02 | CPS2 |
| ATOM | 1433 | C | LYS | 62 | 73.084 | 37.922 | 3.985 | 1.00 | 22.13 | CPS2 |
| ATOM | 1434 | O | LYS | 62 | 73.546 | 39.009 | 3.638 | 1.00 | 22.23 | CPS2 |
| ATOM | 1435 | N | ALA | 63 | 72.929 | 37.581 | 5.264 | 1.00 | 21.23 | CPS2 |
| ATOM | 1436 | CA | ALA | 63 | 73.329 | 38.488 | 6.335 | 1.00 | 20.30 | CPS2 |
| ATOM | 1437 | CB | ALA | 63 | 72.813 | 37.988 | 7.694 | 1.00 | 21.99 | CPS2 |
| ATOM | 1438 | C | ALA | 63 | 74.851 | 38.541 | 6.337 | 1.00 | 22.63 | CPS2 |
| ATOM | 1439 | O | ALA | 63 | 75.439 | 39.604 | 6.541 | 1.00 | 22.47 | CPS2 |
| ATOM | 1440 | N | PHE | 64 | 75.473 | 37.387 | 6.092 | 1.00 | 23.43 | CPS2 |
| ATOM | 1441 | CA | PHE | 64 | 76.934 | 37.257 | 6.040 | 1.00 | 26.03 | CPS2 |
| ATOM | 1442 | CB | PHE | 64 | 77.315 | 35.788 | 5.814 | 1.00 | 28.19 | CPS2 |
| ATOM | 1443 | CG | PHE | 64 | 78.780 | 35.482 | 6.042 | 1.00 | 31.14 | CPS2 |
| ATOM | 1444 | CD1 | PHE | 64 | 79.301 | 35.418 | 7.329 | 1.00 | 33.14 | CPS2 |
| ATOM | 1445 | CD2 | PHE | 64 | 79.624 | 35.224 | 4.965 | 1.00 | 32.47 | CPS2 |
| ATOM | 1446 | CE1 | PHE | 64 | 80.652 | 35.094 | 7.545 | 1.00 | 34.43 | CPS2 |
| ATOM | 1447 | CE2 | PHE | 64 | 80.969 | 34.900 | 5.163 | 1.00 | 33.63 | CPS2 |
| ATOM | 1448 | CZ | PHE | 64 | 81.484 | 34.834 | 6.457 | 1.00 | 33.53 | CPS2 |
| ATOM | 1449 | C | PHE | 64 | 77.481 | 38.136 | 4.905 | 1.00 | 27.97 | CPS2 |
| ATOM | 1450 | O | PHE | 64 | 78.645 | 38.549 | 4.935 | 1.00 | 29.10 | CPS2 |
| ATOM | 1451 | N | GLY | 65 | 76.642 | 38.388 | 3.901 | 1.00 | 28.14 | CPS2 |
| ATOM | 1452 | CA | GLY | 65 | 76.999 | 39.256 | 2.786 | 1.00 | 29.01 | CPS2 |
| ATOM | 1453 | C | GLY | 65 | 77.588 | 38.652 | 1.523 | 1.00 | 30.18 | CPS2 |
| ATOM | 1454 | O | GLY | 65 | 77.945 | 39.377 | 0.596 | 1.00 | 31.12 | CPS2 |
| ATOM | 1455 | N | THR | 66 | 77.660 | 37.332 | 1.454 | 1.00 | 30.26 | CPS2 |
| ATOM | 1456 | CA | THR | 66 | 78.268 | 36.684 | 0.302 | 1.00 | 30.90 | CPS2 |
| ATOM | 1457 | CB | THR | 66 | 79.499 | 35.898 | 0.744 | 1.00 | 30.61 | CPS2 |
| ATOM | 1458 | OG1 | THR | 66 | 79.078 | 34.838 | 1.607 | 1.00 | 32.42 | CPS2 |
| ATOM | 1459 | CG2 | THR | 66 | 80.457 | 36.790 | 1.525 | 1.00 | 31.71 | CPS2 |
| ATOM | 1460 | C | THR | 66 | 77.362 | 35.697 | -0.410 | 1.00 | 31.06 | CPS2 |
| ATOM | 1461 | O | THR | 66 | 77.601 | 35.355 | -1.573 | 1.00 | 32.11 | CPS2 |
| ATOM | 1462 | N | GLY | 67 | 76.332 | 35.232 | 0.288 | 1.00 | 30.08 | CPS2 |
| ATOM | 1463 | CA | GLY | 67 | 75.460 | 34.226 | -0.285 | 1.00 | 29.32 | CPS2 |
| ATOM | 1464 | C | GLY | 67 | 76.230 | 32.923 | -0.146 | 1.00 | 29.07 | CPS2 |
| ATOM | 1465 | O | GLY | 67 | 77.357 | 32.929 | 0.354 | 1.00 | 28.18 | CPS2 |
| ATOM | 1466 | N | ILE | 68 | 75.640 | 31.809 | -0.566 | 1.00 | 29.24 | CPS2 |
| ATOM | 1467 | CA | ILE | 68 | 76.315 | 30.518 | -0.477 | 1.00 | 30.11 | CPS2 |
| ATOM | 1468 | CB | ILE | 68 | 75.293 | 29.347 | -0.467 | 1.00 | 29.33 | CPS2 |
| ATOM | 1469 | CG2 | ILE | 68 | 76.018 | 28.010 | -0.446 | 1.00 | 29.51 | CPS2 |
| ATOM | 1470 | CG1 | ILE | 68 | 74.388 | 29.434 | 0.769 | 1.00 | 28.22 | CPS2 |
| ATOM | 1471 | CD1 | ILE | 68 | 75.100 | 29.195 | 2.089 | 1.00 | 25.10 | CPS2 |
| ATOM | 1472 | C | ILE | 68 | 77.237 | 30.385 | -1.697 | 1.00 | 32.39 | CPS2 |
| ATOM | 1473 | O | ILE | 68 | 76.831 | 30.654 | -2.827 | 1.00 | 32.91 | CPS2 |
| ATOM | 1474 | N | GLY | 69 | 78.476 | 29.979 | -1.460 | 1.00 | 32.97 | CPS2 |
| ATOM | 1475 | CA | GLY | 69 | 79.419 | 29.834 | -2.552 | 1.00 | 35.33 | CPS2 |
| ATOM | 1476 | C | GLY | 69 | 80.810 | 29.564 | -2.028 | 1.00 | 36.14 | CPS2 |
| ATOM | 1477 | O | GLY | 69 | 80.970 | 28.924 | -0.992 | 1.00 | 36.01 | CPS2 |
| ATOM | 1478 | N | ALA | 70 | 81.814 | 30.065 | -2.742 | 1.00 | 37.62 | CPS2 |
| ATOM | 1479 | CA | ALA | 70 | 83.212 | 29.872 | -2.379 | 1.00 | 38.31 | CPS2 |
| ATOM | 1480 | CB | ALA | 70 | 84.110 | 30.468 | -3.473 | 1.00 | 38.64 | CPS2 |
| ATOM | 1481 | C | ALA | 70 | 83.577 | 30.474 | -1.025 | 1.00 | 38.65 | CPS2 |

FIG. 1A-26

| ATOM | 1482 | O   | ALA | 70 | 84.488 | 29.999 | -0.345 | 1.00 | 39.72 | CPS2 |
|------|------|-----|-----|-----|--------|--------|--------|------|-------|------|
| ATOM | 1483 | N   | GLN | 71 | 82.858 | 31.515 | -0.628 | 1.00 | 38.67 | CPS2 |
| ATOM | 1484 | CA  | GLN | 71 | 83.130 | 32.197 | 0.630  | 1.00 | 37.32 | CPS2 |
| ATOM | 1485 | CB  | GLN | 71 | 82.744 | 33.666 | 0.472  | 1.00 | 40.43 | CPS2 |
| ATOM | 1486 | CG  | GLN | 71 | 83.693 | 34.659 | 1.118  | 1.00 | 44.57 | CPS2 |
| ATOM | 1487 | CD  | GLN | 71 | 83.654 | 36.018 | 0.431  | 1.00 | 46.06 | CPS2 |
| ATOM | 1488 | OE1 | GLN | 71 | 84.175 | 37.004 | 0.952  | 1.00 | 48.20 | CPS2 |
| ATOM | 1489 | NE2 | GLN | 71 | 83.044 | 36.069 | -0.754 | 1.00 | 47.40 | CPS2 |
| ATOM | 1490 | C   | GLN | 71 | 82.391 | 31.578 | 1.824  | 1.00 | 35.81 | CPS2 |
| ATOM | 1491 | O   | GLN | 71 | 82.851 | 31.656 | 2.962  | 1.00 | 36.15 | CPS2 |
| ATOM | 1492 | N   | LEU | 72 | 81.257 | 30.944 | 1.561  | 1.00 | 32.57 | CPS2 |
| ATOM | 1493 | CA  | LEU | 72 | 80.461 | 30.353 | 2.630  | 1.00 | 30.34 | CPS2 |
| ATOM | 1494 | CB  | LEU | 72 | 79.503 | 31.400 | 3.196  | 1.00 | 29.93 | CPS2 |
| ATOM | 1495 | CG  | LEU | 72 | 78.560 | 30.935 | 4.303  | 1.00 | 29.85 | CPS2 |
| ATOM | 1496 | CD1 | LEU | 72 | 79.352 | 30.712 | 5.585  | 1.00 | 29.87 | CPS2 |
| ATOM | 1497 | CD2 | LEU | 72 | 77.482 | 31.998 | 4.515  | 1.00 | 30.13 | CPS2 |
| ATOM | 1498 | C   | LEU | 72 | 79.670 | 29.165 | 2.117  | 1.00 | 28.96 | CPS2 |
| ATOM | 1499 | O   | LEU | 72 | 78.925 | 29.270 | 1.146  | 1.00 | 29.65 | CPS2 |
| ATOM | 1500 | N   | SER | 73 | 79.828 | 28.037 | 2.791  | 1.00 | 26.89 | CPS2 |
| ATOM | 1501 | CA  | SER | 73 | 79.163 | 26.805 | 2.405  | 1.00 | 26.28 | CPS2 |
| ATOM | 1502 | CB  | SER | 73 | 80.176 | 25.656 | 2.498  | 1.00 | 27.70 | CPS2 |
| ATOM | 1503 | OG  | SER | 73 | 79.571 | 24.385 | 2.324  | 1.00 | 31.43 | CPS2 |
| ATOM | 1504 | C   | SER | 73 | 77.970 | 26.491 | 3.300  | 1.00 | 25.59 | CPS2 |
| ATOM | 1505 | O   | SER | 73 | 77.912 | 26.952 | 4.441  | 1.00 | 23.26 | CPS2 |
| ATOM | 1506 | N   | PHE | 74 | 77.016 | 25.718 | 2.780  | 1.00 | 24.61 | CPS2 |
| ATOM | 1507 | CA  | PHE | 74 | 75.874 | 25.292 | 3.591  | 1.00 | 24.32 | CPS2 |
| ATOM | 1508 | CB  | PHE | 74 | 74.974 | 24.333 | 2.813  | 1.00 | 24.91 | CPS2 |
| ATOM | 1509 | CG  | PHE | 74 | 74.016 | 25.012 | 1.887  | 1.00 | 27.32 | CPS2 |
| ATOM | 1510 | CD1 | PHE | 74 | 73.041 | 25.873 | 2.385  | 1.00 | 26.95 | CPS2 |
| ATOM | 1511 | CD2 | PHE | 74 | 74.079 | 24.787 | 0.511  | 1.00 | 28.10 | CPS2 |
| ATOM | 1512 | CE1 | PHE | 74 | 72.142 | 26.501 | 1.528  | 1.00 | 28.03 | CPS2 |
| ATOM | 1513 | CE2 | PHE | 74 | 73.185 | 25.411 | -0.350 | 1.00 | 29.15 | CPS2 |
| ATOM | 1514 | CZ  | PHE | 74 | 72.214 | 26.271 | 0.160  | 1.00 | 27.71 | CPS2 |
| ATOM | 1515 | C   | PHE | 74 | 76.433 | 24.527 | 4.788  | 1.00 | 25.14 | CPS2 |
| ATOM | 1516 | O   | PHE | 74 | 75.841 | 24.490 | 5.868  | 1.00 | 23.71 | CPS2 |
| ATOM | 1517 | N   | GLN | 75 | 77.577 | 23.886 | 4.571  | 1.00 | 25.35 | CPS2 |
| ATOM | 1518 | CA  | GLN | 75 | 78.212 | 23.099 | 5.618  | 1.00 | 26.61 | CPS2 |
| ATOM | 1519 | CB  | GLN | 75 | 79.212 | 22.115 | 4.998  | 1.00 | 26.65 | CPS2 |
| ATOM | 1520 | CG  | GLN | 75 | 78.580 | 21.089 | 4.063  | 1.00 | 27.20 | CPS2 |
| ATOM | 1521 | CD  | GLN | 75 | 77.513 | 20.259 | 4.742  | 1.00 | 26.33 | CPS2 |
| ATOM | 1522 | OE1 | GLN | 75 | 77.695 | 19.797 | 5.864  | 1.00 | 26.93 | CPS2 |
| ATOM | 1523 | NE2 | GLN | 75 | 76.390 | 20.057 | 4.056  | 1.00 | 27.72 | CPS2 |
| ATOM | 1524 | C   | GLN | 75 | 78.918 | 23.944 | 6.674  | 1.00 | 27.33 | CPS2 |
| ATOM | 1525 | O   | GLN | 75 | 79.380 | 23.413 | 7.684  | 1.00 | 30.23 | CPS2 |
| ATOM | 1526 | N   | ASP | 76 | 79.020 | 25.250 | 6.455  | 1.00 | 28.01 | CPS2 |
| ATOM | 1527 | CA  | ASP | 76 | 79.676 | 26.113 | 7.441  | 1.00 | 26.83 | CPS2 |
| ATOM | 1528 | CB  | ASP | 76 | 80.334 | 27.317 | 6.769  | 1.00 | 28.17 | CPS2 |
| ATOM | 1529 | CG  | ASP | 76 | 81.508 | 26.933 | 5.900  | 1.00 | 29.80 | CPS2 |
| ATOM | 1530 | OD1 | ASP | 76 | 82.291 | 26.066 | 6.330  | 1.00 | 29.26 | CPS2 |
| ATOM | 1531 | OD2 | ASP | 76 | 81.649 | 27.514 | 4.800  | 1.00 | 30.74 | CPS2 |
| ATOM | 1532 | C   | ASP | 76 | 78.657 | 26.648 | 8.429  | 1.00 | 27.59 | CPS2 |
| ATOM | 1533 | O   | ASP | 76 | 79.015 | 27.306 | 9.412  | 1.00 | 26.97 | CPS2 |
| ATOM | 1534 | N   | ILE | 77 | 77.389 | 26.352 | 8.164  | 1.00 | 26.05 | CPS2 |
| ATOM | 1535 | CA  | ILE | 77 | 76.280 | 26.859 | 8.970  | 1.00 | 25.04 | CPS2 |
| ATOM | 1536 | CB  | ILE | 77 | 75.306 | 27.678 | 8.079  | 1.00 | 23.67 | CPS2 |
| ATOM | 1537 | CG2 | ILE | 77 | 74.270 | 28.414 | 8.942  | 1.00 | 24.94 | CPS2 |
| ATOM | 1538 | CG1 | ILE | 77 | 76.085 | 28.674 | 7.218  | 1.00 | 23.77 | CPS2 |

FIG. 1A-27

| ATOM | 1539 | CD1 | ILE | 77 | 75.276 | 29.187 | 6.019 | 1.00 | 23.94 | CPS2 |
|------|------|-----|-----|-----|--------|--------|--------|------|-------|------|
| ATOM | 1540 | C | ILE | 77 | 75.487 | 25.717 | 9.586 | 1.00 | 25.85 | CPS2 |
| ATOM | 1541 | O | ILE | 77 | 75.077 | 24.796 | 8.887 | 1.00 | 26.62 | CPS2 |
| ATOM | 1542 | N | GLU | 78 | 75.260 | 25.773 | 10.892 | 1.00 | 24.57 | CPS2 |
| ATOM | 1543 | CA | GLU | 78 | 74.483 | 24.727 | 11.529 | 1.00 | 24.12 | CPS2 |
| ATOM | 1544 | CB | GLU | 78 | 75.366 | 23.875 | 12.450 | 1.00 | 24.96 | CPS2 |
| ATOM | 1545 | CG | GLU | 78 | 74.631 | 22.661 | 13.039 | 1.00 | 26.74 | CPS2 |
| ATOM | 1546 | CD | GLU | 78 | 75.579 | 21.638 | 13.643 | 1.00 | 30.06 | CPS2 |
| ATOM | 1547 | OE1 | GLU | 78 | 75.989 | 21.815 | 14.805 | 1.00 | 30.41 | CPS2 |
| ATOM | 1548 | OE2 | GLU | 78 | 75.930 | 20.656 | 12.942 | 1.00 | 30.57 | CPS2 |
| ATOM | 1549 | C | GLU | 78 | 73.314 | 25.285 | 12.326 | 1.00 | 25.19 | CPS2 |
| ATOM | 1550 | O | GLU | 78 | 73.467 | 26.243 | 13.096 | 1.00 | 24.62 | CPS2 |
| ATOM | 1551 | N | ILE | 79 | 72.139 | 24.697 | 12.124 | 1.00 | 23.01 | CPS2 |
| ATOM | 1552 | CA | ILE | 79 | 70.969 | 25.113 | 12.866 | 1.00 | 22.64 | CPS2 |
| ATOM | 1553 | CB | ILE | 79 | 69.673 | 25.081 | 12.014 | 1.00 | 23.46 | CPS2 |
| ATOM | 1554 | CG2 | ILE | 79 | 68.519 | 25.648 | 12.832 | 1.00 | 25.86 | CPS2 |
| ATOM | 1555 | CG1 | ILE | 79 | 69.868 | 25.835 | 10.688 | 1.00 | 25.21 | CPS2 |
| ATOM | 1556 | CD1 | ILE | 79 | 70.337 | 27.256 | 10.820 | 1.00 | 27.02 | CPS2 |
| ATOM | 1557 | C | ILE | 79 | 70.832 | 24.078 | 13.970 | 1.00 | 23.01 | CPS2 |
| ATOM | 1558 | O | ILE | 79 | 70.679 | 22.882 | 13.691 | 1.00 | 22.93 | CPS2 |
| ATOM | 1559 | N | ARG | 80 | 70.912 | 24.524 | 15.217 | 1.00 | 21.65 | CPS2 |
| ATOM | 1560 | CA | ARG | 80 | 70.765 | 23.624 | 16.348 | 1.00 | 23.25 | CPS2 |
| ATOM | 1561 | CB | ARG | 80 | 71.928 | 23.793 | 17.322 | 1.00 | 22.55 | CPS2 |
| ATOM | 1562 | CG | ARG | 80 | 73.275 | 23.474 | 16.692 | 1.00 | 22.62 | CPS2 |
| ATOM | 1563 | CD | ARG | 80 | 74.373 | 23.461 | 17.742 | 1.00 | 22.35 | CPS2 |
| ATOM | 1564 | NE | ARG | 80 | 75.680 | 23.201 | 17.147 | 1.00 | 21.40 | CPS2 |
| ATOM | 1565 | CZ | ARG | 80 | 76.820 | 23.280 | 17.823 | 1.00 | 22.68 | CPS2 |
| ATOM | 1566 | NH1 | ARG | 80 | 76.802 | 23.614 | 19.110 | 1.00 | 20.04 | CPS2 |
| ATOM | 1567 | NH2 | ARG | 80 | 77.971 | 23.020 | 17.216 | 1.00 | 22.34 | CPS2 |
| ATOM | 1568 | C | ARG | 80 | 69.456 | 23.947 | 17.044 | 1.00 | 24.16 | CPS2 |
| ATOM | 1569 | O | ARG | 80 | 68.837 | 24.965 | 16.757 | 1.00 | 23.92 | CPS2 |
| ATOM | 1570 | N | LYS | 81 | 69.028 | 23.074 | 17.947 | 1.00 | 26.40 | CPS2 |
| ATOM | 1571 | CA | LYS | 81 | 67.789 | 23.290 | 18.684 | 1.00 | 27.93 | CPS2 |
| ATOM | 1572 | CB | LYS | 81 | 66.840 | 22.108 | 18.466 | 1.00 | 30.60 | CPS2 |
| ATOM | 1573 | CG | LYS | 81 | 66.517 | 21.865 | 17.000 | 1.00 | 32.31 | CPS2 |
| ATOM | 1574 | CD | LYS | 81 | 65.759 | 20.561 | 16.767 | 1.00 | 36.54 | CPS2 |
| ATOM | 1575 | CE | LYS | 81 | 64.326 | 20.645 | 17.248 | 1.00 | 39.00 | CPS2 |
| ATOM | 1576 | NZ | LYS | 81 | 63.553 | 19.423 | 16.848 | 1.00 | 41.89 | CPS2 |
| ATOM | 1577 | C | LYS | 81 | 68.113 | 23.428 | 20.168 | 1.00 | 28.77 | CPS2 |
| ATOM | 1578 | O | LYS | 81 | 68.933 | 22.671 | 20.696 | 1.00 | 28.58 | CPS2 |
| ATOM | 1579 | N | ASP | 82 | 67.487 | 24.391 | 20.837 | 1.00 | 27.27 | CPS2 |
| ATOM | 1580 | CA | ASP | 82 | 67.741 | 24.576 | 22.258 | 1.00 | 29.97 | CPS2 |
| ATOM | 1581 | CB | ASP | 82 | 67.521 | 26.039 | 22.666 | 1.00 | 28.54 | CPS2 |
| ATOM | 1582 | CG | ASP | 82 | 66.074 | 26.488 | 22.541 | 1.00 | 30.11 | CPS2 |
| ATOM | 1583 | OD1 | ASP | 82 | 65.846 | 27.715 | 22.575 | 1.00 | 28.52 | CPS2 |
| ATOM | 1584 | OD2 | ASP | 82 | 65.170 | 25.633 | 22.424 | 1.00 | 30.87 | CPS2 |
| ATOM | 1585 | C | ASP | 82 | 66.887 | 23.619 | 23.095 | 1.00 | 30.91 | CPS2 |
| ATOM | 1586 | O | ASP | 82 | 66.268 | 22.707 | 22.546 | 1.00 | 30.68 | CPS2 |
| ATOM | 1587 | N | GLN | 83 | 66.867 | 23.819 | 24.411 | 1.00 | 33.59 | CPS2 |
| ATOM | 1588 | CA | GLN | 83 | 66.120 | 22.941 | 25.313 | 1.00 | 36.28 | CPS2 |
| ATOM | 1589 | CB | GLN | 83 | 66.334 | 23.356 | 26.772 | 1.00 | 37.73 | CPS2 |
| ATOM | 1590 | CG | GLN | 83 | 65.575 | 24.608 | 27.198 | 1.00 | 41.41 | CPS2 |
| ATOM | 1591 | CD | GLN | 83 | 66.435 | 25.862 | 27.228 | 1.00 | 43.65 | CPS2 |
| ATOM | 1592 | OE1 | GLN | 83 | 66.892 | 26.355 | 26.187 | 1.00 | 44.27 | CPS2 |
| ATOM | 1593 | NE2 | GLN | 83 | 66.659 | 26.389 | 28.432 | 1.00 | 43.27 | CPS2 |
| ATOM | 1594 | C | GLN | 83 | 64.626 | 22.892 | 25.022 | 1.00 | 37.29 | CPS2 |
| ATOM | 1595 | O | GLN | 83 | 63.943 | 21.933 | 25.398 | 1.00 | 38.48 | CPS2 |

FIG. 1A-28

| ATOM | 1596 | N | ASN | 84 | 64.120 | 23.927 | 24.362 | 1.00 | 36.62 | CPS2 |
|------|------|---|-----|----|--------|--------|--------|------|-------|------|
| ATOM | 1597 | CA | ASN | 84 | 62.707 | 23.996 | 24.024 | 1.00 | 36.63 | CPS2 |
| ATOM | 1598 | CB | ASN | 84 | 62.168 | 25.389 | 24.347 | 1.00 | 37.40 | CPS2 |
| ATOM | 1599 | CG | ASN | 84 | 62.263 | 25.716 | 25.828 | 1.00 | 38.82 | CPS2 |
| ATOM | 1600 | OD1 | ASN | 84 | 61.807 | 24.945 | 26.675 | 1.00 | 39.51 | CPS2 |
| ATOM | 1601 | ND2 | ASN | 84 | 62.856 | 26.857 | 26.148 | 1.00 | 38.34 | CPS2 |
| ATOM | 1602 | C | ASN | 84 | 62.456 | 23.661 | 22.556 | 1.00 | 36.23 | CPS2 |
| ATOM | 1603 | O | ASN | 84 | 61.345 | 23.839 | 22.052 | 1.00 | 36.16 | CPS2 |
| ATOM | 1604 | N | GLY | 85 | 63.492 | 23.173 | 21.879 | 1.00 | 34.68 | CPS2 |
| ATOM | 1605 | CA | GLY | 85 | 63.370 | 22.814 | 20.476 | 1.00 | 33.60 | CPS2 |
| ATOM | 1606 | C | GLY | 85 | 63.425 | 23.999 | 19.523 | 1.00 | 32.91 | CPS2 |
| ATOM | 1607 | O | GLY | 85 | 63.210 | 23.841 | 18.323 | 1.00 | 34.92 | CPS2 |
| ATOM | 1608 | N | LYS | 86 | 63.726 | 25.184 | 20.041 | 1.00 | 31.20 | CPS2 |
| ATOM | 1609 | CA | LYS | 86 | 63.781 | 26.379 | 19.203 | 1.00 | 29.67 | CPS2 |
| ATOM | 1610 | CB | LYS | 86 | 63.454 | 27.605 | 20.052 | 1.00 | 31.80 | CPS2 |
| ATOM | 1611 | CG | LYS | 86 | 62.137 | 27.394 | 20.790 | 1.00 | 34.73 | CPS2 |
| ATOM | 1612 | CD | LYS | 86 | 61.614 | 28.628 | 21.486 | 1.00 | 39.19 | CPS2 |
| ATOM | 1613 | CE | LYS | 86 | 60.239 | 28.331 | 22.094 | 1.00 | 41.01 | CPS2 |
| ATOM | 1614 | NZ | LYS | 86 | 59.558 | 29.559 | 22.592 | 1.00 | 43.57 | CPS2 |
| ATOM | 1615 | C | LYS | 86 | 65.144 | 26.492 | 18.541 | 1.00 | 28.23 | CPS2 |
| ATOM | 1616 | O | LYS | 86 | 66.169 | 26.212 | 19.159 | 1.00 | 27.95 | CPS2 |
| ATOM | 1617 | N | PRO | 87 | 65.173 | 26.922 | 17.272 | 1.00 | 27.01 | CPS2 |
| ATOM | 1618 | CD | PRO | 87 | 64.035 | 27.381 | 16.447 | 1.00 | 26.75 | CPS2 |
| ATOM | 1619 | CA | PRO | 87 | 66.427 | 27.050 | 16.534 | 1.00 | 25.49 | CPS2 |
| ATOM | 1620 | CB | PRO | 87 | 65.951 | 27.164 | 15.085 | 1.00 | 25.44 | CPS2 |
| ATOM | 1621 | CG | PRO | 87 | 64.735 | 28.043 | 15.239 | 1.00 | 27.74 | CPS2 |
| ATOM | 1622 | C | PRO | 87 | 67.379 | 28.185 | 16.881 | 1.00 | 24.72 | CPS2 |
| ATOM | 1623 | O | PRO | 87 | 66.979 | 29.270 | 17.306 | 1.00 | 23.36 | CPS2 |
| ATOM | 1624 | N | TYR | 88 | 68.664 | 27.904 | 16.716 | 1.00 | 22.58 | CPS2 |
| ATOM | 1625 | CA | TYR | 88 | 69.685 | 28.924 | 16.879 | 1.00 | 22.24 | CPS2 |
| ATOM | 1626 | CB | TYR | 88 | 70.208 | 29.052 | 18.324 | 1.00 | 22.46 | CPS2 |
| ATOM | 1627 | CG | TYR | 88 | 70.921 | 27.860 | 18.913 | 1.00 | 21.40 | CPS2 |
| ATOM | 1628 | CD1 | TYR | 88 | 70.213 | 26.859 | 19.577 | 1.00 | 21.74 | CPS2 |
| ATOM | 1629 | CE1 | TYR | 88 | 70.881 | 25.796 | 20.194 | 1.00 | 21.69 | CPS2 |
| ATOM | 1630 | CD2 | TYR | 88 | 72.317 | 27.769 | 18.871 | 1.00 | 21.96 | CPS2 |
| ATOM | 1631 | CE2 | TYR | 88 | 72.989 | 26.708 | 19.480 | 1.00 | 20.78 | CPS2 |
| ATOM | 1632 | CZ | TYR | 88 | 72.262 | 25.731 | 20.141 | 1.00 | 21.27 | CPS2 |
| ATOM | 1633 | OH | TYR | 88 | 72.923 | 24.699 | 20.772 | 1.00 | 20.50 | CPS2 |
| ATOM | 1634 | C | TYR | 88 | 70.781 | 28.522 | 15.912 | 1.00 | 22.02 | CPS2 |
| ATOM | 1635 | O | TYR | 88 | 70.897 | 27.352 | 15.550 | 1.00 | 23.05 | CPS2 |
| ATOM | 1636 | N | ILE | 89 | 71.577 | 29.485 | 15.480 | 1.00 | 21.04 | CPS2 |
| ATOM | 1637 | CA | ILE | 89 | 72.623 | 29.198 | 14.524 | 1.00 | 21.06 | CPS2 |
| ATOM | 1638 | CB | ILE | 89 | 72.573 | 30.209 | 13.369 | 1.00 | 21.84 | CPS2 |
| ATOM | 1639 | CG2 | ILE | 89 | 73.842 | 30.099 | 12.513 | 1.00 | 22.28 | CPS2 |
| ATOM | 1640 | CG1 | ILE | 89 | 71.324 | 29.982 | 12.522 | 1.00 | 22.51 | CPS2 |
| ATOM | 1641 | CD1 | ILE | 89 | 71.172 | 31.035 | 11.407 | 1.00 | 23.39 | CPS2 |
| ATOM | 1642 | C | ILE | 89 | 74.043 | 29.228 | 15.072 | 1.00 | 22.40 | CPS2 |
| ATOM | 1643 | O | ILE | 89 | 74.401 | 30.123 | 15.847 | 1.00 | 21.51 | CPS2 |
| ATOM | 1644 | N | ILE | 90 | 74.839 | 28.248 | 14.644 | 1.00 | 21.66 | CPS2 |
| ATOM | 1645 | CA | ILE | 90 | 76.255 | 28.184 | 14.988 | 1.00 | 21.61 | CPS2 |
| ATOM | 1646 | CB | ILE | 90 | 76.641 | 26.878 | 15.727 | 1.00 | 21.37 | CPS2 |
| ATOM | 1647 | CG2 | ILE | 90 | 78.169 | 26.743 | 15.791 | 1.00 | 22.23 | CPS2 |
| ATOM | 1648 | CG1 | ILE | 90 | 76.032 | 26.875 | 17.134 | 1.00 | 20.39 | CPS2 |
| ATOM | 1649 | CD1 | ILE | 90 | 76.542 | 27.991 | 18.041 | 1.00 | 20.47 | CPS2 |
| ATOM | 1650 | C | ILE | 90 | 77.019 | 28.232 | 13.664 | 1.00 | 22.97 | CPS2 |
| ATOM | 1651 | O | ILE | 90 | 76.763 | 27.437 | 12.742 | 1.00 | 22.67 | CPS2 |
| ATOM | 1652 | N | CYS | 91 | 77.922 | 29.195 | 13.559 | 1.00 | 23.95 | CPS2 |

FIG. 1A-29

| ATOM | 1653 | CA | CYS | 91 | 78.769 | 29.344 | 12.384 | 1.00 | 26.82 | CPS2 |
|------|------|-----|-----|----|--------|--------|--------|------|-------|------|
| ATOM | 1654 | CB | CYS | 91 | 78.229 | 30.414 | 11.432 | 1.00 | 26.17 | CPS2 |
| ATOM | 1655 | SG | CYS | 91 | 79.260 | 30.612 | 9.945 | 1.00 | 27.83 | CPS2 |
| ATOM | 1656 | C | CYS | 91 | 80.139 | 29.760 | 12.912 | 1.00 | 29.07 | CPS2 |
| ATOM | 1657 | O | CYS | 91 | 80.392 | 30.933 | 13.149 | 1.00 | 29.81 | CPS2 |
| ATOM | 1658 | N | THR | 92 | 81.011 | 28.784 | 13.114 | 1.00 | 33.43 | CPS2 |
| ATOM | 1659 | CA | THR | 92 | 82.347 | 29.049 | 13.637 | 1.00 | 37.11 | CPS2 |
| ATOM | 1660 | CB | THR | 92 | 83.080 | 27.726 | 13.883 | 1.00 | 38.23 | CPS2 |
| ATOM | 1661 | OG1 | THR | 92 | 82.422 | 27.027 | 14.947 | 1.00 | 38.10 | CPS2 |
| ATOM | 1662 | CG2 | THR | 92 | 84.536 | 27.971 | 14.260 | 1.00 | 40.35 | CPS2 |
| ATOM | 1663 | C | THR | 92 | 83.172 | 29.947 | 12.719 | 1.00 | 39.54 | CPS2 |
| ATOM | 1664 | O | THR | 92 | 84.071 | 30.663 | 13.177 | 1.00 | 40.49 | CPS2 |
| ATOM | 1665 | N | LYS | 93 | 82.846 | 29.916 | 11.432 | 1.00 | 40.59 | CPS2 |
| ATOM | 1666 | CA | LYS | 93 | 83.536 | 30.712 | 10.428 | 1.00 | 44.01 | CPS2 |
| ATOM | 1667 | CB | LYS | 93 | 83.024 | 30.334 | 9.040 | 1.00 | 45.12 | CPS2 |
| ATOM | 1668 | CG | LYS | 93 | 83.944 | 30.689 | 7.889 | 1.00 | 47.31 | CPS2 |
| ATOM | 1669 | CD | LYS | 93 | 83.519 | 29.921 | 6.650 | 1.00 | 47.58 | CPS2 |
| ATOM | 1670 | CE | LYS | 93 | 84.638 | 29.817 | 5.630 | 1.00 | 48.24 | CPS2 |
| ATOM | 1671 | NZ | LYS | 93 | 84.290 | 28.834 | 4.556 | 1.00 | 48.73 | CPS2 |
| ATOM | 1672 | C | LYS | 93 | 83.269 | 32.183 | 10.690 | 1.00 | 44.95 | CPS2 |
| ATOM | 1673 | O | LYS | 93 | 83.901 | 33.063 | 10.112 | 1.00 | 46.05 | CPS2 |
| ATOM | 1674 | N | LEU | 94 | 82.322 | 32.443 | 11.575 | 1.00 | 45.51 | CPS2 |
| ATOM | 1675 | CA | LEU | 94 | 81.964 | 33.803 | 11.910 | 1.00 | 46.37 | CPS2 |
| ATOM | 1676 | CB | LEU | 94 | 80.452 | 33.898 | 12.120 | 1.00 | 46.46 | CPS2 |
| ATOM | 1677 | CG | LEU | 94 | 79.830 | 35.271 | 12.344 | 1.00 | 46.35 | CPS2 |
| ATOM | 1678 | CD1 | LEU | 94 | 80.037 | 36.148 | 11.121 | 1.00 | 47.12 | CPS2 |
| ATOM | 1679 | CD2 | LEU | 94 | 78.352 | 35.094 | 12.615 | 1.00 | 46.47 | CPS2 |
| ATOM | 1680 | C | LEU | 94 | 82.685 | 34.233 | 13.172 | 1.00 | 47.39 | CPS2 |
| ATOM | 1681 | O | LEU | 94 | 82.690 | 33.511 | 14.173 | 1.00 | 47.30 | CPS2 |
| ATOM | 1682 | N | SER | 95 | 83.319 | 35.401 | 13.116 | 1.00 | 48.63 | CPS2 |
| ATOM | 1683 | CA | SER | 95 | 84.015 | 35.941 | 14.278 | 1.00 | 48.81 | CPS2 |
| ATOM | 1684 | CB | SER | 95 | 84.347 | 37.420 | 14.037 | 1.00 | 49.86 | CPS2 |
| ATOM | 1685 | OG | SER | 95 | 83.229 | 38.121 | 13.511 | 1.00 | 51.01 | CPS2 |
| ATOM | 1686 | C | SER | 95 | 83.038 | 35.771 | 15.448 | 1.00 | 48.31 | CPS2 |
| ATOM | 1687 | O | SER | 95 | 81.843 | 35.585 | 15.221 | 1.00 | 48.26 | CPS2 |
| ATOM | 1688 | N | PRO | 96 | 83.524 | 35.840 | 16.704 | 1.00 | 46.89 | CPS2 |
| ATOM | 1689 | CD | PRO | 96 | 84.845 | 36.379 | 17.068 | 1.00 | 46.79 | CPS2 |
| ATOM | 1690 | CA | PRO | 96 | 82.693 | 35.682 | 17.909 | 1.00 | 45.46 | CPS2 |
| ATOM | 1691 | CB | PRO | 96 | 83.678 | 35.966 | 19.040 | 1.00 | 45.87 | CPS2 |
| ATOM | 1692 | CG | PRO | 96 | 84.573 | 36.988 | 18.434 | 1.00 | 45.85 | CPS2 |
| ATOM | 1693 | C | PRO | 96 | 81.431 | 36.544 | 18.033 | 1.00 | 44.28 | CPS2 |
| ATOM | 1694 | O | PRO | 96 | 81.041 | 36.911 | 19.141 | 1.00 | 45.08 | CPS2 |
| ATOM | 1695 | N | ALA | 97 | 80.782 | 36.839 | 16.913 | 1.00 | 41.71 | CPS2 |
| ATOM | 1696 | CA | ALA | 97 | 79.577 | 37.671 | 16.900 | 1.00 | 38.60 | CPS2 |
| ATOM | 1697 | CB | ALA | 97 | 79.384 | 38.246 | 15.507 | 1.00 | 39.14 | CPS2 |
| ATOM | 1698 | C | ALA | 97 | 78.288 | 36.977 | 17.347 | 1.00 | 36.55 | CPS2 |
| ATOM | 1699 | O | ALA | 97 | 78.208 | 35.752 | 17.405 | 1.00 | 36.57 | CPS2 |
| ATOM | 1700 | N | ALA | 98 | 77.274 | 37.784 | 17.651 | 1.00 | 33.65 | CPS2 |
| ATOM | 1701 | CA | ALA | 98 | 75.973 | 37.270 | 18.065 | 1.00 | 30.93 | CPS2 |
| ATOM | 1702 | CB | ALA | 98 | 75.295 | 38.239 | 19.026 | 1.00 | 29.97 | CPS2 |
| ATOM | 1703 | C | ALA | 98 | 75.125 | 37.106 | 16.804 | 1.00 | 28.95 | CPS2 |
| ATOM | 1704 | O | ALA | 98 | 75.077 | 37.990 | 15.949 | 1.00 | 28.62 | CPS2 |
| ATOM | 1705 | N | VAL | 99 | 74.454 | 35.969 | 16.709 | 1.00 | 26.50 | CPS2 |
| ATOM | 1706 | CA | VAL | 99 | 73.616 | 35.659 | 15.566 | 1.00 | 23.47 | CPS2 |
| ATOM | 1707 | CB | VAL | 99 | 74.179 | 34.437 | 14.806 | 1.00 | 23.08 | CPS2 |
| ATOM | 1708 | CG1 | VAL | 99 | 73.323 | 34.125 | 13.590 | 1.00 | 23.46 | CPS2 |
| ATOM | 1709 | CG2 | VAL | 99 | 75.617 | 34.718 | 14.381 | 1.00 | 24.82 | CPS2 |

FIG. 1A-30

| ATOM | 1710 | C   | VAL | 99  | 72.209 | 35.335 | 16.054 | 1.00 | 22.87 | CPS2 |
|------|------|-----|-----|-----|--------|--------|--------|------|-------|------|
| ATOM | 1711 | O   | VAL | 99  | 72.034 | 34.549 | 16.980 | 1.00 | 23.69 | CPS2 |
| ATOM | 1712 | N   | HIS | 100 | 71.208 | 35.941 | 15.430 | 1.00 | 21.88 | CPS2 |
| ATOM | 1713 | CA  | HIS | 100 | 69.819 | 35.685 | 15.800 | 1.00 | 20.93 | CPS2 |
| ATOM | 1714 | CB  | HIS | 100 | 69.152 | 36.987 | 16.248 | 1.00 | 22.65 | CPS2 |
| ATOM | 1715 | CG  | HIS | 100 | 69.930 | 37.726 | 17.296 | 1.00 | 24.71 | CPS2 |
| ATOM | 1716 | CD2 | HIS | 100 | 70.837 | 38.727 | 17.191 | 1.00 | 26.85 | CPS2 |
| ATOM | 1717 | ND1 | HIS | 100 | 69.841 | 37.430 | 18.639 | 1.00 | 26.27 | CPS2 |
| ATOM | 1718 | CE1 | HIS | 100 | 70.658 | 38.217 | 19.318 | 1.00 | 28.01 | CPS2 |
| ATOM | 1719 | NE2 | HIS | 100 | 71.276 | 39.012 | 18.462 | 1.00 | 25.52 | CPS2 |
| ATOM | 1720 | C   | HIS | 100 | 69.124 | 35.150 | 14.553 | 1.00 | 19.66 | CPS2 |
| ATOM | 1721 | O   | HIS | 100 | 69.414 | 35.596 | 13.445 | 1.00 | 19.28 | CPS2 |
| ATOM | 1722 | N   | VAL | 101 | 68.208 | 34.203 | 14.729 | 1.00 | 20.06 | CPS2 |
| ATOM | 1723 | CA  | VAL | 101 | 67.500 | 33.628 | 13.586 | 1.00 | 18.60 | CPS2 |
| ATOM | 1724 | CB  | VAL | 101 | 68.111 | 32.251 | 13.166 | 1.00 | 18.24 | CPS2 |
| ATOM | 1725 | CG1 | VAL | 101 | 67.973 | 31.236 | 14.313 | 1.00 | 19.48 | CPS2 |
| ATOM | 1726 | CG2 | VAL | 101 | 67.436 | 31.719 | 11.884 | 1.00 | 16.59 | CPS2 |
| ATOM | 1727 | C   | VAL | 101 | 66.053 | 33.403 | 13.982 | 1.00 | 19.22 | CPS2 |
| ATOM | 1728 | O   | VAL | 101 | 65.753 | 33.247 | 15.160 | 1.00 | 20.38 | CPS2 |
| ATOM | 1729 | N   | SER | 102 | 65.155 | 33.451 | 13.001 | 1.00 | 18.44 | CPS2 |
| ATOM | 1730 | CA  | SER | 102 | 63.748 | 33.140 | 13.241 | 1.00 | 18.74 | CPS2 |
| ATOM | 1731 | CB  | SER | 102 | 62.900 | 34.393 | 13.455 | 1.00 | 18.54 | CPS2 |
| ATOM | 1732 | OG  | SER | 102 | 61.588 | 33.984 | 13.804 | 1.00 | 18.22 | CPS2 |
| ATOM | 1733 | C   | SER | 102 | 63.270 | 32.398 | 12.006 | 1.00 | 18.15 | CPS2 |
| ATOM | 1734 | O   | SER | 102 | 63.568 | 32.801 | 10.883 | 1.00 | 18.21 | CPS2 |
| ATOM | 1735 | N   | ILE | 103 | 62.552 | 31.300 | 12.207 | 1.00 | 18.86 | CPS2 |
| ATOM | 1736 | CA  | ILE | 103 | 62.054 | 30.511 | 11.079 | 1.00 | 18.76 | CPS2 |
| ATOM | 1737 | CB  | ILE | 103 | 62.653 | 29.079 | 11.109 | 1.00 | 19.67 | CPS2 |
| ATOM | 1738 | CG2 | ILE | 103 | 62.224 | 28.298 | 9.869  | 1.00 | 21.39 | CPS2 |
| ATOM | 1739 | CG1 | ILE | 103 | 64.184 | 29.155 | 11.156 | 1.00 | 19.93 | CPS2 |
| ATOM | 1740 | CD1 | ILE | 103 | 64.862 | 27.789 | 11.269 | 1.00 | 21.07 | CPS2 |
| ATOM | 1741 | C   | ILE | 103 | 60.537 | 30.418 | 11.198 | 1.00 | 19.92 | CPS2 |
| ATOM | 1742 | O   | ILE | 103 | 60.004 | 30.291 | 12.307 | 1.00 | 21.12 | CPS2 |
| ATOM | 1743 | N   | THR | 104 | 59.840 | 30.486 | 10.066 | 1.00 | 19.86 | CPS2 |
| ATOM | 1744 | CA  | THR | 104 | 58.388 | 30.396 | 10.077 | 1.00 | 19.62 | CPS2 |
| ATOM | 1745 | CB  | THR | 104 | 57.743 | 31.799 | 9.944  | 1.00 | 21.91 | CPS2 |
| ATOM | 1746 | OG1 | THR | 104 | 56.323 | 31.708 | 10.159 | 1.00 | 22.12 | CPS2 |
| ATOM | 1747 | CG2 | THR | 104 | 58.018 | 32.390 | 8.573  | 1.00 | 20.48 | CPS2 |
| ATOM | 1748 | C   | THR | 104 | 57.945 | 29.487 | 8.934  | 1.00 | 20.91 | CPS2 |
| ATOM | 1749 | O   | THR | 104 | 58.722 | 29.210 | 8.016  | 1.00 | 18.89 | CPS2 |
| ATOM | 1750 | N   | HIS | 105 | 56.705 | 29.015 | 8.999  | 1.00 | 20.52 | CPS2 |
| ATOM | 1751 | CA  | HIS | 105 | 56.179 | 28.108 | 7.973  | 1.00 | 24.14 | CPS2 |
| ATOM | 1752 | CB  | HIS | 105 | 56.224 | 26.647 | 8.474  | 1.00 | 27.48 | CPS2 |
| ATOM | 1753 | CG  | HIS | 105 | 57.594 | 26.134 | 8.811  | 1.00 | 32.26 | CPS2 |
| ATOM | 1754 | CD2 | HIS | 105 | 58.267 | 26.095 | 9.987  | 1.00 | 33.69 | CPS2 |
| ATOM | 1755 | ND1 | HIS | 105 | 58.428 | 25.559 | 7.874  | 1.00 | 34.33 | CPS2 |
| ATOM | 1756 | CE1 | HIS | 105 | 59.555 | 25.191 | 8.457  | 1.00 | 33.58 | CPS2 |
| ATOM | 1757 | NE2 | HIS | 105 | 59.484 | 25.504 | 9.738  | 1.00 | 34.93 | CPS2 |
| ATOM | 1758 | C   | HIS | 105 | 54.702 | 28.393 | 7.653  | 1.00 | 23.87 | CPS2 |
| ATOM | 1759 | O   | HIS | 105 | 53.974 | 28.944 | 8.476  | 1.00 | 23.81 | CPS2 |
| ATOM | 1760 | N   | THR | 106 | 54.284 | 28.013 | 6.449  | 1.00 | 23.91 | CPS2 |
| ATOM | 1761 | CA  | THR | 106 | 52.875 | 28.065 | 6.054  | 1.00 | 24.84 | CPS2 |
| ATOM | 1762 | CB  | THR | 106 | 52.484 | 29.199 | 5.058  | 1.00 | 24.13 | CPS2 |
| ATOM | 1763 | OG1 | THR | 106 | 53.116 | 28.984 | 3.792  | 1.00 | 25.72 | CPS2 |
| ATOM | 1764 | CG2 | THR | 106 | 52.841 | 30.571 | 5.616  | 1.00 | 24.87 | CPS2 |
| ATOM | 1765 | C   | THR | 106 | 52.737 | 26.722 | 5.339  | 1.00 | 26.22 | CPS2 |
| ATOM | 1766 | O   | THR | 106 | 53.716 | 25.971 | 5.224  | 1.00 | 25.93 | CPS2 |

FIG. 1A-31

| ATOM | 1767 | N   | LYS | 107 | 51.544 | 26.408 | 4.857  | 1.00 | 27.42 | CPS2 |
|------|------|-----|-----|-----|--------|--------|--------|------|-------|------|
| ATOM | 1768 | CA  | LYS | 107 | 51.355 | 25.135 | 4.177  | 1.00 | 29.72 | CPS2 |
| ATOM | 1769 | CB  | LYS | 107 | 49.913 | 25.013 | 3.676  | 1.00 | 32.60 | CPS2 |
| ATOM | 1770 | CG  | LYS | 107 | 49.554 | 23.612 | 3.186  | 1.00 | 36.45 | CPS2 |
| ATOM | 1771 | CD  | LYS | 107 | 48.151 | 23.568 | 2.586  | 1.00 | 39.60 | CPS2 |
| ATOM | 1772 | CE  | LYS | 107 | 48.079 | 24.346 | 1.277  | 1.00 | 42.78 | CPS2 |
| ATOM | 1773 | NZ  | LYS | 107 | 46.750 | 24.224 | 0.594  | 1.00 | 44.82 | CPS2 |
| ATOM | 1774 | C   | LYS | 107 | 52.319 | 24.941 | 3.003  | 1.00 | 28.95 | CPS2 |
| ATOM | 1775 | O   | LYS | 107 | 52.889 | 23.863 | 2.833  | 1.00 | 29.55 | CPS2 |
| ATOM | 1776 | N   | GLU | 108 | 52.524 | 25.993 | 2.216  | 1.00 | 27.06 | CPS2 |
| ATOM | 1777 | CA  | GLU | 108 | 53.374 | 25.916 | 1.033  | 1.00 | 27.06 | CPS2 |
| ATOM | 1778 | CB  | GLU | 108 | 52.639 | 26.548 | -0.155 | 1.00 | 29.33 | CPS2 |
| ATOM | 1779 | CG  | GLU | 108 | 51.301 | 25.907 | -0.494 | 1.00 | 36.04 | CPS2 |
| ATOM | 1780 | CD  | GLU | 108 | 51.394 | 24.407 | -0.723 | 1.00 | 39.96 | CPS2 |
| ATOM | 1781 | OE1 | GLU | 108 | 52.416 | 23.935 | -1.270 | 1.00 | 43.61 | CPS2 |
| ATOM | 1782 | OE2 | GLU | 108 | 50.430 | 23.694 | -0.370 | 1.00 | 43.92 | CPS2 |
| ATOM | 1783 | C   | GLU | 108 | 54.771 | 26.532 | 1.092  | 1.00 | 25.54 | CPS2 |
| ATOM | 1784 | O   | GLU | 108 | 55.581 | 26.311 | 0.180  | 1.00 | 25.56 | CPS2 |
| ATOM | 1785 | N   | TYR | 109 | 55.055 | 27.305 | 2.138  | 1.00 | 24.09 | CPS2 |
| ATOM | 1786 | CA  | TYR | 109 | 56.350 | 27.982 | 2.250  | 1.00 | 21.97 | CPS2 |
| ATOM | 1787 | CB  | TYR | 109 | 56.175 | 29.480 | 2.012  | 1.00 | 23.30 | CPS2 |
| ATOM | 1788 | CG  | TYR | 109 | 55.611 | 29.823 | 0.664  | 1.00 | 24.68 | CPS2 |
| ATOM | 1789 | CD1 | TYR | 109 | 56.427 | 29.842 | -0.467 | 1.00 | 24.47 | CPS2 |
| ATOM | 1790 | CE1 | TYR | 109 | 55.895 | 30.083 | -1.731 | 1.00 | 25.63 | CPS2 |
| ATOM | 1791 | CD2 | TYR | 109 | 54.248 | 30.062 | 0.505  | 1.00 | 25.42 | CPS2 |
| ATOM | 1792 | CE2 | TYR | 109 | 53.704 | 30.303 | -0.761 | 1.00 | 26.80 | CPS2 |
| ATOM | 1793 | CZ  | TYR | 109 | 54.530 | 30.307 | -1.866 | 1.00 | 25.17 | CPS2 |
| ATOM | 1794 | OH  | TYR | 109 | 53.996 | 30.501 | -3.118 | 1.00 | 28.15 | CPS2 |
| ATOM | 1795 | C   | TYR | 109 | 57.069 | 27.849 | 3.578  | 1.00 | 21.24 | CPS2 |
| ATOM | 1796 | O   | TYR | 109 | 56.465 | 27.578 | 4.616  | 1.00 | 20.80 | CPS2 |
| ATOM | 1797 | N   | ALA | 110 | 58.379 | 28.067 | 3.518  | 1.00 | 21.00 | CPS2 |
| ATOM | 1798 | CA  | ALA | 110 | 59.230 | 28.102 | 4.705  | 1.00 | 21.72 | CPS2 |
| ATOM | 1799 | CB  | ALA | 110 | 60.238 | 26.966 | 4.686  | 1.00 | 22.11 | CPS2 |
| ATOM | 1800 | C   | ALA | 110 | 59.945 | 29.450 | 4.560  | 1.00 | 21.05 | CPS2 |
| ATOM | 1801 | O   | ALA | 110 | 60.301 | 29.852 | 3.451  | 1.00 | 20.79 | CPS2 |
| ATOM | 1802 | N   | ALA | 111 | 60.141 | 30.165 | 5.657  | 1.00 | 20.04 | CPS2 |
| ATOM | 1803 | CA  | ALA | 111 | 60.822 | 31.446 | 5.557  | 1.00 | 18.91 | CPS2 |
| ATOM | 1804 | CB  | ALA | 111 | 59.802 | 32.577 | 5.431  | 1.00 | 18.42 | CPS2 |
| ATOM | 1805 | C   | ALA | 111 | 61.683 | 31.648 | 6.785  | 1.00 | 17.86 | CPS2 |
| ATOM | 1806 | O   | ALA | 111 | 61.400 | 31.111 | 7.847  | 1.00 | 17.82 | CPS2 |
| ATOM | 1807 | N   | ALA | 112 | 62.754 | 32.411 | 6.638  | 1.00 | 18.38 | CPS2 |
| ATOM | 1808 | CA  | ALA | 112 | 63.627 | 32.642 | 7.777  | 1.00 | 17.98 | CPS2 |
| ATOM | 1809 | CB  | ALA | 112 | 64.718 | 31.564 | 7.820  | 1.00 | 19.37 | CPS2 |
| ATOM | 1810 | C   | ALA | 112 | 64.278 | 33.992 | 7.650  | 1.00 | 18.20 | CPS2 |
| ATOM | 1811 | O   | ALA | 112 | 64.414 | 34.527 | 6.543  | 1.00 | 17.80 | CPS2 |
| ATOM | 1812 | N   | GLN | 113 | 64.686 | 34.540 | 8.787  | 1.00 | 16.99 | CPS2 |
| ATOM | 1813 | CA  | GLN | 113 | 65.406 | 35.802 | 8.775  | 1.00 | 19.02 | CPS2 |
| ATOM | 1814 | CB  | GLN | 113 | 64.511 | 36.964 | 9.178  | 1.00 | 21.92 | CPS2 |
| ATOM | 1815 | CG  | GLN | 113 | 64.045 | 36.908 | 10.593 | 1.00 | 24.71 | CPS2 |
| ATOM | 1816 | CD  | GLN | 113 | 63.223 | 38.120 | 10.979 | 1.00 | 27.15 | CPS2 |
| ATOM | 1817 | OE1 | GLN | 113 | 62.785 | 38.239 | 12.117 | 1.00 | 29.66 | CPS2 |
| ATOM | 1818 | NE2 | GLN | 113 | 63.001 | 39.019 | 10.028 | 1.00 | 31.94 | CPS2 |
| ATOM | 1819 | C   | GLN | 113 | 66.554 | 35.662 | 9.764  | 1.00 | 18.49 | CPS2 |
| ATOM | 1820 | O   | GLN | 113 | 66.463 | 34.908 | 10.738 | 1.00 | 18.27 | CPS2 |
| ATOM | 1821 | N   | VAL | 114 | 67.626 | 36.395 | 9.506  | 1.00 | 18.07 | CPS2 |
| ATOM | 1822 | CA  | VAL | 114 | 68.811 | 36.355 | 10.358 | 1.00 | 18.90 | CPS2 |
| ATOM | 1823 | CB  | VAL | 114 | 69.939 | 35.488 | 9.698  | 1.00 | 19.24 | CPS2 |

FIG. 1A-32

| ATOM | 1824 | CG1 | VAL | 114 | 71.288 | 35.715 | 10.406 | 1.00 | 20.55 | CPS2 |
|------|------|-----|-----|-----|--------|--------|--------|------|-------|------|
| ATOM | 1825 | CG2 | VAL | 114 | 69.575 | 34.007 | 9.753 | 1.00 | 20.65 | CPS2 |
| ATOM | 1826 | C | VAL | 114 | 69.369 | 37.757 | 10.551 | 1.00 | 18.95 | CPS2 |
| ATOM | 1827 | O | VAL | 114 | 69.283 | 38.595 | 9.653 | 1.00 | 18.70 | CPS2 |
| ATOM | 1828 | N | VAL | 115 | 69.918 | 38.015 | 11.733 | 1.00 | 18.92 | CPS2 |
| ATOM | 1829 | CA | VAL | 115 | 70.580 | 39.291 | 11.989 | 1.00 | 19.34 | CPS2 |
| ATOM | 1830 | CB | VAL | 115 | 69.805 | 40.208 | 12.970 | 1.00 | 19.17 | CPS2 |
| ATOM | 1831 | CG1 | VAL | 115 | 70.668 | 41.445 | 13.298 | 1.00 | 20.91 | CPS2 |
| ATOM | 1832 | CG2 | VAL | 115 | 68.499 | 40.688 | 12.334 | 1.00 | 18.48 | CPS2 |
| ATOM | 1833 | C | VAL | 115 | 71.915 | 38.927 | 12.633 | 1.00 | 21.35 | CPS2 |
| ATOM | 1834 | O | VAL | 115 | 71.949 | 38.164 | 13.590 | 1.00 | 21.11 | CPS2 |
| ATOM | 1835 | N | ILE | 116 | 73.009 | 39.428 | 12.074 | 1.00 | 22.97 | CPS2 |
| ATOM | 1836 | CA | ILE | 116 | 74.333 | 39.174 | 12.641 | 1.00 | 25.35 | CPS2 |
| ATOM | 1837 | CB | ILE | 116 | 75.359 | 38.779 | 11.554 | 1.00 | 24.57 | CPS2 |
| ATOM | 1838 | CG2 | ILE | 116 | 76.752 | 38.641 | 12.177 | 1.00 | 25.34 | CPS2 |
| ATOM | 1839 | CG1 | ILE | 116 | 74.945 | 37.468 | 10.880 | 1.00 | 23.64 | CPS2 |
| ATOM | 1840 | CD1 | ILE | 116 | 75.862 | 37.065 | 9.734 | 1.00 | 24.45 | CPS2 |
| ATOM | 1841 | C | ILE | 116 | 74.763 | 40.511 | 13.243 | 1.00 | 27.82 | CPS2 |
| ATOM | 1842 | O | ILE | 116 | 74.692 | 41.531 | 12.569 | 1.00 | 26.14 | CPS2 |
| ATOM | 1843 | N | GLU | 117 | 75.176 | 40.508 | 14.508 | 1.00 | 31.83 | CPS2 |
| ATOM | 1844 | CA | GLU | 117 | 75.620 | 41.741 | 15.162 | 1.00 | 38.95 | CPS2 |
| ATOM | 1845 | CB | GLU | 117 | 75.075 | 41.848 | 16.583 | 1.00 | 40.48 | CPS2 |
| ATOM | 1846 | CG | GLU | 117 | 73.585 | 41.670 | 16.763 | 1.00 | 42.57 | CPS2 |
| ATOM | 1847 | CD | GLU | 117 | 73.180 | 41.900 | 18.211 | 1.00 | 43.48 | CPS2 |
| ATOM | 1848 | OE1 | GLU | 117 | 73.040 | 43.075 | 18.613 | 1.00 | 45.02 | CPS2 |
| ATOM | 1849 | OE2 | GLU | 117 | 73.029 | 40.909 | 18.956 | 1.00 | 43.86 | CPS2 |
| ATOM | 1850 | C | GLU | 117 | 77.140 | 41.701 | 15.260 | 1.00 | 42.69 | CPS2 |
| ATOM | 1851 | O | GLU | 117 | 77.707 | 40.665 | 15.598 | 1.00 | 44.02 | CPS2 |
| ATOM | 1852 | N | ARG | 118 | 77.803 | 42.820 | 14.989 | 1.00 | 46.91 | CPS2 |
| ATOM | 1853 | CA | ARG | 118 | 79.259 | 42.843 | 15.069 | 1.00 | 50.26 | CPS2 |
| ATOM | 1854 | CB | ARG | 118 | 79.824 | 43.901 | 14.124 | 1.00 | 52.17 | CPS2 |
| ATOM | 1855 | CG | ARG | 118 | 79.547 | 45.337 | 14.529 | 1.00 | 54.69 | CPS2 |
| ATOM | 1856 | CD | ARG | 118 | 79.478 | 46.208 | 13.288 | 1.00 | 57.22 | CPS2 |
| ATOM | 1857 | NE | ARG | 118 | 80.501 | 45.827 | 12.319 | 1.00 | 59.20 | CPS2 |
| ATOM | 1858 | CZ | ARG | 118 | 80.479 | 46.170 | 11.034 | 1.00 | 60.31 | CPS2 |
| ATOM | 1859 | NH1 | ARG | 118 | 79.483 | 46.906 | 10.556 | 1.00 | 60.38 | CPS2 |
| ATOM | 1860 | NH2 | ARG | 118 | 81.451 | 45.769 | 10.224 | 1.00 | 60.45 | CPS2 |
| ATOM | 1861 | C | ARG | 118 | 79.722 | 43.108 | 16.499 | 1.00 | 51.12 | CPS2 |
| ATOM | 1862 | OT1 | ARG | 118 | 78.849 | 43.285 | 17.380 | 1.00 | 51.54 | CPS2 |
| ATOM | 1863 | OT2 | ARG | 118 | 80.952 | 43.125 | 16.721 | 1.00 | 52.39 | CPS2 |
| ATOM | 1864 | C | GLY | 1 | 70.826 | 44.611 | 21.183 | 1.00 | 31.20 | CPS3 |
| ATOM | 1865 | O | GLY | 1 | 69.832 | 44.954 | 21.818 | 1.00 | 30.54 | CPS3 |
| ATOM | 1866 | N | GLY | 1 | 72.197 | 46.046 | 22.695 | 1.00 | 34.55 | CPS3 |
| ATOM | 1867 | CA | GLY | 1 | 72.168 | 45.285 | 21.411 | 1.00 | 32.26 | CPS3 |
| ATOM | 1868 | N | ILE | 2 | 70.797 | 43.643 | 20.274 | 1.00 | 29.14 | CPS3 |
| ATOM | 1869 | CA | ILE | 2 | 69.562 | 42.935 | 19.973 | 1.00 | 27.23 | CPS3 |
| ATOM | 1870 | CB | ILE | 2 | 69.544 | 42.452 | 18.510 | 1.00 | 28.42 | CPS3 |
| ATOM | 1871 | CG2 | ILE | 2 | 68.334 | 41.538 | 18.271 | 1.00 | 29.40 | CPS3 |
| ATOM | 1872 | CG1 | ILE | 2 | 69.495 | 43.670 | 17.576 | 1.00 | 28.86 | CPS3 |
| ATOM | 1873 | CD1 | ILE | 2 | 69.507 | 43.331 | 16.115 | 1.00 | 31.24 | CPS3 |
| ATOM | 1874 | C | ILE | 2 | 69.332 | 41.748 | 20.883 | 1.00 | 26.26 | CPS3 |
| ATOM | 1875 | O | ILE | 2 | 70.213 | 40.893 | 21.040 | 1.00 | 25.80 | CPS3 |
| ATOM | 1876 | N | TYR | 3 | 68.147 | 41.713 | 21.489 | 1.00 | 24.05 | CPS3 |
| ATOM | 1877 | CA | TYR | 3 | 67.752 | 40.622 | 22.369 | 1.00 | 24.41 | CPS3 |
| ATOM | 1878 | CB | TYR | 3 | 66.682 | 41.080 | 23.352 | 1.00 | 26.14 | CPS3 |
| ATOM | 1879 | CG | TYR | 3 | 66.254 | 39.967 | 24.268 | 1.00 | 28.89 | CPS3 |
| ATOM | 1880 | CD1 | TYR | 3 | 67.098 | 39.514 | 25.290 | 1.00 | 29.65 | CPS3 |

FIG. 1A-33

| ATOM | 1881 | CE1 | TYR | 3 | 66.736 | 38.442 | 26.092 | 1.00 | 32.21 | CPS3 |
|---|---|---|---|---|---|---|---|---|---|---|
| ATOM | 1882 | CD2 | TYR | 3 | 65.037 | 39.316 | 24.080 | 1.00 | 29.35 | CPS3 |
| ATOM | 1883 | CE2 | TYR | 3 | 64.667 | 38.235 | 24.883 | 1.00 | 31.35 | CPS3 |
| ATOM | 1884 | CZ | TYR | 3 | 65.520 | 37.806 | 25.881 | 1.00 | 32.89 | CPS3 |
| ATOM | 1885 | OH | TYR | 3 | 65.160 | 36.730 | 26.660 | 1.00 | 35.01 | CPS3 |
| ATOM | 1886 | C | TYR | 3 | 67.190 | 39.454 | 21.551 | 1.00 | 23.32 | CPS3 |
| ATOM | 1887 | O | TYR | 3 | 67.604 | 38.305 | 21.720 | 1.00 | 22.34 | CPS3 |
| ATOM | 1888 | N | GLY | 4 | 66.240 | 39.755 | 20.667 | 1.00 | 21.28 | CPS3 |
| ATOM | 1889 | CA | GLY | 4 | 65.655 | 38.705 | 19.848 | 1.00 | 20.37 | CPS3 |
| ATOM | 1890 | C | GLY | 4 | 64.945 | 39.231 | 18.614 | 1.00 | 18.42 | CPS3 |
| ATOM | 1891 | O | GLY | 4 | 64.636 | 40.411 | 18.527 | 1.00 | 18.04 | CPS3 |
| ATOM | 1892 | N | ILE | 5 | 64.694 | 38.350 | 17.656 | 1.00 | 17.82 | CPS3 |
| ATOM | 1893 | CA | ILE | 5 | 63.990 | 38.736 | 16.432 | 1.00 | 17.02 | CPS3 |
| ATOM | 1894 | CB | ILE | 5 | 64.939 | 38.802 | 15.206 | 1.00 | 16.53 | CPS3 |
| ATOM | 1895 | CG2 | ILE | 5 | 66.110 | 39.753 | 15.514 | 1.00 | 17.11 | CPS3 |
| ATOM | 1896 | CG1 | ILE | 5 | 65.457 | 37.398 | 14.841 | 1.00 | 16.93 | CPS3 |
| ATOM | 1897 | CD1 | ILE | 5 | 66.404 | 37.390 | 13.622 | 1.00 | 18.91 | CPS3 |
| ATOM | 1898 | C | ILE | 5 | 62.932 | 37.669 | 16.202 | 1.00 | 17.16 | CPS3 |
| ATOM | 1899 | O | ILE | 5 | 63.033 | 36.555 | 16.737 | 1.00 | 16.49 | CPS3 |
| ATOM | 1900 | N | GLY | 6 | 61.900 | 38.010 | 15.441 | 1.00 | 16.65 | CPS3 |
| ATOM | 1901 | CA | GLY | 6 | 60.847 | 37.041 | 15.187 | 1.00 | 17.04 | CPS3 |
| ATOM | 1902 | C | GLY | 6 | 60.217 | 37.338 | 13.844 | 1.00 | 17.86 | CPS3 |
| ATOM | 1903 | O | GLY | 6 | 60.070 | 38.500 | 13.472 | 1.00 | 16.46 | CPS3 |
| ATOM | 1904 | N | LEU | 7 | 59.865 | 36.283 | 13.110 | 1.00 | 18.17 | CPS3 |
| ATOM | 1905 | CA | LEU | 7 | 59.257 | 36.432 | 11.795 | 1.00 | 18.15 | CPS3 |
| ATOM | 1906 | CB | LEU | 7 | 60.258 | 36.047 | 10.698 | 1.00 | 17.40 | CPS3 |
| ATOM | 1907 | CG | LEU | 7 | 59.723 | 35.991 | 9.257 | 1.00 | 17.71 | CPS3 |
| ATOM | 1908 | CD1 | LEU | 7 | 59.370 | 37.420 | 8.785 | 1.00 | 18.00 | CPS3 |
| ATOM | 1909 | CD2 | LEU | 7 | 60.775 | 35.357 | 8.330 | 1.00 | 18.26 | CPS3 |
| ATOM | 1910 | C | LEU | 7 | 58.068 | 35.482 | 11.718 | 1.00 | 18.31 | CPS3 |
| ATOM | 1911 | O | LEU | 7 | 58.121 | 34.371 | 12.236 | 1.00 | 18.61 | CPS3 |
| ATOM | 1912 | N | ASP | 8 | 56.992 | 35.923 | 11.083 | 1.00 | 18.46 | CPS3 |
| ATOM | 1913 | CA | ASP | 8 | 55.849 | 35.043 | 10.911 | 1.00 | 18.86 | CPS3 |
| ATOM | 1914 | CB | ASP | 8 | 54.871 | 35.157 | 12.082 | 1.00 | 19.63 | CPS3 |
| ATOM | 1915 | CG | ASP | 8 | 53.642 | 34.294 | 11.881 | 1.00 | 22.43 | CPS3 |
| ATOM | 1916 | OD1 | ASP | 8 | 52.653 | 34.768 | 11.281 | 1.00 | 23.32 | CPS3 |
| ATOM | 1917 | OD2 | ASP | 8 | 53.683 | 33.126 | 12.294 | 1.00 | 24.61 | CPS3 |
| ATOM | 1918 | C | ASP | 8 | 55.107 | 35.350 | 9.632 | 1.00 | 19.01 | CPS3 |
| ATOM | 1919 | O | ASP | 8 | 54.955 | 36.507 | 9.251 | 1.00 | 19.92 | CPS3 |
| ATOM | 1920 | N | ILE | 9 | 54.671 | 34.302 | 8.946 | 1.00 | 18.64 | CPS3 |
| ATOM | 1921 | CA | ILE | 9 | 53.871 | 34.490 | 7.747 | 1.00 | 20.14 | CPS3 |
| ATOM | 1922 | CB | ILE | 9 | 54.565 | 33.982 | 6.468 | 1.00 | 19.98 | CPS3 |
| ATOM | 1923 | CG2 | ILE | 9 | 53.605 | 34.144 | 5.283 | 1.00 | 20.49 | CPS3 |
| ATOM | 1924 | CG1 | ILE | 9 | 55.843 | 34.782 | 6.213 | 1.00 | 20.86 | CPS3 |
| ATOM | 1925 | CD1 | ILE | 9 | 56.635 | 34.318 | 4.987 | 1.00 | 23.49 | CPS3 |
| ATOM | 1926 | C | ILE | 9 | 52.642 | 33.649 | 8.032 | 1.00 | 20.08 | CPS3 |
| ATOM | 1927 | O | ILE | 9 | 52.760 | 32.500 | 8.472 | 1.00 | 21.18 | CPS3 |
| ATOM | 1928 | N | THR | 10 | 51.470 | 34.224 | 7.793 | 1.00 | 20.82 | CPS3 |
| ATOM | 1929 | CA | THR | 10 | 50.218 | 33.543 | 8.064 | 1.00 | 22.22 | CPS3 |
| ATOM | 1930 | CB | THR | 10 | 49.502 | 34.213 | 9.267 | 1.00 | 23.80 | CPS3 |
| ATOM | 1931 | OG1 | THR | 10 | 50.237 | 33.942 | 10.478 | 1.00 | 22.74 | CPS3 |
| ATOM | 1932 | CG2 | THR | 10 | 48.088 | 33.667 | 9.413 | 1.00 | 24.86 | CPS3 |
| ATOM | 1933 | C | THR | 10 | 49.310 | 33.548 | 6.838 | 1.00 | 22.47 | CPS3 |
| ATOM | 1934 | O | THR | 10 | 49.106 | 34.581 | 6.197 | 1.00 | 22.06 | CPS3 |
| ATOM | 1935 | N | GLU | 11 | 48.784 | 32.377 | 6.508 | 1.00 | 23.62 | CPS3 |
| ATOM | 1936 | CA | GLU | 11 | 47.894 | 32.230 | 5.359 | 1.00 | 25.07 | CPS3 |
| ATOM | 1937 | CB | GLU | 11 | 47.846 | 30.757 | 4.940 | 1.00 | 25.66 | CPS3 |

FIG. 1A-34

```
ATOM   1938  CG   GLU  11    46.898  30.463   3.793  1.00 29.78      CPS3
ATOM   1939  CD   GLU  11    46.798  28.980   3.481  1.00 32.43      CPS3
ATOM   1940  OE1  GLU  11    47.101  28.151   4.373  1.00 34.21      CPS3
ATOM   1941  OE2  GLU  11    46.396  28.643   2.346  1.00 34.51      CPS3
ATOM   1942  C    GLU  11    46.502  32.708   5.771  1.00 25.06      CPS3
ATOM   1943  O    GLU  11    45.922  32.173   6.714  1.00 25.54      CPS3
ATOM   1944  N    LEU  12    45.963  33.701   5.069  1.00 25.35      CPS3
ATOM   1945  CA   LEU  12    44.642  34.234   5.403  1.00 26.43      CPS3
ATOM   1946  CB   LEU  12    44.225  35.329   4.408  1.00 28.34      CPS3
ATOM   1947  CG   LEU  12    44.432  36.787   4.846  1.00 30.12      CPS3
ATOM   1948  CD1  LEU  12    45.896  37.051   5.095  1.00 29.84      CPS3
ATOM   1949  CD2  LEU  12    43.898  37.731   3.771  1.00 31.67      CPS3
ATOM   1950  C    LEU  12    43.552  33.163   5.459  1.00 27.18      CPS3
ATOM   1951  O    LEU  12    42.700  33.183   6.350  1.00 25.07      CPS3
ATOM   1952  N    ALA  13    43.585  32.231   4.511  1.00 26.60      CPS3
ATOM   1953  CA   ALA  13    42.602  31.160   4.467  1.00 27.39      CPS3
ATOM   1954  CB   ALA  13    42.836  30.296   3.227  1.00 28.53      CPS3
ATOM   1955  C    ALA  13    42.616  30.293   5.730  1.00 28.85      CPS3
ATOM   1956  O    ALA  13    41.569  29.793   6.158  1.00 29.11      CPS3
ATOM   1957  N    ARG  14    43.790  30.115   6.332  1.00 28.68      CPS3
ATOM   1958  CA   ARG  14    43.898  29.303   7.536  1.00 29.64      CPS3
ATOM   1959  CB   ARG  14    45.361  28.961   7.844  1.00 31.16      CPS3
ATOM   1960  CG   ARG  14    45.520  27.811   8.831  1.00 33.62      CPS3
ATOM   1961  CD   ARG  14    46.961  27.333   8.931  1.00 36.46      CPS3
ATOM   1962  NE   ARG  14    47.813  28.263   9.669  1.00 39.10      CPS3
ATOM   1963  CZ   ARG  14    47.809  28.400  10.993  1.00 39.42      CPS3
ATOM   1964  NH1  ARG  14    46.998  27.665  11.741  1.00 41.04      CPS3
ATOM   1965  NH2  ARG  14    48.618  29.273  11.572  1.00 39.96      CPS3
ATOM   1966  C    ARG  14    43.277  30.067   8.693  1.00 30.10      CPS3
ATOM   1967  O    ARG  14    42.619  29.473   9.549  1.00 30.68      CPS3
ATOM   1968  N    ILE  15    43.490  31.382   8.721  1.00 28.50      CPS3
ATOM   1969  CA   ILE  15    42.904  32.220   9.765  1.00 29.44      CPS3
ATOM   1970  CB   ILE  15    43.322  33.708   9.611  1.00 28.52      CPS3
ATOM   1971  CG2  ILE  15    42.492  34.596  10.544  1.00 27.32      CPS3
ATOM   1972  CG1  ILE  15    44.809  33.865   9.955  1.00 27.87      CPS3
ATOM   1973  CD1  ILE  15    45.145  33.454  11.384  1.00 29.13      CPS3
ATOM   1974  C    ILE  15    41.383  32.116   9.656  1.00 30.89      CPS3
ATOM   1975  O    ILE  15    40.689  31.904  10.654  1.00 31.81      CPS3
ATOM   1976  N    ALA  16    40.868  32.271   8.439  1.00 31.30      CPS3
ATOM   1977  CA   ALA  16    39.427  32.180   8.223  1.00 33.08      CPS3
ATOM   1978  CB   ALA  16    39.096  32.463   6.760  1.00 33.09      CPS3
ATOM   1979  C    ALA  16    38.902  30.802   8.634  1.00 34.30      CPS3
ATOM   1980  O    ALA  16    37.800  30.695   9.169  1.00 35.45      CPS3
ATOM   1981  N    SER  17    39.689  29.753   8.395  1.00 35.66      CPS3
ATOM   1982  CA   SER  17    39.282  28.396   8.764  1.00 38.32      CPS3
ATOM   1983  CB   SER  17    40.271  27.356   8.227  1.00 39.07      CPS3
ATOM   1984  OG   SER  17    40.290  27.332   6.810  1.00 40.78      CPS3
ATOM   1985  C    SER  17    39.187  28.242  10.277  1.00 40.41      CPS3
ATOM   1986  O    SER  17    38.202  27.704  10.789  1.00 40.87      CPS3
ATOM   1987  N    MET  18    40.215  28.704  10.989  1.00 41.04      CPS3
ATOM   1988  CA   MET  18    40.238  28.621  12.449  1.00 42.44      CPS3
ATOM   1989  CB   MET  18    41.582  29.110  13.004  1.00 42.96      CPS3
ATOM   1990  CG   MET  18    42.774  28.251  12.617  1.00 44.33      CPS3
ATOM   1991  SD   MET  18    44.266  28.670  13.558  1.00 48.01      CPS3
ATOM   1992  CE   MET  18    44.718  30.192  12.791  1.00 43.96      CPS3
ATOM   1993  C    MET  18    39.115  29.448  13.055  1.00 42.50      CPS3
ATOM   1994  O    MET  18    38.472  29.026  14.014  1.00 43.21      CPS3
```

FIG. 1A-35

| ATOM | 1995 | N   | ALA | 19 | 38.886 | 30.629 | 12.496 | 1.00 | 43.10 | CPS3 |
| ATOM | 1996 | CA  | ALA | 19 | 37.838 | 31.517 | 12.981 | 1.00 | 44.50 | CPS3 |
| ATOM | 1997 | CB  | ALA | 19 | 37.901 | 32.844 | 12.233 | 1.00 | 45.06 | CPS3 |
| ATOM | 1998 | C   | ALA | 19 | 36.453 | 30.889 | 12.816 | 1.00 | 46.48 | CPS3 |
| ATOM | 1999 | O   | ALA | 19 | 35.541 | 31.155 | 13.603 | 1.00 | 46.54 | CPS3 |
| ATOM | 2000 | N   | GLY | 20 | 36.296 | 30.061 | 11.788 | 1.00 | 47.19 | CPS3 |
| ATOM | 2001 | CA  | GLY | 20 | 35.015 | 29.417 | 11.558 | 1.00 | 48.52 | CPS3 |
| ATOM | 2002 | C   | GLY | 20 | 34.838 | 28.190 | 12.429 | 1.00 | 48.97 | CPS3 |
| ATOM | 2003 | O   | GLY | 20 | 33.754 | 27.928 | 12.945 | 1.00 | 49.64 | CPS3 |
| ATOM | 2004 | N   | ARG | 21 | 35.921 | 27.443 | 12.599 | 1.00 | 49.96 | CPS3 |
| ATOM | 2005 | CA  | ARG | 21 | 35.915 | 26.227 | 13.397 | 1.00 | 50.93 | CPS3 |
| ATOM | 2006 | CB  | ARG | 21 | 37.083 | 25.336 | 12.963 | 1.00 | 52.93 | CPS3 |
| ATOM | 2007 | CG  | ARG | 21 | 37.367 | 24.152 | 13.872 | 1.00 | 55.96 | CPS3 |
| ATOM | 2008 | CD  | ARG | 21 | 36.136 | 23.278 | 14.055 | 1.00 | 58.49 | CPS3 |
| ATOM | 2009 | NE  | ARG | 21 | 36.396 | 22.145 | 14.940 | 1.00 | 60.33 | CPS3 |
| ATOM | 2010 | CZ  | ARG | 21 | 35.448 | 21.371 | 15.457 | 1.00 | 60.98 | CPS3 |
| ATOM | 2011 | NH1 | ARG | 21 | 34.171 | 21.611 | 15.179 | 1.00 | 61.06 | CPS3 |
| ATOM | 2012 | NH2 | ARG | 21 | 35.776 | 20.356 | 16.247 | 1.00 | 61.52 | CPS3 |
| ATOM | 2013 | C   | ARG | 21 | 35.987 | 26.469 | 14.904 | 1.00 | 51.00 | CPS3 |
| ATOM | 2014 | O   | ARG | 21 | 35.437 | 25.698 | 15.693 | 1.00 | 51.31 | CPS3 |
| ATOM | 2015 | N   | GLN | 22 | 36.655 | 27.543 | 15.307 | 1.00 | 50.09 | CPS3 |
| ATOM | 2016 | CA  | GLN | 22 | 36.807 | 27.835 | 16.725 | 1.00 | 49.10 | CPS3 |
| ATOM | 2017 | CB  | GLN | 22 | 38.224 | 28.330 | 17.011 | 1.00 | 48.88 | CPS3 |
| ATOM | 2018 | CG  | GLN | 22 | 39.273 | 27.241 | 16.967 | 1.00 | 49.46 | CPS3 |
| ATOM | 2019 | CD  | GLN | 22 | 40.653 | 27.759 | 17.297 | 1.00 | 49.87 | CPS3 |
| ATOM | 2020 | OE1 | GLN | 22 | 40.828 | 28.529 | 18.242 | 1.00 | 50.04 | CPS3 |
| ATOM | 2021 | NE2 | GLN | 22 | 41.648 | 27.330 | 16.526 | 1.00 | 50.52 | CPS3 |
| ATOM | 2022 | C   | GLN | 22 | 35.822 | 28.816 | 17.328 | 1.00 | 47.67 | CPS3 |
| ATOM | 2023 | O   | GLN | 22 | 35.309 | 29.716 | 16.660 | 1.00 | 48.35 | CPS3 |
| ATOM | 2024 | N   | LYS | 23 | 35.580 | 28.626 | 18.619 | 1.00 | 46.19 | CPS3 |
| ATOM | 2025 | CA  | LYS | 23 | 34.683 | 29.477 | 19.384 | 1.00 | 44.06 | CPS3 |
| ATOM | 2026 | CB  | LYS | 23 | 34.086 | 28.701 | 20.569 | 1.00 | 45.41 | CPS3 |
| ATOM | 2027 | CG  | LYS | 23 | 34.474 | 27.218 | 20.651 | 1.00 | 48.30 | CPS3 |
| ATOM | 2028 | CD  | LYS | 23 | 35.983 | 27.019 | 20.828 | 1.00 | 50.15 | CPS3 |
| ATOM | 2029 | CE  | LYS | 23 | 36.341 | 25.554 | 21.037 | 1.00 | 51.50 | CPS3 |
| ATOM | 2030 | NZ  | LYS | 23 | 35.720 | 25.007 | 22.285 | 1.00 | 51.24 | CPS3 |
| ATOM | 2031 | C   | LYS | 23 | 35.490 | 30.659 | 19.918 | 1.00 | 40.79 | CPS3 |
| ATOM | 2032 | O   | LYS | 23 | 36.523 | 30.457 | 20.558 | 1.00 | 40.61 | CPS3 |
| ATOM | 2033 | N   | ARG | 24 | 35.029 | 31.878 | 19.630 | 1.00 | 36.53 | CPS3 |
| ATOM | 2034 | CA  | ARG | 24 | 35.671 | 33.110 | 20.103 | 1.00 | 33.31 | CPS3 |
| ATOM | 2035 | CB  | ARG | 24 | 35.675 | 33.153 | 21.630 | 1.00 | 32.78 | CPS3 |
| ATOM | 2036 | CG  | ARG | 24 | 34.367 | 32.793 | 22.310 | 1.00 | 34.25 | CPS3 |
| ATOM | 2037 | CD  | ARG | 24 | 33.299 | 33.846 | 22.126 | 1.00 | 35.40 | CPS3 |
| ATOM | 2038 | NE  | ARG | 24 | 32.105 | 33.476 | 22.883 | 1.00 | 38.23 | CPS3 |
| ATOM | 2039 | CZ  | ARG | 24 | 30.866 | 33.783 | 22.520 | 1.00 | 38.00 | CPS3 |
| ATOM | 2040 | NH1 | ARG | 24 | 30.653 | 34.474 | 21.405 | 1.00 | 38.06 | CPS3 |
| ATOM | 2041 | NH2 | ARG | 24 | 29.841 | 33.375 | 23.259 | 1.00 | 39.67 | CPS3 |
| ATOM | 2042 | C   | ARG | 24 | 37.116 | 33.301 | 19.641 | 1.00 | 31.71 | CPS3 |
| ATOM | 2043 | O   | ARG | 24 | 37.930 | 33.845 | 20.393 | 1.00 | 27.62 | CPS3 |
| ATOM | 2044 | N   | PHE | 25 | 37.441 | 32.880 | 18.421 | 1.00 | 29.27 | CPS3 |
| ATOM | 2045 | CA  | PHE | 25 | 38.816 | 33.016 | 17.950 | 1.00 | 28.40 | CPS3 |
| ATOM | 2046 | CB  | PHE | 25 | 38.958 | 32.446 | 16.539 | 1.00 | 28.43 | CPS3 |
| ATOM | 2047 | CG  | PHE | 25 | 40.370 | 32.482 | 16.011 | 1.00 | 28.82 | CPS3 |
| ATOM | 2048 | CD1 | PHE | 25 | 40.758 | 33.450 | 15.097 | 1.00 | 29.33 | CPS3 |
| ATOM | 2049 | CD2 | PHE | 25 | 41.311 | 31.556 | 16.445 | 1.00 | 30.13 | CPS3 |
| ATOM | 2050 | CE1 | PHE | 25 | 42.067 | 33.500 | 14.618 | 1.00 | 30.52 | CPS3 |
| ATOM | 2051 | CE2 | PHE | 25 | 42.625 | 31.597 | 15.970 | 1.00 | 30.21 | CPS3 |

FIG. 1A-36

| ATOM | 2052 | CZ | PHE | 25 | 42.997 | 32.570 | 15.059 | 1.00 | 29.47 | CPS3 |
|---|---|---|---|---|---|---|---|---|---|---|
| ATOM | 2053 | C | PHE | 25 | 39.325 | 34.455 | 17.992 | 1.00 | 27.06 | CPS3 |
| ATOM | 2054 | O | PHE | 25 | 40.394 | 34.716 | 18.531 | 1.00 | 27.13 | CPS3 |
| ATOM | 2055 | N | ALA | 26 | 38.569 | 35.394 | 17.433 | 1.00 | 27.40 | CPS3 |
| ATOM | 2056 | CA | ALA | 26 | 38.996 | 36.793 | 17.441 | 1.00 | 26.90 | CPS3 |
| ATOM | 2057 | CB | ALA | 26 | 37.987 | 37.661 | 16.692 | 1.00 | 27.98 | CPS3 |
| ATOM | 2058 | C | ALA | 26 | 39.174 | 37.302 | 18.869 | 1.00 | 26.90 | CPS3 |
| ATOM | 2059 | O | ALA | 26 | 40.131 | 38.027 | 19.170 | 1.00 | 25.61 | CPS3 |
| ATOM | 2060 | N | GLU | 27 | 38.254 | 36.912 | 19.753 | 1.00 | 25.63 | CPS3 |
| ATOM | 2061 | CA | GLU | 27 | 38.314 | 37.329 | 21.143 | 1.00 | 25.29 | CPS3 |
| ATOM | 2062 | CB | GLU | 27 | 37.070 | 36.864 | 21.908 | 1.00 | 25.87 | CPS3 |
| ATOM | 2063 | CG | GLU | 27 | 35.815 | 37.656 | 21.612 | 1.00 | 26.46 | CPS3 |
| ATOM | 2064 | CD | GLU | 27 | 35.199 | 37.336 | 20.266 | 1.00 | 28.64 | CPS3 |
| ATOM | 2065 | OE1 | GLU | 27 | 35.569 | 36.324 | 19.633 | 1.00 | 29.62 | CPS3 |
| ATOM | 2066 | OE2 | GLU | 27 | 34.319 | 38.106 | 19.845 | 1.00 | 31.82 | CPS3 |
| ATOM | 2067 | C | GLU | 27 | 39.548 | 36.770 | 21.835 | 1.00 | 24.48 | CPS3 |
| ATOM | 2068 | O | GLU | 27 | 40.026 | 37.340 | 22.812 | 1.00 | 23.69 | CPS3 |
| ATOM | 2069 | N | ARG | 28 | 40.057 | 35.652 | 21.336 | 1.00 | 24.10 | CPS3 |
| ATOM | 2070 | CA | ARG | 28 | 41.235 | 35.046 | 21.937 | 1.00 | 25.35 | CPS3 |
| ATOM | 2071 | CB | ARG | 28 | 41.286 | 33.561 | 21.588 | 1.00 | 26.74 | CPS3 |
| ATOM | 2072 | CG | ARG | 28 | 42.365 | 32.796 | 22.331 | 1.00 | 30.57 | CPS3 |
| ATOM | 2073 | CD | ARG | 28 | 42.064 | 31.303 | 22.339 | 1.00 | 33.01 | CPS3 |
| ATOM | 2074 | NE | ARG | 28 | 42.094 | 30.724 | 21.001 | 1.00 | 34.13 | CPS3 |
| ATOM | 2075 | CZ | ARG | 28 | 43.212 | 30.481 | 20.327 | 1.00 | 36.89 | CPS3 |
| ATOM | 2076 | NH1 | ARG | 28 | 44.389 | 30.768 | 20.871 | 1.00 | 37.04 | CPS3 |
| ATOM | 2077 | NH2 | ARG | 28 | 43.157 | 29.946 | 19.111 | 1.00 | 37.15 | CPS3 |
| ATOM | 2078 | C | ARG | 28 | 42.529 | 35.736 | 21.488 | 1.00 | 24.56 | CPS3 |
| ATOM | 2079 | O | ARG | 28 | 43.450 | 35.930 | 22.282 | 1.00 | 24.22 | CPS3 |
| ATOM | 2080 | N | ILE | 29 | 42.574 | 36.130 | 20.225 | 1.00 | 23.52 | CPS3 |
| ATOM | 2081 | CA | ILE | 29 | 43.760 | 36.773 | 19.657 | 1.00 | 24.20 | CPS3 |
| ATOM | 2082 | CB | ILE | 29 | 43.788 | 36.591 | 18.122 | 1.00 | 24.82 | CPS3 |
| ATOM | 2083 | CG2 | ILE | 29 | 45.074 | 37.184 | 17.538 | 1.00 | 25.66 | CPS3 |
| ATOM | 2084 | CG1 | ILE | 29 | 43.627 | 35.107 | 17.768 | 1.00 | 26.45 | CPS3 |
| ATOM | 2085 | CD1 | ILE | 29 | 44.675 | 34.207 | 18.357 | 1.00 | 26.17 | CPS3 |
| ATOM | 2086 | C | ILE | 29 | 43.866 | 38.270 | 19.932 | 1.00 | 24.20 | CPS3 |
| ATOM | 2087 | O | ILE | 29 | 44.964 | 38.795 | 20.164 | 1.00 | 23.59 | CPS3 |
| ATOM | 2088 | N | LEU | 30 | 42.722 | 38.952 | 19.913 | 1.00 | 22.23 | CPS3 |
| ATOM | 2089 | CA | LEU | 30 | 42.683 | 40.401 | 20.076 | 1.00 | 22.20 | CPS3 |
| ATOM | 2090 | CB | LEU | 30 | 41.643 | 40.977 | 19.106 | 1.00 | 21.52 | CPS3 |
| ATOM | 2091 | CG | LEU | 30 | 41.738 | 40.518 | 17.649 | 1.00 | 22.01 | CPS3 |
| ATOM | 2092 | CD1 | LEU | 30 | 40.591 | 41.151 | 16.857 | 1.00 | 22.54 | CPS3 |
| ATOM | 2093 | CD2 | LEU | 30 | 43.104 | 40.926 | 17.051 | 1.00 | 22.99 | CPS3 |
| ATOM | 2094 | C | LEU | 30 | 42.387 | 40.940 | 21.467 | 1.00 | 22.82 | CPS3 |
| ATOM | 2095 | O | LEU | 30 | 41.622 | 40.342 | 22.216 | 1.00 | 22.70 | CPS3 |
| ATOM | 2096 | N | THR | 31 | 42.995 | 42.080 | 21.798 | 1.00 | 22.58 | CPS3 |
| ATOM | 2097 | CA | THR | 31 | 42.752 | 42.741 | 23.076 | 1.00 | 23.08 | CPS3 |
| ATOM | 2098 | CB | THR | 31 | 43.781 | 43.846 | 23.374 | 1.00 | 22.96 | CPS3 |
| ATOM | 2099 | OG1 | THR | 31 | 43.666 | 44.871 | 22.377 | 1.00 | 23.51 | CPS3 |
| ATOM | 2100 | CG2 | THR | 31 | 45.200 | 43.283 | 23.406 | 1.00 | 23.16 | CPS3 |
| ATOM | 2101 | C | THR | 31 | 41.400 | 43.438 | 22.944 | 1.00 | 23.05 | CPS3 |
| ATOM | 2102 | O | THR | 31 | 40.840 | 43.499 | 21.850 | 1.00 | 20.90 | CPS3 |
| ATOM | 2103 | N | ARG | 32 | 40.887 | 43.992 | 24.042 | 1.00 | 23.64 | CPS3 |
| ATOM | 2104 | CA | ARG | 32 | 39.593 | 44.672 | 23.984 | 1.00 | 25.29 | CPS3 |
| ATOM | 2105 | CB | ARG | 32 | 39.224 | 45.258 | 25.346 | 1.00 | 24.83 | CPS3 |
| ATOM | 2106 | CG | ARG | 32 | 39.005 | 44.220 | 26.419 | 1.00 | 26.80 | CPS3 |
| ATOM | 2107 | CD | ARG | 32 | 38.684 | 44.890 | 27.752 | 1.00 | 25.11 | CPS3 |
| ATOM | 2108 | NE | ARG | 32 | 38.513 | 43.908 | 28.819 | 1.00 | 25.70 | CPS3 |

FIG. 1A-37

| ATOM | 2109 | CZ  | ARG | 32 | 38.361 | 44.218 | 30.101 | 1.00 | 25.97 | CPS3 |
|------|------|-----|-----|----|--------|--------|--------|------|-------|------|
| ATOM | 2110 | NH1 | ARG | 32 | 38.357 | 45.492 | 30.481 | 1.00 | 26.33 | CPS3 |
| ATOM | 2111 | NH2 | ARG | 32 | 38.224 | 43.256 | 31.005 | 1.00 | 27.07 | CPS3 |
| ATOM | 2112 | C   | ARG | 32 | 39.570 | 45.789 | 22.953 | 1.00 | 25.39 | CPS3 |
| ATOM | 2113 | O   | ARG | 32 | 38.608 | 45.912 | 22.187 | 1.00 | 24.58 | CPS3 |
| ATOM | 2114 | N   | SER | 33 | 40.622 | 46.605 | 22.935 | 1.00 | 24.96 | CPS3 |
| ATOM | 2115 | CA  | SER | 33 | 40.699 | 47.715 | 21.988 | 1.00 | 25.69 | CPS3 |
| ATOM | 2116 | CB  | SER | 33 | 41.909 | 48.603 | 22.284 | 1.00 | 27.21 | CPS3 |
| ATOM | 2117 | OG  | SER | 33 | 41.714 | 49.345 | 23.469 | 1.00 | 28.30 | CPS3 |
| ATOM | 2118 | C   | SER | 33 | 40.766 | 47.250 | 20.544 | 1.00 | 25.41 | CPS3 |
| ATOM | 2119 | O   | SER | 33 | 40.180 | 47.870 | 19.664 | 1.00 | 25.68 | CPS3 |
| ATOM | 2120 | N   | GLU | 34 | 41.492 | 46.169 | 20.290 | 1.00 | 24.03 | CPS3 |
| ATOM | 2121 | CA  | GLU | 34 | 41.597 | 45.640 | 18.935 | 1.00 | 23.95 | CPS3 |
| ATOM | 2122 | CB  | GLU | 34 | 42.699 | 44.574 | 18.879 | 1.00 | 23.46 | CPS3 |
| ATOM | 2123 | CG  | GLU | 34 | 44.089 | 45.163 | 19.059 | 1.00 | 21.69 | CPS3 |
| ATOM | 2124 | CD  | GLU | 34 | 45.182 | 44.105 | 19.221 | 1.00 | 22.84 | CPS3 |
| ATOM | 2125 | OE1 | GLU | 34 | 46.328 | 44.405 | 18.837 | 1.00 | 21.34 | CPS3 |
| ATOM | 2126 | OE2 | GLU | 34 | 44.900 | 42.996 | 19.740 | 1.00 | 20.06 | CPS3 |
| ATOM | 2127 | C   | GLU | 34 | 40.244 | 45.051 | 18.516 | 1.00 | 25.26 | CPS3 |
| ATOM | 2128 | O   | GLU | 34 | 39.846 | 45.151 | 17.353 | 1.00 | 25.38 | CPS3 |
| ATOM | 2129 | N   | LEU | 35 | 39.548 | 44.433 | 19.472 | 1.00 | 24.79 | CPS3 |
| ATOM | 2130 | CA  | LEU | 35 | 38.231 | 43.849 | 19.211 | 1.00 | 25.97 | CPS3 |
| ATOM | 2131 | CB  | LEU | 35 | 37.678 | 43.160 | 20.462 | 1.00 | 27.07 | CPS3 |
| ATOM | 2132 | CG  | LEU | 35 | 37.717 | 41.639 | 20.630 | 1.00 | 30.32 | CPS3 |
| ATOM | 2133 | CD1 | LEU | 35 | 36.834 | 41.312 | 21.844 | 1.00 | 30.54 | CPS3 |
| ATOM | 2134 | CD2 | LEU | 35 | 37.201 | 40.893 | 19.391 | 1.00 | 28.41 | CPS3 |
| ATOM | 2135 | C   | LEU | 35 | 37.264 | 44.947 | 18.806 | 1.00 | 25.13 | CPS3 |
| ATOM | 2136 | O   | LEU | 35 | 36.471 | 44.778 | 17.885 | 1.00 | 26.21 | CPS3 |
| ATOM | 2137 | N   | ASP | 36 | 37.310 | 46.066 | 19.518 | 1.00 | 25.47 | CPS3 |
| ATOM | 2138 | CA  | ASP | 36 | 36.432 | 47.180 | 19.189 | 1.00 | 26.39 | CPS3 |
| ATOM | 2139 | CB  | ASP | 36 | 36.696 | 48.383 | 20.111 | 1.00 | 27.06 | CPS3 |
| ATOM | 2140 | CG  | ASP | 36 | 36.203 | 48.148 | 21.531 | 1.00 | 30.18 | CPS3 |
| ATOM | 2141 | OD1 | ASP | 36 | 35.336 | 47.272 | 21.710 | 1.00 | 28.81 | CPS3 |
| ATOM | 2142 | OD2 | ASP | 36 | 36.667 | 48.843 | 22.464 | 1.00 | 29.67 | CPS3 |
| ATOM | 2143 | C   | ASP | 36 | 36.638 | 47.580 | 17.733 | 1.00 | 28.21 | CPS3 |
| ATOM | 2144 | O   | ASP | 36 | 35.674 | 47.866 | 17.024 | 1.00 | 27.00 | CPS3 |
| ATOM | 2145 | N   | GLN | 37 | 37.892 | 47.580 | 17.281 | 1.00 | 28.66 | CPS3 |
| ATOM | 2146 | CA  | GLN | 37 | 38.200 | 47.939 | 15.895 | 1.00 | 28.46 | CPS3 |
| ATOM | 2147 | CB  | GLN | 37 | 39.712 | 48.129 | 15.705 | 1.00 | 31.40 | CPS3 |
| ATOM | 2148 | CG  | GLN | 37 | 40.309 | 49.384 | 16.315 | 1.00 | 34.73 | CPS3 |
| ATOM | 2149 | CD  | GLN | 37 | 41.820 | 49.462 | 16.104 | 1.00 | 37.78 | CPS3 |
| ATOM | 2150 | OE1 | GLN | 37 | 42.601 | 48.806 | 16.803 | 1.00 | 38.25 | CPS3 |
| ATOM | 2151 | NE2 | GLN | 37 | 42.233 | 50.256 | 15.128 | 1.00 | 40.09 | CPS3 |
| ATOM | 2152 | C   | GLN | 37 | 37.729 | 46.838 | 14.954 | 1.00 | 28.42 | CPS3 |
| ATOM | 2153 | O   | GLN | 37 | 37.107 | 47.097 | 13.918 | 1.00 | 28.25 | CPS3 |
| ATOM | 2154 | N   | TYR | 38 | 38.040 | 45.602 | 15.322 | 1.00 | 25.92 | CPS3 |
| ATOM | 2155 | CA  | TYR | 38 | 37.676 | 44.445 | 14.526 | 1.00 | 27.76 | CPS3 |
| ATOM | 2156 | CB  | TYR | 38 | 38.124 | 43.179 | 15.268 | 1.00 | 26.65 | CPS3 |
| ATOM | 2157 | CG  | TYR | 38 | 37.674 | 41.867 | 14.666 | 1.00 | 28.74 | CPS3 |
| ATOM | 2158 | CD1 | TYR | 38 | 36.522 | 41.225 | 15.130 | 1.00 | 27.49 | CPS3 |
| ATOM | 2159 | CE1 | TYR | 38 | 36.105 | 40.013 | 14.583 | 1.00 | 29.24 | CPS3 |
| ATOM | 2160 | CD2 | TYR | 38 | 38.397 | 41.264 | 13.636 | 1.00 | 27.76 | CPS3 |
| ATOM | 2161 | CE2 | TYR | 38 | 37.986 | 40.046 | 13.081 | 1.00 | 29.24 | CPS3 |
| ATOM | 2162 | CZ  | TYR | 38 | 36.840 | 39.430 | 13.565 | 1.00 | 29.43 | CPS3 |
| ATOM | 2163 | OH  | TYR | 38 | 36.440 | 38.218 | 13.057 | 1.00 | 30.36 | CPS3 |
| ATOM | 2164 | C   | TYR | 38 | 36.177 | 44.398 | 14.219 | 1.00 | 28.73 | CPS3 |
| ATOM | 2165 | O   | TYR | 38 | 35.776 | 44.169 | 13.075 | 1.00 | 28.54 | CPS3 |

FIG. 1A-38

| | | | | | | | | | |
|---|---|---|---|---|---|---|---|---|---|
| ATOM | 2166 | N | TYR | 39 | 35.349 | 44.637 | 15.228 | 1.00 29.50 | CPS3 |
| ATOM | 2167 | CA | TYR | 39 | 33.910 | 44.575 | 15.018 | 1.00 31.58 | CPS3 |
| ATOM | 2168 | CB | TYR | 39 | 33.195 | 44.515 | 16.367 | 1.00 31.24 | CPS3 |
| ATOM | 2169 | CG | TYR | 39 | 33.219 | 43.106 | 16.896 | 1.00 31.89 | CPS3 |
| ATOM | 2170 | CD1 | TYR | 39 | 32.839 | 42.054 | 16.068 | 1.00 34.16 | CPS3 |
| ATOM | 2171 | CE1 | TYR | 39 | 32.897 | 40.744 | 16.491 | 1.00 34.63 | CPS3 |
| ATOM | 2172 | CD2 | TYR | 39 | 33.658 | 42.808 | 18.185 | 1.00 32.76 | CPS3 |
| ATOM | 2173 | CE2 | TYR | 39 | 33.722 | 41.472 | 18.627 | 1.00 32.49 | CPS3 |
| ATOM | 2174 | CZ | TYR | 39 | 33.339 | 40.455 | 17.760 | 1.00 33.06 | CPS3 |
| ATOM | 2175 | OH | TYR | 39 | 33.404 | 39.126 | 18.112 | 1.00 36.81 | CPS3 |
| ATOM | 2176 | C | TYR | 39 | 33.277 | 45.627 | 14.110 | 1.00 33.88 | CPS3 |
| ATOM | 2177 | O | TYR | 39 | 32.122 | 45.484 | 13.715 | 1.00 34.54 | CPS3 |
| ATOM | 2178 | N | GLU | 40 | 34.026 | 46.666 | 13.766 | 1.00 35.41 | CPS3 |
| ATOM | 2179 | CA | GLU | 40 | 33.509 | 47.709 | 12.882 | 1.00 37.60 | CPS3 |
| ATOM | 2180 | CB | GLU | 40 | 34.045 | 49.077 | 13.302 | 1.00 39.04 | CPS3 |
| ATOM | 2181 | CG | GLU | 40 | 33.553 | 49.545 | 14.656 | 1.00 41.70 | CPS3 |
| ATOM | 2182 | CD | GLU | 40 | 32.040 | 49.515 | 14.755 | 1.00 44.23 | CPS3 |
| ATOM | 2183 | OE1 | GLU | 40 | 31.374 | 50.110 | 13.879 | 1.00 46.21 | CPS3 |
| ATOM | 2184 | OE2 | GLU | 40 | 31.515 | 48.895 | 15.706 | 1.00 44.59 | CPS3 |
| ATOM | 2185 | C | GLU | 40 | 33.888 | 47.452 | 11.423 | 1.00 38.62 | CPS3 |
| ATOM | 2186 | O | GLU | 40 | 33.491 | 48.200 | 10.530 | 1.00 39.31 | CPS3 |
| ATOM | 2187 | N | LEU | 41 | 34.651 | 46.388 | 11.189 | 1.00 38.25 | CPS3 |
| ATOM | 2188 | CA | LEU | 41 | 35.120 | 46.028 | 9.851 | 1.00 37.52 | CPS3 |
| ATOM | 2189 | CB | LEU | 41 | 36.507 | 45.380 | 9.954 | 1.00 36.60 | CPS3 |
| ATOM | 2190 | CG | LEU | 41 | 37.764 | 46.251 | 10.003 | 1.00 37.26 | CPS3 |
| ATOM | 2191 | CD1 | LEU | 41 | 37.520 | 47.514 | 10.794 | 1.00 38.83 | CPS3 |
| ATOM | 2192 | CD2 | LEU | 41 | 38.906 | 45.436 | 10.604 | 1.00 35.48 | CPS3 |
| ATOM | 2193 | C | LEU | 41 | 34.206 | 45.080 | 9.079 | 1.00 37.57 | CPS3 |
| ATOM | 2194 | O | LEU | 41 | 33.441 | 44.317 | 9.662 | 1.00 36.05 | CPS3 |
| ATOM | 2195 | N | SER | 42 | 34.312 | 45.127 | 7.755 | 1.00 38.63 | CPS3 |
| ATOM | 2196 | CA | SER | 42 | 33.537 | 44.251 | 6.890 | 1.00 38.96 | CPS3 |
| ATOM | 2197 | CB | SER | 42 | 33.712 | 44.668 | 5.434 | 1.00 40.14 | CPS3 |
| ATOM | 2198 | OG | SER | 42 | 35.078 | 44.585 | 5.055 | 1.00 42.27 | CPS3 |
| ATOM | 2199 | C | SER | 42 | 34.102 | 42.849 | 7.077 | 1.00 39.70 | CPS3 |
| ATOM | 2200 | O | SER | 42 | 35.183 | 42.685 | 7.641 | 1.00 39.21 | CPS3 |
| ATOM | 2201 | N | ALA | 43 | 33.385 | 41.842 | 6.596 | 1.00 39.38 | CPS3 |
| ATOM | 2202 | CA | ALA | 43 | 33.844 | 40.463 | 6.721 | 1.00 40.19 | CPS3 |
| ATOM | 2203 | CB | ALA | 43 | 32.854 | 39.521 | 6.040 | 1.00 41.29 | CPS3 |
| ATOM | 2204 | C | ALA | 43 | 35.247 | 40.268 | 6.128 | 1.00 40.48 | CPS3 |
| ATOM | 2205 | O | ALA | 43 | 36.084 | 39.569 | 6.706 | 1.00 39.82 | CPS3 |
| ATOM | 2206 | N | LYS | 44 | 35.495 | 40.884 | 4.974 | 1.00 40.37 | CPS3 |
| ATOM | 2207 | CA | LYS | 44 | 36.786 | 40.767 | 4.305 | 1.00 40.57 | CPS3 |
| ATOM | 2208 | CB | LYS | 44 | 36.722 | 41.379 | 2.904 | 1.00 42.89 | CPS3 |
| ATOM | 2209 | CG | LYS | 44 | 38.039 | 41.314 | 2.139 | 1.00 45.09 | CPS3 |
| ATOM | 2210 | CD | LYS | 44 | 37.958 | 42.106 | 0.840 | 1.00 47.76 | CPS3 |
| ATOM | 2211 | CE | LYS | 44 | 39.309 | 42.177 | 0.145 | 1.00 49.05 | CPS3 |
| ATOM | 2212 | NZ | LYS | 44 | 39.300 | 43.158 | -0.980 | 1.00 50.90 | CPS3 |
| ATOM | 2213 | C | LYS | 44 | 37.886 | 41.454 | 5.097 | 1.00 39.09 | CPS3 |
| ATOM | 2214 | O | LYS | 44 | 38.955 | 40.881 | 5.308 | 1.00 39.00 | CPS3 |
| ATOM | 2215 | N | ARG | 45 | 37.625 | 42.687 | 5.518 | 1.00 37.74 | CPS3 |
| ATOM | 2216 | CA | ARG | 45 | 38.594 | 43.460 | 6.291 | 1.00 36.13 | CPS3 |
| ATOM | 2217 | CB | ARG | 45 | 38.073 | 44.882 | 6.517 | 1.00 37.61 | CPS3 |
| ATOM | 2218 | CG | ARG | 45 | 38.223 | 45.805 | 5.314 | 1.00 41.25 | CPS3 |
| ATOM | 2219 | CD | ARG | 45 | 39.693 | 46.134 | 5.076 | 1.00 43.51 | CPS3 |
| ATOM | 2220 | NE | ARG | 45 | 40.264 | 46.872 | 6.203 | 1.00 45.35 | CPS3 |
| ATOM | 2221 | CZ | ARG | 45 | 41.392 | 46.536 | 6.826 | 1.00 46.41 | CPS3 |
| ATOM | 2222 | NH1 | ARG | 45 | 42.078 | 45.469 | 6.435 | 1.00 46.39 | CPS3 |

FIG. 1A-39

| ATOM | 2223 | NH2 | ARG | 45 | 41.833 | 47.269 | 7.843 | 1.00 | 46.62 | CPS3 |
|---|---|---|---|---|---|---|---|---|---|---|
| ATOM | 2224 | C | ARG | 45 | 38.909 | 42.799 | 7.634 | 1.00 | 34.32 | CPS3 |
| ATOM | 2225 | O | ARG | 45 | 40.049 | 42.842 | 8.097 | 1.00 | 32.42 | CPS3 |
| ATOM | 2226 | N | LYS | 46 | 37.899 | 42.188 | 8.251 | 1.00 | 32.83 | CPS3 |
| ATOM | 2227 | CA | LYS | 46 | 38.075 | 41.509 | 9.532 | 1.00 | 31.12 | CPS3 |
| ATOM | 2228 | CB | LYS | 46 | 36.775 | 40.842 | 9.987 | 1.00 | 31.02 | CPS3 |
| ATOM | 2229 | CG | LYS | 46 | 35.746 | 41.775 | 10.599 | 1.00 | 30.98 | CPS3 |
| ATOM | 2230 | CD | LYS | 46 | 34.553 | 40.977 | 11.100 | 1.00 | 32.86 | CPS3 |
| ATOM | 2231 | CE | LYS | 46 | 33.524 | 41.861 | 11.785 | 1.00 | 34.98 | CPS3 |
| ATOM | 2232 | NZ | LYS | 46 | 32.360 | 41.053 | 12.230 | 1.00 | 37.21 | CPS3 |
| ATOM | 2233 | C | LYS | 46 | 39.148 | 40.438 | 9.434 | 1.00 | 30.57 | CPS3 |
| ATOM | 2234 | O | LYS | 46 | 40.025 | 40.352 | 10.293 | 1.00 | 28.78 | CPS3 |
| ATOM | 2235 | N | ASN | 47 | 39.061 | 39.612 | 8.392 | 1.00 | 29.54 | CPS3 |
| ATOM | 2236 | CA | ASN | 47 | 40.020 | 38.533 | 8.186 | 1.00 | 29.84 | CPS3 |
| ATOM | 2237 | CB | ASN | 47 | 39.589 | 37.671 | 6.989 | 1.00 | 31.31 | CPS3 |
| ATOM | 2238 | CG | ASN | 47 | 40.603 | 36.588 | 6.635 | 1.00 | 33.49 | CPS3 |
| ATOM | 2239 | OD1 | ASN | 47 | 40.838 | 35.651 | 7.400 | 1.00 | 34.63 | CPS3 |
| ATOM | 2240 | ND2 | ASN | 47 | 41.201 | 36.713 | 5.461 | 1.00 | 34.30 | CPS3 |
| ATOM | 2241 | C | ASN | 47 | 41.436 | 39.083 | 7.976 | 1.00 | 28.84 | CPS3 |
| ATOM | 2242 | O | ASN | 47 | 42.401 | 38.521 | 8.501 | 1.00 | 27.85 | CPS3 |
| ATOM | 2243 | N | GLU | 48 | 41.562 | 40.174 | 7.224 | 1.00 | 27.20 | CPS3 |
| ATOM | 2244 | CA | GLU | 48 | 42.881 | 40.779 | 6.988 | 1.00 | 27.86 | CPS3 |
| ATOM | 2245 | CB | GLU | 48 | 42.795 | 41.910 | 5.955 | 1.00 | 30.08 | CPS3 |
| ATOM | 2246 | CG | GLU | 48 | 42.315 | 41.492 | 4.580 | 1.00 | 34.36 | CPS3 |
| ATOM | 2247 | CD | GLU | 48 | 41.937 | 42.687 | 3.716 | 1.00 | 38.77 | CPS3 |
| ATOM | 2248 | OE1 | GLU | 48 | 41.356 | 42.477 | 2.627 | 1.00 | 40.99 | CPS3 |
| ATOM | 2249 | OE2 | GLU | 48 | 42.221 | 43.835 | 4.124 | 1.00 | 39.72 | CPS3 |
| ATOM | 2250 | C | GLU | 48 | 43.451 | 41.363 | 8.285 | 1.00 | 25.90 | CPS3 |
| ATOM | 2251 | O | GLU | 48 | 44.633 | 41.197 | 8.589 | 1.00 | 24.51 | CPS3 |
| ATOM | 2252 | N | PHE | 49 | 42.601 | 42.065 | 9.030 | 1.00 | 24.05 | CPS3 |
| ATOM | 2253 | CA | PHE | 49 | 42.995 | 42.688 | 10.293 | 1.00 | 24.45 | CPS3 |
| ATOM | 2254 | CB | PHE | 49 | 41.809 | 43.473 | 10.866 | 1.00 | 25.52 | CPS3 |
| ATOM | 2255 | CG | PHE | 49 | 42.073 | 44.119 | 12.203 | 1.00 | 26.02 | CPS3 |
| ATOM | 2256 | CD1 | PHE | 49 | 42.503 | 45.440 | 12.285 | 1.00 | 26.53 | CPS3 |
| ATOM | 2257 | CD2 | PHE | 49 | 41.842 | 43.419 | 13.385 | 1.00 | 26.09 | CPS3 |
| ATOM | 2258 | CE1 | PHE | 49 | 42.688 | 46.061 | 13.529 | 1.00 | 26.57 | CPS3 |
| ATOM | 2259 | CE2 | PHE | 49 | 42.028 | 44.027 | 14.630 | 1.00 | 25.34 | CPS3 |
| ATOM | 2260 | CZ | PHE | 49 | 42.448 | 45.350 | 14.702 | 1.00 | 24.86 | CPS3 |
| ATOM | 2261 | C | PHE | 49 | 43.431 | 41.603 | 11.278 | 1.00 | 24.05 | CPS3 |
| ATOM | 2262 | O | PHE | 49 | 44.499 | 41.691 | 11.885 | 1.00 | 22.16 | CPS3 |
| ATOM | 2263 | N | LEU | 50 | 42.597 | 40.577 | 11.429 | 1.00 | 23.09 | CPS3 |
| ATOM | 2264 | CA | LEU | 50 | 42.894 | 39.478 | 12.342 | 1.00 | 23.23 | CPS3 |
| ATOM | 2265 | CB | LEU | 50 | 41.727 | 38.488 | 12.348 | 1.00 | 24.42 | CPS3 |
| ATOM | 2266 | CG | LEU | 50 | 41.788 | 37.294 | 13.297 | 1.00 | 26.20 | CPS3 |
| ATOM | 2267 | CD1 | LEU | 50 | 42.039 | 37.735 | 14.751 | 1.00 | 26.62 | CPS3 |
| ATOM | 2268 | CD2 | LEU | 50 | 40.468 | 36.551 | 13.182 | 1.00 | 27.72 | CPS3 |
| ATOM | 2269 | C | LEU | 50 | 44.191 | 38.758 | 11.970 | 1.00 | 22.25 | CPS3 |
| ATOM | 2270 | O | LEU | 50 | 45.033 | 38.483 | 12.835 | 1.00 | 21.88 | CPS3 |
| ATOM | 2271 | N | ALA | 51 | 44.359 | 38.455 | 10.685 | 1.00 | 21.04 | CPS3 |
| ATOM | 2272 | CA | ALA | 51 | 45.564 | 37.773 | 10.223 | 1.00 | 20.88 | CPS3 |
| ATOM | 2273 | CB | ALA | 51 | 45.460 | 37.467 | 8.727 | 1.00 | 21.96 | CPS3 |
| ATOM | 2274 | C | ALA | 51 | 46.815 | 38.615 | 10.497 | 1.00 | 21.09 | CPS3 |
| ATOM | 2275 | O | ALA | 51 | 47.860 | 38.077 | 10.863 | 1.00 | 20.76 | CPS3 |
| ATOM | 2276 | N | GLY | 52 | 46.698 | 39.929 | 10.321 | 1.00 | 21.47 | CPS3 |
| ATOM | 2277 | CA | GLY | 52 | 47.830 | 40.814 | 10.559 | 1.00 | 20.85 | CPS3 |
| ATOM | 2278 | C | GLY | 52 | 48.230 | 40.871 | 12.026 | 1.00 | 21.87 | CPS3 |
| ATOM | 2279 | O | GLY | 52 | 49.420 | 40.891 | 12.355 | 1.00 | 20.94 | CPS3 |

FIG. 1A-40

| ATOM | 2280 | N   | ARG | 53 | 47.234 | 40.907 | 12.908 | 1.00 | 20.71 | CPS3 |
| ATOM | 2281 | CA  | ARG | 53 | 47.489 | 40.953 | 14.344 | 1.00 | 19.99 | CPS3 |
| ATOM | 2282 | CB  | ARG | 53 | 46.188 | 41.249 | 15.102 | 1.00 | 21.12 | CPS3 |
| ATOM | 2283 | CG  | ARG | 53 | 45.749 | 42.697 | 15.023 | 1.00 | 25.14 | CPS3 |
| ATOM | 2284 | CD  | ARG | 53 | 46.854 | 43.589 | 15.542 | 1.00 | 26.59 | CPS3 |
| ATOM | 2285 | NE  | ARG | 53 | 46.364 | 44.864 | 16.046 | 1.00 | 29.01 | CPS3 |
| ATOM | 2286 | CZ  | ARG | 53 | 46.020 | 45.905 | 15.293 | 1.00 | 29.46 | CPS3 |
| ATOM | 2287 | NH1 | ARG | 53 | 46.104 | 45.841 | 13.967 | 1.00 | 29.27 | CPS3 |
| ATOM | 2288 | NH2 | ARG | 53 | 45.615 | 47.028 | 15.882 | 1.00 | 26.91 | CPS3 |
| ATOM | 2289 | C   | ARG | 53 | 48.067 | 39.628 | 14.802 | 1.00 | 18.67 | CPS3 |
| ATOM | 2290 | O   | ARG | 53 | 48.983 | 39.585 | 15.623 | 1.00 | 19.03 | CPS3 |
| ATOM | 2291 | N   | PHE | 54 | 47.524 | 38.541 | 14.274 | 1.00 | 19.10 | CPS3 |
| ATOM | 2292 | CA  | PHE | 54 | 48.001 | 37.214 | 14.639 | 1.00 | 18.17 | CPS3 |
| ATOM | 2293 | CB  | PHE | 54 | 47.145 | 36.157 | 13.926 | 1.00 | 20.62 | CPS3 |
| ATOM | 2294 | CG  | PHE | 54 | 47.514 | 34.736 | 14.248 | 1.00 | 21.61 | CPS3 |
| ATOM | 2295 | CD1 | PHE | 54 | 48.429 | 34.050 | 13.462 | 1.00 | 22.92 | CPS3 |
| ATOM | 2296 | CD2 | PHE | 54 | 46.903 | 34.068 | 15.305 | 1.00 | 23.51 | CPS3 |
| ATOM | 2297 | CE1 | PHE | 54 | 48.731 | 32.726 | 13.713 | 1.00 | 24.49 | CPS3 |
| ATOM | 2298 | CE2 | PHE | 54 | 47.196 | 32.735 | 15.572 | 1.00 | 24.31 | CPS3 |
| ATOM | 2299 | CZ  | PHE | 54 | 48.113 | 32.061 | 14.773 | 1.00 | 26.02 | CPS3 |
| ATOM | 2300 | C   | PHE | 54 | 49.480 | 37.082 | 14.254 | 1.00 | 18.48 | CPS3 |
| ATOM | 2301 | O   | PHE | 54 | 50.296 | 36.615 | 15.049 | 1.00 | 16.83 | CPS3 |
| ATOM | 2302 | N   | ALA | 55 | 49.818 | 37.512 | 13.042 | 1.00 | 18.82 | CPS3 |
| ATOM | 2303 | CA  | ALA | 55 | 51.202 | 37.426 | 12.564 | 1.00 | 19.23 | CPS3 |
| ATOM | 2304 | CB  | ALA | 55 | 51.291 | 37.903 | 11.110 | 1.00 | 19.19 | CPS3 |
| ATOM | 2305 | C   | ALA | 55 | 52.121 | 38.271 | 13.439 | 1.00 | 17.75 | CPS3 |
| ATOM | 2306 | O   | ALA | 55 | 53.210 | 37.833 | 13.822 | 1.00 | 17.44 | CPS3 |
| ATOM | 2307 | N   | ALA | 56 | 51.678 | 39.481 | 13.755 | 1.00 | 17.64 | CPS3 |
| ATOM | 2308 | CA  | ALA | 56 | 52.490 | 40.382 | 14.572 | 1.00 | 17.27 | CPS3 |
| ATOM | 2309 | CB  | ALA | 56 | 51.828 | 41.769 | 14.651 | 1.00 | 17.54 | CPS3 |
| ATOM | 2310 | C   | ALA | 56 | 52.745 | 39.840 | 15.978 | 1.00 | 18.48 | CPS3 |
| ATOM | 2311 | O   | ALA | 56 | 53.869 | 39.927 | 16.492 | 1.00 | 16.93 | CPS3 |
| ATOM | 2312 | N   | LYS | 57 | 51.710 | 39.278 | 16.600 | 1.00 | 17.56 | CPS3 |
| ATOM | 2313 | CA  | LYS | 57 | 51.864 | 38.758 | 17.953 | 1.00 | 17.39 | CPS3 |
| ATOM | 2314 | CB  | LYS | 57 | 50.484 | 38.545 | 18.593 | 1.00 | 17.01 | CPS3 |
| ATOM | 2315 | CG  | LYS | 57 | 49.741 | 39.852 | 18.728 | 1.00 | 17.00 | CPS3 |
| ATOM | 2316 | CD  | LYS | 57 | 48.445 | 39.709 | 19.516 | 1.00 | 17.39 | CPS3 |
| ATOM | 2317 | CE  | LYS | 57 | 47.650 | 41.015 | 19.466 | 1.00 | 17.65 | CPS3 |
| ATOM | 2318 | NZ  | LYS | 57 | 46.589 | 41.049 | 20.526 | 1.00 | 18.42 | CPS3 |
| ATOM | 2319 | C   | LYS | 57 | 52.694 | 37.492 | 17.958 | 1.00 | 18.30 | CPS3 |
| ATOM | 2320 | O   | LYS | 57 | 53.456 | 37.248 | 18.895 | 1.00 | 17.97 | CPS3 |
| ATOM | 2321 | N   | GLU | 58 | 52.555 | 36.692 | 16.903 | 1.00 | 19.29 | CPS3 |
| ATOM | 2322 | CA  | GLU | 58 | 53.343 | 35.477 | 16.770 | 1.00 | 21.29 | CPS3 |
| ATOM | 2323 | CB  | GLU | 58 | 52.885 | 34.710 | 15.518 | 1.00 | 25.54 | CPS3 |
| ATOM | 2324 | CG  | GLU | 58 | 52.985 | 33.214 | 15.639 | 1.00 | 35.02 | CPS3 |
| ATOM | 2325 | CD  | GLU | 58 | 52.321 | 32.682 | 16.899 | 1.00 | 36.12 | CPS3 |
| ATOM | 2326 | OE1 | GLU | 58 | 51.079 | 32.744 | 17.033 | 1.00 | 40.18 | CPS3 |
| ATOM | 2327 | OE2 | GLU | 58 | 53.059 | 32.207 | 17.772 | 1.00 | 38.83 | CPS3 |
| ATOM | 2328 | C   | GLU | 58 | 54.818 | 35.900 | 16.644 | 1.00 | 20.21 | CPS3 |
| ATOM | 2329 | O   | GLU | 58 | 55.696 | 35.365 | 17.335 | 1.00 | 19.40 | CPS3 |
| ATOM | 2330 | N   | ALA | 59 | 55.089 | 36.867 | 15.768 | 1.00 | 16.40 | CPS3 |
| ATOM | 2331 | CA  | ALA | 59 | 56.458 | 37.353 | 15.580 | 1.00 | 17.36 | CPS3 |
| ATOM | 2332 | CB  | ALA | 59 | 56.491 | 38.461 | 14.521 | 1.00 | 17.44 | CPS3 |
| ATOM | 2333 | C   | ALA | 59 | 57.011 | 37.883 | 16.900 | 1.00 | 17.42 | CPS3 |
| ATOM | 2334 | O   | ALA | 59 | 58.160 | 37.595 | 17.271 | 1.00 | 17.74 | CPS3 |
| ATOM | 2335 | N   | PHE | 60 | 56.200 | 38.657 | 17.613 | 1.00 | 16.51 | CPS3 |
| ATOM | 2336 | CA  | PHE | 60 | 56.655 | 39.219 | 18.882 | 1.00 | 17.55 | CPS3 |

FIG. 1A-41

| ATOM | 2337 | CB  | PHE | 60 | 55.586 | 40.128 | 19.502 | 1.00 | 17.91 | CPS3 |
| ATOM | 2338 | CG  | PHE | 60 | 55.984 | 40.684 | 20.847 | 1.00 | 18.76 | CPS3 |
| ATOM | 2339 | CD1 | PHE | 60 | 56.755 | 41.838 | 20.933 | 1.00 | 18.58 | CPS3 |
| ATOM | 2340 | CD2 | PHE | 60 | 55.659 | 40.001 | 22.021 | 1.00 | 19.49 | CPS3 |
| ATOM | 2341 | CE1 | PHE | 60 | 57.212 | 42.309 | 22.172 | 1.00 | 20.20 | CPS3 |
| ATOM | 2342 | CE2 | PHE | 60 | 56.107 | 40.459 | 23.266 | 1.00 | 20.93 | CPS3 |
| ATOM | 2343 | CZ  | PHE | 60 | 56.886 | 41.612 | 23.341 | 1.00 | 20.99 | CPS3 |
| ATOM | 2344 | C   | PHE | 60 | 57.008 | 38.118 | 19.883 | 1.00 | 18.91 | CPS3 |
| ATOM | 2345 | O   | PHE | 60 | 58.053 | 38.173 | 20.543 | 1.00 | 18.95 | CPS3 |
| ATOM | 2346 | N   | SER | 61 | 56.137 | 37.123 | 20.001 | 1.00 | 18.23 | CPS3 |
| ATOM | 2347 | CA  | SER | 61 | 56.370 | 36.036 | 20.946 | 1.00 | 19.91 | CPS3 |
| ATOM | 2348 | CB  | SER | 61 | 55.167 | 35.081 | 20.978 | 1.00 | 20.94 | CPS3 |
| ATOM | 2349 | OG  | SER | 61 | 55.170 | 34.217 | 19.851 | 1.00 | 25.41 | CPS3 |
| ATOM | 2350 | C   | SER | 61 | 57.642 | 35.256 | 20.618 | 1.00 | 21.39 | CPS3 |
| ATOM | 2351 | O   | SER | 61 | 58.278 | 34.697 | 21.511 | 1.00 | 21.46 | CPS3 |
| ATOM | 2352 | N   | LYS | 62 | 58.011 | 35.206 | 19.345 | 1.00 | 20.86 | CPS3 |
| ATOM | 2353 | CA  | LYS | 62 | 59.227 | 34.500 | 18.958 | 1.00 | 23.14 | CPS3 |
| ATOM | 2354 | CB  | LYS | 62 | 59.239 | 34.237 | 17.455 | 1.00 | 24.31 | CPS3 |
| ATOM | 2355 | CG  | LYS | 62 | 58.295 | 33.143 | 17.003 | 1.00 | 28.06 | CPS3 |
| ATOM | 2356 | CD  | LYS | 62 | 58.340 | 33.057 | 15.490 | 1.00 | 32.02 | CPS3 |
| ATOM | 2357 | CE  | LYS | 62 | 58.060 | 31.655 | 14.987 | 1.00 | 34.92 | CPS3 |
| ATOM | 2358 | NZ  | LYS | 62 | 58.159 | 31.623 | 13.510 | 1.00 | 35.49 | CPS3 |
| ATOM | 2359 | C   | LYS | 62 | 60.444 | 35.343 | 19.340 | 1.00 | 22.30 | CPS3 |
| ATOM | 2360 | O   | LYS | 62 | 61.464 | 34.815 | 19.788 | 1.00 | 23.20 | CPS3 |
| ATOM | 2361 | N   | ALA | 63 | 60.337 | 36.654 | 19.156 | 1.00 | 19.62 | CPS3 |
| ATOM | 2362 | CA  | ALA | 63 | 61.437 | 37.547 | 19.512 | 1.00 | 20.06 | CPS3 |
| ATOM | 2363 | CB  | ALA | 63 | 61.145 | 38.960 | 19.019 | 1.00 | 20.10 | CPS3 |
| ATOM | 2364 | C   | ALA | 63 | 61.603 | 37.543 | 21.035 | 1.00 | 21.63 | CPS3 |
| ATOM | 2365 | O   | ALA | 63 | 62.724 | 37.529 | 21.550 | 1.00 | 23.66 | CPS3 |
| ATOM | 2366 | N   | PHE | 64 | 60.480 | 37.536 | 21.749 | 1.00 | 20.52 | CPS3 |
| ATOM | 2367 | CA  | PHE | 64 | 60.502 | 37.548 | 23.209 | 1.00 | 23.24 | CPS3 |
| ATOM | 2368 | CB  | PHE | 64 | 59.079 | 37.690 | 23.752 | 1.00 | 23.53 | CPS3 |
| ATOM | 2369 | CG  | PHE | 64 | 59.023 | 38.051 | 25.211 | 1.00 | 24.99 | CPS3 |
| ATOM | 2370 | CD1 | PHE | 64 | 59.492 | 39.283 | 25.653 | 1.00 | 26.02 | CPS3 |
| ATOM | 2371 | CD2 | PHE | 64 | 58.488 | 37.163 | 26.135 | 1.00 | 25.12 | CPS3 |
| ATOM | 2372 | CE1 | PHE | 64 | 59.423 | 39.632 | 27.008 | 1.00 | 28.33 | CPS3 |
| ATOM | 2373 | CE2 | PHE | 64 | 58.412 | 37.495 | 27.484 | 1.00 | 26.52 | CPS3 |
| ATOM | 2374 | CZ  | PHE | 64 | 58.877 | 38.729 | 27.924 | 1.00 | 27.24 | CPS3 |
| ATOM | 2375 | C   | PHE | 64 | 61.140 | 36.251 | 23.718 | 1.00 | 25.44 | CPS3 |
| ATOM | 2376 | O   | PHE | 64 | 61.688 | 36.204 | 24.826 | 1.00 | 24.64 | CPS3 |
| ATOM | 2377 | N   | GLY | 65 | 61.039 | 35.202 | 22.910 | 1.00 | 26.62 | CPS3 |
| ATOM | 2378 | CA  | GLY | 65 | 61.662 | 33.938 | 23.255 | 1.00 | 30.83 | CPS3 |
| ATOM | 2379 | C   | GLY | 65 | 60.802 | 32.879 | 23.912 | 1.00 | 32.24 | CPS3 |
| ATOM | 2380 | O   | GLY | 65 | 61.209 | 31.719 | 23.980 | 1.00 | 33.69 | CPS3 |
| ATOM | 2381 | N   | THR | 66 | 59.616 | 33.256 | 24.376 | 1.00 | 32.78 | CPS3 |
| ATOM | 2382 | CA  | THR | 66 | 58.733 | 32.302 | 25.043 | 1.00 | 34.27 | CPS3 |
| ATOM | 2383 | CB  | THR | 66 | 57.991 | 32.969 | 26.200 | 1.00 | 35.66 | CPS3 |
| ATOM | 2384 | OG1 | THR | 66 | 57.122 | 33.978 | 25.668 | 1.00 | 37.64 | CPS3 |
| ATOM | 2385 | CG2 | THR | 66 | 58.969 | 33.610 | 27.179 | 1.00 | 34.33 | CPS3 |
| ATOM | 2386 | C   | THR | 66 | 57.663 | 31.691 | 24.143 | 1.00 | 34.55 | CPS3 |
| ATOM | 2387 | O   | THR | 66 | 57.154 | 30.610 | 24.431 | 1.00 | 34.19 | CPS3 |
| ATOM | 2388 | N   | GLY | 67 | 57.320 | 32.376 | 23.054 | 1.00 | 34.33 | CPS3 |
| ATOM | 2389 | CA  | GLY | 67 | 56.256 | 31.877 | 22.198 | 1.00 | 34.53 | CPS3 |
| ATOM | 2390 | C   | GLY | 67 | 54.962 | 32.175 | 22.945 | 1.00 | 34.85 | CPS3 |
| ATOM | 2391 | O   | GLY | 67 | 55.012 | 32.656 | 24.080 | 1.00 | 34.24 | CPS3 |
| ATOM | 2392 | N   | ILE | 68 | 53.808 | 31.915 | 22.338 | 1.00 | 35.31 | CPS3 |
| ATOM | 2393 | CA  | ILE | 68 | 52.537 | 32.175 | 23.016 | 1.00 | 35.28 | CPS3 |

FIG. 1A-42

| ATOM | 2394 | CB | ILE | 68 | 51.389 | 32.407 | 22.011 | 1.00 | 34.11 | CPS3 |
|---|---|---|---|---|---|---|---|---|---|---|
| ATOM | 2395 | CG2 | ILE | 68 | 50.052 | 32.474 | 22.755 | 1.00 | 32.62 | CPS3 |
| ATOM | 2396 | CG1 | ILE | 68 | 51.640 | 33.690 | 21.219 | 1.00 | 32.54 | CPS3 |
| ATOM | 2397 | CD1 | ILE | 68 | 51.647 | 34.958 | 22.063 | 1.00 | 32.72 | CPS3 |
| ATOM | 2398 | C | ILE | 68 | 52.161 | 30.999 | 23.910 | 1.00 | 36.56 | CPS3 |
| ATOM | 2399 | O | ILE | 68 | 52.085 | 29.862 | 23.447 | 1.00 | 36.53 | CPS3 |
| ATOM | 2400 | N | GLY | 69 | 51.922 | 31.279 | 25.187 | 1.00 | 36.84 | CPS3 |
| ATOM | 2401 | CA | GLY | 69 | 51.565 | 30.221 | 26.115 | 1.00 | 38.40 | CPS3 |
| ATOM | 2402 | C | GLY | 69 | 51.481 | 30.700 | 27.550 | 1.00 | 38.69 | CPS3 |
| ATOM | 2403 | O | GLY | 69 | 50.987 | 31.797 | 27.820 | 1.00 | 38.83 | CPS3 |
| ATOM | 2404 | N | ALA | 70 | 51.978 | 29.882 | 28.474 | 1.00 | 38.37 | CPS3 |
| ATOM | 2405 | CA | ALA | 70 | 51.949 | 30.215 | 29.895 | 1.00 | 37.89 | CPS3 |
| ATOM | 2406 | CB | ALA | 70 | 52.510 | 29.043 | 30.710 | 1.00 | 38.76 | CPS3 |
| ATOM | 2407 | C | ALA | 70 | 52.684 | 31.506 | 30.270 | 1.00 | 37.56 | CPS3 |
| ATOM | 2408 | O | ALA | 70 | 52.225 | 32.262 | 31.122 | 1.00 | 37.72 | CPS3 |
| ATOM | 2409 | N | GLN | 71 | 53.817 | 31.769 | 29.634 | 1.00 | 36.91 | CPS3 |
| ATOM | 2410 | CA | GLN | 71 | 54.590 | 32.965 | 29.954 | 1.00 | 36.41 | CPS3 |
| ATOM | 2411 | CB | GLN | 71 | 56.072 | 32.593 | 29.697 | 1.00 | 38.98 | CPS3 |
| ATOM | 2412 | CG | GLN | 71 | 56.540 | 31.358 | 30.251 | 1.00 | 42.83 | CPS3 |
| ATOM | 2413 | CD | GLN | 71 | 58.024 | 31.132 | 30.053 | 1.00 | 45.56 | CPS3 |
| ATOM | 2414 | OE1 | GLN | 71 | 58.854 | 31.783 | 30.695 | 1.00 | 47.59 | CPS3 |
| ATOM | 2415 | NE2 | GLN | 71 | 58.369 | 30.211 | 29.156 | 1.00 | 47.26 | CPS3 |
| ATOM | 2416 | C | GLN | 71 | 54.167 | 34.225 | 29.192 | 1.00 | 33.99 | CPS3 |
| ATOM | 2417 | O | GLN | 71 | 54.514 | 35.332 | 29.585 | 1.00 | 34.52 | CPS3 |
| ATOM | 2418 | N | LEU | 72 | 53.422 | 34.056 | 28.107 | 1.00 | 30.98 | CPS3 |
| ATOM | 2419 | CA | LEU | 72 | 52.993 | 35.195 | 27.304 | 1.00 | 27.97 | CPS3 |
| ATOM | 2420 | CB | LEU | 72 | 54.108 | 35.592 | 26.333 | 1.00 | 26.71 | CPS3 |
| ATOM | 2421 | CG | LEU | 72 | 53.888 | 36.797 | 25.415 | 1.00 | 25.21 | CPS3 |
| ATOM | 2422 | CD1 | LEU | 72 | 54.008 | 38.103 | 26.212 | 1.00 | 25.07 | CPS3 |
| ATOM | 2423 | CD2 | LEU | 72 | 54.930 | 36.760 | 24.299 | 1.00 | 26.26 | CPS3 |
| ATOM | 2424 | C | LEU | 72 | 51.727 | 34.852 | 26.532 | 1.00 | 26.94 | CPS3 |
| ATOM | 2425 | O | LEU | 72 | 51.679 | 33.877 | 25.779 | 1.00 | 27.79 | CPS3 |
| ATOM | 2426 | N | SER | 73 | 50.706 | 35.673 | 26.723 | 1.00 | 24.63 | CPS3 |
| ATOM | 2427 | CA | SER | 73 | 49.416 | 35.486 | 26.081 | 1.00 | 24.89 | CPS3 |
| ATOM | 2428 | CB | SER | 73 | 48.318 | 35.677 | 27.135 | 1.00 | 26.50 | CPS3 |
| ATOM | 2429 | OG | SER | 73 | 47.068 | 35.913 | 26.531 | 1.00 | 28.99 | CPS3 |
| ATOM | 2430 | C | SER | 73 | 49.228 | 36.504 | 24.957 | 1.00 | 23.56 | CPS3 |
| ATOM | 2431 | O | SER | 73 | 49.903 | 37.537 | 24.942 | 1.00 | 22.03 | CPS3 |
| ATOM | 2432 | N | PHE | 74 | 48.324 | 36.211 | 24.017 | 1.00 | 22.96 | CPS3 |
| ATOM | 2433 | CA | PHE | 74 | 48.016 | 37.150 | 22.933 | 1.00 | 21.51 | CPS3 |
| ATOM | 2434 | CB | PHE | 74 | 46.922 | 36.599 | 22.010 | 1.00 | 23.03 | CPS3 |
| ATOM | 2435 | CG | PHE | 74 | 47.386 | 35.535 | 21.060 | 1.00 | 24.56 | CPS3 |
| ATOM | 2436 | CD1 | PHE | 74 | 48.330 | 35.820 | 20.079 | 1.00 | 25.15 | CPS3 |
| ATOM | 2437 | CD2 | PHE | 74 | 46.854 | 34.246 | 21.127 | 1.00 | 26.66 | CPS3 |
| ATOM | 2438 | CE1 | PHE | 74 | 48.740 | 34.837 | 19.175 | 1.00 | 25.67 | CPS3 |
| ATOM | 2439 | CE2 | PHE | 74 | 47.257 | 33.251 | 20.226 | 1.00 | 27.19 | CPS3 |
| ATOM | 2440 | CZ | PHE | 74 | 48.200 | 33.547 | 19.251 | 1.00 | 26.99 | CPS3 |
| ATOM | 2441 | C | PHE | 74 | 47.476 | 38.424 | 23.573 | 1.00 | 22.00 | CPS3 |
| ATOM | 2442 | O | PHE | 74 | 47.624 | 39.519 | 23.038 | 1.00 | 20.92 | CPS3 |
| ATOM | 2443 | N | GLN | 75 | 46.830 | 38.270 | 24.726 | 1.00 | 22.26 | CPS3 |
| ATOM | 2444 | CA | GLN | 75 | 46.246 | 39.402 | 25.431 | 1.00 | 22.41 | CPS3 |
| ATOM | 2445 | CB | GLN | 75 | 45.313 | 38.895 | 26.543 | 1.00 | 23.41 | CPS3 |
| ATOM | 2446 | CG | GLN | 75 | 44.119 | 38.109 | 26.025 | 1.00 | 25.20 | CPS3 |
| ATOM | 2447 | CD | GLN | 75 | 43.257 | 38.954 | 25.118 | 1.00 | 26.61 | CPS3 |
| ATOM | 2448 | OE1 | GLN | 75 | 42.891 | 40.080 | 25.476 | 1.00 | 27.48 | CPS3 |
| ATOM | 2449 | NE2 | GLN | 75 | 42.928 | 38.429 | 23.938 | 1.00 | 25.82 | CPS3 |
| ATOM | 2450 | C | GLN | 75 | 47.287 | 40.350 | 26.028 | 1.00 | 22.75 | CPS3 |

FIG. 1A-43

| ATOM | 2451 | O | GLN | 75 | 46.962 | 41.486 | 26.389 | 1.00 | 21.60 | CPS3 |
|------|------|-----|-----|----|--------|--------|--------|------|-------|------|
| ATOM | 2452 | N | ASP | 76 | 48.532 | 39.890 | 26.146 | 1.00 | 21.97 | CPS3 |
| ATOM | 2453 | CA | ASP | 76 | 49.595 | 40.730 | 26.710 | 1.00 | 22.16 | CPS3 |
| ATOM | 2454 | CB | ASP | 76 | 50.738 | 39.876 | 27.279 | 1.00 | 22.82 | CPS3 |
| ATOM | 2455 | CG | ASP | 76 | 50.332 | 39.058 | 28.494 | 1.00 | 25.52 | CPS3 |
| ATOM | 2456 | OD1 | ASP | 76 | 49.557 | 39.565 | 29.332 | 1.00 | 25.20 | CPS3 |
| ATOM | 2457 | OD2 | ASP | 76 | 50.823 | 37.915 | 28.614 | 1.00 | 24.81 | CPS3 |
| ATOM | 2458 | C | ASP | 76 | 50.223 | 41.635 | 25.661 | 1.00 | 21.66 | CPS3 |
| ATOM | 2459 | O | ASP | 76 | 51.059 | 42.481 | 25.982 | 1.00 | 19.63 | CPS3 |
| ATOM | 2460 | N | ILE | 77 | 49.826 | 41.450 | 24.405 | 1.00 | 21.29 | CPS3 |
| ATOM | 2461 | CA | ILE | 77 | 50.416 | 42.202 | 23.301 | 1.00 | 19.67 | CPS3 |
| ATOM | 2462 | CB | ILE | 77 | 51.088 | 41.225 | 22.318 | 1.00 | 19.23 | CPS3 |
| ATOM | 2463 | CG2 | ILE | 77 | 51.893 | 41.995 | 21.253 | 1.00 | 18.53 | CPS3 |
| ATOM | 2464 | CG1 | ILE | 77 | 51.987 | 40.247 | 23.084 | 1.00 | 17.28 | CPS3 |
| ATOM | 2465 | CD1 | ILE | 77 | 52.313 | 38.989 | 22.257 | 1.00 | 19.10 | CPS3 |
| ATOM | 2466 | C | ILE | 77 | 49.379 | 42.988 | 22.520 | 1.00 | 20.27 | CPS3 |
| ATOM | 2467 | O | ILE | 77 | 48.401 | 42.416 | 22.062 | 1.00 | 20.00 | CPS3 |
| ATOM | 2468 | N | GLU | 78 | 49.603 | 44.288 | 22.354 | 1.00 | 21.09 | CPS3 |
| ATOM | 2469 | CA | GLU | 78 | 48.670 | 45.106 | 21.591 | 1.00 | 20.73 | CPS3 |
| ATOM | 2470 | CB | GLU | 78 | 47.909 | 46.082 | 22.496 | 1.00 | 22.17 | CPS3 |
| ATOM | 2471 | CG | GLU | 78 | 46.819 | 46.843 | 21.737 | 1.00 | 24.01 | CPS3 |
| ATOM | 2472 | CD | GLU | 78 | 45.862 | 47.584 | 22.651 | 1.00 | 27.03 | CPS3 |
| ATOM | 2473 | OE1 | GLU | 78 | 46.036 | 48.806 | 22.844 | 1.00 | 28.55 | CPS3 |
| ATOM | 2474 | OE2 | GLU | 78 | 44.937 | 46.934 | 23.181 | 1.00 | 28.54 | CPS3 |
| ATOM | 2475 | C | GLU | 78 | 49.384 | 45.892 | 20.508 | 1.00 | 20.37 | CPS3 |
| ATOM | 2476 | O | GLU | 78 | 50.431 | 46.485 | 20.749 | 1.00 | 20.67 | CPS3 |
| ATOM | 2477 | N | ILE | 79 | 48.826 | 45.877 | 19.303 | 1.00 | 19.96 | CPS3 |
| ATOM | 2478 | CA | ILE | 79 | 49.420 | 46.642 | 18.212 | 1.00 | 19.14 | CPS3 |
| ATOM | 2479 | CB | ILE | 79 | 49.368 | 45.860 | 16.850 | 1.00 | 19.23 | CPS3 |
| ATOM | 2480 | CG2 | ILE | 79 | 49.577 | 46.830 | 15.678 | 1.00 | 19.82 | CPS3 |
| ATOM | 2481 | CG1 | ILE | 79 | 50.477 | 44.798 | 16.795 | 1.00 | 21.31 | CPS3 |
| ATOM | 2482 | CD1 | ILE | 79 | 50.318 | 43.645 | 17.758 | 1.00 | 22.36 | CPS3 |
| ATOM | 2483 | C | ILE | 79 | 48.629 | 47.942 | 18.090 | 1.00 | 20.00 | CPS3 |
| ATOM | 2484 | O | ILE | 79 | 47.389 | 47.928 | 18.088 | 1.00 | 20.09 | CPS3 |
| ATOM | 2485 | N | ARG | 80 | 49.340 | 49.068 | 18.028 | 1.00 | 19.20 | CPS3 |
| ATOM | 2486 | CA | ARG | 80 | 48.703 | 50.380 | 17.861 | 1.00 | 20.32 | CPS3 |
| ATOM | 2487 | CB | ARG | 80 | 48.924 | 51.258 | 19.107 | 1.00 | 20.53 | CPS3 |
| ATOM | 2488 | CG | ARG | 80 | 48.340 | 50.644 | 20.380 | 1.00 | 21.77 | CPS3 |
| ATOM | 2489 | CD | ARG | 80 | 48.505 | 51.527 | 21.617 | 1.00 | 23.01 | CPS3 |
| ATOM | 2490 | NE | ARG | 80 | 47.957 | 50.833 | 22.780 | 1.00 | 23.15 | CPS3 |
| ATOM | 2491 | CZ | ARG | 80 | 48.032 | 51.267 | 24.038 | 1.00 | 25.30 | CPS3 |
| ATOM | 2492 | NH1 | ARG | 80 | 48.634 | 52.412 | 24.321 | 1.00 | 20.84 | CPS3 |
| ATOM | 2493 | NH2 | ARG | 80 | 47.511 | 50.536 | 25.014 | 1.00 | 26.37 | CPS3 |
| ATOM | 2494 | C | ARG | 80 | 49.349 | 51.037 | 16.640 | 1.00 | 20.88 | CPS3 |
| ATOM | 2495 | O | ARG | 80 | 50.362 | 50.550 | 16.138 | 1.00 | 20.01 | CPS3 |
| ATOM | 2496 | N | LYS | 81 | 48.755 | 52.123 | 16.148 | 1.00 | 21.43 | CPS3 |
| ATOM | 2497 | CA | LYS | 81 | 49.316 | 52.839 | 14.998 | 1.00 | 22.45 | CPS3 |
| ATOM | 2498 | CB | LYS | 81 | 48.327 | 52.868 | 13.829 | 1.00 | 25.71 | CPS3 |
| ATOM | 2499 | CG | LYS | 81 | 47.907 | 51.512 | 13.309 | 1.00 | 31.70 | CPS3 |
| ATOM | 2500 | CD | LYS | 81 | 49.057 | 50.788 | 12.665 | 1.00 | 34.29 | CPS3 |
| ATOM | 2501 | CE | LYS | 81 | 48.582 | 49.508 | 11.996 | 1.00 | 36.91 | CPS3 |
| ATOM | 2502 | NZ | LYS | 81 | 47.631 | 49.799 | 10.888 | 1.00 | 38.59 | CPS3 |
| ATOM | 2503 | C | LYS | 81 | 49.591 | 54.269 | 15.423 | 1.00 | 22.25 | CPS3 |
| ATOM | 2504 | O | LYS | 81 | 48.757 | 54.882 | 16.095 | 1.00 | 21.74 | CPS3 |
| ATOM | 2505 | N | ASP | 82 | 50.750 | 54.801 | 15.048 | 1.00 | 21.32 | CPS3 |
| ATOM | 2506 | CA | ASP | 82 | 51.055 | 56.169 | 15.411 | 1.00 | 24.29 | CPS3 |
| ATOM | 2507 | CB | ASP | 82 | 52.568 | 56.396 | 15.564 | 1.00 | 23.73 | CPS3 |

FIG. 1A-44

| ATOM | 2508 | CG | ASP | 82 | 53.340 | 56.303 | 14.253 | 1.00 | 25.37 | CPS3 |
|---|---|---|---|---|---|---|---|---|---|---|
| ATOM | 2509 | OD1 | ASP | 82 | 52.736 | 56.371 | 13.161 | 1.00 | 25.70 | CPS3 |
| ATOM | 2510 | OD2 | ASP | 82 | 54.585 | 56.182 | 14.331 | 1.00 | 27.40 | CPS3 |
| ATOM | 2511 | C | ASP | 82 | 50.446 | 57.129 | 14.394 | 1.00 | 26.03 | CPS3 |
| ATOM | 2512 | O | ASP | 82 | 49.682 | 56.711 | 13.518 | 1.00 | 25.08 | CPS3 |
| ATOM | 2513 | N | GLN | 83 | 50.783 | 58.406 | 14.521 | 1.00 | 27.30 | CPS3 |
| ATOM | 2514 | CA | GLN | 83 | 50.243 | 59.439 | 13.648 | 1.00 | 30.37 | CPS3 |
| ATOM | 2515 | CB | GLN | 83 | 50.694 | 60.810 | 14.158 | 1.00 | 32.92 | CPS3 |
| ATOM | 2516 | CG | GLN | 83 | 50.035 | 61.193 | 15.481 | 1.00 | 36.66 | CPS3 |
| ATOM | 2517 | CD | GLN | 83 | 48.633 | 61.738 | 15.292 | 1.00 | 40.09 | CPS3 |
| ATOM | 2518 | OE1 | GLN | 83 | 48.448 | 62.940 | 15.079 | 1.00 | 42.06 | CPS3 |
| ATOM | 2519 | NE2 | GLN | 83 | 47.637 | 60.859 | 15.354 | 1.00 | 40.07 | CPS3 |
| ATOM | 2520 | C | GLN | 83 | 50.587 | 59.276 | 12.167 | 1.00 | 30.09 | CPS3 |
| ATOM | 2521 | O | GLN | 83 | 49.900 | 59.834 | 11.308 | 1.00 | 30.34 | CPS3 |
| ATOM | 2522 | N | ASN | 84 | 51.647 | 58.532 | 11.865 | 1.00 | 29.03 | CPS3 |
| ATOM | 2523 | CA | ASN | 84 | 52.024 | 58.296 | 10.471 | 1.00 | 29.59 | CPS3 |
| ATOM | 2524 | CB | ASN | 84 | 53.544 | 58.202 | 10.303 | 1.00 | 31.65 | CPS3 |
| ATOM | 2525 | CG | ASN | 84 | 54.239 | 59.536 | 10.457 | 1.00 | 34.87 | CPS3 |
| ATOM | 2526 | OD1 | ASN | 84 | 53.732 | 60.566 | 10.022 | 1.00 | 36.47 | CPS3 |
| ATOM | 2527 | ND2 | ASN | 84 | 55.425 | 59.520 | 11.060 | 1.00 | 36.00 | CPS3 |
| ATOM | 2528 | C | ASN | 84 | 51.419 | 56.990 | 9.974 | 1.00 | 28.93 | CPS3 |
| ATOM | 2529 | O | ASN | 84 | 51.609 | 56.613 | 8.815 | 1.00 | 30.32 | CPS3 |
| ATOM | 2530 | N | GLY | 85 | 50.712 | 56.286 | 10.852 | 1.00 | 26.33 | CPS3 |
| ATOM | 2531 | CA | GLY | 85 | 50.116 | 55.019 | 10.464 | 1.00 | 24.71 | CPS3 |
| ATOM | 2532 | C | GLY | 85 | 51.063 | 53.851 | 10.697 | 1.00 | 23.82 | CPS3 |
| ATOM | 2533 | O | GLY | 85 | 50.759 | 52.713 | 10.341 | 1.00 | 24.11 | CPS3 |
| ATOM | 2534 | N | LYS | 86 | 52.214 | 54.131 | 11.302 | 1.00 | 21.10 | CPS3 |
| ATOM | 2535 | CA | LYS | 86 | 53.204 | 53.096 | 11.582 | 1.00 | 21.62 | CPS3 |
| ATOM | 2536 | CB | LYS | 86 | 54.561 | 53.738 | 11.883 | 1.00 | 21.42 | CPS3 |
| ATOM | 2537 | CG | LYS | 86 | 55.625 | 52.760 | 12.401 | 1.00 | 23.00 | CPS3 |
| ATOM | 2538 | CD | LYS | 86 | 56.097 | 51.789 | 11.325 | 1.00 | 22.60 | CPS3 |
| ATOM | 2539 | CE | LYS | 86 | 57.073 | 50.766 | 11.921 | 1.00 | 21.76 | CPS3 |
| ATOM | 2540 | NZ | LYS | 86 | 57.761 | 49.970 | 10.852 | 1.00 | 21.43 | CPS3 |
| ATOM | 2541 | C | LYS | 86 | 52.782 | 52.244 | 12.783 | 1.00 | 20.36 | CPS3 |
| ATOM | 2542 | O | LYS | 86 | 52.468 | 52.776 | 13.843 | 1.00 | 20.19 | CPS3 |
| ATOM | 2543 | N | PRO | 87 | 52.770 | 50.912 | 12.632 | 1.00 | 20.59 | CPS3 |
| ATOM | 2544 | CD | PRO | 87 | 52.925 | 50.084 | 11.423 | 1.00 | 21.13 | CPS3 |
| ATOM | 2545 | CA | PRO | 87 | 52.375 | 50.091 | 13.781 | 1.00 | 20.38 | CPS3 |
| ATOM | 2546 | CB | PRO | 87 | 52.082 | 48.729 | 13.160 | 1.00 | 22.01 | CPS3 |
| ATOM | 2547 | CG | PRO | 87 | 53.044 | 48.675 | 12.009 | 1.00 | 23.44 | CPS3 |
| ATOM | 2548 | C | PRO | 87 | 53.481 | 49.991 | 14.812 | 1.00 | 18.94 | CPS3 |
| ATOM | 2549 | O | PRO | 87 | 54.662 | 49.996 | 14.468 | 1.00 | 18.59 | CPS3 |
| ATOM | 2550 | N | TYR | 88 | 53.092 | 49.938 | 16.082 | 1.00 | 18.68 | CPS3 |
| ATOM | 2551 | CA | TYR | 88 | 54.064 | 49.757 | 17.155 | 1.00 | 18.87 | CPS3 |
| ATOM | 2552 | CB | TYR | 88 | 54.566 | 51.093 | 17.734 | 1.00 | 19.03 | CPS3 |
| ATOM | 2553 | CG | TYR | 88 | 53.531 | 51.940 | 18.426 | 1.00 | 19.37 | CPS3 |
| ATOM | 2554 | CD1 | TYR | 88 | 53.395 | 51.915 | 19.804 | 1.00 | 19.95 | CPS3 |
| ATOM | 2555 | CE1 | TYR | 88 | 52.413 | 52.683 | 20.449 | 1.00 | 20.13 | CPS3 |
| ATOM | 2556 | CD2 | TYR | 88 | 52.665 | 52.756 | 17.693 | 1.00 | 19.40 | CPS3 |
| ATOM | 2557 | CE2 | TYR | 88 | 51.690 | 53.519 | 18.315 | 1.00 | 19.13 | CPS3 |
| ATOM | 2558 | CZ | TYR | 88 | 51.562 | 53.479 | 19.691 | 1.00 | 18.55 | CPS3 |
| ATOM | 2559 | OH | TYR | 88 | 50.568 | 54.204 | 20.299 | 1.00 | 19.71 | CPS3 |
| ATOM | 2560 | C | TYR | 88 | 53.385 | 48.899 | 18.211 | 1.00 | 18.42 | CPS3 |
| ATOM | 2561 | O | TYR | 88 | 52.159 | 48.825 | 18.277 | 1.00 | 18.60 | CPS3 |
| ATOM | 2562 | N | ILE | 89 | 54.196 | 48.233 | 19.020 | 1.00 | 17.79 | CPS3 |
| ATOM | 2563 | CA | ILE | 89 | 53.675 | 47.331 | 20.022 | 1.00 | 18.21 | CPS3 |
| ATOM | 2564 | CB | ILE | 89 | 54.406 | 45.966 | 19.939 | 1.00 | 17.33 | CPS3 |

FIG. 1A-45

| ATOM | 2565 | CG2 | ILE | 89 | 54.146 | 45.145 | 21.217 | 1.00 | 18.20 | CPS3 |
| ATOM | 2566 | CG1 | ILE | 89 | 53.938 | 45.192 | 18.696 | 1.00 | 18.54 | CPS3 |
| ATOM | 2567 | CD1 | ILE | 89 | 54.805 | 43.948 | 18.365 | 1.00 | 18.01 | CPS3 |
| ATOM | 2568 | C | ILE | 89 | 53.775 | 47.829 | 21.450 | 1.00 | 18.41 | CPS3 |
| ATOM | 2569 | O | ILE | 89 | 54.749 | 48.465 | 21.832 | 1.00 | 18.45 | CPS3 |
| ATOM | 2570 | N | ILE | 90 | 52.737 | 47.539 | 22.221 | 1.00 | 19.17 | CPS3 |
| ATOM | 2571 | CA | ILE | 90 | 52.722 | 47.852 | 23.645 | 1.00 | 20.34 | CPS3 |
| ATOM | 2572 | CB | ILE | 90 | 51.485 | 48.700 | 24.062 | 1.00 | 21.03 | CPS3 |
| ATOM | 2573 | CG2 | ILE | 90 | 51.364 | 48.738 | 25.608 | 1.00 | 21.79 | CPS3 |
| ATOM | 2574 | CG1 | ILE | 90 | 51.605 | 50.128 | 23.516 | 1.00 | 21.44 | CPS3 |
| ATOM | 2575 | CD1 | ILE | 90 | 52.787 | 50.918 | 24.079 | 1.00 | 22.03 | CPS3 |
| ATOM | 2576 | C | ILE | 90 | 52.618 | 46.483 | 24.314 | 1.00 | 20.90 | CPS3 |
| ATOM | 2577 | O | ILE | 90 | 51.722 | 45.704 | 23.994 | 1.00 | 22.15 | CPS3 |
| ATOM | 2578 | N | CYS | 91 | 53.557 | 46.177 | 25.208 | 1.00 | 21.50 | CPS3 |
| ATOM | 2579 | CA | CYS | 91 | 53.565 | 44.918 | 25.968 | 1.00 | 22.56 | CPS3 |
| ATOM | 2580 | CB | CYS | 91 | 54.379 | 43.834 | 25.252 | 1.00 | 22.42 | CPS3 |
| ATOM | 2581 | SG | CYS | 91 | 54.522 | 42.300 | 26.235 | 1.00 | 25.18 | CPS3 |
| ATOM | 2582 | C | CYS | 91 | 54.251 | 45.307 | 27.279 | 1.00 | 23.27 | CPS3 |
| ATOM | 2583 | O | CYS | 91 | 55.450 | 45.584 | 27.292 | 1.00 | 23.16 | CPS3 |
| ATOM | 2584 | N | THR | 92 | 53.500 | 45.337 | 28.372 | 1.00 | 26.40 | CPS3 |
| ATOM | 2585 | CA | THR | 92 | 54.076 | 45.784 | 29.638 | 1.00 | 28.79 | CPS3 |
| ATOM | 2586 | CB | THR | 92 | 52.983 | 46.002 | 30.713 | 1.00 | 29.85 | CPS3 |
| ATOM | 2587 | OG1 | THR | 92 | 52.347 | 44.760 | 31.033 | 1.00 | 31.45 | CPS3 |
| ATOM | 2588 | CG2 | THR | 92 | 51.934 | 46.993 | 30.195 | 1.00 | 30.30 | CPS3 |
| ATOM | 2589 | C | THR | 92 | 55.203 | 44.945 | 30.217 | 1.00 | 30.27 | CPS3 |
| ATOM | 2590 | O | THR | 92 | 55.787 | 45.313 | 31.237 | 1.00 | 29.37 | CPS3 |
| ATOM | 2591 | N | LYS | 93 | 55.520 | 43.828 | 29.571 | 1.00 | 30.96 | CPS3 |
| ATOM | 2592 | CA | LYS | 93 | 56.618 | 42.991 | 30.031 | 1.00 | 32.02 | CPS3 |
| ATOM | 2593 | CB | LYS | 93 | 56.521 | 41.608 | 29.397 | 1.00 | 33.43 | CPS3 |
| ATOM | 2594 | CG | LYS | 93 | 55.509 | 40.711 | 30.098 | 1.00 | 36.42 | CPS3 |
| ATOM | 2595 | CD | LYS | 93 | 55.253 | 39.426 | 29.337 | 1.00 | 38.18 | CPS3 |
| ATOM | 2596 | CE | LYS | 93 | 54.583 | 38.385 | 30.227 | 1.00 | 40.38 | CPS3 |
| ATOM | 2597 | NZ | LYS | 93 | 53.482 | 38.941 | 31.059 | 1.00 | 41.16 | CPS3 |
| ATOM | 2598 | C | LYS | 93 | 57.956 | 43.657 | 29.701 | 1.00 | 31.94 | CPS3 |
| ATOM | 2599 | O | LYS | 93 | 58.998 | 43.287 | 30.233 | 1.00 | 32.81 | CPS3 |
| ATOM | 2600 | N | LEU | 94 | 57.924 | 44.655 | 28.824 | 1.00 | 31.18 | CPS3 |
| ATOM | 2601 | CA | LEU | 94 | 59.139 | 45.378 | 28.473 | 1.00 | 30.06 | CPS3 |
| ATOM | 2602 | CB | LEU | 94 | 59.903 | 44.637 | 27.376 | 1.00 | 31.03 | CPS3 |
| ATOM | 2603 | CG | LEU | 94 | 59.121 | 43.973 | 26.240 | 1.00 | 31.49 | CPS3 |
| ATOM | 2604 | CD1 | LEU | 94 | 58.228 | 44.977 | 25.551 | 1.00 | 33.11 | CPS3 |
| ATOM | 2605 | CD2 | LEU | 94 | 60.109 | 43.366 | 25.258 | 1.00 | 31.24 | CPS3 |
| ATOM | 2606 | C | LEU | 94 | 58.822 | 46.801 | 28.042 | 1.00 | 29.42 | CPS3 |
| ATOM | 2607 | O | LEU | 94 | 57.657 | 47.165 | 27.909 | 1.00 | 28.23 | CPS3 |
| ATOM | 2608 | N | SER | 95 | 59.852 | 47.618 | 27.841 | 1.00 | 28.87 | CPS3 |
| ATOM | 2609 | CA | SER | 95 | 59.616 | 48.993 | 27.423 | 1.00 | 29.31 | CPS3 |
| ATOM | 2610 | CB | SER | 95 | 60.853 | 49.867 | 27.631 | 1.00 | 30.92 | CPS3 |
| ATOM | 2611 | OG | SER | 95 | 60.671 | 51.106 | 26.950 | 1.00 | 31.74 | CPS3 |
| ATOM | 2612 | C | SER | 95 | 59.244 | 49.062 | 25.953 | 1.00 | 28.31 | CPS3 |
| ATOM | 2613 | O | SER | 95 | 59.835 | 48.376 | 25.127 | 1.00 | 27.86 | CPS3 |
| ATOM | 2614 | N | PRO | 96 | 58.269 | 49.914 | 25.611 | 1.00 | 28.41 | CPS3 |
| ATOM | 2615 | CD | PRO | 96 | 57.504 | 50.793 | 26.516 | 1.00 | 29.30 | CPS3 |
| ATOM | 2616 | CA | PRO | 96 | 57.829 | 50.074 | 24.221 | 1.00 | 27.35 | CPS3 |
| ATOM | 2617 | CB | PRO | 96 | 56.749 | 51.155 | 24.312 | 1.00 | 28.52 | CPS3 |
| ATOM | 2618 | CG | PRO | 96 | 56.259 | 51.056 | 25.722 | 1.00 | 29.70 | CPS3 |
| ATOM | 2619 | C | PRO | 96 | 58.997 | 50.532 | 23.344 | 1.00 | 26.87 | CPS3 |
| ATOM | 2620 | O | PRO | 96 | 59.060 | 50.209 | 22.156 | 1.00 | 25.42 | CPS3 |
| ATOM | 2621 | N | ALA | 97 | 59.922 | 51.283 | 23.940 | 1.00 | 26.21 | CPS3 |

FIG. 1A-46

| ATOM | 2622 | CA | ALA | 97 | 61.073 | 51.804 | 23.203 | 1.00 | 26.00 | CPS3 |
|---|---|---|---|---|---|---|---|---|---|---|
| ATOM | 2623 | CB | ALA | 97 | 61.821 | 52.824 | 24.060 | 1.00 | 28.49 | CPS3 |
| ATOM | 2624 | C | ALA | 97 | 62.031 | 50.709 | 22.744 | 1.00 | 25.63 | CPS3 |
| ATOM | 2625 | O | ALA | 97 | 62.858 | 50.921 | 21.858 | 1.00 | 24.95 | CPS3 |
| ATOM | 2626 | N | ALA | 98 | 61.916 | 49.532 | 23.342 | 1.00 | 24.02 | CPS3 |
| ATOM | 2627 | CA | ALA | 98 | 62.793 | 48.426 | 22.986 | 1.00 | 23.40 | CPS3 |
| ATOM | 2628 | CB | ALA | 98 | 63.054 | 47.574 | 24.215 | 1.00 | 25.00 | CPS3 |
| ATOM | 2629 | C | ALA | 98 | 62.208 | 47.553 | 21.880 | 1.00 | 22.32 | CPS3 |
| ATOM | 2630 | O | ALA | 98 | 62.868 | 46.645 | 21.401 | 1.00 | 22.68 | CPS3 |
| ATOM | 2631 | N | VAL | 99 | 60.979 | 47.842 | 21.460 | 1.00 | 21.24 | CPS3 |
| ATOM | 2632 | CA | VAL | 99 | 60.330 | 47.004 | 20.457 | 1.00 | 19.35 | CPS3 |
| ATOM | 2633 | CB | VAL | 99 | 58.965 | 46.511 | 20.982 | 1.00 | 19.94 | CPS3 |
| ATOM | 2634 | CG1 | VAL | 99 | 58.383 | 45.474 | 20.027 | 1.00 | 21.36 | CPS3 |
| ATOM | 2635 | CG2 | VAL | 99 | 59.125 | 45.930 | 22.376 | 1.00 | 23.27 | CPS3 |
| ATOM | 2636 | C | VAL | 99 | 60.100 | 47.691 | 19.121 | 1.00 | 19.01 | CPS3 |
| ATOM | 2637 | O | VAL | 99 | 59.758 | 48.865 | 19.083 | 1.00 | 19.19 | CPS3 |
| ATOM | 2638 | N | HIS | 100 | 60.295 | 46.941 | 18.037 | 1.00 | 18.11 | CPS3 |
| ATOM | 2639 | CA | HIS | 100 | 60.080 | 47.439 | 16.685 | 1.00 | 19.23 | CPS3 |
| ATOM | 2640 | CB | HIS | 100 | 61.426 | 47.732 | 16.029 | 1.00 | 21.42 | CPS3 |
| ATOM | 2641 | CG | HIS | 100 | 62.233 | 48.753 | 16.772 | 1.00 | 24.13 | CPS3 |
| ATOM | 2642 | CD2 | HIS | 100 | 63.223 | 48.613 | 17.686 | 1.00 | 25.59 | CPS3 |
| ATOM | 2643 | ND1 | HIS | 100 | 62.007 | 50.105 | 16.654 | 1.00 | 25.95 | CPS3 |
| ATOM | 2644 | CE1 | HIS | 100 | 62.825 | 50.758 | 17.463 | 1.00 | 26.97 | CPS3 |
| ATOM | 2645 | NE2 | HIS | 100 | 63.572 | 49.874 | 18.100 | 1.00 | 26.97 | CPS3 |
| ATOM | 2646 | C | HIS | 100 | 59.343 | 46.348 | 15.919 | 1.00 | 18.08 | CPS3 |
| ATOM | 2647 | O | HIS | 100 | 59.707 | 45.178 | 16.027 | 1.00 | 17.62 | CPS3 |
| ATOM | 2648 | N | VAL | 101 | 58.313 | 46.731 | 15.161 | 1.00 | 17.20 | CPS3 |
| ATOM | 2649 | CA | VAL | 101 | 57.525 | 45.765 | 14.382 | 1.00 | 16.42 | CPS3 |
| ATOM | 2650 | CB | VAL | 101 | 56.149 | 45.472 | 15.080 | 1.00 | 16.35 | CPS3 |
| ATOM | 2651 | CG1 | VAL | 101 | 55.316 | 46.753 | 15.156 | 1.00 | 15.91 | CPS3 |
| ATOM | 2652 | CG2 | VAL | 101 | 55.364 | 44.375 | 14.330 | 1.00 | 17.27 | CPS3 |
| ATOM | 2653 | C | VAL | 101 | 57.244 | 46.312 | 12.982 | 1.00 | 16.80 | CPS3 |
| ATOM | 2654 | O | VAL | 101 | 57.325 | 47.515 | 12.754 | 1.00 | 15.86 | CPS3 |
| ATOM | 2655 | N | SER | 102 | 56.948 | 45.414 | 12.046 | 1.00 | 16.94 | CPS3 |
| ATOM | 2656 | CA | SER | 102 | 56.554 | 45.816 | 10.694 | 1.00 | 17.40 | CPS3 |
| ATOM | 2657 | CB | SER | 102 | 57.733 | 45.889 | 9.723 | 1.00 | 18.13 | CPS3 |
| ATOM | 2658 | OG | SER | 102 | 57.255 | 46.343 | 8.454 | 1.00 | 19.88 | CPS3 |
| ATOM | 2659 | C | SER | 102 | 55.566 | 44.752 | 10.240 | 1.00 | 17.06 | CPS3 |
| ATOM | 2660 | O | SER | 102 | 55.738 | 43.569 | 10.531 | 1.00 | 16.38 | CPS3 |
| ATOM | 2661 | N | ILE | 103 | 54.508 | 45.180 | 9.562 | 1.00 | 16.71 | CPS3 |
| ATOM | 2662 | CA | ILE | 103 | 53.476 | 44.259 | 9.109 | 1.00 | 16.77 | CPS3 |
| ATOM | 2663 | CB | ILE | 103 | 52.138 | 44.533 | 9.851 | 1.00 | 19.32 | CPS3 |
| ATOM | 2664 | CG2 | ILE | 103 | 51.062 | 43.538 | 9.386 | 1.00 | 20.27 | CPS3 |
| ATOM | 2665 | CG1 | ILE | 103 | 52.340 | 44.398 | 11.366 | 1.00 | 18.63 | CPS3 |
| ATOM | 2666 | CD1 | ILE | 103 | 51.099 | 44.754 | 12.195 | 1.00 | 17.98 | CPS3 |
| ATOM | 2667 | C | ILE | 103 | 53.261 | 44.475 | 7.615 | 1.00 | 17.09 | CPS3 |
| ATOM | 2668 | O | ILE | 103 | 53.304 | 45.608 | 7.140 | 1.00 | 18.12 | CPS3 |
| ATOM | 2669 | N | THR | 104 | 53.038 | 43.390 | 6.880 | 1.00 | 18.52 | CPS3 |
| ATOM | 2670 | CA | THR | 104 | 52.802 | 43.475 | 5.438 | 1.00 | 19.66 | CPS3 |
| ATOM | 2671 | CB | THR | 104 | 54.116 | 43.197 | 4.636 | 1.00 | 20.60 | CPS3 |
| ATOM | 2672 | OG1 | THR | 104 | 53.888 | 43.430 | 3.246 | 1.00 | 21.77 | CPS3 |
| ATOM | 2673 | CG2 | THR | 104 | 54.583 | 41.763 | 4.822 | 1.00 | 20.35 | CPS3 |
| ATOM | 2674 | C | THR | 104 | 51.694 | 42.494 | 5.020 | 1.00 | 20.81 | CPS3 |
| ATOM | 2675 | O | THR | 104 | 51.347 | 41.586 | 5.770 | 1.00 | 19.47 | CPS3 |
| ATOM | 2676 | N | HIS | 105 | 51.142 | 42.688 | 3.825 | 1.00 | 21.19 | CPS3 |
| ATOM | 2677 | CA | HIS | 105 | 50.066 | 41.838 | 3.320 | 1.00 | 23.77 | CPS3 |
| ATOM | 2678 | CB | HIS | 105 | 48.701 | 42.514 | 3.515 | 1.00 | 25.55 | CPS3 |

FIG. 1A-47

| ATOM | 2679 | CG | HIS | 105 | 48.344 | 42.814 | 4.937 | 1.00 | 30.17 | CPS3 |
| ATOM | 2680 | CD2 | HIS | 105 | 48.668 | 43.859 | 5.737 | 1.00 | 31.35 | CPS3 |
| ATOM | 2681 | ND1 | HIS | 105 | 47.507 | 42.008 | 5.676 | 1.00 | 31.23 | CPS3 |
| ATOM | 2682 | CE1 | HIS | 105 | 47.327 | 42.544 | 6.872 | 1.00 | 33.22 | CPS3 |
| ATOM | 2683 | NE2 | HIS | 105 | 48.020 | 43.668 | 6.935 | 1.00 | 32.63 | CPS3 |
| ATOM | 2684 | C | HIS | 105 | 50.178 | 41.619 | 1.817 | 1.00 | 22.69 | CPS3 |
| ATOM | 2685 | O | HIS | 105 | 50.784 | 42.413 | 1.105 | 1.00 | 22.84 | CPS3 |
| ATOM | 2686 | N | THR | 106 | 49.565 | 40.536 | 1.359 | 1.00 | 24.26 | CPS3 |
| ATOM | 2687 | CA | THR | 106 | 49.426 | 40.244 | -0.066 | 1.00 | 25.12 | CPS3 |
| ATOM | 2688 | CB | THR | 106 | 50.338 | 39.107 | -0.598 | 1.00 | 25.65 | CPS3 |
| ATOM | 2689 | OG1 | THR | 106 | 49.928 | 37.848 | -0.047 | 1.00 | 25.72 | CPS3 |
| ATOM | 2690 | CG2 | THR | 106 | 51.805 | 39.395 | -0.275 | 1.00 | 24.63 | CPS3 |
| ATOM | 2691 | C | THR | 106 | 47.970 | 39.769 | -0.097 | 1.00 | 25.84 | CPS3 |
| ATOM | 2692 | O | THR | 106 | 47.290 | 39.753 | 0.934 | 1.00 | 24.47 | CPS3 |
| ATOM | 2693 | N | ALA | 107 | 47.484 | 39.388 | -1.265 | 1.00 | 25.43 | CPS3 |
| ATOM | 2694 | CA | ALA | 107 | 46.108 | 38.937 | -1.362 | 1.00 | 26.46 | CPS3 |
| ATOM | 2695 | CB | ALA | 107 | 45.790 | 38.570 | -2.820 | 1.00 | 27.17 | CPS3 |
| ATOM | 2696 | C | ALA | 107 | 45.812 | 37.750 | -0.444 | 1.00 | 26.57 | CPS3 |
| ATOM | 2697 | O | ALA | 107 | 44.769 | 37.707 | 0.213 | 1.00 | 27.71 | CPS3 |
| ATOM | 2698 | N | GLU | 108 | 46.738 | 36.799 | -0.384 | 1.00 | 26.04 | CPS3 |
| ATOM | 2699 | CA | GLU | 108 | 46.542 | 35.594 | 0.404 | 1.00 | 25.62 | CPS3 |
| ATOM | 2700 | CB | GLU | 108 | 46.833 | 34.374 | -0.475 | 1.00 | 29.10 | CPS3 |
| ATOM | 2701 | CG | GLU | 108 | 46.172 | 34.475 | -1.846 | 1.00 | 35.56 | CPS3 |
| ATOM | 2702 | CD | GLU | 108 | 46.174 | 33.171 | -2.616 | 1.00 | 40.28 | CPS3 |
| ATOM | 2703 | OE1 | GLU | 108 | 47.145 | 32.395 | -2.485 | 1.00 | 42.87 | CPS3 |
| ATOM | 2704 | OE2 | GLU | 108 | 45.201 | 32.932 | -3.369 | 1.00 | 44.28 | CPS3 |
| ATOM | 2705 | C | GLU | 108 | 47.325 | 35.460 | 1.706 | 1.00 | 25.50 | CPS3 |
| ATOM | 2706 | O | GLU | 108 | 47.087 | 34.520 | 2.463 | 1.00 | 23.92 | CPS3 |
| ATOM | 2707 | N | TYR | 109 | 48.239 | 36.389 | 1.978 | 1.00 | 23.47 | CPS3 |
| ATOM | 2708 | CA | TYR | 109 | 49.048 | 36.281 | 3.189 | 1.00 | 22.84 | CPS3 |
| ATOM | 2709 | CB | TYR | 109 | 50.471 | 35.833 | 2.822 | 1.00 | 23.00 | CPS3 |
| ATOM | 2710 | CG | TYR | 109 | 50.552 | 34.480 | 2.176 | 1.00 | 23.82 | CPS3 |
| ATOM | 2711 | CD1 | TYR | 109 | 50.485 | 33.317 | 2.936 | 1.00 | 23.06 | CPS3 |
| ATOM | 2712 | CE1 | TYR | 109 | 50.532 | 32.063 | 2.334 | 1.00 | 24.49 | CPS3 |
| ATOM | 2713 | CD2 | TYR | 109 | 50.668 | 34.361 | 0.793 | 1.00 | 23.15 | CPS3 |
| ATOM | 2714 | CE2 | TYR | 109 | 50.710 | 33.122 | 0.184 | 1.00 | 24.59 | CPS3 |
| ATOM | 2715 | CZ | TYR | 109 | 50.641 | 31.980 | 0.956 | 1.00 | 24.33 | CPS3 |
| ATOM | 2716 | OH | TYR | 109 | 50.655 | 30.756 | 0.341 | 1.00 | 26.41 | CPS3 |
| ATOM | 2717 | C | TYR | 109 | 49.187 | 37.551 | 4.000 | 1.00 | 21.41 | CPS3 |
| ATOM | 2718 | O | TYR | 109 | 49.021 | 38.659 | 3.477 | 1.00 | 21.21 | CPS3 |
| ATOM | 2719 | N | ALA | 110 | 49.478 | 37.366 | 5.293 | 1.00 | 19.67 | CPS3 |
| ATOM | 2720 | CA | ALA | 110 | 49.781 | 38.470 | 6.204 | 1.00 | 19.04 | CPS3 |
| ATOM | 2721 | CB | ALA | 110 | 48.753 | 38.588 | 7.334 | 1.00 | 18.93 | CPS3 |
| ATOM | 2722 | C | ALA | 110 | 51.137 | 38.048 | 6.776 | 1.00 | 19.30 | CPS3 |
| ATOM | 2723 | O | ALA | 110 | 51.375 | 36.861 | 6.985 | 1.00 | 20.91 | CPS3 |
| ATOM | 2724 | N | ALA | 111 | 52.038 | 38.997 | 7.014 | 1.00 | 18.04 | CPS3 |
| ATOM | 2725 | CA | ALA | 111 | 53.337 | 38.631 | 7.565 | 1.00 | 17.63 | CPS3 |
| ATOM | 2726 | CB | ALA | 111 | 54.347 | 38.376 | 6.434 | 1.00 | 16.29 | CPS3 |
| ATOM | 2727 | C | ALA | 111 | 53.819 | 39.758 | 8.469 | 1.00 | 17.67 | CPS3 |
| ATOM | 2728 | O | ALA | 111 | 53.404 | 40.903 | 8.312 | 1.00 | 18.51 | CPS3 |
| ATOM | 2729 | N | ALA | 112 | 54.672 | 39.424 | 9.428 | 1.00 | 16.56 | CPS3 |
| ATOM | 2730 | CA | ALA | 112 | 55.181 | 40.433 | 10.342 | 1.00 | 15.86 | CPS3 |
| ATOM | 2731 | CB | ALA | 112 | 54.203 | 40.636 | 11.489 | 1.00 | 15.01 | CPS3 |
| ATOM | 2732 | C | ALA | 112 | 56.533 | 40.033 | 10.896 | 1.00 | 17.34 | CPS3 |
| ATOM | 2733 | O | ALA | 112 | 56.885 | 38.856 | 10.913 | 1.00 | 16.61 | CPS3 |
| ATOM | 2734 | N | GLN | 113 | 57.294 | 41.021 | 11.352 | 1.00 | 16.50 | CPS3 |
| ATOM | 2735 | CA | GLN | 113 | 58.591 | 40.732 | 11.952 | 1.00 | 18.53 | CPS3 |

FIG. 1A-48

| ATOM | 2736 | CB | GLN | 113 | 59.735 | 40.962 | 10.956 | 1.00 | 18.24 | CPS3 |
|---|---|---|---|---|---|---|---|---|---|---|
| ATOM | 2737 | CG | GLN | 113 | 59.926 | 42.406 | 10.544 | 1.00 | 22.84 | CPS3 |
| ATOM | 2738 | CD | GLN | 113 | 61.095 | 42.611 | 9.578 | 1.00 | 26.07 | CPS3 |
| ATOM | 2739 | OE1 | GLN | 113 | 61.504 | 43.738 | 9.326 | 1.00 | 28.00 | CPS3 |
| ATOM | 2740 | NE2 | GLN | 113 | 61.624 | 41.521 | 9.033 | 1.00 | 28.26 | CPS3 |
| ATOM | 2741 | C | GLN | 113 | 58.724 | 41.667 | 13.144 | 1.00 | 16.72 | CPS3 |
| ATOM | 2742 | O | GLN | 113 | 58.108 | 42.728 | 13.182 | 1.00 | 16.09 | CPS3 |
| ATOM | 2743 | N | VAL | 114 | 59.513 | 41.252 | 14.124 | 1.00 | 17.10 | CPS3 |
| ATOM | 2744 | CA | VAL | 114 | 59.707 | 42.051 | 15.329 | 1.00 | 17.04 | CPS3 |
| ATOM | 2745 | CB | VAL | 114 | 58.882 | 41.484 | 16.538 | 1.00 | 17.59 | CPS3 |
| ATOM | 2746 | CG1 | VAL | 114 | 59.307 | 42.160 | 17.853 | 1.00 | 17.11 | CPS3 |
| ATOM | 2747 | CG2 | VAL | 114 | 57.392 | 41.703 | 16.320 | 1.00 | 16.91 | CPS3 |
| ATOM | 2748 | C | VAL | 114 | 61.173 | 41.971 | 15.710 | 1.00 | 18.24 | CPS3 |
| ATOM | 2749 | O | VAL | 114 | 61.826 | 40.948 | 15.493 | 1.00 | 16.19 | CPS3 |
| ATOM | 2750 | N | VAL | 115 | 61.691 | 43.068 | 16.251 | 1.00 | 18.16 | CPS3 |
| ATOM | 2751 | CA | VAL | 115 | 63.053 | 43.072 | 16.763 | 1.00 | 19.36 | CPS3 |
| ATOM | 2752 | CB | VAL | 115 | 64.021 | 43.925 | 15.920 | 1.00 | 20.69 | CPS3 |
| ATOM | 2753 | CG1 | VAL | 115 | 65.394 | 44.014 | 16.637 | 1.00 | 20.85 | CPS3 |
| ATOM | 2754 | CG2 | VAL | 115 | 64.184 | 43.305 | 14.529 | 1.00 | 18.29 | CPS3 |
| ATOM | 2755 | C | VAL | 115 | 62.916 | 43.691 | 18.148 | 1.00 | 20.16 | CPS3 |
| ATOM | 2756 | O | VAL | 115 | 62.268 | 44.728 | 18.309 | 1.00 | 21.78 | CPS3 |
| ATOM | 2757 | N | ILE | 116 | 63.463 | 43.018 | 19.152 | 1.00 | 20.33 | CPS3 |
| ATOM | 2758 | CA | ILE | 116 | 63.438 | 43.527 | 20.517 | 1.00 | 21.08 | CPS3 |
| ATOM | 2759 | CB | ILE | 116 | 62.911 | 42.491 | 21.517 | 1.00 | 21.66 | CPS3 |
| ATOM | 2760 | CG2 | ILE | 116 | 63.081 | 43.042 | 22.960 | 1.00 | 21.13 | CPS3 |
| ATOM | 2761 | CG1 | ILE | 116 | 61.439 | 42.174 | 21.215 | 1.00 | 21.09 | CPS3 |
| ATOM | 2762 | CD1 | ILE | 116 | 60.806 | 41.091 | 22.118 | 1.00 | 19.60 | CPS3 |
| ATOM | 2763 | C | ILE | 116 | 64.881 | 43.835 | 20.885 | 1.00 | 24.39 | CPS3 |
| ATOM | 2764 | O | ILE | 116 | 65.764 | 42.993 | 20.697 | 1.00 | 22.81 | CPS3 |
| ATOM | 2765 | N | GLU | 117 | 65.131 | 45.041 | 21.381 | 1.00 | 26.58 | CPS3 |
| ATOM | 2766 | CA | GLU | 117 | 66.487 | 45.410 | 21.767 | 1.00 | 31.31 | CPS3 |
| ATOM | 2767 | CB | GLU | 117 | 66.824 | 46.834 | 21.346 | 1.00 | 32.50 | CPS3 |
| ATOM | 2768 | CG | GLU | 117 | 66.641 | 47.178 | 19.901 | 1.00 | 37.84 | CPS3 |
| ATOM | 2769 | CD | GLU | 117 | 67.052 | 48.616 | 19.638 | 1.00 | 40.98 | CPS3 |
| ATOM | 2770 | OE1 | GLU | 117 | 68.271 | 48.872 | 19.516 | 1.00 | 42.89 | CPS3 |
| ATOM | 2771 | OE2 | GLU | 117 | 66.160 | 49.491 | 19.578 | 1.00 | 43.15 | CPS3 |
| ATOM | 2772 | C | GLU | 117 | 66.653 | 45.367 | 23.275 | 1.00 | 33.73 | CPS3 |
| ATOM | 2773 | O | GLU | 117 | 65.679 | 45.454 | 24.026 | 1.00 | 33.05 | CPS3 |
| ATOM | 2774 | N | ARG | 118 | 67.904 | 45.244 | 23.708 | 1.00 | 37.38 | CPS3 |
| ATOM | 2775 | CA | ARG | 118 | 68.224 | 45.267 | 25.124 | 1.00 | 41.10 | CPS3 |
| ATOM | 2776 | CB | ARG | 118 | 69.512 | 44.496 | 25.407 | 1.00 | 42.40 | CPS3 |
| ATOM | 2777 | CG | ARG | 118 | 69.311 | 43.126 | 26.025 | 1.00 | 44.67 | CPS3 |
| ATOM | 2778 | CD | ARG | 118 | 70.649 | 42.566 | 26.483 | 1.00 | 45.83 | CPS3 |
| ATOM | 2779 | NE | ARG | 118 | 71.614 | 42.542 | 25.389 | 1.00 | 47.03 | CPS3 |
| ATOM | 2780 | CZ | ARG | 118 | 71.609 | 41.652 | 24.402 | 1.00 | 47.03 | CPS3 |
| ATOM | 2781 | NH1 | ARG | 118 | 70.690 | 40.694 | 24.367 | 1.00 | 46.54 | CPS3 |
| ATOM | 2782 | NH2 | ARG | 118 | 72.520 | 41.729 | 23.446 | 1.00 | 46.88 | CPS3 |
| ATOM | 2783 | C | ARG | 118 | 68.452 | 46.744 | 25.399 | 1.00 | 42.76 | CPS3 |
| ATOM | 2784 | O | ARG | 118 | 69.227 | 47.392 | 24.697 | 1.00 | 44.45 | CPS3 |
| ATOM | 2785 | N | LEU | 119 | 67.765 | 47.289 | 26.392 | 1.00 | 45.54 | CPS3 |
| ATOM | 2786 | CA | LEU | 119 | 67.928 | 48.699 | 26.722 | 1.00 | 47.93 | CPS3 |
| ATOM | 2787 | CB | LEU | 119 | 66.563 | 49.328 | 27.014 | 1.00 | 48.16 | CPS3 |
| ATOM | 2788 | CG | LEU | 119 | 65.944 | 50.257 | 25.963 | 1.00 | 47.88 | CPS3 |
| ATOM | 2789 | CD1 | LEU | 119 | 66.182 | 49.739 | 24.548 | 1.00 | 47.81 | CPS3 |
| ATOM | 2790 | CD2 | LEU | 119 | 64.460 | 50.385 | 26.260 | 1.00 | 47.26 | CPS3 |
| ATOM | 2791 | C | LEU | 119 | 68.845 | 48.862 | 27.928 | 1.00 | 49.49 | CPS3 |
| ATOM | 2792 | OT1 | LEU | 119 | 70.001 | 49.296 | 27.728 | 1.00 | 50.38 | CPS3 |

FIG. 1A-49

| ATOM | 2793 | OT2 | LEU | 119 | 68.399 | 48.537 | 29.052 | 1.00 | 51.04 | CPS3 |
|---|---|---|---|---|---|---|---|---|---|---|
| ATOM | 2794 | C   | GLY | 0 | 33.524 | 21.933 | 24.405 | 1.00 | 41.93 | CPS4 |
| ATOM | 2795 | O   | GLY | 0 | 33.109 | 21.427 | 23.356 | 1.00 | 43.93 | CPS4 |
| ATOM | 2796 | N   | GLY | 0 | 35.967 | 22.519 | 24.212 | 1.00 | 43.67 | CPS4 |
| ATOM | 2797 | CA  | GLY | 0 | 34.574 | 23.033 | 24.374 | 1.00 | 42.80 | CPS4 |
| ATOM | 2798 | N   | GLY | 1 | 33.089 | 21.565 | 25.607 | 1.00 | 38.91 | CPS4 |
| ATOM | 2799 | CA  | GLY | 1 | 32.082 | 20.530 | 25.746 | 1.00 | 34.29 | CPS4 |
| ATOM | 2800 | C   | GLY | 1 | 30.697 | 21.104 | 25.995 | 1.00 | 31.42 | CPS4 |
| ATOM | 2801 | O   | GLY | 1 | 29.713 | 20.369 | 26.051 | 1.00 | 30.75 | CPS4 |
| ATOM | 2802 | N   | ILE | 2 | 30.618 | 22.419 | 26.172 | 1.00 | 28.92 | CPS4 |
| ATOM | 2803 | CA  | ILE | 2 | 29.328 | 23.068 | 26.405 | 1.00 | 26.32 | CPS4 |
| ATOM | 2804 | CB  | ILE | 2 | 29.309 | 23.809 | 27.765 | 1.00 | 26.73 | CPS4 |
| ATOM | 2805 | CG2 | ILE | 2 | 28.044 | 24.683 | 27.891 | 1.00 | 24.71 | CPS4 |
| ATOM | 2806 | CG1 | ILE | 2 | 29.358 | 22.779 | 28.896 | 1.00 | 27.21 | CPS4 |
| ATOM | 2807 | CD1 | ILE | 2 | 29.417 | 23.387 | 30.265 | 1.00 | 28.66 | CPS4 |
| ATOM | 2808 | C   | ILE | 2 | 29.028 | 24.043 | 25.277 | 1.00 | 25.17 | CPS4 |
| ATOM | 2809 | O   | ILE | 2 | 29.861 | 24.874 | 24.922 | 1.00 | 24.41 | CPS4 |
| ATOM | 2810 | N   | TYR | 3 | 27.839 | 23.910 | 24.703 | 1.00 | 24.67 | CPS4 |
| ATOM | 2811 | CA  | TYR | 3 | 27.389 | 24.765 | 23.606 | 1.00 | 24.61 | CPS4 |
| ATOM | 2812 | CB  | TYR | 3 | 26.260 | 24.071 | 22.850 | 1.00 | 27.01 | CPS4 |
| ATOM | 2813 | CG  | TYR | 3 | 25.726 | 24.865 | 21.681 | 1.00 | 29.25 | CPS4 |
| ATOM | 2814 | CD1 | TYR | 3 | 26.385 | 24.861 | 20.452 | 1.00 | 31.33 | CPS4 |
| ATOM | 2815 | CE1 | TYR | 3 | 25.916 | 25.616 | 19.379 | 1.00 | 33.16 | CPS4 |
| ATOM | 2816 | CD2 | TYR | 3 | 24.579 | 25.645 | 21.811 | 1.00 | 31.21 | CPS4 |
| ATOM | 2817 | CE2 | TYR | 3 | 24.101 | 26.409 | 20.740 | 1.00 | 32.57 | CPS4 |
| ATOM | 2818 | CZ  | TYR | 3 | 24.776 | 26.388 | 19.530 | 1.00 | 34.44 | CPS4 |
| ATOM | 2819 | OH  | TYR | 3 | 24.328 | 27.148 | 18.473 | 1.00 | 36.34 | CPS4 |
| ATOM | 2820 | C   | TYR | 3 | 26.881 | 26.103 | 24.151 | 1.00 | 23.47 | CPS4 |
| ATOM | 2821 | O   | TYR | 3 | 27.167 | 27.175 | 23.609 | 1.00 | 22.30 | CPS4 |
| ATOM | 2822 | N   | GLY | 4 | 26.111 | 26.036 | 25.226 | 1.00 | 21.50 | CPS4 |
| ATOM | 2823 | CA  | GLY | 4 | 25.597 | 27.262 | 25.802 | 1.00 | 20.66 | CPS4 |
| ATOM | 2824 | C   | GLY | 4 | 24.775 | 26.974 | 27.036 | 1.00 | 18.15 | CPS4 |
| ATOM | 2825 | O   | GLY | 4 | 24.397 | 25.824 | 27.275 | 1.00 | 17.40 | CPS4 |
| ATOM | 2826 | N   | ILE | 5 | 24.519 | 28.019 | 27.827 | 1.00 | 17.22 | CPS4 |
| ATOM | 2827 | CA  | ILE | 5 | 23.725 | 27.874 | 29.039 | 1.00 | 16.89 | CPS4 |
| ATOM | 2828 | CB  | ILE | 5 | 24.585 | 27.961 | 30.311 | 1.00 | 17.48 | CPS4 |
| ATOM | 2829 | CG2 | ILE | 5 | 25.700 | 26.921 | 30.241 | 1.00 | 16.93 | CPS4 |
| ATOM | 2830 | CG1 | ILE | 5 | 25.166 | 29.374 | 30.472 | 1.00 | 18.44 | CPS4 |
| ATOM | 2831 | CD1 | ILE | 5 | 26.002 | 29.560 | 31.716 | 1.00 | 17.67 | CPS4 |
| ATOM | 2832 | C   | ILE | 5 | 22.673 | 28.972 | 29.079 | 1.00 | 16.76 | CPS4 |
| ATOM | 2833 | O   | ILE | 5 | 22.831 | 30.024 | 28.457 | 1.00 | 17.03 | CPS4 |
| ATOM | 2834 | N   | GLY | 6 | 21.601 | 28.723 | 29.816 | 1.00 | 16.72 | CPS4 |
| ATOM | 2835 | CA  | GLY | 6 | 20.537 | 29.702 | 29.894 | 1.00 | 17.09 | CPS4 |
| ATOM | 2836 | C   | GLY | 6 | 19.874 | 29.687 | 31.246 | 1.00 | 17.29 | CPS4 |
| ATOM | 2837 | O   | GLY | 6 | 19.730 | 28.638 | 31.869 | 1.00 | 17.78 | CPS4 |
| ATOM | 2838 | N   | LEU | 7 | 19.485 | 30.874 | 31.703 | 1.00 | 16.88 | CPS4 |
| ATOM | 2839 | CA  | LEU | 7 | 18.825 | 31.033 | 32.990 | 1.00 | 17.08 | CPS4 |
| ATOM | 2840 | CB  | LEU | 7 | 19.803 | 31.622 | 34.006 | 1.00 | 18.18 | CPS4 |
| ATOM | 2841 | CG  | LEU | 7 | 19.251 | 31.984 | 35.389 | 1.00 | 18.23 | CPS4 |
| ATOM | 2842 | CD1 | LEU | 7 | 18.988 | 30.707 | 36.200 | 1.00 | 17.58 | CPS4 |
| ATOM | 2843 | CD2 | LEU | 7 | 20.282 | 32.875 | 36.126 | 1.00 | 17.74 | CPS4 |
| ATOM | 2844 | C   | LEU | 7 | 17.660 | 31.998 | 32.817 | 1.00 | 18.06 | CPS4 |
| ATOM | 2845 | O   | LEU | 7 | 17.775 | 32.976 | 32.082 | 1.00 | 18.10 | CPS4 |
| ATOM | 2846 | N   | ASP | 8 | 16.539 | 31.712 | 33.471 | 1.00 | 18.02 | CPS4 |
| ATOM | 2847 | CA  | ASP | 8 | 15.394 | 32.612 | 33.413 | 1.00 | 18.03 | CPS4 |
| ATOM | 2848 | CB  | ASP | 8 | 14.426 | 32.202 | 32.305 | 1.00 | 20.37 | CPS4 |
| ATOM | 2849 | CG  | ASP | 8 | 13.195 | 33.108 | 32.250 | 1.00 | 22.41 | CPS4 |

FIG. 1A-50

| ATOM | 2850 | OD1 | ASP | 8 | 12.194 | 32.814 | 32.922 | 1.00 | 25.67 | CPS4 |
|---|---|---|---|---|---|---|---|---|---|---|
| ATOM | 2851 | OD2 | ASP | 8 | 13.245 | 34.131 | 31.551 | 1.00 | 24.39 | CPS4 |
| ATOM | 2852 | C | ASP | 8 | 14.645 | 32.619 | 34.732 | 1.00 | 19.46 | CPS4 |
| ATOM | 2853 | O | ASP | 8 | 14.490 | 31.574 | 35.363 | 1.00 | 17.36 | CPS4 |
| ATOM | 2854 | N | ILE | 9 | 14.239 | 33.806 | 35.183 | 1.00 | 18.34 | CPS4 |
| ATOM | 2855 | CA | ILE | 9 | 13.420 | 33.898 | 36.376 | 1.00 | 19.60 | CPS4 |
| ATOM | 2856 | CB | ILE | 9 | 14.086 | 34.711 | 37.519 | 1.00 | 19.76 | CPS4 |
| ATOM | 2857 | CG2 | ILE | 9 | 13.133 | 34.805 | 38.700 | 1.00 | 21.48 | CPS4 |
| ATOM | 2858 | CG1 | ILE | 9 | 15.366 | 34.012 | 37.982 | 1.00 | 20.86 | CPS4 |
| ATOM | 2859 | CD1 | ILE | 9 | 16.146 | 34.790 | 39.050 | 1.00 | 22.16 | CPS4 |
| ATOM | 2860 | C | ILE | 9 | 12.171 | 34.623 | 35.878 | 1.00 | 20.38 | CPS4 |
| ATOM | 2861 | O | ILE | 9 | 12.277 | 35.629 | 35.167 | 1.00 | 20.64 | CPS4 |
| ATOM | 2862 | N | THR | 10 | 10.996 | 34.086 | 36.205 | 1.00 | 19.99 | CPS4 |
| ATOM | 2863 | CA | THR | 10 | 9.749 | 34.700 | 35.781 | 1.00 | 20.69 | CPS4 |
| ATOM | 2864 | CB | THR | 10 | 8.999 | 33.803 | 34.777 | 1.00 | 21.55 | CPS4 |
| ATOM | 2865 | OG1 | THR | 10 | 9.775 | 33.679 | 33.572 | 1.00 | 23.30 | CPS4 |
| ATOM | 2866 | CG2 | THR | 10 | 7.639 | 34.414 | 34.433 | 1.00 | 23.59 | CPS4 |
| ATOM | 2867 | C | THR | 10 | 8.833 | 34.990 | 36.970 | 1.00 | 20.24 | CPS4 |
| ATOM | 2868 | O | THR | 10 | 8.677 | 34.166 | 37.865 | 1.00 | 18.97 | CPS4 |
| ATOM | 2869 | N | GLU | 11 | 8.233 | 36.173 | 36.971 | 1.00 | 21.51 | CPS4 |
| ATOM | 2870 | CA | GLU | 11 | 7.321 | 36.560 | 38.045 | 1.00 | 23.43 | CPS4 |
| ATOM | 2871 | CB | GLU | 11 | 7.180 | 38.085 | 38.070 | 1.00 | 26.54 | CPS4 |
| ATOM | 2872 | CG | GLU | 11 | 6.189 | 38.601 | 39.095 | 1.00 | 28.77 | CPS4 |
| ATOM | 2873 | CD | GLU | 11 | 6.072 | 40.116 | 39.097 | 1.00 | 30.52 | CPS4 |
| ATOM | 2874 | OE1 | GLU | 11 | 6.416 | 40.744 | 38.078 | 1.00 | 29.88 | CPS4 |
| ATOM | 2875 | OE2 | GLU | 11 | 5.615 | 40.675 | 40.118 | 1.00 | 33.84 | CPS4 |
| ATOM | 2876 | C | GLU | 11 | 5.959 | 35.906 | 37.791 | 1.00 | 24.01 | CPS4 |
| ATOM | 2877 | O | GLU | 11 | 5.344 | 36.137 | 36.750 | 1.00 | 23.79 | CPS4 |
| ATOM | 2878 | N | LEU | 12 | 5.482 | 35.092 | 38.730 | 1.00 | 23.66 | CPS4 |
| ATOM | 2879 | CA | LEU | 12 | 4.191 | 34.416 | 38.556 | 1.00 | 25.00 | CPS4 |
| ATOM | 2880 | CB | LEU | 12 | 3.804 | 33.609 | 39.798 | 1.00 | 26.31 | CPS4 |
| ATOM | 2881 | CG | LEU | 12 | 4.621 | 32.386 | 40.208 | 1.00 | 31.01 | CPS4 |
| ATOM | 2882 | CD1 | LEU | 12 | 3.877 | 31.679 | 41.347 | 1.00 | 31.83 | CPS4 |
| ATOM | 2883 | CD2 | LEU | 12 | 4.808 | 31.435 | 39.028 | 1.00 | 32.20 | CPS4 |
| ATOM | 2884 | C | LEU | 12 | 3.044 | 35.391 | 38.253 | 1.00 | 24.98 | CPS4 |
| ATOM | 2885 | O | LEU | 12 | 2.196 | 35.107 | 37.412 | 1.00 | 24.51 | CPS4 |
| ATOM | 2886 | N | ALA | 13 | 3.019 | 36.524 | 38.950 | 1.00 | 25.40 | CPS4 |
| ATOM | 2887 | CA | ALA | 13 | 1.968 | 37.527 | 38.744 | 1.00 | 25.67 | CPS4 |
| ATOM | 2888 | CB | ALA | 13 | 2.157 | 38.691 | 39.702 | 1.00 | 28.52 | CPS4 |
| ATOM | 2889 | C | ALA | 13 | 1.939 | 38.044 | 37.314 | 1.00 | 26.33 | CPS4 |
| ATOM | 2890 | O | ALA | 13 | 0.871 | 38.344 | 36.781 | 1.00 | 26.54 | CPS4 |
| ATOM | 2891 | N | ARG | 14 | 3.107 | 38.152 | 36.688 | 1.00 | 24.68 | CPS4 |
| ATOM | 2892 | CA | ARG | 14 | 3.179 | 38.644 | 35.318 | 1.00 | 26.32 | CPS4 |
| ATOM | 2893 | CB | ARG | 14 | 4.644 | 38.886 | 34.925 | 1.00 | 28.73 | CPS4 |
| ATOM | 2894 | CG | ARG | 14 | 4.859 | 39.331 | 33.482 | 1.00 | 34.36 | CPS4 |
| ATOM | 2895 | CD | ARG | 14 | 6.328 | 39.142 | 33.058 | 1.00 | 37.57 | CPS4 |
| ATOM | 2896 | NE | ARG | 14 | 6.497 | 39.219 | 31.608 | 1.00 | 41.82 | CPS4 |
| ATOM | 2897 | CZ | ARG | 14 | 7.529 | 38.704 | 30.947 | 1.00 | 42.56 | CPS4 |
| ATOM | 2898 | NH1 | ARG | 14 | 8.491 | 38.070 | 31.603 | 1.00 | 43.08 | CPS4 |
| ATOM | 2899 | NH2 | ARG | 14 | 7.597 | 38.817 | 29.627 | 1.00 | 44.77 | CPS4 |
| ATOM | 2900 | C | ARG | 14 | 2.533 | 37.633 | 34.370 | 1.00 | 25.53 | CPS4 |
| ATOM | 2901 | O | ARG | 14 | 1.783 | 38.001 | 33.465 | 1.00 | 25.68 | CPS4 |
| ATOM | 2902 | N | ILE | 15 | 2.832 | 36.357 | 34.585 | 1.00 | 24.70 | CPS4 |
| ATOM | 2903 | CA | ILE | 15 | 2.278 | 35.284 | 33.763 | 1.00 | 25.07 | CPS4 |
| ATOM | 2904 | CB | ILE | 15 | 2.884 | 33.920 | 34.153 | 1.00 | 24.95 | CPS4 |
| ATOM | 2905 | CG2 | ILE | 15 | 2.169 | 32.782 | 33.390 | 1.00 | 24.82 | CPS4 |
| ATOM | 2906 | CG1 | ILE | 15 | 4.382 | 33.913 | 33.849 | 1.00 | 24.68 | CPS4 |

FIG. 1A-51

| ATOM | 2907 | CD1 | ILE | 15 | 4.714 | 33.980 | 32.358 | 1.00 | 27.32 | CPS4 |
|---|---|---|---|---|---|---|---|---|---|---|
| ATOM | 2908 | C | ILE | 15 | 0.766 | 35.200 | 33.950 | 1.00 | 26.73 | CPS4 |
| ATOM | 2909 | O | ILE | 15 | 0.009 | 34.983 | 32.993 | 1.00 | 25.85 | CPS4 |
| ATOM | 2910 | N | ALA | 16 | 0.324 | 35.352 | 35.193 | 1.00 | 26.46 | CPS4 |
| ATOM | 2911 | CA | ALA | 16 | -1.104 | 35.273 | 35.469 | 1.00 | 27.92 | CPS4 |
| ATOM | 2912 | CB | ALA | 16 | -1.355 | 35.318 | 36.975 | 1.00 | 28.33 | CPS4 |
| ATOM | 2913 | C | ALA | 16 | -1.823 | 36.423 | 34.774 | 1.00 | 29.55 | CPS4 |
| ATOM | 2914 | O | ALA | 16 | -2.928 | 36.252 | 34.240 | 1.00 | 29.47 | CPS4 |
| ATOM | 2915 | N | SER | 17 | -1.191 | 37.592 | 34.772 | 1.00 | 29.18 | CPS4 |
| ATOM | 2916 | CA | SER | 17 | -1.783 | 38.760 | 34.136 | 1.00 | 31.51 | CPS4 |
| ATOM | 2917 | CB | SER | 17 | -0.944 | 40.000 | 34.429 | 1.00 | 33.05 | CPS4 |
| ATOM | 2918 | OG | SER | 17 | -1.421 | 41.104 | 33.672 | 1.00 | 39.63 | CPS4 |
| ATOM | 2919 | C | SER | 17 | -1.922 | 38.574 | 32.624 | 1.00 | 32.08 | CPS4 |
| ATOM | 2920 | O | SER | 17 | -2.974 | 38.874 | 32.045 | 1.00 | 31.35 | CPS4 |
| ATOM | 2921 | N | MET | 18 | -0.871 | 38.078 | 31.982 | 1.00 | 31.52 | CPS4 |
| ATOM | 2922 | CA | MET | 18 | -0.912 | 37.868 | 30.540 | 1.00 | 32.75 | CPS4 |
| ATOM | 2923 | CB | MET | 18 | 0.469 | 37.482 | 30.008 | 1.00 | 34.03 | CPS4 |
| ATOM | 2924 | CG | MET | 18 | 1.504 | 38.580 | 30.147 | 1.00 | 38.00 | CPS4 |
| ATOM | 2925 | SD | MET | 18 | 3.076 | 38.170 | 29.360 | 1.00 | 41.64 | CPS4 |
| ATOM | 2926 | CE | MET | 18 | 3.866 | 37.225 | 30.666 | 1.00 | 38.75 | CPS4 |
| ATOM | 2927 | C | MET | 18 | -1.917 | 36.793 | 30.156 | 1.00 | 32.75 | CPS4 |
| ATOM | 2928 | O | MET | 18 | -2.689 | 36.971 | 29.215 | 1.00 | 32.74 | CPS4 |
| ATOM | 2929 | N | ALA | 19 | -1.906 | 35.686 | 30.893 | 1.00 | 33.01 | CPS4 |
| ATOM | 2930 | CA | ALA | 19 | -2.801 | 34.569 | 30.618 | 1.00 | 34.57 | CPS4 |
| ATOM | 2931 | CB | ALA | 19 | -2.458 | 33.384 | 31.515 | 1.00 | 34.76 | CPS4 |
| ATOM | 2932 | C | ALA | 19 | -4.262 | 34.944 | 30.793 | 1.00 | 36.04 | CPS4 |
| ATOM | 2933 | O | ALA | 19 | -5.140 | 34.338 | 30.176 | 1.00 | 36.08 | CPS4 |
| ATOM | 2934 | N | GLY | 20 | -4.523 | 35.942 | 31.630 | 1.00 | 36.62 | CPS4 |
| ATOM | 2935 | CA | GLY | 20 | -5.896 | 36.360 | 31.852 | 1.00 | 38.42 | CPS4 |
| ATOM | 2936 | C | GLY | 20 | -6.379 | 37.392 | 30.850 | 1.00 | 38.57 | CPS4 |
| ATOM | 2937 | O | GLY | 20 | -7.560 | 37.437 | 30.511 | 1.00 | 38.87 | CPS4 |
| ATOM | 2938 | N | ARG | 21 | -5.460 | 38.210 | 30.355 | 1.00 | 38.64 | CPS4 |
| ATOM | 2939 | CA | ARG | 21 | -5.813 | 39.261 | 29.417 | 1.00 | 39.87 | CPS4 |
| ATOM | 2940 | CB | ARG | 21 | -4.944 | 40.489 | 29.695 | 1.00 | 42.18 | CPS4 |
| ATOM | 2941 | CG | ARG | 21 | -4.955 | 40.913 | 31.156 | 1.00 | 47.12 | CPS4 |
| ATOM | 2942 | CD | ARG | 21 | -4.162 | 42.195 | 31.381 | 1.00 | 50.94 | CPS4 |
| ATOM | 2943 | NE | ARG | 21 | -4.149 | 42.582 | 32.792 | 1.00 | 55.15 | CPS4 |
| ATOM | 2944 | CZ | ARG | 21 | -3.691 | 43.746 | 33.252 | 1.00 | 56.93 | CPS4 |
| ATOM | 2945 | NH1 | ARG | 21 | -3.721 | 44.005 | 34.554 | 1.00 | 57.41 | CPS4 |
| ATOM | 2946 | NH2 | ARG | 21 | -3.211 | 44.656 | 32.412 | 1.00 | 57.54 | CPS4 |
| ATOM | 2947 | C | ARG | 21 | -5.699 | 38.879 | 27.942 | 1.00 | 39.28 | CPS4 |
| ATOM | 2948 | O | ARG | 21 | -6.223 | 39.587 | 27.080 | 1.00 | 39.05 | CPS4 |
| ATOM | 2949 | N | GLN | 22 | -5.030 | 37.764 | 27.655 | 1.00 | 37.77 | CPS4 |
| ATOM | 2950 | CA | GLN | 22 | -4.823 | 37.311 | 26.276 | 1.00 | 37.67 | CPS4 |
| ATOM | 2951 | CB | GLN | 22 | -3.325 | 37.254 | 25.979 | 1.00 | 36.76 | CPS4 |
| ATOM | 2952 | CG | GLN | 22 | -2.634 | 38.603 | 26.038 | 1.00 | 40.23 | CPS4 |
| ATOM | 2953 | CD | GLN | 22 | -1.135 | 38.490 | 25.871 | 1.00 | 41.78 | CPS4 |
| ATOM | 2954 | OE1 | GLN | 22 | -0.652 | 37.746 | 25.018 | 1.00 | 43.79 | CPS4 |
| ATOM | 2955 | NE2 | GLN | 22 | -0.389 | 39.236 | 26.677 | 1.00 | 42.68 | CPS4 |
| ATOM | 2956 | C | GLN | 22 | -5.441 | 35.947 | 25.997 | 1.00 | 37.08 | CPS4 |
| ATOM | 2957 | O | GLN | 22 | -5.004 | 34.936 | 26.560 | 1.00 | 37.84 | CPS4 |
| ATOM | 2958 | N | LYS | 23 | -6.431 | 35.910 | 25.106 | 1.00 | 34.80 | CPS4 |
| ATOM | 2959 | CA | LYS | 23 | -7.114 | 34.661 | 24.781 | 1.00 | 34.70 | CPS4 |
| ATOM | 2960 | CB | LYS | 23 | -8.133 | 34.862 | 23.641 | 1.00 | 35.14 | CPS4 |
| ATOM | 2961 | CG | LYS | 23 | -9.497 | 35.362 | 24.090 | 1.00 | 37.14 | CPS4 |
| ATOM | 2962 | CD | LYS | 23 | -10.626 | 34.901 | 23.159 | 1.00 | 37.66 | CPS4 |
| ATOM | 2963 | CE | LYS | 23 | -10.491 | 35.444 | 21.745 | 1.00 | 36.38 | CPS4 |

FIG. 1A-52

| ATOM | 2964 | NZ  | LYS | 23 | -11.732 | 35.177 | 20.937 | 1.00 | 32.97 | CPS4 |
|------|------|-----|-----|----|---------|--------|--------|------|-------|------|
| ATOM | 2965 | C   | LYS | 23 | -6.211  | 33.491 | 24.403 | 1.00 | 32.65 | CPS4 |
| ATOM | 2966 | O   | LYS | 23 | -6.488  | 32.356 | 24.775 | 1.00 | 33.18 | CPS4 |
| ATOM | 2967 | N   | ARG | 24 | -5.143  | 33.754 | 23.659 | 1.00 | 31.45 | CPS4 |
| ATOM | 2968 | CA  | ARG | 24 | -4.265  | 32.662 | 23.227 | 1.00 | 31.24 | CPS4 |
| ATOM | 2969 | CB  | ARG | 24 | -4.159  | 32.665 | 21.691 | 1.00 | 32.20 | CPS4 |
| ATOM | 2970 | CG  | ARG | 24 | -5.218  | 31.798 | 20.979 | 1.00 | 34.37 | CPS4 |
| ATOM | 2971 | CD  | ARG | 24 | -6.636  | 32.172 | 21.379 | 1.00 | 34.60 | CPS4 |
| ATOM | 2972 | NE  | ARG | 24 | -7.668  | 31.404 | 20.672 | 1.00 | 34.87 | CPS4 |
| ATOM | 2973 | CZ  | ARG | 24 | -8.339  | 30.379 | 21.191 | 1.00 | 34.53 | CPS4 |
| ATOM | 2974 | NH1 | ARG | 24 | -8.095  | 29.976 | 22.428 | 1.00 | 33.25 | CPS4 |
| ATOM | 2975 | NH2 | ARG | 24 | -9.281  | 29.770 | 20.478 | 1.00 | 35.11 | CPS4 |
| ATOM | 2976 | C   | ARG | 24 | -2.864  | 32.603 | 23.832 | 1.00 | 29.23 | CPS4 |
| ATOM | 2977 | O   | ARG | 24 | -1.967  | 31.992 | 23.259 | 1.00 | 28.10 | CPS4 |
| ATOM | 2978 | N   | PHE | 25 | -2.669  | 33.208 | 24.995 | 1.00 | 27.93 | CPS4 |
| ATOM | 2979 | CA  | PHE | 25 | -1.339  | 33.186 | 25.604 | 1.00 | 26.76 | CPS4 |
| ATOM | 2980 | CB  | PHE | 25 | -1.339  | 33.979 | 26.916 | 1.00 | 27.25 | CPS4 |
| ATOM | 2981 | CG  | PHE | 25 | 0.016   | 34.068 | 27.564 | 1.00 | 28.14 | CPS4 |
| ATOM | 2982 | CD1 | PHE | 25 | 0.301   | 33.345 | 28.716 | 1.00 | 29.02 | CPS4 |
| ATOM | 2983 | CD2 | PHE | 25 | 1.023   | 34.837 | 26.986 | 1.00 | 29.76 | CPS4 |
| ATOM | 2984 | CE1 | PHE | 25 | 1.576   | 33.380 | 29.286 | 1.00 | 29.84 | CPS4 |
| ATOM | 2985 | CE2 | PHE | 25 | 2.304   | 34.879 | 27.547 | 1.00 | 31.14 | CPS4 |
| ATOM | 2986 | CZ  | PHE | 25 | 2.579   | 34.146 | 28.699 | 1.00 | 28.80 | CPS4 |
| ATOM | 2987 | C   | PHE | 25 | -0.822  | 31.763 | 25.857 | 1.00 | 24.98 | CPS4 |
| ATOM | 2988 | O   | PHE | 25 | 0.244   | 31.385 | 25.364 | 1.00 | 25.69 | CPS4 |
| ATOM | 2989 | N   | ALA | 26 | -1.569  | 30.979 | 26.627 | 1.00 | 23.55 | CPS4 |
| ATOM | 2990 | CA  | ALA | 26 | -1.158  | 29.609 | 26.932 | 1.00 | 23.50 | CPS4 |
| ATOM | 2991 | CB  | ALA | 26 | -2.187  | 28.935 | 27.812 | 1.00 | 23.29 | CPS4 |
| ATOM | 2992 | C   | ALA | 26 | -0.968  | 28.785 | 25.668 | 1.00 | 23.71 | CPS4 |
| ATOM | 2993 | O   | ALA | 26 | -0.022  | 27.999 | 25.567 | 1.00 | 22.90 | CPS4 |
| ATOM | 2994 | N   | GLU | 27 | -1.887  | 28.951 | 24.719 | 1.00 | 23.56 | CPS4 |
| ATOM | 2995 | CA  | GLU | 27 | -1.837  | 28.211 | 23.460 | 1.00 | 23.91 | CPS4 |
| ATOM | 2996 | CB  | GLU | 27 | -3.114  | 28.471 | 22.645 | 1.00 | 25.46 | CPS4 |
| ATOM | 2997 | CG  | GLU | 27 | -4.387  | 27.805 | 23.184 | 1.00 | 28.50 | CPS4 |
| ATOM | 2998 | CD  | GLU | 27 | -4.892  | 28.403 | 24.499 | 1.00 | 32.43 | CPS4 |
| ATOM | 2999 | OE1 | GLU | 27 | -4.603  | 29.589 | 24.774 | 1.00 | 31.29 | CPS4 |
| ATOM | 3000 | OE2 | GLU | 27 | -5.589  | 27.682 | 25.255 | 1.00 | 33.07 | CPS4 |
| ATOM | 3001 | C   | GLU | 27 | -0.610  | 28.550 | 22.615 | 1.00 | 23.66 | CPS4 |
| ATOM | 3002 | O   | GLU | 27 | -0.152  | 27.734 | 21.822 | 1.00 | 24.71 | CPS4 |
| ATOM | 3003 | N   | ARG | 28 | -0.081  | 29.754 | 22.779 | 1.00 | 24.04 | CPS4 |
| ATOM | 3004 | CA  | ARG | 28 | 1.094   | 30.170 | 22.016 | 1.00 | 25.19 | CPS4 |
| ATOM | 3005 | CB  | ARG | 28 | 1.191   | 31.696 | 22.047 | 1.00 | 28.07 | CPS4 |
| ATOM | 3006 | CG  | ARG | 28 | 1.800   | 32.351 | 20.829 | 1.00 | 33.41 | CPS4 |
| ATOM | 3007 | CD  | ARG | 28 | 0.994   | 33.602 | 20.446 | 1.00 | 34.25 | CPS4 |
| ATOM | 3008 | NE  | ARG | 28 | 0.767   | 34.484 | 21.592 | 1.00 | 35.45 | CPS4 |
| ATOM | 3009 | CZ  | ARG | 28 | -0.389  | 35.097 | 21.853 | 1.00 | 37.30 | CPS4 |
| ATOM | 3010 | NH1 | ARG | 28 | -1.433  | 34.929 | 21.050 | 1.00 | 35.32 | CPS4 |
| ATOM | 3011 | NH2 | ARG | 28 | -0.506  | 35.871 | 22.928 | 1.00 | 37.39 | CPS4 |
| ATOM | 3012 | C   | ARG | 28 | 2.355   | 29.564 | 22.634 | 1.00 | 24.51 | CPS4 |
| ATOM | 3013 | O   | ARG | 28 | 3.295   | 29.188 | 21.933 | 1.00 | 23.41 | CPS4 |
| ATOM | 3014 | N   | ILE | 29 | 2.348   | 29.459 | 23.956 | 1.00 | 22.84 | CPS4 |
| ATOM | 3015 | CA  | ILE | 29 | 3.498   | 28.959 | 24.707 | 1.00 | 23.13 | CPS4 |
| ATOM | 3016 | CB  | ILE | 29 | 3.462   | 29.482 | 26.175 | 1.00 | 24.30 | CPS4 |
| ATOM | 3017 | CG2 | ILE | 29 | 4.666   | 28.961 | 26.957 | 1.00 | 24.45 | CPS4 |
| ATOM | 3018 | CG1 | ILE | 29 | 3.390   | 31.014 | 26.192 | 1.00 | 25.98 | CPS4 |
| ATOM | 3019 | CD1 | ILE | 29 | 4.519   | 31.704 | 25.507 | 1.00 | 27.67 | CPS4 |
| ATOM | 3020 | C   | ILE | 29 | 3.628   | 27.450 | 24.787 | 1.00 | 22.56 | CPS4 |

FIG. 1A-53

| ATOM | 3021 | O | ILE | 29 | 4.739 | 26.914 | 24.700 | 1.00 | 22.11 | CPS4 |
|---|---|---|---|---|---|---|---|---|---|---|
| ATOM | 3022 | N | LEU | 30 | 2.492 | 26.774 | 24.952 | 1.00 | 20.94 | CPS4 |
| ATOM | 3023 | CA | LEU | 30 | 2.456 | 25.334 | 25.150 | 1.00 | 20.47 | CPS4 |
| ATOM | 3024 | CB | LEU | 30 | 1.447 | 25.009 | 26.264 | 1.00 | 20.33 | CPS4 |
| ATOM | 3025 | CG | LEU | 30 | 1.660 | 25.741 | 27.600 | 1.00 | 23.00 | CPS4 |
| ATOM | 3026 | CD1 | LEU | 30 | 0.511 | 25.425 | 28.561 | 1.00 | 23.25 | CPS4 |
| ATOM | 3027 | CD2 | LEU | 30 | 2.999 | 25.331 | 28.199 | 1.00 | 20.84 | CPS4 |
| ATOM | 3028 | C | LEU | 30 | 2.120 | 24.493 | 23.936 | 1.00 | 21.35 | CPS4 |
| ATOM | 3029 | O | LEU | 30 | 1.279 | 24.870 | 23.127 | 1.00 | 22.16 | CPS4 |
| ATOM | 3030 | N | THR | 31 | 2.781 | 23.344 | 23.821 | 1.00 | 21.39 | CPS4 |
| ATOM | 3031 | CA | THR | 31 | 2.505 | 22.428 | 22.727 | 1.00 | 22.79 | CPS4 |
| ATOM | 3032 | CB | THR | 31 | 3.594 | 21.347 | 22.587 | 1.00 | 23.24 | CPS4 |
| ATOM | 3033 | OG1 | THR | 31 | 3.631 | 20.550 | 23.778 | 1.00 | 24.29 | CPS4 |
| ATOM | 3034 | CG2 | THR | 31 | 4.960 | 21.996 | 22.356 | 1.00 | 24.52 | CPS4 |
| ATOM | 3035 | C | THR | 31 | 1.186 | 21.736 | 23.052 | 1.00 | 25.13 | CPS4 |
| ATOM | 3036 | O | THR | 31 | 0.646 | 21.868 | 24.158 | 1.00 | 24.76 | CPS4 |
| ATOM | 3037 | N | ARG | 32 | 0.672 | 20.974 | 22.096 | 1.00 | 27.56 | CPS4 |
| ATOM | 3038 | CA | ARG | 32 | -0.594 | 20.289 | 22.298 | 1.00 | 30.79 | CPS4 |
| ATOM | 3039 | CB | ARG | 32 | -0.951 | 19.489 | 21.041 | 1.00 | 33.62 | CPS4 |
| ATOM | 3040 | CG | ARG | 32 | -2.328 | 19.807 | 20.476 | 1.00 | 38.29 | CPS4 |
| ATOM | 3041 | CD | ARG | 32 | -3.419 | 18.876 | 21.014 | 1.00 | 42.11 | CPS4 |
| ATOM | 3042 | NE | ARG | 32 | -4.044 | 19.329 | 22.259 | 1.00 | 45.08 | CPS4 |
| ATOM | 3043 | CZ | ARG | 32 | -4.676 | 20.491 | 22.409 | 1.00 | 46.06 | CPS4 |
| ATOM | 3044 | NH1 | ARG | 32 | -4.774 | 21.348 | 21.393 | 1.00 | 45.64 | CPS4 |
| ATOM | 3045 | NH2 | ARG | 32 | -5.224 | 20.792 | 23.577 | 1.00 | 45.73 | CPS4 |
| ATOM | 3046 | C | ARG | 32 | -0.577 | 19.384 | 23.524 | 1.00 | 30.10 | CPS4 |
| ATOM | 3047 | O | ARG | 32 | -1.527 | 19.388 | 24.310 | 1.00 | 30.78 | CPS4 |
| ATOM | 3048 | N | SER | 33 | 0.499 | 18.620 | 23.699 | 1.00 | 30.30 | CPS4 |
| ATOM | 3049 | CA | SER | 33 | 0.615 | 17.722 | 24.850 | 1.00 | 31.44 | CPS4 |
| ATOM | 3050 | CB | SER | 33 | 1.853 | 16.833 | 24.715 | 1.00 | 32.43 | CPS4 |
| ATOM | 3051 | OG | SER | 33 | 1.709 | 15.944 | 23.620 | 1.00 | 37.42 | CPS4 |
| ATOM | 3052 | C | SER | 33 | 0.684 | 18.489 | 26.168 | 1.00 | 30.59 | CPS4 |
| ATOM | 3053 | O | SER | 33 | 0.054 | 18.108 | 27.153 | 1.00 | 31.00 | CPS4 |
| ATOM | 3054 | N | GLU | 34 | 1.464 | 19.564 | 26.191 | 1.00 | 28.83 | CPS4 |
| ATOM | 3055 | CA | GLU | 34 | 1.589 | 20.370 | 27.400 | 1.00 | 27.36 | CPS4 |
| ATOM | 3056 | CB | GLU | 34 | 2.621 | 21.487 | 27.192 | 1.00 | 26.46 | CPS4 |
| ATOM | 3057 | CG | GLU | 34 | 4.048 | 20.963 | 27.099 | 1.00 | 24.49 | CPS4 |
| ATOM | 3058 | CD | GLU | 34 | 5.074 | 22.029 | 26.712 | 1.00 | 24.80 | CPS4 |
| ATOM | 3059 | OE1 | GLU | 34 | 6.223 | 21.934 | 27.196 | 1.00 | 23.27 | CPS4 |
| ATOM | 3060 | OE2 | GLU | 34 | 4.748 | 22.943 | 25.920 | 1.00 | 23.10 | CPS4 |
| ATOM | 3061 | C | GLU | 34 | 0.232 | 20.962 | 27.757 | 1.00 | 27.85 | CPS4 |
| ATOM | 3062 | O | GLU | 34 | -0.138 | 21.028 | 28.928 | 1.00 | 27.48 | CPS4 |
| ATOM | 3063 | N | LEU | 35 | -0.513 | 21.392 | 26.742 | 1.00 | 28.18 | CPS4 |
| ATOM | 3064 | CA | LEU | 35 | -1.840 | 21.960 | 26.968 | 1.00 | 29.32 | CPS4 |
| ATOM | 3065 | CB | LEU | 35 | -2.428 | 22.478 | 25.657 | 1.00 | 27.71 | CPS4 |
| ATOM | 3066 | CG | LEU | 35 | -1.986 | 23.882 | 25.261 | 1.00 | 28.10 | CPS4 |
| ATOM | 3067 | CD1 | LEU | 35 | -2.379 | 24.130 | 23.810 | 1.00 | 28.81 | CPS4 |
| ATOM | 3068 | CD2 | LEU | 35 | -2.629 | 24.928 | 26.202 | 1.00 | 25.30 | CPS4 |
| ATOM | 3069 | C | LEU | 35 | -2.782 | 20.931 | 27.572 | 1.00 | 30.93 | CPS4 |
| ATOM | 3070 | O | LEU | 35 | -3.617 | 21.263 | 28.417 | 1.00 | 31.38 | CPS4 |
| ATOM | 3071 | N | ASP | 36 | -2.659 | 19.681 | 27.135 | 1.00 | 33.94 | CPS4 |
| ATOM | 3072 | CA | ASP | 36 | -3.513 | 18.632 | 27.673 | 1.00 | 35.97 | CPS4 |
| ATOM | 3073 | CB | ASP | 36 | -3.206 | 17.274 | 27.025 | 1.00 | 37.70 | CPS4 |
| ATOM | 3074 | CG | ASP | 36 | -3.763 | 17.156 | 25.612 | 1.00 | 39.64 | CPS4 |
| ATOM | 3075 | OD1 | ASP | 36 | -4.838 | 17.727 | 25.332 | 1.00 | 41.16 | CPS4 |
| ATOM | 3076 | OD2 | ASP | 36 | -3.134 | 16.475 | 24.778 | 1.00 | 42.22 | CPS4 |
| ATOM | 3077 | C | ASP | 36 | -3.306 | 18.560 | 29.182 | 1.00 | 36.01 | CPS4 |

FIG. 1A-54

| ATOM | 3078 | O | ASP | 36 | -4.269 | 18.440 | 29.933 | 1.00 | 36.88 | CPS4 |
|---|---|---|---|---|---|---|---|---|---|---|
| ATOM | 3079 | N | GLN | 37 | -2.054 | 18.645 | 29.626 | 1.00 | 35.23 | CPS4 |
| ATOM | 3080 | CA | GLN | 37 | -1.750 | 18.612 | 31.057 | 1.00 | 34.91 | CPS4 |
| ATOM | 3081 | CB | GLN | 37 | -0.238 | 18.552 | 31.278 | 1.00 | 36.27 | CPS4 |
| ATOM | 3082 | CG | GLN | 37 | 0.417 | 17.271 | 30.798 | 1.00 | 40.16 | CPS4 |
| ATOM | 3083 | CD | GLN | 37 | 1.925 | 17.394 | 30.676 | 1.00 | 41.54 | CPS4 |
| ATOM | 3084 | OE1 | GLN | 37 | 2.436 | 18.146 | 29.845 | 1.00 | 42.68 | CPS4 |
| ATOM | 3085 | NE2 | GLN | 37 | 2.647 | 16.656 | 31.509 | 1.00 | 43.46 | CPS4 |
| ATOM | 3086 | C | GLN | 37 | -2.302 | 19.869 | 31.722 | 1.00 | 33.96 | CPS4 |
| ATOM | 3087 | O | GLN | 37 | -2.985 | 19.810 | 32.743 | 1.00 | 33.94 | CPS4 |
| ATOM | 3088 | N | TYR | 38 | -1.990 | 21.009 | 31.120 | 1.00 | 32.47 | CPS4 |
| ATOM | 3089 | CA | TYR | 38 | -2.422 | 22.315 | 31.601 | 1.00 | 31.95 | CPS4 |
| ATOM | 3090 | CB | TYR | 38 | -1.938 | 23.378 | 30.617 | 1.00 | 30.34 | CPS4 |
| ATOM | 3091 | CG | TYR | 38 | -2.442 | 24.776 | 30.869 | 1.00 | 29.96 | CPS4 |
| ATOM | 3092 | CD1 | TYR | 38 | -3.488 | 25.308 | 30.110 | 1.00 | 30.42 | CPS4 |
| ATOM | 3093 | CE1 | TYR | 38 | -3.905 | 26.618 | 30.287 | 1.00 | 30.73 | CPS4 |
| ATOM | 3094 | CD2 | TYR | 38 | -1.836 | 25.593 | 31.821 | 1.00 | 28.80 | CPS4 |
| ATOM | 3095 | CE2 | TYR | 38 | -2.248 | 26.906 | 32.005 | 1.00 | 29.56 | CPS4 |
| ATOM | 3096 | CZ | TYR | 38 | -3.278 | 27.411 | 31.238 | 1.00 | 31.46 | CPS4 |
| ATOM | 3097 | OH | TYR | 38 | -3.689 | 28.710 | 31.428 | 1.00 | 32.91 | CPS4 |
| ATOM | 3098 | C | TYR | 38 | -3.936 | 22.438 | 31.803 | 1.00 | 32.87 | CPS4 |
| ATOM | 3099 | O | TYR | 38 | -4.388 | 22.888 | 32.854 | 1.00 | 31.90 | CPS4 |
| ATOM | 3100 | N | TYR | 39 | -4.716 | 22.040 | 30.801 | 1.00 | 34.25 | CPS4 |
| ATOM | 3101 | CA | TYR | 39 | -6.167 | 22.151 | 30.905 | 1.00 | 36.14 | CPS4 |
| ATOM | 3102 | CB | TYR | 39 | -6.842 | 21.687 | 29.605 | 1.00 | 36.53 | CPS4 |
| ATOM | 3103 | CG | TYR | 39 | -6.618 | 22.577 | 28.390 | 1.00 | 36.61 | CPS4 |
| ATOM | 3104 | CD1 | TYR | 39 | -6.608 | 23.970 | 28.504 | 1.00 | 36.59 | CPS4 |
| ATOM | 3105 | CE1 | TYR | 39 | -6.471 | 24.791 | 27.378 | 1.00 | 37.06 | CPS4 |
| ATOM | 3106 | CD2 | TYR | 39 | -6.483 | 22.021 | 27.115 | 1.00 | 36.55 | CPS4 |
| ATOM | 3107 | CE2 | TYR | 39 | -6.347 | 22.830 | 25.980 | 1.00 | 37.48 | CPS4 |
| ATOM | 3108 | CZ | TYR | 39 | -6.343 | 24.213 | 26.118 | 1.00 | 37.69 | CPS4 |
| ATOM | 3109 | OH | TYR | 39 | -6.224 | 25.011 | 24.998 | 1.00 | 37.54 | CPS4 |
| ATOM | 3110 | C | TYR | 39 | -6.734 | 21.354 | 32.080 | 1.00 | 37.42 | CPS4 |
| ATOM | 3111 | O | TYR | 39 | -7.809 | 21.667 | 32.584 | 1.00 | 38.66 | CPS4 |
| ATOM | 3112 | N | GLU | 40 | -6.010 | 20.334 | 32.524 | 1.00 | 39.15 | CPS4 |
| ATOM | 3113 | CA | GLU | 40 | -6.476 | 19.491 | 33.622 | 1.00 | 41.54 | CPS4 |
| ATOM | 3114 | CB | GLU | 40 | -5.862 | 18.094 | 33.502 | 1.00 | 43.99 | CPS4 |
| ATOM | 3115 | CG | GLU | 40 | -6.257 | 17.341 | 32.235 | 1.00 | 48.54 | CPS4 |
| ATOM | 3116 | CD | GLU | 40 | -7.761 | 17.149 | 32.111 | 1.00 | 50.97 | CPS4 |
| ATOM | 3117 | OE1 | GLU | 40 | -8.377 | 16.647 | 33.076 | 1.00 | 53.41 | CPS4 |
| ATOM | 3118 | OE2 | GLU | 40 | -8.329 | 17.495 | 31.050 | 1.00 | 52.53 | CPS4 |
| ATOM | 3119 | C | GLU | 40 | -6.181 | 20.035 | 35.009 | 1.00 | 41.32 | CPS4 |
| ATOM | 3120 | O | GLU | 40 | -6.687 | 19.516 | 36.006 | 1.00 | 41.95 | CPS4 |
| ATOM | 3121 | N | LEU | 41 | -5.374 | 21.085 | 35.075 | 1.00 | 40.03 | CPS4 |
| ATOM | 3122 | CA | LEU | 41 | -4.988 | 21.666 | 36.353 | 1.00 | 38.83 | CPS4 |
| ATOM | 3123 | CB | LEU | 41 | -3.589 | 22.283 | 36.230 | 1.00 | 37.58 | CPS4 |
| ATOM | 3124 | CG | LEU | 41 | -2.457 | 21.303 | 35.908 | 1.00 | 36.93 | CPS4 |
| ATOM | 3125 | CD1 | LEU | 41 | -1.171 | 22.070 | 35.673 | 1.00 | 36.17 | CPS4 |
| ATOM | 3126 | CD2 | LEU | 41 | -2.291 | 20.309 | 37.050 | 1.00 | 36.43 | CPS4 |
| ATOM | 3127 | C | LEU | 41 | -5.939 | 22.709 | 36.916 | 1.00 | 38.96 | CPS4 |
| ATOM | 3128 | O | LEU | 41 | -6.744 | 23.295 | 36.197 | 1.00 | 38.34 | CPS4 |
| ATOM | 3129 | N | SER | 42 | -5.830 | 22.936 | 38.220 | 1.00 | 39.70 | CPS4 |
| ATOM | 3130 | CA | SER | 42 | -6.645 | 23.937 | 38.890 | 1.00 | 41.21 | CPS4 |
| ATOM | 3131 | CB | SER | 42 | -6.456 | 23.849 | 40.408 | 1.00 | 41.87 | CPS4 |
| ATOM | 3132 | OG | SER | 42 | -5.119 | 24.152 | 40.781 | 1.00 | 40.52 | CPS4 |
| ATOM | 3133 | C | SER | 42 | -6.182 | 25.305 | 38.399 | 1.00 | 42.49 | CPS4 |
| ATOM | 3134 | O | SER | 42 | -5.134 | 25.424 | 37.766 | 1.00 | 42.26 | CPS4 |

FIG. 1A-55

| ATOM | 3135 | N   | GLU | 43 | -6.955 | 26.338 | 38.703 | 1.00 | 42.87 | CPS4 |
| ATOM | 3136 | CA  | GLU | 43 | -6.616 | 27.687 | 38.286 | 1.00 | 44.09 | CPS4 |
| ATOM | 3137 | CB  | GLU | 43 | -7.686 | 28.651 | 38.803 | 1.00 | 46.92 | CPS4 |
| ATOM | 3138 | CG  | GLU | 43 | -7.721 | 30.000 | 38.115 | 1.00 | 51.91 | CPS4 |
| ATOM | 3139 | CD  | GLU | 43 | -6.722 | 30.982 | 38.687 | 1.00 | 55.38 | CPS4 |
| ATOM | 3140 | OE1 | GLU | 43 | -6.747 | 31.203 | 39.920 | 1.00 | 57.45 | CPS4 |
| ATOM | 3141 | OE2 | GLU | 43 | -5.920 | 31.543 | 37.905 | 1.00 | 57.72 | CPS4 |
| ATOM | 3142 | C   | GLU | 43 | -5.226 | 28.088 | 38.802 | 1.00 | 43.04 | CPS4 |
| ATOM | 3143 | O   | GLU | 43 | -4.404 | 28.633 | 38.058 | 1.00 | 42.48 | CPS4 |
| ATOM | 3144 | N   | LYS | 44 | -4.965 | 27.805 | 40.074 | 1.00 | 41.59 | CPS4 |
| ATOM | 3145 | CA  | LYS | 44 | -3.684 | 28.136 | 40.690 | 1.00 | 40.46 | CPS4 |
| ATOM | 3146 | CB  | LYS | 44 | -3.758 | 27.910 | 42.201 | 1.00 | 42.16 | CPS4 |
| ATOM | 3147 | CG  | LYS | 44 | -2.528 | 28.378 | 42.960 | 1.00 | 44.29 | CPS4 |
| ATOM | 3148 | CD  | LYS | 44 | -2.684 | 28.137 | 44.457 | 1.00 | 47.29 | CPS4 |
| ATOM | 3149 | CE  | LYS | 44 | -1.439 | 28.574 | 45.218 | 1.00 | 48.62 | CPS4 |
| ATOM | 3150 | NZ  | LYS | 44 | -1.554 | 28.319 | 46.683 | 1.00 | 50.30 | CPS4 |
| ATOM | 3151 | C   | LYS | 44 | -2.537 | 27.311 | 40.107 | 1.00 | 38.58 | CPS4 |
| ATOM | 3152 | O   | LYS | 44 | -1.466 | 27.845 | 39.806 | 1.00 | 37.53 | CPS4 |
| ATOM | 3153 | N   | ARG | 45 | -2.764 | 26.010 | 39.957 | 1.00 | 35.62 | CPS4 |
| ATOM | 3154 | CA  | ARG | 45 | -1.755 | 25.115 | 39.406 | 1.00 | 34.29 | CPS4 |
| ATOM | 3155 | CB  | ARG | 45 | -2.205 | 23.663 | 39.575 | 1.00 | 36.05 | CPS4 |
| ATOM | 3156 | CG  | ARG | 45 | -2.054 | 23.119 | 41.002 | 1.00 | 39.56 | CPS4 |
| ATOM | 3157 | CD  | ARG | 45 | -0.605 | 22.768 | 41.301 | 1.00 | 42.27 | CPS4 |
| ATOM | 3158 | NE  | ARG | 45 | -0.090 | 21.793 | 40.341 | 1.00 | 45.82 | CPS4 |
| ATOM | 3159 | CZ  | ARG | 45 |  1.003 | 21.973 | 39.600 | 1.00 | 48.25 | CPS4 |
| ATOM | 3160 | NH1 | ARG | 45 |  1.711 | 23.093 | 39.707 | 1.00 | 47.45 | CPS4 |
| ATOM | 3161 | NH2 | ARG | 45 |  1.381 | 21.037 | 38.733 | 1.00 | 48.96 | CPS4 |
| ATOM | 3162 | C   | ARG | 45 | -1.491 | 25.422 | 37.926 | 1.00 | 32.63 | CPS4 |
| ATOM | 3163 | O   | ARG | 45 | -0.383 | 25.215 | 37.425 | 1.00 | 30.48 | CPS4 |
| ATOM | 3164 | N   | LYS | 46 | -2.513 | 25.912 | 37.232 | 1.00 | 30.94 | CPS4 |
| ATOM | 3165 | CA  | LYS | 46 | -2.365 | 26.265 | 35.820 | 1.00 | 31.41 | CPS4 |
| ATOM | 3166 | CB  | LYS | 46 | -3.672 | 26.841 | 35.262 | 1.00 | 31.76 | CPS4 |
| ATOM | 3167 | CG  | LYS | 46 | -4.637 | 25.828 | 34.661 | 1.00 | 32.98 | CPS4 |
| ATOM | 3168 | CD  | LYS | 46 | -5.770 | 26.574 | 33.959 | 1.00 | 35.55 | CPS4 |
| ATOM | 3169 | CE  | LYS | 46 | -6.597 | 25.647 | 33.081 | 1.00 | 37.38 | CPS4 |
| ATOM | 3170 | NZ  | LYS | 46 | -7.283 | 24.614 | 33.895 | 1.00 | 39.63 | CPS4 |
| ATOM | 3171 | C   | LYS | 46 | -1.275 | 27.326 | 35.668 | 1.00 | 30.10 | CPS4 |
| ATOM | 3172 | O   | LYS | 46 | -0.365 | 27.197 | 34.843 | 1.00 | 28.86 | CPS4 |
| ATOM | 3173 | N   | ASN | 47 | -1.378 | 28.388 | 36.457 | 1.00 | 29.05 | CPS4 |
| ATOM | 3174 | CA  | ASN | 47 | -0.393 | 29.445 | 36.357 | 1.00 | 29.35 | CPS4 |
| ATOM | 3175 | CB  | ASN | 47 | -0.875 | 30.700 | 37.081 | 1.00 | 32.62 | CPS4 |
| ATOM | 3176 | CG  | ASN | 47 | -1.923 | 31.471 | 36.270 | 1.00 | 36.22 | CPS4 |
| ATOM | 3177 | OD1 | ASN | 47 | -1.748 | 31.710 | 35.065 | 1.00 | 37.87 | CPS4 |
| ATOM | 3178 | ND2 | ASN | 47 | -3.008 | 31.869 | 36.928 | 1.00 | 38.04 | CPS4 |
| ATOM | 3179 | C   | ASN | 47 |  0.998 | 29.033 | 36.822 | 1.00 | 28.34 | CPS4 |
| ATOM | 3180 | O   | ASN | 47 |  1.987 | 29.533 | 36.291 | 1.00 | 26.63 | CPS4 |
| ATOM | 3181 | N   | GLU | 48 |  1.085 | 28.125 | 37.794 | 1.00 | 27.39 | CPS4 |
| ATOM | 3182 | CA  | GLU | 48 |  2.398 | 27.656 | 38.253 | 1.00 | 26.57 | CPS4 |
| ATOM | 3183 | CB  | GLU | 48 |  2.256 | 26.763 | 39.493 | 1.00 | 29.29 | CPS4 |
| ATOM | 3184 | CG  | GLU | 48 |  1.753 | 27.481 | 40.733 | 1.00 | 35.14 | CPS4 |
| ATOM | 3185 | CD  | GLU | 48 |  1.467 | 26.534 | 41.899 | 1.00 | 38.18 | CPS4 |
| ATOM | 3186 | OE1 | GLU | 48 |  1.054 | 27.029 | 42.970 | 1.00 | 39.62 | CPS4 |
| ATOM | 3187 | OE2 | GLU | 48 |  1.654 | 25.301 | 41.747 | 1.00 | 39.49 | CPS4 |
| ATOM | 3188 | C   | GLU | 48 |  3.023 | 26.848 | 37.114 | 1.00 | 24.55 | CPS4 |
| ATOM | 3189 | O   | GLU | 48 |  4.198 | 27.004 | 36.786 | 1.00 | 23.53 | CPS4 |
| ATOM | 3190 | N   | PHE | 49 |  2.215 | 25.984 | 36.513 | 1.00 | 22.65 | CPS4 |
| ATOM | 3191 | CA  | PHE | 49 |  2.643 | 25.136 | 35.400 | 1.00 | 22.71 | CPS4 |

FIG. 1A-56

| ATOM | 3192 | CB | PHE | 49 | 1.474 | 24.235 | 34.972 | 1.00 | 23.78 | CPS4 |
| --- | --- | --- | --- | --- | --- | --- | --- | --- | --- | --- |
| ATOM | 3193 | CG | PHE | 49 | 1.796 | 23.299 | 33.836 | 1.00 | 23.79 | CPS4 |
| ATOM | 3194 | CD1 | PHE | 49 | 2.359 | 22.053 | 34.084 | 1.00 | 25.06 | CPS4 |
| ATOM | 3195 | CD2 | PHE | 49 | 1.525 | 23.660 | 32.522 | 1.00 | 24.25 | CPS4 |
| ATOM | 3196 | CE1 | PHE | 49 | 2.645 | 21.179 | 33.045 | 1.00 | 25.26 | CPS4 |
| ATOM | 3197 | CE2 | PHE | 49 | 1.812 | 22.786 | 31.464 | 1.00 | 25.16 | CPS4 |
| ATOM | 3198 | CZ | PHE | 49 | 2.370 | 21.546 | 31.729 | 1.00 | 26.61 | CPS4 |
| ATOM | 3199 | C | PHE | 49 | 3.089 | 25.980 | 34.201 | 1.00 | 22.04 | CPS4 |
| ATOM | 3200 | O | PHE | 49 | 4.158 | 25.751 | 33.631 | 1.00 | 21.19 | CPS4 |
| ATOM | 3201 | N | LEU | 50 | 2.260 | 26.945 | 33.818 | 1.00 | 21.02 | CPS4 |
| ATOM | 3202 | CA | LEU | 50 | 2.564 | 27.807 | 32.678 | 1.00 | 21.41 | CPS4 |
| ATOM | 3203 | CB | LEU | 50 | 1.386 | 28.749 | 32.389 | 1.00 | 21.73 | CPS4 |
| ATOM | 3204 | CG | LEU | 50 | 1.487 | 29.682 | 31.172 | 1.00 | 24.05 | CPS4 |
| ATOM | 3205 | CD1 | LEU | 50 | 1.697 | 28.873 | 29.891 | 1.00 | 24.04 | CPS4 |
| ATOM | 3206 | CD2 | LEU | 50 | 0.218 | 30.518 | 31.075 | 1.00 | 23.32 | CPS4 |
| ATOM | 3207 | C | LEU | 50 | 3.832 | 28.624 | 32.922 | 1.00 | 21.21 | CPS4 |
| ATOM | 3208 | O | LEU | 50 | 4.680 | 28.724 | 32.039 | 1.00 | 20.96 | CPS4 |
| ATOM | 3209 | N | ALA | 51 | 3.960 | 29.207 | 34.114 | 1.00 | 19.78 | CPS4 |
| ATOM | 3210 | CA | ALA | 51 | 5.150 | 30.005 | 34.432 | 1.00 | 19.68 | CPS4 |
| ATOM | 3211 | CB | ALA | 51 | 5.017 | 30.616 | 35.830 | 1.00 | 20.19 | CPS4 |
| ATOM | 3212 | C | ALA | 51 | 6.417 | 29.151 | 34.350 | 1.00 | 20.59 | CPS4 |
| ATOM | 3213 | O | ALA | 51 | 7.453 | 29.598 | 33.830 | 1.00 | 20.05 | CPS4 |
| ATOM | 3214 | N | GLY | 52 | 6.325 | 27.928 | 34.865 | 1.00 | 20.38 | CPS4 |
| ATOM | 3215 | CA | GLY | 52 | 7.459 | 27.015 | 34.840 | 1.00 | 20.83 | CPS4 |
| ATOM | 3216 | C | GLY | 52 | 7.861 | 26.619 | 33.429 | 1.00 | 20.53 | CPS4 |
| ATOM | 3217 | O | GLY | 52 | 9.048 | 26.587 | 33.104 | 1.00 | 20.29 | CPS4 |
| ATOM | 3218 | N | ARG | 53 | 6.884 | 26.279 | 32.593 | 1.00 | 21.19 | CPS4 |
| ATOM | 3219 | CA | ARG | 53 | 7.187 | 25.916 | 31.207 | 1.00 | 21.65 | CPS4 |
| ATOM | 3220 | CB | ARG | 53 | 5.938 | 25.336 | 30.532 | 1.00 | 23.50 | CPS4 |
| ATOM | 3221 | CG | ARG | 53 | 5.824 | 23.807 | 30.654 | 1.00 | 26.67 | CPS4 |
| ATOM | 3222 | CD | ARG | 53 | 5.988 | 23.291 | 32.077 | 1.00 | 31.06 | CPS4 |
| ATOM | 3223 | NE | ARG | 53 | 5.877 | 21.832 | 32.121 | 1.00 | 35.13 | CPS4 |
| ATOM | 3224 | CZ | ARG | 53 | 6.220 | 21.082 | 33.164 | 1.00 | 38.06 | CPS4 |
| ATOM | 3225 | NH1 | ARG | 53 | 6.702 | 21.649 | 34.267 | 1.00 | 38.57 | CPS4 |
| ATOM | 3226 | NH2 | ARG | 53 | 6.086 | 19.762 | 33.105 | 1.00 | 39.34 | CPS4 |
| ATOM | 3227 | C | ARG | 53 | 7.710 | 27.140 | 30.445 | 1.00 | 20.71 | CPS4 |
| ATOM | 3228 | O | ARG | 53 | 8.598 | 27.030 | 29.606 | 1.00 | 20.01 | CPS4 |
| ATOM | 3229 | N | PHE | 54 | 7.160 | 28.311 | 30.740 | 1.00 | 20.84 | CPS4 |
| ATOM | 3230 | CA | PHE | 54 | 7.613 | 29.545 | 30.090 | 1.00 | 19.84 | CPS4 |
| ATOM | 3231 | CB | PHE | 54 | 6.742 | 30.722 | 30.558 | 1.00 | 19.76 | CPS4 |
| ATOM | 3232 | CG | PHE | 54 | 7.131 | 32.059 | 29.966 | 1.00 | 22.53 | CPS4 |
| ATOM | 3233 | CD1 | PHE | 54 | 7.984 | 32.922 | 30.654 | 1.00 | 21.19 | CPS4 |
| ATOM | 3234 | CD2 | PHE | 54 | 6.638 | 32.457 | 28.728 | 1.00 | 22.55 | CPS4 |
| ATOM | 3235 | CE1 | PHE | 54 | 8.339 | 34.162 | 30.115 | 1.00 | 22.92 | CPS4 |
| ATOM | 3236 | CE2 | PHE | 54 | 6.989 | 33.701 | 28.181 | 1.00 | 24.30 | CPS4 |
| ATOM | 3237 | CZ | PHE | 54 | 7.846 | 34.553 | 28.883 | 1.00 | 22.82 | CPS4 |
| ATOM | 3238 | C | PHE | 54 | 9.086 | 29.791 | 30.452 | 1.00 | 20.51 | CPS4 |
| ATOM | 3239 | O | PHE | 54 | 9.912 | 30.084 | 29.583 | 1.00 | 19.99 | CPS4 |
| ATOM | 3240 | N | ALA | 55 | 9.419 | 29.656 | 31.735 | 1.00 | 19.95 | CPS4 |
| ATOM | 3241 | CA | ALA | 55 | 10.798 | 29.874 | 32.179 | 1.00 | 18.42 | CPS4 |
| ATOM | 3242 | CB | ALA | 55 | 10.885 | 29.789 | 33.712 | 1.00 | 17.59 | CPS4 |
| ATOM | 3243 | C | ALA | 55 | 11.747 | 28.867 | 31.535 | 1.00 | 18.74 | CPS4 |
| ATOM | 3244 | O | ALA | 55 | 12.840 | 29.228 | 31.097 | 1.00 | 17.86 | CPS4 |
| ATOM | 3245 | N | ALA | 56 | 11.329 | 27.608 | 31.470 | 1.00 | 17.67 | CPS4 |
| ATOM | 3246 | CA | ALA | 56 | 12.173 | 26.570 | 30.870 | 1.00 | 17.97 | CPS4 |
| ATOM | 3247 | CB | ALA | 56 | 11.519 | 25.179 | 31.051 | 1.00 | 16.50 | CPS4 |
| ATOM | 3248 | C | ALA | 56 | 12.435 | 26.845 | 29.391 | 1.00 | 17.61 | CPS4 |

FIG. 1A-57

| ATOM | 3249 | O | ALA | 56 | 13.555 | 26.672 | 28.898 | 1.00 | 17.56 | CPS4 |
|---|---|---|---|---|---|---|---|---|---|---|
| ATOM | 3250 | N | LYS | 57 | 11.411 | 27.286 | 28.669 | 1.00 | 17.23 | CPS4 |
| ATOM | 3251 | CA | LYS | 57 | 11.603 | 27.555 | 27.249 | 1.00 | 17.45 | CPS4 |
| ATOM | 3252 | CB | LYS | 57 | 10.243 | 27.657 | 26.535 | 1.00 | 17.90 | CPS4 |
| ATOM | 3253 | CG | LYS | 57 | 9.470 | 26.320 | 26.585 | 1.00 | 17.50 | CPS4 |
| ATOM | 3254 | CD | LYS | 57 | 8.243 | 26.286 | 25.673 | 1.00 | 19.16 | CPS4 |
| ATOM | 3255 | CE | LYS | 57 | 7.453 | 24.998 | 25.915 | 1.00 | 20.14 | CPS4 |
| ATOM | 3256 | NZ | LYS | 57 | 6.468 | 24.688 | 24.832 | 1.00 | 18.82 | CPS4 |
| ATOM | 3257 | C | LYS | 57 | 12.450 | 28.800 | 27.033 | 1.00 | 18.57 | CPS4 |
| ATOM | 3258 | O | LYS | 57 | 13.282 | 28.840 | 26.123 | 1.00 | 18.35 | CPS4 |
| ATOM | 3259 | N | GLU | 58 | 12.254 | 29.815 | 27.863 | 1.00 | 19.33 | CPS4 |
| ATOM | 3260 | CA | GLU | 58 | 13.057 | 31.018 | 27.733 | 1.00 | 19.47 | CPS4 |
| ATOM | 3261 | CB | GLU | 58 | 12.581 | 32.104 | 28.698 | 1.00 | 21.46 | CPS4 |
| ATOM | 3262 | CG | GLU | 58 | 11.276 | 32.786 | 28.308 | 1.00 | 24.96 | CPS4 |
| ATOM | 3263 | CD | GLU | 58 | 11.375 | 33.576 | 27.003 | 1.00 | 28.39 | CPS4 |
| ATOM | 3264 | OE1 | GLU | 58 | 12.482 | 34.040 | 26.654 | 1.00 | 30.73 | CPS4 |
| ATOM | 3265 | OE2 | GLU | 58 | 10.333 | 33.748 | 26.333 | 1.00 | 31.57 | CPS4 |
| ATOM | 3266 | C | GLU | 58 | 14.504 | 30.649 | 28.047 | 1.00 | 19.45 | CPS4 |
| ATOM | 3267 | O | GLU | 58 | 15.424 | 31.075 | 27.338 | 1.00 | 18.48 | CPS4 |
| ATOM | 3268 | N | ALA | 59 | 14.718 | 29.857 | 29.097 | 1.00 | 17.21 | CPS4 |
| ATOM | 3269 | CA | ALA | 59 | 16.095 | 29.458 | 29.434 | 1.00 | 16.93 | CPS4 |
| ATOM | 3270 | CB | ALA | 59 | 16.130 | 28.630 | 30.730 | 1.00 | 16.23 | CPS4 |
| ATOM | 3271 | C | ALA | 59 | 16.704 | 28.663 | 28.288 | 1.00 | 17.64 | CPS4 |
| ATOM | 3272 | O | ALA | 59 | 17.868 | 28.871 | 27.917 | 1.00 | 18.71 | CPS4 |
| ATOM | 3273 | N | PHE | 60 | 15.925 | 27.752 | 27.708 | 1.00 | 17.49 | CPS4 |
| ATOM | 3274 | CA | PHE | 60 | 16.438 | 26.973 | 26.590 | 1.00 | 17.61 | CPS4 |
| ATOM | 3275 | CB | PHE | 60 | 15.404 | 25.953 | 26.093 | 1.00 | 17.74 | CPS4 |
| ATOM | 3276 | CG | PHE | 60 | 15.860 | 25.203 | 24.869 | 1.00 | 19.99 | CPS4 |
| ATOM | 3277 | CD1 | PHE | 60 | 16.682 | 24.085 | 24.992 | 1.00 | 21.60 | CPS4 |
| ATOM | 3278 | CD2 | PHE | 60 | 15.565 | 25.681 | 23.594 | 1.00 | 21.01 | CPS4 |
| ATOM | 3279 | CE1 | PHE | 60 | 17.214 | 23.453 | 23.863 | 1.00 | 21.01 | CPS4 |
| ATOM | 3280 | CE2 | PHE | 60 | 16.092 | 25.059 | 22.452 | 1.00 | 20.43 | CPS4 |
| ATOM | 3281 | CZ | PHE | 60 | 16.922 | 23.941 | 22.595 | 1.00 | 22.76 | CPS4 |
| ATOM | 3282 | C | PHE | 60 | 16.817 | 27.894 | 25.423 | 1.00 | 16.99 | CPS4 |
| ATOM | 3283 | O | PHE | 60 | 17.853 | 27.701 | 24.792 | 1.00 | 18.28 | CPS4 |
| ATOM | 3284 | N | SER | 61 | 15.983 | 28.894 | 25.139 | 1.00 | 17.64 | CPS4 |
| ATOM | 3285 | CA | SER | 61 | 16.263 | 29.801 | 24.026 | 1.00 | 17.54 | CPS4 |
| ATOM | 3286 | CB | SER | 61 | 15.069 | 30.757 | 23.788 | 1.00 | 18.97 | CPS4 |
| ATOM | 3287 | OG | SER | 61 | 15.017 | 31.816 | 24.738 | 1.00 | 20.70 | CPS4 |
| ATOM | 3288 | C | SER | 61 | 17.554 | 30.586 | 24.261 | 1.00 | 18.58 | CPS4 |
| ATOM | 3289 | O | SER | 61 | 18.257 | 30.932 | 23.312 | 1.00 | 19.96 | CPS4 |
| ATOM | 3290 | N | LYS | 62 | 17.873 | 30.856 | 25.520 | 1.00 | 17.38 | CPS4 |
| ATOM | 3291 | CA | LYS | 62 | 19.095 | 31.579 | 25.855 | 1.00 | 18.60 | CPS4 |
| ATOM | 3292 | CB | LYS | 62 | 19.021 | 32.120 | 27.281 | 1.00 | 19.12 | CPS4 |
| ATOM | 3293 | CG | LYS | 62 | 17.939 | 33.199 | 27.436 | 1.00 | 24.19 | CPS4 |
| ATOM | 3294 | CD | LYS | 62 | 17.990 | 33.882 | 28.791 | 1.00 | 27.64 | CPS4 |
| ATOM | 3295 | CE | LYS | 62 | 17.112 | 35.126 | 28.763 | 1.00 | 31.95 | CPS4 |
| ATOM | 3296 | NZ | LYS | 62 | 17.485 | 36.123 | 29.784 | 1.00 | 34.09 | CPS4 |
| ATOM | 3297 | C | LYS | 62 | 20.309 | 30.684 | 25.699 | 1.00 | 18.38 | CPS4 |
| ATOM | 3298 | O | LYS | 62 | 21.375 | 31.133 | 25.259 | 1.00 | 19.22 | CPS4 |
| ATOM | 3299 | N | ALA | 63 | 20.156 | 29.418 | 26.070 | 1.00 | 17.11 | CPS4 |
| ATOM | 3300 | CA | ALA | 63 | 21.248 | 28.460 | 25.934 | 1.00 | 17.76 | CPS4 |
| ATOM | 3301 | CB | ALA | 63 | 20.878 | 27.114 | 26.619 | 1.00 | 16.67 | CPS4 |
| ATOM | 3302 | C | ALA | 63 | 21.497 | 28.239 | 24.445 | 1.00 | 18.66 | CPS4 |
| ATOM | 3303 | O | ALA | 63 | 22.640 | 28.126 | 24.012 | 1.00 | 17.98 | CPS4 |
| ATOM | 3304 | N | PHE | 64 | 20.412 | 28.183 | 23.672 | 1.00 | 18.77 | CPS4 |
| ATOM | 3305 | CA | PHE | 64 | 20.480 | 27.976 | 22.220 | 1.00 | 19.86 | CPS4 |

FIG. 1A-58

| ATOM | 3306 | CB | PHE | 64 | 19.068 | 27.758 | 21.659 | 1.00 | 21.49 | CPS4 |
| ATOM | 3307 | CG | PHE | 64 | 19.049 | 27.258 | 20.239 | 1.00 | 23.19 | CPS4 |
| ATOM | 3308 | CD1 | PHE | 64 | 19.603 | 26.019 | 19.917 | 1.00 | 25.84 | CPS4 |
| ATOM | 3309 | CD2 | PHE | 64 | 18.498 | 28.038 | 19.223 | 1.00 | 24.38 | CPS4 |
| ATOM | 3310 | CE1 | PHE | 64 | 19.612 | 25.558 | 18.592 | 1.00 | 27.01 | CPS4 |
| ATOM | 3311 | CE2 | PHE | 64 | 18.495 | 27.595 | 17.897 | 1.00 | 25.99 | CPS4 |
| ATOM | 3312 | CZ | PHE | 64 | 19.055 | 26.353 | 17.578 | 1.00 | 25.96 | CPS4 |
| ATOM | 3313 | C | PHE | 64 | 21.142 | 29.177 | 21.547 | 1.00 | 21.18 | CPS4 |
| ATOM | 3314 | O | PHE | 64 | 21.687 | 29.057 | 20.446 | 1.00 | 22.00 | CPS4 |
| ATOM | 3315 | N | GLY | 65 | 21.075 | 30.330 | 22.214 | 1.00 | 20.65 | CPS4 |
| ATOM | 3316 | CA | GLY | 65 | 21.711 | 31.547 | 21.735 | 1.00 | 21.45 | CPS4 |
| ATOM | 3317 | C | GLY | 65 | 20.914 | 32.487 | 20.848 | 1.00 | 23.53 | CPS4 |
| ATOM | 3318 | O | GLY | 65 | 21.453 | 33.483 | 20.370 | 1.00 | 24.12 | CPS4 |
| ATOM | 3319 | N | THR | 66 | 19.635 | 32.195 | 20.640 | 1.00 | 22.34 | CPS4 |
| ATOM | 3320 | CA | THR | 66 | 18.807 | 33.016 | 19.755 | 1.00 | 23.68 | CPS4 |
| ATOM | 3321 | CB | THR | 66 | 18.176 | 32.144 | 18.667 | 1.00 | 25.10 | CPS4 |
| ATOM | 3322 | OG1 | THR | 66 | 17.343 | 31.160 | 19.296 | 1.00 | 25.13 | CPS4 |
| ATOM | 3323 | CG2 | THR | 66 | 19.249 | 31.434 | 17.845 | 1.00 | 26.27 | CPS4 |
| ATOM | 3324 | C | THR | 66 | 17.646 | 33.737 | 20.424 | 1.00 | 24.40 | CPS4 |
| ATOM | 3325 | O | THR | 66 | 17.172 | 34.762 | 19.925 | 1.00 | 23.79 | CPS4 |
| ATOM | 3326 | N | GLY | 67 | 17.184 | 33.199 | 21.546 | 1.00 | 23.11 | CPS4 |
| ATOM | 3327 | CA | GLY | 67 | 16.018 | 33.766 | 22.193 | 1.00 | 22.95 | CPS4 |
| ATOM | 3328 | C | GLY | 67 | 14.822 | 33.246 | 21.391 | 1.00 | 23.58 | CPS4 |
| ATOM | 3329 | O | GLY | 67 | 14.997 | 32.581 | 20.369 | 1.00 | 22.81 | CPS4 |
| ATOM | 3330 | N | ILE | 68 | 13.610 | 33.540 | 21.848 | 1.00 | 24.83 | CPS4 |
| ATOM | 3331 | CA | ILE | 68 | 12.401 | 33.107 | 21.150 | 1.00 | 25.43 | CPS4 |
| ATOM | 3332 | CB | ILE | 68 | 11.194 | 33.083 | 22.110 | 1.00 | 25.71 | CPS4 |
| ATOM | 3333 | CG2 | ILE | 68 | 9.899 | 32.729 | 21.345 | 1.00 | 26.85 | CPS4 |
| ATOM | 3334 | CG1 | ILE | 68 | 11.449 | 32.061 | 23.222 | 1.00 | 24.50 | CPS4 |
| ATOM | 3335 | CD1 | ILE | 68 | 11.495 | 30.626 | 22.739 | 1.00 | 24.17 | CPS4 |
| ATOM | 3336 | C | ILE | 68 | 12.129 | 34.086 | 20.007 | 1.00 | 27.56 | CPS4 |
| ATOM | 3337 | O | ILE | 68 | 12.150 | 35.300 | 20.203 | 1.00 | 27.28 | CPS4 |
| ATOM | 3338 | N | GLY | 69 | 11.890 | 33.559 | 18.813 | 1.00 | 27.53 | CPS4 |
| ATOM | 3339 | CA | GLY | 69 | 11.641 | 34.434 | 17.686 | 1.00 | 30.15 | CPS4 |
| ATOM | 3340 | C | GLY | 69 | 11.685 | 33.725 | 16.353 | 1.00 | 30.54 | CPS4 |
| ATOM | 3341 | O | GLY | 69 | 11.274 | 32.575 | 16.240 | 1.00 | 30.54 | CPS4 |
| ATOM | 3342 | N | ALA | 70 | 12.197 | 34.416 | 15.342 | 1.00 | 32.70 | CPS4 |
| ATOM | 3343 | CA | ALA | 70 | 12.272 | 33.860 | 13.998 | 1.00 | 33.34 | CPS4 |
| ATOM | 3344 | CB | ALA | 70 | 12.396 | 34.886 | 13.043 | 1.00 | 35.40 | CPS4 |
| ATOM | 3345 | C | ALA | 70 | 13.038 | 32.551 | 13.917 | 1.00 | 33.51 | CPS4 |
| ATOM | 3346 | O | ALA | 70 | 12.695 | 31.679 | 13.118 | 1.00 | 34.32 | CPS4 |
| ATOM | 3347 | N | GLN | 71 | 14.061 | 32.398 | 14.752 | 1.00 | 32.10 | CPS4 |
| ATOM | 3348 | CA | GLN | 71 | 14.882 | 31.192 | 14.713 | 1.00 | 30.79 | CPS4 |
| ATOM | 3349 | CB | GLN | 71 | 16.334 | 31.545 | 15.039 | 1.00 | 33.45 | CPS4 |
| ATOM | 3350 | CG | GLN | 71 | 16.936 | 32.597 | 14.127 | 1.00 | 37.57 | CPS4 |
| ATOM | 3351 | CD | GLN | 71 | 18.391 | 32.873 | 14.451 | 1.00 | 38.92 | CPS4 |
| ATOM | 3352 | OE1 | GLN | 71 | 19.258 | 32.016 | 14.257 | 1.00 | 40.93 | CPS4 |
| ATOM | 3353 | NE2 | GLN | 71 | 18.665 | 34.069 | 14.961 | 1.00 | 40.14 | CPS4 |
| ATOM | 3354 | C | GLN | 71 | 14.443 | 30.066 | 15.636 | 1.00 | 28.73 | CPS4 |
| ATOM | 3355 | O | GLN | 71 | 14.851 | 28.923 | 15.454 | 1.00 | 28.34 | CPS4 |
| ATOM | 3356 | N | LEU | 72 | 13.626 | 30.384 | 16.633 | 1.00 | 26.49 | CPS4 |
| ATOM | 3357 | CA | LEU | 72 | 13.182 | 29.369 | 17.575 | 1.00 | 24.09 | CPS4 |
| ATOM | 3358 | CB | LEU | 72 | 14.224 | 29.221 | 18.690 | 1.00 | 24.17 | CPS4 |
| ATOM | 3359 | CG | LEU | 72 | 13.988 | 28.183 | 19.791 | 1.00 | 23.09 | CPS4 |
| ATOM | 3360 | CD1 | LEU | 72 | 14.211 | 26.785 | 19.231 | 1.00 | 23.74 | CPS4 |
| ATOM | 3361 | CD2 | LEU | 72 | 14.948 | 28.457 | 20.955 | 1.00 | 25.05 | CPS4 |
| ATOM | 3362 | C | LEU | 72 | 11.847 | 29.777 | 18.169 | 1.00 | 23.32 | CPS4 |

FIG. 1A-59

| ATOM | 3363 | O   | LEU | 72 | 11.699 | 30.876 | 18.688 | 1.00 | 24.09 | CPS4 |
|------|------|-----|-----|----|--------|--------|--------|------|-------|------|
| ATOM | 3364 | N   | SER | 73 | 10.880 | 28.877 | 18.084 | 1.00 | 22.99 | CPS4 |
| ATOM | 3365 | CA  | SER | 73 | 9.542  | 29.112 | 18.601 | 1.00 | 23.16 | CPS4 |
| ATOM | 3366 | CB  | SER | 73 | 8.527  | 28.653 | 17.555 | 1.00 | 23.80 | CPS4 |
| ATOM | 3367 | OG  | SER | 73 | 7.227  | 28.611 | 18.093 | 1.00 | 29.93 | CPS4 |
| ATOM | 3368 | C   | SER | 73 | 9.297  | 28.339 | 19.896 | 1.00 | 22.31 | CPS4 |
| ATOM | 3369 | O   | SER | 73 | 9.976  | 27.353 | 20.175 | 1.00 | 21.09 | CPS4 |
| ATOM | 3370 | N   | PHE | 74 | 8.334  | 28.803 | 20.692 | 1.00 | 22.33 | CPS4 |
| ATOM | 3371 | CA  | PHE | 74 | 7.962  | 28.093 | 21.914 | 1.00 | 21.01 | CPS4 |
| ATOM | 3372 | CB  | PHE | 74 | 6.802  | 28.801 | 22.625 | 1.00 | 21.02 | CPS4 |
| ATOM | 3373 | CG  | PHE | 74 | 7.201  | 30.032 | 23.386 | 1.00 | 23.04 | CPS4 |
| ATOM | 3374 | CD1 | PHE | 74 | 8.018  | 29.937 | 24.508 | 1.00 | 23.64 | CPS4 |
| ATOM | 3375 | CD2 | PHE | 74 | 6.726  | 31.285 | 23.003 | 1.00 | 22.57 | CPS4 |
| ATOM | 3376 | CE1 | PHE | 74 | 8.355  | 31.074 | 25.246 | 1.00 | 25.06 | CPS4 |
| ATOM | 3377 | CE2 | PHE | 74 | 7.057  | 32.423 | 23.728 | 1.00 | 25.56 | CPS4 |
| ATOM | 3378 | CZ  | PHE | 74 | 7.872  | 32.318 | 24.854 | 1.00 | 24.29 | CPS4 |
| ATOM | 3379 | C   | PHE | 74 | 7.470  | 26.714 | 21.479 | 1.00 | 21.66 | CPS4 |
| ATOM | 3380 | O   | PHE | 74 | 7.567  | 25.744 | 22.224 | 1.00 | 20.92 | CPS4 |
| ATOM | 3381 | N   | GLN | 75 | 6.928  | 26.635 | 20.266 | 1.00 | 20.29 | CPS4 |
| ATOM | 3382 | CA  | GLN | 75 | 6.402  | 25.372 | 19.760 | 1.00 | 21.28 | CPS4 |
| ATOM | 3383 | CB  | GLN | 75 | 5.442  | 25.637 | 18.595 | 1.00 | 22.50 | CPS4 |
| ATOM | 3384 | CG  | GLN | 75 | 4.216  | 26.457 | 18.996 | 1.00 | 22.28 | CPS4 |
| ATOM | 3385 | CD  | GLN | 75 | 3.364  | 25.763 | 20.048 | 1.00 | 22.84 | CPS4 |
| ATOM | 3386 | OE1 | GLN | 75 | 2.914  | 26.384 | 21.020 | 1.00 | 25.78 | CPS4 |
| ATOM | 3387 | NE2 | GLN | 75 | 3.133  | 24.471 | 19.858 | 1.00 | 21.79 | CPS4 |
| ATOM | 3388 | C   | GLN | 75 | 7.482  | 24.374 | 19.334 | 1.00 | 21.34 | CPS4 |
| ATOM | 3389 | O   | GLN | 75 | 7.179  | 23.209 | 19.072 | 1.00 | 22.34 | CPS4 |
| ATOM | 3390 | N   | ASP | 76 | 8.732  | 24.835 | 19.277 | 1.00 | 20.43 | CPS4 |
| ATOM | 3391 | CA  | ASP | 76 | 9.872  | 23.989 | 18.903 | 1.00 | 20.89 | CPS4 |
| ATOM | 3392 | CB  | ASP | 76 | 11.006 | 24.827 | 18.294 | 1.00 | 22.04 | CPS4 |
| ATOM | 3393 | CG  | ASP | 76 | 10.672 | 25.375 | 16.922 | 1.00 | 25.59 | CPS4 |
| ATOM | 3394 | OD1 | ASP | 76 | 10.016 | 24.658 | 16.149 | 1.00 | 28.36 | CPS4 |
| ATOM | 3395 | OD2 | ASP | 76 | 11.094 | 26.513 | 16.614 | 1.00 | 25.63 | CPS4 |
| ATOM | 3396 | C   | ASP | 76 | 10.442 | 23.292 | 20.132 | 1.00 | 20.74 | CPS4 |
| ATOM | 3397 | O   | ASP | 76 | 11.380 | 22.499 | 20.025 | 1.00 | 20.53 | CPS4 |
| ATOM | 3398 | N   | ILE | 77 | 9.869  | 23.586 | 21.291 | 1.00 | 19.74 | CPS4 |
| ATOM | 3399 | CA  | ILE | 77 | 10.353 | 23.033 | 22.551 | 1.00 | 19.49 | CPS4 |
| ATOM | 3400 | CB  | ILE | 77 | 10.944 | 24.160 | 23.433 | 1.00 | 18.31 | CPS4 |
| ATOM | 3401 | CG2 | ILE | 77 | 11.700 | 23.554 | 24.627 | 1.00 | 19.88 | CPS4 |
| ATOM | 3402 | CG1 | ILE | 77 | 11.856 | 25.056 | 22.584 | 1.00 | 19.12 | CPS4 |
| ATOM | 3403 | CD1 | ILE | 77 | 12.172 | 26.401 | 23.232 | 1.00 | 18.75 | CPS4 |
| ATOM | 3404 | C   | ILE | 77 | 9.249  | 22.387 | 23.356 | 1.00 | 20.14 | CPS4 |
| ATOM | 3405 | O   | ILE | 77 | 8.162  | 22.932 | 23.474 | 1.00 | 21.52 | CPS4 |
| ATOM | 3406 | N   | GLU | 78 | 9.530  | 21.233 | 23.942 | 1.00 | 20.14 | CPS4 |
| ATOM | 3407 | CA  | GLU | 78 | 8.520  | 20.590 | 24.760 | 1.00 | 21.03 | CPS4 |
| ATOM | 3408 | CB  | GLU | 78 | 7.814  | 19.483 | 23.964 | 1.00 | 22.66 | CPS4 |
| ATOM | 3409 | CG  | GLU | 78 | 6.792  | 18.707 | 24.772 | 1.00 | 23.61 | CPS4 |
| ATOM | 3410 | CD  | GLU | 78 | 5.914  | 17.815 | 23.903 | 1.00 | 26.69 | CPS4 |
| ATOM | 3411 | OE1 | GLU | 78 | 5.039  | 18.352 | 23.195 | 1.00 | 26.76 | CPS4 |
| ATOM | 3412 | OE2 | GLU | 78 | 6.105  | 16.581 | 23.922 | 1.00 | 27.97 | CPS4 |
| ATOM | 3413 | C   | GLU | 78 | 9.153  | 20.025 | 26.014 | 1.00 | 20.86 | CPS4 |
| ATOM | 3414 | O   | GLU | 78 | 10.219 | 19.411 | 25.953 | 1.00 | 20.47 | CPS4 |
| ATOM | 3415 | N   | ILE | 79 | 8.519  | 20.273 | 27.158 | 1.00 | 20.68 | CPS4 |
| ATOM | 3416 | CA  | ILE | 79 | 9.019  | 19.744 | 28.420 | 1.00 | 21.74 | CPS4 |
| ATOM | 3417 | CB  | ILE | 79 | 8.845  | 20.756 | 29.598 | 1.00 | 24.16 | CPS4 |
| ATOM | 3418 | CG2 | ILE | 79 | 9.053  | 20.044 | 30.937 | 1.00 | 23.26 | CPS4 |
| ATOM | 3419 | CG1 | ILE | 79 | 9.868  | 21.891 | 29.485 | 1.00 | 27.28 | CPS4 |

FIG. 1A-60

| ATOM | 3420 | CD1 | ILE | 79 | 9.772 | 22.726 | 28.227 | 1.00 | 28.49 | CPS4 |
|---|---|---|---|---|---|---|---|---|---|---|
| ATOM | 3421 | C | ILE | 79 | 8.234 | 18.478 | 28.748 | 1.00 | 22.41 | CPS4 |
| ATOM | 3422 | O | ILE | 79 | 7.001 | 18.462 | 28.685 | 1.00 | 22.59 | CPS4 |
| ATOM | 3423 | N | ARG | 80 | 8.958 | 17.417 | 29.075 | 1.00 | 22.76 | CPS4 |
| ATOM | 3424 | CA | ARG | 80 | 8.349 | 16.151 | 29.451 | 1.00 | 24.99 | CPS4 |
| ATOM | 3425 | CB | ARG | 80 | 8.684 | 15.081 | 28.419 | 1.00 | 25.33 | CPS4 |
| ATOM | 3426 | CG | ARG | 80 | 8.181 | 15.426 | 27.038 | 1.00 | 28.31 | CPS4 |
| ATOM | 3427 | CD | ARG | 80 | 8.496 | 14.332 | 26.049 | 1.00 | 31.70 | CPS4 |
| ATOM | 3428 | NE | ARG | 80 | 7.736 | 14.538 | 24.828 | 1.00 | 33.61 | CPS4 |
| ATOM | 3429 | CZ | ARG | 80 | 7.701 | 13.677 | 23.820 | 1.00 | 35.93 | CPS4 |
| ATOM | 3430 | NH1 | ARG | 80 | 8.390 | 12.545 | 23.893 | 1.00 | 34.86 | CPS4 |
| ATOM | 3431 | NH2 | ARG | 80 | 6.974 | 13.952 | 22.743 | 1.00 | 35.80 | CPS4 |
| ATOM | 3432 | C | ARG | 80 | 8.938 | 15.777 | 30.802 | 1.00 | 26.08 | CPS4 |
| ATOM | 3433 | O | ARG | 80 | 9.892 | 16.412 | 31.257 | 1.00 | 22.69 | CPS4 |
| ATOM | 3434 | N | LYS | 81 | 8.372 | 14.760 | 31.448 | 1.00 | 27.41 | CPS4 |
| ATOM | 3435 | CA | LYS | 81 | 8.877 | 14.334 | 32.750 | 1.00 | 29.89 | CPS4 |
| ATOM | 3436 | CB | LYS | 81 | 7.866 | 14.652 | 33.858 | 1.00 | 31.74 | CPS4 |
| ATOM | 3437 | CG | LYS | 81 | 7.741 | 16.134 | 34.201 | 1.00 | 36.20 | CPS4 |
| ATOM | 3438 | CD | LYS | 81 | 6.836 | 16.335 | 35.421 | 1.00 | 39.03 | CPS4 |
| ATOM | 3439 | CE | LYS | 81 | 6.576 | 17.813 | 35.724 | 1.00 | 41.06 | CPS4 |
| ATOM | 3440 | NZ | LYS | 81 | 7.812 | 18.590 | 36.021 | 1.00 | 41.14 | CPS4 |
| ATOM | 3441 | C | LYS | 81 | 9.157 | 12.844 | 32.742 | 1.00 | 31.20 | CPS4 |
| ATOM | 3442 | O | LYS | 81 | 8.378 | 12.069 | 32.185 | 1.00 | 30.64 | CPS4 |
| ATOM | 3443 | N | ASP | 82 | 10.270 | 12.432 | 33.341 | 1.00 | 30.63 | CPS4 |
| ATOM | 3444 | CA | ASP | 82 | 10.567 | 11.010 | 33.374 | 1.00 | 31.88 | CPS4 |
| ATOM | 3445 | CB | ASP | 82 | 12.073 | 10.746 | 33.491 | 1.00 | 30.04 | CPS4 |
| ATOM | 3446 | CG | ASP | 82 | 12.670 | 11.248 | 34.788 | 1.00 | 30.81 | CPS4 |
| ATOM | 3447 | OD1 | ASP | 82 | 11.938 | 11.421 | 35.789 | 1.00 | 31.13 | CPS4 |
| ATOM | 3448 | OD2 | ASP | 82 | 13.899 | 11.447 | 34.805 | 1.00 | 31.19 | CPS4 |
| ATOM | 3449 | C | ASP | 82 | 9.820 | 10.351 | 34.523 | 1.00 | 32.86 | CPS4 |
| ATOM | 3450 | O | ASP | 82 | 9.037 | 10.997 | 35.221 | 1.00 | 32.72 | CPS4 |
| ATOM | 3451 | N | GLN | 83 | 10.063 | 9.059 | 34.710 | 1.00 | 35.26 | CPS4 |
| ATOM | 3452 | CA | GLN | 83 | 9.404 | 8.292 | 35.755 | 1.00 | 37.75 | CPS4 |
| ATOM | 3453 | CB | GLN | 83 | 9.861 | 6.827 | 35.684 | 1.00 | 40.68 | CPS4 |
| ATOM | 3454 | CG | GLN | 83 | 11.357 | 6.615 | 35.407 | 1.00 | 45.63 | CPS4 |
| ATOM | 3455 | CD | GLN | 83 | 11.805 | 7.096 | 34.020 | 1.00 | 48.44 | CPS4 |
| ATOM | 3456 | OE1 | GLN | 83 | 11.016 | 7.130 | 33.068 | 1.00 | 49.61 | CPS4 |
| ATOM | 3457 | NE2 | GLN | 83 | 13.086 | 7.447 | 33.901 | 1.00 | 50.02 | CPS4 |
| ATOM | 3458 | C | GLN | 83 | 9.607 | 8.854 | 37.160 | 1.00 | 38.09 | CPS4 |
| ATOM | 3459 | O | GLN | 83 | 8.748 | 8.688 | 38.026 | 1.00 | 38.46 | CPS4 |
| ATOM | 3460 | N | ASN | 84 | 10.733 | 9.528 | 37.386 | 1.00 | 37.38 | CPS4 |
| ATOM | 3461 | CA | ASN | 84 | 11.012 | 10.119 | 38.692 | 1.00 | 36.22 | CPS4 |
| ATOM | 3462 | CB | ASN | 84 | 12.520 | 10.213 | 38.931 | 1.00 | 37.16 | CPS4 |
| ATOM | 3463 | CG | ASN | 84 | 13.170 | 8.858 | 39.110 | 1.00 | 37.93 | CPS4 |
| ATOM | 3464 | OD1 | ASN | 84 | 12.631 | 7.984 | 39.787 | 1.00 | 39.18 | CPS4 |
| ATOM | 3465 | ND2 | ASN | 84 | 14.343 | 8.682 | 38.518 | 1.00 | 39.57 | CPS4 |
| ATOM | 3466 | C | ASN | 84 | 10.404 | 11.512 | 38.834 | 1.00 | 36.01 | CPS4 |
| ATOM | 3467 | O | ASN | 84 | 10.470 | 12.118 | 39.903 | 1.00 | 37.22 | CPS4 |
| ATOM | 3468 | N | GLY | 85 | 9.817 | 12.027 | 37.759 | 1.00 | 34.03 | CPS4 |
| ATOM | 3469 | CA | GLY | 85 | 9.226 | 13.352 | 37.824 | 1.00 | 31.62 | CPS4 |
| ATOM | 3470 | C | GLY | 85 | 10.203 | 14.446 | 37.408 | 1.00 | 29.19 | CPS4 |
| ATOM | 3471 | O | GLY | 85 | 9.904 | 15.632 | 37.517 | 1.00 | 28.96 | CPS4 |
| ATOM | 3472 | N | LYS | 86 | 11.377 | 14.048 | 36.938 | 1.00 | 26.53 | CPS4 |
| ATOM | 3473 | CA | LYS | 86 | 12.394 | 15.009 | 36.507 | 1.00 | 25.85 | CPS4 |
| ATOM | 3474 | CB | LYS | 86 | 13.775 | 14.336 | 36.511 | 1.00 | 26.12 | CPS4 |
| ATOM | 3475 | CG | LYS | 86 | 14.913 | 15.136 | 35.853 | 1.00 | 24.62 | CPS4 |
| ATOM | 3476 | CD | LYS | 86 | 15.358 | 16.357 | 36.678 | 1.00 | 22.52 | CPS4 |

FIG. 1A-61

| ATOM | 3477 | CE  | LYS | 86 | 16.368 | 17.189 | 35.880 | 1.00 | 23.49 | CPS4 |
|------|------|-----|-----|----|--------|--------|--------|------|-------|------|
| ATOM | 3478 | NZ  | LYS | 86 | 17.044 | 18.252 | 36.687 | 1.00 | 21.98 | CPS4 |
| ATOM | 3479 | C   | LYS | 86 | 12.069 | 15.527 | 35.105 | 1.00 | 25.27 | CPS4 |
| ATOM | 3480 | O   | LYS | 86 | 11.868 | 14.746 | 34.175 | 1.00 | 23.72 | CPS4 |
| ATOM | 3481 | N   | PRO | 87 | 11.987 | 16.859 | 34.936 | 1.00 | 24.18 | CPS4 |
| ATOM | 3482 | CD  | PRO | 87 | 12.068 | 17.970 | 35.906 | 1.00 | 24.38 | CPS4 |
| ATOM | 3483 | CA  | PRO | 87 | 11.682 | 17.351 | 33.589 | 1.00 | 23.07 | CPS4 |
| ATOM | 3484 | CB  | PRO | 87 | 11.343 | 18.825 | 33.822 | 1.00 | 24.68 | CPS4 |
| ATOM | 3485 | CG  | PRO | 87 | 12.229 | 19.189 | 34.995 | 1.00 | 24.14 | CPS4 |
| ATOM | 3486 | C   | PRO | 87 | 12.869 | 17.202 | 32.658 | 1.00 | 22.51 | CPS4 |
| ATOM | 3487 | O   | PRO | 87 | 14.028 | 17.182 | 33.098 | 1.00 | 21.21 | CPS4 |
| ATOM | 3488 | N   | TYR | 88 | 12.576 | 17.094 | 31.366 | 1.00 | 21.14 | CPS4 |
| ATOM | 3489 | CA  | TYR | 88 | 13.617 | 17.009 | 30.363 | 1.00 | 21.50 | CPS4 |
| ATOM | 3490 | CB  | TYR | 88 | 14.069 | 15.563 | 30.132 | 1.00 | 23.25 | CPS4 |
| ATOM | 3491 | CG  | TYR | 88 | 13.032 | 14.648 | 29.546 | 1.00 | 24.04 | CPS4 |
| ATOM | 3492 | CD1 | TYR | 88 | 12.953 | 14.449 | 28.165 | 1.00 | 26.52 | CPS4 |
| ATOM | 3493 | CE1 | TYR | 88 | 12.033 | 13.554 | 27.622 | 1.00 | 27.83 | CPS4 |
| ATOM | 3494 | CD2 | TYR | 88 | 12.164 | 13.941 | 30.369 | 1.00 | 25.98 | CPS4 |
| ATOM | 3495 | CE2 | TYR | 88 | 11.241 | 13.048 | 29.840 | 1.00 | 27.07 | CPS4 |
| ATOM | 3496 | CZ  | TYR | 88 | 11.185 | 12.857 | 28.467 | 1.00 | 28.72 | CPS4 |
| ATOM | 3497 | OH  | TYR | 88 | 10.295 | 11.941 | 27.945 | 1.00 | 31.78 | CPS4 |
| ATOM | 3498 | C   | TYR | 88 | 13.049 | 17.631 | 29.105 | 1.00 | 20.69 | CPS4 |
| ATOM | 3499 | O   | TYR | 88 | 11.839 | 17.679 | 28.915 | 1.00 | 20.95 | CPS4 |
| ATOM | 3500 | N   | ILE | 89 | 13.930 | 18.130 | 28.257 | 1.00 | 21.21 | CPS4 |
| ATOM | 3501 | CA  | ILE | 89 | 13.501 | 18.805 | 27.042 | 1.00 | 21.24 | CPS4 |
| ATOM | 3502 | CB  | ILE | 89 | 14.275 | 20.141 | 26.878 | 1.00 | 20.12 | CPS4 |
| ATOM | 3503 | CG2 | ILE | 89 | 14.157 | 20.667 | 25.423 | 1.00 | 21.03 | CPS4 |
| ATOM | 3504 | CG1 | ILE | 89 | 13.757 | 21.164 | 27.900 | 1.00 | 20.90 | CPS4 |
| ATOM | 3505 | CD1 | ILE | 89 | 14.595 | 22.440 | 28.000 | 1.00 | 21.80 | CPS4 |
| ATOM | 3506 | C   | ILE | 89 | 13.698 | 18.011 | 25.767 | 1.00 | 22.30 | CPS4 |
| ATOM | 3507 | O   | ILE | 89 | 14.685 | 17.290 | 25.625 | 1.00 | 22.10 | CPS4 |
| ATOM | 3508 | N   | ILE | 90 | 12.729 | 18.126 | 24.862 | 1.00 | 22.64 | CPS4 |
| ATOM | 3509 | CA  | ILE | 90 | 12.871 | 17.544 | 23.538 | 1.00 | 23.23 | CPS4 |
| ATOM | 3510 | CB  | ILE | 90 | 11.850 | 16.413 | 23.228 | 1.00 | 25.32 | CPS4 |
| ATOM | 3511 | CG2 | ILE | 90 | 11.987 | 15.303 | 24.259 | 1.00 | 25.34 | CPS4 |
| ATOM | 3512 | CG1 | ILE | 90 | 10.424 | 16.946 | 23.187 | 1.00 | 27.66 | CPS4 |
| ATOM | 3513 | CD1 | ILE | 90 |  9.462 | 16.003 | 22.454 | 1.00 | 29.92 | CPS4 |
| ATOM | 3514 | C   | ILE | 90 | 12.609 | 18.760 | 22.654 | 1.00 | 23.57 | CPS4 |
| ATOM | 3515 | O   | ILE | 90 | 11.780 | 19.610 | 22.988 | 1.00 | 23.18 | CPS4 |
| ATOM | 3516 | N   | CYS | 91 | 13.341 | 18.892 | 21.558 | 1.00 | 22.32 | CPS4 |
| ATOM | 3517 | CA  | CYS | 91 | 13.118 | 20.042 | 20.692 | 1.00 | 24.32 | CPS4 |
| ATOM | 3518 | CB  | CYS | 91 | 14.023 | 21.209 | 21.096 | 1.00 | 22.65 | CPS4 |
| ATOM | 3519 | SG  | CYS | 91 | 15.776 | 20.862 | 20.976 | 1.00 | 28.76 | CPS4 |
| ATOM | 3520 | C   | CYS | 91 | 13.367 | 19.670 | 19.244 | 1.00 | 24.59 | CPS4 |
| ATOM | 3521 | O   | CYS | 91 | 13.834 | 18.575 | 18.947 | 1.00 | 26.28 | CPS4 |
| ATOM | 3522 | N   | THR | 92 | 13.064 | 20.591 | 18.344 | 1.00 | 25.08 | CPS4 |
| ATOM | 3523 | CA  | THR | 92 | 13.234 | 20.325 | 16.920 | 1.00 | 25.91 | CPS4 |
| ATOM | 3524 | CB  | THR | 92 | 12.266 | 21.187 | 16.102 | 1.00 | 26.21 | CPS4 |
| ATOM | 3525 | OG1 | THR | 92 | 12.577 | 22.562 | 16.329 | 1.00 | 25.10 | CPS4 |
| ATOM | 3526 | CG2 | THR | 92 | 10.828 | 20.933 | 16.526 | 1.00 | 25.78 | CPS4 |
| ATOM | 3527 | C   | THR | 92 | 14.633 | 20.629 | 16.417 | 1.00 | 26.72 | CPS4 |
| ATOM | 3528 | O   | THR | 92 | 14.938 | 20.371 | 15.255 | 1.00 | 27.72 | CPS4 |
| ATOM | 3529 | N   | LYS | 93 | 15.480 | 21.163 | 17.291 | 1.00 | 26.75 | CPS4 |
| ATOM | 3530 | CA  | LYS | 93 | 16.830 | 21.589 | 16.927 | 1.00 | 28.49 | CPS4 |
| ATOM | 3531 | CB  | LYS | 93 | 17.109 | 22.946 | 17.583 | 1.00 | 30.97 | CPS4 |
| ATOM | 3532 | CG  | LYS | 93 | 16.792 | 24.162 | 16.729 | 1.00 | 36.76 | CPS4 |
| ATOM | 3533 | CD  | LYS | 93 | 15.450 | 24.100 | 16.039 | 1.00 | 38.80 | CPS4 |

FIG. 1A-62

| ATOM | 3534 | CE  | LYS | 93  | 15.212 | 25.376 | 15.229 | 1.00 | 40.84 | CPS4 |
|------|------|-----|-----|-----|--------|--------|--------|------|-------|------|
| ATOM | 3535 | NZ  | LYS | 93  | 14.048 | 25.250 | 14.312 | 1.00 | 43.58 | CPS4 |
| ATOM | 3536 | C   | LYS | 93  | 18.005 | 20.676 | 17.234 | 1.00 | 27.51 | CPS4 |
| ATOM | 3537 | O   | LYS | 93  | 19.005 | 20.676 | 16.509 | 1.00 | 27.46 | CPS4 |
| ATOM | 3538 | N   | LEU | 94  | 17.910 | 19.911 | 18.307 | 1.00 | 26.01 | CPS4 |
| ATOM | 3539 | CA  | LEU | 94  | 19.020 | 19.058 | 18.676 | 1.00 | 25.30 | CPS4 |
| ATOM | 3540 | CB  | LEU | 94  | 20.055 | 19.904 | 19.408 | 1.00 | 27.33 | CPS4 |
| ATOM | 3541 | CG  | LEU | 94  | 19.418 | 20.843 | 20.433 | 1.00 | 28.62 | CPS4 |
| ATOM | 3542 | CD1 | LEU | 94  | 19.228 | 20.074 | 21.712 | 1.00 | 30.37 | CPS4 |
| ATOM | 3543 | CD2 | LEU | 94  | 20.292 | 22.060 | 20.673 | 1.00 | 30.20 | CPS4 |
| ATOM | 3544 | C   | LEU | 94  | 18.556 | 17.889 | 19.524 | 1.00 | 25.14 | CPS4 |
| ATOM | 3545 | O   | LEU | 94  | 17.414 | 17.854 | 19.974 | 1.00 | 24.61 | CPS4 |
| ATOM | 3546 | N   | SER | 95  | 19.460 | 16.944 | 19.755 | 1.00 | 24.28 | CPS4 |
| ATOM | 3547 | CA  | SER | 95  | 19.153 | 15.731 | 20.499 | 1.00 | 26.04 | CPS4 |
| ATOM | 3548 | CB  | SER | 95  | 20.323 | 14.756 | 20.355 | 1.00 | 27.48 | CPS4 |
| ATOM | 3549 | OG  | SER | 95  | 20.100 | 13.586 | 21.116 | 1.00 | 33.27 | CPS4 |
| ATOM | 3550 | C   | SER | 95  | 18.825 | 15.908 | 21.982 | 1.00 | 25.21 | CPS4 |
| ATOM | 3551 | O   | SER | 95  | 19.445 | 16.714 | 22.672 | 1.00 | 26.64 | CPS4 |
| ATOM | 3552 | N   | PRO | 96  | 17.840 | 15.150 | 22.485 | 1.00 | 25.96 | CPS4 |
| ATOM | 3553 | CD  | PRO | 96  | 16.943 | 14.229 | 21.760 | 1.00 | 25.56 | CPS4 |
| ATOM | 3554 | CA  | PRO | 96  | 17.461 | 15.245 | 23.900 | 1.00 | 26.26 | CPS4 |
| ATOM | 3555 | CB  | PRO | 96  | 16.385 | 14.165 | 24.045 | 1.00 | 26.57 | CPS4 |
| ATOM | 3556 | CG  | PRO | 96  | 15.745 | 14.149 | 22.679 | 1.00 | 27.21 | CPS4 |
| ATOM | 3557 | C   | PRO | 96  | 18.677 | 14.961 | 24.787 | 1.00 | 26.31 | CPS4 |
| ATOM | 3558 | O   | PRO | 96  | 18.835 | 15.561 | 25.856 | 1.00 | 24.59 | CPS4 |
| ATOM | 3559 | N   | ALA | 97  | 19.541 | 14.056 | 24.323 | 1.00 | 27.53 | CPS4 |
| ATOM | 3560 | CA  | ALA | 97  | 20.739 | 13.678 | 25.074 | 1.00 | 29.07 | CPS4 |
| ATOM | 3561 | CB  | ALA | 97  | 21.480 | 12.589 | 24.286 | 1.00 | 34.39 | CPS4 |
| ATOM | 3562 | C   | ALA | 97  | 21.690 | 14.853 | 25.314 | 1.00 | 27.61 | CPS4 |
| ATOM | 3563 | O   | ALA | 97  | 22.492 | 14.827 | 26.251 | 1.00 | 26.14 | CPS4 |
| ATOM | 3564 | N   | ALA | 98  | 21.599 | 15.885 | 24.483 | 1.00 | 24.18 | CPS4 |
| ATOM | 3565 | CA  | ALA | 98  | 22.486 | 17.034 | 24.617 | 1.00 | 23.38 | CPS4 |
| ATOM | 3566 | CB  | ALA | 98  | 22.804 | 17.600 | 23.238 | 1.00 | 25.54 | CPS4 |
| ATOM | 3567 | C   | ALA | 98  | 21.943 | 18.150 | 25.500 | 1.00 | 23.06 | CPS4 |
| ATOM | 3568 | O   | ALA | 98  | 22.634 | 19.140 | 25.730 | 1.00 | 23.28 | CPS4 |
| ATOM | 3569 | N   | VAL | 99  | 20.720 | 17.993 | 25.999 | 1.00 | 21.46 | CPS4 |
| ATOM | 3570 | CA  | VAL | 99  | 20.109 | 19.048 | 26.796 | 1.00 | 20.54 | CPS4 |
| ATOM | 3571 | CB  | VAL | 99  | 18.806 | 19.548 | 26.146 | 1.00 | 21.70 | CPS4 |
| ATOM | 3572 | CG1 | VAL | 99  | 18.317 | 20.837 | 26.820 | 1.00 | 20.11 | CPS4 |
| ATOM | 3573 | CG2 | VAL | 99  | 19.026 | 19.777 | 24.692 | 1.00 | 25.15 | CPS4 |
| ATOM | 3574 | C   | VAL | 99  | 19.781 | 18.622 | 28.206 | 1.00 | 20.45 | CPS4 |
| ATOM | 3575 | O   | VAL | 99  | 19.399 | 17.477 | 28.450 | 1.00 | 20.26 | CPS4 |
| ATOM | 3576 | N   | HIS | 100 | 19.924 | 19.572 | 29.123 | 1.00 | 19.96 | CPS4 |
| ATOM | 3577 | CA  | HIS | 100 | 19.634 | 19.349 | 30.531 | 1.00 | 19.64 | CPS4 |
| ATOM | 3578 | CB  | HIS | 100 | 20.935 | 19.210 | 31.318 | 1.00 | 20.91 | CPS4 |
| ATOM | 3579 | CG  | HIS | 100 | 21.844 | 18.154 | 30.773 | 1.00 | 24.67 | CPS4 |
| ATOM | 3580 | CD2 | HIS | 100 | 22.842 | 18.227 | 29.862 | 1.00 | 26.77 | CPS4 |
| ATOM | 3581 | ND1 | HIS | 100 | 21.715 | 16.820 | 31.096 | 1.00 | 26.53 | CPS4 |
| ATOM | 3582 | CE1 | HIS | 100 | 22.593 | 16.115 | 30.403 | 1.00 | 26.82 | CPS4 |
| ATOM | 3583 | NE2 | HIS | 100 | 23.288 | 16.946 | 29.646 | 1.00 | 28.13 | CPS4 |
| ATOM | 3584 | C   | HIS | 100 | 18.864 | 20.561 | 31.020 | 1.00 | 18.58 | CPS4 |
| ATOM | 3585 | O   | HIS | 100 | 19.141 | 21.683 | 30.602 | 1.00 | 18.37 | CPS4 |
| ATOM | 3586 | N   | VAL | 101 | 17.907 | 20.336 | 31.911 | 1.00 | 18.87 | CPS4 |
| ATOM | 3587 | CA  | VAL | 101 | 17.103 | 21.434 | 32.431 | 1.00 | 17.84 | CPS4 |
| ATOM | 3588 | CB  | VAL | 101 | 15.800 | 21.590 | 31.608 | 1.00 | 16.78 | CPS4 |
| ATOM | 3589 | CG1 | VAL | 101 | 14.930 | 20.345 | 31.770 | 1.00 | 18.44 | CPS4 |
| ATOM | 3590 | CG2 | VAL | 101 | 15.029 | 22.840 | 32.049 | 1.00 | 18.77 | CPS4 |

FIG. 1A-63

| ATOM | 3591 | C   | VAL | 101 | 16.723 | 21.199 | 33.879 | 1.00 | 18.74 | CPS4 |
|------|------|-----|-----|-----|--------|--------|--------|------|-------|------|
| ATOM | 3592 | O   | VAL | 101 | 16.711 | 20.069 | 34.350 | 1.00 | 17.29 | CPS4 |
| ATOM | 3593 | N   | SER | 102 | 16.441 | 22.287 | 34.590 | 1.00 | 18.62 | CPS4 |
| ATOM | 3594 | CA  | SER | 102 | 15.980 | 22.193 | 35.963 | 1.00 | 18.53 | CPS4 |
| ATOM | 3595 | CB  | SER | 102 | 17.117 | 22.333 | 36.970 | 1.00 | 19.00 | CPS4 |
| ATOM | 3596 | OG  | SER | 102 | 16.596 | 22.169 | 38.289 | 1.00 | 19.73 | CPS4 |
| ATOM | 3597 | C   | SER | 102 | 15.004 | 23.348 | 36.139 | 1.00 | 19.67 | CPS4 |
| ATOM | 3598 | O   | SER | 102 | 15.250 | 24.446 | 35.638 | 1.00 | 18.04 | CPS4 |
| ATOM | 3599 | N   | ILE | 103 | 13.901 | 23.092 | 36.841 | 1.00 | 19.50 | CPS4 |
| ATOM | 3600 | CA  | ILE | 103 | 12.886 | 24.105 | 37.082 | 1.00 | 19.92 | CPS4 |
| ATOM | 3601 | CB  | ILE | 103 | 11.552 | 23.731 | 36.386 | 1.00 | 22.07 | CPS4 |
| ATOM | 3602 | CG2 | ILE | 103 | 10.527 | 24.867 | 36.551 | 1.00 | 23.01 | CPS4 |
| ATOM | 3603 | CG1 | ILE | 103 | 11.804 | 23.454 | 34.905 | 1.00 | 21.39 | CPS4 |
| ATOM | 3604 | CD1 | ILE | 103 | 10.570 | 22.958 | 34.144 | 1.00 | 21.32 | CPS4 |
| ATOM | 3605 | C   | ILE | 103 | 12.642 | 24.173 | 38.590 | 1.00 | 20.11 | CPS4 |
| ATOM | 3606 | O   | ILE | 103 | 12.633 | 23.137 | 39.277 | 1.00 | 20.14 | CPS4 |
| ATOM | 3607 | N   | THR | 104 | 12.462 | 25.386 | 39.098 | 1.00 | 18.69 | CPS4 |
| ATOM | 3608 | CA  | THR | 104 | 12.205 | 25.588 | 40.517 | 1.00 | 21.54 | CPS4 |
| ATOM | 3609 | CB  | THR | 104 | 13.492 | 26.019 | 41.274 | 1.00 | 23.15 | CPS4 |
| ATOM | 3610 | OG1 | THR | 104 | 13.245 | 26.008 | 42.686 | 1.00 | 23.24 | CPS4 |
| ATOM | 3611 | CG2 | THR | 104 | 13.927 | 27.418 | 40.856 | 1.00 | 22.71 | CPS4 |
| ATOM | 3612 | C   | THR | 104 | 11.113 | 26.639 | 40.698 | 1.00 | 21.91 | CPS4 |
| ATOM | 3613 | O   | THR | 104 | 10.790 | 27.376 | 39.772 | 1.00 | 19.56 | CPS4 |
| ATOM | 3614 | N   | HIS | 105 | 10.542 | 26.701 | 41.899 | 1.00 | 22.60 | CPS4 |
| ATOM | 3615 | CA  | HIS | 105 | 9.465  | 27.639 | 42.189 | 1.00 | 24.01 | CPS4 |
| ATOM | 3616 | CB  | HIS | 105 | 8.110  | 26.927 | 42.112 | 1.00 | 26.53 | CPS4 |
| ATOM | 3617 | CG  | HIS | 105 | 7.721  | 26.457 | 40.746 | 1.00 | 30.77 | CPS4 |
| ATOM | 3618 | CD2 | HIS | 105 | 7.892  | 25.262 | 40.130 | 1.00 | 32.51 | CPS4 |
| ATOM | 3619 | ND1 | HIS | 105 | 6.995  | 27.237 | 39.871 | 1.00 | 32.62 | CPS4 |
| ATOM | 3620 | CE1 | HIS | 105 | 6.731  | 26.543 | 38.778 | 1.00 | 32.63 | CPS4 |
| ATOM | 3621 | NE2 | HIS | 105 | 7.264  | 25.341 | 38.909 | 1.00 | 33.46 | CPS4 |
| ATOM | 3622 | C   | HIS | 105 | 9.558  | 28.179 | 43.613 | 1.00 | 24.17 | CPS4 |
| ATOM | 3623 | O   | HIS | 105 | 10.135 | 27.537 | 44.491 | 1.00 | 22.69 | CPS4 |
| ATOM | 3624 | N   | THR | 106 | 8.992  | 29.366 | 43.816 | 1.00 | 24.57 | CPS4 |
| ATOM | 3625 | CA  | THR | 106 | 8.856  | 29.967 | 45.147 | 1.00 | 24.52 | CPS4 |
| ATOM | 3626 | CB  | THR | 106 | 9.756  | 31.195 | 45.408 | 1.00 | 24.79 | CPS4 |
| ATOM | 3627 | OG1 | THR | 106 | 9.327  | 32.299 | 44.602 | 1.00 | 23.92 | CPS4 |
| ATOM | 3628 | CG2 | THR | 106 | 11.210 | 30.858 | 45.127 | 1.00 | 24.13 | CPS4 |
| ATOM | 3629 | C   | THR | 106 | 7.415  | 30.444 | 45.065 | 1.00 | 26.14 | CPS4 |
| ATOM | 3630 | O   | THR | 106 | 6.756  | 30.249 | 44.034 | 1.00 | 26.11 | CPS4 |
| ATOM | 3631 | N   | LYS | 107 | 6.917  | 31.072 | 46.123 | 1.00 | 26.83 | CPS4 |
| ATOM | 3632 | CA  | LYS | 107 | 5.539  | 31.546 | 46.115 | 1.00 | 27.90 | CPS4 |
| ATOM | 3633 | CB  | LYS | 107 | 5.200  | 32.186 | 47.464 | 1.00 | 30.86 | CPS4 |
| ATOM | 3634 | CG  | LYS | 107 | 3.756  | 32.658 | 47.573 | 1.00 | 34.83 | CPS4 |
| ATOM | 3635 | CD  | LYS | 107 | 3.490  | 33.278 | 48.940 | 1.00 | 39.94 | CPS4 |
| ATOM | 3636 | CE  | LYS | 107 | 2.024  | 33.649 | 49.117 | 1.00 | 42.44 | CPS4 |
| ATOM | 3637 | NZ  | LYS | 107 | 1.755  | 34.215 | 50.479 | 1.00 | 45.42 | CPS4 |
| ATOM | 3638 | C   | LYS | 107 | 5.250  | 32.541 | 44.994 | 1.00 | 26.50 | CPS4 |
| ATOM | 3639 | O   | LYS | 107 | 4.169  | 32.511 | 44.402 | 1.00 | 27.10 | CPS4 |
| ATOM | 3640 | N   | GLU | 108 | 6.222  | 33.396 | 44.684 | 1.00 | 24.12 | CPS4 |
| ATOM | 3641 | CA  | GLU | 108 | 6.050  | 34.436 | 43.672 | 1.00 | 23.55 | CPS4 |
| ATOM | 3642 | CB  | GLU | 108 | 6.476  | 35.783 | 44.256 | 1.00 | 27.75 | CPS4 |
| ATOM | 3643 | CG  | GLU | 108 | 5.755  | 36.152 | 45.530 | 1.00 | 34.21 | CPS4 |
| ATOM | 3644 | CD  | GLU | 108 | 4.301  | 36.440 | 45.297 | 1.00 | 39.02 | CPS4 |
| ATOM | 3645 | OE1 | GLU | 108 | 3.639  | 35.645 | 44.593 | 1.00 | 43.65 | CPS4 |
| ATOM | 3646 | OE2 | GLU | 108 | 3.813  | 37.463 | 45.823 | 1.00 | 44.70 | CPS4 |
| ATOM | 3647 | C   | GLU | 108 | 6.794  | 34.267 | 42.352 | 1.00 | 23.22 | CPS4 |

FIG. 1A-64

```
ATOM   3648  O    GLU  108     6.553  35.023  41.400  1.00 22.15      CPS4
ATOM   3649  N    TYR  109     7.711  33.308  42.293  1.00 21.80      CPS4
ATOM   3650  CA   TYR  109     8.509  33.129  41.077  1.00 22.23      CPS4
ATOM   3651  CB   TYR  109     9.940  33.626  41.317  1.00 22.18      CPS4
ATOM   3652  CG   TYR  109    10.035  35.082  41.674  1.00 22.99      CPS4
ATOM   3653  CD1  TYR  109     9.984  36.062  40.688  1.00 22.71      CPS4
ATOM   3654  CE1  TYR  109    10.017  37.418  41.018  1.00 25.19      CPS4
ATOM   3655  CD2  TYR  109    10.127  35.485  43.008  1.00 25.01      CPS4
ATOM   3656  CE2  TYR  109    10.158  36.833  43.350  1.00 26.56      CPS4
ATOM   3657  CZ   TYR  109    10.101  37.793  42.349  1.00 26.58      CPS4
ATOM   3658  OH   TYR  109    10.114  39.128  42.677  1.00 29.10      CPS4
ATOM   3659  C    TYR  109     8.625  31.713  40.569  1.00 20.65      CPS4
ATOM   3660  O    TYR  109     8.402  30.757  41.297  1.00 20.79      CPS4
ATOM   3661  N    ALA  110     8.989  31.609  39.294  1.00 21.05      CPS4
ATOM   3662  CA   ALA  110     9.280  30.334  38.654  1.00 19.88      CPS4
ATOM   3663  CB   ALA  110     8.267  29.999  37.567  1.00 21.21      CPS4
ATOM   3664  C    ALA  110    10.638  30.617  38.028  1.00 19.33      CPS4
ATOM   3665  O    ALA  110    10.887  31.730  37.568  1.00 20.58      CPS4
ATOM   3666  N    ALA  111    11.525  29.626  38.008  1.00 18.54      CPS4
ATOM   3667  CA   ALA  111    12.842  29.834  37.423  1.00 17.54      CPS4
ATOM   3668  CB   ALA  111    13.840  30.291  38.498  1.00 17.07      CPS4
ATOM   3669  C    ALA  111    13.314  28.540  36.786  1.00 16.63      CPS4
ATOM   3670  O    ALA  111    12.873  27.454  37.160  1.00 17.51      CPS4
ATOM   3671  N    ALA  112    14.218  28.654  35.826  1.00 17.15      CPS4
ATOM   3672  CA   ALA  112    14.721  27.471  35.161  1.00 16.51      CPS4
ATOM   3673  CB   ALA  112    13.771  27.054  34.046  1.00 17.29      CPS4
ATOM   3674  C    ALA  112    16.092  27.742  34.583  1.00 16.61      CPS4
ATOM   3675  O    ALA  112    16.476  28.887  34.363  1.00 15.97      CPS4
ATOM   3676  N    GLN  113    16.842  26.677  34.356  1.00 17.66      CPS4
ATOM   3677  CA   GLN  113    18.148  26.829  33.754  1.00 17.26      CPS4
ATOM   3678  CB   GLN  113    19.257  26.820  34.811  1.00 19.62      CPS4
ATOM   3679  CG   GLN  113    19.419  25.510  35.538  1.00 23.20      CPS4
ATOM   3680  CD   GLN  113    20.569  25.522  36.537  1.00 26.68      CPS4
ATOM   3681  OE1  GLN  113    20.942  24.480  37.077  1.00 29.56      CPS4
ATOM   3682  NE2  GLN  113    21.121  26.697  36.798  1.00 29.78      CPS4
ATOM   3683  C    GLN  113    18.314  25.678  32.789  1.00 17.26      CPS4
ATOM   3684  O    GLN  113    17.741  24.609  32.975  1.00 16.60      CPS4
ATOM   3685  N    VAL  114    19.093  25.910  31.746  1.00 16.61      CPS4
ATOM   3686  CA   VAL  114    19.329  24.880  30.744  1.00 17.56      CPS4
ATOM   3687  CB   VAL  114    18.523  25.161  29.436  1.00 17.29      CPS4
ATOM   3688  CG1  VAL  114    19.016  24.268  28.275  1.00 18.95      CPS4
ATOM   3689  CG2  VAL  114    17.058  24.895  29.671  1.00 19.12      CPS4
ATOM   3690  C    VAL  114    20.795  24.886  30.386  1.00 17.66      CPS4
ATOM   3691  O    VAL  114    21.454  25.938  30.404  1.00 17.69      CPS4
ATOM   3692  N    VAL  115    21.309  23.696  30.104  1.00 18.00      CPS4
ATOM   3693  CA   VAL  115    22.673  23.566  29.629  1.00 18.27      CPS4
ATOM   3694  CB   VAL  115    23.611  22.872  30.635  1.00 19.25      CPS4
ATOM   3695  CG1  VAL  115    24.962  22.560  29.939  1.00 19.98      CPS4
ATOM   3696  CG2  VAL  115    23.845  23.762  31.841  1.00 17.55      CPS4
ATOM   3697  C    VAL  115    22.597  22.696  28.378  1.00 19.07      CPS4
ATOM   3698  O    VAL  115    21.987  21.626  28.394  1.00 20.13      CPS4
ATOM   3699  N    ILE  116    23.197  23.170  27.293  1.00 18.54      CPS4
ATOM   3700  CA   ILE  116    23.236  22.407  26.053  1.00 21.10      CPS4
ATOM   3701  CB   ILE  116    22.762  23.239  24.850  1.00 21.01      CPS4
ATOM   3702  CG2  ILE  116    22.921  22.420  23.563  1.00 20.56      CPS4
ATOM   3703  CG1  ILE  116    21.298  23.652  25.046  1.00 19.07      CPS4
ATOM   3704  CD1  ILE  116    20.775  24.599  23.943  1.00 18.68      CPS4
```

FIG. 1A-65

| ATOM | 3705 | C | ILE | 116 | 24.692 | 22.029 | 25.851 | 1.00 | 22.03 | CPS4 |
|---|---|---|---|---|---|---|---|---|---|---|
| ATOM | 3706 | O | ILE | 116 | 25.570 | 22.884 | 25.856 | 1.00 | 21.24 | CPS4 |
| ATOM | 3707 | N | GLU | 117 | 24.951 | 20.736 | 25.702 | 1.00 | 25.15 | CPS4 |
| ATOM | 3708 | CA | GLU | 117 | 26.317 | 20.266 | 25.509 | 1.00 | 28.51 | CPS4 |
| ATOM | 3709 | CB | GLU | 117 | 26.469 | 18.835 | 26.012 | 1.00 | 28.70 | CPS4 |
| ATOM | 3710 | CG | GLU | 117 | 26.237 | 18.661 | 27.490 | 1.00 | 33.10 | CPS4 |
| ATOM | 3711 | CD | GLU | 117 | 26.513 | 17.240 | 27.929 | 1.00 | 34.43 | CPS4 |
| ATOM | 3712 | OE1 | GLU | 117 | 27.702 | 16.908 | 28.114 | 1.00 | 36.09 | CPS4 |
| ATOM | 3713 | OE2 | GLU | 117 | 25.545 | 16.458 | 28.070 | 1.00 | 35.59 | CPS4 |
| ATOM | 3714 | C | GLU | 117 | 26.677 | 20.279 | 24.041 | 1.00 | 30.50 | CPS4 |
| ATOM | 3715 | O | GLU | 117 | 25.815 | 20.420 | 23.186 | 1.00 | 29.91 | CPS4 |
| ATOM | 3716 | N | ARG | 118 | 27.960 | 20.137 | 23.747 | 1.00 | 34.16 | CPS4 |
| ATOM | 3717 | CA | ARG | 118 | 28.371 | 20.085 | 22.355 | 1.00 | 38.48 | CPS4 |
| ATOM | 3718 | CB | ARG | 118 | 29.800 | 20.597 | 22.182 | 1.00 | 41.53 | CPS4 |
| ATOM | 3719 | CG | ARG | 118 | 29.971 | 22.069 | 22.549 | 1.00 | 45.64 | CPS4 |
| ATOM | 3720 | CD | ARG | 118 | 30.881 | 22.808 | 21.567 | 1.00 | 47.97 | CPS4 |
| ATOM | 3721 | NE | ARG | 118 | 30.154 | 23.472 | 20.477 | 1.00 | 50.66 | CPS4 |
| ATOM | 3722 | CZ | ARG | 118 | 29.372 | 22.860 | 19.585 | 1.00 | 50.73 | CPS4 |
| ATOM | 3723 | NH1 | ARG | 118 | 29.188 | 21.550 | 19.633 | 1.00 | 52.65 | CPS4 |
| ATOM | 3724 | NH2 | ARG | 118 | 28.786 | 23.560 | 18.622 | 1.00 | 51.12 | CPS4 |
| ATOM | 3725 | C | ARG | 118 | 28.285 | 18.615 | 21.984 | 1.00 | 40.15 | CPS4 |
| ATOM | 3726 | OT1 | ARG | 118 | 27.421 | 18.274 | 21.156 | 1.00 | 41.62 | CPS4 |
| ATOM | 3727 | OT2 | ARG | 118 | 29.063 | 17.816 | 22.555 | 1.00 | 41.20 | CPS4 |
| ATOM | 3728 | C | GLY | 1 | 28.742 | 14.952 | 31.117 | 1.00 | 33.66 | CPS5 |
| ATOM | 3729 | O | GLY | 1 | 29.119 | 14.581 | 32.234 | 1.00 | 34.07 | CPS5 |
| ATOM | 3730 | N | GLY | 1 | 30.561 | 13.536 | 30.129 | 1.00 | 37.12 | CPS5 |
| ATOM | 3731 | CA | GLY | 1 | 29.506 | 14.565 | 29.858 | 1.00 | 34.50 | CPS5 |
| ATOM | 3732 | N | ILE | 2 | 27.654 | 15.692 | 30.948 | 1.00 | 31.08 | CPS5 |
| ATOM | 3733 | CA | ILE | 2 | 26.856 | 16.110 | 32.095 | 1.00 | 28.11 | CPS5 |
| ATOM | 3734 | CB | ILE | 2 | 26.178 | 17.462 | 31.826 | 1.00 | 27.63 | CPS5 |
| ATOM | 3735 | CG2 | ILE | 2 | 25.128 | 17.747 | 32.899 | 1.00 | 24.45 | CPS5 |
| ATOM | 3736 | CG1 | ILE | 2 | 27.244 | 18.559 | 31.785 | 1.00 | 28.90 | CPS5 |
| ATOM | 3737 | CD1 | ILE | 2 | 26.695 | 19.935 | 31.484 | 1.00 | 31.41 | CPS5 |
| ATOM | 3738 | C | ILE | 2 | 25.797 | 15.083 | 32.441 | 1.00 | 27.43 | CPS5 |
| ATOM | 3739 | O | ILE | 2 | 25.067 | 14.611 | 31.567 | 1.00 | 27.84 | CPS5 |
| ATOM | 3740 | N | TYR | 3 | 25.719 | 14.735 | 33.723 | 1.00 | 27.08 | CPS5 |
| ATOM | 3741 | CA | TYR | 3 | 24.737 | 13.768 | 34.198 | 1.00 | 27.10 | CPS5 |
| ATOM | 3742 | CB | TYR | 3 | 25.220 | 13.087 | 35.476 | 1.00 | 30.18 | CPS5 |
| ATOM | 3743 | CG | TYR | 3 | 24.212 | 12.108 | 36.033 | 1.00 | 34.88 | CPS5 |
| ATOM | 3744 | CD1 | TYR | 3 | 24.012 | 10.862 | 35.428 | 1.00 | 36.41 | CPS5 |
| ATOM | 3745 | CE1 | TYR | 3 | 23.063 | 9.963 | 35.920 | 1.00 | 38.43 | CPS5 |
| ATOM | 3746 | CD2 | TYR | 3 | 23.435 | 12.433 | 37.146 | 1.00 | 36.11 | CPS5 |
| ATOM | 3747 | CE2 | TYR | 3 | 22.484 | 11.542 | 37.646 | 1.00 | 38.38 | CPS5 |
| ATOM | 3748 | CZ | TYR | 3 | 22.305 | 10.309 | 37.029 | 1.00 | 39.52 | CPS5 |
| ATOM | 3749 | OH | TYR | 3 | 21.378 | 9.418 | 37.530 | 1.00 | 42.62 | CPS5 |
| ATOM | 3750 | C | TYR | 3 | 23.418 | 14.475 | 34.485 | 1.00 | 26.49 | CPS5 |
| ATOM | 3751 | O | TYR | 3 | 22.340 | 13.985 | 34.130 | 1.00 | 24.87 | CPS5 |
| ATOM | 3752 | N | GLY | 4 | 23.499 | 15.624 | 35.153 | 1.00 | 24.12 | CPS5 |
| ATOM | 3753 | CA | GLY | 4 | 22.284 | 16.355 | 35.449 | 1.00 | 22.31 | CPS5 |
| ATOM | 3754 | C | GLY | 4 | 22.562 | 17.715 | 36.047 | 1.00 | 20.04 | CPS5 |
| ATOM | 3755 | O | GLY | 4 | 23.667 | 17.966 | 36.509 | 1.00 | 20.64 | CPS5 |
| ATOM | 3756 | N | ILE | 5 | 21.572 | 18.602 | 36.011 | 1.00 | 19.86 | CPS5 |
| ATOM | 3757 | CA | ILE | 5 | 21.730 | 19.932 | 36.592 | 1.00 | 18.90 | CPS5 |
| ATOM | 3758 | CB | ILE | 5 | 21.865 | 21.055 | 35.523 | 1.00 | 18.93 | CPS5 |
| ATOM | 3759 | CG2 | ILE | 5 | 22.936 | 20.676 | 34.510 | 1.00 | 18.22 | CPS5 |
| ATOM | 3760 | CG1 | ILE | 5 | 20.521 | 21.321 | 34.835 | 1.00 | 19.13 | CPS5 |
| ATOM | 3761 | CD1 | ILE | 5 | 20.582 | 22.454 | 33.780 | 1.00 | 18.31 | CPS5 |

FIG. 1A-66

| ATOM | 3762 | C | ILE | 5 | 20.532 | 20.234 | 37.471 | 1.00 | 18.47 | CPS5 |
|---|---|---|---|---|---|---|---|---|---|---|
| ATOM | 3763 | O | ILE | 5 | 19.456 | 19.655 | 37.309 | 1.00 | 17.95 | CPS5 |
| ATOM | 3764 | N | GLY | 6 | 20.727 | 21.149 | 38.410 | 1.00 | 18.51 | CPS5 |
| ATOM | 3765 | CA | GLY | 6 | 19.654 | 21.489 | 39.318 | 1.00 | 18.44 | CPS5 |
| ATOM | 3766 | C | GLY | 6 | 19.741 | 22.925 | 39.766 | 1.00 | 18.43 | CPS5 |
| ATOM | 3767 | O | GLY | 6 | 20.829 | 23.461 | 39.972 | 1.00 | 18.58 | CPS5 |
| ATOM | 3768 | N | LEU | 7 | 18.572 | 23.530 | 39.916 | 1.00 | 17.51 | CPS5 |
| ATOM | 3769 | CA | LEU | 7 | 18.429 | 24.910 | 40.337 | 1.00 | 18.75 | CPS5 |
| ATOM | 3770 | CB | LEU | 7 | 17.977 | 25.769 | 39.146 | 1.00 | 20.12 | CPS5 |
| ATOM | 3771 | CG | LEU | 7 | 17.715 | 27.246 | 39.457 | 1.00 | 20.05 | CPS5 |
| ATOM | 3772 | CD1 | LEU | 7 | 19.056 | 27.945 | 39.706 | 1.00 | 18.90 | CPS5 |
| ATOM | 3773 | CD2 | LEU | 7 | 16.967 | 27.907 | 38.298 | 1.00 | 19.78 | CPS5 |
| ATOM | 3774 | C | LEU | 7 | 17.366 | 24.991 | 41.428 | 1.00 | 19.75 | CPS5 |
| ATOM | 3775 | O | LEU | 7 | 16.329 | 24.330 | 41.353 | 1.00 | 18.94 | CPS5 |
| ATOM | 3776 | N | ASP | 8 | 17.626 | 25.797 | 42.450 | 1.00 | 18.42 | CPS5 |
| ATOM | 3777 | CA | ASP | 8 | 16.644 | 25.985 | 43.491 | 1.00 | 20.59 | CPS5 |
| ATOM | 3778 | CB | ASP | 8 | 16.823 | 24.969 | 44.625 | 1.00 | 22.60 | CPS5 |
| ATOM | 3779 | CG | ASP | 8 | 15.838 | 25.199 | 45.764 | 1.00 | 25.07 | CPS5 |
| ATOM | 3780 | OD1 | ASP | 8 | 16.142 | 26.008 | 46.666 | 1.00 | 26.32 | CPS5 |
| ATOM | 3781 | OD2 | ASP | 8 | 14.749 | 24.597 | 45.742 | 1.00 | 26.96 | CPS5 |
| ATOM | 3782 | C | ASP | 8 | 16.700 | 27.391 | 44.066 | 1.00 | 19.95 | CPS5 |
| ATOM | 3783 | O | ASP | 8 | 17.768 | 27.957 | 44.243 | 1.00 | 21.00 | CPS5 |
| ATOM | 3784 | N | ILE | 9 | 15.533 | 27.966 | 44.309 | 1.00 | 19.58 | CPS5 |
| ATOM | 3785 | CA | ILE | 9 | 15.456 | 29.275 | 44.949 | 1.00 | 19.88 | CPS5 |
| ATOM | 3786 | CB | ILE | 9 | 14.814 | 30.352 | 44.055 | 1.00 | 19.43 | CPS5 |
| ATOM | 3787 | CG2 | ILE | 9 | 14.757 | 31.674 | 44.820 | 1.00 | 19.92 | CPS5 |
| ATOM | 3788 | CG1 | ILE | 9 | 15.640 | 30.524 | 42.776 | 1.00 | 18.89 | CPS5 |
| ATOM | 3789 | CD1 | ILE | 9 | 15.018 | 31.488 | 41.770 | 1.00 | 19.11 | CPS5 |
| ATOM | 3790 | C | ILE | 9 | 14.538 | 29.012 | 46.121 | 1.00 | 20.96 | CPS5 |
| ATOM | 3791 | O | ILE | 9 | 13.482 | 28.392 | 45.964 | 1.00 | 20.32 | CPS5 |
| ATOM | 3792 | N | THR | 10 | 14.950 | 29.453 | 47.301 | 1.00 | 20.95 | CPS5 |
| ATOM | 3793 | CA | THR | 10 | 14.145 | 29.250 | 48.491 | 1.00 | 22.53 | CPS5 |
| ATOM | 3794 | CB | THR | 10 | 14.837 | 28.265 | 49.452 | 1.00 | 23.91 | CPS5 |
| ATOM | 3795 | OG1 | THR | 10 | 14.913 | 26.976 | 48.821 | 1.00 | 24.32 | CPS5 |
| ATOM | 3796 | CG2 | THR | 10 | 14.045 | 28.138 | 50.764 | 1.00 | 24.45 | CPS5 |
| ATOM | 3797 | C | THR | 10 | 13.893 | 30.567 | 49.207 | 1.00 | 23.06 | CPS5 |
| ATOM | 3798 | O | THR | 10 | 14.810 | 31.375 | 49.398 | 1.00 | 22.57 | CPS5 |
| ATOM | 3799 | N | GLU | 11 | 12.641 | 30.782 | 49.588 | 1.00 | 23.52 | CPS5 |
| ATOM | 3800 | CA | GLU | 11 | 12.260 | 31.997 | 50.302 | 1.00 | 24.89 | CPS5 |
| ATOM | 3801 | CB | GLU | 11 | 10.747 | 32.212 | 50.168 | 1.00 | 25.23 | CPS5 |
| ATOM | 3802 | CG | GLU | 11 | 10.217 | 33.456 | 50.870 | 1.00 | 27.69 | CPS5 |
| ATOM | 3803 | CD | GLU | 11 | 8.701 | 33.491 | 50.901 | 1.00 | 29.32 | CPS5 |
| ATOM | 3804 | OE1 | GLU | 11 | 8.079 | 32.418 | 50.756 | 1.00 | 30.90 | CPS5 |
| ATOM | 3805 | OE2 | GLU | 11 | 8.129 | 34.584 | 51.089 | 1.00 | 33.76 | CPS5 |
| ATOM | 3806 | C | GLU | 11 | 12.668 | 31.858 | 51.781 | 1.00 | 24.72 | CPS5 |
| ATOM | 3807 | O | GLU | 11 | 12.246 | 30.925 | 52.469 | 1.00 | 25.10 | CPS5 |
| ATOM | 3808 | N | LEU | 12 | 13.510 | 32.772 | 52.252 | 1.00 | 24.85 | CPS5 |
| ATOM | 3809 | CA | LEU | 12 | 13.988 | 32.756 | 53.633 | 1.00 | 24.83 | CPS5 |
| ATOM | 3810 | CB | LEU | 12 | 14.850 | 33.997 | 53.895 | 1.00 | 25.59 | CPS5 |
| ATOM | 3811 | CG | LEU | 12 | 16.371 | 33.834 | 53.933 | 1.00 | 28.80 | CPS5 |
| ATOM | 3812 | CD1 | LEU | 12 | 16.851 | 32.954 | 52.799 | 1.00 | 28.80 | CPS5 |
| ATOM | 3813 | CD2 | LEU | 12 | 17.018 | 35.199 | 53.858 | 1.00 | 30.41 | CPS5 |
| ATOM | 3814 | C | LEU | 12 | 12.856 | 32.691 | 54.661 | 1.00 | 26.18 | CPS5 |
| ATOM | 3815 | O | LEU | 12 | 12.947 | 31.983 | 55.658 | 1.00 | 25.34 | CPS5 |
| ATOM | 3816 | N | LYS | 13 | 11.788 | 33.432 | 54.403 | 1.00 | 27.19 | CPS5 |
| ATOM | 3817 | CA | LYS | 13 | 10.644 | 33.479 | 55.304 | 1.00 | 29.15 | CPS5 |
| ATOM | 3818 | CB | LYS | 13 | 9.634 | 34.508 | 54.777 | 1.00 | 31.29 | CPS5 |

FIG. 1A-67

| ATOM | 3819 | CG | LYS | 13 | 8.429 | 34.734 | 55.668 | 1.00 | 36.36 | CPS5 |
|---|---|---|---|---|---|---|---|---|---|---|
| ATOM | 3820 | CD | LYS | 13 | 7.596 | 35.907 | 55.154 | 1.00 | 40.04 | CPS5 |
| ATOM | 3821 | CE | LYS | 13 | 6.387 | 36.178 | 56.041 | 1.00 | 42.34 | CPS5 |
| ATOM | 3822 | NZ | LYS | 13 | 5.660 | 37.416 | 55.611 | 1.00 | 44.27 | CPS5 |
| ATOM | 3823 | C | LYS | 13 | 9.989 | 32.108 | 55.449 | 1.00 | 29.23 | CPS5 |
| ATOM | 3824 | O | LYS | 13 | 9.513 | 31.742 | 56.525 | 1.00 | 27.84 | CPS5 |
| ATOM | 3825 | N | ARG | 14 | 9.971 | 31.345 | 54.362 | 1.00 | 28.90 | CPS5 |
| ATOM | 3826 | CA | ARG | 14 | 9.371 | 30.019 | 54.384 | 1.00 | 29.32 | CPS5 |
| ATOM | 3827 | CB | ARG | 14 | 9.264 | 29.486 | 52.958 | 1.00 | 30.67 | CPS5 |
| ATOM | 3828 | CG | ARG | 14 | 8.489 | 28.186 | 52.828 | 1.00 | 33.67 | CPS5 |
| ATOM | 3829 | CD | ARG | 14 | 8.693 | 27.591 | 51.442 | 1.00 | 36.77 | CPS5 |
| ATOM | 3830 | NE | ARG | 14 | 8.435 | 26.157 | 51.442 | 1.00 | 40.83 | CPS5 |
| ATOM | 3831 | CZ | ARG | 14 | 9.204 | 25.259 | 50.836 | 1.00 | 42.06 | CPS5 |
| ATOM | 3832 | NH1 | ARG | 14 | 10.289 | 25.640 | 50.176 | 1.00 | 40.50 | CPS5 |
| ATOM | 3833 | NH2 | ARG | 14 | 8.882 | 23.973 | 50.891 | 1.00 | 43.70 | CPS5 |
| ATOM | 3834 | C | ARG | 14 | 10.210 | 29.072 | 55.257 | 1.00 | 28.72 | CPS5 |
| ATOM | 3835 | O | ARG | 14 | 9.665 | 28.242 | 55.994 | 1.00 | 28.02 | CPS5 |
| ATOM | 3836 | N | ILE | 15 | 11.533 | 29.199 | 55.170 | 1.00 | 28.10 | CPS5 |
| ATOM | 3837 | CA | ILE | 15 | 12.439 | 28.378 | 55.972 | 1.00 | 27.56 | CPS5 |
| ATOM | 3838 | CB | ILE | 15 | 13.916 | 28.640 | 55.587 | 1.00 | 28.43 | CPS5 |
| ATOM | 3839 | CG2 | ILE | 15 | 14.863 | 28.021 | 56.623 | 1.00 | 27.74 | CPS5 |
| ATOM | 3840 | CG1 | ILE | 15 | 14.201 | 28.042 | 54.204 | 1.00 | 26.73 | CPS5 |
| ATOM | 3841 | CD1 | ILE | 15 | 14.052 | 26.517 | 54.159 | 1.00 | 29.51 | CPS5 |
| ATOM | 3842 | C | ILE | 15 | 12.226 | 28.739 | 57.441 | 1.00 | 29.85 | CPS5 |
| ATOM | 3843 | O | ILE | 15 | 12.131 | 27.860 | 58.300 | 1.00 | 28.01 | CPS5 |
| ATOM | 3844 | N | ALA | 16 | 12.145 | 30.039 | 57.724 | 1.00 | 30.25 | CPS5 |
| ATOM | 3845 | CA | ALA | 16 | 11.929 | 30.508 | 59.097 | 1.00 | 31.84 | CPS5 |
| ATOM | 3846 | CB | ALA | 16 | 11.937 | 32.038 | 59.142 | 1.00 | 31.96 | CPS5 |
| ATOM | 3847 | C | ALA | 16 | 10.607 | 29.966 | 59.644 | 1.00 | 32.73 | CPS5 |
| ATOM | 3848 | O | ALA | 16 | 10.534 | 29.550 | 60.802 | 1.00 | 33.57 | CPS5 |
| ATOM | 3849 | N | SER | 17 | 9.564 | 29.958 | 58.820 | 1.00 | 33.10 | CPS5 |
| ATOM | 3850 | CA | SER | 17 | 8.276 | 29.435 | 59.269 | 1.00 | 35.41 | CPS5 |
| ATOM | 3851 | CB | SER | 17 | 7.206 | 29.639 | 58.201 | 1.00 | 36.49 | CPS5 |
| ATOM | 3852 | OG | SER | 17 | 6.988 | 31.024 | 57.990 | 1.00 | 40.91 | CPS5 |
| ATOM | 3853 | C | SER | 17 | 8.369 | 27.954 | 59.617 | 1.00 | 35.50 | CPS5 |
| ATOM | 3854 | O | SER | 17 | 7.938 | 27.532 | 60.696 | 1.00 | 35.16 | CPS5 |
| ATOM | 3855 | N | MET | 18 | 8.927 | 27.164 | 58.705 | 1.00 | 35.27 | CPS5 |
| ATOM | 3856 | CA | MET | 18 | 9.073 | 25.731 | 58.942 | 1.00 | 36.03 | CPS5 |
| ATOM | 3857 | CB | MET | 18 | 9.701 | 25.045 | 57.726 | 1.00 | 36.24 | CPS5 |
| ATOM | 3858 | CG | MET | 18 | 8.794 | 24.994 | 56.519 | 1.00 | 38.74 | CPS5 |
| ATOM | 3859 | SD | MET | 18 | 9.503 | 24.027 | 55.178 | 1.00 | 44.39 | CPS5 |
| ATOM | 3860 | CE | MET | 18 | 10.534 | 25.241 | 54.428 | 1.00 | 38.98 | CPS5 |
| ATOM | 3861 | C | MET | 18 | 9.918 | 25.462 | 60.180 | 1.00 | 35.92 | CPS5 |
| ATOM | 3862 | O | MET | 18 | 9.597 | 24.580 | 60.979 | 1.00 | 37.63 | CPS5 |
| ATOM | 3863 | N | ALA | 19 | 10.995 | 26.220 | 60.348 | 1.00 | 35.18 | CPS5 |
| ATOM | 3864 | CA | ALA | 19 | 11.859 | 26.033 | 61.504 | 1.00 | 35.87 | CPS5 |
| ATOM | 3865 | CB | ALA | 19 | 13.081 | 26.932 | 61.401 | 1.00 | 35.73 | CPS5 |
| ATOM | 3866 | C | ALA | 19 | 11.087 | 26.348 | 62.783 | 1.00 | 38.24 | CPS5 |
| ATOM | 3867 | O | ALA | 19 | 11.367 | 25.787 | 63.844 | 1.00 | 36.83 | CPS5 |
| ATOM | 3868 | N | GLY | 20 | 10.106 | 27.239 | 62.669 | 1.00 | 38.64 | CPS5 |
| ATOM | 3869 | CA | GLY | 20 | 9.320 | 27.619 | 63.827 | 1.00 | 40.77 | CPS5 |
| ATOM | 3870 | C | GLY | 20 | 8.203 | 26.663 | 64.196 | 1.00 | 41.91 | CPS5 |
| ATOM | 3871 | O | GLY | 20 | 7.826 | 26.580 | 65.361 | 1.00 | 43.62 | CPS5 |
| ATOM | 3872 | N | ARG | 21 | 7.668 | 25.935 | 63.225 | 1.00 | 42.69 | CPS5 |
| ATOM | 3873 | CA | ARG | 21 | 6.580 | 25.012 | 63.511 | 1.00 | 44.15 | CPS5 |
| ATOM | 3874 | CB | ARG | 21 | 5.574 | 25.026 | 62.362 | 1.00 | 46.42 | CPS5 |
| ATOM | 3875 | CG | ARG | 21 | 6.018 | 24.224 | 61.156 | 1.00 | 50.19 | CPS5 |

FIG. 1A-68

| ATOM | 3876 | CD  | ARG | 21 | 5.388  | 24.747 | 59.879 | 1.00 | 53.16 | CPS5 |
| ATOM | 3877 | NE  | ARG | 21 | 5.589  | 23.833 | 58.759 | 1.00 | 54.93 | CPS5 |
| ATOM | 3878 | CZ  | ARG | 21 | 5.372  | 24.159 | 57.490 | 1.00 | 56.47 | CPS5 |
| ATOM | 3879 | NH1 | ARG | 21 | 4.956  | 25.383 | 57.184 | 1.00 | 57.16 | CPS5 |
| ATOM | 3880 | NH2 | ARG | 21 | 5.554  | 23.258 | 56.533 | 1.00 | 56.82 | CPS5 |
| ATOM | 3881 | C   | ARG | 21 | 7.051  | 23.579 | 63.753 | 1.00 | 44.27 | CPS5 |
| ATOM | 3882 | O   | ARG | 21 | 6.367  | 22.803 | 64.420 | 1.00 | 44.45 | CPS5 |
| ATOM | 3883 | N   | GLN | 22 | 8.213  | 23.226 | 63.209 | 1.00 | 42.85 | CPS5 |
| ATOM | 3884 | CA  | GLN | 22 | 8.741  | 21.874 | 63.369 | 1.00 | 41.63 | CPS5 |
| ATOM | 3885 | CB  | GLN | 22 | 9.212  | 21.351 | 62.011 | 1.00 | 41.96 | CPS5 |
| ATOM | 3886 | CG  | GLN | 22 | 8.182  | 21.567 | 60.906 | 1.00 | 42.25 | CPS5 |
| ATOM | 3887 | CD  | GLN | 22 | 8.610  | 21.008 | 59.560 | 1.00 | 44.24 | CPS5 |
| ATOM | 3888 | OE1 | GLN | 22 | 7.988  | 21.293 | 58.533 | 1.00 | 45.66 | CPS5 |
| ATOM | 3889 | NE2 | GLN | 22 | 9.664  | 20.202 | 59.557 | 1.00 | 42.69 | CPS5 |
| ATOM | 3890 | C   | GLN | 22 | 9.882  | 21.862 | 64.387 | 1.00 | 41.06 | CPS5 |
| ATOM | 3891 | O   | GLN | 22 | 10.853 | 22.607 | 64.255 | 1.00 | 41.24 | CPS5 |
| ATOM | 3892 | N   | LYS | 23 | 9.764  | 20.995 | 65.390 | 1.00 | 39.60 | CPS5 |
| ATOM | 3893 | CA  | LYS | 23 | 10.750 | 20.903 | 66.466 | 1.00 | 38.55 | CPS5 |
| ATOM | 3894 | CB  | LYS | 23 | 10.439 | 19.695 | 67.357 | 1.00 | 39.83 | CPS5 |
| ATOM | 3895 | CG  | LYS | 23 | 11.370 | 19.589 | 68.551 | 1.00 | 41.79 | CPS5 |
| ATOM | 3896 | CD  | LYS | 23 | 10.771 | 18.745 | 69.654 | 1.00 | 43.79 | CPS5 |
| ATOM | 3897 | CE  | LYS | 23 | 10.448 | 17.353 | 69.161 | 1.00 | 44.48 | CPS5 |
| ATOM | 3898 | NZ  | LYS | 23 | 10.028 | 16.518 | 70.294 | 1.00 | 46.17 | CPS5 |
| ATOM | 3899 | C   | LYS | 23 | 12.236 | 20.885 | 66.106 | 1.00 | 37.06 | CPS5 |
| ATOM | 3900 | O   | LYS | 23 | 12.982 | 21.787 | 66.501 | 1.00 | 40.33 | CPS5 |
| ATOM | 3901 | N   | ARG | 24 | 12.679 | 19.862 | 65.389 | 1.00 | 32.83 | CPS5 |
| ATOM | 3902 | CA  | ARG | 24 | 14.093 | 19.767 | 65.025 | 1.00 | 28.69 | CPS5 |
| ATOM | 3903 | CB  | ARG | 24 | 14.693 | 18.448 | 65.537 | 1.00 | 27.47 | CPS5 |
| ATOM | 3904 | CG  | ARG | 24 | 15.128 | 18.477 | 67.012 | 1.00 | 26.46 | CPS5 |
| ATOM | 3905 | CD  | ARG | 24 | 15.742 | 17.141 | 67.435 | 1.00 | 26.25 | CPS5 |
| ATOM | 3906 | NE  | ARG | 24 | 14.723 | 16.093 | 67.528 | 1.00 | 26.94 | CPS5 |
| ATOM | 3907 | CZ  | ARG | 24 | 14.061 | 15.783 | 68.640 | 1.00 | 26.62 | CPS5 |
| ATOM | 3908 | NH1 | ARG | 24 | 14.304 | 16.423 | 69.781 | 1.00 | 28.42 | CPS5 |
| ATOM | 3909 | NH2 | ARG | 24 | 13.128 | 14.851 | 68.605 | 1.00 | 27.58 | CPS5 |
| ATOM | 3910 | C   | ARG | 24 | 14.269 | 19.874 | 63.519 | 1.00 | 26.86 | CPS5 |
| ATOM | 3911 | O   | ARG | 24 | 14.863 | 19.008 | 62.872 | 1.00 | 24.69 | CPS5 |
| ATOM | 3912 | N   | PHE | 25 | 13.747 | 20.953 | 62.957 | 1.00 | 24.39 | CPS5 |
| ATOM | 3913 | CA  | PHE | 25 | 13.848 | 21.148 | 61.515 | 1.00 | 24.06 | CPS5 |
| ATOM | 3914 | CB  | PHE | 25 | 13.089 | 22.408 | 61.103 | 1.00 | 25.10 | CPS5 |
| ATOM | 3915 | CG  | PHE | 25 | 13.220 | 22.738 | 59.645 | 1.00 | 25.01 | CPS5 |
| ATOM | 3916 | CD1 | PHE | 25 | 14.065 | 23.754 | 59.224 | 1.00 | 26.44 | CPS5 |
| ATOM | 3917 | CD2 | PHE | 25 | 12.502 | 22.029 | 58.695 | 1.00 | 26.17 | CPS5 |
| ATOM | 3918 | CE1 | PHE | 25 | 14.192 | 24.063 | 57.867 | 1.00 | 26.84 | CPS5 |
| ATOM | 3919 | CE2 | PHE | 25 | 12.624 | 22.330 | 57.338 | 1.00 | 27.83 | CPS5 |
| ATOM | 3920 | CZ  | PHE | 25 | 13.470 | 23.348 | 56.929 | 1.00 | 26.25 | CPS5 |
| ATOM | 3921 | C   | PHE | 25 | 15.289 | 21.241 | 61.034 | 1.00 | 23.02 | CPS5 |
| ATOM | 3922 | O   | PHE | 25 | 15.669 | 20.583 | 60.067 | 1.00 | 23.63 | CPS5 |
| ATOM | 3923 | N   | ALA | 26 | 16.096 | 22.055 | 61.702 | 1.00 | 21.62 | CPS5 |
| ATOM | 3924 | CA  | ALA | 26 | 17.481 | 22.211 | 61.272 | 1.00 | 22.64 | CPS5 |
| ATOM | 3925 | CB  | ALA | 26 | 18.200 | 23.213 | 62.171 | 1.00 | 21.17 | CPS5 |
| ATOM | 3926 | C   | ALA | 26 | 18.203 | 20.868 | 61.295 | 1.00 | 22.18 | CPS5 |
| ATOM | 3927 | O   | ALA | 26 | 18.962 | 20.542 | 60.382 | 1.00 | 21.14 | CPS5 |
| ATOM | 3928 | N   | GLU | 27 | 17.967 | 20.098 | 62.356 | 1.00 | 21.95 | CPS5 |
| ATOM | 3929 | CA  | GLU | 27 | 18.595 | 18.784 | 62.499 | 1.00 | 22.37 | CPS5 |
| ATOM | 3930 | CB  | GLU | 27 | 18.231 | 18.176 | 63.862 | 1.00 | 21.57 | CPS5 |
| ATOM | 3931 | CG  | GLU | 27 | 18.935 | 18.817 | 65.089 | 1.00 | 23.00 | CPS5 |
| ATOM | 3932 | CD  | GLU | 27 | 18.465 | 20.233 | 65.452 | 1.00 | 24.81 | CPS5 |

FIG. 1A-69

```
ATOM   3933  OE1  GLU  27   17.353  20.647  65.056  1.00 23.58      CPS5
ATOM   3934  OE2  GLU  27   19.218  20.932  66.172  1.00 25.05      CPS5
ATOM   3935  C    GLU  27   18.184  17.831  61.369  1.00 23.57      CPS5
ATOM   3936  O    GLU  27   18.937  16.934  61.000  1.00 23.93      CPS5
ATOM   3937  N    ARG  28   16.981  18.015  60.833  1.00 23.21      CPS5
ATOM   3938  CA   ARG  28   16.502  17.173  59.742  1.00 25.30      CPS5
ATOM   3939  CB   ARG  28   14.995  17.391  59.530  1.00 28.97      CPS5
ATOM   3940  CG   ARG  28   14.413  16.636  58.327  1.00 31.14      CPS5
ATOM   3941  CD   ARG  28   12.911  16.353  58.503  1.00 35.90      CPS5
ATOM   3942  NE   ARG  28   12.063  17.535  58.340  1.00 36.29      CPS5
ATOM   3943  CZ   ARG  28   11.774  18.089  57.165  1.00 38.49      CPS5
ATOM   3944  NH1  ARG  28   12.264  17.571  56.045  1.00 37.03      CPS5
ATOM   3945  NH2  ARG  28   10.980  19.154  57.105  1.00 38.67      CPS5
ATOM   3946  C    ARG  28   17.245  17.488  58.439  1.00 24.41      CPS5
ATOM   3947  O    ARG  28   17.582  16.596  57.666  1.00 24.06      CPS5
ATOM   3948  N    ILE  29   17.517  18.765  58.218  1.00 23.36      CPS5
ATOM   3949  CA   ILE  29   18.183  19.212  56.997  1.00 24.49      CPS5
ATOM   3950  CB   ILE  29   17.817  20.693  56.704  1.00 24.90      CPS5
ATOM   3951  CG2  ILE  29   18.374  21.123  55.334  1.00 26.73      CPS5
ATOM   3952  CG1  ILE  29   16.305  20.880  56.773  1.00 24.80      CPS5
ATOM   3953  CD1  ILE  29   15.527  19.982  55.843  1.00 23.16      CPS5
ATOM   3954  C    ILE  29   19.708  19.121  56.983  1.00 24.05      CPS5
ATOM   3955  O    ILE  29   20.313  18.817  55.949  1.00 23.72      CPS5
ATOM   3956  N    LEU  30   20.323  19.383  58.132  1.00 23.56      CPS5
ATOM   3957  CA   LEU  30   21.778  19.444  58.240  1.00 23.33      CPS5
ATOM   3958  CB   LEU  30   22.151  20.701  59.035  1.00 22.47      CPS5
ATOM   3959  CG   LEU  30   21.503  22.020  58.591  1.00 23.18      CPS5
ATOM   3960  CD1  LEU  30   21.940  23.141  59.519  1.00 23.77      CPS5
ATOM   3961  CD2  LEU  30   21.901  22.348  57.157  1.00 22.19      CPS5
ATOM   3962  C    LEU  30   22.492  18.238  58.854  1.00 24.18      CPS5
ATOM   3963  O    LEU  30   21.966  17.577  59.753  1.00 24.62      CPS5
ATOM   3964  N    THR  31   23.704  17.976  58.363  1.00 24.03      CPS5
ATOM   3965  CA   THR  31   24.531  16.878  58.862  1.00 24.72      CPS5
ATOM   3966  CB   THR  31   25.626  16.494  57.850  1.00 25.78      CPS5
ATOM   3967  OG1  THR  31   26.575  17.563  57.761  1.00 26.99      CPS5
ATOM   3968  CG2  THR  31   25.022  16.234  56.466  1.00 24.96      CPS5
ATOM   3969  C    THR  31   25.228  17.351  60.140  1.00 24.37      CPS5
ATOM   3970  O    THR  31   25.134  18.520  60.514  1.00 24.09      CPS5
ATOM   3971  N    ARG  32   25.943  16.452  60.806  1.00 25.54      CPS5
ATOM   3972  CA   ARG  32   26.642  16.832  62.031  1.00 27.17      CPS5
ATOM   3973  CB   ARG  32   27.429  15.651  62.590  1.00 28.99      CPS5
ATOM   3974  CG   ARG  32   26.583  14.597  63.261  1.00 31.34      CPS5
ATOM   3975  CD   ARG  32   27.476  13.684  64.109  1.00 34.50      CPS5
ATOM   3976  NE   ARG  32   26.701  12.698  64.853  1.00 38.58      CPS5
ATOM   3977  CZ   ARG  32   27.200  11.916  65.809  1.00 40.34      CPS5
ATOM   3978  NH1  ARG  32   26.419  11.044  66.435  1.00 37.96      CPS5
ATOM   3979  NH2  ARG  32   28.480  12.009  66.145  1.00 42.21      CPS5
ATOM   3980  C    ARG  32   27.589  18.014  61.865  1.00 27.70      CPS5
ATOM   3981  O    ARG  32   27.562  18.940  62.666  1.00 28.37      CPS5
ATOM   3982  N    SER  33   28.439  17.987  60.841  1.00 27.97      CPS5
ATOM   3983  CA   SER  33   29.379  19.088  60.652  1.00 28.23      CPS5
ATOM   3984  CB   SER  33   30.397  18.746  59.556  1.00 30.14      CPS5
ATOM   3985  OG   SER  33   29.759  18.525  58.309  1.00 34.75      CPS5
ATOM   3986  C    SER  33   28.661  20.398  60.330  1.00 27.70      CPS5
ATOM   3987  O    SER  33   29.082  21.464  60.776  1.00 27.19      CPS5
ATOM   3988  N    GLU  34   27.578  20.319  59.560  1.00 27.25      CPS5
ATOM   3989  CA   GLU  34   26.804  21.511  59.212  1.00 27.47      CPS5
```

FIG. 1A-70

| ATOM | 3990 | CB | GLU | 34 | 25.759 | 21.171 | 58.148 | 1.00 | 27.07 | CPS5 |
|---|---|---|---|---|---|---|---|---|---|---|
| ATOM | 3991 | CG | GLU | 34 | 26.368 | 20.872 | 56.783 | 1.00 | 28.76 | CPS5 |
| ATOM | 3992 | CD | GLU | 34 | 25.376 | 20.290 | 55.782 | 1.00 | 28.74 | CPS5 |
| ATOM | 3993 | OE1 | GLU | 34 | 25.664 | 20.350 | 54.569 | 1.00 | 31.36 | CPS5 |
| ATOM | 3994 | OE2 | GLU | 34 | 24.320 | 19.764 | 56.192 | 1.00 | 26.92 | CPS5 |
| ATOM | 3995 | C | GLU | 34 | 26.121 | 22.080 | 60.454 | 1.00 | 27.58 | CPS5 |
| ATOM | 3996 | O | GLU | 34 | 26.028 | 23.300 | 60.624 | 1.00 | 26.80 | CPS5 |
| ATOM | 3997 | N | LEU | 35 | 25.629 | 21.196 | 61.319 | 1.00 | 26.86 | CPS5 |
| ATOM | 3998 | CA | LEU | 35 | 24.988 | 21.653 | 62.545 | 1.00 | 27.86 | CPS5 |
| ATOM | 3999 | CB | LEU | 35 | 24.322 | 20.476 | 63.272 | 1.00 | 26.37 | CPS5 |
| ATOM | 4000 | CG | LEU | 35 | 23.004 | 19.992 | 62.650 | 1.00 | 26.60 | CPS5 |
| ATOM | 4001 | CD1 | LEU | 35 | 22.597 | 18.649 | 63.255 | 1.00 | 27.30 | CPS5 |
| ATOM | 4002 | CD2 | LEU | 35 | 21.906 | 21.050 | 62.890 | 1.00 | 25.07 | CPS5 |
| ATOM | 4003 | C | LEU | 35 | 26.032 | 22.333 | 63.442 | 1.00 | 28.95 | CPS5 |
| ATOM | 4004 | O | LEU | 35 | 25.727 | 23.317 | 64.104 | 1.00 | 29.27 | CPS5 |
| ATOM | 4005 | N | ASP | 36 | 27.264 | 21.825 | 63.458 | 1.00 | 31.26 | CPS5 |
| ATOM | 4006 | CA | ASP | 36 | 28.306 | 22.453 | 64.279 | 1.00 | 33.66 | CPS5 |
| ATOM | 4007 | CB | ASP | 36 | 29.649 | 21.740 | 64.127 | 1.00 | 36.86 | CPS5 |
| ATOM | 4008 | CG | ASP | 36 | 29.668 | 20.386 | 64.795 | 1.00 | 39.66 | CPS5 |
| ATOM | 4009 | OD1 | ASP | 36 | 28.990 | 20.235 | 65.833 | 1.00 | 43.45 | CPS5 |
| ATOM | 4010 | OD2 | ASP | 36 | 30.373 | 19.479 | 64.297 | 1.00 | 41.30 | CPS5 |
| ATOM | 4011 | C | ASP | 36 | 28.481 | 23.905 | 63.871 | 1.00 | 34.39 | CPS5 |
| ATOM | 4012 | O | ASP | 36 | 28.608 | 24.794 | 64.722 | 1.00 | 34.60 | CPS5 |
| ATOM | 4013 | N | GLN | 37 | 28.488 | 24.140 | 62.563 | 1.00 | 33.83 | CPS5 |
| ATOM | 4014 | CA | GLN | 37 | 28.639 | 25.483 | 62.015 | 1.00 | 35.12 | CPS5 |
| ATOM | 4015 | CB | GLN | 37 | 28.809 | 25.394 | 60.499 | 1.00 | 36.30 | CPS5 |
| ATOM | 4016 | CG | GLN | 37 | 30.079 | 24.660 | 60.055 | 1.00 | 41.36 | CPS5 |
| ATOM | 4017 | CD | GLN | 37 | 29.944 | 24.026 | 58.676 | 1.00 | 43.00 | CPS5 |
| ATOM | 4018 | OE1 | GLN | 37 | 29.434 | 24.646 | 57.746 | 1.00 | 44.80 | CPS5 |
| ATOM | 4019 | NE2 | GLN | 37 | 30.408 | 22.786 | 58.541 | 1.00 | 44.26 | CPS5 |
| ATOM | 4020 | C | GLN | 37 | 27.409 | 26.328 | 62.344 | 1.00 | 34.18 | CPS5 |
| ATOM | 4021 | O | GLN | 37 | 27.513 | 27.470 | 62.794 | 1.00 | 33.82 | CPS5 |
| ATOM | 4022 | N | TYR | 38 | 26.240 | 25.736 | 62.126 | 1.00 | 32.84 | CPS5 |
| ATOM | 4023 | CA | TYR | 38 | 24.963 | 26.395 | 62.349 | 1.00 | 32.66 | CPS5 |
| ATOM | 4024 | CB | TYR | 38 | 23.846 | 25.419 | 61.961 | 1.00 | 29.71 | CPS5 |
| ATOM | 4025 | CG | TYR | 38 | 22.433 | 25.884 | 62.224 | 1.00 | 29.29 | CPS5 |
| ATOM | 4026 | CD1 | TYR | 38 | 21.721 | 25.404 | 63.317 | 1.00 | 29.80 | CPS5 |
| ATOM | 4027 | CE1 | TYR | 38 | 20.401 | 25.776 | 63.541 | 1.00 | 31.00 | CPS5 |
| ATOM | 4028 | CD2 | TYR | 38 | 21.788 | 26.763 | 61.355 | 1.00 | 28.96 | CPS5 |
| ATOM | 4029 | CE2 | TYR | 38 | 20.459 | 27.146 | 61.571 | 1.00 | 28.65 | CPS5 |
| ATOM | 4030 | CZ | TYR | 38 | 19.776 | 26.644 | 62.665 | 1.00 | 29.30 | CPS5 |
| ATOM | 4031 | OH | TYR | 38 | 18.462 | 26.985 | 62.885 | 1.00 | 28.92 | CPS5 |
| ATOM | 4032 | C | TYR | 38 | 24.746 | 26.939 | 63.765 | 1.00 | 34.02 | CPS5 |
| ATOM | 4033 | O | TYR | 38 | 24.292 | 28.068 | 63.936 | 1.00 | 34.37 | CPS5 |
| ATOM | 4034 | N | TYR | 39 | 25.076 | 26.154 | 64.780 | 1.00 | 36.23 | CPS5 |
| ATOM | 4035 | CA | TYR | 39 | 24.860 | 26.613 | 66.144 | 1.00 | 38.88 | CPS5 |
| ATOM | 4036 | CB | TYR | 39 | 24.762 | 25.414 | 67.082 | 1.00 | 38.30 | CPS5 |
| ATOM | 4037 | CG | TYR | 39 | 23.371 | 24.847 | 67.036 | 1.00 | 38.06 | CPS5 |
| ATOM | 4038 | CD1 | TYR | 39 | 22.273 | 25.658 | 67.338 | 1.00 | 38.93 | CPS5 |
| ATOM | 4039 | CE1 | TYR | 39 | 20.974 | 25.194 | 67.203 | 1.00 | 39.58 | CPS5 |
| ATOM | 4040 | CD2 | TYR | 39 | 23.134 | 23.546 | 66.608 | 1.00 | 37.49 | CPS5 |
| ATOM | 4041 | CE2 | TYR | 39 | 21.837 | 23.064 | 66.469 | 1.00 | 37.88 | CPS5 |
| ATOM | 4042 | CZ | TYR | 39 | 20.760 | 23.893 | 66.763 | 1.00 | 39.42 | CPS5 |
| ATOM | 4043 | OH | TYR | 39 | 19.470 | 23.450 | 66.592 | 1.00 | 38.55 | CPS5 |
| ATOM | 4044 | C | TYR | 39 | 25.816 | 27.658 | 66.692 | 1.00 | 41.19 | CPS5 |
| ATOM | 4045 | O | TYR | 39 | 25.662 | 28.109 | 67.822 | 1.00 | 42.90 | CPS5 |
| ATOM | 4046 | N | GLU | 40 | 26.789 | 28.060 | 65.887 | 1.00 | 43.80 | CPS5 |

FIG. 1A-71

| ATOM | 4047 | CA | GLU | 40 | 27.731 | 29.090 | 66.304 | 1.00 | 46.08 | CPS5 |
|---|---|---|---|---|---|---|---|---|---|---|
| ATOM | 4048 | CB | GLU | 40 | 29.140 | 28.737 | 65.834 | 1.00 | 48.41 | CPS5 |
| ATOM | 4049 | CG | GLU | 40 | 29.806 | 27.639 | 66.639 | 1.00 | 52.50 | CPS5 |
| ATOM | 4050 | CD | GLU | 40 | 31.155 | 27.248 | 66.063 | 1.00 | 54.95 | CPS5 |
| ATOM | 4051 | OE1 | GLU | 40 | 31.969 | 28.154 | 65.774 | 1.00 | 56.23 | CPS5 |
| ATOM | 4052 | OE2 | GLU | 40 | 31.403 | 26.033 | 65.904 | 1.00 | 57.17 | CPS5 |
| ATOM | 4053 | C | GLU | 40 | 27.322 | 30.446 | 65.721 | 1.00 | 46.24 | CPS5 |
| ATOM | 4054 | O | GLU | 40 | 27.932 | 31.475 | 66.023 | 1.00 | 46.47 | CPS5 |
| ATOM | 4055 | N | LEU | 41 | 26.279 | 30.443 | 64.896 | 1.00 | 45.08 | CPS5 |
| ATOM | 4056 | CA | LEU | 41 | 25.803 | 31.664 | 64.254 | 1.00 | 44.90 | CPS5 |
| ATOM | 4057 | CB | LEU | 41 | 25.304 | 31.348 | 62.840 | 1.00 | 44.02 | CPS5 |
| ATOM | 4058 | CG | LEU | 41 | 26.227 | 30.623 | 61.859 | 1.00 | 43.61 | CPS5 |
| ATOM | 4059 | CD1 | LEU | 41 | 25.443 | 30.306 | 60.591 | 1.00 | 42.67 | CPS5 |
| ATOM | 4060 | CD2 | LEU | 41 | 27.439 | 31.480 | 61.530 | 1.00 | 43.84 | CPS5 |
| ATOM | 4061 | C | LEU | 41 | 24.685 | 32.376 | 65.013 | 1.00 | 45.61 | CPS5 |
| ATOM | 4062 | O | LEU | 41 | 24.021 | 31.789 | 65.869 | 1.00 | 45.79 | CPS5 |
| ATOM | 4063 | N | SER | 42 | 24.479 | 33.648 | 64.677 | 1.00 | 46.42 | CPS5 |
| ATOM | 4064 | CA | SER | 42 | 23.432 | 34.456 | 65.288 | 1.00 | 47.43 | CPS5 |
| ATOM | 4065 | CB | SER | 42 | 23.615 | 35.924 | 64.915 | 1.00 | 48.22 | CPS5 |
| ATOM | 4066 | OG | SER | 42 | 23.440 | 36.106 | 63.520 | 1.00 | 48.72 | CPS5 |
| ATOM | 4067 | C | SER | 42 | 22.105 | 33.963 | 64.734 | 1.00 | 47.92 | CPS5 |
| ATOM | 4068 | O | SER | 42 | 22.081 | 33.205 | 63.763 | 1.00 | 47.71 | CPS5 |
| ATOM | 4069 | N | GLU | 43 | 21.000 | 34.399 | 65.328 | 1.00 | 48.18 | CPS5 |
| ATOM | 4070 | CA | GLU | 43 | 19.689 | 33.959 | 64.861 | 1.00 | 48.69 | CPS5 |
| ATOM | 4071 | CB | GLU | 43 | 18.581 | 34.563 | 65.728 | 1.00 | 50.88 | CPS5 |
| ATOM | 4072 | CG | GLU | 43 | 17.286 | 33.765 | 65.683 | 1.00 | 53.85 | CPS5 |
| ATOM | 4073 | CD | GLU | 43 | 16.099 | 34.579 | 65.201 | 1.00 | 56.30 | CPS5 |
| ATOM | 4074 | OE1 | GLU | 43 | 16.189 | 35.176 | 64.105 | 1.00 | 57.99 | CPS5 |
| ATOM | 4075 | OE2 | GLU | 43 | 15.073 | 34.614 | 65.916 | 1.00 | 56.86 | CPS5 |
| ATOM | 4076 | C | GLU | 43 | 19.449 | 34.308 | 63.389 | 1.00 | 47.59 | CPS5 |
| ATOM | 4077 | O | GLU | 43 | 18.899 | 33.503 | 62.635 | 1.00 | 46.68 | CPS5 |
| ATOM | 4078 | N | LYS | 44 | 19.861 | 35.504 | 62.979 | 1.00 | 46.55 | CPS5 |
| ATOM | 4079 | CA | LYS | 44 | 19.680 | 35.926 | 61.591 | 1.00 | 46.07 | CPS5 |
| ATOM | 4080 | CB | LYS | 44 | 19.973 | 37.422 | 61.439 | 1.00 | 47.29 | CPS5 |
| ATOM | 4081 | CG | LYS | 44 | 19.730 | 37.935 | 60.031 | 1.00 | 49.35 | CPS5 |
| ATOM | 4082 | CD | LYS | 44 | 20.148 | 39.384 | 59.857 | 1.00 | 50.89 | CPS5 |
| ATOM | 4083 | CE | LYS | 44 | 19.837 | 39.855 | 58.440 | 1.00 | 52.29 | CPS5 |
| ATOM | 4084 | NZ | LYS | 44 | 20.265 | 41.261 | 58.188 | 1.00 | 53.26 | CPS5 |
| ATOM | 4085 | C | LYS | 44 | 20.597 | 35.130 | 60.660 | 1.00 | 44.52 | CPS5 |
| ATOM | 4086 | O | LYS | 44 | 20.185 | 34.698 | 59.579 | 1.00 | 43.62 | CPS5 |
| ATOM | 4087 | N | ARG | 45 | 21.842 | 34.944 | 61.084 | 1.00 | 42.61 | CPS5 |
| ATOM | 4088 | CA | ARG | 45 | 22.816 | 34.195 | 60.297 | 1.00 | 41.42 | CPS5 |
| ATOM | 4089 | CB | ARG | 45 | 24.193 | 34.284 | 60.957 | 1.00 | 43.69 | CPS5 |
| ATOM | 4090 | CG | ARG | 45 | 25.001 | 35.512 | 60.552 | 1.00 | 47.18 | CPS5 |
| ATOM | 4091 | CD | ARG | 45 | 26.039 | 35.120 | 59.517 | 1.00 | 50.46 | CPS5 |
| ATOM | 4092 | NE | ARG | 45 | 25.455 | 34.243 | 58.506 | 1.00 | 53.21 | CPS5 |
| ATOM | 4093 | CZ | ARG | 45 | 26.141 | 33.355 | 57.794 | 1.00 | 54.22 | CPS5 |
| ATOM | 4094 | NH1 | ARG | 45 | 27.450 | 33.219 | 57.975 | 1.00 | 54.73 | CPS5 |
| ATOM | 4095 | NH2 | ARG | 45 | 25.514 | 32.593 | 56.909 | 1.00 | 54.37 | CPS5 |
| ATOM | 4096 | C | ARG | 45 | 22.385 | 32.735 | 60.156 | 1.00 | 39.25 | CPS5 |
| ATOM | 4097 | O | ARG | 45 | 22.620 | 32.100 | 59.128 | 1.00 | 37.24 | CPS5 |
| ATOM | 4098 | N | LYS | 46 | 21.748 | 32.209 | 61.196 | 1.00 | 36.43 | CPS5 |
| ATOM | 4099 | CA | LYS | 46 | 21.273 | 30.830 | 61.175 | 1.00 | 34.18 | CPS5 |
| ATOM | 4100 | CB | LYS | 46 | 20.618 | 30.472 | 62.511 | 1.00 | 34.58 | CPS5 |
| ATOM | 4101 | CG | LYS | 46 | 21.608 | 30.164 | 63.630 | 1.00 | 35.23 | CPS5 |
| ATOM | 4102 | CD | LYS | 46 | 20.871 | 29.751 | 64.894 | 1.00 | 37.58 | CPS5 |
| ATOM | 4103 | CE | LYS | 46 | 21.842 | 29.392 | 66.010 | 1.00 | 39.36 | CPS5 |

FIG. 1A-72

| ATOM | 4104 | NZ | LYS | 46 | 21.100 | 29.022 | 67.241 | 1.00 | 40.50 | CPS5 |
|---|---|---|---|---|---|---|---|---|---|---|
| ATOM | 4105 | C | LYS | 46 | 20.267 | 30.612 | 60.047 | 1.00 | 33.30 | CPS5 |
| ATOM | 4106 | O | LYS | 46 | 20.350 | 29.631 | 59.310 | 1.00 | 31.70 | CPS5 |
| ATOM | 4107 | N | ASN | 47 | 19.313 | 31.531 | 59.924 | 1.00 | 31.25 | CPS5 |
| ATOM | 4108 | CA | ASN | 47 | 18.295 | 31.424 | 58.892 | 1.00 | 30.79 | CPS5 |
| ATOM | 4109 | CB | ASN | 47 | 17.298 | 32.575 | 59.020 | 1.00 | 32.61 | CPS5 |
| ATOM | 4110 | CG | ASN | 47 | 16.216 | 32.532 | 57.963 | 1.00 | 33.88 | CPS5 |
| ATOM | 4111 | OD1 | ASN | 47 | 15.427 | 31.588 | 57.896 | 1.00 | 34.99 | CPS5 |
| ATOM | 4112 | ND2 | ASN | 47 | 16.176 | 33.558 | 57.121 | 1.00 | 36.56 | CPS5 |
| ATOM | 4113 | C | ASN | 47 | 18.944 | 31.440 | 57.513 | 1.00 | 31.05 | CPS5 |
| ATOM | 4114 | O | ASN | 47 | 18.588 | 30.637 | 56.648 | 1.00 | 30.48 | CPS5 |
| ATOM | 4115 | N | GLU | 48 | 19.888 | 32.358 | 57.311 | 1.00 | 28.97 | CPS5 |
| ATOM | 4116 | CA | GLU | 48 | 20.588 | 32.468 | 56.031 | 1.00 | 29.63 | CPS5 |
| ATOM | 4117 | CB | GLU | 48 | 21.570 | 33.640 | 56.061 | 1.00 | 31.86 | CPS5 |
| ATOM | 4118 | CG | GLU | 48 | 20.921 | 34.975 | 56.372 | 1.00 | 37.62 | CPS5 |
| ATOM | 4119 | CD | GLU | 48 | 21.936 | 36.092 | 56.540 | 1.00 | 40.25 | CPS5 |
| ATOM | 4120 | OE1 | GLU | 48 | 21.525 | 37.217 | 56.898 | 1.00 | 42.86 | CPS5 |
| ATOM | 4121 | OE2 | GLU | 48 | 23.141 | 35.845 | 56.313 | 1.00 | 41.40 | CPS5 |
| ATOM | 4122 | C | GLU | 48 | 21.358 | 31.187 | 55.726 | 1.00 | 27.51 | CPS5 |
| ATOM | 4123 | O | GLU | 48 | 21.281 | 30.644 | 54.622 | 1.00 | 26.82 | CPS5 |
| ATOM | 4124 | N | PHE | 49 | 22.106 | 30.712 | 56.711 | 1.00 | 25.07 | CPS5 |
| ATOM | 4125 | CA | PHE | 49 | 22.886 | 29.497 | 56.552 | 1.00 | 25.50 | CPS5 |
| ATOM | 4126 | CB | PHE | 49 | 23.636 | 29.194 | 57.844 | 1.00 | 25.32 | CPS5 |
| ATOM | 4127 | CG | PHE | 49 | 24.519 | 27.986 | 57.765 | 1.00 | 26.38 | CPS5 |
| ATOM | 4128 | CD1 | PHE | 49 | 25.798 | 28.077 | 57.233 | 1.00 | 27.15 | CPS5 |
| ATOM | 4129 | CD2 | PHE | 49 | 24.080 | 26.757 | 58.249 | 1.00 | 24.90 | CPS5 |
| ATOM | 4130 | CE1 | PHE | 49 | 26.640 | 26.954 | 57.189 | 1.00 | 28.06 | CPS5 |
| ATOM | 4131 | CE2 | PHE | 49 | 24.903 | 25.635 | 58.211 | 1.00 | 25.87 | CPS5 |
| ATOM | 4132 | CZ | PHE | 49 | 26.195 | 25.736 | 57.678 | 1.00 | 26.35 | CPS5 |
| ATOM | 4133 | C | PHE | 49 | 21.991 | 28.312 | 56.203 | 1.00 | 24.96 | CPS5 |
| ATOM | 4134 | O | PHE | 49 | 22.255 | 27.581 | 55.248 | 1.00 | 24.24 | CPS5 |
| ATOM | 4135 | N | LEU | 50 | 20.939 | 28.114 | 56.995 | 1.00 | 23.68 | CPS5 |
| ATOM | 4136 | CA | LEU | 50 | 20.024 | 27.005 | 56.773 | 1.00 | 23.00 | CPS5 |
| ATOM | 4137 | CB | LEU | 50 | 18.974 | 26.962 | 57.892 | 1.00 | 24.58 | CPS5 |
| ATOM | 4138 | CG | LEU | 50 | 17.860 | 25.903 | 57.864 | 1.00 | 24.45 | CPS5 |
| ATOM | 4139 | CD1 | LEU | 50 | 18.431 | 24.483 | 57.785 | 1.00 | 24.94 | CPS5 |
| ATOM | 4140 | CD2 | LEU | 50 | 17.022 | 26.072 | 59.142 | 1.00 | 23.53 | CPS5 |
| ATOM | 4141 | C | LEU | 50 | 19.349 | 27.082 | 55.403 | 1.00 | 22.61 | CPS5 |
| ATOM | 4142 | O | LEU | 50 | 19.268 | 26.083 | 54.693 | 1.00 | 21.59 | CPS5 |
| ATOM | 4143 | N | ALA | 51 | 18.865 | 28.260 | 55.021 | 1.00 | 21.89 | CPS5 |
| ATOM | 4144 | CA | ALA | 51 | 18.213 | 28.390 | 53.723 | 1.00 | 21.84 | CPS5 |
| ATOM | 4145 | CB | ALA | 51 | 17.637 | 29.799 | 53.556 | 1.00 | 21.05 | CPS5 |
| ATOM | 4146 | C | ALA | 51 | 19.191 | 28.076 | 52.585 | 1.00 | 21.23 | CPS5 |
| ATOM | 4147 | O | ALA | 51 | 18.813 | 27.458 | 51.587 | 1.00 | 21.60 | CPS5 |
| ATOM | 4148 | N | GLY | 52 | 20.442 | 28.506 | 52.734 | 1.00 | 21.20 | CPS5 |
| ATOM | 4149 | CA | GLY | 52 | 21.437 | 28.245 | 51.700 | 1.00 | 21.20 | CPS5 |
| ATOM | 4150 | C | GLY | 52 | 21.769 | 26.767 | 51.563 | 1.00 | 22.06 | CPS5 |
| ATOM | 4151 | O | GLY | 52 | 21.929 | 26.252 | 50.452 | 1.00 | 20.70 | CPS5 |
| ATOM | 4152 | N | ARG | 53 | 21.888 | 26.074 | 52.693 | 1.00 | 21.88 | CPS5 |
| ATOM | 4153 | CA | ARG | 53 | 22.188 | 24.645 | 52.659 | 1.00 | 21.58 | CPS5 |
| ATOM | 4154 | CB | ARG | 53 | 22.565 | 24.152 | 54.065 | 1.00 | 23.65 | CPS5 |
| ATOM | 4155 | CG | ARG | 53 | 24.066 | 24.127 | 54.329 | 1.00 | 27.20 | CPS5 |
| ATOM | 4156 | CD | ARG | 53 | 24.751 | 25.409 | 53.912 | 1.00 | 30.18 | CPS5 |
| ATOM | 4157 | NE | ARG | 53 | 26.181 | 25.365 | 54.194 | 1.00 | 32.58 | CPS5 |
| ATOM | 4158 | CZ | ARG | 53 | 27.072 | 26.204 | 53.677 | 1.00 | 35.33 | CPS5 |
| ATOM | 4159 | NH1 | ARG | 53 | 26.690 | 27.163 | 52.836 | 1.00 | 37.77 | CPS5 |
| ATOM | 4160 | NH2 | ARG | 53 | 28.350 | 26.089 | 54.006 | 1.00 | 37.90 | CPS5 |

FIG. 1A-73

| ATOM | 4161 | C   | ARG | 53 | 20.976 | 23.890 | 52.125 | 1.00 | 21.40 | CPS5 |
|------|------|-----|-----|----|--------|--------|--------|------|-------|------|
| ATOM | 4162 | O   | ARG | 53 | 21.106 | 22.921 | 51.365 | 1.00 | 20.53 | CPS5 |
| ATOM | 4163 | N   | PHE | 54 | 19.795 | 24.341 | 52.528 | 1.00 | 19.73 | CPS5 |
| ATOM | 4164 | CA  | PHE | 54 | 18.548 | 23.745 | 52.070 | 1.00 | 19.35 | CPS5 |
| ATOM | 4165 | CB  | PHE | 54 | 17.364 | 24.482 | 52.724 | 1.00 | 19.38 | CPS5 |
| ATOM | 4166 | CG  | PHE | 54 | 16.023 | 23.926 | 52.353 | 1.00 | 20.72 | CPS5 |
| ATOM | 4167 | CD1 | PHE | 54 | 15.330 | 24.414 | 51.245 | 1.00 | 22.15 | CPS5 |
| ATOM | 4168 | CD2 | PHE | 54 | 15.448 | 22.903 | 53.107 | 1.00 | 21.41 | CPS5 |
| ATOM | 4169 | CE1 | PHE | 54 | 14.080 | 23.891 | 50.893 | 1.00 | 22.91 | CPS5 |
| ATOM | 4170 | CE2 | PHE | 54 | 14.196 | 22.371 | 52.762 | 1.00 | 22.41 | CPS5 |
| ATOM | 4171 | CZ  | PHE | 54 | 13.513 | 22.868 | 51.654 | 1.00 | 22.38 | CPS5 |
| ATOM | 4172 | C   | PHE | 54 | 18.484 | 23.873 | 50.537 | 1.00 | 19.62 | CPS5 |
| ATOM | 4173 | O   | PHE | 54 | 18.223 | 22.901 | 49.821 | 1.00 | 18.89 | CPS5 |
| ATOM | 4174 | N   | ALA | 55 | 18.736 | 25.082 | 50.046 | 1.00 | 19.98 | CPS5 |
| ATOM | 4175 | CA  | ALA | 55 | 18.690 | 25.348 | 48.608 | 1.00 | 19.92 | CPS5 |
| ATOM | 4176 | CB  | ALA | 55 | 18.930 | 26.839 | 48.347 | 1.00 | 18.81 | CPS5 |
| ATOM | 4177 | C   | ALA | 55 | 19.721 | 24.515 | 47.859 | 1.00 | 19.28 | CPS5 |
| ATOM | 4178 | O   | ALA | 55 | 19.442 | 23.972 | 46.788 | 1.00 | 19.25 | CPS5 |
| ATOM | 4179 | N   | ALA | 56 | 20.916 | 24.398 | 48.422 | 1.00 | 19.74 | CPS5 |
| ATOM | 4180 | CA  | ALA | 56 | 21.954 | 23.621 | 47.755 | 1.00 | 20.82 | CPS5 |
| ATOM | 4181 | CB  | ALA | 56 | 23.299 | 23.838 | 48.446 | 1.00 | 20.78 | CPS5 |
| ATOM | 4182 | C   | ALA | 56 | 21.622 | 22.130 | 47.693 | 1.00 | 20.48 | CPS5 |
| ATOM | 4183 | O   | ALA | 56 | 21.944 | 21.459 | 46.702 | 1.00 | 20.22 | CPS5 |
| ATOM | 4184 | N   | LYS | 57 | 20.993 | 21.600 | 48.746 | 1.00 | 19.44 | CPS5 |
| ATOM | 4185 | CA  | LYS | 57 | 20.642 | 20.187 | 48.754 | 1.00 | 19.12 | CPS5 |
| ATOM | 4186 | CB  | LYS | 57 | 20.336 | 19.718 | 50.191 | 1.00 | 18.95 | CPS5 |
| ATOM | 4187 | CG  | LYS | 57 | 21.571 | 19.809 | 51.077 | 1.00 | 18.78 | CPS5 |
| ATOM | 4188 | CD  | LYS | 57 | 21.395 | 19.116 | 52.429 | 1.00 | 22.43 | CPS5 |
| ATOM | 4189 | CE  | LYS | 57 | 22.575 | 19.458 | 53.329 | 1.00 | 22.68 | CPS5 |
| ATOM | 4190 | NZ  | LYS | 57 | 22.712 | 18.541 | 54.502 | 1.00 | 21.60 | CPS5 |
| ATOM | 4191 | C   | LYS | 57 | 19.465 | 19.937 | 47.821 | 1.00 | 20.77 | CPS5 |
| ATOM | 4192 | O   | LYS | 57 | 19.401 | 18.900 | 47.160 | 1.00 | 20.15 | CPS5 |
| ATOM | 4193 | N   | GLU | 58 | 18.535 | 20.885 | 47.757 | 1.00 | 19.45 | CPS5 |
| ATOM | 4194 | CA  | GLU | 58 | 17.410 | 20.738 | 46.845 | 1.00 | 21.16 | CPS5 |
| ATOM | 4195 | CB  | GLU | 58 | 16.409 | 21.887 | 47.020 | 1.00 | 21.14 | CPS5 |
| ATOM | 4196 | CG  | GLU | 58 | 15.520 | 21.769 | 48.247 | 1.00 | 25.24 | CPS5 |
| ATOM | 4197 | CD  | GLU | 58 | 14.558 | 20.605 | 48.153 | 1.00 | 29.18 | CPS5 |
| ATOM | 4198 | OE1 | GLU | 58 | 14.482 | 19.993 | 47.066 | 1.00 | 31.68 | CPS5 |
| ATOM | 4199 | OE2 | GLU | 58 | 13.875 | 20.305 | 49.156 | 1.00 | 29.87 | CPS5 |
| ATOM | 4200 | C   | GLU | 58 | 17.943 | 20.741 | 45.410 | 1.00 | 20.35 | CPS5 |
| ATOM | 4201 | O   | GLU | 58 | 17.543 | 19.908 | 44.590 | 1.00 | 20.00 | CPS5 |
| ATOM | 4202 | N   | ALA | 59 | 18.848 | 21.675 | 45.113 | 1.00 | 20.46 | CPS5 |
| ATOM | 4203 | CA  | ALA | 59 | 19.418 | 21.765 | 43.769 | 1.00 | 20.45 | CPS5 |
| ATOM | 4204 | CB  | ALA | 59 | 20.353 | 22.971 | 43.655 | 1.00 | 20.63 | CPS5 |
| ATOM | 4205 | C   | ALA | 59 | 20.175 | 20.489 | 43.436 | 1.00 | 20.79 | CPS5 |
| ATOM | 4206 | O   | ALA | 59 | 20.104 | 19.985 | 42.312 | 1.00 | 20.80 | CPS5 |
| ATOM | 4207 | N   | PHE | 60 | 20.916 | 19.965 | 44.404 | 1.00 | 19.71 | CPS5 |
| ATOM | 4208 | CA  | PHE | 60 | 21.643 | 18.730 | 44.153 | 1.00 | 19.50 | CPS5 |
| ATOM | 4209 | CB  | PHE | 60 | 22.511 | 18.349 | 45.361 | 1.00 | 20.28 | CPS5 |
| ATOM | 4210 | CG  | PHE | 60 | 23.252 | 17.057 | 45.172 | 1.00 | 22.22 | CPS5 |
| ATOM | 4211 | CD1 | PHE | 60 | 24.498 | 17.034 | 44.548 | 1.00 | 22.07 | CPS5 |
| ATOM | 4212 | CD2 | PHE | 60 | 22.657 | 15.850 | 45.538 | 1.00 | 23.50 | CPS5 |
| ATOM | 4213 | CE1 | PHE | 60 | 25.145 | 15.810 | 44.285 | 1.00 | 25.08 | CPS5 |
| ATOM | 4214 | CE2 | PHE | 60 | 23.287 | 14.629 | 45.282 | 1.00 | 26.22 | CPS5 |
| ATOM | 4215 | CZ  | PHE | 60 | 24.534 | 14.614 | 44.652 | 1.00 | 24.97 | CPS5 |
| ATOM | 4216 | C   | PHE | 60 | 20.665 | 17.588 | 43.857 | 1.00 | 19.97 | CPS5 |
| ATOM | 4217 | O   | PHE | 60 | 20.893 | 16.774 | 42.946 | 1.00 | 20.76 | CPS5 |

FIG. 1A-74

| ATOM | 4218 | N | SER | 61 | 19.575 | 17.530 | 44.615 | 1.00 | 19.93 | CPS5 |
| ATOM | 4219 | CA | SER | 61 | 18.596 | 16.461 | 44.437 | 1.00 | 22.05 | CPS5 |
| ATOM | 4220 | CB | SER | 61 | 17.542 | 16.505 | 45.550 | 1.00 | 21.89 | CPS5 |
| ATOM | 4221 | OG | SER | 61 | 16.571 | 17.505 | 45.308 | 1.00 | 22.40 | CPS5 |
| ATOM | 4222 | C | SER | 61 | 17.931 | 16.519 | 43.067 | 1.00 | 22.70 | CPS5 |
| ATOM | 4223 | O | SER | 61 | 17.482 | 15.494 | 42.540 | 1.00 | 23.10 | CPS5 |
| ATOM | 4224 | N | LYS | 62 | 17.874 | 17.716 | 42.487 | 1.00 | 21.75 | CPS5 |
| ATOM | 4225 | CA | LYS | 62 | 17.292 | 17.888 | 41.158 | 1.00 | 22.11 | CPS5 |
| ATOM | 4226 | CB | LYS | 62 | 16.914 | 19.349 | 40.932 | 1.00 | 23.25 | CPS5 |
| ATOM | 4227 | CG | LYS | 62 | 15.636 | 19.790 | 41.661 | 1.00 | 26.97 | CPS5 |
| ATOM | 4228 | CD | LYS | 62 | 15.515 | 21.316 | 41.597 | 1.00 | 29.60 | CPS5 |
| ATOM | 4229 | CE | LYS | 62 | 14.085 | 21.787 | 41.383 | 1.00 | 33.49 | CPS5 |
| ATOM | 4230 | NZ | LYS | 62 | 13.174 | 21.402 | 42.470 | 1.00 | 35.09 | CPS5 |
| ATOM | 4231 | C | LYS | 62 | 18.290 | 17.431 | 40.095 | 1.00 | 22.61 | CPS5 |
| ATOM | 4232 | O | LYS | 62 | 17.897 | 16.841 | 39.079 | 1.00 | 22.72 | CPS5 |
| ATOM | 4233 | N | ALA | 63 | 19.577 | 17.695 | 40.333 | 1.00 | 21.05 | CPS5 |
| ATOM | 4234 | CA | ALA | 63 | 20.627 | 17.283 | 39.408 | 1.00 | 21.93 | CPS5 |
| ATOM | 4235 | CB | ALA | 63 | 21.965 | 17.909 | 39.801 | 1.00 | 21.40 | CPS5 |
| ATOM | 4236 | C | ALA | 63 | 20.737 | 15.767 | 39.476 | 1.00 | 23.26 | CPS5 |
| ATOM | 4237 | O | ALA | 63 | 21.006 | 15.113 | 38.473 | 1.00 | 22.70 | CPS5 |
| ATOM | 4238 | N | PHE | 64 | 20.525 | 15.225 | 40.672 | 1.00 | 23.91 | CPS5 |
| ATOM | 4239 | CA | PHE | 64 | 20.591 | 13.782 | 40.916 | 1.00 | 25.22 | CPS5 |
| ATOM | 4240 | CB | PHE | 64 | 20.463 | 13.512 | 42.419 | 1.00 | 24.79 | CPS5 |
| ATOM | 4241 | CG | PHE | 64 | 20.781 | 12.097 | 42.818 | 1.00 | 27.22 | CPS5 |
| ATOM | 4242 | CD1 | PHE | 64 | 22.094 | 11.642 | 42.822 | 1.00 | 28.51 | CPS5 |
| ATOM | 4243 | CD2 | PHE | 64 | 19.768 | 11.233 | 43.217 | 1.00 | 27.62 | CPS5 |
| ATOM | 4244 | CE1 | PHE | 64 | 22.398 | 10.343 | 43.224 | 1.00 | 30.62 | CPS5 |
| ATOM | 4245 | CE2 | PHE | 64 | 20.061 | 9.931 | 43.622 | 1.00 | 28.83 | CPS5 |
| ATOM | 4246 | CZ | PHE | 64 | 21.377 | 9.489 | 43.625 | 1.00 | 28.53 | CPS5 |
| ATOM | 4247 | C | PHE | 64 | 19.453 | 13.109 | 40.147 | 1.00 | 26.39 | CPS5 |
| ATOM | 4248 | O | PHE | 64 | 19.554 | 11.941 | 39.766 | 1.00 | 28.07 | CPS5 |
| ATOM | 4249 | N | GLY | 65 | 18.381 | 13.862 | 39.911 | 1.00 | 26.10 | CPS5 |
| ATOM | 4250 | CA | GLY | 65 | 17.251 | 13.368 | 39.143 | 1.00 | 27.17 | CPS5 |
| ATOM | 4251 | C | GLY | 65 | 16.088 | 12.768 | 39.905 | 1.00 | 28.46 | CPS5 |
| ATOM | 4252 | O | GLY | 65 | 15.117 | 12.317 | 39.298 | 1.00 | 28.55 | CPS5 |
| ATOM | 4253 | N | THR | 66 | 16.157 | 12.789 | 41.231 | 1.00 | 28.12 | CPS5 |
| ATOM | 4254 | CA | THR | 66 | 15.099 | 12.191 | 42.037 | 1.00 | 29.33 | CPS5 |
| ATOM | 4255 | CB | THR | 66 | 15.663 | 11.062 | 42.903 | 1.00 | 29.96 | CPS5 |
| ATOM | 4256 | OG1 | THR | 66 | 16.635 | 11.608 | 43.804 | 1.00 | 29.92 | CPS5 |
| ATOM | 4257 | CG2 | THR | 66 | 16.326 | 10.009 | 42.038 | 1.00 | 30.68 | CPS5 |
| ATOM | 4258 | C | THR | 66 | 14.410 | 13.148 | 42.984 | 1.00 | 28.71 | CPS5 |
| ATOM | 4259 | O | THR | 66 | 13.269 | 12.915 | 43.378 | 1.00 | 28.56 | CPS5 |
| ATOM | 4260 | N | GLY | 67 | 15.098 | 14.227 | 43.343 | 1.00 | 27.58 | CPS5 |
| ATOM | 4261 | CA | GLY | 67 | 14.530 | 15.150 | 44.305 | 1.00 | 27.06 | CPS5 |
| ATOM | 4262 | C | GLY | 67 | 14.741 | 14.479 | 45.657 | 1.00 | 27.43 | CPS5 |
| ATOM | 4263 | O | GLY | 67 | 15.278 | 13.367 | 45.712 | 1.00 | 26.28 | CPS5 |
| ATOM | 4264 | N | ILE | 68 | 14.343 | 15.145 | 46.737 | 1.00 | 26.71 | CPS5 |
| ATOM | 4265 | CA | ILE | 68 | 14.491 | 14.593 | 48.082 | 1.00 | 28.68 | CPS5 |
| ATOM | 4266 | CB | ILE | 68 | 14.470 | 15.715 | 49.166 | 1.00 | 27.25 | CPS5 |
| ATOM | 4267 | CG2 | ILE | 68 | 14.574 | 15.098 | 50.569 | 1.00 | 27.25 | CPS5 |
| ATOM | 4268 | CG1 | ILE | 68 | 15.630 | 16.697 | 48.936 | 1.00 | 24.63 | CPS5 |
| ATOM | 4269 | CD1 | ILE | 68 | 17.030 | 16.084 | 49.112 | 1.00 | 23.40 | CPS5 |
| ATOM | 4270 | C | ILE | 68 | 13.335 | 13.629 | 48.342 | 1.00 | 30.86 | CPS5 |
| ATOM | 4271 | O | ILE | 68 | 12.167 | 13.982 | 48.169 | 1.00 | 31.01 | CPS5 |
| ATOM | 4272 | N | GLY | 69 | 13.671 | 12.412 | 48.752 | 1.00 | 33.01 | CPS5 |
| ATOM | 4273 | CA | GLY | 69 | 12.654 | 11.415 | 49.022 | 1.00 | 34.73 | CPS5 |
| ATOM | 4274 | C | GLY | 69 | 13.291 | 10.115 | 49.470 | 1.00 | 36.57 | CPS5 |

FIG. 1A-75

| ATOM | 4275 | O | GLY | 69 | 14.363 | 10.112 | 50.079 | 1.00 | 36.27 | CPS5 |
|---|---|---|---|---|---|---|---|---|---|---|
| ATOM | 4276 | N | ARG | 70 | 12.653 | 8.997 | 49.152 | 1.00 | 38.18 | CPS5 |
| ATOM | 4277 | CA | ARG | 70 | 13.203 | 7.724 | 49.579 | 1.00 | 39.66 | CPS5 |
| ATOM | 4278 | CB | ARG | 70 | 12.137 | 6.627 | 49.493 | 1.00 | 43.12 | CPS5 |
| ATOM | 4279 | CG | ARG | 70 | 11.182 | 6.661 | 50.696 | 1.00 | 47.23 | CPS5 |
| ATOM | 4280 | CD | ARG | 70 | 11.972 | 6.780 | 52.019 | 1.00 | 49.65 | CPS5 |
| ATOM | 4281 | NE | ARG | 70 | 11.469 | 7.858 | 52.870 | 1.00 | 51.86 | CPS5 |
| ATOM | 4282 | CZ | ARG | 70 | 12.239 | 8.672 | 53.590 | 1.00 | 52.77 | CPS5 |
| ATOM | 4283 | NH1 | ARG | 70 | 13.558 | 8.540 | 53.569 | 1.00 | 53.05 | CPS5 |
| ATOM | 4284 | NH2 | ARG | 70 | 11.691 | 9.627 | 54.328 | 1.00 | 52.96 | CPS5 |
| ATOM | 4285 | C | ARG | 70 | 14.468 | 7.317 | 48.855 | 1.00 | 37.80 | CPS5 |
| ATOM | 4286 | O | ARG | 70 | 15.221 | 6.478 | 49.345 | 1.00 | 37.07 | CPS5 |
| ATOM | 4287 | N | GLN | 71 | 14.726 | 7.926 | 47.703 | 1.00 | 36.29 | CPS5 |
| ATOM | 4288 | CA | GLN | 71 | 15.932 | 7.598 | 46.959 | 1.00 | 35.22 | CPS5 |
| ATOM | 4289 | CB | GLN | 71 | 15.707 | 7.778 | 45.453 | 1.00 | 36.48 | CPS5 |
| ATOM | 4290 | CG | GLN | 71 | 14.534 | 6.985 | 44.889 | 1.00 | 38.95 | CPS5 |
| ATOM | 4291 | CD | GLN | 71 | 14.402 | 7.129 | 43.379 | 1.00 | 40.20 | CPS5 |
| ATOM | 4292 | OE1 | GLN | 71 | 15.236 | 6.631 | 42.622 | 1.00 | 40.67 | CPS5 |
| ATOM | 4293 | NE2 | GLN | 71 | 13.355 | 7.827 | 42.937 | 1.00 | 40.72 | CPS5 |
| ATOM | 4294 | C | GLN | 71 | 17.084 | 8.483 | 47.412 | 1.00 | 33.38 | CPS5 |
| ATOM | 4295 | O | GLN | 71 | 18.248 | 8.110 | 47.276 | 1.00 | 33.43 | CPS5 |
| ATOM | 4296 | N | LEU | 72 | 16.759 | 9.650 | 47.966 | 1.00 | 30.70 | CPS5 |
| ATOM | 4297 | CA | LEU | 72 | 17.786 | 10.591 | 48.409 | 1.00 | 27.96 | CPS5 |
| ATOM | 4298 | CB | LEU | 72 | 18.204 | 11.478 | 47.231 | 1.00 | 26.31 | CPS5 |
| ATOM | 4299 | CG | LEU | 72 | 19.285 | 12.532 | 47.448 | 1.00 | 26.21 | CPS5 |
| ATOM | 4300 | CD1 | LEU | 72 | 20.626 | 11.867 | 47.673 | 1.00 | 27.19 | CPS5 |
| ATOM | 4301 | CD2 | LEU | 72 | 19.338 | 13.446 | 46.213 | 1.00 | 25.53 | CPS5 |
| ATOM | 4302 | C | LEU | 72 | 17.279 | 11.469 | 49.556 | 1.00 | 27.62 | CPS5 |
| ATOM | 4303 | O | LEU | 72 | 16.203 | 12.070 | 49.470 | 1.00 | 27.05 | CPS5 |
| ATOM | 4304 | N | SER | 73 | 18.076 | 11.545 | 50.616 | 1.00 | 26.31 | CPS5 |
| ATOM | 4305 | CA | SER | 73 | 17.735 | 12.323 | 51.805 | 1.00 | 25.42 | CPS5 |
| ATOM | 4306 | CB | SER | 73 | 17.889 | 11.441 | 53.051 | 1.00 | 26.75 | CPS5 |
| ATOM | 4307 | OG | SER | 73 | 17.970 | 12.228 | 54.231 | 1.00 | 27.96 | CPS5 |
| ATOM | 4308 | C | SER | 73 | 18.633 | 13.539 | 51.965 | 1.00 | 24.08 | CPS5 |
| ATOM | 4309 | O | SER | 73 | 19.733 | 13.581 | 51.419 | 1.00 | 23.91 | CPS5 |
| ATOM | 4310 | N | PHE | 74 | 18.165 | 14.525 | 52.721 | 1.00 | 23.49 | CPS5 |
| ATOM | 4311 | CA | PHE | 74 | 18.975 | 15.707 | 52.995 | 1.00 | 23.97 | CPS5 |
| ATOM | 4312 | CB | PHE | 74 | 18.246 | 16.657 | 53.955 | 1.00 | 24.68 | CPS5 |
| ATOM | 4313 | CG | PHE | 74 | 17.124 | 17.430 | 53.319 | 1.00 | 25.48 | CPS5 |
| ATOM | 4314 | CD1 | PHE | 74 | 17.392 | 18.421 | 52.371 | 1.00 | 26.10 | CPS5 |
| ATOM | 4315 | CD2 | PHE | 74 | 15.801 | 17.176 | 53.672 | 1.00 | 26.28 | CPS5 |
| ATOM | 4316 | CE1 | PHE | 74 | 16.347 | 19.151 | 51.786 | 1.00 | 25.75 | CPS5 |
| ATOM | 4317 | CE2 | PHE | 74 | 14.750 | 17.896 | 53.092 | 1.00 | 26.75 | CPS5 |
| ATOM | 4318 | CZ | PHE | 74 | 15.028 | 18.886 | 52.148 | 1.00 | 25.31 | CPS5 |
| ATOM | 4319 | C | PHE | 74 | 20.260 | 15.241 | 53.674 | 1.00 | 23.42 | CPS5 |
| ATOM | 4320 | O | PHE | 74 | 21.334 | 15.804 | 53.459 | 1.00 | 23.30 | CPS5 |
| ATOM | 4321 | N | GLN | 75 | 20.141 | 14.207 | 54.504 | 1.00 | 24.48 | CPS5 |
| ATOM | 4322 | CA | GLN | 75 | 21.284 | 13.688 | 55.245 | 1.00 | 24.75 | CPS5 |
| ATOM | 4323 | CB | GLN | 75 | 20.804 | 12.774 | 56.382 | 1.00 | 24.94 | CPS5 |
| ATOM | 4324 | CG | GLN | 75 | 20.012 | 13.515 | 57.455 | 1.00 | 24.64 | CPS5 |
| ATOM | 4325 | CD | GLN | 75 | 20.838 | 14.550 | 58.200 | 1.00 | 24.25 | CPS5 |
| ATOM | 4326 | OE1 | GLN | 75 | 20.304 | 15.559 | 58.674 | 1.00 | 28.14 | CPS5 |
| ATOM | 4327 | NE2 | GLN | 75 | 22.141 | 14.308 | 58.319 | 1.00 | 22.66 | CPS5 |
| ATOM | 4328 | C | GLN | 75 | 22.316 | 12.958 | 54.390 | 1.00 | 26.96 | CPS5 |
| ATOM | 4329 | O | GLN | 75 | 23.423 | 12.684 | 54.861 | 1.00 | 27.29 | CPS5 |
| ATOM | 4330 | N | ASP | 76 | 21.965 | 12.651 | 53.144 | 1.00 | 27.28 | CPS5 |
| ATOM | 4331 | CA | ASP | 76 | 22.906 | 11.976 | 52.245 | 1.00 | 28.96 | CPS5 |

FIG. 1A-76

| ATOM | 4332 | CB  | ASP | 76 | 22.171 | 11.187 | 51.157 | 1.00 | 28.71 | CPS5 |
|------|------|-----|-----|----|--------|--------|--------|------|-------|------|
| ATOM | 4333 | CG  | ASP | 76 | 21.422 | 10.002 | 51.695 | 1.00 | 30.19 | CPS5 |
| ATOM | 4334 | OD1 | ASP | 76 | 21.971 | 9.327  | 52.593 | 1.00 | 30.44 | CPS5 |
| ATOM | 4335 | OD2 | ASP | 76 | 20.296 | 9.733  | 51.211 | 1.00 | 30.21 | CPS5 |
| ATOM | 4336 | C   | ASP | 76 | 23.787 | 13.007 | 51.552 | 1.00 | 29.00 | CPS5 |
| ATOM | 4337 | O   | ASP | 76 | 24.738 | 12.652 | 50.856 | 1.00 | 30.49 | CPS5 |
| ATOM | 4338 | N   | ILE | 77 | 23.472 | 14.284 | 51.743 | 1.00 | 28.00 | CPS5 |
| ATOM | 4339 | CA  | ILE | 77 | 24.207 | 15.354 | 51.080 | 1.00 | 27.42 | CPS5 |
| ATOM | 4340 | CB  | ILE | 77 | 23.251 | 16.214 | 50.213 | 1.00 | 25.93 | CPS5 |
| ATOM | 4341 | CG2 | ILE | 77 | 24.067 | 17.152 | 49.328 | 1.00 | 26.70 | CPS5 |
| ATOM | 4342 | CG1 | ILE | 77 | 22.345 | 15.310 | 49.370 | 1.00 | 24.69 | CPS5 |
| ATOM | 4343 | CD1 | ILE | 77 | 21.036 | 15.971 | 48.941 | 1.00 | 25.15 | CPS5 |
| ATOM | 4344 | C   | ILE | 77 | 24.910 | 16.287 | 52.046 | 1.00 | 28.47 | CPS5 |
| ATOM | 4345 | O   | ILE | 77 | 24.287 | 16.853 | 52.943 | 1.00 | 29.75 | CPS5 |
| ATOM | 4346 | N   | GLU | 78 | 26.206 | 16.472 | 51.864 | 1.00 | 27.86 | CPS5 |
| ATOM | 4347 | CA  | GLU | 78 | 26.920 | 17.367 | 52.751 | 1.00 | 31.23 | CPS5 |
| ATOM | 4348 | CB  | GLU | 78 | 27.892 | 16.591 | 53.638 | 1.00 | 32.64 | CPS5 |
| ATOM | 4349 | CG  | GLU | 78 | 28.558 | 17.466 | 54.681 | 1.00 | 34.90 | CPS5 |
| ATOM | 4350 | CD  | GLU | 78 | 29.270 | 16.647 | 55.734 | 1.00 | 37.57 | CPS5 |
| ATOM | 4351 | OE1 | GLU | 78 | 30.334 | 16.072 | 55.425 | 1.00 | 38.97 | CPS5 |
| ATOM | 4352 | OE2 | GLU | 78 | 28.753 | 16.568 | 56.866 | 1.00 | 38.56 | CPS5 |
| ATOM | 4353 | C   | GLU | 78 | 27.676 | 18.468 | 52.042 | 1.00 | 31.73 | CPS5 |
| ATOM | 4354 | O   | GLU | 78 | 28.415 | 18.224 | 51.090 | 1.00 | 32.74 | CPS5 |
| ATOM | 4355 | N   | ILE | 79 | 27.481 | 19.691 | 52.508 | 1.00 | 32.96 | CPS5 |
| ATOM | 4356 | CA  | ILE | 79 | 28.177 | 20.821 | 51.932 | 1.00 | 35.99 | CPS5 |
| ATOM | 4357 | CB  | ILE | 79 | 27.265 | 22.044 | 51.818 | 1.00 | 36.51 | CPS5 |
| ATOM | 4358 | CG2 | ILE | 79 | 28.066 | 23.252 | 51.363 | 1.00 | 35.93 | CPS5 |
| ATOM | 4359 | CG1 | ILE | 79 | 26.129 | 21.738 | 50.842 | 1.00 | 37.54 | CPS5 |
| ATOM | 4360 | CD1 | ILE | 79 | 25.122 | 22.836 | 50.754 | 1.00 | 42.06 | CPS5 |
| ATOM | 4361 | C   | ILE | 79 | 29.342 | 21.145 | 52.842 | 1.00 | 38.38 | CPS5 |
| ATOM | 4362 | O   | ILE | 79 | 29.166 | 21.432 | 54.026 | 1.00 | 37.01 | CPS5 |
| ATOM | 4363 | N   | ARG | 80 | 30.543 | 21.075 | 52.290 | 1.00 | 42.32 | CPS5 |
| ATOM | 4364 | CA  | ARG | 80 | 31.729 | 21.371 | 53.070 | 1.00 | 46.50 | CPS5 |
| ATOM | 4365 | CB  | ARG | 80 | 32.690 | 20.180 | 53.091 | 1.00 | 46.70 | CPS5 |
| ATOM | 4366 | CG  | ARG | 80 | 32.116 | 18.913 | 53.670 | 1.00 | 48.52 | CPS5 |
| ATOM | 4367 | CD  | ARG | 80 | 33.151 | 17.798 | 53.687 | 1.00 | 49.02 | CPS5 |
| ATOM | 4368 | NE  | ARG | 80 | 32.519 | 16.508 | 53.945 | 1.00 | 50.86 | CPS5 |
| ATOM | 4369 | CZ  | ARG | 80 | 33.159 | 15.345 | 53.970 | 1.00 | 50.68 | CPS5 |
| ATOM | 4370 | NH1 | ARG | 80 | 34.465 | 15.303 | 53.757 | 1.00 | 50.94 | CPS5 |
| ATOM | 4371 | NH2 | ARG | 80 | 32.485 | 14.221 | 54.185 | 1.00 | 51.63 | CPS5 |
| ATOM | 4372 | C   | ARG | 80 | 32.444 | 22.545 | 52.459 | 1.00 | 48.41 | CPS5 |
| ATOM | 4373 | O   | ARG | 80 | 31.955 | 23.189 | 51.529 | 1.00 | 48.48 | CPS5 |
| ATOM | 4374 | N   | LYS | 81 | 33.616 | 22.820 | 53.003 | 1.00 | 51.83 | CPS5 |
| ATOM | 4375 | CA  | LYS | 81 | 34.448 | 23.892 | 52.507 | 1.00 | 54.26 | CPS5 |
| ATOM | 4376 | CB  | LYS | 81 | 34.388 | 25.099 | 53.445 | 1.00 | 55.70 | CPS5 |
| ATOM | 4377 | CG  | LYS | 81 | 32.994 | 25.704 | 53.578 | 1.00 | 58.10 | CPS5 |
| ATOM | 4378 | CD  | LYS | 81 | 33.014 | 26.958 | 54.439 | 1.00 | 59.69 | CPS5 |
| ATOM | 4379 | CE  | LYS | 81 | 31.606 | 27.467 | 54.730 | 1.00 | 61.09 | CPS5 |
| ATOM | 4380 | NZ  | LYS | 81 | 30.801 | 26.502 | 55.540 | 1.00 | 61.28 | CPS5 |
| ATOM | 4381 | C   | LYS | 81 | 35.847 | 23.307 | 52.459 | 1.00 | 54.90 | CPS5 |
| ATOM | 4382 | O   | LYS | 81 | 36.305 | 22.695 | 53.427 | 1.00 | 54.56 | CPS5 |
| ATOM | 4383 | N   | ASP | 82 | 36.504 | 23.452 | 51.314 | 1.00 | 55.76 | CPS5 |
| ATOM | 4384 | CA  | ASP | 82 | 37.855 | 22.940 | 51.151 | 1.00 | 56.67 | CPS5 |
| ATOM | 4385 | CB  | ASP | 82 | 38.281 | 23.026 | 49.683 | 1.00 | 56.75 | CPS5 |
| ATOM | 4386 | CG  | ASP | 82 | 37.874 | 24.337 | 49.031 | 1.00 | 56.88 | CPS5 |
| ATOM | 4387 | OD1 | ASP | 82 | 37.980 | 25.399 | 49.687 | 1.00 | 55.92 | CPS5 |
| ATOM | 4388 | OD2 | ASP | 82 | 37.457 | 24.301 | 47.853 | 1.00 | 57.36 | CPS5 |

FIG. 1A-77

| ATOM | 4389 | C | ASP | 82 | 38.810 | 23.753 | 52.015 | 1.00 | 57.41 | CPS5 |
|---|---|---|---|---|---|---|---|---|---|---|
| ATOM | 4390 | O | ASP | 82 | 38.377 | 24.523 | 52.874 | 1.00 | 56.93 | CPS5 |
| ATOM | 4391 | N | GLN | 83 | 40.107 | 23.580 | 51.785 | 1.00 | 58.43 | CPS5 |
| ATOM | 4392 | CA | GLN | 83 | 41.119 | 24.306 | 52.543 | 1.00 | 59.77 | CPS5 |
| ATOM | 4393 | CB | GLN | 83 | 42.505 | 23.717 | 52.275 | 1.00 | 60.54 | CPS5 |
| ATOM | 4394 | CG | GLN | 83 | 42.754 | 22.364 | 52.916 | 1.00 | 61.21 | CPS5 |
| ATOM | 4395 | CD | GLN | 83 | 42.737 | 22.424 | 54.432 | 1.00 | 61.78 | CPS5 |
| ATOM | 4396 | OE1 | GLN | 83 | 41.674 | 22.447 | 55.054 | 1.00 | 62.24 | CPS5 |
| ATOM | 4397 | NE2 | GLN | 83 | 43.921 | 22.462 | 55.035 | 1.00 | 61.85 | CPS5 |
| ATOM | 4398 | C | GLN | 83 | 41.117 | 25.793 | 52.189 | 1.00 | 60.23 | CPS5 |
| ATOM | 4399 | O | GLN | 83 | 41.792 | 26.598 | 52.837 | 1.00 | 60.80 | CPS5 |
| ATOM | 4400 | N | ASN | 84 | 40.359 | 26.153 | 51.157 | 1.00 | 59.89 | CPS5 |
| ATOM | 4401 | CA | ASN | 84 | 40.268 | 27.543 | 50.730 | 1.00 | 59.63 | CPS5 |
| ATOM | 4402 | CB | ASN | 84 | 40.373 | 27.636 | 49.207 | 1.00 | 60.60 | CPS5 |
| ATOM | 4403 | CG | ASN | 84 | 41.707 | 27.140 | 48.685 | 1.00 | 61.37 | CPS5 |
| ATOM | 4404 | OD1 | ASN | 84 | 42.761 | 27.667 | 49.044 | 1.00 | 61.62 | CPS5 |
| ATOM | 4405 | ND2 | ASN | 84 | 41.669 | 26.120 | 47.834 | 1.00 | 61.98 | CPS5 |
| ATOM | 4406 | C | ASN | 84 | 38.956 | 28.160 | 51.199 | 1.00 | 59.10 | CPS5 |
| ATOM | 4407 | O | ASN | 84 | 38.731 | 29.361 | 51.037 | 1.00 | 59.66 | CPS5 |
| ATOM | 4408 | N | GLY | 85 | 38.095 | 27.330 | 51.780 | 1.00 | 57.75 | CPS5 |
| ATOM | 4409 | CA | GLY | 85 | 36.818 | 27.809 | 52.272 | 1.00 | 56.41 | CPS5 |
| ATOM | 4410 | C | GLY | 85 | 35.731 | 27.794 | 51.213 | 1.00 | 55.75 | CPS5 |
| ATOM | 4411 | O | GLY | 85 | 34.643 | 28.331 | 51.425 | 1.00 | 56.16 | CPS5 |
| ATOM | 4412 | N | LYS | 86 | 36.022 | 27.180 | 50.070 | 1.00 | 54.26 | CPS5 |
| ATOM | 4413 | CA | LYS | 86 | 35.058 | 27.107 | 48.978 | 1.00 | 52.12 | CPS5 |
| ATOM | 4414 | CB | LYS | 86 | 35.775 | 26.812 | 47.657 | 1.00 | 53.72 | CPS5 |
| ATOM | 4415 | CG | LYS | 86 | 34.948 | 27.105 | 46.406 | 1.00 | 55.30 | CPS5 |
| ATOM | 4416 | CD | LYS | 86 | 34.812 | 28.604 | 46.171 | 1.00 | 56.46 | CPS5 |
| ATOM | 4417 | CE | LYS | 86 | 34.012 | 28.910 | 44.905 | 1.00 | 56.79 | CPS5 |
| ATOM | 4418 | NZ | LYS | 86 | 32.619 | 28.397 | 45.007 | 1.00 | 57.01 | CPS5 |
| ATOM | 4419 | C | LYS | 86 | 34.057 | 25.999 | 49.279 | 1.00 | 49.78 | CPS5 |
| ATOM | 4420 | O | LYS | 86 | 34.420 | 24.944 | 49.806 | 1.00 | 49.58 | CPS5 |
| ATOM | 4421 | N | PRO | 87 | 32.777 | 26.222 | 48.952 | 1.00 | 47.09 | CPS5 |
| ATOM | 4422 | CD | PRO | 87 | 32.162 | 27.432 | 48.380 | 1.00 | 46.07 | CPS5 |
| ATOM | 4423 | CA | PRO | 87 | 31.764 | 25.198 | 49.214 | 1.00 | 44.34 | CPS5 |
| ATOM | 4424 | CB | PRO | 87 | 30.469 | 25.995 | 49.177 | 1.00 | 44.60 | CPS5 |
| ATOM | 4425 | CG | PRO | 87 | 30.745 | 26.967 | 48.074 | 1.00 | 45.82 | CPS5 |
| ATOM | 4426 | C | PRO | 87 | 31.776 | 24.098 | 48.158 | 1.00 | 40.83 | CPS5 |
| ATOM | 4427 | O | PRO | 87 | 31.837 | 24.382 | 46.961 | 1.00 | 40.94 | CPS5 |
| ATOM | 4428 | N | TYR | 88 | 31.731 | 22.846 | 48.598 | 1.00 | 37.82 | CPS5 |
| ATOM | 4429 | CA | TYR | 88 | 31.690 | 21.737 | 47.662 | 1.00 | 34.81 | CPS5 |
| ATOM | 4430 | CB | TYR | 88 | 33.111 | 21.229 | 47.335 | 1.00 | 35.73 | CPS5 |
| ATOM | 4431 | CG | TYR | 88 | 33.795 | 20.385 | 48.390 | 1.00 | 34.31 | CPS5 |
| ATOM | 4432 | CD1 | TYR | 88 | 33.648 | 19.002 | 48.399 | 1.00 | 34.27 | CPS5 |
| ATOM | 4433 | CE1 | TYR | 88 | 34.303 | 18.212 | 49.339 | 1.00 | 34.82 | CPS5 |
| ATOM | 4434 | CD2 | TYR | 88 | 34.615 | 20.966 | 49.354 | 1.00 | 35.40 | CPS5 |
| ATOM | 4435 | CE2 | TYR | 88 | 35.275 | 20.187 | 50.304 | 1.00 | 33.64 | CPS5 |
| ATOM | 4436 | CZ | TYR | 88 | 35.112 | 18.812 | 50.290 | 1.00 | 35.08 | CPS5 |
| ATOM | 4437 | OH | TYR | 88 | 35.730 | 18.028 | 51.239 | 1.00 | 35.18 | CPS5 |
| ATOM | 4438 | C | TYR | 88 | 30.807 | 20.668 | 48.279 | 1.00 | 33.39 | CPS5 |
| ATOM | 4439 | O | TYR | 88 | 30.627 | 20.633 | 49.497 | 1.00 | 32.83 | CPS5 |
| ATOM | 4440 | N | ILE | 89 | 30.238 | 19.817 | 47.435 | 1.00 | 31.13 | CPS5 |
| ATOM | 4441 | CA | ILE | 89 | 29.321 | 18.778 | 47.882 | 1.00 | 30.93 | CPS5 |
| ATOM | 4442 | CB | ILE | 89 | 28.043 | 18.780 | 47.010 | 1.00 | 29.10 | CPS5 |
| ATOM | 4443 | CG2 | ILE | 89 | 27.189 | 17.547 | 47.303 | 1.00 | 27.98 | CPS5 |
| ATOM | 4444 | CG1 | ILE | 89 | 27.253 | 20.065 | 47.253 | 1.00 | 27.68 | CPS5 |
| ATOM | 4445 | CD1 | ILE | 89 | 26.041 | 20.215 | 46.364 | 1.00 | 27.97 | CPS5 |

FIG. 1A-78

| ATOM | 4446 | C | ILE | 89 | 29.873 | 17.362 | 47.863 | 1.00 | 32.51 | CPS5 |
|---|---|---|---|---|---|---|---|---|---|---|
| ATOM | 4447 | O | ILE | 89 | 30.637 | 16.987 | 46.973 | 1.00 | 31.03 | CPS5 |
| ATOM | 4448 | N | ILE | 90 | 29.462 | 16.582 | 48.858 | 1.00 | 33.80 | CPS5 |
| ATOM | 4449 | CA | ILE | 90 | 29.837 | 15.180 | 48.960 | 1.00 | 35.56 | CPS5 |
| ATOM | 4450 | CB | ILE | 90 | 30.776 | 14.928 | 50.144 | 1.00 | 37.43 | CPS5 |
| ATOM | 4451 | CG2 | ILE | 90 | 30.959 | 13.418 | 50.359 | 1.00 | 37.12 | CPS5 |
| ATOM | 4452 | CG1 | ILE | 90 | 32.116 | 15.608 | 49.875 | 1.00 | 38.91 | CPS5 |
| ATOM | 4453 | CD1 | ILE | 90 | 33.093 | 15.508 | 51.006 | 1.00 | 42.45 | CPS5 |
| ATOM | 4454 | C | ILE | 90 | 28.564 | 14.363 | 49.156 | 1.00 | 36.47 | CPS5 |
| ATOM | 4455 | O | ILE | 90 | 27.782 | 14.624 | 50.076 | 1.00 | 35.64 | CPS5 |
| ATOM | 4456 | N | CYS | 91 | 28.348 | 13.400 | 48.269 | 1.00 | 36.91 | CPS5 |
| ATOM | 4457 | CA | CYS | 91 | 27.189 | 12.520 | 48.340 | 1.00 | 40.22 | CPS5 |
| ATOM | 4458 | CB | CYS | 91 | 26.132 | 12.945 | 47.328 | 1.00 | 37.91 | CPS5 |
| ATOM | 4459 | SG | CYS | 91 | 24.623 | 11.970 | 47.401 | 1.00 | 39.23 | CPS5 |
| ATOM | 4460 | C | CYS | 91 | 27.643 | 11.094 | 48.035 | 1.00 | 42.93 | CPS5 |
| ATOM | 4461 | O | CYS | 91 | 27.983 | 10.771 | 46.895 | 1.00 | 42.83 | CPS5 |
| ATOM | 4462 | N | THR | 92 | 27.648 | 10.245 | 49.056 | 1.00 | 46.74 | CPS5 |
| ATOM | 4463 | CA | THR | 92 | 28.070 | 8.858 | 48.881 | 1.00 | 50.26 | CPS5 |
| ATOM | 4464 | CB | THR | 92 | 28.080 | 8.106 | 50.238 | 1.00 | 51.61 | CPS5 |
| ATOM | 4465 | OG1 | THR | 92 | 28.496 | 6.748 | 50.035 | 1.00 | 52.93 | CPS5 |
| ATOM | 4466 | CG2 | THR | 92 | 26.693 | 8.130 | 50.876 | 1.00 | 52.67 | CPS5 |
| ATOM | 4467 | C | THR | 92 | 27.175 | 8.110 | 47.890 | 1.00 | 51.62 | CPS5 |
| ATOM | 4468 | O | THR | 92 | 27.656 | 7.285 | 47.108 | 1.00 | 51.98 | CPS5 |
| ATOM | 4469 | N | LYS | 93 | 25.879 | 8.413 | 47.914 | 1.00 | 52.57 | CPS5 |
| ATOM | 4470 | CA | LYS | 93 | 24.918 | 7.769 | 47.020 | 1.00 | 53.74 | CPS5 |
| ATOM | 4471 | CB | LYS | 93 | 23.503 | 8.289 | 47.296 | 1.00 | 54.52 | CPS5 |
| ATOM | 4472 | CG | LYS | 93 | 23.041 | 8.147 | 48.742 | 1.00 | 56.49 | CPS5 |
| ATOM | 4473 | CD | LYS | 93 | 22.706 | 6.708 | 49.101 | 1.00 | 57.62 | CPS5 |
| ATOM | 4474 | CE | LYS | 93 | 21.372 | 6.279 | 48.501 | 1.00 | 58.57 | CPS5 |
| ATOM | 4475 | NZ | LYS | 93 | 20.218 | 7.009 | 49.109 | 1.00 | 59.31 | CPS5 |
| ATOM | 4476 | C | LYS | 93 | 25.262 | 8.027 | 45.556 | 1.00 | 53.90 | CPS5 |
| ATOM | 4477 | O | LYS | 93 | 24.681 | 7.419 | 44.656 | 1.00 | 54.01 | CPS5 |
| ATOM | 4478 | N | LEU | 94 | 26.213 | 8.926 | 45.322 | 1.00 | 53.85 | CPS5 |
| ATOM | 4479 | CA | LEU | 94 | 26.605 | 9.283 | 43.967 | 1.00 | 54.05 | CPS5 |
| ATOM | 4480 | CB | LEU | 94 | 26.967 | 10.770 | 43.904 | 1.00 | 54.55 | CPS5 |
| ATOM | 4481 | CG | LEU | 94 | 26.620 | 11.562 | 42.640 | 1.00 | 54.80 | CPS5 |
| ATOM | 4482 | CD1 | LEU | 94 | 27.225 | 12.951 | 42.751 | 1.00 | 54.69 | CPS5 |
| ATOM | 4483 | CD2 | LEU | 94 | 27.143 | 10.857 | 41.405 | 1.00 | 55.41 | CPS5 |
| ATOM | 4484 | C | LEU | 94 | 27.780 | 8.466 | 43.452 | 1.00 | 54.05 | CPS5 |
| ATOM | 4485 | O | LEU | 94 | 28.797 | 8.322 | 44.130 | 1.00 | 54.64 | CPS5 |
| ATOM | 4486 | N | SER | 95 | 27.626 | 7.934 | 42.246 | 1.00 | 53.47 | CPS5 |
| ATOM | 4487 | CA | SER | 95 | 28.673 | 7.155 | 41.603 | 1.00 | 53.51 | CPS5 |
| ATOM | 4488 | CB | SER | 95 | 28.131 | 6.559 | 40.299 | 1.00 | 54.31 | CPS5 |
| ATOM | 4489 | OG | SER | 95 | 29.138 | 5.881 | 39.574 | 1.00 | 56.70 | CPS5 |
| ATOM | 4490 | C | SER | 95 | 29.812 | 8.134 | 41.315 | 1.00 | 52.59 | CPS5 |
| ATOM | 4491 | O | SER | 95 | 29.589 | 9.345 | 41.279 | 1.00 | 53.14 | CPS5 |
| ATOM | 4492 | N | PRO | 96 | 31.046 | 7.636 | 41.121 | 1.00 | 51.05 | CPS5 |
| ATOM | 4493 | CD | PRO | 96 | 31.511 | 6.248 | 40.992 | 1.00 | 51.64 | CPS5 |
| ATOM | 4494 | CA | PRO | 96 | 32.140 | 8.572 | 40.843 | 1.00 | 49.02 | CPS5 |
| ATOM | 4495 | CB | PRO | 96 | 33.252 | 7.670 | 40.285 | 1.00 | 50.01 | CPS5 |
| ATOM | 4496 | CG | PRO | 96 | 32.537 | 6.387 | 39.898 | 1.00 | 51.26 | CPS5 |
| ATOM | 4497 | C | PRO | 96 | 31.731 | 9.680 | 39.878 | 1.00 | 47.02 | CPS5 |
| ATOM | 4498 | O | PRO | 96 | 31.238 | 9.425 | 38.775 | 1.00 | 46.21 | CPS5 |
| ATOM | 4499 | N | ALA | 97 | 31.931 | 10.917 | 40.313 | 1.00 | 44.30 | CPS5 |
| ATOM | 4500 | CA | ALA | 97 | 31.566 | 12.063 | 39.499 | 1.00 | 41.77 | CPS5 |
| ATOM | 4501 | CB | ALA | 97 | 30.055 | 12.176 | 39.425 | 1.00 | 40.64 | CPS5 |
| ATOM | 4502 | C | ALA | 97 | 32.140 | 13.342 | 40.071 | 1.00 | 40.33 | CPS5 |

FIG. 1A-79

| ATOM | 4503 | O | ALA | 97 | 32.593 | 13.382 | 41.216 | 1.00 | 40.58 | CPS5 |
| ATOM | 4504 | N | ALA | 98 | 32.121 | 14.387 | 39.256 | 1.00 | 37.31 | CPS5 |
| ATOM | 4505 | CA | ALA | 98 | 32.597 | 15.688 | 39.676 | 1.00 | 34.75 | CPS5 |
| ATOM | 4506 | CB | ALA | 98 | 33.398 | 16.340 | 38.561 | 1.00 | 35.64 | CPS5 |
| ATOM | 4507 | C | ALA | 98 | 31.308 | 16.463 | 39.941 | 1.00 | 32.51 | CPS5 |
| ATOM | 4508 | O | ALA | 98 | 30.407 | 16.478 | 39.107 | 1.00 | 31.77 | CPS5 |
| ATOM | 4509 | N | VAL | 99 | 31.204 | 17.061 | 41.119 | 1.00 | 29.38 | CPS5 |
| ATOM | 4510 | CA | VAL | 99 | 30.017 | 17.823 | 41.476 | 1.00 | 26.77 | CPS5 |
| ATOM | 4511 | CB | VAL | 99 | 29.409 | 17.320 | 42.808 | 1.00 | 26.38 | CPS5 |
| ATOM | 4512 | CG1 | VAL | 99 | 28.128 | 18.089 | 43.132 | 1.00 | 25.70 | CPS5 |
| ATOM | 4513 | CG2 | VAL | 99 | 29.110 | 15.821 | 42.708 | 1.00 | 26.03 | CPS5 |
| ATOM | 4514 | C | VAL | 99 | 30.460 | 19.270 | 41.632 | 1.00 | 25.29 | CPS5 |
| ATOM | 4515 | O | VAL | 99 | 31.518 | 19.541 | 42.192 | 1.00 | 24.54 | CPS5 |
| ATOM | 4516 | N | HIS | 100 | 29.655 | 20.190 | 41.113 | 1.00 | 23.97 | CPS5 |
| ATOM | 4517 | CA | HIS | 100 | 29.949 | 21.615 | 41.203 | 1.00 | 23.10 | CPS5 |
| ATOM | 4518 | CB | HIS | 100 | 30.225 | 22.176 | 39.819 | 1.00 | 24.86 | CPS5 |
| ATOM | 4519 | CG | HIS | 100 | 31.328 | 21.468 | 39.105 | 1.00 | 26.57 | CPS5 |
| ATOM | 4520 | CD2 | HIS | 100 | 31.297 | 20.480 | 38.181 | 1.00 | 27.57 | CPS5 |
| ATOM | 4521 | ND1 | HIS | 100 | 32.660 | 21.719 | 39.358 | 1.00 | 28.54 | CPS5 |
| ATOM | 4522 | CE1 | HIS | 100 | 33.403 | 20.915 | 38.618 | 1.00 | 28.60 | CPS5 |
| ATOM | 4523 | NE2 | HIS | 100 | 32.599 | 20.155 | 37.894 | 1.00 | 28.27 | CPS5 |
| ATOM | 4524 | C | HIS | 100 | 28.728 | 22.293 | 41.791 | 1.00 | 22.08 | CPS5 |
| ATOM | 4525 | O | HIS | 100 | 27.602 | 21.917 | 41.475 | 1.00 | 21.49 | CPS5 |
| ATOM | 4526 | N | VAL | 101 | 28.944 | 23.288 | 42.640 | 1.00 | 20.70 | CPS5 |
| ATOM | 4527 | CA | VAL | 101 | 27.823 | 23.980 | 43.254 | 1.00 | 20.32 | CPS5 |
| ATOM | 4528 | CB | VAL | 101 | 27.503 | 23.372 | 44.672 | 1.00 | 21.79 | CPS5 |
| ATOM | 4529 | CG1 | VAL | 101 | 28.687 | 23.560 | 45.614 | 1.00 | 21.73 | CPS5 |
| ATOM | 4530 | CG2 | VAL | 101 | 26.253 | 24.021 | 45.281 | 1.00 | 20.57 | CPS5 |
| ATOM | 4531 | C | VAL | 101 | 28.137 | 25.462 | 43.385 | 1.00 | 20.62 | CPS5 |
| ATOM | 4532 | O | VAL | 101 | 29.299 | 25.863 | 43.370 | 1.00 | 20.26 | CPS5 |
| ATOM | 4533 | N | SER | 102 | 27.091 | 26.281 | 43.448 | 1.00 | 18.85 | CPS5 |
| ATOM | 4534 | CA | SER | 102 | 27.256 | 27.709 | 43.670 | 1.00 | 18.73 | CPS5 |
| ATOM | 4535 | CB | SER | 102 | 27.292 | 28.509 | 42.363 | 1.00 | 19.66 | CPS5 |
| ATOM | 4536 | OG | SER | 102 | 27.474 | 29.886 | 42.685 | 1.00 | 19.70 | CPS5 |
| ATOM | 4537 | C | SER | 102 | 26.037 | 28.118 | 44.489 | 1.00 | 19.25 | CPS5 |
| ATOM | 4538 | O | SER | 102 | 24.931 | 27.684 | 44.200 | 1.00 | 17.98 | CPS5 |
| ATOM | 4539 | N | ILE | 103 | 26.246 | 28.928 | 45.520 | 1.00 | 19.07 | CPS5 |
| ATOM | 4540 | CA | ILE | 103 | 25.153 | 29.374 | 46.377 | 1.00 | 20.39 | CPS5 |
| ATOM | 4541 | CB | ILE | 103 | 25.347 | 28.876 | 47.833 | 1.00 | 22.16 | CPS5 |
| ATOM | 4542 | CG2 | ILE | 103 | 24.216 | 29.404 | 48.736 | 1.00 | 22.36 | CPS5 |
| ATOM | 4543 | CG1 | ILE | 103 | 25.363 | 27.350 | 47.865 | 1.00 | 21.89 | CPS5 |
| ATOM | 4544 | CD1 | ILE | 103 | 25.821 | 26.762 | 49.214 | 1.00 | 24.06 | CPS5 |
| ATOM | 4545 | C | ILE | 103 | 25.157 | 30.892 | 46.358 | 1.00 | 21.36 | CPS5 |
| ATOM | 4546 | O | ILE | 103 | 26.225 | 31.512 | 46.304 | 1.00 | 21.80 | CPS5 |
| ATOM | 4547 | N | THR | 104 | 23.968 | 31.489 | 46.374 | 1.00 | 21.34 | CPS5 |
| ATOM | 4548 | CA | THR | 104 | 23.839 | 32.938 | 46.347 | 1.00 | 22.25 | CPS5 |
| ATOM | 4549 | CB | THR | 104 | 23.591 | 33.450 | 44.901 | 1.00 | 24.00 | CPS5 |
| ATOM | 4550 | OG1 | THR | 104 | 23.661 | 34.887 | 44.864 | 1.00 | 24.60 | CPS5 |
| ATOM | 4551 | CG2 | THR | 104 | 22.235 | 32.998 | 44.399 | 1.00 | 23.88 | CPS5 |
| ATOM | 4552 | C | THR | 104 | 22.705 | 33.376 | 47.276 | 1.00 | 23.21 | CPS5 |
| ATOM | 4553 | O | THR | 104 | 21.831 | 32.579 | 47.641 | 1.00 | 21.95 | CPS5 |
| ATOM | 4554 | N | HIS | 105 | 22.728 | 34.645 | 47.664 | 1.00 | 24.23 | CPS5 |
| ATOM | 4555 | CA | HIS | 105 | 21.723 | 35.181 | 48.578 | 1.00 | 26.22 | CPS5 |
| ATOM | 4556 | CB | HIS | 105 | 22.287 | 35.276 | 50.003 | 1.00 | 27.67 | CPS5 |
| ATOM | 4557 | CG | HIS | 105 | 22.810 | 33.988 | 50.555 | 1.00 | 30.95 | CPS5 |
| ATOM | 4558 | CD2 | HIS | 105 | 24.036 | 33.417 | 50.475 | 1.00 | 32.56 | CPS5 |
| ATOM | 4559 | ND1 | HIS | 105 | 22.046 | 33.146 | 51.333 | 1.00 | 32.46 | CPS5 |

FIG. 1A-80

```
ATOM   4560  CE1  HIS  105    22.777  32.114  51.713  1.00  32.44    CPS5
ATOM   4561  NE2  HIS  105    23.990  32.253  51.206  1.00  32.77    CPS5
ATOM   4562  C    HIS  105    21.291  36.596  48.218  1.00  25.94    CPS5
ATOM   4563  O    HIS  105    22.037  37.344  47.584  1.00  25.81    CPS5
ATOM   4564  N    THR  106    20.077  36.944  48.630  1.00  25.98    CPS5
ATOM   4565  CA   THR  106    19.569  38.305  48.498  1.00  26.59    CPS5
ATOM   4566  CB   THR  106    18.474  38.498  47.436  1.00  26.91    CPS5
ATOM   4567  OG1  THR  106    17.305  37.771  47.813  1.00  26.20    CPS5
ATOM   4568  CG2  THR  106    18.963  38.070  46.062  1.00  25.16    CPS5
ATOM   4569  C    THR  106    18.946  38.516  49.870  1.00  27.65    CPS5
ATOM   4570  O    THR  106    19.024  37.638  50.733  1.00  26.71    CPS5
ATOM   4571  N    LYS  107    18.330  39.667  50.086  1.00  28.18    CPS5
ATOM   4572  CA   LYS  107    17.716  39.938  51.377  1.00  29.86    CPS5
ATOM   4573  CB   LYS  107    17.103  41.345  51.366  1.00  32.21    CPS5
ATOM   4574  CG   LYS  107    16.495  41.791  52.690  1.00  36.65    CPS5
ATOM   4575  CD   LYS  107    15.848  43.171  52.540  1.00  40.32    CPS5
ATOM   4576  CE   LYS  107    15.282  43.682  53.860  1.00  42.28    CPS5
ATOM   4577  NZ   LYS  107    14.641  45.026  53.709  1.00  45.02    CPS5
ATOM   4578  C    LYS  107    16.645  38.910  51.754  1.00  29.02    CPS5
ATOM   4579  O    LYS  107    16.576  38.484  52.908  1.00  29.89    CPS5
ATOM   4580  N    GLU  108    15.830  38.495  50.785  1.00  27.24    CPS5
ATOM   4581  CA   GLU  108    14.733  37.568  51.063  1.00  26.97    CPS5
ATOM   4582  CB   GLU  108    13.428  38.156  50.525  1.00  29.17    CPS5
ATOM   4583  CG   GLU  108    13.129  39.552  51.030  1.00  35.90    CPS5
ATOM   4584  CD   GLU  108    11.758  40.043  50.612  1.00  40.16    CPS5
ATOM   4585  OE1  GLU  108    11.459  40.044  49.397  1.00  43.68    CPS5
ATOM   4586  OE2  GLU  108    10.975  40.436  51.505  1.00  44.69    CPS5
ATOM   4587  C    GLU  108    14.855  36.149  50.527  1.00  24.76    CPS5
ATOM   4588  O    GLU  108    14.007  35.300  50.823  1.00  23.74    CPS5
ATOM   4589  N    TYR  109    15.889  35.888  49.738  1.00  23.62    CPS5
ATOM   4590  CA   TYR  109    16.045  34.564  49.137  1.00  23.16    CPS5
ATOM   4591  CB   TYR  109    15.695  34.627  47.645  1.00  23.09    CPS5
ATOM   4592  CG   TYR  109    14.286  35.052  47.352  1.00  23.49    CPS5
ATOM   4593  CD1  TYR  109    13.243  34.135  47.403  1.00  24.28    CPS5
ATOM   4594  CE1  TYR  109    11.931  34.529  47.199  1.00  24.85    CPS5
ATOM   4595  CD2  TYR  109    13.982  36.390  47.080  1.00  26.20    CPS5
ATOM   4596  CE2  TYR  109    12.667  36.797  46.874  1.00  25.83    CPS5
ATOM   4597  CZ   TYR  109    11.648  35.861  46.937  1.00  25.55    CPS5
ATOM   4598  OH   TYR  109    10.341  36.243  46.769  1.00  26.59    CPS5
ATOM   4599  C    TYR  109    17.438  33.976  49.230  1.00  22.83    CPS5
ATOM   4600  O    TYR  109    18.421  34.691  49.403  1.00  23.71    CPS5
ATOM   4601  N    ALA  110    17.490  32.650  49.128  1.00  21.41    CPS5
ATOM   4602  CA   ALA  110    18.744  31.912  49.055  1.00  21.16    CPS5
ATOM   4603  CB   ALA  110    18.924  30.988  50.258  1.00  20.41    CPS5
ATOM   4604  C    ALA  110    18.536  31.089  47.785  1.00  20.71    CPS5
ATOM   4605  O    ALA  110    17.415  30.635  47.508  1.00  21.39    CPS5
ATOM   4606  N    ALA  111    19.589  30.915  46.991  1.00  19.32    CPS5
ATOM   4607  CA   ALA  111    19.467  30.131  45.771  1.00  18.05    CPS5
ATOM   4608  CB   ALA  111    19.215  31.033  44.575  1.00  18.98    CPS5
ATOM   4609  C    ALA  111    20.734  29.344  45.550  1.00  19.39    CPS5
ATOM   4610  O    ALA  111    21.800  29.707  46.050  1.00  18.83    CPS5
ATOM   4611  N    ALA  112    20.623  28.269  44.786  1.00  18.45    CPS5
ATOM   4612  CA   ALA  112    21.784  27.451  44.508  1.00  19.52    CPS5
ATOM   4613  CB   ALA  112    22.008  26.481  45.655  1.00  19.65    CPS5
ATOM   4614  C    ALA  112    21.617  26.679  43.212  1.00  18.81    CPS5
ATOM   4615  O    ALA  112    20.502  26.442  42.764  1.00  17.20    CPS5
ATOM   4616  N    GLN  113    22.733  26.311  42.599  1.00  19.37    CPS5
```

FIG. 1A-81

| ATOM | 4617 | CA | GLN | 113 | 22.663 | 25.499 | 41.400 | 1.00 | 20.01 | CPS5 |
|---|---|---|---|---|---|---|---|---|---|---|
| ATOM | 4618 | CB | GLN | 113 | 22.890 | 26.321 | 40.135 | 1.00 | 23.47 | CPS5 |
| ATOM | 4619 | CG | GLN | 113 | 24.249 | 26.942 | 40.040 | 1.00 | 26.43 | CPS5 |
| ATOM | 4620 | CD | GLN | 113 | 24.463 | 27.640 | 38.705 | 1.00 | 30.41 | CPS5 |
| ATOM | 4621 | OE1 | GLN | 113 | 25.506 | 28.234 | 38.467 | 1.00 | 29.83 | CPS5 |
| ATOM | 4622 | NE2 | GLN | 113 | 23.466 | 27.567 | 37.831 | 1.00 | 33.75 | CPS5 |
| ATOM | 4623 | C | GLN | 113 | 23.735 | 24.439 | 41.518 | 1.00 | 19.96 | CPS5 |
| ATOM | 4624 | O | GLN | 113 | 24.753 | 24.633 | 42.177 | 1.00 | 19.44 | CPS5 |
| ATOM | 4625 | N | VAL | 114 | 23.504 | 23.312 | 40.869 | 1.00 | 19.35 | CPS5 |
| ATOM | 4626 | CA | VAL | 114 | 24.462 | 22.221 | 40.924 | 1.00 | 19.11 | CPS5 |
| ATOM | 4627 | CB | VAL | 114 | 23.960 | 21.111 | 41.897 | 1.00 | 18.72 | CPS5 |
| ATOM | 4628 | CG1 | VAL | 114 | 24.791 | 19.828 | 41.721 | 1.00 | 20.30 | CPS5 |
| ATOM | 4629 | CG2 | VAL | 114 | 24.043 | 21.603 | 43.344 | 1.00 | 20.16 | CPS5 |
| ATOM | 4630 | C | VAL | 114 | 24.589 | 21.611 | 39.538 | 1.00 | 19.40 | CPS5 |
| ATOM | 4631 | O | VAL | 114 | 23.618 | 21.590 | 38.781 | 1.00 | 19.86 | CPS5 |
| ATOM | 4632 | N | VAL | 115 | 25.792 | 21.159 | 39.201 | 1.00 | 19.59 | CPS5 |
| ATOM | 4633 | CA | VAL | 115 | 26.017 | 20.436 | 37.956 | 1.00 | 19.26 | CPS5 |
| ATOM | 4634 | CB | VAL | 115 | 26.879 | 21.202 | 36.928 | 1.00 | 20.70 | CPS5 |
| ATOM | 4635 | CG1 | VAL | 115 | 27.182 | 20.280 | 35.725 | 1.00 | 19.97 | CPS5 |
| ATOM | 4636 | CG2 | VAL | 115 | 26.131 | 22.443 | 36.433 | 1.00 | 19.15 | CPS5 |
| ATOM | 4637 | C | VAL | 115 | 26.780 | 19.172 | 38.359 | 1.00 | 22.16 | CPS5 |
| ATOM | 4638 | O | VAL | 115 | 27.765 | 19.248 | 39.092 | 1.00 | 21.19 | CPS5 |
| ATOM | 4639 | N | ILE | 116 | 26.291 | 18.018 | 37.920 | 1.00 | 23.19 | CPS5 |
| ATOM | 4640 | CA | ILE | 116 | 26.965 | 16.749 | 38.201 | 1.00 | 25.23 | CPS5 |
| ATOM | 4641 | CB | ILE | 116 | 25.983 | 15.681 | 38.761 | 1.00 | 24.21 | CPS5 |
| ATOM | 4642 | CG2 | ILE | 116 | 26.717 | 14.347 | 38.952 | 1.00 | 24.03 | CPS5 |
| ATOM | 4643 | CG1 | ILE | 116 | 25.401 | 16.139 | 40.106 | 1.00 | 24.21 | CPS5 |
| ATOM | 4644 | CD1 | ILE | 116 | 24.294 | 15.209 | 40.635 | 1.00 | 22.70 | CPS5 |
| ATOM | 4645 | C | ILE | 116 | 27.521 | 16.243 | 36.866 | 1.00 | 26.72 | CPS5 |
| ATOM | 4646 | O | ILE | 116 | 26.788 | 16.165 | 35.881 | 1.00 | 25.85 | CPS5 |
| ATOM | 4647 | N | GLU | 117 | 28.809 | 15.914 | 36.835 | 1.00 | 30.40 | CPS5 |
| ATOM | 4648 | CA | GLU | 117 | 29.447 | 15.401 | 35.615 | 1.00 | 35.53 | CPS5 |
| ATOM | 4649 | CB | GLU | 117 | 30.792 | 16.064 | 35.352 | 1.00 | 36.89 | CPS5 |
| ATOM | 4650 | CG | GLU | 117 | 30.816 | 17.554 | 35.274 | 1.00 | 39.07 | CPS5 |
| ATOM | 4651 | CD | GLU | 117 | 32.168 | 18.036 | 34.808 | 1.00 | 39.75 | CPS5 |
| ATOM | 4652 | OE1 | GLU | 117 | 32.457 | 17.877 | 33.605 | 1.00 | 40.89 | CPS5 |
| ATOM | 4653 | OE2 | GLU | 117 | 32.948 | 18.547 | 35.641 | 1.00 | 40.65 | CPS5 |
| ATOM | 4654 | C | GLU | 117 | 29.735 | 13.915 | 35.771 | 1.00 | 38.76 | CPS5 |
| ATOM | 4655 | O | GLU | 117 | 30.317 | 13.501 | 36.782 | 1.00 | 38.92 | CPS5 |
| ATOM | 4656 | N | ALA | 118 | 29.364 | 13.131 | 34.761 | 1.00 | 41.50 | CPS5 |
| ATOM | 4657 | CA | ALA | 118 | 29.596 | 11.689 | 34.784 | 1.00 | 44.75 | CPS5 |
| ATOM | 4658 | CB | ALA | 118 | 29.047 | 11.049 | 33.508 | 1.00 | 45.12 | CPS5 |
| ATOM | 4659 | C | ALA | 118 | 31.095 | 11.422 | 34.899 | 1.00 | 46.14 | CPS5 |
| ATOM | 4660 | OT1 | ALA | 118 | 31.885 | 12.266 | 34.413 | 1.00 | 46.30 | CPS5 |
| ATOM | 4661 | OT2 | ALA | 118 | 31.460 | 10.367 | 35.466 | 1.00 | 48.44 | CPS5 |
| ATOM | 4662 | C | GLY | 1 | 34.929 | 20.508 | 32.382 | 1.00 | 33.16 | CPS6 |
| ATOM | 4663 | O | GLY | 1 | 35.455 | 21.500 | 31.885 | 1.00 | 34.15 | CPS6 |
| ATOM | 4664 | N | GLY | 1 | 36.363 | 18.424 | 32.401 | 1.00 | 38.41 | CPS6 |
| ATOM | 4665 | CA | GLY | 1 | 35.171 | 19.118 | 31.815 | 1.00 | 34.91 | CPS6 |
| ATOM | 4666 | N | ILE | 2 | 34.133 | 20.587 | 33.435 | 1.00 | 30.97 | CPS6 |
| ATOM | 4667 | CA | ILE | 2 | 33.824 | 21.875 | 34.039 | 1.00 | 28.64 | CPS6 |
| ATOM | 4668 | CB | ILE | 2 | 32.405 | 21.855 | 34.627 | 1.00 | 27.89 | CPS6 |
| ATOM | 4669 | CG2 | ILE | 2 | 32.168 | 23.101 | 35.474 | 1.00 | 27.12 | CPS6 |
| ATOM | 4670 | CG1 | ILE | 2 | 31.386 | 21.726 | 33.490 | 1.00 | 28.03 | CPS6 |
| ATOM | 4671 | CD1 | ILE | 2 | 29.965 | 21.432 | 33.954 | 1.00 | 28.46 | CPS6 |
| ATOM | 4672 | C | ILE | 2 | 34.810 | 22.262 | 35.134 | 1.00 | 28.03 | CPS6 |
| ATOM | 4673 | O | ILE | 2 | 35.117 | 21.463 | 36.011 | 1.00 | 27.12 | CPS6 |

FIG. 1A-82

| | | | | | | | | | |
|---|---|---|---|---|---|---|---|---|---|
| ATOM | 4674 | N | TYR | 3 | 35.305 | 23.492 | 35.080 | 1.00 26.59 | CPS6 |
| ATOM | 4675 | CA | TYR | 3 | 36.234 | 23.970 | 36.101 | 1.00 26.25 | CPS6 |
| ATOM | 4676 | CB | TYR | 3 | 37.102 | 25.091 | 35.540 | 1.00 27.53 | CPS6 |
| ATOM | 4677 | CG | TYR | 3 | 38.027 | 25.703 | 36.570 | 1.00 31.25 | CPS6 |
| ATOM | 4678 | CD1 | TYR | 3 | 39.171 | 25.027 | 36.999 | 1.00 32.43 | CPS6 |
| ATOM | 4679 | CE1 | TYR | 3 | 40.006 | 25.568 | 37.978 | 1.00 35.68 | CPS6 |
| ATOM | 4680 | CD2 | TYR | 3 | 37.738 | 26.937 | 37.146 | 1.00 31.55 | CPS6 |
| ATOM | 4681 | CE2 | TYR | 3 | 38.563 | 27.489 | 38.126 | 1.00 35.40 | CPS6 |
| ATOM | 4682 | CZ | TYR | 3 | 39.697 | 26.800 | 38.537 | 1.00 36.39 | CPS6 |
| ATOM | 4683 | OH | TYR | 3 | 40.525 | 27.355 | 39.488 | 1.00 39.51 | CPS6 |
| ATOM | 4684 | C | TYR | 3 | 35.451 | 24.482 | 37.316 | 1.00 25.81 | CPS6 |
| ATOM | 4685 | O | TYR | 3 | 35.762 | 24.145 | 38.469 | 1.00 24.16 | CPS6 |
| ATOM | 4686 | N | GLY | 4 | 34.437 | 25.301 | 37.058 | 1.00 22.42 | CPS6 |
| ATOM | 4687 | CA | GLY | 4 | 33.630 | 25.823 | 38.147 | 1.00 22.32 | CPS6 |
| ATOM | 4688 | C | GLY | 4 | 32.365 | 26.494 | 37.642 | 1.00 20.34 | CPS6 |
| ATOM | 4689 | O | GLY | 4 | 32.280 | 26.799 | 36.461 | 1.00 19.69 | CPS6 |
| ATOM | 4690 | N | ILE | 5 | 31.389 | 26.704 | 38.525 | 1.00 20.01 | CPS6 |
| ATOM | 4691 | CA | ILE | 5 | 30.140 | 27.366 | 38.143 | 1.00 20.35 | CPS6 |
| ATOM | 4692 | CB | ILE | 5 | 28.947 | 26.382 | 38.097 | 1.00 20.14 | CPS6 |
| ATOM | 4693 | CG2 | ILE | 5 | 29.291 | 25.224 | 37.159 | 1.00 19.26 | CPS6 |
| ATOM | 4694 | CG1 | ILE | 5 | 28.600 | 25.876 | 39.507 | 1.00 19.61 | CPS6 |
| ATOM | 4695 | CD1 | ILE | 5 | 27.418 | 24.871 | 39.535 | 1.00 21.63 | CPS6 |
| ATOM | 4696 | C | ILE | 5 | 29.832 | 28.481 | 39.119 | 1.00 20.43 | CPS6 |
| ATOM | 4697 | O | ILE | 5 | 30.337 | 28.505 | 40.242 | 1.00 20.18 | CPS6 |
| ATOM | 4698 | N | GLY | 6 | 29.009 | 29.426 | 38.686 | 1.00 19.58 | CPS6 |
| ATOM | 4699 | CA | GLY | 6 | 28.681 | 30.532 | 39.560 | 1.00 19.69 | CPS6 |
| ATOM | 4700 | C | GLY | 6 | 27.279 | 31.023 | 39.287 | 1.00 19.25 | CPS6 |
| ATOM | 4701 | O | GLY | 6 | 26.842 | 31.080 | 38.135 | 1.00 17.69 | CPS6 |
| ATOM | 4702 | N | LEU | 7 | 26.581 | 31.374 | 40.358 | 1.00 19.31 | CPS6 |
| ATOM | 4703 | CA | LEU | 7 | 25.214 | 31.865 | 40.262 | 1.00 20.65 | CPS6 |
| ATOM | 4704 | CB | LEU | 7 | 24.249 | 30.808 | 40.811 | 1.00 20.48 | CPS6 |
| ATOM | 4705 | CG | LEU | 7 | 22.781 | 31.222 | 40.967 | 1.00 21.08 | CPS6 |
| ATOM | 4706 | CD1 | LEU | 7 | 22.175 | 31.455 | 39.576 | 1.00 22.40 | CPS6 |
| ATOM | 4707 | CD2 | LEU | 7 | 22.017 | 30.132 | 41.724 | 1.00 21.05 | CPS6 |
| ATOM | 4708 | C | LEU | 7 | 25.108 | 33.114 | 41.116 | 1.00 20.36 | CPS6 |
| ATOM | 4709 | O | LEU | 7 | 25.687 | 33.180 | 42.193 | 1.00 21.58 | CPS6 |
| ATOM | 4710 | N | ASP | 8 | 24.387 | 34.114 | 40.631 | 1.00 20.16 | CPS6 |
| ATOM | 4711 | CA | ASP | 8 | 24.188 | 35.310 | 41.423 | 1.00 21.86 | CPS6 |
| ATOM | 4712 | CB | ASP | 8 | 25.261 | 36.368 | 41.151 | 1.00 23.79 | CPS6 |
| ATOM | 4713 | CG | ASP | 8 | 25.018 | 37.637 | 41.948 | 1.00 26.23 | CPS6 |
| ATOM | 4714 | OD1 | ASP | 8 | 24.287 | 38.523 | 41.462 | 1.00 26.66 | CPS6 |
| ATOM | 4715 | OD2 | ASP | 8 | 25.523 | 37.725 | 43.081 | 1.00 27.19 | CPS6 |
| ATOM | 4716 | C | ASP | 8 | 22.838 | 35.935 | 41.173 | 1.00 21.30 | CPS6 |
| ATOM | 4717 | O | ASP | 8 | 22.379 | 35.977 | 40.041 | 1.00 20.01 | CPS6 |
| ATOM | 4718 | N | ILE | 9 | 22.184 | 36.384 | 42.242 | 1.00 20.98 | CPS6 |
| ATOM | 4719 | CA | ILE | 9 | 20.911 | 37.081 | 42.099 | 1.00 20.91 | CPS6 |
| ATOM | 4720 | CB | ILE | 9 | 19.733 | 36.347 | 42.787 | 1.00 21.99 | CPS6 |
| ATOM | 4721 | CG2 | ILE | 9 | 18.456 | 37.172 | 42.639 | 1.00 20.05 | CPS6 |
| ATOM | 4722 | CG1 | ILE | 9 | 19.543 | 34.963 | 42.159 | 1.00 20.50 | CPS6 |
| ATOM | 4723 | CD1 | ILE | 9 | 18.405 | 34.165 | 42.754 | 1.00 21.55 | CPS6 |
| ATOM | 4724 | C | ILE | 9 | 21.160 | 38.402 | 42.803 | 1.00 22.15 | CPS6 |
| ATOM | 4725 | O | ILE | 9 | 21.683 | 38.420 | 43.918 | 1.00 23.20 | CPS6 |
| ATOM | 4726 | N | THR | 10 | 20.813 | 39.505 | 42.148 | 1.00 24.06 | CPS6 |
| ATOM | 4727 | CA | THR | 10 | 21.033 | 40.826 | 42.722 | 1.00 25.03 | CPS6 |
| ATOM | 4728 | CB | THR | 10 | 22.125 | 41.578 | 41.915 | 1.00 27.35 | CPS6 |
| ATOM | 4729 | OG1 | THR | 10 | 23.375 | 40.882 | 42.054 | 1.00 27.27 | CPS6 |
| ATOM | 4730 | CG2 | THR | 10 | 22.299 | 43.006 | 42.413 | 1.00 28.83 | CPS6 |

FIG. 1A-83

| ATOM | 4731 | C | THR | 10 | 19.734 | 41.626 | 42.734 | 1.00 | 25.30 | CPS6 |
|---|---|---|---|---|---|---|---|---|---|---|
| ATOM | 4732 | O | THR | 10 | 18.978 | 41.620 | 41.762 | 1.00 | 24.09 | CPS6 |
| ATOM | 4733 | N | GLU | 11 | 19.475 | 42.290 | 43.857 | 1.00 | 24.60 | CPS6 |
| ATOM | 4734 | CA | GLU | 11 | 18.278 | 43.112 | 44.025 | 1.00 | 25.85 | CPS6 |
| ATOM | 4735 | CB | GLU | 11 | 18.012 | 43.306 | 45.525 | 1.00 | 26.85 | CPS6 |
| ATOM | 4736 | CG | GLU | 11 | 16.635 | 43.843 | 45.872 | 1.00 | 30.57 | CPS6 |
| ATOM | 4737 | CD | GLU | 11 | 16.506 | 44.224 | 47.342 | 1.00 | 33.54 | CPS6 |
| ATOM | 4738 | OE1 | GLU | 11 | 17.435 | 43.928 | 48.136 | 1.00 | 34.46 | CPS6 |
| ATOM | 4739 | OE2 | GLU | 11 | 15.469 | 44.821 | 47.701 | 1.00 | 34.21 | CPS6 |
| ATOM | 4740 | C | GLU | 11 | 18.533 | 44.467 | 43.354 | 1.00 | 25.21 | CPS6 |
| ATOM | 4741 | O | GLU | 11 | 19.499 | 45.150 | 43.694 | 1.00 | 26.16 | CPS6 |
| ATOM | 4742 | N | LEU | 12 | 17.687 | 44.855 | 42.402 | 1.00 | 26.01 | CPS6 |
| ATOM | 4743 | CA | LEU | 12 | 17.870 | 46.138 | 41.713 | 1.00 | 28.08 | CPS6 |
| ATOM | 4744 | CB | LEU | 12 | 16.733 | 46.381 | 40.707 | 1.00 | 28.52 | CPS6 |
| ATOM | 4745 | CG | LEU | 12 | 16.880 | 45.889 | 39.264 | 1.00 | 31.49 | CPS6 |
| ATOM | 4746 | CD1 | LEU | 12 | 17.467 | 44.495 | 39.234 | 1.00 | 30.71 | CPS6 |
| ATOM | 4747 | CD2 | LEU | 12 | 15.530 | 45.921 | 38.573 | 1.00 | 32.17 | CPS6 |
| ATOM | 4748 | C | LEU | 12 | 17.926 | 47.301 | 42.708 | 1.00 | 29.26 | CPS6 |
| ATOM | 4749 | O | LEU | 12 | 18.732 | 48.223 | 42.553 | 1.00 | 29.98 | CPS6 |
| ATOM | 4750 | N | ALA | 13 | 17.067 | 47.258 | 43.725 | 1.00 | 29.78 | CPS6 |
| ATOM | 4751 | CA | ALA | 13 | 17.027 | 48.315 | 44.733 | 1.00 | 30.29 | CPS6 |
| ATOM | 4752 | CB | ALA | 13 | 15.901 | 48.042 | 45.741 | 1.00 | 31.01 | CPS6 |
| ATOM | 4753 | C | ALA | 13 | 18.364 | 48.447 | 45.460 | 1.00 | 31.44 | CPS6 |
| ATOM | 4754 | O | ALA | 13 | 18.774 | 49.551 | 45.825 | 1.00 | 31.56 | CPS6 |
| ATOM | 4755 | N | ARG | 14 | 19.048 | 47.327 | 45.669 | 1.00 | 32.19 | CPS6 |
| ATOM | 4756 | CA | ARG | 14 | 20.338 | 47.357 | 46.352 | 1.00 | 32.76 | CPS6 |
| ATOM | 4757 | CB | ARG | 14 | 20.745 | 45.940 | 46.768 | 1.00 | 35.66 | CPS6 |
| ATOM | 4758 | CG | ARG | 14 | 22.097 | 45.852 | 47.437 | 1.00 | 39.95 | CPS6 |
| ATOM | 4759 | CD | ARG | 14 | 22.314 | 44.493 | 48.078 | 1.00 | 42.90 | CPS6 |
| ATOM | 4760 | NE | ARG | 14 | 23.727 | 44.261 | 48.363 | 1.00 | 46.95 | CPS6 |
| ATOM | 4761 | CZ | ARG | 14 | 24.577 | 43.675 | 47.524 | 1.00 | 48.91 | CPS6 |
| ATOM | 4762 | NH1 | ARG | 14 | 24.163 | 43.247 | 46.338 | 1.00 | 50.22 | CPS6 |
| ATOM | 4763 | NH2 | ARG | 14 | 25.850 | 43.523 | 47.868 | 1.00 | 50.46 | CPS6 |
| ATOM | 4764 | C | ARG | 14 | 21.415 | 48.002 | 45.469 | 1.00 | 32.36 | CPS6 |
| ATOM | 4765 | O | ARG | 14 | 22.268 | 48.747 | 45.961 | 1.00 | 31.82 | CPS6 |
| ATOM | 4766 | N | ILE | 15 | 21.381 | 47.719 | 44.171 | 1.00 | 31.44 | CPS6 |
| ATOM | 4767 | CA | ILE | 15 | 22.337 | 48.326 | 43.247 | 1.00 | 31.99 | CPS6 |
| ATOM | 4768 | CB | ILE | 15 | 22.153 | 47.777 | 41.817 | 1.00 | 32.07 | CPS6 |
| ATOM | 4769 | CG2 | ILE | 15 | 22.311 | 48.638 | 40.813 | 1.00 | 31.65 | CPS6 |
| ATOM | 4770 | CG1 | ILE | 15 | 22.655 | 46.333 | 41.752 | 1.00 | 32.16 | CPS6 |
| ATOM | 4771 | CD1 | ILE | 15 | 24.156 | 46.184 | 42.013 | 1.00 | 33.75 | CPS6 |
| ATOM | 4772 | C | ILE | 15 | 22.113 | 49.843 | 43.236 | 1.00 | 32.92 | CPS6 |
| ATOM | 4773 | O | ILE | 15 | 23.062 | 50.627 | 43.265 | 1.00 | 32.09 | CPS6 |
| ATOM | 4774 | N | ALA | 16 | 20.851 | 50.254 | 43.201 | 1.00 | 33.77 | CPS6 |
| ATOM | 4775 | CA | ALA | 16 | 20.520 | 51.677 | 43.194 | 1.00 | 36.34 | CPS6 |
| ATOM | 4776 | CB | ALA | 16 | 19.014 | 51.860 | 43.063 | 1.00 | 36.06 | CPS6 |
| ATOM | 4777 | C | ALA | 16 | 21.030 | 52.356 | 44.467 | 1.00 | 38.13 | CPS6 |
| ATOM | 4778 | O | ALA | 16 | 21.491 | 53.498 | 44.427 | 1.00 | 38.48 | CPS6 |
| ATOM | 4779 | N | SER | 17 | 20.951 | 51.648 | 45.590 | 1.00 | 40.20 | CPS6 |
| ATOM | 4780 | CA | SER | 17 | 21.415 | 52.175 | 46.871 | 1.00 | 43.01 | CPS6 |
| ATOM | 4781 | CB | SER | 17 | 20.959 | 51.268 | 48.017 | 1.00 | 43.08 | CPS6 |
| ATOM | 4782 | OG | SER | 17 | 19.549 | 51.302 | 48.157 | 1.00 | 45.35 | CPS6 |
| ATOM | 4783 | C | SER | 17 | 22.934 | 52.320 | 46.919 | 1.00 | 44.34 | CPS6 |
| ATOM | 4784 | O | SER | 17 | 23.456 | 53.311 | 47.432 | 1.00 | 44.28 | CPS6 |
| ATOM | 4785 | N | MET | 18 | 23.644 | 51.323 | 46.402 | 1.00 | 45.43 | CPS6 |
| ATOM | 4786 | CA | MET | 18 | 25.100 | 51.370 | 46.390 | 1.00 | 47.02 | CPS6 |
| ATOM | 4787 | CB | MET | 18 | 25.678 | 50.035 | 45.917 | 1.00 | 48.11 | CPS6 |

FIG. 1A-84

| ATOM | 4788 | CG | MET | 18 | 25.502 | 48.901 | 46.906 | 1.00 | 49.87 | CPS6 |
|---|---|---|---|---|---|---|---|---|---|---|
| ATOM | 4789 | SD | MET | 18 | 26.307 | 47.401 | 46.338 | 1.00 | 54.02 | CPS6 |
| ATOM | 4790 | CE | MET | 18 | 24.997 | 46.663 | 45.390 | 1.00 | 52.20 | CPS6 |
| ATOM | 4791 | C | MET | 18 | 25.586 | 52.485 | 45.475 | 1.00 | 47.28 | CPS6 |
| ATOM | 4792 | O | MET | 18 | 26.533 | 53.196 | 45.799 | 1.00 | 47.27 | CPS6 |
| ATOM | 4793 | N | ALA | 19 | 24.923 | 52.636 | 44.334 | 1.00 | 47.28 | CPS6 |
| ATOM | 4794 | CA | ALA | 19 | 25.284 | 53.658 | 43.361 | 1.00 | 48.35 | CPS6 |
| ATOM | 4795 | CB | ALA | 19 | 24.558 | 53.397 | 42.049 | 1.00 | 47.94 | CPS6 |
| ATOM | 4796 | C | ALA | 19 | 24.956 | 55.059 | 43.867 | 1.00 | 49.67 | CPS6 |
| ATOM | 4797 | O | ALA | 19 | 25.644 | 56.031 | 43.539 | 1.00 | 48.84 | CPS6 |
| ATOM | 4798 | N | GLY | 20 | 23.895 | 55.159 | 44.659 | 1.00 | 50.28 | CPS6 |
| ATOM | 4799 | CA | GLY | 20 | 23.501 | 56.448 | 45.188 | 1.00 | 52.81 | CPS6 |
| ATOM | 4800 | C | GLY | 20 | 24.379 | 56.884 | 46.342 | 1.00 | 53.84 | CPS6 |
| ATOM | 4801 | O | GLY | 20 | 24.504 | 58.077 | 46.612 | 1.00 | 54.96 | CPS6 |
| ATOM | 4802 | N | ARG | 21 | 24.996 | 55.919 | 47.017 | 1.00 | 54.88 | CPS6 |
| ATOM | 4803 | CA | ARG | 21 | 25.853 | 56.215 | 48.157 | 1.00 | 56.13 | CPS6 |
| ATOM | 4804 | CB | ARG | 21 | 25.694 | 55.134 | 49.228 | 1.00 | 57.83 | CPS6 |
| ATOM | 4805 | CG | ARG | 21 | 24.308 | 55.086 | 49.857 | 1.00 | 60.18 | CPS6 |
| ATOM | 4806 | CD | ARG | 21 | 24.275 | 54.226 | 51.123 | 1.00 | 62.40 | CPS6 |
| ATOM | 4807 | NE | ARG | 21 | 24.085 | 52.797 | 50.866 | 1.00 | 64.82 | CPS6 |
| ATOM | 4808 | CZ | ARG | 21 | 25.003 | 51.979 | 50.352 | 1.00 | 65.81 | CPS6 |
| ATOM | 4809 | NH1 | ARG | 21 | 26.207 | 52.434 | 50.024 | 1.00 | 66.03 | CPS6 |
| ATOM | 4810 | NH2 | ARG | 21 | 24.714 | 50.695 | 50.175 | 1.00 | 65.70 | CPS6 |
| ATOM | 4811 | C | ARG | 21 | 27.327 | 56.359 | 47.802 | 1.00 | 56.17 | CPS6 |
| ATOM | 4812 | O | ARG | 21 | 28.113 | 56.882 | 48.591 | 1.00 | 56.98 | CPS6 |
| ATOM | 4813 | N | GLN | 22 | 27.710 | 55.896 | 46.619 | 1.00 | 55.40 | CPS6 |
| ATOM | 4814 | CA | GLN | 22 | 29.104 | 55.992 | 46.207 | 1.00 | 54.24 | CPS6 |
| ATOM | 4815 | CB | GLN | 22 | 29.637 | 54.619 | 45.795 | 1.00 | 55.16 | CPS6 |
| ATOM | 4816 | CG | GLN | 22 | 29.456 | 53.533 | 46.836 | 1.00 | 57.52 | CPS6 |
| ATOM | 4817 | CD | GLN | 22 | 30.179 | 52.251 | 46.467 | 1.00 | 58.37 | CPS6 |
| ATOM | 4818 | OE1 | GLN | 22 | 30.060 | 51.236 | 47.154 | 1.00 | 59.62 | CPS6 |
| ATOM | 4819 | NE2 | GLN | 22 | 30.940 | 52.294 | 45.378 | 1.00 | 59.05 | CPS6 |
| ATOM | 4820 | C | GLN | 22 | 29.281 | 56.953 | 45.044 | 1.00 | 52.16 | CPS6 |
| ATOM | 4821 | O | GLN | 22 | 28.312 | 57.363 | 44.402 | 1.00 | 51.84 | CPS6 |
| ATOM | 4822 | N | LYS | 23 | 30.531 | 57.325 | 44.793 | 1.00 | 49.79 | CPS6 |
| ATOM | 4823 | CA | LYS | 23 | 30.848 | 58.203 | 43.679 | 1.00 | 47.03 | CPS6 |
| ATOM | 4824 | CB | LYS | 23 | 31.906 | 59.240 | 44.078 | 1.00 | 48.67 | CPS6 |
| ATOM | 4825 | CG | LYS | 23 | 32.117 | 60.319 | 43.025 | 1.00 | 50.00 | CPS6 |
| ATOM | 4826 | CD | LYS | 23 | 33.404 | 61.106 | 43.232 | 1.00 | 51.39 | CPS6 |
| ATOM | 4827 | CE | LYS | 23 | 33.384 | 61.925 | 44.506 | 1.00 | 52.42 | CPS6 |
| ATOM | 4828 | NZ | LYS | 23 | 34.570 | 62.835 | 44.558 | 1.00 | 53.74 | CPS6 |
| ATOM | 4829 | C | LYS | 23 | 31.406 | 57.280 | 42.595 | 1.00 | 43.64 | CPS6 |
| ATOM | 4830 | O | LYS | 23 | 32.259 | 56.433 | 42.866 | 1.00 | 43.39 | CPS6 |
| ATOM | 4831 | N | ARG | 24 | 30.898 | 57.421 | 41.379 | 1.00 | 40.62 | CPS6 |
| ATOM | 4832 | CA | ARG | 24 | 31.363 | 56.603 | 40.266 | 1.00 | 38.09 | CPS6 |
| ATOM | 4833 | CB | ARG | 24 | 32.806 | 56.991 | 39.919 | 1.00 | 38.24 | CPS6 |
| ATOM | 4834 | CG | ARG | 24 | 32.935 | 58.400 | 39.340 | 1.00 | 38.55 | CPS6 |
| ATOM | 4835 | CD | ARG | 24 | 34.348 | 58.672 | 38.853 | 1.00 | 38.30 | CPS6 |
| ATOM | 4836 | NE | ARG | 24 | 35.297 | 58.859 | 39.948 | 1.00 | 39.05 | CPS6 |
| ATOM | 4837 | CZ | ARG | 24 | 35.511 | 60.019 | 40.561 | 1.00 | 39.71 | CPS6 |
| ATOM | 4838 | NH1 | ARG | 24 | 34.846 | 61.108 | 40.190 | 1.00 | 39.61 | CPS6 |
| ATOM | 4839 | NH2 | ARG | 24 | 36.396 | 60.092 | 41.543 | 1.00 | 39.47 | CPS6 |
| ATOM | 4840 | C | ARG | 24 | 31.266 | 55.086 | 40.500 | 1.00 | 35.99 | CPS6 |
| ATOM | 4841 | O | ARG | 24 | 32.202 | 54.339 | 40.206 | 1.00 | 34.55 | CPS6 |
| ATOM | 4842 | N | PHE | 25 | 30.135 | 54.627 | 41.026 | 1.00 | 33.55 | CPS6 |
| ATOM | 4843 | CA | PHE | 25 | 29.959 | 53.196 | 41.251 | 1.00 | 31.77 | CPS6 |
| ATOM | 4844 | CB | PHE | 25 | 28.647 | 52.938 | 42.012 | 1.00 | 32.24 | CPS6 |

FIG. 1A-85

| | | | | | | | | | |
|---|---|---|---|---|---|---|---|---|---|
| ATOM | 4845 | CG | PHE | 25 | 28.331 | 51.481 | 42.211 | 1.00 31.39 | CPS6 |
| ATOM | 4846 | CD1 | PHE | 25 | 27.306 | 50.879 | 41.495 | 1.00 33.76 | CPS6 |
| ATOM | 4847 | CD2 | PHE | 25 | 29.069 | 50.709 | 43.102 | 1.00 32.67 | CPS6 |
| ATOM | 4848 | CE1 | PHE | 25 | 27.021 | 49.524 | 41.663 | 1.00 32.84 | CPS6 |
| ATOM | 4849 | CE2 | PHE | 25 | 28.794 | 49.354 | 43.277 | 1.00 32.53 | CPS6 |
| ATOM | 4850 | CZ | PHE | 25 | 27.764 | 48.763 | 42.553 | 1.00 32.75 | CPS6 |
| ATOM | 4851 | C | PHE | 25 | 29.943 | 52.489 | 39.887 | 1.00 30.17 | CPS6 |
| ATOM | 4852 | O | PHE | 25 | 30.573 | 51.446 | 39.706 | 1.00 28.44 | CPS6 |
| ATOM | 4853 | N | ALA | 26 | 29.236 | 53.074 | 38.923 | 1.00 29.20 | CPS6 |
| ATOM | 4854 | CA | ALA | 26 | 29.158 | 52.484 | 37.592 | 1.00 28.94 | CPS6 |
| ATOM | 4855 | CB | ALA | 26 | 28.244 | 53.319 | 36.697 | 1.00 29.36 | CPS6 |
| ATOM | 4856 | C | ALA | 26 | 30.540 | 52.376 | 36.961 | 1.00 28.91 | CPS6 |
| ATOM | 4857 | O | ALA | 26 | 30.857 | 51.378 | 36.325 | 1.00 26.93 | CPS6 |
| ATOM | 4858 | N | GLU | 27 | 31.358 | 53.411 | 37.144 | 1.00 28.69 | CPS6 |
| ATOM | 4859 | CA | GLU | 27 | 32.701 | 53.434 | 36.576 | 1.00 29.76 | CPS6 |
| ATOM | 4860 | CB | GLU | 27 | 33.317 | 54.829 | 36.730 | 1.00 30.26 | CPS6 |
| ATOM | 4861 | CG | GLU | 27 | 32.737 | 55.916 | 35.822 | 1.00 32.04 | CPS6 |
| ATOM | 4862 | CD | GLU | 27 | 31.325 | 56.344 | 36.195 | 1.00 33.96 | CPS6 |
| ATOM | 4863 | OE1 | GLU | 27 | 30.902 | 56.135 | 37.353 | 1.00 32.41 | CPS6 |
| ATOM | 4864 | OE2 | GLU | 27 | 30.638 | 56.914 | 35.318 | 1.00 37.48 | CPS6 |
| ATOM | 4865 | C | GLU | 27 | 33.622 | 52.399 | 37.224 | 1.00 29.59 | CPS6 |
| ATOM | 4866 | O | GLU | 27 | 34.661 | 52.040 | 36.673 | 1.00 29.53 | CPS6 |
| ATOM | 4867 | N | ARG | 28 | 33.243 | 51.927 | 38.402 | 1.00 30.48 | CPS6 |
| ATOM | 4868 | CA | ARG | 28 | 34.040 | 50.934 | 39.107 | 1.00 32.10 | CPS6 |
| ATOM | 4869 | CB | ARG | 28 | 33.782 | 51.051 | 40.611 | 1.00 35.59 | CPS6 |
| ATOM | 4870 | CG | ARG | 28 | 34.480 | 50.013 | 41.467 | 1.00 40.15 | CPS6 |
| ATOM | 4871 | CD | ARG | 28 | 34.042 | 50.172 | 42.911 | 1.00 44.70 | CPS6 |
| ATOM | 4872 | NE | ARG | 28 | 33.719 | 48.891 | 43.529 | 1.00 48.06 | CPS6 |
| ATOM | 4873 | CZ | ARG | 28 | 33.004 | 48.764 | 44.642 | 1.00 50.43 | CPS6 |
| ATOM | 4874 | NH1 | ARG | 28 | 32.535 | 49.845 | 45.258 | 1.00 51.09 | CPS6 |
| ATOM | 4875 | NH2 | ARG | 28 | 32.755 | 47.558 | 45.139 | 1.00 51.52 | CPS6 |
| ATOM | 4876 | C | ARG | 28 | 33.677 | 49.526 | 38.621 | 1.00 30.71 | CPS6 |
| ATOM | 4877 | O | ARG | 28 | 34.546 | 48.659 | 38.464 | 1.00 32.13 | CPS6 |
| ATOM | 4878 | N | ILE | 29 | 32.391 | 49.316 | 38.364 | 1.00 28.03 | CPS6 |
| ATOM | 4879 | CA | ILE | 29 | 31.891 | 48.016 | 37.922 | 1.00 26.37 | CPS6 |
| ATOM | 4880 | CB | ILE | 29 | 30.387 | 47.854 | 38.270 | 1.00 25.85 | CPS6 |
| ATOM | 4881 | CG2 | ILE | 29 | 29.886 | 46.496 | 37.802 | 1.00 25.90 | CPS6 |
| ATOM | 4882 | CG1 | ILE | 29 | 30.164 | 48.051 | 39.776 | 1.00 27.54 | CPS6 |
| ATOM | 4883 | CD1 | ILE | 29 | 30.962 | 47.113 | 40.667 | 1.00 27.66 | CPS6 |
| ATOM | 4884 | C | ILE | 29 | 32.030 | 47.746 | 36.421 | 1.00 25.65 | CPS6 |
| ATOM | 4885 | O | ILE | 29 | 32.327 | 46.617 | 36.017 | 1.00 24.93 | CPS6 |
| ATOM | 4886 | N | LEU | 30 | 31.820 | 48.784 | 35.609 | 1.00 23.77 | CPS6 |
| ATOM | 4887 | CA | LEU | 30 | 31.844 | 48.651 | 34.158 | 1.00 24.32 | CPS6 |
| ATOM | 4888 | CB | LEU | 30 | 30.665 | 49.429 | 33.567 | 1.00 24.16 | CPS6 |
| ATOM | 4889 | CG | LEU | 30 | 29.282 | 49.141 | 34.169 | 1.00 25.20 | CPS6 |
| ATOM | 4890 | CD1 | LEU | 30 | 28.251 | 50.068 | 33.540 | 1.00 24.33 | CPS6 |
| ATOM | 4891 | CD2 | LEU | 30 | 28.898 | 47.695 | 33.927 | 1.00 23.57 | CPS6 |
| ATOM | 4892 | C | LEU | 30 | 33.121 | 49.071 | 33.433 | 1.00 24.24 | CPS6 |
| ATOM | 4893 | O | LEU | 30 | 33.820 | 49.996 | 33.845 | 1.00 23.43 | CPS6 |
| ATOM | 4894 | N | THR | 31 | 33.404 | 48.376 | 32.341 | 1.00 23.91 | CPS6 |
| ATOM | 4895 | CA | THR | 31 | 34.573 | 48.676 | 31.523 | 1.00 25.21 | CPS6 |
| ATOM | 4896 | CB | THR | 31 | 34.999 | 47.461 | 30.695 | 1.00 25.51 | CPS6 |
| ATOM | 4897 | OG1 | THR | 31 | 33.972 | 47.150 | 29.739 | 1.00 24.34 | CPS6 |
| ATOM | 4898 | CG2 | THR | 31 | 35.245 | 46.265 | 31.597 | 1.00 24.28 | CPS6 |
| ATOM | 4899 | C | THR | 31 | 34.219 | 49.798 | 30.553 | 1.00 26.00 | CPS6 |
| ATOM | 4900 | O | THR | 31 | 33.071 | 50.247 | 30.490 | 1.00 25.37 | CPS6 |
| ATOM | 4901 | N | ARG | 32 | 35.202 | 50.240 | 29.782 | 1.00 27.55 | CPS6 |

FIG. 1A-86

| ATOM | 4902 | CA | ARG | 32 | 34.976 | 51.310 | 28.818 | 1.00 | 29.54 | CPS6 |
|---|---|---|---|---|---|---|---|---|---|---|
| ATOM | 4903 | CB | ARG | 32 | 36.290 | 51.626 | 28.091 | 1.00 | 32.98 | CPS6 |
| ATOM | 4904 | CG | ARG | 32 | 36.198 | 52.721 | 27.040 | 1.00 | 38.34 | CPS6 |
| ATOM | 4905 | CD | ARG | 32 | 37.595 | 53.116 | 26.557 | 1.00 | 42.64 | CPS6 |
| ATOM | 4906 | NE | ARG | 32 | 38.282 | 53.987 | 27.513 | 1.00 | 45.62 | CPS6 |
| ATOM | 4907 | CZ | ARG | 32 | 38.009 | 55.281 | 27.677 | 1.00 | 47.09 | CPS6 |
| ATOM | 4908 | NH1 | ARG | 32 | 37.065 | 55.865 | 26.946 | 1.00 | 48.54 | CPS6 |
| ATOM | 4909 | NH2 | ARG | 32 | 38.675 | 55.992 | 28.576 | 1.00 | 48.16 | CPS6 |
| ATOM | 4910 | C | ARG | 32 | 33.879 | 50.928 | 27.815 | 1.00 | 28.32 | CPS6 |
| ATOM | 4911 | O | ARG | 32 | 32.969 | 51.711 | 27.544 | 1.00 | 27.76 | CPS6 |
| ATOM | 4912 | N | SER | 33 | 33.966 | 49.719 | 27.275 | 1.00 | 27.75 | CPS6 |
| ATOM | 4913 | CA | SER | 33 | 32.988 | 49.238 | 26.303 | 1.00 | 28.81 | CPS6 |
| ATOM | 4914 | CB | SER | 33 | 33.386 | 47.828 | 25.835 | 1.00 | 30.61 | CPS6 |
| ATOM | 4915 | OG | SER | 33 | 32.421 | 47.266 | 24.963 | 1.00 | 33.62 | CPS6 |
| ATOM | 4916 | C | SER | 33 | 31.586 | 49.211 | 26.926 | 1.00 | 28.93 | CPS6 |
| ATOM | 4917 | O | SER | 33 | 30.599 | 49.614 | 26.302 | 1.00 | 28.74 | CPS6 |
| ATOM | 4918 | N | GLU | 34 | 31.508 | 48.733 | 28.160 | 1.00 | 26.50 | CPS6 |
| ATOM | 4919 | CA | GLU | 34 | 30.237 | 48.650 | 28.866 | 1.00 | 27.17 | CPS6 |
| ATOM | 4920 | CB | GLU | 34 | 30.405 | 47.814 | 30.137 | 1.00 | 25.92 | CPS6 |
| ATOM | 4921 | CG | GLU | 34 | 30.649 | 46.339 | 29.830 | 1.00 | 25.85 | CPS6 |
| ATOM | 4922 | CD | GLU | 34 | 30.989 | 45.521 | 31.064 | 1.00 | 25.48 | CPS6 |
| ATOM | 4923 | OE1 | GLU | 34 | 30.771 | 44.290 | 31.035 | 1.00 | 24.91 | CPS6 |
| ATOM | 4924 | OE2 | GLU | 34 | 31.479 | 46.102 | 32.057 | 1.00 | 23.64 | CPS6 |
| ATOM | 4925 | C | GLU | 34 | 29.688 | 50.029 | 29.193 | 1.00 | 27.92 | CPS6 |
| ATOM | 4926 | O | GLU | 34 | 28.492 | 50.276 | 29.026 | 1.00 | 28.34 | CPS6 |
| ATOM | 4927 | N | LEU | 35 | 30.556 | 50.929 | 29.648 | 1.00 | 27.84 | CPS6 |
| ATOM | 4928 | CA | LEU | 35 | 30.137 | 52.286 | 29.977 | 1.00 | 30.69 | CPS6 |
| ATOM | 4929 | CB | LEU | 35 | 31.310 | 53.081 | 30.557 | 1.00 | 30.33 | CPS6 |
| ATOM | 4930 | CG | LEU | 35 | 31.719 | 52.712 | 31.981 | 1.00 | 30.63 | CPS6 |
| ATOM | 4931 | CD1 | LEU | 35 | 33.062 | 53.354 | 32.327 | 1.00 | 30.22 | CPS6 |
| ATOM | 4932 | CD2 | LEU | 35 | 30.631 | 53.170 | 32.943 | 1.00 | 30.10 | CPS6 |
| ATOM | 4933 | C | LEU | 35 | 29.583 | 53.012 | 28.756 | 1.00 | 32.12 | CPS6 |
| ATOM | 4934 | O | LEU | 35 | 28.669 | 53.826 | 28.880 | 1.00 | 32.67 | CPS6 |
| ATOM | 4935 | N | ASP | 36 | 30.140 | 52.730 | 27.579 | 1.00 | 34.02 | CPS6 |
| ATOM | 4936 | CA | ASP | 36 | 29.656 | 53.376 | 26.362 | 1.00 | 36.28 | CPS6 |
| ATOM | 4937 | CB | ASP | 36 | 30.457 | 52.928 | 25.131 | 1.00 | 38.02 | CPS6 |
| ATOM | 4938 | CG | ASP | 36 | 31.801 | 53.636 | 25.016 | 1.00 | 41.17 | CPS6 |
| ATOM | 4939 | OD1 | ASP | 36 | 31.924 | 54.767 | 25.538 | 1.00 | 42.30 | CPS6 |
| ATOM | 4940 | OD2 | ASP | 36 | 32.730 | 53.073 | 24.391 | 1.00 | 43.23 | CPS6 |
| ATOM | 4941 | C | ASP | 36 | 28.177 | 53.071 | 26.152 | 1.00 | 37.04 | CPS6 |
| ATOM | 4942 | O | ASP | 36 | 27.411 | 53.945 | 25.756 | 1.00 | 38.21 | CPS6 |
| ATOM | 4943 | N | GLN | 37 | 27.772 | 51.836 | 26.427 | 1.00 | 36.14 | CPS6 |
| ATOM | 4944 | CA | GLN | 37 | 26.376 | 51.449 | 26.261 | 1.00 | 37.10 | CPS6 |
| ATOM | 4945 | CB | GLN | 37 | 26.253 | 49.928 | 26.271 | 1.00 | 39.04 | CPS6 |
| ATOM | 4946 | CG | GLN | 37 | 27.296 | 49.234 | 25.424 | 1.00 | 43.60 | CPS6 |
| ATOM | 4947 | CD | GLN | 37 | 27.084 | 47.741 | 25.357 | 1.00 | 47.47 | CPS6 |
| ATOM | 4948 | OE1 | GLN | 37 | 26.134 | 47.268 | 24.726 | 1.00 | 50.58 | CPS6 |
| ATOM | 4949 | NE2 | GLN | 37 | 27.960 | 46.983 | 26.016 | 1.00 | 47.62 | CPS6 |
| ATOM | 4950 | C | GLN | 37 | 25.535 | 52.042 | 27.389 | 1.00 | 36.39 | CPS6 |
| ATOM | 4951 | O | GLN | 37 | 24.466 | 52.607 | 27.159 | 1.00 | 36.41 | CPS6 |
| ATOM | 4952 | N | TYR | 38 | 26.045 | 51.909 | 28.608 | 1.00 | 35.09 | CPS6 |
| ATOM | 4953 | CA | TYR | 38 | 25.395 | 52.405 | 29.813 | 1.00 | 35.03 | CPS6 |
| ATOM | 4954 | CB | TYR | 38 | 26.346 | 52.199 | 31.000 | 1.00 | 33.56 | CPS6 |
| ATOM | 4955 | CG | TYR | 38 | 25.868 | 52.724 | 32.330 | 1.00 | 32.55 | CPS6 |
| ATOM | 4956 | CD1 | TYR | 38 | 26.296 | 53.958 | 32.810 | 1.00 | 32.33 | CPS6 |
| ATOM | 4957 | CE1 | TYR | 38 | 25.882 | 54.427 | 34.057 | 1.00 | 33.78 | CPS6 |
| ATOM | 4958 | CD2 | TYR | 38 | 25.008 | 51.969 | 33.127 | 1.00 | 31.82 | CPS6 |

FIG. 1A-87

| ATOM | 4959 | CE2 | TYR | 38 | 24.590 | 52.423 | 34.367 | 1.00 | 32.17 | CPS6 |
|------|------|-----|-----|----|--------|--------|--------|------|-------|------|
| ATOM | 4960 | CZ  | TYR | 38 | 25.029 | 53.652 | 34.829 | 1.00 | 33.51 | CPS6 |
| ATOM | 4961 | OH  | TYR | 38 | 24.611 | 54.099 | 36.060 | 1.00 | 34.37 | CPS6 |
| ATOM | 4962 | C   | TYR | 38 | 24.978 | 53.872 | 29.714 | 1.00 | 36.19 | CPS6 |
| ATOM | 4963 | O   | TYR | 38 | 23.825 | 54.213 | 29.974 | 1.00 | 35.32 | CPS6 |
| ATOM | 4964 | N   | TYR | 39 | 25.917 | 54.733 | 29.335 | 1.00 | 37.73 | CPS6 |
| ATOM | 4965 | CA  | TYR | 39 | 25.649 | 56.168 | 29.229 | 1.00 | 39.75 | CPS6 |
| ATOM | 4966 | CB  | TYR | 39 | 26.922 | 56.925 | 28.838 | 1.00 | 39.88 | CPS6 |
| ATOM | 4967 | CG  | TYR | 39 | 28.029 | 56.896 | 29.873 | 1.00 | 40.44 | CPS6 |
| ATOM | 4968 | CD1 | TYR | 39 | 27.742 | 56.963 | 31.239 | 1.00 | 39.77 | CPS6 |
| ATOM | 4969 | CE1 | TYR | 39 | 28.762 | 56.991 | 32.188 | 1.00 | 39.44 | CPS6 |
| ATOM | 4970 | CD2 | TYR | 39 | 29.370 | 56.855 | 29.481 | 1.00 | 40.21 | CPS6 |
| ATOM | 4971 | CE2 | TYR | 39 | 30.399 | 56.884 | 30.420 | 1.00 | 39.93 | CPS6 |
| ATOM | 4972 | CZ  | TYR | 39 | 30.089 | 56.954 | 31.773 | 1.00 | 40.43 | CPS6 |
| ATOM | 4973 | OH  | TYR | 39 | 31.109 | 57.010 | 32.702 | 1.00 | 40.54 | CPS6 |
| ATOM | 4974 | C   | TYR | 39 | 24.538 | 56.546 | 28.254 | 1.00 | 41.06 | CPS6 |
| ATOM | 4975 | O   | TYR | 39 | 23.957 | 57.627 | 28.357 | 1.00 | 42.29 | CPS6 |
| ATOM | 4976 | N   | GLU | 40 | 24.239 | 55.668 | 27.307 | 1.00 | 42.33 | CPS6 |
| ATOM | 4977 | CA  | GLU | 40 | 23.199 | 55.965 | 26.331 | 1.00 | 44.33 | CPS6 |
| ATOM | 4978 | CB  | GLU | 40 | 23.541 | 55.323 | 24.986 | 1.00 | 46.05 | CPS6 |
| ATOM | 4979 | CG  | GLU | 40 | 24.916 | 55.689 | 24.466 | 1.00 | 50.15 | CPS6 |
| ATOM | 4980 | CD  | GLU | 40 | 25.203 | 55.088 | 23.105 | 1.00 | 52.92 | CPS6 |
| ATOM | 4981 | OE1 | GLU | 40 | 25.040 | 53.857 | 22.948 | 1.00 | 55.32 | CPS6 |
| ATOM | 4982 | OE2 | GLU | 40 | 25.599 | 55.848 | 22.191 | 1.00 | 54.91 | CPS6 |
| ATOM | 4983 | C   | GLU | 40 | 21.827 | 55.488 | 26.780 | 1.00 | 44.19 | CPS6 |
| ATOM | 4984 | O   | GLU | 40 | 20.854 | 55.629 | 26.041 | 1.00 | 44.77 | CPS6 |
| ATOM | 4985 | N   | LEU | 41 | 21.743 | 54.941 | 27.991 | 1.00 | 42.63 | CPS6 |
| ATOM | 4986 | CA  | LEU | 41 | 20.474 | 54.427 | 28.499 | 1.00 | 42.23 | CPS6 |
| ATOM | 4987 | CB  | LEU | 41 | 20.696 | 53.114 | 29.259 | 1.00 | 41.12 | CPS6 |
| ATOM | 4988 | CG  | LEU | 41 | 21.294 | 51.934 | 28.486 | 1.00 | 40.93 | CPS6 |
| ATOM | 4989 | CD1 | LEU | 41 | 21.524 | 50.777 | 29.446 | 1.00 | 39.97 | CPS6 |
| ATOM | 4990 | CD2 | LEU | 41 | 20.362 | 51.514 | 27.360 | 1.00 | 40.04 | CPS6 |
| ATOM | 4991 | C   | LEU | 41 | 19.736 | 55.392 | 29.410 | 1.00 | 41.84 | CPS6 |
| ATOM | 4992 | O   | LEU | 41 | 20.317 | 56.335 | 29.934 | 1.00 | 41.86 | CPS6 |
| ATOM | 4993 | N   | SER | 42 | 18.447 | 55.129 | 29.597 | 1.00 | 42.32 | CPS6 |
| ATOM | 4994 | CA  | SER | 42 | 17.602 | 55.937 | 30.465 | 1.00 | 43.65 | CPS6 |
| ATOM | 4995 | CB  | SER | 42 | 16.134 | 55.578 | 30.252 | 1.00 | 43.85 | CPS6 |
| ATOM | 4996 | OG  | SER | 42 | 15.871 | 54.269 | 30.726 | 1.00 | 44.29 | CPS6 |
| ATOM | 4997 | C   | SER | 42 | 17.983 | 55.620 | 31.902 | 1.00 | 43.88 | CPS6 |
| ATOM | 4998 | O   | SER | 42 | 18.661 | 54.626 | 32.157 | 1.00 | 44.22 | CPS6 |
| ATOM | 4999 | N   | GLU | 43 | 17.540 | 56.447 | 32.843 | 1.00 | 43.94 | CPS6 |
| ATOM | 5000 | CA  | GLU | 43 | 17.860 | 56.216 | 34.248 | 1.00 | 44.69 | CPS6 |
| ATOM | 5001 | CB  | GLU | 43 | 17.195 | 57.266 | 35.147 | 1.00 | 47.52 | CPS6 |
| ATOM | 5002 | CG  | GLU | 43 | 17.466 | 57.033 | 36.632 | 1.00 | 51.04 | CPS6 |
| ATOM | 5003 | CD  | GLU | 43 | 16.733 | 58.002 | 37.546 | 1.00 | 53.92 | CPS6 |
| ATOM | 5004 | OE1 | GLU | 43 | 15.480 | 57.965 | 37.596 | 1.00 | 55.09 | CPS6 |
| ATOM | 5005 | OE2 | GLU | 43 | 17.418 | 58.802 | 38.221 | 1.00 | 55.13 | CPS6 |
| ATOM | 5006 | C   | GLU | 43 | 17.411 | 54.828 | 34.687 | 1.00 | 43.76 | CPS6 |
| ATOM | 5007 | O   | GLU | 43 | 18.123 | 54.143 | 35.419 | 1.00 | 43.62 | CPS6 |
| ATOM | 5008 | N   | LYS | 44 | 16.227 | 54.419 | 34.244 | 1.00 | 42.65 | CPS6 |
| ATOM | 5009 | CA  | LYS | 44 | 15.699 | 53.110 | 34.601 | 1.00 | 42.18 | CPS6 |
| ATOM | 5010 | CB  | LYS | 44 | 14.244 | 52.980 | 34.151 | 1.00 | 43.86 | CPS6 |
| ATOM | 5011 | CG  | LYS | 44 | 13.612 | 51.643 | 34.508 | 1.00 | 45.75 | CPS6 |
| ATOM | 5012 | CD  | LYS | 44 | 12.155 | 51.590 | 34.086 | 1.00 | 47.40 | CPS6 |
| ATOM | 5013 | CE  | LYS | 44 | 11.521 | 50.267 | 34.474 | 1.00 | 48.83 | CPS6 |
| ATOM | 5014 | NZ  | LYS | 44 | 10.076 | 50.213 | 34.107 | 1.00 | 50.91 | CPS6 |
| ATOM | 5015 | C   | LYS | 44 | 16.521 | 51.994 | 33.966 | 1.00 | 40.95 | CPS6 |

FIG. 1A-88

| ATOM | 5016 | O | LYS | 44 | 16.952 | 51.064 | 34.645 | 1.00 | 40.09 | CPS6 |
| --- | --- | --- | --- | --- | --- | --- | --- | --- | --- | --- |
| ATOM | 5017 | N | ARG | 45 | 16.722 | 52.091 | 32.656 | 1.00 | 39.93 | CPS6 |
| ATOM | 5018 | CA | ARG | 45 | 17.490 | 51.095 | 31.923 | 1.00 | 38.26 | CPS6 |
| ATOM | 5019 | CB | ARG | 45 | 17.518 | 51.437 | 30.434 | 1.00 | 40.94 | CPS6 |
| ATOM | 5020 | CG | ARG | 45 | 16.178 | 51.285 | 29.736 | 1.00 | 45.37 | CPS6 |
| ATOM | 5021 | CD | ARG | 45 | 15.796 | 49.825 | 29.572 | 1.00 | 48.47 | CPS6 |
| ATOM | 5022 | NE | ARG | 45 | 16.746 | 49.092 | 28.732 | 1.00 | 52.03 | CPS6 |
| ATOM | 5023 | CZ | ARG | 45 | 17.047 | 49.411 | 27.475 | 1.00 | 54.07 | CPS6 |
| ATOM | 5024 | NH1 | ARG | 45 | 16.480 | 50.459 | 26.888 | 1.00 | 55.15 | CPS6 |
| ATOM | 5025 | NH2 | ARG | 45 | 17.917 | 48.672 | 26.796 | 1.00 | 55.63 | CPS6 |
| ATOM | 5026 | C | ARG | 45 | 18.915 | 50.992 | 32.441 | 1.00 | 35.74 | CPS6 |
| ATOM | 5027 | O | ARG | 45 | 19.524 | 49.926 | 32.374 | 1.00 | 33.44 | CPS6 |
| ATOM | 5028 | N | LYS | 46 | 19.456 | 52.098 | 32.945 | 1.00 | 33.77 | CPS6 |
| ATOM | 5029 | CA | LYS | 46 | 20.814 | 52.075 | 33.466 | 1.00 | 32.86 | CPS6 |
| ATOM | 5030 | CB | LYS | 46 | 21.311 | 53.489 | 33.787 | 1.00 | 33.65 | CPS6 |
| ATOM | 5031 | CG | LYS | 46 | 21.636 | 54.270 | 32.529 | 1.00 | 35.15 | CPS6 |
| ATOM | 5032 | CD | LYS | 46 | 22.700 | 55.318 | 32.752 | 1.00 | 38.55 | CPS6 |
| ATOM | 5033 | CE | LYS | 46 | 22.185 | 56.492 | 33.528 | 1.00 | 38.97 | CPS6 |
| ATOM | 5034 | NZ | LYS | 46 | 22.923 | 57.716 | 33.075 | 1.00 | 40.88 | CPS6 |
| ATOM | 5035 | C | LYS | 46 | 20.904 | 51.196 | 34.693 | 1.00 | 31.44 | CPS6 |
| ATOM | 5036 | O | LYS | 46 | 21.841 | 50.415 | 34.832 | 1.00 | 30.69 | CPS6 |
| ATOM | 5037 | N | ASN | 47 | 19.927 | 51.310 | 35.585 | 1.00 | 30.34 | CPS6 |
| ATOM | 5038 | CA | ASN | 47 | 19.935 | 50.486 | 36.788 | 1.00 | 29.82 | CPS6 |
| ATOM | 5039 | CB | ASN | 47 | 18.779 | 50.880 | 37.713 | 1.00 | 30.59 | CPS6 |
| ATOM | 5040 | CG | ASN | 47 | 18.683 | 49.983 | 38.935 | 1.00 | 32.30 | CPS6 |
| ATOM | 5041 | OD1 | ASN | 47 | 19.510 | 50.057 | 39.851 | 1.00 | 33.45 | CPS6 |
| ATOM | 5042 | ND2 | ASN | 47 | 17.675 | 49.119 | 38.950 | 1.00 | 34.07 | CPS6 |
| ATOM | 5043 | C | ASN | 47 | 19.821 | 49.003 | 36.401 | 1.00 | 28.64 | CPS6 |
| ATOM | 5044 | O | ASN | 47 | 20.503 | 48.154 | 36.970 | 1.00 | 28.65 | CPS6 |
| ATOM | 5045 | N | GLU | 48 | 18.972 | 48.700 | 35.424 | 1.00 | 28.08 | CPS6 |
| ATOM | 5046 | CA | GLU | 48 | 18.796 | 47.319 | 34.969 | 1.00 | 28.15 | CPS6 |
| ATOM | 5047 | CB | GLU | 48 | 17.680 | 47.234 | 33.927 | 1.00 | 31.68 | CPS6 |
| ATOM | 5048 | CG | GLU | 48 | 16.301 | 47.618 | 34.448 | 1.00 | 36.94 | CPS6 |
| ATOM | 5049 | CD | GLU | 48 | 15.246 | 47.631 | 33.352 | 1.00 | 40.49 | CPS6 |
| ATOM | 5050 | OE1 | GLU | 48 | 14.076 | 47.950 | 33.661 | 1.00 | 42.57 | CPS6 |
| ATOM | 5051 | OE2 | GLU | 48 | 15.585 | 47.325 | 32.185 | 1.00 | 40.94 | CPS6 |
| ATOM | 5052 | C | GLU | 48 | 20.085 | 46.783 | 34.344 | 1.00 | 27.02 | CPS6 |
| ATOM | 5053 | O | GLU | 48 | 20.489 | 45.646 | 34.598 | 1.00 | 25.06 | CPS6 |
| ATOM | 5054 | N | PHE | 49 | 20.714 | 47.613 | 33.515 | 1.00 | 25.48 | CPS6 |
| ATOM | 5055 | CA | PHE | 49 | 21.949 | 47.243 | 32.830 | 1.00 | 26.00 | CPS6 |
| ATOM | 5056 | CB | PHE | 49 | 22.351 | 48.358 | 31.858 | 1.00 | 26.69 | CPS6 |
| ATOM | 5057 | CG | PHE | 49 | 23.585 | 48.058 | 31.057 | 1.00 | 27.23 | CPS6 |
| ATOM | 5058 | CD1 | PHE | 49 | 23.497 | 47.397 | 29.838 | 1.00 | 28.29 | CPS6 |
| ATOM | 5059 | CD2 | PHE | 49 | 24.835 | 48.455 | 31.515 | 1.00 | 26.82 | CPS6 |
| ATOM | 5060 | CE1 | PHE | 49 | 24.640 | 47.142 | 29.081 | 1.00 | 28.93 | CPS6 |
| ATOM | 5061 | CE2 | PHE | 49 | 25.987 | 48.202 | 30.765 | 1.00 | 27.94 | CPS6 |
| ATOM | 5062 | CZ | PHE | 49 | 25.886 | 47.548 | 29.550 | 1.00 | 28.38 | CPS6 |
| ATOM | 5063 | C | PHE | 49 | 23.066 | 46.997 | 33.837 | 1.00 | 24.84 | CPS6 |
| ATOM | 5064 | O | PHE | 49 | 23.739 | 45.966 | 33.789 | 1.00 | 25.50 | CPS6 |
| ATOM | 5065 | N | LEU | 50 | 23.264 | 47.946 | 34.747 | 1.00 | 24.16 | CPS6 |
| ATOM | 5066 | CA | LEU | 50 | 24.296 | 47.824 | 35.773 | 1.00 | 22.97 | CPS6 |
| ATOM | 5067 | CB | LEU | 50 | 24.304 | 49.088 | 36.647 | 1.00 | 24.37 | CPS6 |
| ATOM | 5068 | CG | LEU | 50 | 25.348 | 49.178 | 37.759 | 1.00 | 25.79 | CPS6 |
| ATOM | 5069 | CD1 | LEU | 50 | 26.760 | 49.145 | 37.149 | 1.00 | 26.03 | CPS6 |
| ATOM | 5070 | CD2 | LEU | 50 | 25.141 | 50.471 | 38.537 | 1.00 | 26.29 | CPS6 |
| ATOM | 5071 | C | LEU | 50 | 24.081 | 46.583 | 36.653 | 1.00 | 21.87 | CPS6 |
| ATOM | 5072 | O | LEU | 50 | 25.022 | 45.839 | 36.939 | 1.00 | 21.43 | CPS6 |

FIG. 1A-89

| ATOM | 5073 | N | ALA | 51 | 22.844 | 46.364 | 37.089 | 1.00 | 21.05 | CPS6 |
|---|---|---|---|---|---|---|---|---|---|---|
| ATOM | 5074 | CA | ALA | 51 | 22.524 | 45.218 | 37.940 | 1.00 | 21.01 | CPS6 |
| ATOM | 5075 | CB | ALA | 51 | 21.038 | 45.271 | 38.346 | 1.00 | 20.12 | CPS6 |
| ATOM | 5076 | C | ALA | 51 | 22.829 | 43.894 | 37.223 | 1.00 | 20.25 | CPS6 |
| ATOM | 5077 | O | ALA | 51 | 23.351 | 42.955 | 37.825 | 1.00 | 20.85 | CPS6 |
| ATOM | 5078 | N | GLY | 52 | 22.493 | 43.830 | 35.943 | 1.00 | 21.02 | CPS6 |
| ATOM | 5079 | CA | GLY | 52 | 22.742 | 42.624 | 35.164 | 1.00 | 20.99 | CPS6 |
| ATOM | 5080 | C | GLY | 52 | 24.232 | 42.376 | 34.989 | 1.00 | 22.24 | CPS6 |
| ATOM | 5081 | O | GLY | 52 | 24.688 | 41.232 | 35.044 | 1.00 | 21.77 | CPS6 |
| ATOM | 5082 | N | ARG | 53 | 24.992 | 43.444 | 34.764 | 1.00 | 22.45 | CPS6 |
| ATOM | 5083 | CA | ARG | 53 | 26.442 | 43.317 | 34.600 | 1.00 | 22.02 | CPS6 |
| ATOM | 5084 | CB | ARG | 53 | 27.051 | 44.624 | 34.093 | 1.00 | 23.58 | CPS6 |
| ATOM | 5085 | CG | ARG | 53 | 26.831 | 44.875 | 32.628 | 1.00 | 26.56 | CPS6 |
| ATOM | 5086 | CD | ARG | 53 | 27.406 | 43.749 | 31.834 | 1.00 | 28.57 | CPS6 |
| ATOM | 5087 | NE | ARG | 53 | 27.764 | 44.164 | 30.483 | 1.00 | 32.59 | CPS6 |
| ATOM | 5088 | CZ | ARG | 53 | 26.903 | 44.301 | 29.481 | 1.00 | 32.51 | CPS6 |
| ATOM | 5089 | NH1 | ARG | 53 | 25.606 | 44.053 | 29.676 | 1.00 | 29.51 | CPS6 |
| ATOM | 5090 | NH2 | ARG | 53 | 27.352 | 44.666 | 28.277 | 1.00 | 29.31 | CPS6 |
| ATOM | 5091 | C | ARG | 53 | 27.081 | 42.951 | 35.926 | 1.00 | 22.03 | CPS6 |
| ATOM | 5092 | O | ARG | 53 | 28.014 | 42.159 | 35.983 | 1.00 | 22.12 | CPS6 |
| ATOM | 5093 | N | PHE | 54 | 26.576 | 43.541 | 37.000 | 1.00 | 20.72 | CPS6 |
| ATOM | 5094 | CA | PHE | 54 | 27.089 | 43.253 | 38.322 | 1.00 | 21.84 | CPS6 |
| ATOM | 5095 | CB | PHE | 54 | 26.391 | 44.144 | 39.347 | 1.00 | 23.57 | CPS6 |
| ATOM | 5096 | CG | PHE | 54 | 26.843 | 43.925 | 40.756 | 1.00 | 24.76 | CPS6 |
| ATOM | 5097 | CD1 | PHE | 54 | 26.202 | 42.996 | 41.571 | 1.00 | 26.78 | CPS6 |
| ATOM | 5098 | CD2 | PHE | 54 | 27.896 | 44.666 | 41.282 | 1.00 | 26.87 | CPS6 |
| ATOM | 5099 | CE1 | PHE | 54 | 26.603 | 42.815 | 42.886 | 1.00 | 27.91 | CPS6 |
| ATOM | 5100 | CE2 | PHE | 54 | 28.302 | 44.491 | 42.592 | 1.00 | 26.99 | CPS6 |
| ATOM | 5101 | CZ | PHE | 54 | 27.656 | 43.567 | 43.397 | 1.00 | 27.41 | CPS6 |
| ATOM | 5102 | C | PHE | 54 | 26.865 | 41.777 | 38.647 | 1.00 | 21.21 | CPS6 |
| ATOM | 5103 | O | PHE | 54 | 27.768 | 41.097 | 39.123 | 1.00 | 20.78 | CPS6 |
| ATOM | 5104 | N | ALA | 55 | 25.665 | 41.277 | 38.381 | 1.00 | 20.89 | CPS6 |
| ATOM | 5105 | CA | ALA | 55 | 25.374 | 39.872 | 38.669 | 1.00 | 20.22 | CPS6 |
| ATOM | 5106 | CB | ALA | 55 | 23.892 | 39.574 | 38.441 | 1.00 | 19.35 | CPS6 |
| ATOM | 5107 | C | ALA | 55 | 26.224 | 38.955 | 37.805 | 1.00 | 18.66 | CPS6 |
| ATOM | 5108 | O | ALA | 55 | 26.716 | 37.923 | 38.278 | 1.00 | 19.74 | CPS6 |
| ATOM | 5109 | N | ALA | 56 | 26.395 | 39.314 | 36.538 | 1.00 | 18.06 | CPS6 |
| ATOM | 5110 | CA | ALA | 56 | 27.195 | 38.488 | 35.639 | 1.00 | 18.21 | CPS6 |
| ATOM | 5111 | CB | ALA | 56 | 27.134 | 39.041 | 34.198 | 1.00 | 18.23 | CPS6 |
| ATOM | 5112 | C | ALA | 56 | 28.648 | 38.387 | 36.101 | 1.00 | 18.83 | CPS6 |
| ATOM | 5113 | O | ALA | 56 | 29.259 | 37.307 | 36.057 | 1.00 | 17.66 | CPS6 |
| ATOM | 5114 | N | LYS | 57 | 29.207 | 39.508 | 36.549 | 1.00 | 19.03 | CPS6 |
| ATOM | 5115 | CA | LYS | 57 | 30.592 | 39.513 | 37.012 | 1.00 | 18.37 | CPS6 |
| ATOM | 5116 | CB | LYS | 57 | 31.101 | 40.958 | 37.085 | 1.00 | 19.18 | CPS6 |
| ATOM | 5117 | CG | LYS | 57 | 31.179 | 41.574 | 35.689 | 1.00 | 19.49 | CPS6 |
| ATOM | 5118 | CD | LYS | 57 | 31.775 | 42.975 | 35.676 | 1.00 | 23.00 | CPS6 |
| ATOM | 5119 | CE | LYS | 57 | 31.663 | 43.579 | 34.285 | 1.00 | 20.60 | CPS6 |
| ATOM | 5120 | NZ | LYS | 57 | 32.580 | 44.729 | 34.103 | 1.00 | 21.27 | CPS6 |
| ATOM | 5121 | C | LYS | 57 | 30.745 | 38.785 | 38.344 | 1.00 | 19.47 | CPS6 |
| ATOM | 5122 | O | LYS | 57 | 31.739 | 38.084 | 38.557 | 1.00 | 20.88 | CPS6 |
| ATOM | 5123 | N | GLU | 58 | 29.773 | 38.942 | 39.245 | 1.00 | 19.43 | CPS6 |
| ATOM | 5124 | CA | GLU | 58 | 29.821 | 38.212 | 40.512 | 1.00 | 21.77 | CPS6 |
| ATOM | 5125 | CB | GLU | 58 | 28.640 | 38.591 | 41.419 | 1.00 | 22.85 | CPS6 |
| ATOM | 5126 | CG | GLU | 58 | 28.746 | 39.965 | 42.066 | 1.00 | 27.74 | CPS6 |
| ATOM | 5127 | CD | GLU | 58 | 29.884 | 40.060 | 43.079 | 1.00 | 30.88 | CPS6 |
| ATOM | 5128 | OE1 | GLU | 58 | 30.148 | 41.173 | 43.580 | 1.00 | 34.74 | CPS6 |
| ATOM | 5129 | OE2 | GLU | 58 | 30.517 | 39.028 | 43.378 | 1.00 | 34.50 | CPS6 |

FIG. 1A-90

| ATOM | 5130 | C | GLU | 58 | 29.745 | 36.711 | 40.199 | 1.00 | 21.81 | CPS6 |
|---|---|---|---|---|---|---|---|---|---|---|
| ATOM | 5131 | O | GLU | 58 | 30.494 | 35.900 | 40.767 | 1.00 | 21.58 | CPS6 |
| ATOM | 5132 | N | ALA | 59 | 28.833 | 36.332 | 39.305 | 1.00 | 20.31 | CPS6 |
| ATOM | 5133 | CA | ALA | 59 | 28.704 | 34.917 | 38.958 | 1.00 | 20.01 | CPS6 |
| ATOM | 5134 | CB | ALA | 59 | 27.557 | 34.709 | 37.956 | 1.00 | 19.39 | CPS6 |
| ATOM | 5135 | C | ALA | 59 | 30.015 | 34.398 | 38.370 | 1.00 | 20.62 | CPS6 |
| ATOM | 5136 | O | ALA | 59 | 30.463 | 33.289 | 38.693 | 1.00 | 21.08 | CPS6 |
| ATOM | 5137 | N | PHE | 60 | 30.625 | 35.192 | 37.497 | 1.00 | 18.52 | CPS6 |
| ATOM | 5138 | CA | PHE | 60 | 31.886 | 34.784 | 36.891 | 1.00 | 20.21 | CPS6 |
| ATOM | 5139 | CB | PHE | 60 | 32.359 | 35.819 | 35.863 | 1.00 | 19.79 | CPS6 |
| ATOM | 5140 | CG | PHE | 60 | 33.690 | 35.482 | 35.248 | 1.00 | 21.99 | CPS6 |
| ATOM | 5141 | CD1 | PHE | 60 | 33.768 | 34.653 | 34.133 | 1.00 | 19.74 | CPS6 |
| ATOM | 5142 | CD2 | PHE | 60 | 34.874 | 35.925 | 35.842 | 1.00 | 22.16 | CPS6 |
| ATOM | 5143 | CE1 | PHE | 60 | 35.010 | 34.264 | 33.618 | 1.00 | 23.98 | CPS6 |
| ATOM | 5144 | CE2 | PHE | 60 | 36.117 | 35.542 | 35.339 | 1.00 | 23.86 | CPS6 |
| ATOM | 5145 | CZ | PHE | 60 | 36.187 | 34.709 | 34.227 | 1.00 | 23.24 | CPS6 |
| ATOM | 5146 | C | PHE | 60 | 32.970 | 34.614 | 37.961 | 1.00 | 21.37 | CPS6 |
| ATOM | 5147 | O | PHE | 60 | 33.724 | 33.638 | 37.938 | 1.00 | 22.00 | CPS6 |
| ATOM | 5148 | N | SER | 61 | 33.048 | 35.565 | 38.891 | 1.00 | 21.71 | CPS6 |
| ATOM | 5149 | CA | SER | 61 | 34.065 | 35.516 | 39.945 | 1.00 | 23.80 | CPS6 |
| ATOM | 5150 | CB | SER | 61 | 34.003 | 36.772 | 40.824 | 1.00 | 23.70 | CPS6 |
| ATOM | 5151 | OG | SER | 61 | 32.938 | 36.694 | 41.753 | 1.00 | 25.60 | CPS6 |
| ATOM | 5152 | C | SER | 61 | 33.912 | 34.284 | 40.824 | 1.00 | 24.14 | CPS6 |
| ATOM | 5153 | O | SER | 61 | 34.897 | 33.786 | 41.386 | 1.00 | 25.44 | CPS6 |
| ATOM | 5154 | N | LYS | 62 | 32.683 | 33.800 | 40.957 | 1.00 | 23.98 | CPS6 |
| ATOM | 5155 | CA | LYS | 62 | 32.425 | 32.609 | 41.764 | 1.00 | 25.63 | CPS6 |
| ATOM | 5156 | CB | LYS | 62 | 30.946 | 32.566 | 42.174 | 1.00 | 25.79 | CPS6 |
| ATOM | 5157 | CG | LYS | 62 | 30.601 | 33.735 | 43.097 | 1.00 | 29.14 | CPS6 |
| ATOM | 5158 | CD | LYS | 62 | 29.112 | 33.966 | 43.281 | 1.00 | 32.29 | CPS6 |
| ATOM | 5159 | CE | LYS | 62 | 28.492 | 32.995 | 44.255 | 1.00 | 34.95 | CPS6 |
| ATOM | 5160 | NZ | LYS | 62 | 27.224 | 33.584 | 44.793 | 1.00 | 38.32 | CPS6 |
| ATOM | 5161 | C | LYS | 62 | 32.830 | 31.358 | 40.995 | 1.00 | 26.22 | CPS6 |
| ATOM | 5162 | O | LYS | 62 | 33.397 | 30.424 | 41.568 | 1.00 | 25.89 | CPS6 |
| ATOM | 5163 | N | ALA | 63 | 32.556 | 31.343 | 39.693 | 1.00 | 24.67 | CPS6 |
| ATOM | 5164 | CA | ALA | 63 | 32.936 | 30.209 | 38.861 | 1.00 | 24.83 | CPS6 |
| ATOM | 5165 | CB | ALA | 63 | 32.345 | 30.359 | 37.464 | 1.00 | 24.34 | CPS6 |
| ATOM | 5166 | C | ALA | 63 | 34.459 | 30.174 | 38.780 | 1.00 | 26.66 | CPS6 |
| ATOM | 5167 | O | ALA | 63 | 35.064 | 29.105 | 38.737 | 1.00 | 26.11 | CPS6 |
| ATOM | 5168 | N | PHE | 64 | 35.071 | 31.354 | 38.762 | 1.00 | 26.12 | CPS6 |
| ATOM | 5169 | CA | PHE | 64 | 36.526 | 31.467 | 38.692 | 1.00 | 28.50 | CPS6 |
| ATOM | 5170 | CB | PHE | 64 | 36.919 | 32.925 | 38.445 | 1.00 | 28.06 | CPS6 |
| ATOM | 5171 | CG | PHE | 64 | 38.341 | 33.104 | 37.992 | 1.00 | 29.52 | CPS6 |
| ATOM | 5172 | CD1 | PHE | 64 | 38.760 | 32.606 | 36.765 | 1.00 | 29.61 | CPS6 |
| ATOM | 5173 | CD2 | PHE | 64 | 39.251 | 33.787 | 38.787 | 1.00 | 29.01 | CPS6 |
| ATOM | 5174 | CE1 | PHE | 64 | 40.072 | 32.787 | 36.329 | 1.00 | 32.11 | CPS6 |
| ATOM | 5175 | CE2 | PHE | 64 | 40.565 | 33.973 | 38.362 | 1.00 | 30.85 | CPS6 |
| ATOM | 5176 | CZ | PHE | 64 | 40.975 | 33.473 | 37.130 | 1.00 | 31.27 | CPS6 |
| ATOM | 5177 | C | PHE | 64 | 37.176 | 30.953 | 39.981 | 1.00 | 29.90 | CPS6 |
| ATOM | 5178 | O | PHE | 64 | 38.376 | 30.661 | 40.003 | 1.00 | 30.91 | CPS6 |
| ATOM | 5179 | N | GLY | 65 | 36.377 | 30.858 | 41.043 | 1.00 | 31.52 | CPS6 |
| ATOM | 5180 | CA | GLY | 65 | 36.845 | 30.349 | 42.322 | 1.00 | 34.23 | CPS6 |
| ATOM | 5181 | C | GLY | 65 | 37.435 | 31.337 | 43.315 | 1.00 | 36.45 | CPS6 |
| ATOM | 5182 | O | GLY | 65 | 37.726 | 30.968 | 44.456 | 1.00 | 37.62 | CPS6 |
| ATOM | 5183 | N | THR | 66 | 37.593 | 32.592 | 42.902 | 1.00 | 36.65 | CPS6 |
| ATOM | 5184 | CA | THR | 66 | 38.195 | 33.616 | 43.755 | 1.00 | 36.52 | CPS6 |
| ATOM | 5185 | CB | THR | 66 | 39.272 | 34.385 | 42.978 | 1.00 | 36.52 | CPS6 |
| ATOM | 5186 | OG1 | THR | 66 | 38.648 | 35.112 | 41.908 | 1.00 | 36.34 | CPS6 |

FIG. 1A-91

| ATOM | 5187 | CG2 | THR | 66 | 40.297 | 33.429 | 42.389 | 1.00 | 36.79 | CPS6 |
|---|---|---|---|---|---|---|---|---|---|---|
| ATOM | 5188 | C | THR | 66 | 37.243 | 34.666 | 44.329 | 1.00 | 36.19 | CPS6 |
| ATOM | 5189 | O | THR | 66 | 37.475 | 35.193 | 45.419 | 1.00 | 35.77 | CPS6 |
| ATOM | 5190 | N | GLY | 67 | 36.175 | 34.973 | 43.599 | 1.00 | 35.09 | CPS6 |
| ATOM | 5191 | CA | GLY | 67 | 35.266 | 36.011 | 44.046 | 1.00 | 33.07 | CPS6 |
| ATOM | 5192 | C | GLY | 67 | 35.944 | 37.308 | 43.634 | 1.00 | 32.90 | CPS6 |
| ATOM | 5193 | O | GLY | 67 | 37.083 | 37.269 | 43.168 | 1.00 | 32.07 | CPS6 |
| ATOM | 5194 | N | ILE | 68 | 35.264 | 38.446 | 43.766 | 1.00 | 32.48 | CPS6 |
| ATOM | 5195 | CA | ILE | 68 | 35.878 | 39.721 | 43.397 | 1.00 | 32.14 | CPS6 |
| ATOM | 5196 | CB | ILE | 68 | 34.821 | 40.823 | 43.170 | 1.00 | 31.75 | CPS6 |
| ATOM | 5197 | CG2 | ILE | 68 | 35.509 | 42.167 | 42.928 | 1.00 | 32.21 | CPS6 |
| ATOM | 5198 | CG1 | ILE | 68 | 33.941 | 40.463 | 41.967 | 1.00 | 30.11 | CPS6 |
| ATOM | 5199 | CD1 | ILE | 68 | 34.697 | 40.354 | 40.642 | 1.00 | 30.32 | CPS6 |
| ATOM | 5200 | C | ILE | 68 | 36.796 | 40.150 | 44.536 | 1.00 | 33.67 | CPS6 |
| ATOM | 5201 | O | ILE | 68 | 36.370 | 40.206 | 45.692 | 1.00 | 33.24 | CPS6 |
| ATOM | 5202 | N | GLY | 69 | 38.050 | 40.443 | 44.207 | 1.00 | 34.42 | CPS6 |
| ATOM | 5203 | CA | GLY | 69 | 39.002 | 40.845 | 45.226 | 1.00 | 37.25 | CPS6 |
| ATOM | 5204 | C | GLY | 69 | 40.431 | 40.946 | 44.719 | 1.00 | 38.28 | CPS6 |
| ATOM | 5205 | O | GLY | 69 | 40.669 | 41.302 | 43.567 | 1.00 | 38.30 | CPS6 |
| ATOM | 5206 | N | ALA | 70 | 41.386 | 40.609 | 45.579 | 1.00 | 38.96 | CPS6 |
| ATOM | 5207 | CA | ALA | 70 | 42.800 | 40.684 | 45.233 | 1.00 | 39.69 | CPS6 |
| ATOM | 5208 | CB | ALA | 70 | 43.644 | 40.198 | 46.415 | 1.00 | 40.64 | CPS6 |
| ATOM | 5209 | C | ALA | 70 | 43.208 | 39.939 | 43.965 | 1.00 | 39.83 | CPS6 |
| ATOM | 5210 | O | ALA | 70 | 44.175 | 40.322 | 43.311 | 1.00 | 40.54 | CPS6 |
| ATOM | 5211 | N | GLN | 71 | 42.481 | 38.885 | 43.605 | 1.00 | 39.94 | CPS6 |
| ATOM | 5212 | CA | GLN | 71 | 42.834 | 38.115 | 42.411 | 1.00 | 39.34 | CPS6 |
| ATOM | 5213 | CB | GLN | 71 | 42.773 | 36.614 | 42.709 | 1.00 | 41.56 | CPS6 |
| ATOM | 5214 | CG | GLN | 71 | 43.429 | 36.181 | 44.006 | 1.00 | 43.98 | CPS6 |
| ATOM | 5215 | CD | GLN | 71 | 43.299 | 34.684 | 44.233 | 1.00 | 45.96 | CPS6 |
| ATOM | 5216 | OE1 | GLN | 71 | 43.901 | 33.880 | 43.515 | 1.00 | 48.14 | CPS6 |
| ATOM | 5217 | NE2 | GLN | 71 | 42.502 | 34.302 | 45.224 | 1.00 | 46.92 | CPS6 |
| ATOM | 5218 | C | GLN | 71 | 41.972 | 38.381 | 41.176 | 1.00 | 37.54 | CPS6 |
| ATOM | 5219 | O | GLN | 71 | 42.286 | 37.886 | 40.096 | 1.00 | 37.40 | CPS6 |
| ATOM | 5220 | N | LEU | 72 | 40.898 | 39.154 | 41.326 | 1.00 | 35.40 | CPS6 |
| ATOM | 5221 | CA | LEU | 72 | 39.998 | 39.428 | 40.204 | 1.00 | 33.24 | CPS6 |
| ATOM | 5222 | CB | LEU | 72 | 39.029 | 38.257 | 40.026 | 1.00 | 31.49 | CPS6 |
| ATOM | 5223 | CG | LEU | 72 | 38.647 | 37.600 | 38.692 | 1.00 | 32.42 | CPS6 |
| ATOM | 5224 | CD1 | LEU | 72 | 37.168 | 37.243 | 38.788 | 1.00 | 28.80 | CPS6 |
| ATOM | 5225 | CD2 | LEU | 72 | 38.919 | 38.478 | 37.487 | 1.00 | 30.34 | CPS6 |
| ATOM | 5226 | C | LEU | 72 | 39.174 | 40.680 | 40.483 | 1.00 | 31.78 | CPS6 |
| ATOM | 5227 | O | LEU | 72 | 38.496 | 40.758 | 41.502 | 1.00 | 32.54 | CPS6 |
| ATOM | 5228 | N | SER | 73 | 39.217 | 41.652 | 39.583 | 1.00 | 30.85 | CPS6 |
| ATOM | 5229 | CA | SER | 73 | 38.428 | 42.866 | 39.784 | 1.00 | 29.39 | CPS6 |
| ATOM | 5230 | CB | SER | 73 | 39.289 | 44.113 | 39.615 | 1.00 | 30.61 | CPS6 |
| ATOM | 5231 | OG | SER | 73 | 39.523 | 44.366 | 38.246 | 1.00 | 30.25 | CPS6 |
| ATOM | 5232 | C | SER | 73 | 37.309 | 42.898 | 38.752 | 1.00 | 27.96 | CPS6 |
| ATOM | 5233 | O | SER | 73 | 37.333 | 42.147 | 37.775 | 1.00 | 27.49 | CPS6 |
| ATOM | 5234 | N | PHE | 74 | 36.322 | 43.760 | 38.975 | 1.00 | 26.79 | CPS6 |
| ATOM | 5235 | CA | PHE | 74 | 35.213 | 43.888 | 38.034 | 1.00 | 26.21 | CPS6 |
| ATOM | 5236 | CB | PHE | 74 | 34.219 | 44.938 | 38.534 | 1.00 | 25.48 | CPS6 |
| ATOM | 5237 | CG | PHE | 74 | 33.366 | 44.472 | 39.676 | 1.00 | 26.75 | CPS6 |
| ATOM | 5238 | CD1 | PHE | 74 | 32.329 | 43.568 | 39.460 | 1.00 | 27.07 | CPS6 |
| ATOM | 5239 | CD2 | PHE | 74 | 33.582 | 44.949 | 40.967 | 1.00 | 27.57 | CPS6 |
| ATOM | 5240 | CE1 | PHE | 74 | 31.511 | 43.148 | 40.515 | 1.00 | 27.84 | CPS6 |
| ATOM | 5241 | CE2 | PHE | 74 | 32.770 | 44.534 | 42.030 | 1.00 | 28.92 | CPS6 |
| ATOM | 5242 | CZ | PHE | 74 | 31.732 | 43.634 | 41.801 | 1.00 | 27.85 | CPS6 |
| ATOM | 5243 | C | PHE | 74 | 35.731 | 44.301 | 36.659 | 1.00 | 26.17 | CPS6 |

FIG. 1A-92

| ATOM | 5244 | O   | PHE | 74 | 35.186 | 43.903 | 35.638 | 1.00 | 25.99 | CPS6 |
| ATOM | 5245 | N   | GLN | 75 | 36.793 | 45.103 | 36.638 | 1.00 | 25.96 | CPS6 |
| ATOM | 5246 | CA  | GLN | 75 | 37.365 | 45.583 | 35.384 | 1.00 | 27.32 | CPS6 |
| ATOM | 5247 | CB  | GLN | 75 | 38.374 | 46.703 | 35.665 | 1.00 | 27.52 | CPS6 |
| ATOM | 5248 | CG  | GLN | 75 | 37.754 | 47.960 | 36.271 | 1.00 | 30.15 | CPS6 |
| ATOM | 5249 | CD  | GLN | 75 | 36.770 | 48.648 | 35.339 | 1.00 | 30.80 | CPS6 |
| ATOM | 5250 | OE1 | GLN | 75 | 37.052 | 48.857 | 34.159 | 1.00 | 31.37 | CPS6 |
| ATOM | 5251 | NE2 | GLN | 75 | 35.618 | 49.019 | 35.871 | 1.00 | 34.02 | CPS6 |
| ATOM | 5252 | C   | GLN | 75 | 38.024 | 44.498 | 34.530 | 1.00 | 26.97 | CPS6 |
| ATOM | 5253 | O   | GLN | 75 | 38.199 | 44.679 | 33.329 | 1.00 | 26.86 | CPS6 |
| ATOM | 5254 | N   | ASP | 76 | 38.382 | 43.377 | 35.150 | 1.00 | 27.98 | CPS6 |
| ATOM | 5255 | CA  | ASP | 76 | 39.004 | 42.258 | 34.437 | 1.00 | 27.78 | CPS6 |
| ATOM | 5256 | CB  | ASP | 76 | 39.644 | 41.271 | 35.421 | 1.00 | 29.90 | CPS6 |
| ATOM | 5257 | CG  | ASP | 76 | 40.883 | 41.813 | 36.091 | 1.00 | 31.18 | CPS6 |
| ATOM | 5258 | OD1 | ASP | 76 | 41.690 | 42.457 | 35.397 | 1.00 | 35.07 | CPS6 |
| ATOM | 5259 | OD2 | ASP | 76 | 41.059 | 41.570 | 37.307 | 1.00 | 32.81 | CPS6 |
| ATOM | 5260 | C   | ASP | 76 | 37.969 | 41.474 | 33.633 | 1.00 | 27.27 | CPS6 |
| ATOM | 5261 | O   | ASP | 76 | 38.314 | 40.671 | 32.764 | 1.00 | 26.16 | CPS6 |
| ATOM | 5262 | N   | ILE | 77 | 36.696 | 41.705 | 33.930 | 1.00 | 26.25 | CPS6 |
| ATOM | 5263 | CA  | ILE | 77 | 35.616 | 40.966 | 33.272 | 1.00 | 25.67 | CPS6 |
| ATOM | 5264 | CB  | ILE | 77 | 34.682 | 40.360 | 34.335 | 1.00 | 25.40 | CPS6 |
| ATOM | 5265 | CG2 | ILE | 77 | 33.688 | 39.404 | 33.681 | 1.00 | 24.95 | CPS6 |
| ATOM | 5266 | CG1 | ILE | 77 | 35.511 | 39.639 | 35.400 | 1.00 | 23.36 | CPS6 |
| ATOM | 5267 | CD1 | ILE | 77 | 34.798 | 39.549 | 36.758 | 1.00 | 23.84 | CPS6 |
| ATOM | 5268 | C   | ILE | 77 | 34.785 | 41.871 | 32.372 | 1.00 | 25.23 | CPS6 |
| ATOM | 5269 | O   | ILE | 77 | 34.326 | 42.916 | 32.809 | 1.00 | 26.66 | CPS6 |
| ATOM | 5270 | N   | GLU | 78 | 34.579 | 41.473 | 31.123 | 1.00 | 24.36 | CPS6 |
| ATOM | 5271 | CA  | GLU | 78 | 33.794 | 42.296 | 30.217 | 1.00 | 23.95 | CPS6 |
| ATOM | 5272 | CB  | GLU | 78 | 34.689 | 42.928 | 29.151 | 1.00 | 23.23 | CPS6 |
| ATOM | 5273 | CG  | GLU | 78 | 33.936 | 43.867 | 28.231 | 1.00 | 25.47 | CPS6 |
| ATOM | 5274 | CD  | GLU | 78 | 34.858 | 44.740 | 27.406 | 1.00 | 28.41 | CPS6 |
| ATOM | 5275 | OE1 | GLU | 78 | 35.313 | 44.287 | 26.331 | 1.00 | 28.29 | CPS6 |
| ATOM | 5276 | OE2 | GLU | 78 | 35.133 | 45.880 | 27.844 | 1.00 | 29.93 | CPS6 |
| ATOM | 5277 | C   | GLU | 78 | 32.698 | 41.501 | 29.523 | 1.00 | 23.31 | CPS6 |
| ATOM | 5278 | O   | GLU | 78 | 32.951 | 40.411 | 29.013 | 1.00 | 23.66 | CPS6 |
| ATOM | 5279 | N   | ILE | 79 | 31.481 | 42.045 | 29.519 | 1.00 | 23.40 | CPS6 |
| ATOM | 5280 | CA  | ILE | 79 | 30.376 | 41.377 | 28.843 | 1.00 | 22.82 | CPS6 |
| ATOM | 5281 | CB  | ILE | 79 | 29.074 | 41.348 | 29.696 | 1.00 | 22.78 | CPS6 |
| ATOM | 5282 | CG2 | ILE | 79 | 27.899 | 40.913 | 28.834 | 1.00 | 23.83 | CPS6 |
| ATOM | 5283 | CG1 | ILE | 79 | 29.214 | 40.370 | 30.871 | 1.00 | 23.62 | CPS6 |
| ATOM | 5284 | CD1 | ILE | 79 | 29.978 | 40.908 | 32.041 | 1.00 | 26.29 | CPS6 |
| ATOM | 5285 | C   | ILE | 79 | 30.081 | 42.125 | 27.551 | 1.00 | 22.89 | CPS6 |
| ATOM | 5286 | O   | ILE | 79 | 29.992 | 43.352 | 27.547 | 1.00 | 21.79 | CPS6 |
| ATOM | 5287 | N   | ARG | 80 | 29.969 | 41.383 | 26.456 | 1.00 | 22.11 | CPS6 |
| ATOM | 5288 | CA  | ARG | 80 | 29.625 | 41.957 | 25.152 | 1.00 | 24.89 | CPS6 |
| ATOM | 5289 | CB  | ARG | 80 | 30.781 | 41.821 | 24.147 | 1.00 | 28.30 | CPS6 |
| ATOM | 5290 | CG  | ARG | 80 | 32.171 | 41.662 | 24.758 | 1.00 | 34.49 | CPS6 |
| ATOM | 5291 | CD  | ARG | 80 | 33.065 | 42.894 | 24.630 | 1.00 | 37.92 | CPS6 |
| ATOM | 5292 | NE  | ARG | 80 | 33.175 | 43.397 | 23.267 | 1.00 | 39.97 | CPS6 |
| ATOM | 5293 | CZ  | ARG | 80 | 34.078 | 44.291 | 22.857 | 1.00 | 39.55 | CPS6 |
| ATOM | 5294 | NH1 | ARG | 80 | 34.981 | 44.787 | 23.697 | 1.00 | 38.56 | CPS6 |
| ATOM | 5295 | NH2 | ARG | 80 | 34.050 | 44.724 | 21.604 | 1.00 | 37.96 | CPS6 |
| ATOM | 5296 | C   | ARG | 80 | 28.445 | 41.119 | 24.657 | 1.00 | 24.70 | CPS6 |
| ATOM | 5297 | O   | ARG | 80 | 28.130 | .40.095 | 25.249 | 1.00 | 22.24 | CPS6 |
| ATOM | 5298 | N   | LYS | 81 | 27.776 | 41.551 | 23.592 | 1.00 | 26.22 | CPS6 |
| ATOM | 5299 | CA  | LYS | 81 | 26.664 | 40.770 | 23.055 | 1.00 | 28.06 | CPS6 |
| ATOM | 5300 | CB  | LYS | 81 | 25.346 | 41.547 | 23.140 | 1.00 | 30.47 | CPS6 |

FIG. 1A-93

| ATOM | 5301 | CG | LYS | 81 | 24.745 | 41.614 | 24.542 | 1.00 | 34.14 | CPS6 |
|---|---|---|---|---|---|---|---|---|---|---|
| ATOM | 5302 | CD | LYS | 81 | 23.460 | 42.439 | 24.545 | 1.00 | 37.71 | CPS6 |
| ATOM | 5303 | CE | LYS | 81 | 22.985 | 42.787 | 25.963 | 1.00 | 39.78 | CPS6 |
| ATOM | 5304 | NZ | LYS | 81 | 22.435 | 41.636 | 26.736 | 1.00 | 39.75 | CPS6 |
| ATOM | 5305 | C | LYS | 81 | 26.962 | 40.409 | 21.608 | 1.00 | 29.13 | CPS6 |
| ATOM | 5306 | O | LYS | 81 | 27.536 | 41.222 | 20.876 | 1.00 | 29.46 | CPS6 |
| ATOM | 5307 | N | ASP | 82 | 26.602 | 39.193 | 21.197 | 1.00 | 29.17 | CPS6 |
| ATOM | 5308 | CA | ASP | 82 | 26.861 | 38.783 | 19.824 | 1.00 | 31.09 | CPS6 |
| ATOM | 5309 | CB | ASP | 82 | 27.044 | 37.255 | 19.707 | 1.00 | 29.73 | CPS6 |
| ATOM | 5310 | CG | ASP | 82 | 25.751 | 36.464 | 19.877 | 1.00 | 28.91 | CPS6 |
| ATOM | 5311 | OD1 | ASP | 82 | 24.646 | 37.045 | 19.861 | 1.00 | 26.18 | CPS6 |
| ATOM | 5312 | OD2 | ASP | 82 | 25.861 | 35.226 | 20.012 | 1.00 | 28.29 | CPS6 |
| ATOM | 5313 | C | ASP | 82 | 25.775 | 39.283 | 18.891 | 1.00 | 31.70 | CPS6 |
| ATOM | 5314 | O | ASP | 82 | 24.909 | 40.051 | 19.306 | 1.00 | 32.19 | CPS6 |
| ATOM | 5315 | N | GLN | 83 | 25.821 | 38.852 | 17.634 | 1.00 | 35.43 | CPS6 |
| ATOM | 5316 | CA | GLN | 83 | 24.854 | 39.300 | 16.634 | 1.00 | 37.80 | CPS6 |
| ATOM | 5317 | CB | GLN | 83 | 25.222 | 38.738 | 15.252 | 1.00 | 40.89 | CPS6 |
| ATOM | 5318 | CG | GLN | 83 | 25.267 | 37.219 | 15.164 | 1.00 | 44.70 | CPS6 |
| ATOM | 5319 | CD | GLN | 83 | 26.534 | 36.612 | 15.755 | 1.00 | 47.79 | CPS6 |
| ATOM | 5320 | OE1 | GLN | 83 | 26.642 | 35.388 | 15.889 | 1.00 | 49.81 | CPS6 |
| ATOM | 5321 | NE2 | GLN | 83 | 27.503 | 37.461 | 16.101 | 1.00 | 48.69 | CPS6 |
| ATOM | 5322 | C | GLN | 83 | 23.400 | 38.966 | 16.965 | 1.00 | 38.04 | CPS6 |
| ATOM | 5323 | O | GLN | 83 | 22.481 | 39.641 | 16.499 | 1.00 | 38.72 | CPS6 |
| ATOM | 5324 | N | ASN | 84 | 23.182 | 37.933 | 17.772 | 1.00 | 36.73 | CPS6 |
| ATOM | 5325 | CA | ASN | 84 | 21.822 | 37.564 | 18.146 | 1.00 | 35.24 | CPS6 |
| ATOM | 5326 | CB | ASN | 84 | 21.701 | 36.049 | 18.292 | 1.00 | 35.98 | CPS6 |
| ATOM | 5327 | CG | ASN | 84 | 21.864 | 35.331 | 16.979 | 1.00 | 37.29 | CPS6 |
| ATOM | 5328 | OD1 | ASN | 84 | 21.242 | 35.699 | 15.977 | 1.00 | 39.43 | CPS6 |
| ATOM | 5329 | ND2 | ASN | 84 | 22.694 | 34.298 | 16.968 | 1.00 | 36.91 | CPS6 |
| ATOM | 5330 | C | ASN | 84 | 21.400 | 38.234 | 19.447 | 1.00 | 33.77 | CPS6 |
| ATOM | 5331 | O | ASN | 84 | 20.262 | 38.088 | 19.882 | 1.00 | 34.74 | CPS6 |
| ATOM | 5332 | N | GLY | 85 | 22.322 | 38.963 | 20.067 | 1.00 | 31.96 | CPS6 |
| ATOM | 5333 | CA | GLY | 85 | 22.011 | 39.635 | 21.315 | 1.00 | 30.32 | CPS6 |
| ATOM | 5334 | C | GLY | 85 | 22.360 | 38.777 | 22.520 | 1.00 | 28.59 | CPS6 |
| ATOM | 5335 | O | GLY | 85 | 22.022 | 39.112 | 23.655 | 1.00 | 28.08 | CPS6 |
| ATOM | 5336 | N | LYS | 86 | 23.041 | 37.664 | 22.265 | 1.00 | 26.87 | CPS6 |
| ATOM | 5337 | CA | LYS | 86 | 23.451 | 36.743 | 23.323 | 1.00 | 24.77 | CPS6 |
| ATOM | 5338 | CB | LYS | 86 | 23.760 | 35.365 | 22.719 | 1.00 | 24.34 | CPS6 |
| ATOM | 5339 | CG | LYS | 86 | 24.446 | 34.376 | 23.663 | 1.00 | 23.41 | CPS6 |
| ATOM | 5340 | CD | LYS | 86 | 23.518 | 33.886 | 24.783 | 1.00 | 22.54 | CPS6 |
| ATOM | 5341 | CE | LYS | 86 | 24.296 | 33.008 | 25.778 | 1.00 | 21.86 | CPS6 |
| ATOM | 5342 | NZ | LYS | 86 | 23.395 | 32.379 | 26.784 | 1.00 | 21.67 | CPS6 |
| ATOM | 5343 | C | LYS | 86 | 24.690 | 37.282 | 24.028 | 1.00 | 23.40 | CPS6 |
| ATOM | 5344 | O | LYS | 86 | 25.709 | 37.558 | 23.390 | 1.00 | 22.20 | CPS6 |
| ATOM | 5345 | N | PRO | 87 | 24.628 | 37.443 | 25.359 | 1.00 | 22.90 | CPS6 |
| ATOM | 5346 | CD | PRO | 87 | 23.483 | 37.328 | 26.283 | 1.00 | 23.21 | CPS6 |
| ATOM | 5347 | CA | PRO | 87 | 25.820 | 37.956 | 26.050 | 1.00 | 21.73 | CPS6 |
| ATOM | 5348 | CB | PRO | 87 | 25.281 | 38.351 | 27.427 | 1.00 | 23.57 | CPS6 |
| ATOM | 5349 | CG | PRO | 87 | 24.166 | 37.350 | 27.648 | 1.00 | 23.73 | CPS6 |
| ATOM | 5350 | C | PRO | 87 | 26.945 | 36.924 | 26.167 | 1.00 | 21.97 | CPS6 |
| ATOM | 5351 | O | PRO | 87 | 26.693 | 35.724 | 26.260 | 1.00 | 19.28 | CPS6 |
| ATOM | 5352 | N | TYR | 88 | 28.192 | 37.393 | 26.124 | 1.00 | 21.22 | CPS6 |
| ATOM | 5353 | CA | TYR | 88 | 29.333 | 36.504 | 26.308 | 1.00 | 20.65 | CPS6 |
| ATOM | 5354 | CB | TYR | 88 | 29.881 | 35.972 | 24.980 | 1.00 | 22.01 | CPS6 |
| ATOM | 5355 | CG | TYR | 88 | 30.434 | 37.009 | 24.036 | 1.00 | 21.99 | CPS6 |
| ATOM | 5356 | CD1 | TYR | 88 | 31.796 | 37.317 | 24.021 | 1.00 | 25.46 | CPS6 |
| ATOM | 5357 | CE1 | TYR | 88 | 32.310 | 38.251 | 23.121 | 1.00 | 24.59 | CPS6 |

FIG. 1A-94

| ATOM | 5358 | CD2 | TYR | 88 | 29.600 | 37.666 | 23.132 | 1.00 | 25.11 | CPS6 |
|------|------|-----|-----|----|--------|--------|--------|------|-------|------|
| ATOM | 5359 | CE2 | TYR | 88 | 30.105 | 38.601 | 22.234 | 1.00 | 25.50 | CPS6 |
| ATOM | 5360 | CZ  | TYR | 88 | 31.459 | 38.887 | 22.235 | 1.00 | 26.13 | CPS6 |
| ATOM | 5361 | OH  | TYR | 88 | 31.947 | 39.824 | 21.351 | 1.00 | 28.03 | CPS6 |
| ATOM | 5362 | C   | TYR | 88 | 30.382 | 37.287 | 27.062 | 1.00 | 21.33 | CPS6 |
| ATOM | 5363 | O   | TYR | 88 | 30.415 | 38.512 | 27.009 | 1.00 | 22.02 | CPS6 |
| ATOM | 5364 | N   | ILE | 89 | 31.238 | 36.571 | 27.769 | 1.00 | 22.15 | CPS6 |
| ATOM | 5365 | CA  | ILE | 89 | 32.263 | 37.187 | 28.581 | 1.00 | 22.97 | CPS6 |
| ATOM | 5366 | CB  | ILE | 89 | 32.244 | 36.555 | 30.001 | 1.00 | 22.83 | CPS6 |
| ATOM | 5367 | CG2 | ILE | 89 | 33.564 | 36.820 | 30.736 | 1.00 | 22.49 | CPS6 |
| ATOM | 5368 | CG1 | ILE | 89 | 31.036 | 37.080 | 30.779 | 1.00 | 23.07 | CPS6 |
| ATOM | 5369 | CD1 | ILE | 89 | 30.876 | 36.460 | 32.168 | 1.00 | 23.21 | CPS6 |
| ATOM | 5370 | C   | ILE | 89 | 33.670 | 37.026 | 28.027 | 1.00 | 24.96 | CPS6 |
| ATOM | 5371 | O   | ILE | 89 | 33.990 | 35.997 | 27.435 | 1.00 | 24.10 | CPS6 |
| ATOM | 5372 | N   | ILE | 90 | 34.489 | 38.064 | 28.193 | 1.00 | 24.59 | CPS6 |
| ATOM | 5373 | CA  | ILE | 90 | 35.898 | 37.956 | 27.833 | 1.00 | 25.62 | CPS6 |
| ATOM | 5374 | CB  | ILE | 90 | 36.305 | 38.796 | 26.589 | 1.00 | 26.38 | CPS6 |
| ATOM | 5375 | CG2 | ILE | 90 | 35.630 | 38.229 | 25.360 | 1.00 | 26.74 | CPS6 |
| ATOM | 5376 | CG1 | ILE | 90 | 35.984 | 40.273 | 26.787 | 1.00 | 27.06 | CPS6 |
| ATOM | 5377 | CD1 | ILE | 90 | 36.410 | 41.147 | 25.584 | 1.00 | 30.06 | CPS6 |
| ATOM | 5378 | C   | ILE | 90 | 36.657 | 38.407 | 29.079 | 1.00 | 26.15 | CPS6 |
| ATOM | 5379 | O   | ILE | 90 | 36.241 | 39.337 | 29.783 | 1.00 | 25.40 | CPS6 |
| ATOM | 5380 | N   | CYS | 91 | 37.742 | 37.702 | 29.376 | 1.00 | 26.82 | CPS6 |
| ATOM | 5381 | CA  | CYS | 91 | 38.574 | 37.975 | 30.543 | 1.00 | 28.62 | CPS6 |
| ATOM | 5382 | CB  | CYS | 91 | 38.041 | 37.191 | 31.749 | 1.00 | 27.71 | CPS6 |
| ATOM | 5383 | SG  | CYS | 91 | 39.031 | 37.333 | 33.261 | 1.00 | 30.47 | CPS6 |
| ATOM | 5384 | C   | CYS | 91 | 39.998 | 37.516 | 30.194 | 1.00 | 29.98 | CPS6 |
| ATOM | 5385 | O   | CYS | 91 | 40.213 | 36.361 | 29.839 | 1.00 | 29.65 | CPS6 |
| ATOM | 5386 | N   | THR | 92 | 40.966 | 38.419 | 30.291 | 1.00 | 32.42 | CPS6 |
| ATOM | 5387 | CA  | THR | 92 | 42.344 | 38.078 | 29.948 | 1.00 | 34.14 | CPS6 |
| ATOM | 5388 | CB  | THR | 92 | 43.264 | 39.303 | 30.103 | 1.00 | 36.33 | CPS6 |
| ATOM | 5389 | OG1 | THR | 92 | 43.150 | 39.810 | 31.439 | 1.00 | 38.35 | CPS6 |
| ATOM | 5390 | CG2 | THR | 92 | 42.872 | 40.393 | 29.104 | 1.00 | 35.90 | CPS6 |
| ATOM | 5391 | C   | THR | 92 | 42.931 | 36.932 | 30.761 | 1.00 | 35.10 | CPS6 |
| ATOM | 5392 | O   | THR | 92 | 43.960 | 36.359 | 30.380 | 1.00 | 36.58 | CPS6 |
| ATOM | 5393 | N   | LYS | 93 | 42.291 | 36.582 | 31.870 | 1.00 | 33.97 | CPS6 |
| ATOM | 5394 | CA  | LYS | 93 | 42.808 | 35.503 | 32.698 | 1.00 | 34.28 | CPS6 |
| ATOM | 5395 | CB  | LYS | 93 | 42.231 | 35.596 | 34.105 | 1.00 | 35.19 | CPS6 |
| ATOM | 5396 | CG  | LYS | 93 | 42.654 | 36.867 | 34.827 | 1.00 | 38.98 | CPS6 |
| ATOM | 5397 | CD  | LYS | 93 | 42.107 | 36.924 | 36.240 | 1.00 | 40.89 | CPS6 |
| ATOM | 5398 | CE  | LYS | 93 | 42.416 | 38.263 | 36.898 | 1.00 | 41.92 | CPS6 |
| ATOM | 5399 | NZ  | LYS | 93 | 43.879 | 38.529 | 36.966 | 1.00 | 43.76 | CPS6 |
| ATOM | 5400 | C   | LYS | 93 | 42.575 | 34.111 | 32.126 | 1.00 | 33.08 | CPS6 |
| ATOM | 5401 | O   | LYS | 93 | 43.143 | 33.137 | 32.613 | 1.00 | 33.58 | CPS6 |
| ATOM | 5402 | N   | LEU | 94 | 41.743 | 34.005 | 31.098 | 1.00 | 31.56 | CPS6 |
| ATOM | 5403 | CA  | LEU | 94 | 41.489 | 32.702 | 30.487 | 1.00 | 29.96 | CPS6 |
| ATOM | 5404 | CB  | LEU | 94 | 40.553 | 31.853 | 31.363 | 1.00 | 31.34 | CPS6 |
| ATOM | 5405 | CG  | LEU | 94 | 39.321 | 32.481 | 32.035 | 1.00 | 33.01 | CPS6 |
| ATOM | 5406 | CD1 | LEU | 94 | 38.520 | 33.306 | 31.062 | 1.00 | 32.91 | CPS6 |
| ATOM | 5407 | CD2 | LEU | 94 | 38.465 | 31.368 | 32.625 | 1.00 | 35.31 | CPS6 |
| ATOM | 5408 | C   | LEU | 94 | 40.917 | 32.822 | 29.091 | 1.00 | 28.50 | CPS6 |
| ATOM | 5409 | O   | LEU | 94 | 40.531 | 33.909 | 28.654 | 1.00 | 28.02 | CPS6 |
| ATOM | 5410 | N   | SER | 95 | 40.861 | 31.692 | 28.398 | 1.00 | 27.95 | CPS6 |
| ATOM | 5411 | CA  | SER | 95 | 40.341 | 31.636 | 27.040 | 1.00 | 27.87 | CPS6 |
| ATOM | 5412 | CB  | SER | 95 | 40.579 | 30.261 | 26.426 | 1.00 | 28.47 | CPS6 |
| ATOM | 5413 | OG  | SER | 95 | 39.846 | 30.141 | 25.218 | 1.00 | 30.54 | CPS6 |
| ATOM | 5414 | C   | SER | 95 | 38.849 | 31.905 | 27.011 | 1.00 | 26.60 | CPS6 |

FIG. 1A-95

| ATOM | 5415 | O   | SER | 95  | 38.098 | 31.331 | 27.793 | 1.00 | 25.68 | CPS6 |
|------|------|-----|-----|-----|--------|--------|--------|------|-------|------|
| ATOM | 5416 | N   | PRO | 96  | 38.401 | 32.762 | 26.082 | 1.00 | 25.92 | CPS6 |
| ATOM | 5417 | CD  | PRO | 96  | 39.206 | 33.567 | 25.144 | 1.00 | 25.77 | CPS6 |
| ATOM | 5418 | CA  | PRO | 96  | 36.978 | 33.085 | 25.978 | 1.00 | 25.00 | CPS6 |
| ATOM | 5419 | CB  | PRO | 96  | 36.947 | 34.199 | 24.922 | 1.00 | 25.69 | CPS6 |
| ATOM | 5420 | CG  | PRO | 96  | 38.197 | 33.949 | 24.093 | 1.00 | 25.08 | CPS6 |
| ATOM | 5421 | C   | PRO | 96  | 36.129 | 31.873 | 25.602 | 1.00 | 25.28 | CPS6 |
| ATOM | 5422 | O   | PRO | 96  | 34.942 | 31.810 | 25.922 | 1.00 | 23.78 | CPS6 |
| ATOM | 5423 | N   | ALA | 97  | 36.741 | 30.902 | 24.934 | 1.00 | 24.13 | CPS6 |
| ATOM | 5424 | CA  | ALA | 97  | 36.023 | 29.701 | 24.534 | 1.00 | 24.78 | CPS6 |
| ATOM | 5425 | CB  | ALA | 97  | 36.873 | 28.890 | 23.569 | 1.00 | 25.54 | CPS6 |
| ATOM | 5426 | C   | ALA | 97  | 35.650 | 28.846 | 25.746 | 1.00 | 24.39 | CPS6 |
| ATOM | 5427 | O   | ALA | 97  | 34.783 | 27.980 | 25.657 | 1.00 | 25.77 | CPS6 |
| ATOM | 5428 | N   | ALA | 98  | 36.300 | 29.093 | 26.879 | 1.00 | 23.13 | CPS6 |
| ATOM | 5429 | CA  | ALA | 98  | 36.033 | 28.320 | 28.094 | 1.00 | 23.12 | CPS6 |
| ATOM | 5430 | CB  | ALA | 98  | 37.285 | 28.277 | 28.947 | 1.00 | 23.94 | CPS6 |
| ATOM | 5431 | C   | ALA | 98  | 34.875 | 28.867 | 28.937 | 1.00 | 23.29 | CPS6 |
| ATOM | 5432 | O   | ALA | 98  | 34.418 | 28.217 | 29.883 | 1.00 | 23.78 | CPS6 |
| ATOM | 5433 | N   | VAL | 99  | 34.398 | 30.055 | 28.593 | 1.00 | 22.50 | CPS6 |
| ATOM | 5434 | CA  | VAL | 99  | 33.353 | 30.693 | 29.386 | 1.00 | 22.03 | CPS6 |
| ATOM | 5435 | CB  | VAL | 99  | 33.776 | 32.130 | 29.747 | 1.00 | 22.74 | CPS6 |
| ATOM | 5436 | CG1 | VAL | 99  | 32.850 | 32.710 | 30.799 | 1.00 | 22.51 | CPS6 |
| ATOM | 5437 | CG2 | VAL | 99  | 35.207 | 32.132 | 30.250 | 1.00 | 24.89 | CPS6 |
| ATOM | 5438 | C   | VAL | 99  | 31.978 | 30.757 | 28.739 | 1.00 | 20.85 | CPS6 |
| ATOM | 5439 | O   | VAL | 99  | 31.850 | 30.969 | 27.534 | 1.00 | 20.38 | CPS6 |
| ATOM | 5440 | N   | HIS | 100 | 30.950 | 30.580 | 29.568 | 1.00 | 20.29 | CPS6 |
| ATOM | 5441 | CA  | HIS | 100 | 29.563 | 30.652 | 29.132 | 1.00 | 18.65 | CPS6 |
| ATOM | 5442 | CB  | HIS | 100 | 28.988 | 29.251 | 29.029 | 1.00 | 20.06 | CPS6 |
| ATOM | 5443 | CG  | HIS | 100 | 29.786 | 28.360 | 28.139 | 1.00 | 23.66 | CPS6 |
| ATOM | 5444 | CD2 | HIS | 100 | 30.802 | 27.509 | 28.412 | 1.00 | 26.19 | CPS6 |
| ATOM | 5445 | ND1 | HIS | 100 | 29.626 | 28.343 | 26.772 | 1.00 | 25.30 | CPS6 |
| ATOM | 5446 | CE1 | HIS | 100 | 30.511 | 27.518 | 26.239 | 1.00 | 26.78 | CPS6 |
| ATOM | 5447 | NE2 | HIS | 100 | 31.237 | 27.000 | 27.214 | 1.00 | 27.25 | CPS6 |
| ATOM | 5448 | C   | HIS | 100 | 28.806 | 31.440 | 30.186 | 1.00 | 18.48 | CPS6 |
| ATOM | 5449 | O   | HIS | 100 | 29.071 | 31.297 | 31.378 | 1.00 | 17.96 | CPS6 |
| ATOM | 5450 | N   | VAL | 101 | 27.852 | 32.261 | 29.753 | 1.00 | 17.67 | CPS6 |
| ATOM | 5451 | CA  | VAL | 101 | 27.092 | 33.060 | 30.697 | 1.00 | 17.87 | CPS6 |
| ATOM | 5452 | CB  | VAL | 101 | 27.749 | 34.455 | 30.846 | 1.00 | 19.43 | CPS6 |
| ATOM | 5453 | CG1 | VAL | 101 | 27.766 | 35.151 | 29.492 | 1.00 | 19.75 | CPS6 |
| ATOM | 5454 | CG2 | VAL | 101 | 26.984 | 35.314 | 31.860 | 1.00 | 19.30 | CPS6 |
| ATOM | 5455 | C   | VAL | 101 | 25.650 | 33.255 | 30.229 | 1.00 | 17.14 | CPS6 |
| ATOM | 5456 | O   | VAL | 101 | 25.356 | 33.139 | 29.046 | 1.00 | 16.92 | CPS6 |
| ATOM | 5457 | N   | SER | 102 | 24.752 | 33.522 | 31.173 | 1.00 | 17.82 | CPS6 |
| ATOM | 5458 | CA  | SER | 102 | 23.365 | 33.821 | 30.837 | 1.00 | 18.24 | CPS6 |
| ATOM | 5459 | CB  | SER | 102 | 22.450 | 32.592 | 30.926 | 1.00 | 18.94 | CPS6 |
| ATOM | 5460 | OG  | SER | 102 | 21.131 | 32.955 | 30.513 | 1.00 | 19.02 | CPS6 |
| ATOM | 5461 | C   | SER | 102 | 22.932 | 34.853 | 31.855 | 1.00 | 17.95 | CPS6 |
| ATOM | 5462 | O   | SER | 102 | 23.335 | 34.792 | 33.025 | 1.00 | 16.39 | CPS6 |
| ATOM | 5463 | N   | ILE | 103 | 22.112 | 35.802 | 31.414 | 1.00 | 16.51 | CPS6 |
| ATOM | 5464 | CA  | ILE | 103 | 21.630 | 36.864 | 32.291 | 1.00 | 17.17 | CPS6 |
| ATOM | 5465 | CB  | ILE | 103 | 22.243 | 38.240 | 31.884 | 1.00 | 17.60 | CPS6 |
| ATOM | 5466 | CG2 | ILE | 103 | 21.761 | 39.341 | 32.845 | 1.00 | 19.81 | CPS6 |
| ATOM | 5467 | CG1 | ILE | 103 | 23.769 | 38.152 | 31.899 | 1.00 | 19.89 | CPS6 |
| ATOM | 5468 | CD1 | ILE | 103 | 24.483 | 39.402 | 31.357 | 1.00 | 19.80 | CPS6 |
| ATOM | 5469 | C   | ILE | 103 | 20.112 | 36.933 | 32.131 | 1.00 | 17.69 | CPS6 |
| ATOM | 5470 | O   | ILE | 103 | 19.595 | 36.760 | 31.021 | 1.00 | 17.52 | CPS6 |
| ATOM | 5471 | N   | THR | 104 | 19.414 | 37.173 | 33.237 | 1.00 | 18.18 | CPS6 |

FIG. 1A-96

| ATOM | 5472 | CA | THR | 104 | 17.954 | 37.283 | 33.226 | 1.00 | 18.92 | CPS6 |
|---|---|---|---|---|---|---|---|---|---|---|
| ATOM | 5473 | CB | THR | 104 | 17.285 | 35.948 | 33.660 | 1.00 | 20.47 | CPS6 |
| ATOM | 5474 | OG1 | THR | 104 | 15.864 | 36.026 | 33.456 | 1.00 | 20.23 | CPS6 |
| ATOM | 5475 | CG2 | THR | 104 | 17.578 | 35.648 | 35.130 | 1.00 | 17.86 | CPS6 |
| ATOM | 5476 | C | THR | 104 | 17.523 | 38.429 | 34.159 | 1.00 | 20.41 | CPS6 |
| ATOM | 5477 | O | THR | 104 | 18.306 | 38.901 | 34.990 | 1.00 | 19.19 | CPS6 |
| ATOM | 5478 | N | HIS | 105 | 16.280 | 38.880 | 34.001 | 1.00 | 21.31 | CPS6 |
| ATOM | 5479 | CA | HIS | 105 | 15.751 | 39.984 | 34.799 | 1.00 | 22.86 | CPS6 |
| ATOM | 5480 | CB | HIS | 105 | 15.802 | 41.299 | 33.998 | 1.00 | 26.24 | CPS6 |
| ATOM | 5481 | CG | HIS | 105 | 17.175 | 41.721 | 33.578 | 1.00 | 30.59 | CPS6 |
| ATOM | 5482 | CD2 | HIS | 105 | 17.889 | 41.444 | 32.461 | 1.00 | 32.14 | CPS6 |
| ATOM | 5483 | ND1 | HIS | 105 | 17.974 | 42.534 | 34.355 | 1.00 | 33.04 | CPS6 |
| ATOM | 5484 | CE1 | HIS | 105 | 19.122 | 42.739 | 33.733 | 1.00 | 33.19 | CPS6 |
| ATOM | 5485 | NE2 | HIS | 105 | 19.097 | 42.089 | 32.582 | 1.00 | 32.49 | CPS6 |
| ATOM | 5486 | C | HIS | 105 | 14.278 | 39.762 | 35.129 | 1.00 | 23.27 | CPS6 |
| ATOM | 5487 | O | HIS | 105 | 13.575 | 39.039 | 34.417 | 1.00 | 21.93 | CPS6 |
| ATOM | 5488 | N | THR | 106 | 13.837 | 40.393 | 36.212 | 1.00 | 23.40 | CPS6 |
| ATOM | 5489 | CA | THR | 106 | 12.430 | 40.421 | 36.605 | 1.00 | 25.56 | CPS6 |
| ATOM | 5490 | CB | THR | 106 | 12.067 | 39.537 | 37.816 | 1.00 | 27.06 | CPS6 |
| ATOM | 5491 | OG1 | THR | 106 | 12.664 | 40.059 | 39.015 | 1.00 | 26.80 | CPS6 |
| ATOM | 5492 | CG2 | THR | 106 | 12.496 | 38.102 | 37.567 | 1.00 | 25.79 | CPS6 |
| ATOM | 5493 | C | THR | 106 | 12.266 | 41.879 | 37.013 | 1.00 | 27.51 | CPS6 |
| ATOM | 5494 | O | THR | 106 | 13.230 | 42.651 | 36.964 | 1.00 | 26.39 | CPS6 |
| ATOM | 5495 | N | LYS | 107 | 11.069 | 42.272 | 37.423 | 1.00 | 28.29 | CPS6 |
| ATOM | 5496 | CA | LYS | 107 | 10.880 | 43.662 | 37.810 | 1.00 | 29.88 | CPS6 |
| ATOM | 5497 | CB | LYS | 107 | 9.440 | 43.899 | 38.268 | 1.00 | 32.33 | CPS6 |
| ATOM | 5498 | CG | LYS | 107 | 9.155 | 45.357 | 38.599 | 1.00 | 36.25 | CPS6 |
| ATOM | 5499 | CD | LYS | 107 | 7.745 | 45.549 | 39.147 | 1.00 | 39.84 | CPS6 |
| ATOM | 5500 | CE | LYS | 107 | 7.473 | 47.024 | 39.442 | 1.00 | 41.42 | CPS6 |
| ATOM | 5501 | NZ | LYS | 107 | 6.102 | 47.246 | 39.995 | 1.00 | 45.05 | CPS6 |
| ATOM | 5502 | C | LYS | 107 | 11.839 | 44.132 | 38.905 | 1.00 | 29.50 | CPS6 |
| ATOM | 5503 | O | LYS | 107 | 12.367 | 45.243 | 38.823 | 1.00 | 29.28 | CPS6 |
| ATOM | 5504 | N | GLU | 108 | 12.081 | 43.289 | 39.912 | 1.00 | 27.21 | CPS6 |
| ATOM | 5505 | CA | GLU | 108 | 12.945 | 43.667 | 41.033 | 1.00 | 26.33 | CPS6 |
| ATOM | 5506 | CB | GLU | 108 | 12.239 | 43.363 | 42.358 | 1.00 | 30.27 | CPS6 |
| ATOM | 5507 | CG | GLU | 108 | 10.841 | 43.953 | 42.480 | 1.00 | 36.27 | CPS6 |
| ATOM | 5508 | CD | GLU | 108 | 10.259 | 43.782 | 43.874 | 1.00 | 41.02 | CPS6 |
| ATOM | 5509 | OE1 | GLU | 108 | 10.158 | 42.632 | 44.354 | 1.00 | 44.74 | CPS6 |
| ATOM | 5510 | OE2 | GLU | 108 | 9.897 | 44.803 | 44.497 | 1.00 | 45.09 | CPS6 |
| ATOM | 5511 | C | GLU | 108 | 14.333 | 43.033 | 41.108 | 1.00 | 25.31 | CPS6 |
| ATOM | 5512 | O | GLU | 108 | 15.145 | 43.437 | 41.936 | 1.00 | 22.62 | CPS6 |
| ATOM | 5513 | N | TYR | 109 | 14.609 | 42.043 | 40.266 | 1.00 | 22.54 | CPS6 |
| ATOM | 5514 | CA | TYR | 109 | 15.900 | 41.368 | 40.333 | 1.00 | 22.99 | CPS6 |
| ATOM | 5515 | CB | TYR | 109 | 15.728 | 39.954 | 40.909 | 1.00 | 22.64 | CPS6 |
| ATOM | 5516 | CG | TYR | 109 | 15.175 | 39.906 | 42.310 | 1.00 | 24.37 | CPS6 |
| ATOM | 5517 | CD1 | TYR | 109 | 15.988 | 40.167 | 43.411 | 1.00 | 24.51 | CPS6 |
| ATOM | 5518 | CE1 | TYR | 109 | 15.465 | 40.190 | 44.701 | 1.00 | 26.40 | CPS6 |
| ATOM | 5519 | CD2 | TYR | 109 | 13.821 | 39.661 | 42.531 | 1.00 | 24.67 | CPS6 |
| ATOM | 5520 | CE2 | TYR | 109 | 13.286 | 39.683 | 43.809 | 1.00 | 24.88 | CPS6 |
| ATOM | 5521 | CZ | TYR | 109 | 14.106 | 39.946 | 44.884 | 1.00 | 26.56 | CPS6 |
| ATOM | 5522 | OH | TYR | 109 | 13.576 | 39.968 | 46.144 | 1.00 | 29.07 | CPS6 |
| ATOM | 5523 | C | TYR | 109 | 16.609 | 41.211 | 39.008 | 1.00 | 21.70 | CPS6 |
| ATOM | 5524 | O | TYR | 109 | 15.993 | 41.280 | 37.945 | 1.00 | 22.54 | CPS6 |
| ATOM | 5525 | N | ALA | 110 | 17.926 | 41.012 | 39.103 | 1.00 | 21.84 | CPS6 |
| ATOM | 5526 | CA | ALA | 110 | 18.770 | 40.702 | 37.950 | 1.00 | 20.16 | CPS6 |
| ATOM | 5527 | CB | ALA | 110 | 19.785 | 41.803 | 37.666 | 1.00 | 21.73 | CPS6 |
| ATOM | 5528 | C | ALA | 110 | 19.492 | 39.445 | 38.443 | 1.00 | 20.44 | CPS6 |

FIG. 1A-97

| ATOM | 5529 | O | ALA | 110 | 19.824 | 39.345 | 39.621 | 1.00 | 21.38 | CPS6 |
| ATOM | 5530 | N | ALA | 111 | 19.714 | 38.476 | 37.560 | 1.00 | 19.56 | CPS6 |
| ATOM | 5531 | CA | ALA | 111 | 20.415 | 37.272 | 37.962 | 1.00 | 17.92 | CPS6 |
| ATOM | 5532 | CB | ALA | 111 | 19.410 | 36.180 | 38.358 | 1.00 | 18.78 | CPS6 |
| ATOM | 5533 | C | ALA | 111 | 21.286 | 36.791 | 36.808 | 1.00 | 18.10 | CPS6 |
| ATOM | 5534 | O | ALA | 111 | 21.044 | 37.114 | 35.654 | 1.00 | 19.16 | CPS6 |
| ATOM | 5535 | N | ALA | 112 | 22.319 | 36.033 | 37.128 | 1.00 | 18.13 | CPS6 |
| ATOM | 5536 | CA | ALA | 112 | 23.175 | 35.509 | 36.083 | 1.00 | 18.42 | CPS6 |
| ATOM | 5537 | CB | ALA | 112 | 24.206 | 36.565 | 35.659 | 1.00 | 16.42 | CPS6 |
| ATOM | 5538 | C | ALA | 112 | 23.882 | 34.260 | 36.569 | 1.00 | 17.57 | CPS6 |
| ATOM | 5539 | O | ALA | 112 | 24.000 | 34.017 | 37.778 | 1.00 | 18.87 | CPS6 |
| ATOM | 5540 | N | GLN | 113 | 24.327 | 33.449 | 35.619 | 1.00 | 17.13 | CPS6 |
| ATOM | 5541 | CA | GLN | 113 | 25.065 | 32.247 | 35.971 | 1.00 | 17.77 | CPS6 |
| ATOM | 5542 | CB | GLN | 113 | 24.163 | 31.017 | 35.898 | 1.00 | 19.54 | CPS6 |
| ATOM | 5543 | CG | GLN | 113 | 23.699 | 30.693 | 34.495 | 1.00 | 21.95 | CPS6 |
| ATOM | 5544 | CD | GLN | 113 | 22.787 | 29.472 | 34.435 | 1.00 | 25.73 | CPS6 |
| ATOM | 5545 | OE1 | GLN | 113 | 22.446 | 29.002 | 33.352 | 1.00 | 27.72 | CPS6 |
| ATOM | 5546 | NE2 | GLN | 113 | 22.378 | 28.968 | 35.594 | 1.00 | 27.67 | CPS6 |
| ATOM | 5547 | C | GLN | 113 | 26.205 | 32.133 | 34.968 | 1.00 | 16.69 | CPS6 |
| ATOM | 5548 | O | GLN | 113 | 26.104 | 32.622 | 33.840 | 1.00 | 16.20 | CPS6 |
| ATOM | 5549 | N | VAL | 114 | 27.288 | 31.499 | 35.391 | 1.00 | 17.22 | CPS6 |
| ATOM | 5550 | CA | VAL | 114 | 28.449 | 31.324 | 34.535 | 1.00 | 17.47 | CPS6 |
| ATOM | 5551 | CB | VAL | 114 | 29.605 | 32.300 | 34.948 | 1.00 | 17.72 | CPS6 |
| ATOM | 5552 | CG1 | VAL | 114 | 30.931 | 31.901 | 34.243 | 1.00 | 16.56 | CPS6 |
| ATOM | 5553 | CG2 | VAL | 114 | 29.222 | 33.738 | 34.581 | 1.00 | 17.27 | CPS6 |
| ATOM | 5554 | C | VAL | 114 | 28.964 | 29.911 | 34.693 | 1.00 | 18.72 | CPS6 |
| ATOM | 5555 | O | VAL | 114 | 28.880 | 29.338 | 35.776 | 1.00 | 19.21 | CPS6 |
| ATOM | 5556 | N | VAL | 115 | 29.461 | 29.338 | 33.604 | 1.00 | 18.94 | CPS6 |
| ATOM | 5557 | CA | VAL | 115 | 30.090 | 28.027 | 33.684 | 1.00 | 19.93 | CPS6 |
| ATOM | 5558 | CB | VAL | 115 | 29.311 | 26.916 | 32.928 | 1.00 | 19.40 | CPS6 |
| ATOM | 5559 | CG1 | VAL | 115 | 30.143 | 25.631 | 32.901 | 1.00 | 20.42 | CPS6 |
| ATOM | 5560 | CG2 | VAL | 115 | 27.981 | 26.638 | 33.628 | 1.00 | 19.61 | CPS6 |
| ATOM | 5561 | C | VAL | 115 | 31.453 | 28.231 | 33.023 | 1.00 | 20.14 | CPS6 |
| ATOM | 5562 | O | VAL | 115 | 31.562 | 28.860 | 31.958 | 1.00 | 19.69 | CPS6 |
| ATOM | 5563 | N | ILE | 116 | 32.498 | 27.750 | 33.680 | 1.00 | 19.47 | CPS6 |
| ATOM | 5564 | CA | ILE | 116 | 33.839 | 27.853 | 33.121 | 1.00 | 21.42 | CPS6 |
| ATOM | 5565 | CB | ILE | 116 | 34.806 | 28.617 | 34.068 | 1.00 | 21.08 | CPS6 |
| ATOM | 5566 | CG2 | ILE | 116 | 36.235 | 28.577 | 33.505 | 1.00 | 23.06 | CPS6 |
| ATOM | 5567 | CG1 | ILE | 116 | 34.365 | 30.082 | 34.195 | 1.00 | 21.71 | CPS6 |
| ATOM | 5568 | CD1 | ILE | 116 | 35.180 | 30.906 | 35.213 | 1.00 | 21.07 | CPS6 |
| ATOM | 5569 | C | ILE | 116 | 34.320 | 26.420 | 32.940 | 1.00 | 24.10 | CPS6 |
| ATOM | 5570 | O | ILE | 116 | 34.264 | 25.615 | 33.872 | 1.00 | 23.26 | CPS6 |
| ATOM | 5571 | N | GLU | 117 | 34.759 | 26.103 | 31.731 | 1.00 | 25.26 | CPS6 |
| ATOM | 5572 | CA | GLU | 117 | 35.243 | 24.769 | 31.424 | 1.00 | 29.11 | CPS6 |
| ATOM | 5573 | CB | GLU | 117 | 34.878 | 24.369 | 30.001 | 1.00 | 30.47 | CPS6 |
| ATOM | 5574 | CG | GLU | 117 | 33.446 | 24.548 | 29.587 | 1.00 | 33.45 | CPS6 |
| ATOM | 5575 | CD | GLU | 117 | 33.226 | 24.007 | 28.194 | 1.00 | 36.82 | CPS6 |
| ATOM | 5576 | OE1 | GLU | 117 | 33.345 | 22.776 | 28.022 | 1.00 | 39.37 | CPS6 |
| ATOM | 5577 | OE2 | GLU | 117 | 32.959 | 24.804 | 27.271 | 1.00 | 38.14 | CPS6 |
| ATOM | 5578 | C | GLU | 117 | 36.754 | 24.698 | 31.503 | 1.00 | 31.19 | CPS6 |
| ATOM | 5579 | O | GLU | 117 | 37.445 | 25.712 | 31.392 | 1.00 | 28.72 | CPS6 |
| ATOM | 5580 | N | ARG | 118 | 37.259 | 23.484 | 31.686 | 1.00 | 34.06 | CPS6 |
| ATOM | 5581 | CA | ARG | 118 | 38.692 | 23.267 | 31.686 | 1.00 | 39.18 | CPS6 |
| ATOM | 5582 | CB | ARG | 118 | 39.089 | 22.180 | 32.703 | 1.00 | 40.91 | CPS6 |
| ATOM | 5583 | CG | ARG | 118 | 38.327 | 20.872 | 32.574 | 1.00 | 46.37 | CPS6 |
| ATOM | 5584 | CD | ARG | 118 | 38.840 | 19.776 | 33.528 | 1.00 | 49.12 | CPS6 |
| ATOM | 5585 | NE | ARG | 118 | 38.479 | 19.996 | 34.930 | 1.00 | 50.78 | CPS6 |

FIG. 1A-98

| ATOM | 5586 | CZ | ARG | 118 | 39.095 | 20.849 | 35.744 | 1.00 | 51.80 | CPS6 |
|---|---|---|---|---|---|---|---|---|---|---|
| ATOM | 5587 | NH1 | ARG | 118 | 40.113 | 21.575 | 35.304 | 1.00 | 53.03 | CPS6 |
| ATOM | 5588 | NH2 | ARG | 118 | 38.692 | 20.977 | 37.003 | 1.00 | 51.56 | CPS6 |
| ATOM | 5589 | C | ARG | 118 | 38.895 | 22.789 | 30.250 | 1.00 | 40.50 | CPS6 |
| ATOM | 5590 | O | ARG | 118 | 38.365 | 21.750 | 29.862 | 1.00 | 41.56 | CPS6 |
| ATOM | 5591 | N | LEU | 119 | 39.615 | 23.562 | 29.445 | 1.00 | 42.65 | CPS6 |
| ATOM | 5592 | CA | LEU | 119 | 39.833 | 23.176 | 28.055 | 1.00 | 44.91 | CPS6 |
| ATOM | 5593 | CB | LEU | 119 | 40.106 | 24.414 | 27.196 | 1.00 | 45.15 | CPS6 |
| ATOM | 5594 | CG | LEU | 119 | 38.970 | 25.432 | 27.070 | 1.00 | 45.37 | CPS6 |
| ATOM | 5595 | CD1 | LEU | 119 | 39.442 | 26.618 | 26.246 | 1.00 | 44.17 | CPS6 |
| ATOM | 5596 | CD2 | LEU | 119 | 37.752 | 24.776 | 26.427 | 1.00 | 45.02 | CPS6 |
| ATOM | 5597 | C | LEU | 119 | 40.991 | 22.193 | 27.918 | 1.00 | 46.41 | CPS6 |
| ATOM | 5598 | OT1 | LEU | 119 | 41.823 | 22.138 | 28.848 | 1.00 | 47.25 | CPS6 |
| ATOM | 5599 | OT2 | LEU | 119 | 41.055 | 21.501 | 26.874 | 1.00 | 47.76 | CPS6 |
| ATOM | 5600 | O | HOH | 1 | 74.183 | 58.190 | -19.320 | 1.00 | 16.24 | AT |
| ATOM | 5601 | O | HOH | 2 | 50.451 | 28.498 | 2.245 | 1.00 | 16.26 | AT |
| ATOM | 5602 | O | HOH | 3 | 72.513 | 43.845 | 5.247 | 1.00 | 16.95 | AT |
| ATOM | 5603 | O | HOH | 4 | 59.768 | 49.591 | 13.381 | 1.00 | 18.99 | AT |
| ATOM | 5604 | O | HOH | 5 | 9.919 | 40.963 | 40.359 | 1.00 | 17.22 | AT |
| ATOM | 5605 | O | HOH | 6 | 57.301 | 49.721 | 15.536 | 1.00 | 18.51 | AT |
| ATOM | 5606 | O | HOH | 7 | 72.254 | 36.424 | 22.184 | 1.00 | 19.44 | AT |
| ATOM | 5607 | O | HOH | 8 | 15.486 | 40.288 | 48.189 | 1.00 | 19.00 | AT |
| ATOM | 5608 | O | HOH | 9 | 22.359 | 26.422 | 33.132 | 1.00 | 28.69 | AT |
| ATOM | 5609 | O | HOH | 10 | 62.648 | 41.000 | 12.765 | 1.00 | 26.69 | AT |
| ATOM | 5610 | O | HOH | 11 | 27.253 | 11.532 | 60.836 | 1.00 | 33.03 | AT |
| ATOM | 5611 | O | HOH | 12 | 4.545 | 29.482 | 16.753 | 1.00 | 34.49 | AT |
| ATOM | 5612 | O | HOH | 13 | 14.678 | 33.346 | 17.568 | 1.00 | 28.16 | AT |
| ATOM | 5613 | O | HOH | 14 | 2.443 | 17.966 | 21.642 | 1.00 | 31.50 | AT |
| ATOM | 5614 | O | HOH | 15 | 13.387 | 44.897 | 46.109 | 1.00 | 36.84 | AT |
| ATOM | 5615 | O | HOH | 16 | 64.048 | 43.971 | 9.189 | 1.00 | 27.36 | AT |
| ATOM | 5616 | O | HOH | 17 | 17.153 | 29.081 | 61.693 | 1.00 | 38.80 | AT |
| ATOM | 5617 | O | HOH | 18 | 15.565 | 11.097 | 37.041 | 1.00 | 32.04 | AT |
| ATOM | 5618 | O | HOH | 19 | 66.736 | 39.802 | 9.758 | 1.00 | 31.88 | AT |
| ATOM | 5619 | O | HOH | 20 | 68.806 | 35.163 | 19.609 | 1.00 | 43.12 | AT |
| ATOM | 5620 | O | HOH | 21 | 28.442 | 30.448 | 25.270 | 1.00 | 35.30 | AT |
| ATOM | 5621 | O | HOH | 22 | 20.356 | 37.769 | 28.103 | 1.00 | 40.41 | AT |
| ATOM | 5622 | O | HOH | 23 | 27.784 | 56.284 | 42.007 | 1.00 | 39.44 | AT |
| ATOM | 5623 | O | HOH | 24 | 9.819 | 21.853 | 51.711 | 1.00 | 48.93 | AT |
| ATOM | 5624 | O | HOH | 25 | 18.794 | 48.571 | 49.608 | 1.00 | 38.44 | AT |
| ATOM | 5625 | O | HOH | 26 | 50.953 | 43.970 | 28.198 | 1.00 | 29.58 | AT |
| ATOM | 5626 | O | HOH | 27 | 22.120 | 28.021 | 18.001 | 1.00 | 41.70 | AT |
| ATOM | 5627 | O | HOH | 28 | 18.224 | 7.825 | 50.971 | 1.00 | 37.65 | AT |
| ATOM | 5628 | O | HOH | 29 | 45.010 | 40.785 | 1.909 | 1.00 | 35.18 | AT |
| ATOM | 5629 | O | HOH | 30 | 64.211 | 31.229 | 23.988 | 1.00 | 42.82 | AT |
| ATOM | 5630 | O | HOH | 31 | 55.673 | 59.846 | 2.934 | 1.00 | 40.75 | AT |
| ATOM | 5631 | O | HOH | 32 | 12.144 | 16.656 | 71.990 | 1.00 | 45.41 | AT |
| ATOM | 5632 | O | HOH | 33 | 26.174 | 28.070 | 35.889 | 1.00 | 33.23 | AT |
| ATOM | 5633 | O | HOH | 34 | 23.423 | 24.108 | 37.385 | 1.00 | 33.85 | AT |
| ATOM | 5634 | O | HOH | 35 | 72.206 | 58.375 | 9.452 | 1.00 | 45.41 | AT |
| ATOM | 5635 | O | HOH | 36 | 4.583 | 28.820 | 43.211 | 1.00 | 37.91 | AT |
| ATOM | 5636 | O | HOH | 37 | 54.428 | 31.469 | 26.691 | 1.00 | 40.61 | AT |
| ATOM | 5637 | O | HOH | 38 | 5.129 | 39.360 | 42.159 | 1.00 | 34.31 | AT |
| ATOM | 5638 | O | HOH | 39 | 61.288 | 9.543 | 3.422 | 1.00 | 45.78 | AT |
| ATOM | 5639 | O | HOH | 40 | 41.144 | 21.554 | 50.056 | 1.00 | 46.77 | AT |
| ATOM | 5640 | O | HOH | 41 | 45.899 | 31.375 | 23.218 | 1.00 | 36.69 | AT |
| ATOM | 5641 | O | HOH | 42 | 46.684 | 40.019 | 4.072 | 1.00 | 40.88 | AT |
| ATOM | 5642 | O | HOH | 43 | 32.060 | 30.436 | 24.972 | 1.00 | 38.00 | AT |

FIG. 1A-99

| | | | | | | | | | |
|---|---|---|---|---|---|---|---|---|---|
| ATOM | 5643 | O | HOH | 44 | 27.193 | 55.260 | 39.276 | 1.00 39.83 | AT |
| ATOM | 5644 | O | HOH | 45 | 74.083 | 12.016 | 10.419 | 1.00 37.57 | AT |
| ATOM | 5645 | O | HOH | 46 | 7.161 | 11.806 | 20.918 | 1.00 37.74 | AT |
| ATOM | 5646 | O | HOH | 47 | 37.597 | 37.224 | 10.717 | 1.00 44.06 | AT |
| ATOM | 5647 | O | HOH | 48 | 26.713 | 40.428 | 46.123 | 1.00 47.01 | AT |
| ATOM | 5648 | O | HOH | 49 | 73.327 | 31.524 | 18.039 | 1.00 39.95 | AT |
| ATOM | 5649 | O | HOH | 50 | 6.885 | 35.701 | 48.910 | 1.00 38.11 | AT |
| ATOM | 5650 | O | HOH | 51 | 12.147 | 30.555 | 62.867 | 1.00 45.67 | AT |
| ATOM | 5651 | O | HOH | 52 | 45.035 | 35.126 | 28.209 | 1.00 45.09 | AT |
| ATOM | 5652 | O | HOH | 53 | 45.816 | 30.463 | 0.531 | 1.00 37.06 | AT |
| ATOM | 5653 | O | HOH | 54 | 37.959 | 49.546 | 12.787 | 1.00 41.97 | AT |
| ATOM | 5654 | O | HOH | 55 | 29.307 | 59.252 | 40.586 | 1.00 54.29 | AT |
| ATOM | 5655 | O | HOH | 56 | 33.064 | 30.245 | 14.482 | 1.00 53.18 | AT |
| ATOM | 5656 | O | HOH | 57 | 5.959 | 29.404 | 40.923 | 1.00 42.88 | AT |
| ATOM | 5657 | O | HOH | 58 | 72.015 | 56.594 | 2.111 | 1.00 41.98 | AT |
| ATOM | 5658 | O | HOH | 59 | 34.149 | 9.199 | 46.267 | 1.00 42.25 | AT |
| ATOM | 5659 | O | HOH | 60 | 56.871 | 24.901 | 5.890 | 1.00 43.48 | AT |
| ATOM | 5660 | O | HOH | 61 | 53.366 | 27.278 | 27.533 | 1.00 46.43 | AT |
| ATOM | 5661 | O | HOH | 62 | 51.684 | 37.046 | 30.830 | 1.00 46.25 | AT |
| ATOM | 5662 | O | HOH | 63 | 52.569 | 48.531 | 8.124 | 1.00 42.45 | AT |
| ATOM | 5663 | O | HOH | 64 | 19.990 | 15.518 | 32.236 | 1.00 48.76 | AT |
| ATOM | 5664 | O | HOH | 65 | 64.540 | 44.979 | 26.386 | 1.00 42.49 | AT |
| ATOM | 5665 | O | HOH | 66 | 30.220 | 13.054 | 46.228 | 1.00 52.13 | AT |
| ATOM | 5666 | O | HOH | 67 | 54.239 | 52.985 | 1.438 | 1.00 45.12 | AT |
| ATOM | 5667 | O | HOH | 68 | 20.023 | 54.748 | 37.127 | 1.00 39.76 | AT |
| ATOM | 5668 | O | HOH | 69 | 8.456 | 21.336 | 37.515 | 1.00 48.76 | AT |
| ATOM | 5669 | O | HOH | 70 | 35.909 | 45.522 | 2.599 | 1.00 46.39 | AT |
| ATOM | 5670 | O | HOH | 71 | 53.886 | 30.997 | 19.731 | 1.00 43.92 | AT |
| ATOM | 5671 | O | HOH | 72 | 10.033 | 24.488 | 66.210 | 1.00 53.66 | AT |
| ATOM | 5672 | O | HOH | 73 | 58.903 | 57.250 | 13.037 | 1.00 41.23 | AT |
| ATOM | 5673 | O | HOH | 74 | 62.777 | 15.875 | 1.984 | 1.00 41.20 | AT |
| ATOM | 5674 | O | HOH | 75 | 42.217 | 40.323 | 33.742 | 1.00 43.11 | AT |
| ATOM | 5675 | O | HOH | 76 | 20.956 | 40.692 | 29.179 | 1.00 49.81 | AT |
| ATOM | 5676 | O | HOH | 77 | 46.166 | 43.977 | 11.730 | 1.00 36.26 | AT |
| ATOM | 5677 | O | HOH | 78 | 66.744 | 59.058 | 16.145 | 1.00 56.18 | AT |
| ATOM | 5678 | O | HOH | 79 | 45.851 | 25.881 | 4.391 | 1.00 55.88 | AT |
| ATOM | 5679 | O | HOH | 80 | 75.174 | 49.183 | 6.063 | 1.00 47.74 | AT |
| ATOM | 5680 | O | HOH | 81 | 29.310 | 41.802 | 17.220 | 1.00 55.92 | AT |
| ATOM | 5681 | O | HOH | 82 | 1.927 | 35.649 | 42.778 | 1.00 51.25 | AT |
| ATOM | 5682 | O | HOH | 83 | -1.663 | 38.805 | 38.155 | 1.00 39.95 | AT |
| ATOM | 5683 | O | HOH | 84 | 14.052 | 11.606 | 52.410 | 1.00 45.64 | AT |
| ATOM | 5684 | O | HOH | 85 | 12.374 | 37.222 | 15.756 | 1.00 49.24 | AT |
| ATOM | 5685 | O | HOH | 86 | 31.903 | 41.930 | 45.468 | 1.00 45.19 | AT |
| ATOM | 5686 | O | HOH | 87 | 33.483 | 20.380 | 56.292 | 1.00 53.83 | AT |
| ATOM | 5687 | O | HOH | 88 | 74.639 | 45.461 | 5.020 | 1.00 41.59 | AT |
| ATOM | 5688 | O | HOH | 89 | 37.028 | 19.108 | 53.278 | 1.00 43.77 | AT |
| ATOM | 5689 | O | HOH | 90 | 38.593 | 49.011 | 6.342 | 1.00 51.49 | AT |
| ATOM | 5690 | O | HOH | 91 | 52.402 | 56.617 | 3.593 | 1.00 53.57 | AT |
| ATOM | 5691 | O | HOH | 92 | 5.772 | 28.675 | 61.930 | 1.00 44.14 | AT |
| ATOM | 5692 | O | HOH | 93 | 32.173 | 36.302 | 19.628 | 1.00 45.70 | AT |
| ATOM | 5693 | O | HOH | 94 | 52.026 | 42.123 | 29.953 | 1.00 47.73 | AT |
| ATOM | 5694 | O | HOH | 95 | 47.042 | 40.027 | 29.849 | 1.00 57.66 | AT |
| ATOM | 5695 | O | HOH | 96 | 62.041 | 43.614 | 30.370 | 1.00 49.31 | AT |
| ATOM | 5696 | O | HOH | 97 | 61.630 | 30.997 | 18.476 | 1.00 53.79 | AT |
| ATOM | 5697 | O | HOH | 98 | 11.168 | 13.661 | 45.409 | 1.00 45.46 | AT |
| ATOM | 5698 | O | HOH | 99 | 28.738 | 15.678 | 20.064 | 1.00 63.95 | AT |
| ATOM | 5699 | O | HOH | 100 | 37.162 | 57.858 | 42.839 | 1.00 49.29 | AT |

FIG. 1A-100

| ATOM | 5700 | O | HOH | 101 | 56.970 | 48.398 | 18.183 | 1.00 | 20.07 | AT |
|------|------|---|-----|-----|--------|--------|--------|------|-------|-----|
| ATOM | 5701 | O | HOH | 102 | 16.747 | 17.196 | 32.059 | 1.00 | 21.58 | AT |
| ATOM | 5702 | O | HOH | 103 | 45.835 | 52.603 | 17.631 | 1.00 | 19.92 | AT |
| ATOM | 5703 | O | HOH | 104 | -5.526 | 20.298 | 17.919 | 1.00 | 20.40 | AT |
| ATOM | 5704 | O | HOH | 105 | 16.573 | 18.225 | 29.320 | 1.00 | 21.11 | AT |
| ATOM | 5705 | O | HOH | 106 | 28.084 | 33.122 | 26.572 | 1.00 | 21.96 | AT |
| ATOM | 5706 | O | HOH | 107 | 56.776 | 49.897 | 20.691 | 1.00 | 20.77 | AT |
| ATOM | 5707 | O | HOH | 108 | 61.822 | 31.586 | 15.608 | 1.00 | 22.44 | AT |
| ATOM | 5708 | O | HOH | 109 | 75.499 | 25.254 | 21.262 | 1.00 | 22.49 | AT |
| ATOM | 5709 | O | HOH | 110 | 52.716 | 36.178 | -8.615 | 1.00 | 23.96 | AT |
| ATOM | 5710 | O | HOH | 111 | 30.657 | 33.717 | 27.675 | 1.00 | 22.13 | AT |
| ATOM | 5711 | O | HOH | 112 | 31.857 | 23.322 | 43.883 | 1.00 | 22.91 | AT |
| ATOM | 5712 | O | HOH | 113 | 16.560 | 16.176 | 27.250 | 1.00 | 22.50 | AT |
| ATOM | 5713 | O | HOH | 114 | 48.919 | 55.521 | 18.754 | 1.00 | 22.71 | AT |
| ATOM | 5714 | O | HOH | 115 | 30.469 | 45.806 | 26.160 | 1.00 | 24.06 | AT |
| ATOM | 5715 | O | HOH | 116 | 29.611 | 29.912 | 44.889 | 1.00 | 23.26 | AT |
| ATOM | 5716 | O | HOH | 117 | 14.658 | 45.605 | 43.596 | 1.00 | 25.77 | AT |
| ATOM | 5717 | O | HOH | 118 | 38.482 | 35.704 | 27.602 | 1.00 | 23.84 | AT |
| ATOM | 5718 | O | HOH | 119 | 33.048 | 33.856 | 26.010 | 1.00 | 23.17 | AT |
| ATOM | 5719 | O | HOH | 120 | 11.956 | 35.757 | 52.609 | 1.00 | 26.32 | AT |
| ATOM | 5720 | O | HOH | 121 | 72.585 | 45.998 | 2.976 | 1.00 | 23.39 | AT |
| ATOM | 5721 | O | HOH | 122 | 45.040 | 32.707 | 1.982 | 1.00 | 25.55 | AT |
| ATOM | 5722 | O | HOH | 123 | 71.609 | 48.727 | 2.944 | 1.00 | 24.67 | AT |
| ATOM | 5723 | O | HOH | 124 | 34.369 | 7.558 | 43.913 | 1.00 | 24.87 | AT |
| ATOM | 5724 | O | HOH | 125 | 4.595 | 36.818 | 41.429 | 1.00 | 25.98 | AT |
| ATOM | 5725 | O | HOH | 126 | 11.206 | 23.871 | 43.608 | 1.00 | 25.23 | AT |
| ATOM | 5726 | O | HOH | 127 | 14.284 | 14.636 | 65.129 | 1.00 | 25.02 | AT |
| ATOM | 5727 | O | HOH | 128 | 70.983 | 32.077 | 16.439 | 1.00 | 25.53 | AT |
| ATOM | 5728 | O | HOH | 129 | 15.935 | 10.066 | 59.658 | 1.00 | 25.84 | AT |
| ATOM | 5729 | O | HOH | 130 | 17.042 | 11.420 | 57.203 | 1.00 | 25.22 | AT |
| ATOM | 5730 | O | HOH | 131 | 78.508 | 30.572 | 16.070 | 1.00 | 25.80 | AT |
| ATOM | 5731 | O | HOH | 132 | 31.882 | 25.438 | 41.276 | 1.00 | 25.44 | AT |
| ATOM | 5732 | O | HOH | 133 | 68.333 | 21.576 | 13.174 | 1.00 | 27.25 | AT |
| ATOM | 5733 | O | HOH | 134 | 59.808 | 51.543 | 15.137 | 1.00 | 26.71 | AT |
| ATOM | 5734 | O | HOH | 135 | 51.803 | 45.823 | 2.829 | 1.00 | 28.23 | AT |
| ATOM | 5735 | O | HOH | 136 | 23.948 | 33.437 | 19.543 | 1.00 | 26.93 | AT |
| ATOM | 5736 | O | HOH | 137 | 77.529 | 24.686 | -0.187 | 1.00 | 27.06 | AT |
| ATOM | 5737 | O | HOH | 138 | 36.414 | 47.961 | 27.068 | 1.00 | 26.59 | AT |
| ATOM | 5738 | O | HOH | 139 | 15.210 | 37.727 | 30.916 | 1.00 | 26.63 | AT |
| ATOM | 5739 | O | HOH | 140 | 26.736 | 13.803 | 59.642 | 1.00 | 27.51 | AT |
| ATOM | 5740 | O | HOH | 141 | 59.707 | 29.029 | -5.923 | 1.00 | 28.00 | AT |
| ATOM | 5741 | O | HOH | 142 | 73.385 | 50.907 | 2.916 | 1.00 | 25.70 | AT |
| ATOM | 5742 | O | HOH | 143 | 25.372 | 31.413 | 54.764 | 1.00 | 28.23 | AT |
| ATOM | 5743 | O | HOH | 144 | 8.726 | 40.753 | 36.473 | 1.00 | 28.04 | AT |
| ATOM | 5744 | O | HOH | 145 | 21.631 | 52.226 | 39.835 | 1.00 | 27.68 | AT |
| ATOM | 5745 | O | HOH | 146 | 6.966 | 31.512 | 19.584 | 1.00 | 26.22 | AT |
| ATOM | 5746 | O | HOH | 147 | 33.568 | 23.343 | 41.390 | 1.00 | 28.59 | AT |
| ATOM | 5747 | O | HOH | 148 | 47.104 | 33.497 | 24.474 | 1.00 | 31.57 | AT |
| ATOM | 5748 | O | HOH | 149 | 42.706 | 46.788 | 25.123 | 1.00 | 28.27 | AT |
| ATOM | 5749 | O | HOH | 150 | 15.361 | 13.776 | 53.744 | 1.00 | 28.43 | AT |
| ATOM | 5750 | O | HOH | 151 | 49.210 | 27.704 | 6.023 | 1.00 | 26.48 | AT |
| ATOM | 5751 | O | HOH | 152 | 69.742 | 37.893 | 23.208 | 1.00 | 28.63 | AT |
| ATOM | 5752 | O | HOH | 153 | 62.896 | 46.941 | 28.207 | 1.00 | 29.51 | AT |
| ATOM | 5753 | O | HOH | 154 | 66.194 | 34.304 | -2.754 | 1.00 | 27.04 | AT |
| ATOM | 5754 | O | HOH | 155 | 56.380 | 56.783 | 12.351 | 1.00 | 29.49 | AT |
| ATOM | 5755 | O | HOH | 156 | 62.810 | 23.721 | 9.697 | 1.00 | 29.08 | AT |
| ATOM | 5756 | O | HOH | 157 | 59.600 | 48.626 | -20.735 | 1.00 | 30.39 | AT |

FIG. 1A-101

| ATOM | 5757 | O | HOH | 158 | 63.447 | 33.873 | 17.572 | 1.00 | 29.71 | AT |
|---|---|---|---|---|---|---|---|---|---|---|
| ATOM | 5758 | O | HOH | 159 | 11.724 | 13.599 | 66.211 | 1.00 | 27.82 | AT |
| ATOM | 5759 | O | HOH | 160 | 60.558 | 22.006 | 10.718 | 1.00 | 28.85 | AT |
| ATOM | 5760 | O | HOH | 161 | 46.499 | 54.700 | 19.899 | 1.00 | 29.19 | AT |
| ATOM | 5761 | O | HOH | 162 | 63.410 | 57.441 | -12.830 | 1.00 | 29.14 | AT |
| ATOM | 5762 | O | HOH | 163 | 16.531 | 13.383 | 27.915 | 1.00 | 29.15 | AT |
| ATOM | 5763 | O | HOH | 164 | 57.094 | 58.123 | -5.057 | 1.00 | 30.67 | AT |
| ATOM | 5764 | O | HOH | 165 | 55.029 | 24.601 | -1.884 | 1.00 | 27.07 | AT |
| ATOM | 5765 | O | HOH | 166 | 13.338 | 35.151 | 24.133 | 1.00 | 28.54 | AT |
| ATOM | 5766 | O | HOH | 167 | 35.398 | 47.783 | 6.493 | 1.00 | 28.26 | AT |
| ATOM | 5767 | O | HOH | 168 | 70.174 | 56.885 | -10.515 | 1.00 | 31.78 | AT |
| ATOM | 5768 | O | HOH | 169 | 25.901 | 44.946 | 25.667 | 1.00 | 31.94 | AT |
| ATOM | 5769 | O | HOH | 170 | 50.393 | 53.846 | 23.119 | 1.00 | 28.26 | AT |
| ATOM | 5770 | O | HOH | 171 | 62.156 | 25.716 | 13.450 | 1.00 | 31.00 | AT |
| ATOM | 5771 | O | HOH | 172 | 42.474 | 44.185 | 26.823 | 1.00 | 31.95 | AT |
| ATOM | 5772 | O | HOH | 173 | 77.820 | 49.020 | -5.810 | 1.00 | 32.32 | AT |
| ATOM | 5773 | O | HOH | 174 | 67.420 | 39.148 | -19.340 | 1.00 | 29.68 | AT |
| ATOM | 5774 | O | HOH | 175 | 48.791 | 40.644 | -3.702 | 1.00 | 28.90 | AT |
| ATOM | 5775 | O | HOH | 176 | 33.117 | 16.234 | 43.002 | 1.00 | 31.48 | AT |
| ATOM | 5776 | O | HOH | 177 | 15.122 | 24.092 | 63.819 | 1.00 | 30.47 | AT |
| ATOM | 5777 | O | HOH | 178 | 64.991 | 30.299 | -1.464 | 1.00 | 30.76 | AT |
| ATOM | 5778 | O | HOH | 179 | 15.212 | 16.862 | 21.098 | 1.00 | 32.61 | AT |
| ATOM | 5779 | O | HOH | 180 | 8.026 | 30.440 | 48.746 | 1.00 | 29.36 | AT |
| ATOM | 5780 | O | HOH | 181 | 15.063 | 29.611 | 60.193 | 1.00 | 29.52 | AT |
| ATOM | 5781 | O | HOH | 182 | -4.236 | 31.973 | 27.775 | 1.00 | 33.07 | AT |
| ATOM | 5782 | O | HOH | 183 | 41.379 | 28.581 | 29.607 | 1.00 | 31.08 | AT |
| ATOM | 5783 | O | HOH | 184 | 30.685 | 20.525 | 44.633 | 1.00 | 30.33 | AT |
| ATOM | 5784 | O | HOH | 185 | 25.786 | 35.845 | 47.678 | 1.00 | 31.51 | AT |
| ATOM | 5785 | O | HOH | 186 | 33.235 | 47.941 | 17.895 | 1.00 | 29.68 | AT |
| ATOM | 5786 | O | HOH | 187 | 64.882 | 30.921 | 17.515 | 1.00 | 30.10 | AT |
| ATOM | 5787 | O | HOH | 188 | 5.685 | 13.963 | 30.264 | 1.00 | 32.30 | AT |
| ATOM | 5788 | O | HOH | 189 | -4.735 | 20.413 | 39.978 | 1.00 | 33.19 | AT |
| ATOM | 5789 | O | HOH | 190 | 44.587 | 45.272 | 8.578 | 1.00 | 31.21 | AT |
| ATOM | 5790 | O | HOH | 191 | 57.838 | 12.743 | 11.965 | 1.00 | 31.57 | AT |
| ATOM | 5791 | O | HOH | 192 | 16.393 | 22.844 | 66.100 | 1.00 | 34.23 | AT |
| ATOM | 5792 | O | HOH | 193 | 4.372 | 22.943 | 37.792 | 1.00 | 32.96 | AT |
| ATOM | 5793 | O | HOH | 194 | 71.929 | 20.305 | 14.473 | 1.00 | 32.09 | AT |
| ATOM | 5794 | O | HOH | 195 | 28.925 | 15.553 | 59.281 | 1.00 | 30.49 | AT |
| ATOM | 5795 | O | HOH | 196 | 53.796 | 25.895 | -4.052 | 1.00 | 33.01 | AT |
| ATOM | 5796 | O | HOH | 197 | 6.468 | 23.780 | 36.296 | 1.00 | 34.02 | AT |
| ATOM | 5797 | O | HOH | 198 | 53.710 | 44.972 | -1.506 | 1.00 | 33.84 | AT |
| ATOM | 5798 | O | HOH | 199 | 19.319 | 42.034 | 48.498 | 1.00 | 31.81 | AT |
| ATOM | 5799 | O | HOH | 200 | 24.603 | 12.893 | 57.779 | 1.00 | 32.45 | AT |
| ATOM | 5800 | O | HOH | 201 | 82.186 | 45.693 | -2.681 | 1.00 | 34.17 | AT |
| ATOM | 5801 | O | HOH | 202 | 11.264 | 18.716 | 60.799 | 1.00 | 36.53 | AT |
| ATOM | 5802 | O | HOH | 203 | 79.085 | 17.668 | 9.255 | 1.00 | 31.67 | AT |
| ATOM | 5803 | O | HOH | 204 | 59.866 | 52.931 | 11.834 | 1.00 | 30.91 | AT |
| ATOM | 5804 | O | HOH | 205 | 13.907 | 16.278 | 62.855 | 1.00 | 36.18 | AT |
| ATOM | 5805 | O | HOH | 206 | 16.412 | 14.129 | 56.660 | 1.00 | 32.42 | AT |
| ATOM | 5806 | O | HOH | 207 | 66.234 | 40.890 | -9.847 | 1.00 | 31.86 | AT |
| ATOM | 5807 | O | HOH | 208 | 10.481 | 11.237 | 25.068 | 1.00 | 32.03 | AT |
| ATOM | 5808 | O | HOH | 209 | 5.289 | 19.707 | 30.585 | 1.00 | 33.17 | AT |
| ATOM | 5809 | O | HOH | 210 | 39.446 | 40.017 | 23.668 | 1.00 | 33.18 | AT |
| ATOM | 5810 | O | HOH | 211 | 54.509 | 23.461 | 6.035 | 1.00 | 35.31 | AT |
| ATOM | 5811 | O | HOH | 212 | 51.401 | 31.567 | 11.354 | 1.00 | 32.75 | AT |
| ATOM | 5812 | O | HOH | 213 | 28.205 | 23.736 | 55.152 | 1.00 | 30.83 | AT |
| ATOM | 5813 | O | HOH | 214 | 50.324 | 34.946 | -7.659 | 1.00 | 34.98 | AT |

FIG. 1A-102

| ATOM | 5814 | O | HOH | 215 | 30.129 | 20.719 | 56.661 | 1.00 | 32.37 | AT |
|---|---|---|---|---|---|---|---|---|---|---|
| ATOM | 5815 | O | HOH | 216 | 58.457 | 50.516 | -18.849 | 1.00 | 32.27 | AT |
| ATOM | 5816 | O | HOH | 217 | 44.476 | 34.908 | 24.562 | 1.00 | 35.00 | AT |
| ATOM | 5817 | O | HOH | 218 | 9.990 | 35.693 | 24.724 | 1.00 | 34.96 | AT |
| ATOM | 5818 | O | HOH | 219 | 11.096 | 35.811 | 32.093 | 1.00 | 34.27 | AT |
| ATOM | 5819 | O | HOH | 220 | 12.913 | 17.730 | 46.309 | 1.00 | 34.71 | AT |
| ATOM | 5820 | O | HOH | 221 | 65.231 | 44.053 | -7.852 | 1.00 | 32.99 | AT |
| ATOM | 5821 | O | HOH | 222 | 38.789 | 35.275 | 9.625 | 1.00 | 34.60 | AT |
| ATOM | 5822 | O | HOH | 223 | 12.929 | 25.623 | 47.543 | 1.00 | 32.40 | AT |
| ATOM | 5823 | O | HOH | 224 | 74.529 | 33.737 | 18.589 | 1.00 | 33.85 | AT |
| ATOM | 5824 | O | HOH | 225 | 16.279 | 43.522 | 36.165 | 1.00 | 33.82 | AT |
| ATOM | 5825 | O | HOH | 226 | 13.480 | 14.423 | 55.667 | 1.00 | 35.36 | AT |
| ATOM | 5826 | O | HOH | 227 | 4.656 | 17.272 | 27.720 | 1.00 | 34.90 | AT |
| ATOM | 5827 | O | HOH | 228 | 55.566 | 43.939 | -14.228 | 1.00 | 37.00 | AT |
| ATOM | 5828 | O | HOH | 229 | 18.454 | 21.396 | 68.984 | 1.00 | 35.96 | AT |
| ATOM | 5829 | O | HOH | 230 | 56.014 | 51.348 | -16.697 | 1.00 | 37.91 | AT |
| ATOM | 5830 | O | HOH | 231 | 71.572 | 46.002 | -9.177 | 1.00 | 36.91 | AT |
| ATOM | 5831 | O | HOH | 232 | 39.465 | 30.116 | 20.475 | 1.00 | 46.92 | AT |
| ATOM | 5832 | O | HOH | 233 | 40.113 | 37.155 | 25.795 | 1.00 | 31.64 | AT |
| ATOM | 5833 | O | HOH | 234 | 14.226 | 44.782 | 35.447 | 1.00 | 33.52 | AT |
| ATOM | 5834 | O | HOH | 235 | 20.027 | 45.208 | 30.512 | 1.00 | 33.92 | AT |
| ATOM | 5835 | O | HOH | 236 | 61.895 | 17.484 | 0.210 | 1.00 | 36.39 | AT |
| ATOM | 5836 | O | HOH | 237 | 26.769 | 18.525 | 65.425 | 1.00 | 33.45 | AT |
| ATOM | 5837 | O | HOH | 238 | 30.216 | 49.429 | 23.557 | 1.00 | 38.87 | AT |
| ATOM | 5838 | O | HOH | 239 | 12.005 | 18.680 | 49.514 | 1.00 | 35.80 | AT |
| ATOM | 5839 | O | HOH | 240 | 40.174 | 39.987 | 26.354 | 1.00 | 36.59 | AT |
| ATOM | 5840 | O | HOH | 241 | 19.654 | 14.821 | 28.728 | 1.00 | 35.91 | AT |
| ATOM | 5841 | O | HOH | 242 | 55.447 | 29.046 | 11.959 | 1.00 | 36.10 | AT |
| ATOM | 5842 | O | HOH | 243 | 67.323 | 29.753 | -3.238 | 1.00 | 39.47 | AT |
| ATOM | 5843 | O | HOH | 244 | 84.687 | 32.541 | 17.389 | 1.00 | 39.50 | AT |
| ATOM | 5844 | O | HOH | 245 | 54.503 | 28.663 | -6.976 | 1.00 | 36.28 | AT |
| ATOM | 5845 | O | HOH | 246 | 35.636 | 37.561 | 8.625 | 1.00 | 41.11 | AT |
| ATOM | 5846 | O | HOH | 247 | 10.020 | 25.331 | 46.396 | 1.00 | 38.25 | AT |
| ATOM | 5847 | O | HOH | 248 | 11.151 | 27.733 | 14.203 | 1.00 | 38.20 | AT |
| ATOM | 5848 | O | HOH | 249 | 10.978 | 20.075 | 53.913 | 1.00 | 37.44 | AT |
| ATOM | 5849 | O | HOH | 250 | 77.340 | 21.792 | 0.783 | 1.00 | 40.63 | AT |
| ATOM | 5850 | O | HOH | 251 | 63.681 | 23.994 | 15.360 | 1.00 | 37.38 | AT |
| ATOM | 5851 | O | HOH | 252 | 11.477 | 23.218 | 48.380 | 1.00 | 37.57 | AT |
| ATOM | 5852 | O | HOH | 253 | 24.484 | 40.133 | 44.556 | 1.00 | 37.00 | AT |
| ATOM | 5853 | O | HOH | 254 | 26.870 | 34.997 | 63.642 | 1.00 | 37.28 | AT |
| ATOM | 5854 | O | HOH | 255 | 38.821 | 41.107 | 28.862 | 1.00 | 37.55 | AT |
| ATOM | 5855 | O | HOH | 256 | 17.119 | 53.559 | 27.111 | 1.00 | 35.75 | AT |
| ATOM | 5856 | O | HOH | 257 | 31.732 | 49.464 | 21.724 | 1.00 | 40.71 | AT |
| ATOM | 5857 | O | HOH | 258 | 37.233 | 48.595 | 24.778 | 1.00 | 37.38 | AT |
| ATOM | 5858 | O | HOH | 259 | 64.957 | 31.599 | -4.165 | 1.00 | 34.72 | AT |
| ATOM | 5859 | O | HOH | 260 | 42.059 | 35.767 | 26.985 | 1.00 | 38.69 | AT |
| ATOM | 5860 | O | HOH | 261 | 53.170 | 52.497 | -1.737 | 1.00 | 41.39 | AT |
| ATOM | 5861 | O | HOH | 262 | 15.919 | 8.802 | 51.909 | 1.00 | 37.27 | AT |
| ATOM | 5862 | O | HOH | 263 | 60.591 | 34.941 | -9.345 | 1.00 | 36.16 | AT |
| ATOM | 5863 | O | HOH | 264 | 10.541 | 36.936 | 29.724 | 1.00 | 38.71 | AT |
| ATOM | 5864 | O | HOH | 265 | 31.514 | 44.281 | 21.202 | 1.00 | 36.97 | AT |
| ATOM | 5865 | O | HOH | 266 | 9.564 | 36.687 | 51.380 | 1.00 | 38.68 | AT |
| ATOM | 5866 | O | HOH | 267 | 79.927 | 33.538 | 17.348 | 1.00 | 38.09 | AT |
| ATOM | 5867 | O | HOH | 268 | 52.604 | 28.637 | 11.241 | 1.00 | 38.37 | AT |
| ATOM | 5868 | O | HOH | 269 | 4.383 | 30.021 | 19.676 | 1.00 | 37.95 | AT |
| ATOM | 5869 | O | HOH | 270 | 39.831 | 37.961 | 44.275 | 1.00 | 39.26 | AT |
| ATOM | 5870 | O | HOH | 271 | 76.908 | 49.901 | -8.433 | 1.00 | 40.20 | AT |

FIG. 1A-103

| | | | | | | | | | | |
|---|---|---|---|---|---|---|---|---|---|---|
| ATOM | 5871 | O | HOH | 272 | 18.828 | 14.845 | 36.392 | 1.00 | 40.61 | AT |
| ATOM | 5872 | O | HOH | 273 | 77.377 | 18.239 | 12.575 | 1.00 | 39.42 | AT |
| ATOM | 5873 | O | HOH | 274 | 51.042 | 29.821 | 13.536 | 1.00 | 39.59 | AT |
| ATOM | 5874 | O | HOH | 275 | 64.107 | 14.629 | 14.266 | 1.00 | 39.71 | AT |
| ATOM | 5875 | O | HOH | 276 | 58.267 | 58.162 | -7.799 | 1.00 | 39.43 | AT |
| ATOM | 5876 | O | HOH | 277 | 40.740 | 40.966 | 31.483 | 1.00 | 40.51 | AT |
| ATOM | 5877 | O | HOH | 278 | 15.055 | 10.589 | 55.645 | 1.00 | 39.15 | AT |
| ATOM | 5878 | O | HOH | 279 | 19.789 | 34.347 | 51.860 | 1.00 | 40.37 | AT |
| ATOM | 5879 | O | HOH | 280 | 11.976 | 38.727 | 31.710 | 1.00 | 37.91 | AT |
| ATOM | 5880 | O | HOH | 281 | 31.389 | 28.117 | 42.824 | 1.00 | 40.91 | AT |
| ATOM | 5881 | O | HOH | 282 | 70.878 | 25.270 | -4.197 | 1.00 | 43.53 | AT |
| ATOM | 5882 | O | HOH | 283 | 75.431 | 41.776 | 4.726 | 1.00 | 40.67 | AT |
| ATOM | 5883 | O | HOH | 284 | 62.312 | 53.358 | 28.086 | 1.00 | 40.98 | AT |
| ATOM | 5884 | O | HOH | 285 | 62.124 | 59.105 | 9.640 | 1.00 | 39.55 | AT |
| ATOM | 5885 | O | HOH | 286 | 40.707 | 28.142 | 23.532 | 1.00 | 44.54 | AT |
| ATOM | 5886 | O | HOH | 287 | 33.311 | 41.660 | 3.153 | 1.00 | 41.98 | AT |
| ATOM | 5887 | O | HOH | 288 | 38.680 | 48.495 | 32.258 | 1.00 | 44.14 | AT |
| ATOM | 5888 | O | HOH | 289 | 32.712 | 38.251 | 44.880 | 1.00 | 40.32 | AT |
| ATOM | 5889 | O | HOH | 290 | 12.709 | 24.006 | 64.828 | 1.00 | 40.21 | AT |
| ATOM | 5890 | O | HOH | 291 | 48.861 | 28.304 | 14.453 | 1.00 | 42.61 | AT |
| ATOM | 5891 | O | HOH | 292 | 79.466 | 20.245 | 8.333 | 1.00 | 40.49 | AT |
| ATOM | 5892 | O | HOH | 293 | 50.553 | 45.041 | -0.292 | 1.00 | 42.19 | AT |
| ATOM | 5893 | O | HOH | 294 | 42.897 | 26.326 | 5.722 | 1.00 | 41.10 | AT |
| ATOM | 5894 | O | HOH | 295 | 40.124 | 38.889 | 3.911 | 1.00 | 42.97 | AT |
| ATOM | 5895 | O | HOH | 296 | -9.725 | 26.259 | 40.147 | 1.00 | 43.57 | AT |
| ATOM | 5896 | O | HOH | 297 | 24.463 | 39.296 | 47.536 | 1.00 | 39.76 | AT |
| ATOM | 5897 | O | HOH | 298 | 59.389 | 43.519 | -22.049 | 1.00 | 45.90 | AT |
| ATOM | 5898 | O | HOH | 299 | 58.697 | 26.078 | -8.432 | 1.00 | 42.64 | AT |
| ATOM | 5899 | O | HOH | 300 | 59.168 | 23.233 | -8.586 | 1.00 | 43.13 | AT |
| ATOM | 5900 | O | HOH | 301 | 33.173 | 10.853 | 42.976 | 1.00 | 43.47 | AT |
| ATOM | 5901 | O | HOH | 302 | 38.135 | 51.041 | 21.685 | 1.00 | 40.23 | AT |
| ATOM | 5902 | O | HOH | 303 | 64.003 | 32.204 | 20.781 | 1.00 | 39.51 | AT |
| ATOM | 5903 | O | HOH | 304 | 18.175 | 36.881 | 18.239 | 1.00 | 42.51 | AT |
| ATOM | 5904 | O | HOH | 305 | 35.383 | 27.547 | 41.161 | 1.00 | 46.62 | AT |
| ATOM | 5905 | O | HOH | 306 | -1.325 | 41.441 | 28.735 | 1.00 | 43.36 | AT |
| ATOM | 5906 | O | HOH | 307 | 18.409 | 47.629 | 30.260 | 1.00 | 46.92 | AT |
| ATOM | 5907 | O | HOH | 308 | -0.365 | 41.851 | 31.323 | 1.00 | 43.06 | AT |
| ATOM | 5908 | O | HOH | 309 | 31.846 | 13.357 | 43.817 | 1.00 | 49.55 | AT |
| ATOM | 5909 | O | HOH | 310 | 51.910 | 47.621 | -1.442 | 1.00 | 43.27 | AT |
| ATOM | 5910 | O | HOH | 311 | 29.562 | 44.918 | 17.110 | 1.00 | 52.42 | AT |
| ATOM | 5911 | O | HOH | 312 | 30.495 | 43.251 | 13.422 | 1.00 | 45.47 | AT |
| ATOM | 5912 | O | HOH | 313 | 11.474 | 10.744 | 42.423 | 1.00 | 51.55 | AT |
| ATOM | 5913 | O | HOH | 314 | 14.240 | 10.741 | 46.442 | 1.00 | 43.12 | AT |
| ATOM | 5914 | O | HOH | 315 | 52.861 | 58.416 | 6.793 | 1.00 | 44.59 | AT |
| ATOM | 5915 | O | HOH | 316 | 28.512 | 44.265 | 22.711 | 1.00 | 45.20 | AT |
| ATOM | 5916 | O | HOH | 317 | 72.643 | 46.339 | -17.391 | 1.00 | 46.70 | AT |
| ATOM | 5917 | O | HOH | 318 | 31.387 | 46.123 | 19.248 | 1.00 | 43.61 | AT |
| ATOM | 5918 | O | HOH | 319 | 78.102 | 45.702 | -8.575 | 1.00 | 48.47 | AT |
| ATOM | 5919 | O | HOH | 320 | 53.628 | 13.801 | 9.167 | 1.00 | 49.46 | AT |
| ATOM | 5920 | O | HOH | 321 | 65.846 | 41.632 | -7.173 | 1.00 | 44.55 | AT |
| ATOM | 5921 | O | HOH | 322 | 41.074 | 48.539 | 27.174 | 1.00 | 50.50 | AT |
| ATOM | 5922 | O | HOH | 323 | 30.457 | 41.713 | 20.027 | 1.00 | 47.21 | AT |
| ATOM | 5923 | O | HOH | 324 | 23.888 | 42.661 | 19.783 | 1.00 | 49.37 | AT |
| ATOM | 5924 | O | HOH | 325 | 46.169 | 56.278 | 15.804 | 1.00 | 51.43 | AT |
| ATOM | 5925 | O | HOH | 326 | 64.632 | 36.604 | -9.385 | 1.00 | 48.35 | AT |
| ATOM | 5926 | O | HOH | 327 | 50.410 | 48.704 | -3.435 | 1.00 | 48.93 | AT |
| ATOM | 5927 | O | HOH | 328 | 17.266 | 4.657 | 48.965 | 1.00 | 55.69 | AT |

FIG. 1A-104

| ATOM | 5928 | O | HOH | 329 | 15.343 | 49.959 | 36.887 | 1.00 | 53.08 | AT |
|---|---|---|---|---|---|---|---|---|---|---|
| ATOM | 5929 | O | HOH | 330 | 77.778 | 42.870 | 3.924 | 1.00 | 55.32 | AT |
| ATOM | 5930 | O | HOH | 331 | 68.103 | 40.973 | -5.266 | 1.00 | 57.57 | AT |
| ATOM | 5931 | O | HOH | 332 | 21.493 | 20.139 | 67.130 | 1.00 | 33.16 | AT |
| ATOM | 5932 | O | HOH | 333 | 81.269 | 24.355 | 14.982 | 1.00 | 33.69 | AT |
| ATOM | 5933 | O | HOH | 334 | -5.903 | 30.538 | 26.686 | 1.00 | 40.35 | AT |
| ATOM | 5934 | O | HOH | 335 | 80.030 | 32.515 | -0.810 | 1.00 | 39.92 | AT |
| ATOM | 5935 | O | HOH | 336 | -7.205 | 27.318 | 42.127 | 1.00 | 37.50 | AT |
| ATOM | 5936 | O | HOH | 337 | 0.251 | 35.076 | 40.556 | 1.00 | 41.65 | AT |
| ATOM | 5937 | O | HOH | 338 | 67.263 | 58.975 | -10.701 | 1.00 | 34.16 | AT |
| ATOM | 5938 | O | HOH | 339 | 78.930 | 41.885 | 0.871 | 1.00 | 36.88 | AT |
| ATOM | 5939 | O | HOH | 340 | 81.589 | 22.534 | 9.006 | 1.00 | 32.20 | AT |
| ATOM | 5940 | O | HOH | 341 | -4.841 | 30.109 | 35.827 | 1.00 | 39.55 | AT |
| ATOM | 5941 | O | HOH | 342 | 24.216 | 28.828 | 53.120 | 1.00 | 48.54 | AT |
| ATOM | 5942 | O | HOH | 343 | 58.172 | 44.547 | -15.457 | 1.00 | 37.88 | AT |
| ATOM | 5943 | O | HOH | 344 | 72.009 | 58.325 | -12.680 | 1.00 | 44.56 | AT |
| ATOM | 5944 | O | HOH | 345 | 70.243 | 44.553 | -16.741 | 1.00 | 37.48 | AT |
| ATOM | 5945 | O | HOH | 346 | 63.182 | 47.822 | -22.683 | 1.00 | 47.83 | AT |
| ATOM | 5946 | O | HOH | 347 | 59.201 | 59.513 | -12.511 | 1.00 | 48.60 | AT |
| ATOM | 5947 | O | HOH | 348 | 73.024 | 32.150 | -1.717 | 1.00 | 35.73 | AT |
| ATOM | 5948 | O | HOH | 349 | 36.241 | 17.553 | 55.406 | 1.00 | 43.52 | AT |
| ATOM | 5949 | O | HOH | 351 | 14.204 | 56.480 | 33.327 | 1.00 | 44.23 | AT |
| ATOM | 5950 | O | HOH | 352 | 81.607 | 27.771 | 10.204 | 1.00 | 46.37 | AT |
| ATOM | 5951 | O | HOH | 353 | 72.230 | 29.150 | -2.863 | 1.00 | 44.64 | AT |
| ATOM | 5952 | O | HOH | 354 | 63.965 | 35.398 | -19.062 | 1.00 | 40.75 | AT |
| ATOM | 5953 | O | HOH | 355 | 83.662 | 27.262 | 2.560 | 1.00 | 52.07 | AT |
| ATOM | 5954 | O | HOH | 356 | 54.821 | 57.411 | -7.143 | 1.00 | 47.42 | AT |
| ATOM | 5955 | O | HOH | 357 | 75.827 | 24.345 | -2.592 | 1.00 | 38.53 | AT |
| ATOM | 5956 | O | HOH | 358 | -3.100 | 29.989 | 33.712 | 1.00 | 35.26 | AT |
| ATOM | 5957 | O | HOH | 359 | 76.580 | 32.031 | 17.038 | 1.00 | 45.16 | AT |
| ATOM | 5958 | O | HOH | 360 | 61.004 | 63.374 | -0.717 | 1.00 | 51.75 | AT |
| ATOM | 5959 | O | HOH | 361 | 57.555 | 42.914 | -17.566 | 1.00 | 37.15 | AT |
| ATOM | 5960 | O | HOH | 362 | 46.758 | 41.005 | -9.571 | 1.00 | 49.08 | AT |
| ATOM | 5961 | O | HOH | 363 | 65.046 | 41.921 | 10.931 | 1.00 | 43.73 | AT |
| ATOM | 5962 | O | HOH | 364 | 60.495 | 37.070 | -20.999 | 1.00 | 39.43 | AT |
| ATOM | 5963 | O | HOH | 365 | 24.639 | 46.742 | 50.064 | 1.00 | 49.54 | AT |
| ATOM | 5964 | O | HOH | 366 | 65.360 | 59.537 | -12.244 | 1.00 | 42.08 | AT |
| ATOM | 5965 | O | HOH | 367 | 81.253 | 38.379 | 6.191 | 1.00 | 44.60 | AT |
| ATOM | 5966 | O | HOH | 368 | 20.278 | 58.789 | 32.999 | 1.00 | 51.96 | AT |
| ATOM | 5967 | O | HOH | 369 | 35.754 | 25.608 | 43.846 | 1.00 | 41.69 | AT |
| ATOM | 5968 | O | HOH | 370 | 58.812 | 30.456 | 20.182 | 1.00 | 47.60 | AT |
| ATOM | 5969 | O | HOH | 371 | 62.070 | 60.522 | -12.130 | 1.00 | 38.66 | AT |
| ATOM | 5970 | O | HOH | 372 | 28.704 | 57.271 | 37.789 | 1.00 | 53.91 | AT |
| ATOM | 5971 | O | HOH | 373 | 16.768 | 31.252 | 63.214 | 1.00 | 43.22 | AT |
| ATOM | 5972 | O | HOH | 374 | 17.431 | 24.978 | 67.168 | 1.00 | 45.45 | AT |
| ATOM | 5973 | O | HOH | 375 | 51.911 | 28.483 | -4.087 | 1.00 | 57.67 | AT |
| ATOM | 5974 | O | HOH | 376 | 61.859 | 13.653 | 15.354 | 1.00 | 48.16 | AT |
| ATOM | 5975 | O | HOH | 377 | 60.309 | 37.228 | -7.635 | 1.00 | 40.72 | AT |
| ATOM | 5976 | O | HOH | 378 | 76.341 | 49.000 | 11.927 | 1.00 | 51.08 | AT |
| ATOM | 5977 | O | HOH | 379 | 26.911 | 4.583 | 49.436 | 1.00 | 50.11 | AT |
| ATOM | 5978 | O | HOH | 380 | 60.796 | 28.003 | 14.825 | 1.00 | 41.08 | AT |
| ATOM | 5979 | O | HOH | 381 | 64.912 | 34.210 | -13.805 | 1.00 | 54.13 | AT |
| ATOM | 5980 | O | HOH | 382 | 24.406 | 25.422 | 35.245 | 1.00 | 46.00 | AT |
| ATOM | 5981 | O | HOH | 383 | 27.206 | 10.460 | 58.142 | 1.00 | 48.67 | AT |
| ATOM | 5982 | O | HOH | 384 | 69.870 | 64.847 | 0.287 | 1.00 | 51.86 | AT |
| ATOM | 5983 | O | HOH | 385 | 13.388 | 53.599 | 30.313 | 1.00 | 53.21 | AT |
| ATOM | 5984 | O | HOH | 386 | 65.207 | 44.282 | -23.032 | 1.00 | 44.87 | AT |

FIG. 1A-105

```
ATOM   5985  O  HOH  387   23.812  43.965  31.871  1.00 51.01      AT
ATOM   5986  O  HOH  388   27.925  56.723  25.402  1.00 50.91      AT
ATOM   5987  O  HOH  389   22.429  53.122  37.372  1.00 40.24      AT
ATOM   5988  O  HOH  390   20.340  37.818  64.894  1.00 43.91      AT
ATOM   5989  O  HOH  391    3.772  17.279  18.046  1.00 55.83      AT
ATOM   5990  O  HOH  392   61.560  29.447  -8.011  1.00 48.85      AT
ATOM   5991  O  HOH  393   40.737  49.676  12.185  1.00 48.28      AT
ATOM   5992  O  HOH  394   47.566  44.388  26.446  1.00 47.81      AT
ATOM   5993  O  HOH  395   62.091  37.019  27.629  1.00 53.63      AT
ATOM   5994  O  HOH  396   45.170  49.972  14.734  1.00 52.56      AT
ATOM   5995  O  HOH  397   25.713  56.378  37.487  1.00 46.30      AT
ATOM   5996  O  HOH  398   19.430  54.171  39.827  1.00 43.81      AT
ATOM   5997  O  HOH  399   25.461  13.937  28.867  1.00 46.75      AT
ATOM   5998  O  HOH  400   65.078  42.400  27.343  1.00 58.24      AT
ATOM   5999  O  HOH  401   15.750  35.665  16.140  1.00 49.43      AT
ATOM   6000  O  HOH  402   30.823  49.012   9.778  1.00 49.25      AT
ATOM   6001  O  HOH  403   63.642  30.868  -6.737  1.00 63.10      AT
ATOM   6002  O  HOH  404   -5.102  30.693  29.722  1.00 44.38      AT
ATOM   6003  O  HOH  405    5.998  28.463  48.599  1.00 45.41      AT
ATOM   6004  O  HOH  406   78.918  22.759  14.469  1.00 48.83      AT
ATOM   6005  O  HOH  407   67.800  14.615  -0.774  1.00 47.19      AT
ATOM   6006  O  HOH  408   -8.454  30.970  25.750  1.00 52.46      AT
ATOM   6007  O  HOH  409   39.982  27.102  31.435  1.00 51.86      AT
ATOM   6008  O  HOH  410   73.123  40.475  21.437  1.00 60.13      AT
ATOM   6009  O  HOH  411   60.888  14.040   1.887  1.00 46.41      AT
ATOM   6010  O  HOH  412   36.503  50.699  10.642  1.00 54.16      AT
ATOM   6011  O  HOH  413   59.362  62.211  -6.530  1.00 49.09      AT
ATOM   6012  O  HOH  414   28.103  13.240  52.474  1.00 47.88      AT
ATOM   6013  O  HOH  415   32.010  21.506  60.871  1.00 51.04      AT
ATOM   6014  O  HOH  416   35.534  13.760  51.867  1.00 48.76      AT
ATOM   6015  O  HOH  417   40.198  51.587  23.313  1.00 47.59      AT
ATOM   6016  O  HOH  418   32.582  27.322  18.391  1.00 59.17      AT
ATOM   6017  O  HOH  419   70.979  43.580 -23.023  1.00 62.55      AT
ATOM   6018  O  HOH  420   72.711  52.348 -21.252  1.00 55.53      AT
ATOM   6019  O  HOH  421   51.501  60.903   2.181  1.00 56.42      AT
ATOM   6020  O  HOH  423   53.460  21.733  -0.240  1.00 63.43      AT
ATOM   6021  O  HOH  424   55.865  19.944  -0.930  1.00 45.43      AT
ATOM   6022  O  HOH  425   11.457  18.171  63.981  1.00 40.96      AT
ATOM   6023  O  HOH  426   29.667  28.514  52.029  1.00 40.86      AT
ATOM   6024  O  HOH  427   21.382  43.057  31.379  1.00 37.88      AT
ATOM   6025  O  HOH  428   72.431  56.442 -14.816  1.00 38.78      AT
ATOM   6026  O  HOH  429   13.645  35.387  57.232  1.00 45.75      AT
ATOM   6027  O  HOH  430   47.325  44.655   9.515  1.00 52.79      AT
ATOM   6028  O  HOH  431   12.413   9.161  45.090  1.00 53.71      AT
ATOM   6029  O  HOH  432   69.847  39.107  -2.341  1.00 47.46      AT
ATOM   6030  O  HOH  433   40.580  34.476   3.546  1.00 42.74      AT
ATOM   6031  O  HOH  434   68.590  27.199  -5.061  1.00 50.14      AT
ATOM   6032  O  HOH  435   81.709  33.738  20.448  1.00 51.49      AT
ATOM   6033  O  HOH  436   21.276   6.862  53.221  1.00 43.81      AT
ATOM   6034  O  HOH  437   63.959  28.541  24.084  1.00 48.89      AT
ATOM   6035  O  HOH  438   44.540  42.464  26.796  1.00 45.92      AT
ATOM   6036  O  HOH  439   26.430  12.510  54.374  1.00 41.22      AT
ATOM   6037  O  HOH  440   13.505  42.803  49.080  1.00 49.02      AT
ATOM   6038  O  HOH  441   61.236  27.483  -9.781  1.00 53.99      AT
ATOM   6039  O  HOH  442   48.452  32.235  26.577  1.00 39.84      AT
ATOM   6040  O  HOH  443   -6.734  17.777  28.953  1.00 43.66      AT
ATOM   6041  O  HOH  444   68.689  11.054   1.803  1.00 54.43      AT
```

FIG. 1A-106

| ATOM | 6042 | O | HOH | 445 | 64.733 | 8.182 | 7.092 | 1.00 | 51.11 | AT |
|---|---|---|---|---|---|---|---|---|---|---|
| ATOM | 6043 | O | HOH | 446 | 47.452 | 47.307 | 25.789 | 1.00 | 50.83 | AT |
| ATOM | 6044 | O | HOH | 447 | -5.597 | 17.191 | 22.022 | 1.00 | 62.54 | AT |
| ATOM | 6045 | O | HOH | 448 | 34.703 | 54.274 | 40.793 | 1.00 | 43.46 | AT |
| ATOM | 6046 | O | HOH | 449 | 7.584 | 42.423 | 41.797 | 1.00 | 50.29 | AT |
| ATOM | 6047 | O | HOH | 450 | 68.745 | 9.611 | 12.516 | 1.00 | 44.55 | AT |
| ATOM | 6048 | O | HOH | 451 | 10.345 | 30.448 | 14.624 | 1.00 | 52.09 | AT |
| ATOM | 6049 | O | HOH | 452 | 28.739 | 24.654 | 67.367 | 1.00 | 43.81 | AT |
| ATOM | 6050 | O | HOH | 453 | 59.859 | 15.451 | -0.538 | 1.00 | 50.23 | AT |
| ATOM | 6051 | O | HOH | 454 | 9.715 | 22.615 | 40.260 | 1.00 | 55.68 | AT |
| ATOM | 6052 | O | HOH | 455 | 8.408 | 33.305 | 58.554 | 1.00 | 48.77 | AT |
| ATOM | 6053 | O | HOH | 456 | 82.808 | 20.346 | 7.688 | 1.00 | 64.19 | AT |
| ATOM | 6054 | O | HOH | 457 | 20.676 | 9.525 | 40.046 | 1.00 | 47.64 | AT |
| ATOM | 6055 | O | HOH | 458 | 12.300 | 21.911 | 45.521 | 1.00 | 55.95 | AT |
| ATOM | 6056 | O | HOH | 459 | 12.849 | 37.059 | 54.956 | 1.00 | 47.15 | AT |
| ATOM | 6057 | O | HOH | 460 | 18.947 | 37.315 | 56.296 | 1.00 | 55.87 | AT |
| ATOM | 6058 | O | HOH | 461 | 42.279 | 43.046 | 32.215 | 1.00 | 55.34 | AT |
| ATOM | 6059 | O | HOH | 462 | 58.113 | 60.078 | -9.775 | 1.00 | 41.21 | AT |
| ATOM | 6060 | O | HOH | 463 | -4.882 | 24.186 | 43.569 | 1.00 | 49.34 | AT |
| ATOM | 6061 | O | HOH | 464 | 2.275 | 30.894 | 44.638 | 1.00 | 49.59 | AT |
| ATOM | 6062 | O | HOH | 465 | 11.908 | 42.581 | 46.538 | 1.00 | 54.17 | AT |
| ATOM | 6063 | O | HOH | 466 | 25.196 | 30.973 | 68.678 | 1.00 | 54.36 | AT |
| ATOM | 6064 | O | HOH | 467 | 55.729 | 18.620 | -3.586 | 1.00 | 51.13 | AT |
| ATOM | 6065 | O | HOH | 468 | 12.016 | 5.491 | 40.550 | 1.00 | 54.15 | AT |
| ATOM | 6066 | O | HOH | 469 | 56.711 | 29.214 | 27.406 | 1.00 | 63.41 | AT |
| ATOM | 6067 | O | HOH | 470 | 56.150 | 18.575 | 3.127 | 1.00 | 57.43 | AT |
| ATOM | 6068 | O | HOH | 471 | 18.186 | 11.646 | 26.302 | 1.00 | 54.34 | AT |
| ATOM | 6069 | S1 | DTT | 1 | 74.181 | 38.187 | -0.498 | 1.00 | 67.01 | TT1 |
| ATOM | 6070 | C1 | DTT | 1 | 72.670 | 38.130 | -1.524 | 1.00 | 67.92 | TT1 |
| ATOM | 6071 | C2 | DTT | 1 | 72.656 | 36.968 | -2.590 | 1.00 | 68.22 | TT1 |
| ATOM | 6072 | O2 | DTT | 1 | 71.393 | 37.023 | -3.311 | 1.00 | 68.98 | TT1 |
| ATOM | 6073 | C3 | DTT | 1 | 73.769 | 37.036 | -3.768 | 1.00 | 67.93 | TT1 |
| ATOM | 6074 | O3 | DTT | 1 | 73.674 | 35.873 | -4.701 | 1.00 | 67.85 | TT1 |
| ATOM | 6075 | C4 | DTT | 1 | 75.213 | 37.003 | -3.287 | 1.00 | 67.57 | TT1 |
| ATOM | 6076 | S4 | DTT | 1 | 75.541 | 38.418 | -2.099 | 1.00 | 67.52 | TT1 |
| ATOM | 6077 | S1 | DTT | 2 | 54.935 | 53.026 | 7.820 | 1.00 | 53.56 | TT2 |
| ATOM | 6078 | C1 | DTT | 2 | 53.759 | 51.637 | 7.760 | 1.00 | 53.84 | TT2 |
| ATOM | 6079 | C2 | DTT | 2 | 52.738 | 51.710 | 6.562 | 1.00 | 54.90 | TT2 |
| ATOM | 6080 | O2 | DTT | 2 | 51.885 | 50.534 | 6.613 | 1.00 | 56.10 | TT2 |
| ATOM | 6081 | C3 | DTT | 2 | 51.681 | 52.940 | 6.568 | 1.00 | 54.93 | TT2 |
| ATOM | 6082 | O3 | DTT | 2 | 50.780 | 52.918 | 5.376 | 1.00 | 55.43 | TT2 |
| ATOM | 6083 | C4 | DTT | 2 | 52.313 | 54.325 | 6.524 | 1.00 | 54.51 | TT2 |
| ATOM | 6084 | S4 | DTT | 2 | 53.485 | 54.549 | 7.971 | 1.00 | 54.25 | TT2 |
| ATOM | 6085 | S1 | DTT | 3 | 9.841 | 19.197 | 19.765 | 1.00 | 46.94 | TT3 |
| ATOM | 6086 | C1 | DTT | 3 | 8.080 | 19.681 | 19.855 | 1.00 | 44.23 | TT3 |
| ATOM | 6087 | C2 | DTT | 3 | 7.123 | 18.477 | 20.203 | 1.00 | 45.91 | TT3 |
| ATOM | 6088 | O2 | DTT | 3 | 5.758 | 18.968 | 20.283 | 1.00 | 45.68 | TT3 |
| ATOM | 6089 | C3 | DTT | 3 | 7.023 | 17.285 | 19.113 | 1.00 | 46.42 | TT3 |
| ATOM | 6090 | O3 | DTT | 3 | 6.110 | 16.195 | 19.567 | 1.00 | 49.11 | TT3 |
| ATOM | 6091 | C4 | DTT | 3 | 8.337 | 16.568 | 18.812 | 1.00 | 45.21 | TT3 |
| ATOM | 6092 | S4 | DTT | 3 | 9.629 | 17.785 | 18.211 | 1.00 | 44.44 | TT3 |
| ATOM | 6093 | S1 | DTT | 4 | 19.785 | 34.825 | 23.721 | 1.00 | 49.21 | TT4 |
| ATOM | 6094 | C1 | DTT | 4 | 19.784 | 36.095 | 25.038 | 1.00 | 49.59 | TT4 |
| ATOM | 6095 | C2 | DTT | 4 | 18.556 | 37.084 | 24.993 | 1.00 | 51.01 | TT4 |
| ATOM | 6096 | O2 | DTT | 4 | 18.673 | 38.019 | 26.105 | 1.00 | 52.92 | TT4 |
| ATOM | 6097 | C3 | DTT | 4 | 18.440 | 38.051 | 23.699 | 1.00 | 50.89 | TT4 |
| ATOM | 6098 | O3 | DTT | 4 | 17.234 | 38.926 | 23.759 | 1.00 | 51.66 | TT4 |

FIG. 1A-107

| | | | | | | | | | |
|---|---|---|---|---|---|---|---|---|---|
| ATOM | 6099 | C4 | DTT | 4 | 18.302 | 37.325 | 22.365 | 1.00 50.07 | TT4 |
| ATOM | 6100 | S4 | DTT | 4 | 19.750 | 36.164 | 22.087 | 1.00 49.50 | TT4 |
| ATOM | 6101 | S1 | DTT | 5 | 13.883 | 15.968 | 40.130 | 1.00 53.89 | TT5 |
| ATOM | 6102 | C1 | DTT | 5 | 12.694 | 17.323 | 39.827 | 1.00 54.86 | TT5 |
| ATOM | 6103 | C2 | DTT | 5 | 11.608 | 17.502 | 40.955 | 1.00 55.83 | TT5 |
| ATOM | 6104 | O2 | DTT | 5 | 10.754 | 18.625 | 40.590 | 1.00 57.35 | TT5 |
| ATOM | 6105 | C3 | DTT | 5 | 10.561 | 16.283 | 41.172 | 1.00 55.92 | TT5 |
| ATOM | 6106 | O3 | DTT | 5 | 9.597 | 16.559 | 42.278 | 1.00 56.47 | TT5 |
| ATOM | 6107 | C4 | DTT | 5 | 11.194 | 14.953 | 41.564 | 1.00 55.56 | TT5 |
| ATOM | 6108 | S4 | DTT | 5 | 12.443 | 14.418 | 40.274 | 1.00 55.31 | TT5 |
| ATOM | 6109 | C1 | GOL | 6 | 25.840 | 30.485 | 23.369 | 1.00 60.12 | OL1 |
| ATOM | 6110 | O1 | GOL | 6 | 24.418 | 30.344 | 23.510 | 1.00 58.37 | OL1 |
| ATOM | 6111 | C2 | GOL | 6 | 26.254 | 30.565 | 21.841 | 1.00 60.62 | OL1 |
| ATOM | 6112 | O2 | GOL | 6 | 26.921 | 31.825 | 21.610 | 1.00 61.53 | OL1 |
| ATOM | 6113 | C3 | GOL | 6 | 25.019 | 30.470 | 20.890 | 1.00 60.48 | OL1 |
| ATOM | 6114 | O3 | GOL | 6 | 25.353 | 30.640 | 19.507 | 1.00 60.02 | OL1 |
| ATOM | 6115 | C1 | GOL | 7 | 79.028 | 22.813 | 10.783 | 1.00 59.60 | OL2 |
| ATOM | 6116 | O1 | GOL | 7 | 78.201 | 22.510 | 11.912 | 1.00 61.71 | OL2 |
| ATOM | 6117 | C2 | GOL | 7 | 79.615 | 24.278 | 10.893 | 1.00 59.54 | OL2 |
| ATOM | 6118 | O2 | GOL | 7 | 81.057 | 24.201 | 10.902 | 1.00 59.72 | OL2 |
| ATOM | 6119 | C3 | GOL | 7 | 79.147 | 25.010 | 12.189 | 1.00 58.44 | OL2 |
| ATOM | 6120 | O3 | GOL | 7 | 79.958 | 26.145 | 12.514 | 1.00 56.91 | OL2 |
| ATOM | 6121 | NA+1 | NA1 | 1 | 63.339 | 31.566 | -2.590 | 1.00 26.24 | ONS |
| ATOM | 6122 | NA+1 | NA1 | 2 | 65.507 | 33.113 | 17.476 | 1.00 24.78 | ONS |
| ATOM | 6123 | NA+1 | NA1 | 3 | 52.138 | 43.339 | -0.467 | 1.00 31.32 | ONS |
| ATOM | 6124 | NA+1 | NA1 | 4 | 11.564 | 27.003 | 46.250 | 1.00 28.57 | ONS |
| ATOM | 6125 | NA+1 | NA1 | 5 | 22.858 | 38.903 | 45.868 | 1.00 35.79 | ONS |
| ATOM | 6126 | NA+1 | NA1 | 6 | 12.049 | 37.399 | 33.606 | 1.00 30.07 | ONS |
| ATOM | 6127 | NA+1 | NA1 | 7 | 52.399 | 30.404 | 9.576 | 1.00 28.65 | ONS |
| ATOM | 6128 | NA+1 | NA1 | 8 | 61.322 | 58.273 | -12.969 | 1.00 38.12 | ONS |
| ATOM | 6129 | CL-1 | CL1 | 9 | 74.315 | 48.004 | -8.768 | 1.00 36.69 | ONS |
| ATOM | 6130 | CL-1 | CL1 | 10 | 10.448 | 28.591 | 48.519 | 1.00 26.89 | ONS |
| ATOM | 6131 | CL-1 | CL1 | 11 | 49.897 | 29.847 | 8.163 | 1.00 28.28 | ONS |
| ATOM | 6132 | CL-1 | CL1 | 12 | 68.370 | 32.685 | 17.763 | 1.00 30.08 | ONS |
| ATOM | 6133 | CL-1 | CL1 | 13 | 21.352 | 41.348 | 46.322 | 1.00 33.00 | ONS |
| ATOM | 6134 | CL-1 | CL1 | 14 | 21.514 | 34.817 | 28.080 | 1.00 20.85 | ONS |
| ATOM | 6135 | CL-1 | CL1 | 15 | 70.235 | 40.020 | 0.588 | 1.00 21.12 | ONS |
| ATOM | 6136 | CL-1 | CL1 | 16 | 55.303 | 48.583 | 9.136 | 1.00 22.36 | ONS |
| ATOM | 6137 | CL-1 | CL1 | 17 | 61.816 | 29.359 | -3.630 | 1.00 27.78 | ONS |
| ATOM | 6138 | CL-1 | CL1 | 18 | 66.265 | 35.653 | 18.338 | 1.00 26.36 | ONS |
| ATOM | 6139 | CL-1 | CL1 | 19 | 9.405 | 38.244 | 34.766 | 1.00 27.56 | ONS |
| ATOM | 6140 | CL-1 | CL1 | 20 | 56.075 | 30.580 | -5.205 | 1.00 30.76 | ONS |
| ATOM | 6141 | CL-1 | CL1 | 21 | 51.184 | 42.277 | -2.989 | 1.00 29.31 | ONS |
| ATOM | 6142 | CL-1 | CL1 | 22 | 8.488 | 34.106 | 46.950 | 1.00 31.69 | ONS |
| ATOM | 6143 | CL-1 | CL1 | 23 | 26.255 | 30.563 | 26.909 | 1.00 29.29 | ONS |
| ATOM | 6144 | CL-1 | CL1 | 24 | 14.532 | 19.865 | 38.018 | 1.00 22.44 | ONS |
| ATOM | 6145 | CL-1 | CL1 | 25 | 38.459 | 48.451 | 29.075 | 1.00 41.86 | ONS |
| ATOM | 6146 | CL-1 | CL1 | 26 | 48.969 | 36.502 | -2.659 | 1.00 32.79 | ONS |
| ATOM | 6147 | CL-1 | CL1 | 27 | 19.241 | 17.587 | 34.034 | 1.00 29.08 | ONS |
| END | | | | | | | | | |

FIG. 2

|  | Atom Type | Res. |  | X | Y | Z | OCC | B | MOL |
|---|---|---|---|---|---|---|---|---|---|
| ATOM | 1 C | GLY | 1 | 3.531 | 2.676 | 31.918 | 1.00 | 23.54 | ACPS |
| ATOM | 2 O | GLY | 1 | 2.877 | 3.712 | 32.042 | 1.00 | 24.07 | ACPS |
| ATOM | 3 N | GLY | 1 | 3.058 | 2.705 | 29.459 | 1.00 | 25.97 | ACPS |
| ATOM | 4 CA | GLY | 1 | 3.503 | 1.884 | 30.623 | 1.00 | 24.19 | ACPS |
| ATOM | 5 N | ILE | 2 | 4.299 | 2.191 | 32.884 | 1.00 | 21.88 | ACPS |
| ATOM | 6 CA | ILE | 2 | 4.396 | 2.857 | 34.180 | 1.00 | 20.22 | ACPS |
| ATOM | 7 CB | ILE | 2 | 4.119 | 1.857 | 35.329 | 1.00 | 19.41 | ACPS |
| ATOM | 8 CG2 | ILE | 2 | 4.474 | 2.485 | 36.679 | 1.00 | 18.46 | ACPS |
| ATOM | 9 CG1 | ILE | 2 | 2.647 | 1.429 | 35.289 | 1.00 | 19.13 | ACPS |

FIG. 2A-1

| ATOM | 10 | CD1 | ILE | 2 | 2.303 | 0.294 | 36.250 | 1.00 | 20.56 | ACPS |
|---|---|---|---|---|---|---|---|---|---|---|
| ATOM | 11 | C | ILE | 2 | 5.769 | 3.490 | 34.376 | 1.00 | 19.58 | ACPS |
| ATOM | 12 | O | ILE | 2 | 6.798 | 2.827 | 34.223 | 1.00 | 19.75 | ACPS |
| ATOM | 13 | N | TYR | 3 | 5.779 | 4.780 | 34.704 | 1.00 | 18.83 | ACPS |
| ATOM | 14 | CA | TYR | 3 | 7.024 | 5.493 | 34.942 | 1.00 | 18.94 | ACPS |
| ATOM | 15 | CB | TYR | 3 | 6.814 | 7.004 | 34.809 | 1.00 | 21.16 | ACPS |
| ATOM | 16 | CG | TYR | 3 | 8.059 | 7.808 | 35.103 | 1.00 | 23.30 | ACPS |
| ATOM | 17 | CD1 | TYR | 3 | 9.164 | 7.761 | 34.246 | 1.00 | 24.81 | ACPS |
| ATOM | 18 | CE1 | TYR | 3 | 10.326 | 8.486 | 34.525 | 1.00 | 25.94 | ACPS |
| ATOM | 19 | CD2 | TYR | 3 | 8.145 | 8.601 | 36.246 | 1.00 | 24.18 | ACPS |
| ATOM | 20 | CE2 | TYR | 3 | 9.297 | 9.329 | 36.534 | 1.00 | 25.63 | ACPS |
| ATOM | 21 | CZ | TYR | 3 | 10.384 | 9.267 | 35.672 | 1.00 | 26.92 | ACPS |
| ATOM | 22 | OH | TYR | 3 | 11.524 | 9.974 | 35.970 | 1.00 | 28.98 | ACPS |
| ATOM | 23 | C | TYR | 3 | 7.555 | 5.165 | 36.340 | 1.00 | 17.87 | ACPS |
| ATOM | 24 | O | TYR | 3 | 8.757 | 4.968 | 36.525 | 1.00 | 18.51 | ACPS |
| ATOM | 25 | N | GLY | 4 | 6.657 | 5.107 | 37.325 | 1.00 | 16.17 | ACPS |
| ATOM | 26 | CA | GLY | 4 | 7.088 | 4.789 | 38.678 | 1.00 | 13.94 | ACPS |
| ATOM | 27 | C | GLY | 4 | 5.937 | 4.643 | 39.657 | 1.00 | 13.19 | ACPS |
| ATOM | 28 | O | GLY | 4 | 4.819 | 5.094 | 39.387 | 1.00 | 13.25 | ACPS |
| ATOM | 29 | N | ILE | 5 | 6.217 | 4.001 | 40.794 | 1.00 | 12.43 | ACPS |
| ATOM | 30 | CA | ILE | 5 | 5.209 | 3.822 | 41.841 | 1.00 | 11.10 | ACPS |
| ATOM | 31 | CB | ILE | 5 | 4.718 | 2.326 | 41.963 | 1.00 | 11.22 | ACPS |
| ATOM | 32 | CG2 | ILE | 5 | 4.330 | 1.793 | 40.572 | 1.00 | 12.21 | ACPS |
| ATOM | 33 | CG1 | ILE | 5 | 5.785 | 1.441 | 42.619 | 1.00 | 11.21 | ACPS |
| ATOM | 34 | CD1 | ILE | 5 | 5.338 | -0.010 | 42.831 | 1.00 | 12.31 | ACPS |
| ATOM | 35 | C | ILE | 5 | 5.793 | 4.294 | 43.175 | 1.00 | 10.72 | ACPS |
| ATOM | 36 | O | ILE | 5 | 7.013 | 4.358 | 43.346 | 1.00 | 11.21 | ACPS |
| ATOM | 37 | N | GLY | 6 | 4.910 | 4.644 | 44.108 | 1.00 | 10.20 | ACPS |
| ATOM | 38 | CA | GLY | 6 | 5.347 | 5.102 | 45.414 | 1.00 | 9.68 | ACPS |
| ATOM | 39 | C | GLY | 6 | 4.762 | 4.776 | 46.503 | 1.00 | 10.17 | ACPS |
| ATOM | 40 | O | GLY | 6 | 3.139 | 4.776 | 46.261 | 1.00 | 9.96 | ACPS |
| ATOM | 41 | N | LEU | 7 | 4.859 | 4.459 | 47.697 | 1.00 | 9.09 | ACPS |
| ATOM | 42 | CA | LEU | 7 | 4.024 | 4.109 | 48.852 | 1.00 | 9.72 | ACPS |
| ATOM | 43 | CB | LEU | 7 | 4.058 | 2.588 | 49.078 | 1.00 | 10.10 | ACPS |
| ATOM | 44 | CG | LEU | 7 | 3.308 | 2.001 | 50.285 | 1.00 | 9.72 | ACPS |
| ATOM | 45 | CD1 | LEU | 7 | 1.814 | 2.059 | 50.037 | 1.00 | 12.07 | ACPS |
| ATOM | 46 | CD2 | LEU | 7 | 3.741 | 0.552 | 50.503 | 1.00 | 10.42 | ACPS |
| ATOM | 47 | C | LEU | 7 | 4.530 | 4.804 | 50.121 | 1.00 | 10.28 | ACPS |
| ATOM | 48 | O | LEU | 7 | 5.739 | 4.936 | 50.319 | 1.00 | 10.25 | ACPS |
| ATOM | 49 | N | ASP | 8 | 3.610 | 5.255 | 50.976 | 1.00 | 9.98 | ACPS |
| ATOM | 50 | CA | ASP | 8 | 4.024 | 5.871 | 52.230 | 1.00 | 9.91 | ACPS |
| ATOM | 51 | CB | ASP | 8 | 4.323 | 7.365 | 52.045 | 1.00 | 9.85 | ACPS |
| ATOM | 52 | CG | ASP | 8 | 5.223 | 7.887 | 53.128 | 1.00 | 11.38 | ACPS |
| ATOM | 53 | OD1 | ASP | 8 | 4.723 | 8.465 | 54.110 | 1.00 | 12.14 | ACPS |
| ATOM | 54 | OD2 | ASP | 8 | 6.439 | 7.672 | 53.003 | 1.00 | 13.58 | ACPS |
| ATOM | 55 | C | ASP | 8 | 2.997 | 5.715 | 53.338 | 1.00 | 9.65 | ACPS |
| ATOM | 56 | O | ASP | 8 | 1.792 | 5.822 | 53.101 | 1.00 | 10.65 | ACPS |
| ATOM | 57 | N | ILE | 9 | 3.479 | 5.447 | 54.551 | 1.00 | 9.53 | ACPS |
| ATOM | 58 | CA | ILE | 9 | 2.598 | 5.334 | 55.721 | 1.00 | 9.56 | ACPS |
| ATOM | 59 | CB | ILE | 9 | 2.634 | 3.913 | 56.338 | 1.00 | 9.26 | ACPS |
| ATOM | 60 | CG2 | ILE | 9 | 1.780 | 3.890 | 57.602 | 1.00 | 10.57 | ACPS |
| ATOM | 61 | CG1 | ILE | 9 | 2.101 | 2.881 | 55.338 | 1.00 | 9.47 | ACPS |
| ATOM | 62 | CD1 | ILE | 9 | 2.215 | 1.426 | 55.815 | 1.00 | 10.23 | ACPS |
| ATOM | 63 | C | ILE | 9 | 3.142 | 6.361 | 56.717 | 1.00 | 9.80 | ACPS |
| ATOM | 64 | O | ILE | 9 | 4.233 | 6.206 | 57.245 | 1.00 | 9.76 | ACPS |
| ATOM | 65 | N | THR | 10 | 2.375 | 7.423 | 56.941 | 1.00 | 9.46 | ACPS |
| ATOM | 66 | CA | THR | 10 | 2.768 | 8.527 | 57.819 | 1.00 | 10.38 | ACPS |

FIG. 2A-2

| ATOM | 67 | CB | THR | 10 | 2.428 | 9.871 | 57.089 | 1.00 | 10.26 | ACPS |
|------|----|----|----|----|----|----|----|----|----|----|
| ATOM | 68 | OG1 | THR | 10 | 3.340 | 10.050 | 55.997 | 1.00 | 11.15 | ACPS |
| ATOM | 69 | CG2 | THR | 10 | 2.527 | 11.081 | 58.021 | 1.00 | 11.35 | ACPS |
| ATOM | 70 | C | THR | 10 | 2.113 | 8.453 | 59.211 | 1.00 | 10.55 | ACPS |
| ATOM | 71 | O | THR | 10 | 0.936 | 8.111 | 59.336 | 1.00 | 10.38 | ACPS |
| ATOM | 72 | N | GLU | 11 | 2.897 | 8.773 | 60.246 | 1.00 | 10.75 | ACPS |
| ATOM | 73 | CA | GLU | 11 | 2.463 | 8.743 | 61.654 | 1.00 | 11.46 | ACPS |
| ATOM | 74 | CB | GLU | 11 | 3.708 | 8.583 | 62.544 | 1.00 | 11.49 | ACPS |
| ATOM | 75 | CG | GLU | 11 | 3.454 | 8.435 | 64.044 | 1.00 | 14.01 | ACPS |
| ATOM | 76 | CD | GLU | 11 | 3.151 | 7.005 | 64.449 | 1.00 | 16.01 | ACPS |
| ATOM | 77 | OE1 | GLU | 11 | 3.674 | 6.084 | 63.791 | 1.00 | 17.38 | ACPS |
| ATOM | 78 | OE2 | GLU | 11 | 2.417 | 6.807 | 65.435 | 1.00 | 18.05 | ACPS |
| ATOM | 79 | C | GLU | 11 | 1.697 | 10.012 | 62.065 | 1.00 | 11.12 | ACPS |
| ATOM | 80 | O | GLU | 11 | 2.255 | 11.106 | 62.037 | 1.00 | 11.41 | ACPS |
| ATOM | 81 | N | LEU | 12 | 0.430 | 9.865 | 62.447 | 1.00 | 11.46 | ACPS |
| ATOM | 82 | CA | LEU | 12 | -0.383 | 11.026 | 62.848 | 1.00 | 12.27 | ACPS |
| ATOM | 83 | CB | LEU | 12 | -1.785 | 10.582 | 63.305 | 1.00 | 12.68 | ACPS |
| ATOM | 84 | CG | LEU | 12 | -2.751 | 10.062 | 62.234 | 1.00 | 13.69 | ACPS |
| ATOM | 85 | CD1 | LEU | 12 | -4.049 | 9.642 | 62.918 | 1.00 | 13.86 | ACPS |
| ATOM | 86 | CD2 | LEU | 12 | -3.039 | 11.140 | 61.183 | 1.00 | 14.80 | ACPS |
| ATOM | 87 | C | LEU | 12 | 0.265 | 11.839 | 63.963 | 1.00 | 12.67 | ACPS |
| ATOM | 88 | O | LEU | 12 | 0.270 | 13.066 | 63.915 | 1.00 | 12.56 | ACPS |
| ATOM | 89 | N | LYS | 13 | 0.826 | 11.158 | 64.958 | 1.00 | 13.19 | ACPS |
| ATOM | 90 | CA | LYS | 13 | 1.457 | 11.852 | 66.085 | 1.00 | 14.09 | ACPS |
| ATOM | 91 | CB | LYS | 13 | 1.878 | 10.851 | 67.165 | 1.00 | 15.99 | ACPS |
| ATOM | 92 | CG | LYS | 13 | 0.740 | 10.332 | 68.017 | 1.00 | 20.36 | ACPS |
| ATOM | 93 | CD | LYS | 13 | 1.290 | 9.557 | 69.197 | 1.00 | 23.47 | ACPS |
| ATOM | 94 | CE | LYS | 13 | 0.232 | 9.319 | 70.261 | 1.00 | 25.28 | ACPS |
| ATOM | 95 | NZ | LYS | 13 | 0.840 | 8.690 | 71.473 | 1.00 | 26.94 | ACPS |
| ATOM | 96 | C | LYS | 13 | 2.665 | 12.693 | 65.685 | 1.00 | 13.56 | ACPS |
| ATOM | 97 | O | LYS | 13 | 2.924 | 13.738 | 66.295 | 1.00 | 13.25 | ACPS |
| ATOM | 98 | N | ARG | 14 | 3.423 | 12.237 | 64.692 | 1.00 | 12.75 | ACPS |
| ATOM | 99 | CA | ARG | 14 | 4.579 | 13.009 | 64.233 | 1.00 | 13.17 | ACPS |
| ATOM | 100 | CB | ARG | 14 | 5.436 | 12.178 | 63.270 | 1.00 | 14.59 | ACPS |
| ATOM | 101 | CG | ARG | 14 | 6.598 | 12.936 | 62.661 | 1.00 | 17.45 | ACPS |
| ATOM | 102 | CD | ARG | 14 | 7.572 | 12.010 | 61.933 | 1.00 | 21.04 | ACPS |
| ATOM | 103 | NE | ARG | 14 | 8.623 | 12.770 | 61.254 | 1.00 | 23.74 | ACPS |
| ATOM | 104 | CZ | ARG | 14 | 8.689 | 12.966 | 59.939 | 1.00 | 25.19 | ACPS |
| ATOM | 105 | NH1 | ARG | 14 | 7.768 | 12.450 | 59.134 | 1.00 | 25.79 | ACPS |
| ATOM | 106 | NH2 | ARG | 14 | 9.671 | 13.701 | 59.425 | 1.00 | 15.80 | ACPS |
| ATOM | 107 | C | ARG | 14 | 4.100 | 14.296 | 63.547 | 1.00 | 13.10 | ACPS |
| ATOM | 108 | O | ARG | 14 | 4.636 | 15.377 | 63.798 | 1.00 | 13.21 | ACPS |
| ATOM | 109 | N | ILE | 15 | 3.099 | 14.181 | 62.678 | 1.00 | 11.73 | ACPS |
| ATOM | 110 | CA | ILE | 15 | 2.559 | 15.348 | 61.988 | 1.00 | 12.13 | ACPS |
| ATOM | 111 | CB | ILE | 15 | 1.468 | 14.924 | 60.965 | 1.00 | 12.16 | ACPS |
| ATOM | 112 | CG2 | ILE | 15 | 0.822 | 16.150 | 60.320 | 1.00 | 13.81 | ACPS |
| ATOM | 113 | CG1 | ILE | 15 | 2.095 | 14.050 | 59.875 | 1.00 | 13.13 | ACPS |
| ATOM | 114 | CD1 | ILE | 15 | 3.191 | 14.736 | 59.050 | 1.00 | 15.37 | ACPS |
| ATOM | 115 | C | ILE | 15 | 1.981 | 16.356 | 62.996 | 1.00 | 12.43 | ACPS |
| ATOM | 116 | O | ILE | 15 | 2.165 | 17.571 | 62.845 | 1.00 | 13.17 | ACPS |
| ATOM | 117 | N | ALA | 16 | 1.292 | 15.859 | 64.019 | 1.00 | 12.31 | ACPS |
| ATOM | 118 | CA | ALA | 16 | 0.711 | 16.740 | 65.038 | 1.00 | 13.48 | ACPS |
| ATOM | 119 | CB | ALA | 16 | -0.165 | 15.938 | 66.000 | 1.00 | 13.26 | ACPS |
| ATOM | 120 | C | ALA | 16 | 1.812 | 17.456 | 65.811 | 1.00 | 13.84 | ACPS |
| ATOM | 121 | O | ALA | 16 | 1.679 | 18.631 | 66.159 | 1.00 | 14.13 | ACPS |
| ATOM | 122 | N | SER | 17 | 2.902 | 16.752 | 66.089 | 1.00 | 13.89 | ACPS |
| ATOM | 123 | CA | SER | 17 | 4.013 | 17.356 | 66.809 | 1.00 | 14.78 | ACPS |

FIG. 2A-3

| ATOM | 124 | CB | SER | 17 | 5.041 | 16.291 | 67.199 | 1.00 | 14.52 | ACPS |
|---|---|---|---|---|---|---|---|---|---|---|
| ATOM | 125 | OG | SER | 17 | 6.151 | 16.878 | 67.861 | 1.00 | 15.33 | ACPS |
| ATOM | 126 | C | SER | 17 | 4.686 | 18.440 | 65.971 | 1.00 | 15.57 | ACPS |
| ATOM | 127 | O | SER | 17 | 4.981 | 19.528 | 66.478 | 1.00 | 16.23 | ACPS |
| ATOM | 128 | N | MET | 18 | 4.933 | 18.163 | 64.694 | 1.00 | 15.86 | ACPS |
| ATOM | 129 | CA | MET | 18 | 5.568 | 19.173 | 63.861 | 1.00 | 17.36 | ACPS |
| ATOM | 130 | CB | MET | 18 | 5.920 | 18.593 | 62.491 | 1.00 | 18.79 | ACPS |
| ATOM | 131 | CG | MET | 18 | 6.984 | 17.513 | 62.579 | 1.00 | 21.58 | ACPS |
| ATOM | 132 | SD | MET | 18 | 7.569 | 16.962 | 60.979 | 1.00 | 27.23 | ACPS |
| ATOM | 133 | CE | MET | 18 | 6.322 | 15.823 | 60.550 | 1.00 | 24.77 | ACPS |
| ATOM | 134 | C | MET | 18 | 4.679 | 20.408 | 63.724 | 1.00 | 18.05 | ACPS |
| ATOM | 135 | O | MET | 18 | 5.171 | 21.537 | 63.720 | 1.00 | 17.78 | ACPS |
| ATOM | 136 | N | ALA | 19 | 3.371 | 20.200 | 63.637 | 1.00 | 17.79 | ACPS |
| ATOM | 137 | CA | ALA | 19 | 2.439 | 21.320 | 63.519 | 1.00 | 19.33 | ACPS |
| ATOM | 138 | CB | ALA | 19 | 1.047 | 20.810 | 63.161 | 1.00 | 18.47 | ACPS |
| ATOM | 139 | C | ALA | 19 | 2.391 | 22.119 | 64.827 | 1.00 | 20.49 | ACPS |
| ATOM | 140 | O | ALA | 19 | 2.124 | 23.324 | 64.820 | 1.00 | 21.87 | ACPS |
| ATOM | 141 | N | GLY | 20 | 2.655 | 21.446 | 65.944 | 1.00 | 21.04 | ACPS |
| ATOM | 142 | CA | GLY | 20 | 2.635 | 22.112 | 67.234 | 1.00 | 22.79 | ACPS |
| ATOM | 143 | C | GLY | 20 | 3.916 | 22.879 | 67.506 | 1.00 | 24.03 | ACPS |
| ATOM | 144 | O | GLY | 20 | 3.920 | 23.834 | 68.283 | 1.00 | 25.21 | ACPS |
| ATOM | 145 | N | ARG | 21 | 5.007 | 22.463 | 66.875 | 1.00 | 24.92 | ACPS |
| ATOM | 146 | CA | ARG | 21 | 6.286 | 23.135 | 67.062 | 1.00 | 26.49 | ACPS |
| ATOM | 147 | CB | ARG | 21 | 7.420 | 22.117 | 67.058 | 1.00 | 27.00 | ACPS |
| ATOM | 148 | CG | ARG | 21 | 7.376 | 21.144 | 68.216 | 1.00 | 28.19 | ACPS |
| ATOM | 149 | CD | ARG | 21 | 8.764 | 20.607 | 68.471 | 1.00 | 29.42 | ACPS |
| ATOM | 150 | NE | ARG | 21 | 9.667 | 21.695 | 68.835 | 1.00 | 30.12 | ACPS |
| ATOM | 151 | CZ | ARG | 21 | 10.993 | 21.603 | 68.834 | 1.00 | 29.99 | ACPS |
| ATOM | 152 | NH1 | ARG | 21 | 11.727 | 22.650 | 69.183 | 1.00 | 30.82 | ACPS |
| ATOM | 153 | NH2 | ARG | 21 | 11.584 | 20.469 | 68.481 | 1.00 | 30.49 | ACPS |
| ATOM | 154 | C | ARG | 21 | 6.559 | 24.208 | 66.006 | 1.00 | 27.49 | ACPS |
| ATOM | 155 | O | ARG | 21 | 7.329 | 25.141 | 66.247 | 1.00 | 28.27 | ACPS |
| ATOM | 156 | N | GLN | 22 | 5.935 | 24.073 | 64.840 | 1.00 | 27.79 | ACPS |
| ATOM | 157 | CA | GLN | 22 | 6.103 | 25.039 | 63.757 | 1.00 | 28.18 | ACPS |
| ATOM | 158 | CB | GLN | 22 | 6.697 | 24.364 | 62.515 | 1.00 | 29.33 | ACPS |
| ATOM | 159 | CG | GLN | 22 | 8.186 | 24.075 | 62.625 | 1.00 | 30.67 | ACPS |
| ATOM | 160 | CD | GLN | 22 | 8.839 | 23.775 | 61.284 | 1.00 | 31.99 | ACPS |
| ATOM | 161 | OE1 | GLN | 22 | 10.065 | 23.853 | 61.148 | 1.00 | 33.50 | ACPS |
| ATOM | 162 | NE2 | GLN | 22 | 8.029 | 23.422 | 60.291 | 1.00 | 31.08 | ACPS |
| ATOM | 163 | C | GLN | 22 | 4.765 | 25.686 | 63.406 | 1.00 | 27.71 | ACPS |
| ATOM | 164 | O | GLN | 22 | 3.866 | 25.036 | 62.869 | 1.00 | 27.85 | ACPS |
| ATOM | 165 | N | ALA | 23 | 4.646 | 26.976 | 63.707 | 1.00 | 26.91 | ACPS |
| ATOM | 166 | CA | ALA | 23 | 3.420 | 27.721 | 63.453 | 1.00 | 25.59 | ACPS |
| ATOM | 167 | CB | ALA | 23 | 3.578 | 29.155 | 63.945 | 1.00 | 26.37 | ACPS |
| ATOM | 168 | C | ALA | 23 | 2.966 | 27.722 | 61.994 | 1.00 | 24.20 | ACPS |
| ATOM | 169 | O | ALA | 23 | 1.784 | 27.936 | 61.711 | 1.00 | 25.27 | ACPS |
| ATOM | 170 | N | ARG | 24 | 3.885 | 27.478 | 61.068 | 1.00 | 22.39 | ACPS |
| ATOM | 171 | CA | ARG | 24 | 3.519 | 27.481 | 59.655 | 1.00 | 20.64 | ACPS |
| ATOM | 172 | CB | ARG | 24 | 4.265 | 28.617 | 58.943 | 1.00 | 23.30 | ACPS |
| ATOM | 173 | CG | ARG | 24 | 4.063 | 29.987 | 59.612 | 1.00 | 26.19 | ACPS |
| ATOM | 174 | CD | ARG | 24 | 4.793 | 31.085 | 58.862 | 1.00 | 30.07 | ACPS |
| ATOM | 175 | NE | ARG | 24 | 4.710 | 32.403 | 59.493 | 1.00 | 32.13 | ACPS |
| ATOM | 176 | CZ | ARG | 24 | 5.594 | 32.879 | 60.363 | 1.00 | 32.86 | ACPS |
| ATOM | 177 | NH1 | ARG | 24 | 6.644 | 32.150 | 60.720 | 1.00 | 33.10 | ACPS |
| ATOM | 178 | NH2 | ARG | 24 | 5.435 | 34.097 | 60.867 | 1.00 | 34.22 | ACPS |
| ATOM | 179 | C | ARG | 24 | 3.784 | 26.144 | 58.956 | 1.00 | 19.11 | ACPS |
| ATOM | 180 | O | ARG | 24 | 3.982 | 26.094 | 57.744 | 1.00 | 17.80 | ACPS |

FIG. 2A-4

| ATOM | 181 | N   | PHE | 25 | 3.765  | 25.057 | 59.720 | 1.00 | 16.89 | ACPS |
|------|-----|-----|-----|----|--------|--------|--------|------|-------|------|
| ATOM | 182 | CA  | PHE | 25 | 4.007  | 23.738 | 59.147 | 1.00 | 16.15 | ACPS |
| ATOM | 183 | CB  | PHE | 25 | 3.958  | 22.664 | 60.246 | 1.00 | 16.22 | ACPS |
| ATOM | 184 | CG  | PHE | 25 | 4.308  | 21.282 | 59.757 | 1.00 | 16.81 | ACPS |
| ATOM | 185 | CD1 | PHE | 25 | 3.357  | 20.271 | 59.754 | 1.00 | 17.39 | ACPS |
| ATOM | 186 | CD2 | PHE | 25 | 5.577  | 21.008 | 59.255 | 1.00 | 16.97 | ACPS |
| ATOM | 187 | CE1 | PHE | 25 | 3.662  | 19.001 | 59.253 | 1.00 | 18.39 | ACPS |
| ATOM | 188 | CE2 | PHE | 25 | 5.892  | 19.737 | 58.752 | 1.00 | 18.24 | ACPS |
| ATOM | 189 | CZ  | PHE | 25 | 4.930  | 18.737 | 58.753 | 1.00 | 17.96 | ACPS |
| ATOM | 190 | C   | PHE | 25 | 3.038  | 23.370 | 58.015 | 1.00 | 15.11 | ACPS |
| ATOM | 191 | O   | PHE | 25 | 3.464  | 22.840 | 56.988 | 1.00 | 14.64 | ACPS |
| ATOM | 192 | N   | ALA | 26 | 1.748  | 23.646 | 58.196 | 1.00 | 15.46 | ACPS |
| ATOM | 193 | CA  | ALA | 26 | 0.762  | 23.332 | 57.162 | 1.00 | 15.40 | ACPS |
| ATOM | 194 | CB  | ALA | 26 | -0.658 | 23.670 | 57.642 | 1.00 | 16.24 | ACPS |
| ATOM | 195 | C   | ALA | 26 | 1.075  | 24.093 | 55.881 | 1.00 | 15.52 | ACPS |
| ATOM | 196 | O   | ALA | 26 | 0.941  | 23.551 | 54.787 | 1.00 | 14.18 | ACPS |
| ATOM | 197 | N   | GLU | 27 | 1.512  | 25.345 | 56.011 | 1.00 | 14.73 | ACPS |
| ATOM | 198 | CA  | GLU | 27 | 1.839  | 26.155 | 54.838 | 1.00 | 15.35 | ACPS |
| ATOM | 199 | CB  | GLU | 27 | 2.041  | 27.619 | 55.236 | 1.00 | 16.37 | ACPS |
| ATOM | 200 | CG  | GLU | 27 | 0.782  | 28.381 | 55.603 | 1.00 | 18.60 | ACPS |
| ATOM | 201 | CD  | GLU | 27 | 0.176  | 27.956 | 56.927 | 1.00 | 19.31 | ACPS |
| ATOM | 202 | OE1 | GLU | 27 | 0.899  | 27.430 | 57.796 | 1.00 | 19.16 | ACPS |
| ATOM | 203 | OE2 | GLU | 27 | -1.040 | 28.169 | 57.109 | 1.00 | 22.95 | ACPS |
| ATOM | 204 | C   | GLU | 27 | 3.089  | 25.652 | 54.115 | 1.00 | 14.38 | ACPS |
| ATOM | 205 | O   | GLU | 27 | 3.309  | 25.946 | 52.944 | 1.00 | 14.80 | ACPS |
| ATOM | 206 | N   | ARG | 28 | 3.907  | 24.896 | 54.829 | 1.00 | 15.20 | ACPS |
| ATOM | 207 | CA  | ARG | 28 | 5.119  | 24.330 | 54.268 | 1.00 | 16.00 | ACPS |
| ATOM | 208 | CB  | ARG | 28 | 6.018  | 23.880 | 55.420 | 1.00 | 18.75 | ACPS |
| ATOM | 209 | CG  | ARG | 28 | 7.335  | 23.289 | 55.015 | 1.00 | 22.72 | ACPS |
| ATOM | 210 | CD  | ARG | 28 | 8.158  | 22.968 | 56.250 | 1.00 | 25.44 | ACPS |
| ATOM | 211 | NE  | ARG | 28 | 9.461  | 22.432 | 55.890 | 1.00 | 28.04 | ACPS |
| ATOM | 212 | CZ  | ARG | 28 | 10.382 | 22.070 | 56.775 | 1.00 | 28.40 | ACPS |
| ATOM | 213 | NH1 | ARG | 28 | 11.542 | 21.594 | 56.356 | 1.00 | 29.55 | ACPS |
| ATOM | 214 | NH2 | ARG | 28 | 10.135 | 22.184 | 58.074 | 1.00 | 28.44 | ACPS |
| ATOM | 215 | C   | ARG | 28 | 4.768  | 23.129 | 53.380 | 1.00 | 15.03 | ACPS |
| ATOM | 216 | O   | ARG | 28 | 5.345  | 22.925 | 52.311 | 1.00 | 15.61 | ACPS |
| ATOM | 217 | N   | ILE | 29 | 3.792  | 22.350 | 53.824 | 1.00 | 14.41 | ACPS |
| ATOM | 218 | CA  | ILE | 29 | 3.396  | 21.137 | 53.112 | 1.00 | 14.00 | ACPS |
| ATOM | 219 | CB  | ILE | 29 | 2.883  | 20.066 | 54.121 | 1.00 | 13.17 | ACPS |
| ATOM | 220 | CG2 | ILE | 29 | 2.586  | 18.765 | 53.401 | 1.00 | 13.59 | ACPS |
| ATOM | 221 | CG1 | ILE | 29 | 3.900  | 19.834 | 55.245 | 1.00 | 13.14 | ACPS |
| ATOM | 222 | CD1 | ILE | 29 | 5.307  | 19.516 | 54.785 | 1.00 | 12.95 | ACPS |
| ATOM | 223 | C   | ILE | 29 | 2.313  | 21.299 | 52.034 | 1.00 | 13.32 | ACPS |
| ATOM | 224 | O   | ILE | 29 | 2.370  | 20.650 | 50.993 | 1.00 | 13.97 | ACPS |
| ATOM | 225 | N   | LEU | 30 | 1.350  | 22.181 | 52.275 | 1.00 | 12.58 | ACPS |
| ATOM | 226 | CA  | LEU | 30 | 0.211  | 22.337 | 51.369 | 1.00 | 12.60 | ACPS |
| ATOM | 227 | CB  | LEU | 30 | -1.073 | 22.390 | 52.207 | 1.00 | 12.43 | ACPS |
| ATOM | 228 | CG  | LEU | 30 | -1.309 | 21.263 | 53.220 | 1.00 | 12.14 | ACPS |
| ATOM | 229 | CD1 | LEU | 30 | -2.536 | 21.595 | 54.057 | 1.00 | 13.80 | ACPS |
| ATOM | 230 | CD2 | LEU | 30 | -1.496 | 19.932 | 52.491 | 1.00 | 12.77 | ACPS |
| ATOM | 231 | C   | LEU | 30 | 0.227  | 23.540 | 50.432 | 1.00 | 12.66 | ACPS |
| ATOM | 232 | O   | LEU | 30 | 0.732  | 24.605 | 50.785 | 1.00 | 14.05 | ACPS |
| ATOM | 233 | N   | THR | 31 | -0.342 | 23.359 | 49.242 | 1.00 | 13.04 | ACPS |
| ATOM | 234 | CA  | THR | 31 | -0.456 | 24.450 | 48.265 | 1.00 | 13.14 | ACPS |
| ATOM | 235 | CB  | THR | 31 | -0.746 | 23.921 | 46.859 | 1.00 | 13.54 | ACPS |
| ATOM | 236 | OG1 | THR | 31 | -2.018 | 23.262 | 46.854 | 1.00 | 13.92 | ACPS |
| ATOM | 237 | CG2 | THR | 31 | 0.313  | 22.937 | 46.429 | 1.00 | 14.69 | ACPS |

FIG. 2A-5

| ATOM | 238 | C | THR | 31 | -1.641 | 25.328 | 48.690 | 1.00 | 13.91 | ACPS |
|---|---|---|---|---|---|---|---|---|---|---|
| ATOM | 239 | O | THR | 31 | -2.374 | 24.980 | 49.617 | 1.00 | 13.14 | ACPS |
| ATOM | 240 | N | ARG | 32 | -1.836 | 26.455 | 48.014 | 1.00 | 15.34 | ACPS |
| ATOM | 241 | CA | ARG | 32 | -2.947 | 27.338 | 48.367 | 1.00 | 15.55 | ACPS |
| ATOM | 242 | CB | ARG | 32 | -2.912 | 28.615 | 47.517 | 1.00 | 16.36 | ACPS |
| ATOM | 243 | CG | ARG | 32 | -1.630 | 29.403 | 47.682 | 1.00 | 18.69 | ACPS |
| ATOM | 244 | CD | ARG | 32 | -1.794 | 30.834 | 47.191 | 1.00 | 20.77 | ACPS |
| ATOM | 245 | NE | ARG | 32 | -2.750 | 31.590 | 48.000 | 1.00 | 22.37 | ACPS |
| ATOM | 246 | CZ | ARG | 32 | -3.938 | 32.003 | 47.569 | 1.00 | 23.12 | ACPS |
| ATOM | 247 | NH1 | ARG | 32 | -4.326 | 31.738 | 46.330 | 1.00 | 23.58 | ACPS |
| ATOM | 248 | NH2 | ARG | 32 | -4.738 | 32.686 | 48.380 | 1.00 | 22.27 | ACPS |
| ATOM | 249 | C | ARG | 32 | -4.296 | 26.646 | 48.205 | 1.00 | 15.92 | ACPS |
| ATOM | 250 | O | ARG | 32 | -5.166 | 26.781 | 49.054 | 1.00 | 16.02 | ACPS |
| ATOM | 251 | N | SER | 33 | -4.467 | 25.908 | 47.114 | 1.00 | 16.47 | ACPS |
| ATOM | 252 | CA | SER | 33 | -5.717 | 25.183 | 46.863 | 1.00 | 16.46 | ACPS |
| ATOM | 253 | CB | SER | 33 | -5.638 | 24.465 | 45.513 | 1.00 | 17.75 | ACPS |
| ATOM | 254 | OG | SER | 33 | -6.833 | 23.772 | 45.224 | 1.00 | 24.08 | ACPS |
| ATOM | 255 | C | SER | 33 | -5.981 | 24.154 | 47.967 | 1.00 | 16.53 | ACPS |
| ATOM | 256 | O | SER | 33 | -7.115 | 23.963 | 48.404 | 1.00 | 16.86 | ACPS |
| ATOM | 257 | N | GLU | 34 | -4.926 | 23.484 | 48.413 | 1.00 | 15.70 | ACPS |
| ATOM | 258 | CA | GLU | 34 | -5.058 | 22.480 | 49.458 | 1.00 | 15.77 | ACPS |
| ATOM | 259 | CB | GLU | 34 | -3.753 | 21.677 | 49.573 | 1.00 | 14.72 | ACPS |
| ATOM | 260 | CG | GLU | 34 | -3.578 | 20.659 | 48.459 | 1.00 | 15.35 | ACPS |
| ATOM | 261 | CD | GLU | 34 | -2.174 | 20.079 | 48.369 | 1.00 | 13.75 | ACPS |
| ATOM | 262 | OE1 | GLU | 34 | -2.023 | 19.029 | 47.719 | 1.00 | 13.81 | ACPS |
| ATOM | 263 | OE2 | GLU | 34 | -1.215 | 20.669 | 48.916 | 1.00 | 13.16 | ACPS |
| ATOM | 264 | C | GLU | 34 | -5.397 | 23.134 | 50.789 | 1.00 | 15.99 | ACPS |
| ATOM | 265 | O | GLU | 34 | -6.206 | 22.621 | 51.563 | 1.00 | 17.16 | ACPS |
| ATOM | 266 | N | LEU | 35 | -4.781 | 24.285 | 51.050 | 1.00 | 16.62 | ACPS |
| ATOM | 267 | CA | LEU | 35 | -5.025 | 25.008 | 52.285 | 1.00 | 17.38 | ACPS |
| ATOM | 268 | CB | LEU | 35 | -4.064 | 26.199 | 52.401 | 1.00 | 17.16 | ACPS |
| ATOM | 269 | CG | LEU | 35 | -2.614 | 25.863 | 52.761 | 1.00 | 17.73 | ACPS |
| ATOM | 270 | CD1 | LEU | 35 | -1.722 | 27.078 | 52.532 | 1.00 | 17.25 | ACPS |
| ATOM | 271 | CD2 | LEU | 35 | -2.547 | 25.405 | 54.212 | 1.00 | 17.05 | ACPS |
| ATOM | 272 | C | LEU | 35 | -6.462 | 25.499 | 52.380 | 1.00 | 18.36 | ACPS |
| ATOM | 273 | O | LEU | 35 | -7.035 | 25.535 | 53.466 | 1.00 | 17.94 | ACPS |
| ATOM | 274 | N | ASP | 36 | -7.049 | 25.866 | 51.248 | 1.00 | 19.36 | ACPS |
| ATOM | 275 | CA | ASP | 36 | -8.419 | 26.361 | 51.264 | 1.00 | 21.62 | ACPS |
| ATOM | 276 | CB | ASP | 36 | -8.866 | 26.738 | 49.845 | 1.00 | 22.68 | ACPS |
| ATOM | 277 | CG | ASP | 36 | -9.949 | 27.806 | 49.836 | 1.00 | 24.19 | ACPS |
| ATOM | 278 | OD1 | ASP | 36 | -9.928 | 28.690 | 50.724 | 1.00 | 25.68 | ACPS |
| ATOM | 279 | OD2 | ASP | 36 | -10.807 | 27.773 | 48.927 | 1.00 | 24.47 | ACPS |
| ATOM | 280 | C | ASP | 36 | -9.321 | 25.285 | 51.857 | 1.00 | 22.68 | ACPS |
| ATOM | 281 | O | ASP | 36 | -10.269 | 25.589 | 52.587 | 1.00 | 23.58 | ACPS |
| ATOM | 282 | N | GLN | 37 | -9.003 | 24.024 | 51.572 | 1.00 | 22.62 | ACPS |
| ATOM | 283 | CA | GLN | 37 | -9.784 | 22.899 | 52.087 | 1.00 | 23.62 | ACPS |
| ATOM | 284 | CB | GLN | 37 | -9.514 | 21.653 | 51.236 | 1.00 | 24.76 | ACPS |
| ATOM | 285 | CG | GLN | 37 | -9.899 | 21.812 | 49.769 | 1.00 | 26.90 | ACPS |
| ATOM | 286 | CD | GLN | 37 | -9.264 | 20.761 | 48.867 | 1.00 | 29.15 | ACPS |
| ATOM | 287 | OE1 | GLN | 37 | -9.409 | 19.557 | 49.092 | 1.00 | 30.76 | ACPS |
| ATOM | 288 | NE2 | GLN | 37 | -8.556 | 21.215 | 47.836 | 1.00 | 30.60 | ACPS |
| ATOM | 289 | C | GLN | 37 | -9.445 | 22.617 | 53.554 | 1.00 | 23.33 | ACPS |
| ATOM | 290 | O | GLN | 37 | -10.321 | 22.331 | 54.367 | 1.00 | 23.90 | ACPS |
| ATOM | 291 | N | TYR | 38 | -8.161 | 22.711 | 53.876 | 1.00 | 22.41 | ACPS |
| ATOM | 292 | CA | TYR | 38 | -7.644 | 22.474 | 55.222 | 1.00 | 22.14 | ACPS |
| ATOM | 293 | CB | TYR | 38 | -6.115 | 22.564 | 55.169 | 1.00 | 20.71 | ACPS |
| ATOM | 294 | CG | TYR | 38 | -5.376 | 22.533 | 56.491 | 1.00 | 20.71 | ACPS |

FIG. 2A-6

| ATOM | 295 | CD1 | TYR | 38 | -4.945 | 23.711 | 57.107 | 1.00 | 20.16 | ACPS |
|------|-----|-----|-----|----|--------|--------|--------|------|-------|------|
| ATOM | 296 | CE1 | TYR | 38 | -4.180 | 23.677 | 58.276 | 1.00 | 21.07 | ACPS |
| ATOM | 297 | CD2 | TYR | 38 | -5.033 | 21.322 | 57.084 | 1.00 | 19.25 | ACPS |
| ATOM | 298 | CE2 | TYR | 38 | -4.275 | 21.276 | 58.246 | 1.00 | 20.56 | ACPS |
| ATOM | 299 | CZ | TYR | 38 | -3.848 | 22.451 | 58.837 | 1.00 | 21.15 | ACPS |
| ATOM | 300 | OH | TYR | 38 | -3.079 | 22.392 | 59.976 | 1.00 | 21.86 | ACPS |
| ATOM | 301 | C | TYR | 38 | -8.191 | 23.441 | 56.270 | 1.00 | 22.57 | ACPS |
| ATOM | 302 | O | TYR | 38 | -8.599 | 23.031 | 57.357 | 1.00 | 21.64 | ACPS |
| ATOM | 303 | N | TYR | 39 | -8.201 | 24.727 | 55.933 | 1.00 | 23.00 | ACPS |
| ATOM | 304 | CA | TYR | 39 | -8.669 | 25.750 | 56.854 | 1.00 | 23.93 | ACPS |
| ATOM | 305 | CB | TYR | 39 | -8.540 | 27.139 | 56.212 | 1.00 | 24.42 | ACPS |
| ATOM | 306 | CG | TYR | 39 | -7.117 | 27.588 | 55.948 | 1.00 | 25.39 | ACPS |
| ATOM | 307 | CD1 | TYR | 39 | -6.061 | 27.134 | 56.734 | 1.00 | 26.23 | ACPS |
| ATOM | 308 | CE1 | TYR | 39 | -4.763 | 27.590 | 56.525 | 1.00 | 27.45 | ACPS |
| ATOM | 309 | CD2 | TYR | 39 | -6.836 | 28.512 | 54.939 | 1.00 | 26.81 | ACPS |
| ATOM | 310 | CE2 | TYR | 39 | -5.540 | 28.979 | 54.726 | 1.00 | 26.80 | ACPS |
| ATOM | 311 | CZ | TYR | 39 | -4.508 | 28.516 | 55.522 | 1.00 | 27.95 | ACPS |
| ATOM | 312 | OH | TYR | 39 | -3.224 | 28.999 | 55.337 | 1.00 | 28.86 | ACPS |
| ATOM | 313 | C | TYR | 39 | -10.095 | 25.568 | 57.369 | 1.00 | 24.48 | ACPS |
| ATOM | 314 | O | TYR | 39 | -10.440 | 26.118 | 58.412 | 1.00 | 25.01 | ACPS |
| ATOM | 315 | N | GLU | 40 | -10.916 | 24.802 | 56.656 | 1.00 | 24.88 | ACPS |
| ATOM | 316 | CA | GLU | 40 | -12.307 | 24.591 | 57.067 | 1.00 | 26.05 | ACPS |
| ATOM | 317 | CB | GLU | 40 | -13.180 | 24.249 | 55.854 | 1.00 | 27.82 | ACPS |
| ATOM | 318 | CG | GLU | 40 | -13.036 | 25.174 | 54.661 | 1.00 | 30.61 | ACPS |
| ATOM | 319 | CD | GLU | 40 | -14.017 | 24.833 | 53.551 | 1.00 | 31.77 | ACPS |
| ATOM | 320 | OE1 | GLU | 40 | -14.101 | 23.640 | 53.178 | 1.00 | 32.73 | ACPS |
| ATOM | 321 | OE2 | GLU | 40 | -14.697 | 25.756 | 53.050 | 1.00 | 33.34 | ACPS |
| ATOM | 322 | C | GLU | 40 | -12.487 | 23.467 | 58.086 | 1.00 | 25.59 | ACPS |
| ATOM | 323 | O | GLU | 40 | -13.581 | 23.280 | 58.618 | 1.00 | 26.05 | ACPS |
| ATOM | 324 | N | LEU | 41 | -11.420 | 22.731 | 58.368 | 1.00 | 24.07 | ACPS |
| ATOM | 325 | CA | LEU | 41 | -11.509 | 21.584 | 59.266 | 1.00 | 22.24 | ACPS |
| ATOM | 326 | CB | LEU | 41 | -10.578 | 20.486 | 58.744 | 1.00 | 21.78 | ACPS |
| ATOM | 327 | CG | LEU | 41 | -10.760 | 20.090 | 57.273 | 1.00 | 21.91 | ACPS |
| ATOM | 328 | CD1 | LEU | 41 | -9.666 | 19.107 | 56.881 | 1.00 | 21.70 | ACPS |
| ATOM | 329 | CD2 | LEU | 41 | -12.126 | 19.474 | 57.058 | 1.00 | 22.12 | ACPS |
| ATOM | 330 | C | LEU | 41 | -11.230 | 21.813 | 60.748 | 1.00 | 21.46 | ACPS |
| ATOM | 331 | O | LEU | 41 | -10.614 | 22.800 | 61.141 | 1.00 | 21.25 | ACPS |
| ATOM | 332 | N | SER | 42 | -11.693 | 20.873 | 61.567 | 1.00 | 21.01 | ACPS |
| ATOM | 333 | CA | SER | 42 | -11.476 | 20.926 | 63.009 | 1.00 | 20.67 | ACPS |
| ATOM | 334 | CB | SER | 42 | -12.319 | 19.865 | 63.716 | 1.00 | 21.24 | ACPS |
| ATOM | 335 | OG | SER | 42 | -11.874 | 18.558 | 63.388 | 1.00 | 20.80 | ACPS |
| ATOM | 336 | C | SER | 42 | -10.008 | 20.617 | 63.245 | 1.00 | 20.69 | ACPS |
| ATOM | 337 | O | SER | 42 | -9.309 | 20.184 | 62.328 | 1.00 | 19.86 | ACPS |
| ATOM | 338 | N | GLU | 43 | -9.540 | 20.834 | 64.469 | 1.00 | 19.62 | ACPS |
| ATOM | 339 | CA | GLU | 43 | -8.146 | 20.568 | 64.815 | 1.00 | 19.23 | ACPS |
| ATOM | 340 | CB | GLU | 43 | -7.932 | 20.830 | 66.312 | 1.00 | 20.39 | ACPS |
| ATOM | 341 | CG | GLU | 43 | -6.524 | 20.541 | 66.843 | 1.00 | 22.14 | ACPS |
| ATOM | 342 | CD | GLU | 43 | -6.452 | 20.617 | 68.366 | 1.00 | 23.47 | ACPS |
| ATOM | 343 | OE1 | GLU | 43 | -6.731 | 21.698 | 68.922 | 1.00 | 23.93 | ACPS |
| ATOM | 344 | OE2 | GLU | 43 | -6.118 | 19.594 | 69.004 | 1.00 | 24.66 | ACPS |
| ATOM | 345 | C | GLU | 43 | -7.789 | 19.120 | 64.473 | 1.00 | 18.65 | ACPS |
| ATOM | 346 | O | GLU | 43 | -6.755 | 18.849 | 63.864 | 1.00 | 18.62 | ACPS |
| ATOM | 347 | N | LYS | 44 | -8.653 | 18.190 | 64.853 | 1.00 | 17.32 | ACPS |
| ATOM | 348 | CA | LYS | 44 | -8.403 | 16.777 | 64.591 | 1.00 | 17.24 | ACPS |
| ATOM | 349 | CB | LYS | 44 | -9.441 | 15.931 | 65.326 | 1.00 | 16.54 | ACPS |
| ATOM | 350 | CG | LYS | 44 | -9.404 | 14.452 | 64.984 | 1.00 | 17.99 | ACPS |
| ATOM | 351 | CD | LYS | 44 | -10.561 | 13.732 | 65.664 | 1.00 | 19.56 | ACPS |

FIG. 2A-7

| ATOM | 352 | CE | LYS | 44 | -10.691 | 12.285 | 65.205 | 1.00 | 19.17 | ACPS |
|---|---|---|---|---|---|---|---|---|---|---|
| ATOM | 353 | NZ | LYS | 44 | -11.159 | 12.153 | 63.799 | 1.00 | 19.63 | ACPS |
| ATOM | 354 | C | LYS | 44 | -8.413 | 16.431 | 63.099 | 1.00 | 16.56 | ACPS |
| ATOM | 355 | O | LYS | 44 | -7.530 | 15.719 | 62.613 | 1.00 | 16.25 | ACPS |
| ATOM | 356 | N | ARG | 45 | -9.412 | 16.923 | 62.375 | 1.00 | 16.89 | ACPS |
| ATOM | 357 | CA | ARG | 45 | -9.507 | 16.641 | 60.947 | 1.00 | 17.08 | ACPS |
| ATOM | 358 | CB | ARG | 45 | -10.849 | 17.131 | 60.400 | 1.00 | 19.32 | ACPS |
| ATOM | 359 | CG | ARG | 45 | -12.053 | 16.345 | 60.910 | 1.00 | 21.73 | ACPS |
| ATOM | 360 | CD | ARG | 45 | -12.092 | 14.927 | 60.336 | 1.00 | 25.16 | ACPS |
| ATOM | 361 | NE | ARG | 45 | -13.304 | 14.213 | 60.741 | 1.00 | 28.95 | ACPS |
| ATOM | 362 | CZ | ARG | 45 | -13.616 | 12.977 | 60.360 | 1.00 | 30.49 | ACPS |
| ATOM | 363 | NH1 | ARG | 45 | -14.743 | 12.419 | 60.783 | 1.00 | 31.89 | ACPS |
| ATOM | 364 | NH2 | ARG | 45 | -12.808 | 12.296 | 59.553 | 1.00 | 32.45 | ACPS |
| ATOM | 365 | C | ARG | 45 | -8.353 | 17.284 | 60.189 | 1.00 | 16.29 | ACPS |
| ATOM | 366 | O | ARG | 45 | -7.871 | 16.734 | 59.198 | 1.00 | 15.72 | ACPS |
| ATOM | 367 | N | LYS | 46 | -7.917 | 18.455 | 60.644 | 1.00 | 15.52 | ACPS |
| ATOM | 368 | CA | LYS | 46 | -6.796 | 19.128 | 60.009 | 1.00 | 15.32 | ACPS |
| ATOM | 369 | CB | LYS | 46 | -6.449 | 20.429 | 60.746 | 1.00 | 15.53 | ACPS |
| ATOM | 370 | CG | LYS | 46 | -7.232 | 21.666 | 60.320 | 1.00 | 18.65 | ACPS |
| ATOM | 371 | CD | LYS | 46 | -6.678 | 22.887 | 61.051 | 1.00 | 20.77 | ACPS |
| ATOM | 372 | CE | LYS | 46 | -7.201 | 24.203 | 60.485 | 1.00 | 22.56 | ACPS |
| ATOM | 373 | NZ | LYS | 46 | -8.661 | 24.396 | 60.688 | 1.00 | 24.62 | ACPS |
| ATOM | 374 | C | LYS | 46 | -5.584 | 18.207 | 60.036 | 1.00 | 14.61 | ACPS |
| ATOM | 375 | O | LYS | 46 | -4.892 | 18.051 | 59.033 | 1.00 | 14.78 | ACPS |
| ATOM | 376 | N | ASN | 47 | -5.320 | 17.602 | 61.190 | 1.00 | 14.97 | ACPS |
| ATOM | 377 | CA | ASN | 47 | -4.174 | 16.711 | 61.329 | 1.00 | 14.85 | ACPS |
| ATOM | 378 | CB | ASN | 47 | -4.064 | 16.233 | 62.783 | 1.00 | 16.85 | ACPS |
| ATOM | 379 | CG | ASN | 47 | -2.877 | 15.317 | 63.008 | 1.00 | 19.82 | ACPS |
| ATOM | 380 | OD1 | ASN | 47 | -1.732 | 15.704 | 62.794 | 1.00 | 22.35 | ACPS |
| ATOM | 381 | ND2 | ASN | 47 | -3.149 | 14.093 | 63.439 | 1.00 | 21.62 | ACPS |
| ATOM | 382 | C | ASN | 47 | -4.283 | 15.517 | 60.373 | 1.00 | 14.22 | ACPS |
| ATOM | 383 | O | ASN | 47 | -3.312 | 15.159 | 59.702 | 1.00 | 13.37 | ACPS |
| ATOM | 384 | N | GLU | 48 | -5.461 | 14.915 | 60.289 | 1.00 | 13.02 | ACPS |
| ATOM | 385 | CA | GLU | 48 | -5.650 | 13.774 | 59.392 | 1.00 | 13.33 | ACPS |
| ATOM | 386 | CB | GLU | 48 | -7.005 | 13.122 | 59.666 | 1.00 | 13.97 | ACPS |
| ATOM | 387 | CG | GLU | 48 | -7.094 | 12.540 | 61.075 | 1.00 | 17.87 | ACPS |
| ATOM | 388 | CD | GLU | 48 | -8.518 | 12.306 | 61.525 | 1.00 | 19.35 | ACPS |
| ATOM | 389 | OE1 | GLU | 48 | -8.699 | 11.814 | 62.657 | 1.00 | 22.50 | ACPS |
| ATOM | 390 | OE2 | GLU | 48 | -9.449 | 12.615 | 60.754 | 1.00 | 22.51 | ACPS |
| ATOM | 391 | C | GLU | 48 | -5.531 | 14.180 | 57.925 | 1.00 | 12.99 | ACPS |
| ATOM | 392 | O | GLU | 48 | -4.927 | 13.463 | 57.121 | 1.00 | 12.41 | ACPS |
| ATOM | 393 | N | PHE | 49 | -6.098 | 15.331 | 57.573 | 1.00 | 12.16 | ACPS |
| ATOM | 394 | CA | PHE | 49 | -6.015 | 15.818 | 56.204 | 1.00 | 11.74 | ACPS |
| ATOM | 395 | CB | PHE | 49 | -6.827 | 17.118 | 56.058 | 1.00 | 12.28 | ACPS |
| ATOM | 396 | CG | PHE | 49 | -6.785 | 17.716 | 54.674 | 1.00 | 13.38 | ACPS |
| ATOM | 397 | CD1 | PHE | 49 | -7.742 | 17.379 | 53.724 | 1.00 | 13.30 | ACPS |
| ATOM | 398 | CD2 | PHE | 49 | -5.794 | 18.626 | 54.324 | 1.00 | 12.58 | ACPS |
| ATOM | 399 | CE1 | PHE | 49 | -7.710 | 17.950 | 52.449 | 1.00 | 14.47 | ACPS |
| ATOM | 400 | CE2 | PHE | 49 | -5.754 | 19.197 | 53.058 | 1.00 | 13.76 | ACPS |
| ATOM | 401 | CZ | PHE | 49 | -6.714 | 18.860 | 52.120 | 1.00 | 14.53 | ACPS |
| ATOM | 402 | C | PHE | 49 | -4.549 | 16.076 | 55.846 | 1.00 | 11.65 | ACPS |
| ATOM | 403 | O | PHE | 49 | -4.059 | 15.616 | 54.809 | 1.00 | 11.61 | ACPS |
| ATOM | 404 | N | LEU | 50 | -3.852 | 16.805 | 56.717 | 1.00 | 11.42 | ACPS |
| ATOM | 405 | CA | LEU | 50 | -2.454 | 17.140 | 56.489 | 1.00 | 11.53 | ACPS |
| ATOM | 406 | CB | LEU | 50 | -1.947 | 18.075 | 57.597 | 1.00 | 12.38 | ACPS |
| ATOM | 407 | CG | LEU | 50 | -0.473 | 18.512 | 57.597 | 1.00 | 12.32 | ACPS |
| ATOM | 408 | CD1 | LEU | 50 | -0.131 | 19.277 | 56.323 | 1.00 | 14.40 | ACPS |

FIG. 2A-8

| ATOM | 409 | CD2 | LEU | 50 | -0.213 | 19.390 | 58.824 | 1.00 | 13.78 | ACPS |
|---|---|---|---|---|---|---|---|---|---|---|
| ATOM | 410 | C | LEU | 50 | -1.573 | 15.900 | 56.413 | 1.00 | 10.56 | ACPS |
| ATOM | 411 | O | LEU | 50 | -0.684 | 15.827 | 55.569 | 1.00 | 10.55 | ACPS |
| ATOM | 412 | N | ALA | 51 | -1.806 | 14.936 | 57.301 | 1.00 | 10.65 | ACPS |
| ATOM | 413 | CA | ALA | 51 | -1.001 | 13.711 | 57.291 | 1.00 | 10.86 | ACPS |
| ATOM | 414 | CB | ALA | 51 | -1.330 | 12.847 | 58.510 | 1.00 | 10.65 | ACPS |
| ATOM | 415 | C | ALA | 51 | -1.213 | 12.905 | 56.003 | 1.00 | 11.03 | ACPS |
| ATOM | 416 | O | ALA | 51 | -0.274 | 12.296 | 55.481 | 1.00 | 10.16 | ACPS |
| ATOM | 417 | N | GLY | 52 | -2.441 | 12.913 | 55.490 | 1.00 | 11.30 | ACPS |
| ATOM | 418 | CA | GLY | 52 | -2.742 | 12.186 | 54.267 | 1.00 | 11.27 | ACPS |
| ATOM | 419 | C | GLY | 52 | -2.113 | 12.848 | 53.050 | 1.00 | 11.12 | ACPS |
| ATOM | 420 | O | GLY | 52 | -1.635 | 12.174 | 52.144 | 1.00 | 10.32 | ACPS |
| ATOM | 421 | N | ARG | 53 | -2.118 | 14.177 | 53.026 | 1.00 | 10.73 | ACPS |
| ATOM | 422 | CA | ARG | 53 | -1.521 | 14.896 | 51.906 | 1.00 | 10.83 | ACPS |
| ATOM | 423 | CB | ARG | 53 | -1.919 | 16.385 | 51.943 | 1.00 | 11.05 | ACPS |
| ATOM | 424 | CG | ARG | 53 | -3.089 | 16.756 | 51.012 | 1.00 | 13.36 | ACPS |
| ATOM | 425 | CD | ARG | 53 | -4.316 | 15.894 | 51.232 | 1.00 | 14.65 | ACPS |
| ATOM | 426 | NE | ARG | 53 | -5.419 | 16.229 | 50.322 | 1.00 | 13.75 | ACPS |
| ATOM | 427 | CZ | ARG | 53 | -6.569 | 15.562 | 50.280 | 1.00 | 14.79 | ACPS |
| ATOM | 428 | NH1 | ARG | 53 | -6.761 | 14.525 | 51.087 | 1.00 | 14.78 | ACPS |
| ATOM | 429 | NH2 | ARG | 53 | -7.534 | 15.932 | 49.445 | 1.00 | 15.39 | ACPS |
| ATOM | 430 | C | ARG | 53 | 0.001 | 14.732 | 51.974 | 1.00 | 10.44 | ACPS |
| ATOM | 431 | O | ARG | 53 | 0.654 | 14.603 | 50.938 | 1.00 | 10.68 | ACPS |
| ATOM | 432 | N | PHE | 54 | 0.557 | 14.728 | 53.193 | 1.00 | 10.64 | ACPS |
| ATOM | 433 | CA | PHE | 54 | 1.999 | 14.549 | 53.396 | 1.00 | 9.72 | ACPS |
| ATOM | 434 | CB | PHE | 54 | 2.308 | 14.710 | 54.903 | 1.00 | 10.85 | ACPS |
| ATOM | 435 | CG | PHE | 54 | 3.770 | 14.621 | 55.264 | 1.00 | 11.55 | ACPS |
| ATOM | 436 | CD1 | PHE | 54 | 4.397 | 13.386 | 55.407 | 1.00 | 12.45 | ACPS |
| ATOM | 437 | CD2 | PHE | 54 | 4.505 | 15.780 | 55.522 | 1.00 | 12.56 | ACPS |
| ATOM | 438 | CE1 | PHE | 54 | 5.729 | 13.301 | 55.806 | 1.00 | 12.31 | ACPS |
| ATOM | 439 | CE2 | PHE | 54 | 5.841 | 15.709 | 55.923 | 1.00 | 11.84 | ACPS |
| ATOM | 440 | CZ | PHE | 54 | 6.452 | 14.462 | 56.066 | 1.00 | 13.57 | ACPS |
| ATOM | 441 | C | PHE | 54 | 2.392 | 13.154 | 52.861 | 1.00 | 9.79 | ACPS |
| ATOM | 442 | O | PHE | 54 | 3.377 | 13.010 | 52.123 | 1.00 | 9.57 | ACPS |
| ATOM | 443 | N | ALA | 55 | 1.607 | 12.136 | 53.210 | 1.00 | 9.67 | ACPS |
| ATOM | 444 | CA | ALA | 55 | 1.873 | 10.770 | 52.742 | 1.00 | 9.05 | ACPS |
| ATOM | 445 | CB | ALA | 55 | 0.894 | 9.788 | 53.396 | 1.00 | 9.23 | ACPS |
| ATOM | 446 | C | ALA | 55 | 1.758 | 10.694 | 51.218 | 1.00 | 9.72 | ACPS |
| ATOM | 447 | O | ALA | 55 | 2.578 | 10.070 | 50.550 | 1.00 | 10.39 | ACPS |
| ATOM | 448 | N | ALA | 56 | 0.730 | 11.327 | 50.666 | 1.00 | 9.39 | ACPS |
| ATOM | 449 | CA | ALA | 56 | 0.550 | 11.313 | 49.215 | 1.00 | 9.78 | ACPS |
| ATOM | 450 | CB | ALA | 56 | -0.759 | 12.014 | 48.846 | 1.00 | 10.10 | ACPS |
| ATOM | 451 | C | ALA | 56 | 1.728 | 11.969 | 48.487 | 1.00 | 9.83 | ACPS |
| ATOM | 452 | O | ALA | 56 | 2.158 | 11.479 | 47.451 | 1.00 | 10.05 | ACPS |
| ATOM | 453 | N | LYS | 57 | 2.242 | 13.077 | 49.026 | 1.00 | 9.72 | ACPS |
| ATOM | 454 | CA | LYS | 57 | 3.361 | 13.758 | 48.388 | 1.00 | 10.49 | ACPS |
| ATOM | 455 | CB | LYS | 57 | 3.477 | 15.194 | 48.914 | 1.00 | 9.29 | ACPS |
| ATOM | 456 | CG | LYS | 57 | 2.243 | 16.015 | 48.546 | 1.00 | 9.85 | ACPS |
| ATOM | 457 | CD | LYS | 57 | 2.383 | 17.492 | 48.881 | 1.00 | 10.42 | ACPS |
| ATOM | 458 | CE | LYS | 57 | 1.057 | 18.196 | 48.628 | 1.00 | 10.41 | ACPS |
| ATOM | 459 | NZ | LYS | 57 | 1.214 | 19.689 | 48.629 | 1.00 | 10.56 | ACPS |
| ATOM | 460 | C | LYS | 57 | 4.668 | 12.986 | 48.549 | 1.00 | 10.05 | ACPS |
| ATOM | 461 | O | LYS | 57 | 5.501 | 12.992 | 47.632 | 1.00 | 11.38 | ACPS |
| ATOM | 462 | N | GLU | 58 | 4.863 | 12.322 | 49.687 | 1.00 | 10.76 | ACPS |
| ATOM | 463 | CA | GLU | 58 | 6.073 | 11.513 | 49.846 | 1.00 | 10.03 | ACPS |
| ATOM | 464 | CB | GLU | 58 | 6.270 | 11.064 | 51.304 | 1.00 | 10.79 | ACPS |
| ATOM | 465 | CG | GLU | 58 | 6.674 | 12.221 | 52.234 | 1.00 | 12.67 | ACPS |

FIG. 2A-9

| ATOM | 466 | CD  | GLU | 58 | 7.551  | 11.800 | 53.407 | 1.00 | 14.43 | ACPS |
|------|-----|-----|-----|----|--------|--------|--------|------|-------|------|
| ATOM | 467 | OE1 | GLU | 58 | 7.452  | 10.642 | 53.851 | 1.00 | 12.52 | ACPS |
| ATOM | 468 | OE2 | GLU | 58 | 8.343  | 12.641 | 53.905 | 1.00 | 14.76 | ACPS |
| ATOM | 469 | C   | GLU | 58 | 5.969  | 10.307 | 48.903 | 1.00 | 10.19 | ACPS |
| ATOM | 470 | O   | GLU | 58 | 6.960  | 9.897  | 48.298 | 1.00 | 11.04 | ACPS |
| ATOM | 471 | N   | ALA | 59 | 4.773  | 9.742  | 48.765 | 1.00 | 10.50 | ACPS |
| ATOM | 472 | CA  | ALA | 59 | 4.596  | 8.622  | 47.844 | 1.00 | 10.19 | ACPS |
| ATOM | 473 | CB  | ALA | 59 | 3.178  | 8.031  | 47.965 | 1.00 | 9.73  | ACPS |
| ATOM | 474 | C   | ALA | 59 | 4.866  | 9.100  | 46.415 | 1.00 | 11.21 | ACPS |
| ATOM | 475 | O   | ALA | 59 | 5.510  | 8.402  | 45.641 | 1.00 | 11.07 | ACPS |
| ATOM | 476 | N   | PHE | 60 | 4.377  | 10.289 | 46.071 | 1.00 | 10.97 | ACPS |
| ATOM | 477 | CA  | PHE | 60 | 4.614  | 10.824 | 44.735 | 1.00 | 11.41 | ACPS |
| ATOM | 478 | CB  | PHE | 60 | 3.918  | 12.182 | 44.536 | 1.00 | 11.35 | ACPS |
| ATOM | 479 | CG  | PHE | 60 | 4.213  | 12.810 | 43.191 | 1.00 | 11.93 | ACPS |
| ATOM | 480 | CD1 | PHE | 60 | 3.492  | 12.439 | 42.057 | 1.00 | 11.51 | ACPS |
| ATOM | 481 | CD2 | PHE | 60 | 5.284  | 13.684 | 43.047 | 1.00 | 11.60 | ACPS |
| ATOM | 482 | CE1 | PHE | 60 | 3.841  | 12.926 | 40.793 | 1.00 | 12.57 | ACPS |
| ATOM | 483 | CE2 | PHE | 60 | 5.641  | 14.174 | 41.794 | 1.00 | 12.35 | ACPS |
| ATOM | 484 | CZ  | PHE | 60 | 4.921  | 13.794 | 40.671 | 1.00 | 11.51 | ACPS |
| ATOM | 485 | C   | PHE | 60 | 6.109  | 11.014 | 44.481 | 1.00 | 10.91 | ACPS |
| ATOM | 486 | O   | PHE | 60 | 6.599  | 10.703 | 43.390 | 1.00 | 11.17 | ACPS |
| ATOM | 487 | N   | SER | 61 | 6.828  | 11.529 | 45.483 | 1.00 | 11.07 | ACPS |
| ATOM | 488 | CA  | SER | 61 | 8.262  | 11.775 | 45.336 | 1.00 | 11.40 | ACPS |
| ATOM | 489 | CB  | SER | 61 | 8.815  | 12.510 | 46.561 | 1.00 | 11.56 | ACPS |
| ATOM | 490 | OG  | SER | 61 | 9.026  | 11.642 | 47.660 | 1.00 | 12.07 | ACPS |
| ATOM | 491 | C   | SER | 61 | 9.039  | 10.487 | 45.094 | 1.00 | 12.17 | ACPS |
| ATOM | 492 | O   | SER | 61 | 10.102 | 10.508 | 44.476 | 1.00 | 11.91 | ACPS |
| ATOM | 493 | N   | LYS | 62 | 8.513  | 9.365  | 45.583 | 1.00 | 11.76 | ACPS |
| ATOM | 494 | CA  | LYS | 62 | 9.165  | 8.081  | 45.361 | 1.00 | 11.72 | ACPS |
| ATOM | 495 | CB  | LYS | 62 | 8.687  | 7.051  | 46.395 | 1.00 | 9.91  | ACPS |
| ATOM | 496 | CG  | LYS | 62 | 9.172  | 7.377  | 47.836 | 1.00 | 10.07 | ACPS |
| ATOM | 497 | CD  | LYS | 62 | 8.584  | 6.402  | 48.888 | 1.00 | 8.91  | ACPS |
| ATOM | 498 | CE  | LYS | 62 | 8.901  | 6.838  | 50.320 | 1.00 | 10.72 | ACPS |
| ATOM | 499 | NZ  | LYS | 62 | 8.292  | 5.910  | 51.344 | 1.00 | 10.83 | ACPS |
| ATOM | 500 | C   | LYS | 62 | 8.875  | 7.603  | 43.935 | 1.00 | 11.87 | ACPS |
| ATOM | 501 | O   | LYS | 62 | 9.758  | 7.062  | 43.264 | 1.00 | 12.36 | ACPS |
| ATOM | 502 | N   | ALA | 63 | 7.642  | 7.815  | 43.472 | 1.00 | 12.11 | ACPS |
| ATOM | 503 | CA  | ALA | 63 | 7.266  | 7.408  | 42.119 | 1.00 | 12.83 | ACPS |
| ATOM | 504 | CB  | ALA | 63 | 5.751  | 7.567  | 41.914 | 1.00 | 11.67 | ACPS |
| ATOM | 505 | C   | ALA | 63 | 8.033  | 8.259  | 41.105 | 1.00 | 13.18 | ACPS |
| ATOM | 506 | O   | ALA | 63 | 8.402  | 7.774  | 40.037 | 1.00 | 13.32 | ACPS |
| ATOM | 507 | N   | PHE | 64 | 8.262  | 9.523  | 41.457 | 1.00 | 13.48 | ACPS |
| ATOM | 508 | CA  | PHE | 64 | 8.987  | 10.491 | 40.628 | 1.00 | 14.82 | ACPS |
| ATOM | 509 | CB  | PHE | 64 | 8.856  | 11.878 | 41.290 | 1.00 | 14.97 | ACPS |
| ATOM | 510 | CG  | PHE | 64 | 9.339  | 13.026 | 40.451 | 1.00 | 17.08 | ACPS |
| ATOM | 511 | CD1 | PHE | 64 | 8.715  | 13.350 | 39.253 | 1.00 | 17.78 | ACPS |
| ATOM | 512 | CD2 | PHE | 64 | 10.402 | 13.809 | 40.885 | 1.00 | 17.57 | ACPS |
| ATOM | 513 | CE1 | PHE | 64 | 9.148  | 14.450 | 38.495 | 1.00 | 18.78 | ACPS |
| ATOM | 514 | CE2 | PHE | 64 | 10.838 | 14.904 | 40.137 | 1.00 | 18.89 | ACPS |
| ATOM | 515 | CZ  | PHE | 64 | 10.209 | 15.221 | 38.944 | 1.00 | 18.36 | ACPS |
| ATOM | 516 | C   | PHE | 64 | 10.456 | 10.048 | 40.545 | 1.00 | 14.87 | ACPS |
| ATOM | 517 | O   | PHE | 64 | 11.136 | 10.290 | 39.547 | 1.00 | 16.68 | ACPS |
| ATOM | 518 | N   | GLY | 65 | 10.941 | 9.423  | 41.615 | 1.00 | 14.73 | ACPS |
| ATOM | 519 | CA  | GLY | 65 | 12.302 | 8.907  | 41.652 | 1.00 | 14.56 | ACPS |
| ATOM | 520 | C   | GLY | 65 | 13.370 | 9.729  | 42.351 | 1.00 | 14.92 | ACPS |
| ATOM | 521 | O   | GLY | 65 | 14.542 | 9.351  | 42.348 | 1.00 | 15.63 | ACPS |
| ATOM | 522 | N   | THR | 66 | 12.979 | 10.826 | 42.980 | 1.00 | 16.03 | ACPS |

FIG. 2A-10

| ATOM | 523 | CA  | THR | 66 | 13.945 | 11.700 | 43.643 | 1.00 | 16.17 | ACPS |
| ---- | --- | --- | --- | -- | ------ | ------ | ------ | ---- | ----- | ---- |
| ATOM | 524 | CB  | THR | 66 | 13.908 | 13.103 | 43.038 | 1.00 | 17.57 | ACPS |
| ATOM | 525 | OG1 | THR | 66 | 12.622 | 13.685 | 43.290 | 1.00 | 16.98 | ACPS |
| ATOM | 526 | CG2 | THR | 66 | 14.150 | 13.056 | 41.531 | 1.00 | 18.71 | ACPS |
| ATOM | 527 | C   | THR | 66 | 13.770 | 11.912 | 45.140 | 1.00 | 15.80 | ACPS |
| ATOM | 528 | O   | THR | 66 | 14.713 | 12.315 | 45.825 | 1.00 | 15.38 | ACPS |
| ATOM | 529 | N   | GLY | 67 | 12.572 | 11.652 | 45.649 | 1.00 | 15.62 | ACPS |
| ATOM | 530 | CA  | GLY | 67 | 12.319 | 11.918 | 47.052 | 1.00 | 15.38 | ACPS |
| ATOM | 531 | C   | GLY | 67 | 12.088 | 13.421 | 47.173 | 1.00 | 15.61 | ACPS |
| ATOM | 532 | O   | GLY | 67 | 12.160 | 14.137 | 46.170 | 1.00 | 15.25 | ACPS |
| ATOM | 533 | N   | ILE | 68 | 11.801 | 13.906 | 48.380 | 1.00 | 15.09 | ACPS |
| ATOM | 534 | CA  | ILE | 68 | 11.580 | 15.332 | 48.598 | 1.00 | 16.65 | ACPS |
| ATOM | 535 | CB  | ILE | 68 | 10.578 | 15.590 | 49.762 | 1.00 | 15.30 | ACPS |
| ATOM | 536 | CG2 | ILE | 68 | 10.508 | 17.089 | 50.063 | 1.00 | 16.62 | ACPS |
| ATOM | 537 | CG1 | ILE | 68 | 9.182  | 15.049 | 49.413 | 1.00 | 14.84 | ACPS |
| ATOM | 538 | CD1 | ILE | 68 | 8.484  | 15.785 | 48.269 | 1.00 | 15.16 | ACPS |
| ATOM | 539 | C   | ILE | 68 | 12.927 | 15.967 | 48.945 | 1.00 | 17.33 | ACPS |
| ATOM | 540 | O   | ILE | 68 | 13.610 | 15.520 | 49.862 | 1.00 | 18.29 | ACPS |
| ATOM | 541 | N   | GLY | 69 | 13.305 | 17.002 | 48.202 | 1.00 | 18.32 | ACPS |
| ATOM | 542 | CA  | GLY | 69 | 14.574 | 17.663 | 48.436 | 1.00 | 20.27 | ACPS |
| ATOM | 543 | C   | GLY | 69 | 14.877 | 18.700 | 47.371 | 1.00 | 20.85 | ACPS |
| ATOM | 544 | O   | GLY | 69 | 13.990 | 19.447 | 46.949 | 1.00 | 20.98 | ACPS |
| ATOM | 545 | N   | ALA | 70 | 16.128 | 18.734 | 46.920 | 1.00 | 22.02 | ACPS |
| ATOM | 546 | CA  | ALA | 70 | 16.564 | 19.710 | 45.922 | 1.00 | 22.94 | ACPS |
| ATOM | 547 | CB  | ALA | 70 | 18.064 | 19.575 | 45.690 | 1.00 | 24.19 | ACPS |
| ATOM | 548 | C   | ALA | 70 | 15.834 | 19.655 | 44.582 | 1.00 | 23.39 | ACPS |
| ATOM | 549 | O   | ALA | 70 | 15.623 | 20.688 | 43.950 | 1.00 | 24.35 | ACPS |
| ATOM | 550 | N   | GLN | 71 | 15.446 | 18.457 | 44.153 | 1.00 | 22.46 | ACPS |
| ATOM | 551 | CA  | GLN | 71 | 14.765 | 18.289 | 42.871 | 1.00 | 21.53 | ACPS |
| ATOM | 552 | CB  | GLN | 71 | 15.204 | 16.971 | 42.223 | 1.00 | 23.55 | ACPS |
| ATOM | 553 | CG  | GLN | 71 | 16.683 | 16.924 | 41.843 | 1.00 | 26.32 | ACPS |
| ATOM | 554 | CD  | GLN | 71 | 17.185 | 15.512 | 41.591 | 1.00 | 28.10 | ACPS |
| ATOM | 555 | OE1 | GLN | 71 | 17.349 | 14.722 | 42.523 | 1.00 | 29.41 | ACPS |
| ATOM | 556 | NE2 | GLN | 71 | 17.435 | 15.188 | 40.326 | 1.00 | 29.15 | ACPS |
| ATOM | 557 | C   | GLN | 71 | 13.239 | 18.334 | 42.931 | 1.00 | 20.50 | ACPS |
| ATOM | 558 | O   | GLN | 71 | 12.580 | 18.424 | 41.891 | 1.00 | 20.08 | ACPS |
| ATOM | 559 | N   | LEU | 72 | 12.668 | 18.287 | 44.132 | 1.00 | 18.34 | ACPS |
| ATOM | 560 | CA  | LEU | 72 | 11.210 | 18.292 | 44.261 | 1.00 | 16.54 | ACPS |
| ATOM | 561 | CB  | LEU | 72 | 10.671 | 16.868 | 44.034 | 1.00 | 16.42 | ACPS |
| ATOM | 562 | CG  | LEU | 72 | 9.146  | 16.682 | 44.035 | 1.00 | 15.69 | ACPS |
| ATOM | 563 | CD1 | LEU | 72 | 8.539  | 17.358 | 42.815 | 1.00 | 16.49 | ACPS |
| ATOM | 564 | CD2 | LEU | 72 | 8.811  | 15.186 | 44.032 | 1.00 | 16.39 | ACPS |
| ATOM | 565 | C   | LEU | 72 | 10.752 | 18.786 | 45.632 | 1.00 | 15.95 | ACPS |
| ATOM | 566 | O   | LEU | 72 | 11.177 | 18.260 | 46.654 | 1.00 | 16.86 | ACPS |
| ATOM | 567 | N   | SER | 73 | 9.879  | 19.789 | 45.649 | 1.00 | 15.85 | ACPS |
| ATOM | 568 | CA  | SER | 73 | 9.360  | 20.337 | 46.901 | 1.00 | 15.02 | ACPS |
| ATOM | 569 | CB  | SER | 73 | 9.400  | 21.872 | 46.865 | 1.00 | 16.69 | ACPS |
| ATOM | 570 | OG  | SER | 73 | 8.552  | 22.454 | 47.851 | 1.00 | 18.22 | ACPS |
| ATOM | 571 | C   | SER | 73 | 7.920  | 19.896 | 47.122 | 1.00 | 13.98 | ACPS |
| ATOM | 572 | O   | SER | 73 | 7.227  | 19.531 | 46.175 | 1.00 | 14.35 | ACPS |
| ATOM | 573 | N   | PHE | 74 | 7.469  | 19.926 | 48.373 | 1.00 | 13.59 | ACPS |
| ATOM | 574 | CA  | PHE | 74 | 6.083  | 19.584 | 48.674 | 1.00 | 12.78 | ACPS |
| ATOM | 575 | CB  | PHE | 74 | 5.802  | 19.731 | 50.177 | 1.00 | 12.70 | ACPS |
| ATOM | 576 | CG  | PHE | 74 | 6.274  | 18.566 | 51.010 | 1.00 | 13.35 | ACPS |
| ATOM | 577 | CD1 | PHE | 74 | 5.663  | 17.320 | 50.894 | 1.00 | 14.16 | ACPS |
| ATOM | 578 | CD2 | PHE | 74 | 7.308  | 18.723 | 51.928 | 1.00 | 15.36 | ACPS |
| ATOM | 579 | CE1 | PHE | 74 | 6.071  | 16.246 | 51.679 | 1.00 | 13.54 | ACPS |

FIG. 2A-11

| | | | | | | | | | |
|---|---|---|---|---|---|---|---|---|---|
| ATOM | 580 | CE2 | PHE | 74 | 7.727 | 17.653 | 52.720 | 1.00 14.73 | ACPS |
| ATOM | 581 | CZ | PHE | 74 | 7.104 | 16.412 | 52.592 | 1.00 14.61 | ACPS |
| ATOM | 582 | C | PHE | 74 | 5.172 | 20.539 | 47.894 | 1.00 13.25 | ACPS |
| ATOM | 583 | O | PHE | 74 | 4.070 | 20.179 | 47.500 | 1.00 13.15 | ACPS |
| ATOM | 584 | N | GLN | 75 | 5.642 | 21.764 | 47.665 | 1.00 13.41 | ACPS |
| ATOM | 585 | CA | GLN | 75 | 4.848 | 22.749 | 46.929 | 1.00 13.12 | ACPS |
| ATOM | 586 | CB | GLN | 75 | 5.437 | 24.152 | 47.124 | 1.00 13.58 | ACPS |
| ATOM | 587 | CG | GLN | 75 | 5.338 | 24.667 | 48.545 | 1.00 14.20 | ACPS |
| ATOM | 588 | CD | GLN | 75 | 3.897 | 24.841 | 48.976 | 1.00 15.83 | ACPS |
| ATOM | 589 | OE1 | GLN | 75 | 3.077 | 25.355 | 48.217 | 1.00 17.10 | ACPS |
| ATOM | 590 | NE2 | GLN | 75 | 3.581 | 24.421 | 50.194 | 1.00 15.26 | ACPS |
| ATOM | 591 | C | GLN | 75 | 4.701 | 22.473 | 45.430 | 1.00 13.39 | ACPS |
| ATOM | 592 | O | GLN | 75 | 3.865 | 23.097 | 44.769 | 1.00 14.75 | ACPS |
| ATOM | 593 | N | ASP | 76 | 5.502 | 21.555 | 44.889 | 1.00 13.51 | ACPS |
| ATOM | 594 | CA | ASP | 76 | 5.423 | 21.214 | 43.464 | 1.00 13.36 | ACPS |
| ATOM | 595 | CB | ASP | 76 | 6.760 | 20.670 | 42.950 | 1.00 14.98 | ACPS |
| ATOM | 596 | CG | ASP | 76 | 7.907 | 21.644 | 43.108 | 1.00 15.83 | ACPS |
| ATOM | 597 | OD1 | ASP | 76 | 7.682 | 22.872 | 43.049 | 1.00 17.92 | ACPS |
| ATOM | 598 | OD2 | ASP | 76 | 9.049 | 21.168 | 43.265 | 1.00 16.55 | ACPS |
| ATOM | 599 | C | ASP | 76 | 4.369 | 20.143 | 43.177 | 1.00 13.18 | ACPS |
| ATOM | 600 | O | ASP | 76 | 4.138 | 19.781 | 42.016 | 1.00 13.17 | ACPS |
| ATOM | 601 | N | ILE | 77 | 3.743 | 19.637 | 44.234 | 1.00 12.89 | ACPS |
| ATOM | 602 | CA | ILE | 77 | 2.765 | 18.561 | 44.116 | 1.00 12.84 | ACPS |
| ATOM | 603 | CB | ILE | 77 | 3.248 | 17.339 | 44.932 | 1.00 11.96 | ACPS |
| ATOM | 604 | CG2 | ILE | 77 | 2.405 | 16.122 | 44.608 | 1.00 11.88 | ACPS |
| ATOM | 605 | CG1 | ILE | 77 | 4.722 | 17.053 | 44.638 | 1.00 12.24 | ACPS |
| ATOM | 606 | CD1 | ILE | 77 | 5.413 | 16.211 | 45.724 | 1.00 12.11 | ACPS |
| ATOM | 607 | C | ILE | 77 | 1.414 | 18.999 | 44.664 | 1.00 12.77 | ACPS |
| ATOM | 608 | O | ILE | 77 | 1.330 | 19.552 | 45.766 | 1.00 13.68 | ACPS |
| ATOM | 609 | N | GLU | 78 | 0.349 | 18.748 | 43.910 | 1.00 12.53 | ACPS |
| ATOM | 610 | CA | GLU | 78 | -0.975 | 19.130 | 44.373 | 1.00 12.16 | ACPS |
| ATOM | 611 | CB | GLU | 78 | -1.472 | 20.350 | 43.587 | 1.00 12.59 | ACPS |
| ATOM | 612 | CG | GLU | 78 | -2.722 | 20.983 | 44.167 | 1.00 13.40 | ACPS |
| ATOM | 613 | CD | GLU | 78 | -2.987 | 22.339 | 43.559 | 1.00 14.46 | ACPS |
| ATOM | 614 | OE1 | GLU | 78 | -3.631 | 22.398 | 42.489 | 1.00 16.38 | ACPS |
| ATOM | 615 | OE2 | GLU | 78 | -2.524 | 23.340 | 44.147 | 1.00 15.90 | ACPS |
| ATOM | 616 | C | GLU | 78 | -1.999 | 18.014 | 44.252 | 1.00 11.56 | ACPS |
| ATOM | 617 | O | GLU | 78 | -2.145 | 17.402 | 43.198 | 1.00 12.82 | ACPS |
| ATOM | 618 | N | ILE | 79 | -2.704 | 17.748 | 45.344 | 1.00 11.82 | ACPS |
| ATOM | 619 | CA | ILE | 79 | -3.750 | 16.734 | 45.329 | 1.00 12.32 | ACPS |
| ATOM | 620 | CB | ILE | 79 | -3.893 | 16.000 | 46.698 | 1.00 12.41 | ACPS |
| ATOM | 621 | CG2 | ILE | 79 | -5.201 | 15.191 | 46.723 | 1.00 12.50 | ACPS |
| ATOM | 622 | CG1 | ILE | 79 | -2.737 | 15.010 | 46.913 | 1.00 11.83 | ACPS |
| ATOM | 623 | CD1 | ILE | 79 | -1.372 | 15.660 | 47.132 | 1.00 12.95 | ACPS |
| ATOM | 624 | C | ILE | 79 | -5.053 | 17.483 | 45.048 | 1.00 12.37 | ACPS |
| ATOM | 625 | O | ILE | 79 | -5.389 | 18.439 | 45.747 | 1.00 13.01 | ACPS |
| ATOM | 626 | N | ARG | 80 | -5.753 | 17.059 | 44.003 | 1.00 12.18 | ACPS |
| ATOM | 627 | CA | ARG | 80 | -7.037 | 17.649 | 43.633 | 1.00 13.15 | ACPS |
| ATOM | 628 | CB | ARG | 80 | -6.981 | 18.219 | 42.205 | 1.00 13.40 | ACPS |
| ATOM | 629 | CG | ARG | 80 | -5.887 | 19.278 | 41.989 | 1.00 14.66 | ACPS |
| ATOM | 630 | CD | ARG | 80 | -5.931 | 19.884 | 40.592 | 1.00 16.60 | ACPS |
| ATOM | 631 | NE | ARG | 80 | -4.846 | 20.849 | 40.396 | 1.00 16.81 | ACPS |
| ATOM | 632 | CZ | ARG | 80 | -4.588 | 21.471 | 39.248 | 1.00 18.53 | ACPS |
| ATOM | 633 | NH1 | ARG | 80 | -3.581 | 22.331 | 39.175 | 1.00 18.94 | ACPS |
| ATOM | 634 | NH2 | ARG | 80 | -5.331 | 21.240 | 38.173 | 1.00 17.96 | ACPS |
| ATOM | 635 | C | ARG | 80 | -8.061 | 16.516 | 43.701 | 1.00 13.09 | ACPS |
| ATOM | 636 | O | ARG | 80 | -7.697 | 15.352 | 43.882 | 1.00 13.74 | ACPS |

FIG. 2A-12

| | | | | | | | | | |
|---|---|---|---|---|---|---|---|---|---|
| ATOM | 637 | N | LYS | 81 | -9.339 | 16.837 | 43.577 | 1.00 13.78 | ACPS |
| ATOM | 638 | CA | LYS | 81 | -10.349 | 15.789 | 43.610 | 1.00 15.56 | ACPS |
| ATOM | 639 | CB | LYS | 81 | -10.943 | 15.648 | 45.017 | 1.00 17.86 | ACPS |
| ATOM | 640 | CG | LYS | 81 | -11.693 | 16.852 | 45.502 | 1.00 21.01 | ACPS |
| ATOM | 641 | CD | LYS | 81 | -12.183 | 16.669 | 46.939 | 1.00 23.45 | ACPS |
| ATOM | 642 | CE | LYS | 81 | -12.982 | 17.886 | 47.415 | 1.00 25.03 | ACPS |
| ATOM | 643 | NZ | LYS | 81 | -13.413 | 17.764 | 48.847 | 1.00 28.19 | ACPS |
| ATOM | 644 | C | LYS | 81 | -11.446 | 16.080 | 42.612 | 1.00 15.29 | ACPS |
| ATOM | 645 | O | LYS | 81 | -11.752 | 17.249 | 42.329 | 1.00 15.96 | ACPS |
| ATOM | 646 | N | ASP | 82 | -12.025 | 15.019 | 42.060 | 1.00 14.49 | ACPS |
| ATOM | 647 | CA | ASP | 82 | -13.102 | 15.191 | 41.102 | 1.00 13.96 | ACPS |
| ATOM | 648 | CB | ASP | 82 | -13.140 | 14.042 | 40.067 | 1.00 14.55 | ACPS |
| ATOM | 649 | CG | ASP | 82 | -13.516 | 12.682 | 40.660 | 1.00 14.41 | ACPS |
| ATOM | 650 | OD1 | ASP | 82 | -14.130 | 12.609 | 41.738 | 1.00 13.41 | ACPS |
| ATOM | 651 | OD2 | ASP | 82 | -13.199 | 11.666 | 40.003 | 1.00 16.39 | ACPS |
| ATOM | 652 | C | ASP | 82 | -14.440 | 15.347 | 41.816 | 1.00 14.59 | ACPS |
| ATOM | 653 | O | ASP | 82 | -14.506 | 15.366 | 43.048 | 1.00 13.66 | ACPS |
| ATOM | 654 | N | GLN | 83 | -15.506 | 15.464 | 41.038 | 1.00 16.21 | ACPS |
| ATOM | 655 | CA | GLN | 83 | -16.836 | 15.671 | 41.596 | 1.00 18.34 | ACPS |
| ATOM | 656 | CB | GLN | 83 | -17.809 | 15.984 | 40.454 | 1.00 20.79 | ACPS |
| ATOM | 657 | CG | GLN | 83 | -17.344 | 17.201 | 39.649 | 1.00 25.58 | ACPS |
| ATOM | 658 | CD | GLN | 83 | -18.065 | 17.378 | 38.327 | 1.00 28.04 | ACPS |
| ATOM | 659 | OE1 | GLN | 83 | -17.669 | 18.207 | 37.505 | 1.00 30.79 | ACPS |
| ATOM | 660 | NE2 | GLN | 83 | -19.130 | 16.606 | 38.114 | 1.00 29.51 | ACPS |
| ATOM | 661 | C | GLN | 83 | -17.351 | 14.530 | 42.465 | 1.00 18.31 | ACPS |
| ATOM | 662 | O | GLN | 83 | -18.304 | 14.707 | 43.225 | 1.00 18.85 | ACPS |
| ATOM | 663 | N | ASN | 84 | -16.722 | 13.366 | 42.363 | 1.00 18.00 | ACPS |
| ATOM | 664 | CA | ASN | 84 | -17.126 | 12.220 | 43.178 | 1.00 18.03 | ACPS |
| ATOM | 665 | CB | ASN | 84 | -16.984 | 10.901 | 42.414 | 1.00 19.80 | ACPS |
| ATOM | 666 | CG | ASN | 84 | -17.959 | 10.776 | 41.269 | 1.00 21.78 | ACPS |
| ATOM | 667 | OD1 | ASN | 84 | -19.160 | 10.993 | 41.432 | 1.00 24.79 | ACPS |
| ATOM | 668 | ND2 | ASN | 84 | -17.451 | 10.404 | 40.105 | 1.00 23.27 | ACPS |
| ATOM | 669 | C | ASN | 84 | -16.282 | 12.111 | 44.439 | 1.00 16.61 | ACPS |
| ATOM | 670 | O | ASN | 84 | -16.534 | 11.247 | 45.276 | 1.00 16.49 | ACPS |
| ATOM | 671 | N | GLY | 85 | -15.278 | 12.972 | 44.568 | 1.00 15.58 | ACPS |
| ATOM | 672 | CA | GLY | 85 | -14.424 | 12.920 | 45.741 | 1.00 14.25 | ACPS |
| ATOM | 673 | C | GLY | 85 | -13.153 | 12.107 | 45.539 | 1.00 14.48 | ACPS |
| ATOM | 674 | O | GLY | 85 | -12.368 | 11.945 | 46.475 | 1.00 14.65 | ACPS |
| ATOM | 675 | N | LYS | 86 | -12.941 | 11.597 | 44.330 | 1.00 13.84 | ACPS |
| ATOM | 676 | CA | LYS | 86 | -11.741 | 10.810 | 44.042 | 1.00 12.93 | ACPS |
| ATOM | 677 | CB | LYS | 86 | -11.911 | 10.014 | 42.745 | 1.00 13.87 | ACPS |
| ATOM | 678 | CG | LYS | 86 | -10.672 | 9.204 | 42.353 | 1.00 15.94 | ACPS |
| ATOM | 679 | CD | LYS | 86 | -10.789 | 8.679 | 40.926 | 1.00 19.84 | ACPS |
| ATOM | 680 | CE | LYS | 86 | -9.548 | 7.906 | 40.485 | 1.00 20.40 | ACPS |
| ATOM | 681 | NZ | LYS | 86 | -9.484 | 6.545 | 41.078 | 1.00 21.85 | ACPS |
| ATOM | 682 | C | LYS | 86 | -10.534 | 11.730 | 43.883 | 1.00 13.03 | ACPS |
| ATOM | 683 | O | LYS | 86 | -10.557 | 12.660 | 43.078 | 1.00 12.98 | ACPS |
| ATOM | 684 | N | PRO | 87 | -9.461 | 11.478 | 44.647 | 1.00 11.91 | ACPS |
| ATOM | 685 | CD | PRO | 87 | -9.315 | 10.444 | 45.694 | 1.00 12.38 | ACPS |
| ATOM | 686 | CA | PRO | 87 | -8.262 | 12.308 | 44.551 | 1.00 11.87 | ACPS |
| ATOM | 687 | CB | PRO | 87 | -7.556 | 12.043 | 45.874 | 1.00 10.81 | ACPS |
| ATOM | 688 | CG | PRO | 87 | -7.838 | 10.568 | 46.090 | 1.00 11.34 | ACPS |
| ATOM | 689 | C | PRO | 87 | -7.386 | 11.913 | 43.377 | 1.00 11.68 | ACPS |
| ATOM | 690 | O | PRO | 87 | -7.429 | 10.768 | 42.910 | 1.00 11.62 | ACPS |
| ATOM | 691 | N | TYR | 88 | -6.615 | 12.882 | 42.895 | 1.00 11.62 | ACPS |
| ATOM | 692 | CA | TYR | 88 | -5.639 | 12.674 | 41.830 | 1.00 11.77 | ACPS |
| ATOM | 693 | CB | TYR | 88 | -6.288 | 12.733 | 40.432 | 1.00 13.03 | ACPS |

FIG. 2A-13

| ATOM | 694 | CG  | TYR | 88 | -6.922  | 14.047 | 40.032 | 1.00 | 14.02 | ACPS |
|------|-----|-----|-----|----|---------|--------|--------|------|-------|------|
| ATOM | 695 | CD1 | TYR | 88 | -6.188  | 15.023 | 39.364 | 1.00 | 14.07 | ACPS |
| ATOM | 696 | CE1 | TYR | 88 | -6.787  | 16.222 | 38.963 | 1.00 | 14.84 | ACPS |
| ATOM | 697 | CD2 | TYR | 88 | -8.271  | 14.298 | 40.294 | 1.00 | 14.32 | ACPS |
| ATOM | 698 | CE2 | TYR | 88 | -8.877  | 15.480 | 39.898 | 1.00 | 15.51 | ACPS |
| ATOM | 699 | CZ  | TYR | 88 | -8.131  | 16.442 | 39.232 | 1.00 | 15.27 | ACPS |
| ATOM | 700 | OH  | TYR | 88 | -8.728  | 17.622 | 38.835 | 1.00 | 17.40 | ACPS |
| ATOM | 701 | C   | TYR | 88 | -4.571  | 13.748 | 42.029 | 1.00 | 11.78 | ACPS |
| ATOM | 702 | O   | TYR | 88 | -4.801  | 14.752 | 42.698 | 1.00 | 11.93 | ACPS |
| ATOM | 703 | N   | ILE | 89 | -3.385  | 13.521 | 41.487 | 1.00 | 11.68 | ACPS |
| ATOM | 704 | CA  | ILE | 89 | -2.302  | 14.482 | 41.647 | 1.00 | 12.44 | ACPS |
| ATOM | 705 | CB  | ILE | 89 | -1.037  | 13.765 | 42.199 | 1.00 | 11.85 | ACPS |
| ATOM | 706 | CG2 | ILE | 89 | 0.239   | 14.579 | 41.910 | 1.00 | 11.95 | ACPS |
| ATOM | 707 | CG1 | ILE | 89 | -1.185  | 13.538 | 43.706 | 1.00 | 11.65 | ACPS |
| ATOM | 708 | CD1 | ILE | 89 | -0.021  | 12.751 | 44.320 | 1.00 | 12.93 | ACPS |
| ATOM | 709 | C   | ILE | 89 | -1.921  | 15.214 | 40.371 | 1.00 | 12.52 | ACPS |
| ATOM | 710 | O   | ILE | 89 | -2.000  | 14.662 | 39.271 | 1.00 | 13.59 | ACPS |
| ATOM | 711 | N   | ILE | 90 | -1.527  | 16.470 | 40.539 | 1.00 | 14.09 | ACPS |
| ATOM | 712 | CA  | ILE | 90 | -1.036  | 17.282 | 39.434 | 1.00 | 14.07 | ACPS |
| ATOM | 713 | CB  | ILE | 90 | -1.937  | 18.514 | 39.151 | 1.00 | 14.62 | ACPS |
| ATOM | 714 | CG2 | ILE | 90 | -1.254  | 19.433 | 38.127 | 1.00 | 15.25 | ACPS |
| ATOM | 715 | CG1 | ILE | 90 | -3.313  | 18.067 | 38.636 | 1.00 | 15.67 | ACPS |
| ATOM | 716 | CD1 | ILE | 90 | -3.289  | 17.301 | 37.330 | 1.00 | 16.06 | ACPS |
| ATOM | 717 | C   | ILE | 90 | 0.357   | 17.780 | 39.855 | 1.00 | 14.28 | ACPS |
| ATOM | 718 | O   | ILE | 90 | 0.514   | 18.342 | 40.940 | 1.00 | 13.87 | ACPS |
| ATOM | 719 | N   | CYS | 91 | 1.362   | 17.520 | 39.016 | 1.00 | 15.25 | ACPS |
| ATOM | 720 | CA  | CYS | 91 | 2.737   | 17.974 | 39.242 | 1.00 | 15.44 | ACPS |
| ATOM | 721 | CB  | CYS | 91 | 3.677   | 16.806 | 39.561 | 1.00 | 15.30 | ACPS |
| ATOM | 722 | SG  | CYS | 91 | 5.404   | 17.317 | 39.841 | 1.00 | 14.62 | ACPS |
| ATOM | 723 | C   | CYS | 91 | 3.139   | 18.606 | 37.916 | 1.00 | 16.53 | ACPS |
| ATOM | 724 | O   | CYS | 91 | 3.585   | 17.926 | 36.990 | 1.00 | 17.19 | ACPS |
| ATOM | 725 | N   | THR | 92 | 2.958   | 19.912 | 37.830 | 1.00 | 17.43 | ACPS |
| ATOM | 726 | CA  | THR | 92 | 3.255   | 20.640 | 36.609 | 1.00 | 19.27 | ACPS |
| ATOM | 727 | CB  | THR | 92 | 2.946   | 22.137 | 36.804 | 1.00 | 20.38 | ACPS |
| ATOM | 728 | OG1 | THR | 92 | 1.550   | 22.286 | 37.117 | 1.00 | 22.97 | ACPS |
| ATOM | 729 | CG2 | THR | 92 | 3.257   | 22.920 | 35.542 | 1.00 | 21.13 | ACPS |
| ATOM | 730 | C   | THR | 92 | 4.685   | 20.436 | 36.102 | 1.00 | 19.66 | ACPS |
| ATOM | 731 | O   | THR | 92 | 4.909   | 20.405 | 34.885 | 1.00 | 19.81 | ACPS |
| ATOM | 732 | N   | LYS | 93 | 5.641   | 20.269 | 37.021 | 1.00 | 19.24 | ACPS |
| ATOM | 733 | CA  | LYS | 93 | 7.040   | 20.049 | 36.633 | 1.00 | 20.40 | ACPS |
| ATOM | 734 | CB  | LYS | 93 | 7.950   | 19.936 | 37.869 | 1.00 | 21.00 | ACPS |
| ATOM | 735 | CG  | LYS | 93 | 8.283   | 21.253 | 38.540 | 1.00 | 23.04 | ACPS |
| ATOM | 736 | CD  | LYS | 93 | 9.271   | 21.044 | 39.674 | 1.00 | 23.13 | ACPS |
| ATOM | 737 | CE  | LYS | 93 | 9.590   | 22.347 | 40.394 | 1.00 | 25.70 | ACPS |
| ATOM | 738 | NZ  | LYS | 93 | 10.683  | 22.160 | 41.393 | 1.00 | 27.21 | ACPS |
| ATOM | 739 | C   | LYS | 93 | 7.194   | 18.774 | 35.816 | 1.00 | 19.95 | ACPS |
| ATOM | 740 | O   | LYS | 93 | 8.155   | 18.624 | 35.063 | 1.00 | 19.63 | ACPS |
| ATOM | 741 | N   | LEU | 94 | 6.251   | 17.851 | 35.978 | 1.00 | 20.99 | ACPS |
| ATOM | 742 | CA  | LEU | 94 | 6.279   | 16.575 | 35.264 | 1.00 | 22.26 | ACPS |
| ATOM | 743 | CB  | LEU | 94 | 5.643   | 15.485 | 36.129 | 1.00 | 23.41 | ACPS |
| ATOM | 744 | CG  | LEU | 94 | 5.579   | 14.064 | 35.563 | 1.00 | 24.26 | ACPS |
| ATOM | 745 | CD1 | LEU | 94 | 6.980   | 13.493 | 35.405 | 1.00 | 26.39 | ACPS |
| ATOM | 746 | CD2 | LEU | 94 | 4.761   | 13.194 | 36.507 | 1.00 | 25.01 | ACPS |
| ATOM | 747 | C   | LEU | 94 | 5.530   | 16.674 | 33.936 | 1.00 | 23.14 | ACPS |
| ATOM | 748 | O   | LEU | 94 | 6.110   | 16.499 | 32.862 | 1.00 | 22.82 | ACPS |
| ATOM | 749 | N   | SER | 95 | 4.234   | 16.942 | 34.028 | 1.00 | 23.89 | ACPS |
| ATOM | 750 | CA  | SER | 95 | 3.375   | 17.074 | 32.861 | 1.00 | 25.33 | ACPS |

FIG. 2A-14

| ATOM | 751 | CB | SER | 95 | 3.268 | 15.736 | 32.112 | 1.00 | 26.52 | ACPS |
| --- | --- | --- | --- | --- | --- | --- | --- | --- | --- | --- |
| ATOM | 752 | OG | SER | 95 | 2.573 | 14.752 | 32.861 | 1.00 | 27.95 | ACPS |
| ATOM | 753 | C | SER | 95 | 2.002 | 17.531 | 33.354 | 1.00 | 25.56 | ACPS |
| ATOM | 754 | O | SER | 95 | 1.760 | 17.599 | 34.561 | 1.00 | 24.02 | ACPS |
| ATOM | 755 | N | PRO | 96 | 1.090 | 17.874 | 32.432 | 1.00 | 26.00 | ACPS |
| ATOM | 756 | CD | PRO | 96 | 1.289 | 18.101 | 30.986 | 1.00 | 26.52 | ACPS |
| ATOM | 757 | CA | PRO | 96 | -0.240 | 18.324 | 32.853 | 1.00 | 25.75 | ACPS |
| ATOM | 758 | CB | PRO | 96 | -0.709 | 19.147 | 31.657 | 1.00 | 26.31 | ACPS |
| ATOM | 759 | CG | PRO | 96 | -0.119 | 18.392 | 30.506 | 1.00 | 26.75 | ACPS |
| ATOM | 760 | C | PRO | 96 | -1.201 | 17.179 | 33.176 | 1.00 | 25.06 | ACPS |
| ATOM | 761 | O | PRO | 96 | -2.304 | 17.414 | 33.664 | 1.00 | 25.74 | ACPS |
| ATOM | 762 | N | ALA | 97 | -0.773 | 15.950 | 32.907 | 1.00 | 24.25 | ACPS |
| ATOM | 763 | CA | ALA | 97 | -1.599 | 14.769 | 33.142 | 1.00 | 23.20 | ACPS |
| ATOM | 764 | CB | ALA | 97 | -0.967 | 13.555 | 32.479 | 1.00 | 24.01 | ACPS |
| ATOM | 765 | C | ALA | 97 | -1.872 | 14.463 | 34.611 | 1.00 | 22.43 | ACPS |
| ATOM | 766 | O | ALA | 97 | -1.072 | 14.786 | 35.490 | 1.00 | 22.83 | ACPS |
| ATOM | 767 | N | ALA | 98 | -3.020 | 13.841 | 34.865 | 1.00 | 21.00 | ACPS |
| ATOM | 768 | CA | ALA | 98 | -3.411 | 13.462 | 36.215 | 1.00 | 19.60 | ACPS |
| ATOM | 769 | CB | ALA | 98 | -4.914 | 13.140 | 36.259 | 1.00 | 19.71 | ACPS |
| ATOM | 770 | C | ALA | 98 | -2.597 | 12.232 | 36.601 | 1.00 | 18.50 | ACPS |
| ATOM | 771 | O | ALA | 98 | -2.426 | 11.313 | 35.796 | 1.00 | 19.87 | ACPS |
| ATOM | 772 | N | VAL | 99 | -2.084 | 12.231 | 37.826 | 1.00 | 15.98 | ACPS |
| ATOM | 773 | CA | VAL | 99 | -1.299 | 11.120 | 38.346 | 1.00 | 14.14 | ACPS |
| ATOM | 774 | CB | VAL | 99 | -0.042 | 11.661 | 39.041 | 1.00 | 15.01 | ACPS |
| ATOM | 775 | CG1 | VAL | 99 | 0.630 | 10.575 | 39.854 | 1.00 | 15.26 | ACPS |
| ATOM | 776 | CG2 | VAL | 99 | 0.909 | 12.221 | 37.990 | 1.00 | 14.69 | ACPS |
| ATOM | 777 | C | VAL | 99 | -2.192 | 10.357 | 39.336 | 1.00 | 13.62 | ACPS |
| ATOM | 778 | O | VAL | 99 | -2.935 | 10.971 | 40.098 | 1.00 | 14.19 | ACPS |
| ATOM | 779 | N | HIS | 100 | -2.132 | 9.029 | 39.306 | 1.00 | 12.36 | ACPS |
| ATOM | 780 | CA | HIS | 100 | -2.949 | 8.192 | 40.178 | 1.00 | 12.74 | ACPS |
| ATOM | 781 | CB | HIS | 100 | -2.894 | 6.741 | 39.708 | 1.00 | 13.48 | ACPS |
| ATOM | 782 | CG | HIS | 100 | -3.505 | 6.514 | 38.362 | 1.00 | 14.92 | ACPS |
| ATOM | 783 | CD2 | HIS | 100 | -2.938 | 6.353 | 37.143 | 1.00 | 15.96 | ACPS |
| ATOM | 784 | ND1 | HIS | 100 | -4.868 | 6.432 | 38.165 | 1.00 | 15.90 | ACPS |
| ATOM | 785 | CE1 | HIS | 100 | -5.113 | 6.232 | 36.883 | 1.00 | 17.29 | ACPS |
| ATOM | 786 | NE2 | HIS | 100 | -3.960 | 6.181 | 36.241 | 1.00 | 15.85 | ACPS |
| ATOM | 787 | C | HIS | 100 | -2.513 | 8.233 | 41.630 | 1.00 | 12.24 | ACPS |
| ATOM | 788 | O | HIS | 100 | -1.328 | 8.140 | 41.927 | 1.00 | 12.33 | ACPS |
| ATOM | 789 | N | VAL | 101 | -3.487 | 8.363 | 42.525 | 1.00 | 11.72 | ACPS |
| ATOM | 790 | CA | VAL | 101 | -3.217 | 8.365 | 43.958 | 1.00 | 11.15 | ACPS |
| ATOM | 791 | CB | VAL | 101 | -2.899 | 9.811 | 44.477 | 1.00 | 11.69 | ACPS |
| ATOM | 792 | CG1 | VAL | 101 | -4.142 | 10.694 | 44.373 | 1.00 | 12.75 | ACPS |
| ATOM | 793 | CG2 | VAL | 101 | -2.391 | 9.758 | 45.924 | 1.00 | 12.34 | ACPS |
| ATOM | 794 | C | VAL | 101 | -4.430 | 7.815 | 44.725 | 1.00 | 10.53 | ACPS |
| ATOM | 795 | O | VAL | 101 | -5.565 | 7.914 | 44.253 | 1.00 | 10.71 | ACPS |
| ATOM | 796 | N | SER | 102 | -4.174 | 7.176 | 45.871 | 1.00 | 9.38 | ACPS |
| ATOM | 797 | CA | SER | 102 | -5.243 | 6.698 | 46.748 | 1.00 | 9.83 | ACPS |
| ATOM | 798 | CB | SER | 102 | -5.574 | 5.218 | 46.517 | 1.00 | 10.13 | ACPS |
| ATOM | 799 | OG | SER | 102 | -6.713 | 4.863 | 47.295 | 1.00 | 9.75 | ACPS |
| ATOM | 800 | C | SER | 102 | -4.782 | 6.906 | 48.192 | 1.00 | 9.45 | ACPS |
| ATOM | 801 | O | SER | 102 | -3.608 | 6.730 | 48.493 | 1.00 | 10.30 | ACPS |
| ATOM | 802 | N | ILE | 103 | -5.712 | 7.277 | 49.071 | 1.00 | 9.23 | ACPS |
| ATOM | 803 | CA | ILE | 103 | -5.417 | 7.563 | 50.474 | 1.00 | 9.67 | ACPS |
| ATOM | 804 | CB | ILE | 103 | -5.683 | 9.063 | 50.774 | 1.00 | 9.72 | ACPS |
| ATOM | 805 | CG2 | ILE | 103 | -5.495 | 9.382 | 52.283 | 1.00 | 8.94 | ACPS |
| ATOM | 806 | CG1 | ILE | 103 | -4.778 | 9.912 | 49.885 | 1.00 | 10.44 | ACPS |
| ATOM | 807 | CD1 | ILE | 103 | -5.088 | 11.421 | 49.938 | 1.00 | 11.38 | ACPS |

FIG. 2A-15

| ATOM | 808 | C | ILE | 103 | -6.299 | 6.728 | 51.388 | 1.00 | 9.74 | ACPS |
|---|---|---|---|---|---|---|---|---|---|---|
| ATOM | 809 | O | ILE | 103 | -7.447 | 6.432 | 51.041 | 1.00 | 9.47 | ACPS |
| ATOM | 810 | N | THR | 104 | -5.751 | 6.334 | 52.541 | 1.00 | 9.43 | ACPS |
| ATOM | 811 | CA | THR | 104 | -6.507 | 5.567 | 53.537 | 1.00 | 9.07 | ACPS |
| ATOM | 812 | CB | THR | 104 | -6.323 | 4.034 | 53.329 | 1.00 | 9.49 | ACPS |
| ATOM | 813 | OG1 | THR | 104 | -7.164 | 3.312 | 54.246 | 1.00 | 10.14 | ACPS |
| ATOM | 814 | CG2 | THR | 104 | -4.878 | 3.617 | 53.528 | 1.00 | 8.69 | ACPS |
| ATOM | 815 | C | THR | 104 | -6.067 | 5.976 | 54.949 | 1.00 | 9.89 | ACPS |
| ATOM | 816 | O | THR | 104 | -4.896 | 6.283 | 55.174 | 1.00 | 9.73 | ACPS |
| ATOM | 817 | N | HIS | 105 | -7.006 | 5.978 | 55.891 | 1.00 | 10.13 | ACPS |
| ATOM | 818 | CA | HIS | 105 | -6.734 | 6.384 | 57.266 | 1.00 | 10.93 | ACPS |
| ATOM | 819 | CB | HIS | 105 | -7.632 | 7.572 | 57.622 | 1.00 | 11.25 | ACPS |
| ATOM | 820 | CG | HIS | 105 | -7.371 | 8.805 | 56.817 | 1.00 | 11.60 | ACPS |
| ATOM | 821 | CD2 | HIS | 105 | -7.921 | 9.254 | 55.663 | 1.00 | 13.08 | ACPS |
| ATOM | 822 | ND1 | HIS | 105 | -6.442 | 9.749 | 57.192 | 1.00 | 11.93 | ACPS |
| ATOM | 823 | CE1 | HIS | 105 | -6.427 | 10.729 | 56.305 | 1.00 | 11.86 | ACPS |
| ATOM | 824 | NE2 | HIS | 105 | -7.315 | 10.451 | 55.366 | 1.00 | 12.18 | ACPS |
| ATOM | 825 | C | HIS | 105 | -6.986 | 5.299 | 58.314 | 1.00 | 11.03 | ACPS |
| ATOM | 826 | O | HIS | 105 | -7.888 | 4.471 | 58.165 | 1.00 | 12.54 | ACPS |
| ATOM | 827 | N | THR | 106 | -6.165 | 5.309 | 59.367 | 1.00 | 11.51 | ACPS |
| ATOM | 828 | CA | THR | 106 | -6.349 | 4.411 | 60.509 | 1.00 | 11.59 | ACPS |
| ATOM | 829 | CB | THR | 106 | -5.289 | 3.270 | 60.620 | 1.00 | 11.24 | ACPS |
| ATOM | 830 | OG1 | THR | 106 | -4.065 | 3.780 | 61.169 | 1.00 | 11.20 | ACPS |
| ATOM | 831 | CG2 | THR | 106 | -5.017 | 2.634 | 59.261 | 1.00 | 12.65 | ACPS |
| ATOM | 832 | C | THR | 106 | -6.225 | 5.273 | 61.771 | 1.00 | 12.23 | ACPS |
| ATOM | 833 | O | THR | 106 | -6.002 | 6.482 | 61.692 | 1.00 | 12.54 | ACPS |
| ATOM | 834 | N | LYS | 107 | -6.364 | 4.634 | 62.929 | 1.00 | 12.39 | ACPS |
| ATOM | 835 | CA | LYS | 107 | -6.269 | 5.295 | 64.229 | 1.00 | 12.12 | ACPS |
| ATOM | 836 | CB | LYS | 107 | -6.473 | 4.242 | 65.326 | 1.00 | 12.29 | ACPS |
| ATOM | 837 | CG | LYS | 107 | -5.379 | 3.146 | 65.280 | 1.00 | 13.31 | ACPS |
| ATOM | 838 | CD | LYS | 107 | -5.653 | 1.939 | 66.203 | 1.00 | 14.42 | ACPS |
| ATOM | 839 | CE | LYS | 107 | -4.660 | 0.799 | 65.876 | 1.00 | 15.82 | ACPS |
| ATOM | 840 | NZ | LYS | 107 | -4.895 | -0.473 | 66.648 | 1.00 | 18.55 | ACPS |
| ATOM | 841 | C | LYS | 107 | -4.936 | 5.998 | 64.490 | 1.00 | 12.43 | ACPS |
| ATOM | 842 | O | LYS | 107 | -4.874 | 6.970 | 65.263 | 1.00 | 14.30 | ACPS |
| ATOM | 843 | N | GLU | 108 | -3.871 | 5.516 | 63.857 | 1.00 | 11.38 | ACPS |
| ATOM | 844 | CA | GLU | 108 | -2.540 | 6.061 | 64.099 | 1.00 | 11.08 | ACPS |
| ATOM | 845 | CB | GLU | 108 | -1.692 | 4.997 | 64.823 | 1.00 | 10.76 | ACPS |
| ATOM | 846 | CG | GLU | 108 | -1.320 | 3.790 | 63.936 | 1.00 | 11.72 | ACPS |
| ATOM | 847 | CD | GLU | 108 | -0.835 | 2.550 | 64.706 | 1.00 | 11.82 | ACPS |
| ATOM | 848 | OE1 | GLU | 108 | -0.047 | 2.673 | 65.664 | 1.00 | 12.16 | ACPS |
| ATOM | 849 | OE2 | GLU | 108 | -1.224 | 1.420 | 64.329 | 1.00 | 11.39 | ACPS |
| ATOM | 850 | C | GLU | 108 | -1.788 | 6.517 | 62.858 | 1.00 | 10.37 | ACPS |
| ATOM | 851 | O | GLU | 108 | -0.769 | 7.193 | 62.977 | 1.00 | 10.85 | ACPS |
| ATOM | 852 | N | TYR | 109 | -2.292 | 6.164 | 61.676 | 1.00 | 10.03 | ACPS |
| ATOM | 853 | CA | TYR | 109 | -1.608 | 6.482 | 60.421 | 1.00 | 9.03 | ACPS |
| ATOM | 854 | CB | TYR | 109 | -1.061 | 5.195 | 59.757 | 1.00 | 10.14 | ACPS |
| ATOM | 855 | CG | TYR | 109 | -0.074 | 4.364 | 60.537 | 1.00 | 9.25 | ACPS |
| ATOM | 856 | CD1 | TYR | 109 | 1.091 | 4.927 | 61.043 | 1.00 | 9.05 | ACPS |
| ATOM | 857 | CE1 | TYR | 109 | 2.032 | 4.157 | 61.725 | 1.00 | 10.07 | ACPS |
| ATOM | 858 | CD2 | TYR | 109 | -0.283 | 2.996 | 60.730 | 1.00 | 10.49 | ACPS |
| ATOM | 859 | CE2 | TYR | 109 | 0.649 | 2.217 | 61.410 | 1.00 | 10.01 | ACPS |
| ATOM | 860 | CZ | TYR | 109 | 1.807 | 2.809 | 61.902 | 1.00 | 11.02 | ACPS |
| ATOM | 861 | OH | TYR | 109 | 2.753 | 2.042 | 62.546 | 1.00 | 11.45 | ACPS |
| ATOM | 862 | C | TYR | 109 | -2.487 | 7.101 | 59.343 | 1.00 | 9.01 | ACPS |
| ATOM | 863 | O | TYR | 109 | -3.708 | 6.991 | 59.375 | 1.00 | 9.80 | ACPS |
| ATOM | 864 | N | ALA | 110 | -1.825 | 7.735 | 58.381 | 1.00 | 9.15 | ACPS |

FIG. 2A-16

| ATOM | 865 | CA | ALA | 110 | -2.475 | 8.207 | 57.162 | 1.00 | 10.18 | ACPS |
|---|---|---|---|---|---|---|---|---|---|---|
| ATOM | 866 | CB | ALA | 110 | -2.489 | 9.726 | 57.072 | 1.00 | 9.95 | ACPS |
| ATOM | 867 | C | ALA | 110 | -1.529 | 7.598 | 56.110 | 1.00 | 8.99 | ACPS |
| ATOM | 868 | O | ALA | 110 | -0.322 | 7.843 | 56.143 | 1.00 | 10.23 | ACPS |
| ATOM | 869 | N | ALA | 111 | -2.067 | 6.776 | 55.209 | 1.00 | 9.06 | ACPS |
| ATOM | 870 | CA | ALA | 111 | -1.255 | 6.109 | 54.181 | 1.00 | 9.24 | ACPS |
| ATOM | 871 | CB | ALA | 111 | -1.319 | 4.577 | 54.371 | 1.00 | 9.27 | ACPS |
| ATOM | 872 | C | ALA | 111 | -1.710 | 6.462 | 52.773 | 1.00 | 9.10 | ACPS |
| ATOM | 873 | O | ALA | 111 | -2.877 | 6.780 | 52.551 | 1.00 | 9.14 | ACPS |
| ATOM | 874 | N | ALA | 112 | -0.782 | 6.399 | 51.822 | 1.00 | 9.52 | ACPS |
| ATOM | 875 | CA | ALA | 112 | -1.107 | 6.713 | 50.434 | 1.00 | 9.40 | ACPS |
| ATOM | 876 | CB | ALA | 112 | -0.973 | 8.219 | 50.190 | 1.00 | 10.40 | ACPS |
| ATOM | 877 | C | ALA | 112 | -0.202 | 5.984 | 49.462 | 1.00 | 9.11 | ACPS |
| ATOM | 878 | O | ALA | 112 | 0.890 | 5.548 | 49.814 | 1.00 | 9.27 | ACPS |
| ATOM | 879 | N | GLN | 113 | -0.680 | 5.843 | 48.233 | 1.00 | 10.03 | ACPS |
| ATOM | 880 | CA | GLN | 113 | 0.124 | 5.246 | 47.171 | 1.00 | 10.71 | ACPS |
| ATOM | 881 | CB | GLN | 113 | -0.221 | 3.768 | 46.949 | 1.00 | 12.50 | ACPS |
| ATOM | 882 | CG | GLN | 113 | -1.607 | 3.525 | 46.382 | 1.00 | 14.15 | ACPS |
| ATOM | 883 | CD | GLN | 113 | -1.910 | 2.053 | 46.181 | 1.00 | 16.57 | ACPS |
| ATOM | 884 | OE1 | GLN | 113 | -2.978 | 1.699 | 45.686 | 1.00 | 17.95 | ACPS |
| ATOM | 885 | NE2 | GLN | 113 | -0.978 | 1.187 | 46.581 | 1.00 | 19.32 | ACPS |
| ATOM | 886 | C | GLN | 113 | -0.088 | 6.047 | 45.884 | 1.00 | 10.42 | ACPS |
| ATOM | 887 | O | GLN | 113 | -1.121 | 6.698 | 45.701 | 1.00 | 11.38 | ACPS |
| ATOM | 888 | N | VAL | 114 | 0.905 | 5.998 | 45.002 | 1.00 | 10.88 | ACPS |
| ATOM | 889 | CA | VAL | 114 | 0.872 | 6.727 | 43.742 | 1.00 | 11.50 | ACPS |
| ATOM | 890 | CB | VAL | 114 | 1.770 | 8.002 | 43.834 | 1.00 | 12.48 | ACPS |
| ATOM | 891 | CG1 | VAL | 114 | 1.994 | 8.613 | 42.444 | 1.00 | 12.51 | ACPS |
| ATOM | 892 | CG2 | VAL | 114 | 1.144 | 9.013 | 44.779 | 1.00 | 11.66 | ACPS |
| ATOM | 893 | C | VAL | 114 | 1.409 | 5.888 | 42.589 | 1.00 | 11.78 | ACPS |
| ATOM | 894 | O | VAL | 114 | 2.295 | 5.055 | 42.772 | 1.00 | 11.30 | ACPS |
| ATOM | 895 | N | VAL | 115 | 0.839 | 6.099 | 41.405 | 1.00 | 12.16 | ACPS |
| ATOM | 896 | CA | VAL | 115 | 1.322 | 5.454 | 40.195 | 1.00 | 12.60 | ACPS |
| ATOM | 897 | CB | VAL | 115 | 0.426 | 4.301 | 39.706 | 1.00 | 12.42 | ACPS |
| ATOM | 898 | CG1 | VAL | 115 | 0.957 | 3.778 | 38.377 | 1.00 | 14.70 | ACPS |
| ATOM | 899 | CG2 | VAL | 115 | 0.388 | 3.172 | 40.736 | 1.00 | 12.57 | ACPS |
| ATOM | 900 | C | VAL | 115 | 1.364 | 6.525 | 39.109 | 1.00 | 12.96 | ACPS |
| ATOM | 901 | O | VAL | 115 | 0.351 | 7.167 | 38.821 | 1.00 | 13.15 | ACPS |
| ATOM | 902 | N | ILE | 116 | 2.547 | 6.732 | 38.534 | 1.00 | 13.59 | ACPS |
| ATOM | 903 | CA | ILE | 116 | 2.736 | 7.708 | 37.454 | 1.00 | 15.01 | ACPS |
| ATOM | 904 | CB | ILE | 116 | 4.044 | 8.514 | 37.619 | 1.00 | 15.13 | ACPS |
| ATOM | 905 | CG2 | ILE | 116 | 4.252 | 9.422 | 36.391 | 1.00 | 15.76 | ACPS |
| ATOM | 906 | CG1 | ILE | 116 | 4.011 | 9.353 | 38.901 | 1.00 | 14.74 | ACPS |
| ATOM | 907 | CD1 | ILE | 116 | 5.326 | 10.082 | 39.168 | 1.00 | 15.57 | ACPS |
| ATOM | 908 | C | ILE | 116 | 2.881 | 6.907 | 36.164 | 1.00 | 16.45 | ACPS |
| ATOM | 909 | O | ILE | 116 | 3.750 | 6.032 | 36.076 | 1.00 | 16.35 | ACPS |
| ATOM | 910 | N | GLU | 117 | 2.054 | 7.205 | 35.165 | 1.00 | 18.81 | ACPS |
| ATOM | 911 | CA | GLU | 117 | 2.142 | 6.481 | 33.894 | 1.00 | 21.39 | ACPS |
| ATOM | 912 | CB | GLU | 117 | 0.760 | 6.363 | 33.245 | 1.00 | 22.18 | ACPS |
| ATOM | 913 | CG | GLU | 117 | -0.272 | 5.679 | 34.124 | 1.00 | 23.46 | ACPS |
| ATOM | 914 | CD | GLU | 117 | -1.560 | 5.358 | 33.391 | 1.00 | 24.48 | ACPS |
| ATOM | 915 | OE1 | GLU | 117 | -1.582 | 4.373 | 32.622 | 1.00 | 25.10 | ACPS |
| ATOM | 916 | OE2 | GLU | 117 | -2.550 | 6.092 | 33.580 | 1.00 | 25.49 | ACPS |
| ATOM | 917 | C | GLU | 117 | 3.097 | 7.186 | 32.938 | 1.00 | 23.33 | ACPS |
| ATOM | 918 | O | GLU | 117 | 3.386 | 8.367 | 33.101 | 1.00 | 23.55 | ACPS |
| ATOM | 919 | N | ALA | 118 | 3.596 | 6.460 | 31.943 | 1.00 | 25.38 | ACPS |
| ATOM | 920 | CA | ALA | 118 | 4.516 | 7.055 | 30.979 | 1.00 | 27.43 | ACPS |
| ATOM | 921 | CB | ALA | 118 | 4.977 | 6.002 | 29.985 | 1.00 | 27.34 | ACPS |

FIG. 2A-17

| ATOM | 922 | C | ALA | 118 | 3.841 | 8.208 | 30.244 | 1.00 | 28.57 | ACPS |
|---|---|---|---|---|---|---|---|---|---|---|
| ATOM | 923 | OT1 | ALA | 118 | 2.598 | 8.169 | 30.110 | 1.00 | 29.57 | ACPS |
| ATOM | 924 | OT2 | ALA | 118 | 4.563 | 9.133 | 29.800 | 1.00 | 30.29 | ACPS |
| ATOM | 925 | O | HOH | 1 | 8.184 | 16.571 | 66.146 | 1.00 | 24.49 | WAT |
| ATOM | 926 | O | HOH | 2 | 8.785 | 8.855 | 56.929 | 1.00 | 23.58 | WAT |
| ATOM | 927 | O | HOH | 3 | -6.634 | 6.371 | 40.520 | 1.00 | 13.40 | WAT |
| ATOM | 928 | O | HOH | 4 | 6.850 | 6.588 | 56.334 | 1.00 | 12.56 | WAT |
| ATOM | 929 | O | HOH | 5 | -8.045 | 6.689 | 43.987 | 1.00 | 13.42 | WAT |
| ATOM | 930 | O | HOH | 6 | -5.322 | 9.243 | 59.567 | 1.00 | 14.25 | WAT |
| ATOM | 931 | O | HOH | 7 | -8.408 | 6.897 | 46.767 | 1.00 | 10.54 | WAT |
| ATOM | 932 | O | HOH | 8 | 0.163 | 8.272 | 65.337 | 1.00 | 14.13 | WAT |
| ATOM | 933 | O | HOH | 9 | -14.561 | 9.350 | 40.005 | 1.00 | 16.00 | WAT |
| ATOM | 934 | O | HOH | 10 | 5.984 | 9.787 | 56.562 | 1.00 | 12.10 | WAT |
| ATOM | 935 | O | HOH | 11 | 9.603 | 20.654 | 50.362 | 1.00 | 18.90 | WAT |
| ATOM | 936 | O | HOH | 12 | 9.199 | 12.001 | 56.416 | 1.00 | 20.43 | WAT |
| ATOM | 937 | O | HOH | 13 | -5.501 | 13.397 | 53.431 | 1.00 | 13.06 | WAT |
| ATOM | 938 | O | HOH | 14 | -2.767 | 25.961 | 44.622 | 1.00 | 17.37 | WAT |
| ATOM | 939 | O | HOH | 15 | 1.460 | 20.979 | 40.473 | 1.00 | 16.78 | WAT |
| ATOM | 940 | O | HOH | 16 | -6.412 | 20.992 | 45.756 | 1.00 | 19.74 | WAT |
| ATOM | 941 | O | HOH | 17 | -6.145 | 9.042 | 41.305 | 1.00 | 12.90 | WAT |
| ATOM | 942 | O | HOH | 18 | -0.223 | 24.078 | 42.670 | 1.00 | 18.93 | WAT |
| ATOM | 943 | O | HOH | 19 | -7.596 | 19.455 | 37.156 | 1.00 | 19.34 | WAT |
| ATOM | 944 | O | HOH | 20 | -5.063 | 33.496 | 51.266 | 1.00 | 22.07 | WAT |
| ATOM | 945 | O | HOH | 21 | -1.492 | 0.933 | 67.571 | 1.00 | 14.90 | WAT |
| ATOM | 946 | O | HOH | 22 | 10.843 | 7.091 | 38.836 | 1.00 | 23.19 | WAT |
| ATOM | 947 | O | HOH | 23 | 1.577 | 14.422 | 68.706 | 1.00 | 24.82 | WAT |
| ATOM | 948 | O | HOH | 24 | -7.606 | 8.898 | 61.270 | 1.00 | 18.79 | WAT |
| ATOM | 949 | O | HOH | 25 | 0.081 | 9.327 | 35.513 | 1.00 | 22.45 | WAT |
| ATOM | 950 | O | HOH | 26 | -6.295 | 18.339 | 48.365 | 1.00 | 15.49 | WAT |
| ATOM | 951 | O | HOH | 27 | -0.673 | 19.887 | 66.759 | 1.00 | 21.01 | WAT |
| ATOM | 952 | O | HOH | 28 | 2.234 | 22.708 | 42.588 | 1.00 | 18.21 | WAT |
| ATOM | 953 | O | HOH | 29 | 5.866 | 5.790 | 62.516 | 1.00 | 18.49 | WAT |
| ATOM | 954 | O | HOH | 30 | 0.991 | 15.961 | 36.660 | 1.00 | 18.35 | WAT |
| ATOM | 955 | O | HOH | 31 | -6.406 | 9.357 | 38.563 | 1.00 | 20.48 | WAT |
| ATOM | 956 | O | HOH | 32 | -11.957 | 11.623 | 37.352 | 1.00 | 24.33 | WAT |
| ATOM | 957 | O | HOH | 33 | -10.389 | 14.434 | 49.725 | 1.00 | 27.42 | WAT |
| ATOM | 958 | O | HOH | 34 | -4.448 | 20.165 | 63.854 | 1.00 | 24.32 | WAT |
| ATOM | 959 | O | HOH | 35 | 1.450 | 2.725 | 43.903 | 1.00 | 20.38 | WAT |
| ATOM | 960 | O | HOH | 36 | -9.847 | 19.977 | 43.739 | 1.00 | 23.75 | WAT |
| ATOM | 961 | O | HOH | 37 | -4.274 | 35.006 | 45.404 | 1.00 | 20.66 | WAT |
| ATOM | 962 | O | HOH | 38 | -0.833 | 22.659 | 40.326 | 1.00 | 19.80 | WAT |
| ATOM | 963 | O | HOH | 39 | -10.345 | 18.568 | 67.239 | 1.00 | 20.80 | WAT |
| ATOM | 964 | O | HOH | 40 | -8.477 | 13.551 | 55.975 | 1.00 | 26.24 | WAT |
| ATOM | 965 | O | HOH | 41 | -5.655 | 29.371 | 49.873 | 1.00 | 28.51 | WAT |
| ATOM | 966 | O | HOH | 42 | -10.675 | 16.934 | 50.659 | 1.00 | 24.92 | WAT |
| ATOM | 967 | O | HOH | 43 | -12.936 | 12.520 | 51.596 | 1.00 | 27.30 | WAT |
| ATOM | 968 | O | HOH | 44 | 5.317 | 21.159 | 39.730 | 1.00 | 21.12 | WAT |
| ATOM | 969 | O | HOH | 45 | -16.788 | 9.865 | 48.461 | 1.00 | 26.54 | WAT |
| ATOM | 970 | O | HOH | 46 | -11.077 | 6.886 | 57.927 | 1.00 | 23.02 | WAT |
| ATOM | 971 | O | HOH | 47 | 8.239 | 21.236 | 62.377 | 1.00 | 34.53 | WAT |
| ATOM | 972 | O | HOH | 48 | -12.230 | 29.900 | 51.577 | 1.00 | 21.86 | WAT |
| ATOM | 973 | O | HOH | 49 | 14.440 | 16.080 | 45.556 | 1.00 | 23.96 | WAT |
| ATOM | 974 | O | HOH | 50 | 12.861 | 21.772 | 39.431 | 1.00 | 30.68 | WAT |
| ATOM | 975 | O | HOH | 51 | -14.091 | 19.163 | 60.526 | 1.00 | 27.55 | WAT |
| ATOM | 976 | O | HOH | 52 | 6.663 | 27.800 | 61.179 | 1.00 | 32.84 | WAT |
| ATOM | 977 | O | HOH | 53 | -11.635 | 27.871 | 53.345 | 1.00 | 31.03 | WAT |
| ATOM | 978 | O | HOH | 54 | -6.997 | 7.591 | 67.044 | 1.00 | 25.57 | WAT |

FIG. 2A-18

| ATOM | 979 | O | HOH | 55 | 5.799 | 6.629 | 59.843 | 1.00 | 16.31 | WAT |
|---|---|---|---|---|---|---|---|---|---|---|
| ATOM | 980 | O | HOH | 56 | 2.012 | 25.703 | 66.142 | 1.00 | 35.32 | WAT |
| ATOM | 981 | O | HOH | 57 | 0.121 | 2.727 | 31.610 | 1.00 | 42.03 | WAT |
| ATOM | 982 | O | HOH | 58 | 1.534 | 10.328 | 32.415 | 1.00 | 41.42 | WAT |
| ATOM | 983 | O | HOH | 59 | -16.524 | 4.165 | 56.298 | 1.00 | 21.92 | WAT |
| ATOM | 984 | O | HOH | 60 | -13.305 | 16.632 | 64.615 | 1.00 | 23.56 | WAT |
| ATOM | 985 | O | HOH | 61 | -12.177 | 16.550 | 67.442 | 1.00 | 20.64 | WAT |
| ATOM | 986 | O | HOH | 62 | -14.009 | 9.985 | 52.284 | 1.00 | 25.38 | WAT |
| ATOM | 987 | O | HOH | 63 | -9.900 | 9.225 | 59.680 | 1.00 | 23.49 | WAT |
| ATOM | 988 | O | HOH | 64 | -6.771 | 33.311 | 45.569 | 1.00 | 21.83 | WAT |
| ATOM | 989 | O | HOH | 65 | -2.713 | 20.087 | 61.546 | 1.00 | 24.39 | WAT |
| ATOM | 990 | O | HOH | 66 | -7.980 | 17.897 | 68.615 | 1.00 | 22.87 | WAT |
| ATOM | 991 | O | HOH | 67 | -13.405 | 7.809 | 38.191 | 1.00 | 26.90 | WAT |
| ATOM | 992 | O | HOH | 68 | -4.952 | 28.402 | 44.638 | 1.00 | 33.63 | WAT |
| ATOM | 993 | O | HOH | 69 | -2.685 | 3.686 | 68.288 | 1.00 | 31.25 | WAT |
| ATOM | 994 | O | HOH | 70 | 8.512 | 9.048 | 60.830 | 1.00 | 28.65 | WAT |
| ATOM | 995 | O | HOH | 71 | -1.486 | 18.163 | 62.740 | 1.00 | 32.45 | WAT |
| ATOM | 996 | O | HOH | 72 | 5.603 | 18.678 | 70.084 | 1.00 | 26.38 | WAT |
| ATOM | 997 | O | HOH | 73 | -7.547 | 29.689 | 51.621 | 1.00 | 29.41 | WAT |
| ATOM | 998 | O | HOH | 74 | 10.855 | 19.331 | 52.981 | 1.00 | 26.05 | WAT |
| ATOM | 999 | O | HOH | 75 | -11.689 | 10.901 | 61.337 | 1.00 | 28.27 | WAT |
| ATOM | 1000 | O | HOH | 76 | -0.166 | 23.981 | 38.303 | 1.00 | 33.92 | WAT |
| ATOM | 1001 | O | HOH | 77 | -11.224 | 22.643 | 66.111 | 1.00 | 30.50 | WAT |
| ATOM | 1002 | O | HOH | 78 | 15.942 | 18.609 | 39.466 | 1.00 | 35.09 | WAT |
| ATOM | 1003 | O | HOH | 79 | -9.721 | 15.254 | 57.360 | 1.00 | 23.81 | WAT |
| ATOM | 1004 | O | HOH | 80 | -9.623 | 11.467 | 57.685 | 1.00 | 26.57 | WAT |
| ATOM | 1005 | O | HOH | 81 | -10.600 | 4.395 | 59.079 | 1.00 | 26.62 | WAT |
| ATOM | 1006 | O | HOH | 82 | -8.498 | 10.896 | 38.078 | 1.00 | 35.64 | WAT |
| ATOM | 1007 | O | HOH | 83 | -2.753 | 18.652 | 65.536 | 1.00 | 26.51 | WAT |
| ATOM | 1008 | O | HOH | 84 | 9.568 | 24.455 | 43.921 | 1.00 | 31.56 | WAT |
| ATOM | 1009 | O | HOH | 85 | 19.835 | 12.684 | 45.040 | 1.00 | 35.96 | WAT |
| ATOM | 1010 | O | HOH | 86 | 13.338 | 21.812 | 46.003 | 1.00 | 39.76 | WAT |
| ATOM | 1011 | O | HOH | 87 | 11.096 | 20.032 | 59.974 | 1.00 | 34.99 | WAT |
| ATOM | 1012 | O | HOH | 88 | 3.720 | 23.855 | 40.646 | 1.00 | 31.59 | WAT |
| ATOM | 1013 | O | HOH | 89 | -1.224 | 22.461 | 66.261 | 1.00 | 34.76 | WAT |
| ATOM | 1014 | O | HOH | 90 | -7.691 | 9.770 | 63.766 | 1.00 | 31.45 | WAT |
| ATOM | 1015 | O | HOH | 91 | 17.406 | 11.773 | 44.998 | 1.00 | 29.99 | WAT |
| ATOM | 1016 | O | HOH | 92 | -1.506 | 7.951 | 67.587 | 1.00 | 28.61 | WAT |
| ATOM | 1017 | O | HOH | 93 | -3.462 | 10.383 | 67.429 | 1.00 | 32.97 | WAT |
| ATOM | 1018 | O | HOH | 94 | -2.310 | 12.680 | 66.265 | 1.00 | 27.88 | WAT |
| ATOM | 1019 | O | HOH | 95 | -4.299 | 16.505 | 66.744 | 1.00 | 34.32 | WAT |
| ATOM | 1020 | O | HOH | 96 | 0.990 | 24.911 | 62.972 | 1.00 | 31.02 | WAT |
| ATOM | 1021 | O | HOH | 97 | -13.635 | 13.854 | 63.282 | 1.00 | 15.69 | WAT |
| ATOM | 1022 | O | HOH | 98 | -12.472 | 13.178 | 48.835 | 1.00 | 25.84 | WAT |
| ATOM | 1023 | O | HOH | 99 | 0.796 | 0.192 | 42.865 | 1.00 | 28.22 | WAT |
| ATOM | 1024 | N1 | COA | 120 | -12.948 | 7.608 | 44.920 | 1.00 | 13.13 | COA |
| ATOM | 1025 | C2 | COA | 120 | -11.643 | 7.336 | 45.414 | 1.00 | 12.29 | COA |
| ATOM | 1026 | N3 | COA | 120 | -11.182 | 7.731 | 46.667 | 1.00 | 13.13 | COA |
| ATOM | 1027 | C4 | COA | 120 | -12.090 | 8.415 | 47.420 | 1.00 | 12.87 | COA |
| ATOM | 1028 | C5 | COA | 120 | -13.461 | 8.771 | 47.064 | 1.00 | 12.68 | COA |
| ATOM | 1029 | C6 | COA | 120 | -13.899 | 8.321 | 45.698 | 1.00 | 13.32 | COA |
| ATOM | 1030 | N6 | COA | 120 | -15.094 | 8.573 | 45.246 | 1.00 | 13.97 | COA |
| ATOM | 1031 | N7 | COA | 120 | -14.087 | 9.450 | 48.042 | 1.00 | 13.45 | COA |
| ATOM | 1032 | C8 | COA | 120 | -13.179 | 9.555 | 49.021 | 1.00 | 14.05 | COA |
| ATOM | 1033 | N9 | COA | 120 | -11.940 | 8.949 | 48.707 | 1.00 | 12.82 | COA |
| ATOM | 1034 | C1* | COA | 120 | -10.508 | 8.739 | 49.433 | 1.00 | 12.92 | COA |
| ATOM | 1035 | C2* | COA | 120 | -10.131 | 10.063 | 49.988 | 1.00 | 12.61 | COA |

FIG. 2A-19

| | | | | | | | | | |
|---|---|---|---|---|---|---|---|---|---|
| ATOM | 1036 | O2* | COA | 120 | -8.885 | 10.585 | 49.617 | 1.00 13.09 | COA |
| ATOM | 1037 | C3* | COA | 120 | -10.321 | 9.967 | 51.470 | 1.00 12.95 | COA |
| ATOM | 1038 | O3* | COA | 120 | -9.269 | 10.478 | 52.488 | 1.00 12.93 | COA |
| ATOM | 1039 | P3* | COA | 120 | -9.182 | 12.127 | 52.589 | 1.00 13.47 | COA |
| ATOM | 1040 | O7 | COA | 120 | -8.835 | 12.768 | 51.184 | 1.00 13.51 | COA |
| ATOM | 1041 | O8 | COA | 120 | -8.049 | 12.448 | 53.626 | 1.00 13.28 | COA |
| ATOM | 1042 | O9 | COA | 120 | -10.609 | 12.596 | 53.131 | 1.00 14.44 | COA |
| ATOM | 1043 | C4* | COA | 120 | -10.208 | 8.375 | 51.725 | 1.00 13.08 | COA |
| ATOM | 1044 | O4* | COA | 120 | -10.977 | 7.897 | 50.509 | 1.00 12.26 | COA |
| ATOM | 1045 | C5* | COA | 120 | -10.401 | 7.949 | 53.127 | 1.00 14.58 | COA |
| ATOM | 1046 | O5* | COA | 120 | -10.469 | 6.473 | 52.938 | 1.00 13.48 | COA |
| ATOM | 1047 | P1 | COA | 120 | -10.652 | 5.672 | 54.364 | 1.00 12.56 | COA |
| ATOM | 1048 | O1 | COA | 120 | -9.729 | 6.240 | 55.365 | 1.00 13.21 | COA |
| ATOM | 1049 | O2 | COA | 120 | -10.459 | 4.226 | 54.119 | 1.00 15.04 | COA |
| ATOM | 1050 | O3 | COA | 120 | -12.029 | 6.083 | 54.854 | 1.00 16.52 | COA |
| ATOM | 1051 | P2 | COA | 120 | -13.553 | 5.541 | 54.845 | 1.00 22.65 | COA |
| ATOM | 1052 | O4 | COA | 120 | -13.663 | 4.249 | 55.488 | 1.00 23.91 | COA |
| ATOM | 1053 | O5 | COA | 120 | -14.429 | 6.530 | 55.551 | 1.00 25.17 | COA |
| ATOM | 1054 | O6 | COA | 120 | -13.926 | 5.591 | 53.277 | 1.00 23.32 | COA |
| ATOM | 1055 | C11 | COA | 120 | -14.755 | 4.650 | 51.149 | 1.00 25.32 | COA |
| ATOM | 1056 | C12 | COA | 120 | -13.824 | 4.473 | 52.426 | 1.00 24.46 | COA |
| ATOM | 1057 | C13 | COA | 120 | -14.105 | 5.689 | 50.154 | 1.00 25.05 | COA |
| ATOM | 1058 | C14 | COA | 120 | -14.799 | 3.243 | 50.564 | 1.00 25.09 | COA |
| ATOM | 1059 | C10 | COA | 120 | -16.252 | 5.244 | 51.556 | 1.00 26.37 | COA |
| ATOM | 1060 | O10 | COA | 120 | -17.086 | 5.395 | 50.361 | 1.00 26.75 | COA |
| ATOM | 1061 | C9 | COA | 120 | -17.067 | 4.353 | 52.553 | 1.00 27.72 | COA |
| ATOM | 1062 | O39 | COA | 120 | -16.649 | 4.199 | 53.819 | 1.00 28.04 | COA |
| ATOM | 1063 | N8 | COA | 120 | -18.144 | 3.780 | 52.101 | 1.00 30.34 | COA |
| ATOM | 1064 | C7 | COA | 120 | -19.329 | 3.490 | 52.916 | 1.00 32.23 | COA |
| ATOM | 1065 | C42 | COA | 120 | -19.224 | 2.064 | 53.477 | 1.00 33.78 | COA |
| ATOM | 1066 | C43 | COA | 120 | -19.805 | 1.971 | 54.888 | 1.00 34.86 | COA |
| ATOM | 1067 | O44 | COA | 120 | -20.414 | 2.967 | 55.487 | 1.00 36.24 | COA |
| ATOM | 1068 | N4 | COA | 120 | -19.632 | 0.789 | 55.446 | 1.00 34.84 | COA |
| ATOM | 1069 | C3 | COA | 120 | -20.112 | 0.432 | 56.852 | 1.00 34.67 | COA |
| ATOM | 1070 | C47 | COA | 120 | -19.736 | -0.998 | 57.112 | 1.00 34.47 | COA |
| ATOM | 1071 | S1 | COA | 120 | -20.877 | -2.208 | 56.301 | 1.00 33.46 | COA |
| ATOM | 1072 | CA+2 | CA2 | 1 | 7.365 | 8.523 | 54.928 | 1.00 11.64 | IONS |
| ATOM | 1073 | CL-1 | CL1 | 2 | 5.841 | 9.868 | 59.601 | 1.00 16.02 | IONS |
| ATOM | 1074 | CA+2 | CA2 | 3 | 0.000 | 0.000 | 65.920 | 0.33 1.00 | IONS |

END

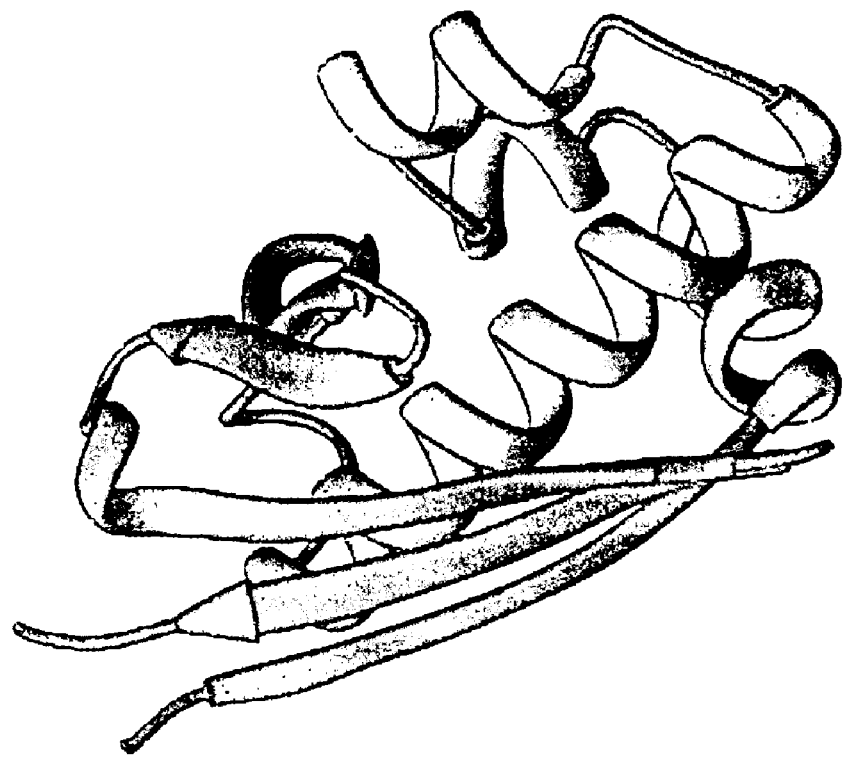
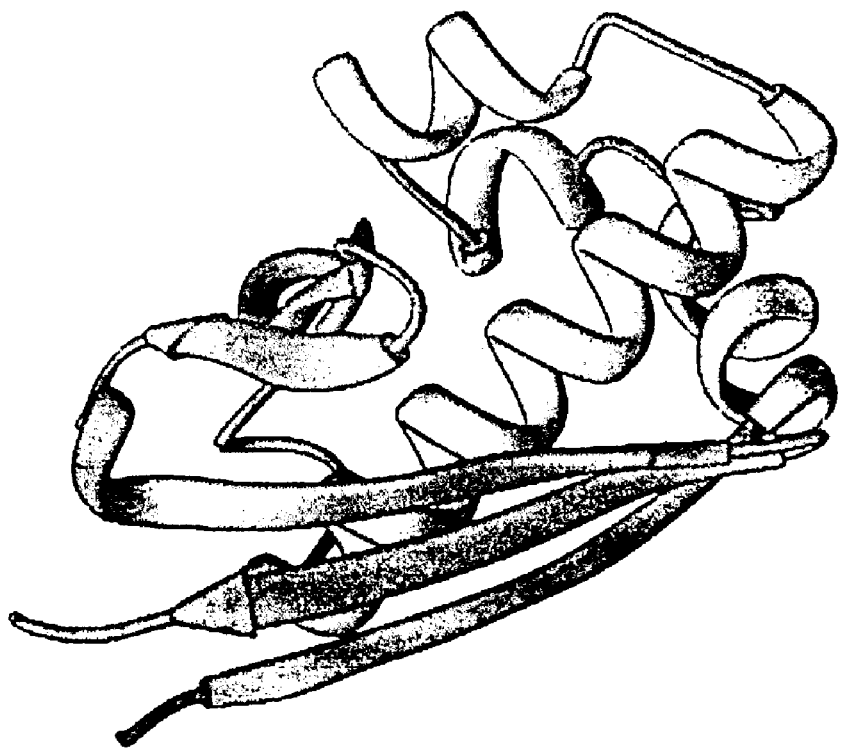
FIG. 3B

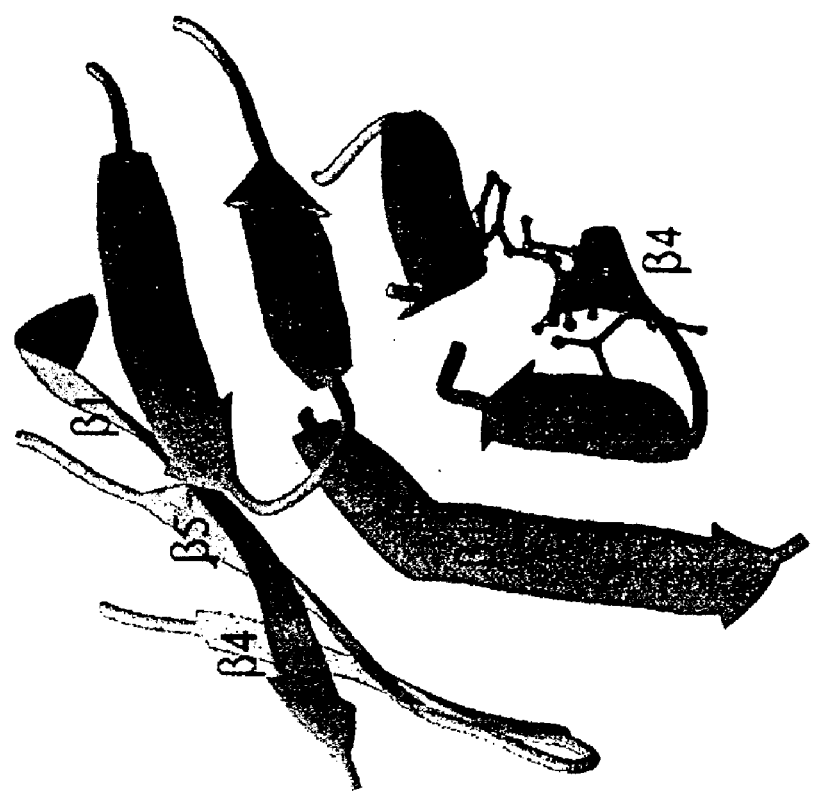
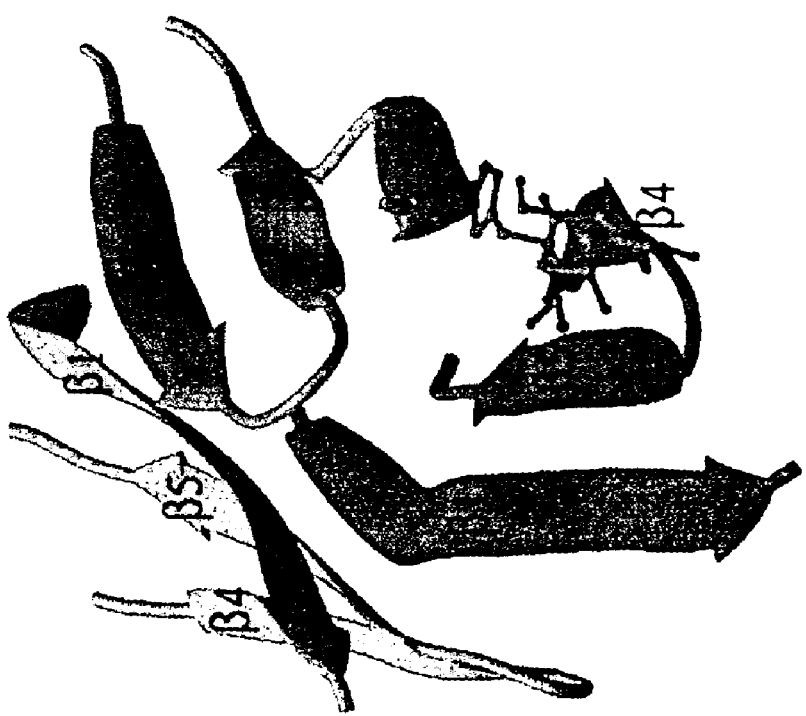
FIG. 4

15% Non-reducing, denaturing gel of ACPS samples before and after analytical centrifugation

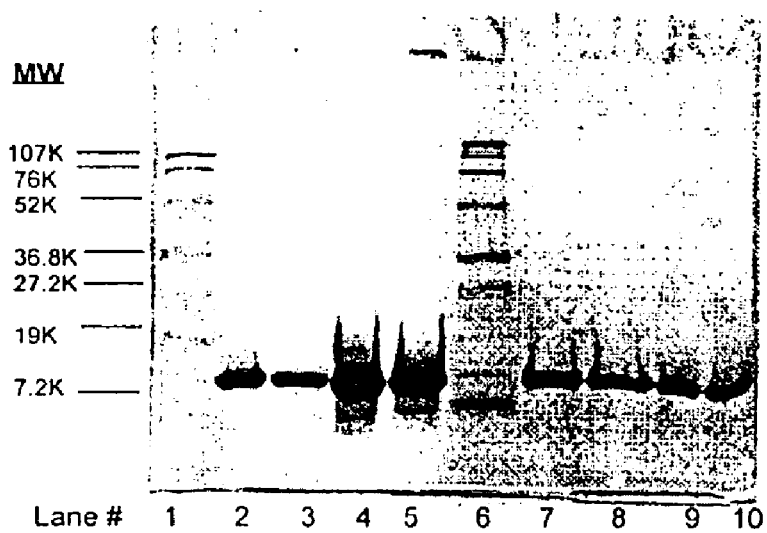

| Lane # | ACPS samples |
|---|---|
| 2 | pH 5.2 |
| 3 | pH 5.2, heated 10 min at 100 deg in gel sample buffer |
| 4 | pH 6.4, after sedimentation equilibrium expt. |
| 5 | pH 6.4, after equilibrium expt, heated 10 min at 100deg in gel buffer |
| 7 | pH 7.4 |
| 8 | pH 7.4, heated 10 min at 100 deg in gel buffer |
| 9 | pH 6.4 |
| 10 | pH 6.4, heated 10 min at 100 deg in gel sample buffer |

Lanes 2, 3, 7, 8, 9, 10: 20 uL of a freshly prepared 32 ujM ACPS sample was added
Lanes 4, 5: 20 uL of the 100 uM ACPS pH 6.4 solution from the sedimentation equilbrium experiment was used

FIG. 7

MIYGI GLDIT ELKRI ASMAG RQKRF AERIL
TRSEL DQYYE LSEKR KNEFL AGRFA AKEAF
SKAFG TGIGR QLSFQ DIEIR KDQNG KPYII
CTKLS QAAVH VSITH TKEYA AAQVV IERLS
S

FIG. 8

```
Aquifex         1   ----MIGVDIVKNERIKDALERFGDKFLDRIYTKRELEYCY----AHCDFLPCLAARWAG
Chlamydophila   1   MEIIHIGTDIIEISRIREAIATHGNRLLNRIFTEAEQKYCL----EKTDPIPSFAGRFAG
Helicobacter    1   ----MIGIDIVSIARIEKCVKRFKMKFLERFLSPSEIVLCK----DKSS---SIAGFFAL
Staphylococcus  1   -MIHGIGVDLIEIDRIQALYSKQ-PKLVERILTKNEQHKFNN-FTHEQRKIEFLAGRFAT
Thermotoga      1   -MIVGVGIDVLEVERVP-------EKFAERILGESEKRLF---LTRKRRR-EFIAGRFAL
Escherichia     1   MAILGLGTDIVEIARIEAVIARSGDRLARRVLSDNEWAIWK---THHQPV-RFLAKRFAY
Rickettsia      1   -MLIGVGTDIVQIPRIEKILNIYQELFAKKILALKELKQFT--LLNKTNHATFLAKRFSA
Streptomyces    1   MSIIGVGIDVAEVERFGA-ALERTPALAGRLFLESELLLP----GGERRGVASLAARFAA
Treponema       1   -MIIGVGIDIVEIERFVS-WTHNVRLLR-RFFHQEEIVDF----FKNHMRAQFLATRFAA
Bacillus        1   -MIYGIGLDITELKRIAS-MAGRQKRFAERILTRSELDQYY--ELSEKRKNEFLAGRFAA
Bradyrhizobium  1   -MIIGIGSDLIDITRVGKVIERHGERFLDRIFTAAERAKAERRAKNEKMVVATYAKRFAA
Mycobacterium   1   MGIVGVGIDLVSIPDFAEQVSQPGTVFM-TIFTPGERRDAS---VKSSSAVCHLAARWAV
consensus       1              G D                       E                    A
                1   1........10........20........30........40........50........

Aquifex         53  KEAVLKAFYTEFKIFL-------RFKEIEILGNRGRPPTVVINRE--GVEEILKNY----E
Chlamydophila   57  KEAVAKALGTGIGSVV------AWKDIEVFKVSHGPEVLLPS----HVYAKIGIS----K
Helicobacter    50  KEACSKALQVGIGKEL------SFLDIKISKSPKNAPLITLSK---EKMDYFNIQ----S
Staphylococcus  58  KEAFSKALGTGLGKHV------AFNDIDCYNDELGKPKI---------DYEGF-----I
Thermotoga      49  KEAFFKALGTGLNGH-------SFTDVEFLESN-GKPVLCVH------KDFGFFN----Y
Escherichia     57  KEAAAKAFGTGIRNGL------AFNQFEVFNDELGKPRLRLWGEALKLAEKLGVA----N
Rickettsia      58  KEAVSKAFGVGIGRGI------NFKDITILNDNLGKPTVEISS---HYTNKLAPF----N
Streptomyces    56  KEALAKALGAPAG--L------LWTDAEVWVEAGGRPRLRVTGTVAARAAELGVA----S
Treponema       54  KEAFGKALGTGLRN-M------ELRNIRVCQNGWGKPRLEVYGAAQAMLAATGGT----H
Bacillus        57  KEAFSKAFGTGIGRQL------SFQDIEIRKDQNGKPYIICT--------KLSQA----A
Bradyrhizobium  60  KEACSKALGTGIRRGV------WWRDMGVVNLPGGRPTMQLTGGALARLQALTPDGFEAR
Mycobacterium   57  KEAVIKAWSGSRFAQRPMLPENIHRDIEVVNDMWGRPRVRLTG---AIAKHLTDV----T
consensus       61  KEA   KA
                61  61........70........80........90........100.......110........

Aquifex        101  VIVSLSHERDYSVAVAYIKKKS-------------------
Chlamydophila  103  VILSISHCKEYATATAIALA---------------------
Helicobacter    97  LSASISHDAGFAIAVVVSSSNE-------------------
Staphylococcus  97  VHVSISHTEHYAMSQVVLEK----------SAF--------
Thermotoga      91  AHVSLSH-DRFAVALVVLEKRKGDIIVEGDESFLRKRFEVLERSVEGWEIETSLPPFTLK
Escherichia    107  MHVTLADERHYACATVIIES---------------------
Rickettsia     105  IHLSLSDDYPICIAFAIIESNC-------------------
Streptomyces   104  WHVSLSHDAGIASAVVIAEG---------------------
Treponema      103  IQVSLTHEREVASAIVIIEGEPL------------------
Cacillus        99  VHVSITHTKEYAAAQVVIERLSS------------------
Bradyrhizobium 114  IDVSITDDWPLAQAFVIISAVPLAKS---------------
Mycobacterium  110  IHVSLTHEGDIAAAVVILEVL--------------------
consensus      121
               121  121......130.......140.......150.......160.......170........

Aquifex             -------------------
Chlamydophila       -------------------
Helicobacter        -------------------
Staphylococcus      -------------------
Thermotoga     150  KLLESSGCRLVRYGNILIGE
Excherichia         -------------------
Rickettsia          -------------------
Streptomyces        -------------------
Treponema           -------------------
Bacillus            -------------------
Bradyrhizobium      -------------------
Mycobacterium       -------------------
consensus      181
               181  181......190........
```

FIG. 9

METHODS FOR IDENTIFYING AN AGENT THAT INTERACTS WITH AN ACTIVE SITE OF ACYL CARRIER PROTEIN SYNTHASE OR ACYL CARRIER PROTEIN SYNTHASE COMPLEX

This application claims the benefit of U.S. Provisional Application No. 60/178,639 filed Jan. 28, 2000.

BACKGROUND OF THE INVENTION

Acyl Carrier Proteins (ACPs) play important roles in a number of biosynthetic pathways that are dependent upon acyl group transfers. They are most often associated with the biosynthesis of fatty acids [1,2], but they are also utilized in the synthesis of polyketide antibiotics [3,4], non-ribosomal peptides [5,6], and of intermediates used in the synthesis of vitamins such as the protein-bound coenzymes, lipoic acid [7] and biotin [8]. The ACP in each of these pathways is composed of 80–100 residues and is either an integrated domain in a larger multi-functional protein (Type I) or is a structurally independent protein that is part of a non-aggregated multi-enzyme system (Type II). Type I ACPs are found in mammals, fungi and certain Mycobacteria while type II ACPs are utilized by plants and most bacteria. The fact that these proteins are essential for the maturation of the organism has led to their investigation as targets for the development of new anti-microbial agents [9–12].

ACPs require post-translational modification for activity. They are converted from an inactive apo-form to an active holo-form by the transfer of the 4'-phosphopantetheinyl (P-pant) moiety of coenzyme A to a conserved serine on the ACP. Evidence now suggests [13] that each ACP that is dependent upon P-pant attachment for activation has its own acyl carrier protein synthase responsible for this attachment.

The post-translational modification of the fatty acid synthase ACP is performed by holo-[acyl carrier protein] synthase (hereinafter defined as "ACPS"; Enzyme Commission No. 2.7.8.7). ACPS produces holo-fatty acid synthase ACP by transferring the P-pant moiety to Ser-36 of the apo-fatty acid synthase ACP in a magnesium dependent reaction [14] as follows:

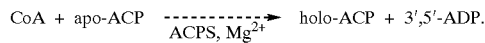

The over-expression and purification of the ACPS from *Escherichia coli* has been described [15] and this protein has been classified as a member of a new enzyme superfamily, the phosphopantetheinyl transferases [13]. Other members of this superfamily have low similarity with *E. coli* ACPS (12–22%), but each has been shown to possess P-pant transferase activity. Alignment of these proteins show that two regions, residues 5–13 and 51–65 (*E. coli* ACPS numbering), are highly conserved with eight of the residues in these regions being strictly conserved.

While numerous members of the phosphopantetheinyl transferase superfamily have been identified and sequenced, until the present invention, no one, to the inventors' knowledge, has discovered the crystal structure of an ACPS-like phosphopantetheinyl transferase or has characterized the three dimensional structure of the molecule's Co-A active site. Determination of the three dimensional structure of ACPS and its CoA active site is critical to the rational identification and/or design of therapeutic or antibiotic agents that may act as inhibitors or activators of ACPS enzymatic activity. Alternatively, using conventional drug assay techniques, the only way to identify such an agent is to screen thousands of test compounds, either in culture or by administration to suitable animal models in a laboratory setting, until an agent having the desired inhibitory or activating effect on a target compound is identified. Necessarily, such conventional screening methods are expensive, time consuming, and do not elucidate the method of action of the identified agent on the target compound.

However, advancing X-ray, spectroscopic and computer modeling technologies allow researchers to visualize the three dimensional structure of a targeted compound. Using such a three dimensional structure, researchers identify putative binding sites and then identify or design agents to interact with these binding sites. These agents are then screened for an activating or inhibitory effect upon the target molecule. In this manner, not only are the number of agents to be screened for the desired activity greatly reduced, but the mechanism of action on the target compound is better understood. Further, the three dimensional structure of one compound determined using these techniques can be used to ascertain the three dimensional structure of other related compounds.

Recently, Reuter, et al. have disclosed the crystal structure of another member of the P-pant transferase superfamily, Sfp, complexed with CoA [22]. Sfp converts the inactive apo forms of the seven PCP domains of surfactin synthetase to their active holo-forms by transfer of the 4'-phosphopantetheinyl moiety of CoA to the side chain hydroxyl of a serine residue found in PCP domains. Thus, Sfp is essential in the production of lipoheptapeptide antibiotic surfactin in *B. subtilis* [22].

The "Sfp-like" P-pant transferases are very different than the "ACPS-like" P-pant transferases. In particular, the Sfp-like P-pant transferases activate PCP (peptidyl carrier protein) domains of various non-ribosomal peptide synthetases and are present in monomeric form. Further, Sfp shows a pseudo 2-fold symmetry dividing the molecule into two similarly folded halves of roughly identical size. In contrast, the ACPS-like P-pant transferases, which form homodimers, activate the ACP domains or subunits of fatty acid synthetases, polyketide synthases and other enzymes, and are about half the size of Sfp-like transferases. While the pseudo 2-fold symmetry of the Sfp synthetase activating enzyme disclosed by Reuter, et al. suggests that dimerization may be necessary for the formation of an intact ACPS-like P-pant transferase [22], the crystal structure of Sfp, alone or complexed with CoA, is not sufficient to generate a three dimensional model of an ACPS-like P-pant transferase nor is it useful for designing or identifying agents which may activate or inhibit ACPS enzymatic activity. Furthermore, as discussed below, there are significant differences between the Sfp and ACPS structures that clearly place the two enzymes in different functional groups of the P-pant transferase superfamily.

SUMMARY OF THE INVENTION

The present invention relates to a crystallized ACPS-like phosphopantetheinyl (P-pant) transferase, and in particular, to an acyl carrier protein synthase (ACPS), as well as to a crystallized complex comprising acyl carrier protein synthase and coenzyme A (CoA) (hereinafter referred to as "ACPS-CoA complex"). The invention is further directed to the three dimensional structure of the ACPS-like P-pant transferases, including ACPS and the ACPS-CoA complex, as determined using crystallographic analysis (with or without sedimentation analysis) of ACPS and the ACPS-COA complex. Particularly, the invention is directed to the three dimensional structure of the CoA binding site present in ACPS and other ACPS-like P-pant transferases that mediates P-pant attachment from CoA to various carrier proteins, alone and as complexed with CoA or other agents that interact with the CoA binding site of said transferases. Identification of the three dimensional structure of the CoA binding site will be valuable for the design of antibiotics and other agents that interfere with P-pant attachment, thereby preventing activation of corresponding carrier proteins.

The invention additionally provides a method for identifying an agent that interacts with any active site of ACPS, comprising the steps of determining a putative active site of ACPS from a three dimensional model of the ACPS enzyme, and by performing various computer fitting analyses to identify an agent which interacts with the putative active site. Such agents may act as inhibitors or activators of ACPS activity, as determined by obtaining the identified agent, contacting the same with ACPS and measuring the agent's effect on ACPS activity. Similarly, the present invention also provides a method for identifying an agent that interacts with any active site of an ACPS-CoA complex, comprising the steps of determining a putative active site of an ACPS-COA complex from a three dimensional model of the ACPS-CoA complex, and performing various computer fitting analyses to identify an agent which interacts with the putative active site. Again, such agents may act as inhibitors or activators of ACPS-CoA complex activity, as determined by obtaining the identified agent, contacting the same with ACPS-CoA complex, and measuring the agent's effect on ACPS-CoA complex activity.

Yet another aspect of the present invention is a method for identifying an activator or inhibitor of any molecule or molecular complex which comprises a CoA binding site, including any member of the ACPS-like P-pant transferases, comprising the steps of generating a three dimensional model of said molecule or molecular complex using the relative structural coordinates according to FIGS. 1 and 1A-1 to 1A-107 or FIGS. 2 and 2A-1 to 2A-19 of residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR 66, GLY67, ILE68 and PHE74 from a second monomer of ACPS, ± a root mean square deviation from the backbone atoms of said residues of not more than 1.5 Å, and then selecting or designing a candidate activator or inhibitor that interacts with said molecule or molecular complex using computer fitting analyses of interactions between the three dimensional model of the molecule or molecular complex and the candidate activator or inhibitor. The effect of the candidate activator or inhibitor may be evaluated by obtaining the candidate activator or inhibitor, contacting the same with the molecule or molecular complex, and measuring the effect of the candidate activator or inhibitor on molecular or molecular complex activity.

Alternatively, the three dimensional model of the molecule or molecular complex comprising a CoA binding site may be determined using the relative structural coordinates according to FIGS. 1 and 1A-1 to 1A-107 or FIGS. 2 and 2A-1 to 2A-19 of residues ARG53, ASN84, GLY85, LYS86, PRO87, ILE103, THR104, and HIS105 from one monomer of ACPS and ASP8, PHE25, ARG28, ILE29, PHE54, GLU58, SER61, LYS62, GLY65, THR66, GLY67, ILE68 and PHE74 from a second monomer of ACPS, or alternatively, of residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, in each case ± a root mean square deviation from the backbone atoms of said amino acids of not more than 1.5 Å. Also provided by the present invention are the activators or inhibitors selected or designed using the above-noted methods.

Still further, the present invention is directed to a method of determining the three dimensional structure of a molecule or molecular complex whose structure is unknown, comprising the steps of first obtaining crystals of the molecule or molecular complex whose structure is unknown, and then generating X-ray diffraction data from the crystallized molecule or molecular complex. The X-ray diffraction data from the molecule or molecular complex is compared with the known three dimensional structures determined from the ACPS and/or ACPS-CoA crystals of the present invention, and molecular replacement analysis is used to conform the known three dimensional structures to the X-ray diffraction data from the crystallized molecule or molecular complex.

Finally, the present invention provides the CoA active site of an ACPS-like P-pant transferase, including, but not limited to, an ACPS, comprising, alternatively, (a) the relative structural coordinates according to FIG. 1 and 1A-1 to 1A-107 of ARG45, PHE49, ARG53, LYS81, ASN84, GLY85, LYS86, PRO87, ILE103, THR104 and HIS105 from one monomer of ACPS, and ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, (b) the structural coordinates according to FIG. 1 and 1A-1 to 1A-107 of residues ARG53, ASN84, GLY85, LYS86, PRO87, ILE103, THR104, and HIS105 from one monomer of ACPS and ASP8, PHE25, ARG28, ILE29, PHE54, GLU58, SER61, LYS62, GLY65, THR66, GLY67, ILE68 and PHE74 from a second monomer of AGPS, in each case ± a root mean square deviation from the backbone atoms of said amino acids of not more than 1.5 Å, or (c) the structural coordinates according to FIGS. 1 and 1A-1 to 1A-107 of residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, in each case ± a root mean square deviation from the backbone atoms of said amino acids of not more than 1.5 Å.

In an additional embodiment, the present invention provides the CoA active site of an ACPS-like P-pant transferase, including, but not limited to, an ACPS, wherein said active site is in its bound configuration, and comprising alternatively, (a) the relative structural coordinates according to FIGS. 2 and 2A-1 to 2A-19 of ARG45, PHE49, ARG53, LYS81, ASN84, GLY85, LYS86, PRO87, ILE103, THR104 and HIS105 from one monomer of ACPS, and ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, (b) the structural coordinates according to FIGS. 2 and 2A-1 to 2A-19 of residues ARG53, ASN84, GLY85, LYS86, PRO87, ILE103, THR104, and HIS105 from one monomer of ACPS and ASP8, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, or (c) the structural coordinates according to FIGS. 2 and 2A-1 to 2A-19 of residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, in each case ± a root mean square deviation from the backbone atoms of said amino acids of not more than 1.5 Å.

BRIEF DESCRIPTION OF THE FIGURES

FIGS. 1 and 1A-1 to 1A-107 lists the atomic structure coordinates for ACPS as derived by X-ray diffraction of an ACPS crystal. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure (Å$^2$). "MOL" indicates the segment identification used to uniquely identify each molecule.

FIGS. 2 and 2A-1 to 2A-19 lists the atomic structure coordinates for ACPS and CoA as derived by X-ray diffraction of an AGPS-CoA crystal. Figure headings are as noted above.

FIG. 3B is the stereo image of the ribbon diagram of the ACPS molecule from the ACPS-CoA complex structure, with the secondary structure elements labeled according to the Richardson diagram shown in FIG. 3C.

FIG. 4 is a stereo diagram showing how the β-sheets from the ACPS molecule interact to form a three-faced β-sandwich in the trimer.

FIG. 5 illustrates interactions among the coenzyme A molecule, the ACPS protein and solvent molecules.

FIG. 7 depicts a non-reducing, denaturing gel of ACPS samples before and after analytical centrifugation experiments.

FIG. 8 depicts the amino acid sequence of ACPS (SEQ ID NO:1) isolated from *B. subtilis,* deposited as SWISS-PROT accession number P96618.

FIG. 9 illustrates the alignment of amino acid sequences for twelve members of the ACPS family, including the consensus sequence. Depicted are amino acid sequences for *Aquifex 1 (SEQ ID NO:*2), *Chiamydophila* (SEQ ID NO:3), *Helicobacter* (SEQ ID NO:4), *Staphylococcus* (SEQ ID NO:5), *Thermotoga* (SEQ ID NO:6), *Escherichia* (SEQ ID NO:7), *Rickettsia* (SEQ ID NO:8), *Streptomyces* (SEQ ID NO:9), *Treponema* (SEQ ID NO:10), *Bacillus* (SEQ ID NO:11), *Bradyrhizobium* (SEQ ID NO:12), and *Mycobacterium* (SEQ ID NO:13).

DETAILED DESCRIPTION OF THE INVENTION

Figure 3A:
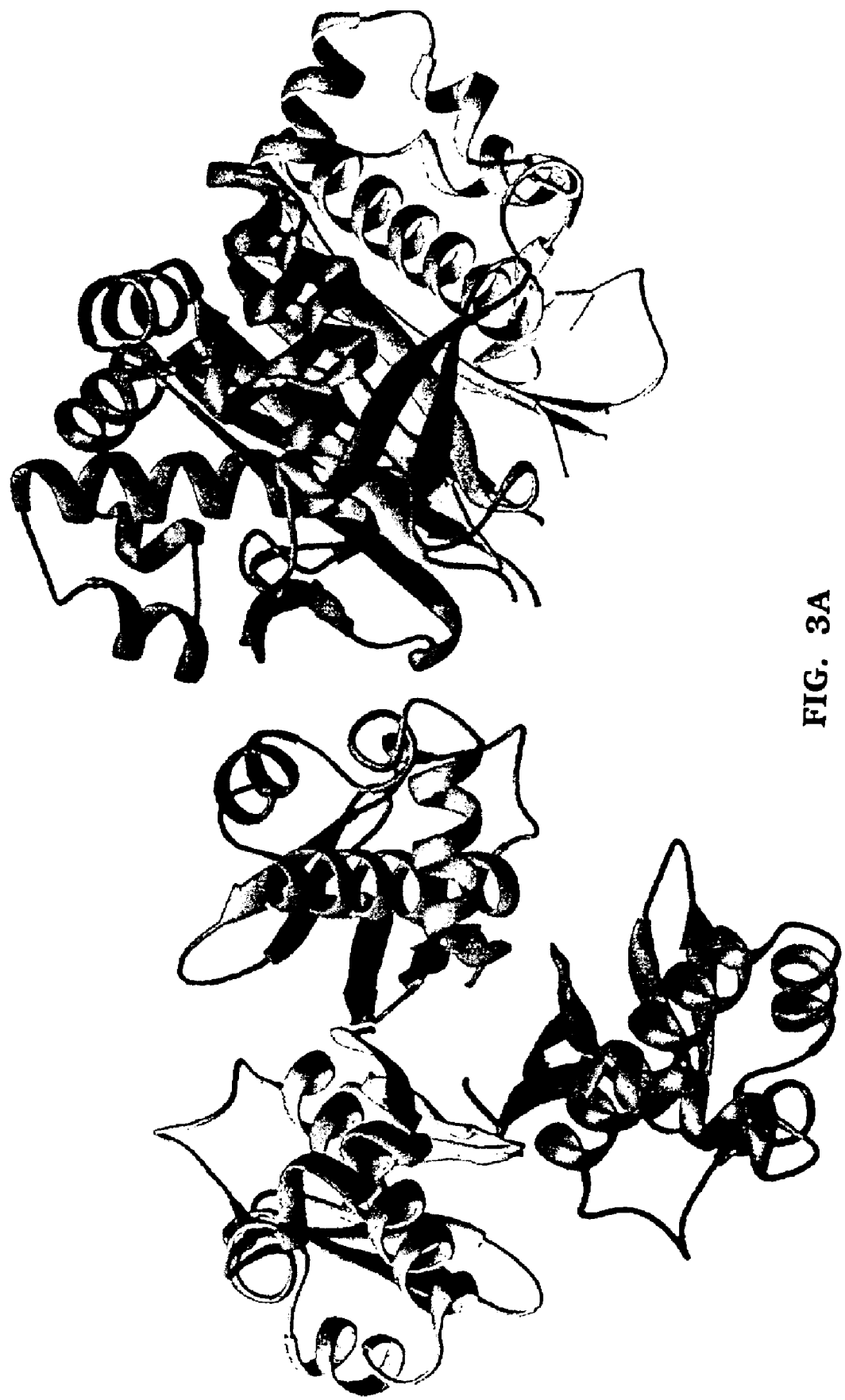
FIG. 3A is a diagram showing the arrangement of the six monomers in the monoclinic ACPS structure into two trimers in the asymmetric unit.
Figure 3C:
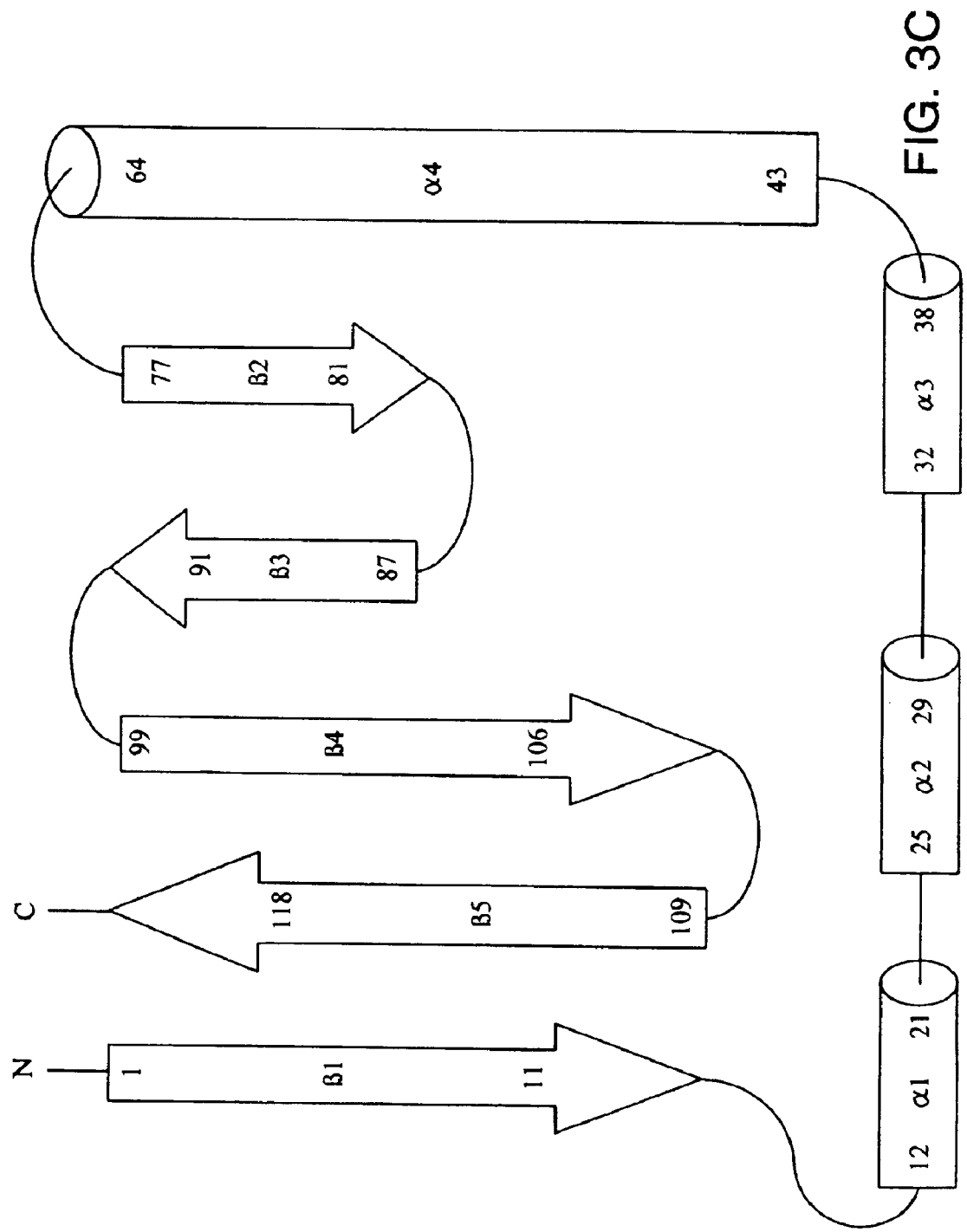

As used herein, the following terms and phrases shall have the meanings set forth below:

"ACPS" includes acyl carrier protein synthases as well as "ACPS-like" P-pant transferases. Acyl carrier protein synthases produce a holo-fatty acid synthase ACP by transferring the P-pant moiety to Ser-36 (or equivalent Serine) of an apo-fatty acid synthase ACP in a magnesium dependent reaction. "ACPS-like" P-pant transferases are those enzymes having P-pant transferase activity (i.e., that transfer the 4'-phosphopantetheinyl moiety of CoA to a conserved serine on the corresponding target molecule) which form homodimers and activate the ACP domains or subunits of fatty acid synthases, polyketide synthases or other enzymes.

Unless otherwise indicated, "protein" shall include a protein, polypeptide or peptide.

An "agent" shall include a protein, polypeptide, peptide, nucleic acid, including DNA or RNA, molecule, compound, antibiotic or drug.

"Root mean square deviation" is the square root of the arithmetic mean of the squares of the deviations from the mean, and is a way of expressing deviation or variation from the structural coordinates of ACPS and ACPS-CoA described herein.

It will be obvious to the skilled practitioner that the numbering of the amino acid residues in the various isoforms of ACPS or in other ACPS-like P-pant transferases may be different than that set forth herein. Corresponding amino acids and conservative substitutions in other isoforms or P-pant transferases are easily identified by visual inspection of the relevant amino acid sequences or by using commercially available homology software programs. "Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic).

The present invention is directed to a crystallized ACPS-like P-pant transferase, and more specifically, to a crystallized acyl carrier protein synthase enzyme, that effectively diffracts X-rays for the determination of the structural coordinates of the enzyme. The invention further provides a crystallized ACPS-COA complex that effectively diffracts X-rays for the determination of the structural coordinates of the ACPS-CoA complex.

As used herein, the protein used in the ACPS crystals and crystal complexes of the present invention includes any protein (i.e., as used herein, any protein, polypeptide or peptide), isolated from any source (including, but not limited to, a protein isolated from *Aquifex, Chiamydophila, Helicobacter, Staphylococcus, Thermotoga, Escherichia, Rickertsia, Streptomyces, Treponema, Bacillus, Bradyrhizobium,* and *Mycobacterium*), wherein said protein has ACPS-like P-pant transferase activity, and further comprises the consensus sequence as shown in FIG. 9. Additionally, the protein used in the ACPS crystals and crystal complexes of the present invention includes proteins having ACPS-like P-pant transferase activity which comprise the relative structural coordinates according to FIGS. 1 and 1A-1 to 1A-107 or FIGS. 2 and 2A-1 to 2A-19 for the residues GLY6, ASP8, ALA51, LYS57, GLU58, ARG53, ALA59, LYS62 and ALA63, ± a root mean square deviation from the backbone atoms of said amino acids of not more than 1.5 Å, or more preferably not more than 1.5 Å, or most preferably, not more than 0.5 Å. In a preferred embodiment of the invention and as exemplified below, ACPS is cloned and isolated from *B. subtilis,* and then overexpressed in a commercially available *E. coli* system.

In an alternate embodiment of the present invention, the ACPS used to generate the crystals and/or crystal complexes of the present invention comprises amino acid residues ASP8, GLU11, ARG14, MET18, PHE25, ARG28, ILE29, ARG45, PHE49, ARG53, PHE54, GLU58, SER61, LYS62, GLY65, THR66, GLY67, ILE68, PHE74, LYS81, ASN84, GLY85, LYS86, PRO87, ILE103, THR104, and HIS105, or conservative substitutions thereof. These amino acids constitute a depression which defines the CoA active site in the three dimensional structure of the ACPS enzyme, wherein the depression is more particularly comprised of the relative structural coordinates according to FIGS. 1 and 1A-1 to 1A-107 or FIGS. 2 and 2A-1 to 2A-19 of residues ARG45, PHE49, ARG53, LYS81, ASN84, GLY85, LYS86, PRO87, ILE103, THR104 and HIS105 from one monomer of ACPS, and residues ASP8, GLU11, ARG14, MET18, PHE25, ARG28, ILE29, PHE54, GLU58, SER61, LYS62, GLY65, THR66, GLY67, ILE68 and PHE74 from a second molecule of ACPS, ± a root mean square deviation from the backbone atoms of said amino acids of not more than 1.5 Å, or more preferably not more than 1.5 Å, or most preferably, not more than 0.5 Å.

There are six ACPS molecules in the asymmetric unit of the ACPS crystal. In one embodiment of the invention, the relative structural coordinates according to FIGS. 1 and 1A-1 to 1A-107 of the two monomers forming the depression defining the CoA active site are of residues ARG45, PHE49, ARG53, LYS81, ASN84, GLY85, LYS86, PRO87, ILE103, THR104 and HIS105 from ACPS1, and residues ASP8, GLU11, ARG14, MET18, PHE25, ARG28, ILE29, PHE54, GLU58, SER61, LYS62, GLY65, THR66, GLY67, ILE68 and PHE74 from ACPS2. In alternate embodiments, the relative structural coordinates according to FIGS. 1 and 1A-1 to 1A-107 are from ACPS2 and ACPS3, respectively; from ACPS1 and ACPS3, respectively; from ACPS4 and ACPS5, respectively; from ACPS5 and ACPS6, respectively; and from ACPS4 and ACPS6, respectively.

In an alternate preferred embodiment, the ACPS used to generate the crystals and/or crystal complexes of the present invention comprises amino acid residues which are within 4 Å of the CoA molecule associated with the ACPS CoA binding site. In a specific embodiment, the ACPS comprises amino acid residues ASP8, PHE25, ARG28, ILE29, ARG53, PHE54, GLU58, SER61, LYS62, GLY65, THR66, GLY67, ILE68, PHE74, ASN84, GLY85, LYS86, PRO87, ILE103, THR104, and HIS105, or conservative substitutions thereof. Such residues specifically comprise the relative structural coordinates according to FIGS. 1 and 1A-1 to 1A-107 or FIGS. 2 and 2A-1 to 2A-19 of residues ARG53, ASN84, GLY85, LYS86, PRO87, ILE103, THR104, and HIS105 from one monomer of ACPS and ASP8, PHE25, ARG28, ILE29, PHE24, GLU58, SER61, LYS62, GLY65, THR66, GLY67, ILE68, and PHE74 from a second monomer of ACPS, ± a root mean square deviation from the backbone atoms of said amino acids of not more than 1.5 Å, or more preferably not more than 1.0 Å, or most preferably, not more than 0.5 Å. In alternate embodiments, the relative structural coordinates according to FIGS. 1 and 1A-1 to 1A-107 are from ACPS1 and ACPS2, respectively; from ACPS2 and ACPS3, respectively; from ACPS1 and ACPS3, respectively; from ACPS4 and ACPS5, respectively; from ACPS5 and ACPS6, respectively; and from ACPS4 and ACPS6, respectively.

In yet another alternate preferred embodiment, the ACPS used to generate the crystals and/or crystal complexes of the present invention comprises amino acid residues which are within 4 Å to 8 Å of the CoA molecule associated with the ACPS CoA binding site. Specifically, such residues include ILE5, GLY6, LEU7, ILE9, THR10, ARG14, ILE15, MET18, GLN22, LEU41, ARG45, GLU48, PHE49, LEU50, ALA51, GLY52, ALA55, LYS57, ALA59, PHE60, ALA63, PHE64, GLY69, ARG70, GLN71, LEU72, ILE79, ARG80, LYS81, ASP82, GLN83, TYR88, VAL101, SER102, THR106, TYR109, ALA110, and ALA111, or conservative substitutions thereof. Such residues more particularly comprise the relative structural coordinates according to FIGS. 1 and 1A-1 to 1A-107 or FIGS. 2 and 2A-1 to 2A-19 of residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, ± a root mean square deviation from the backbone atoms of said amino acids of not more than 1.5 Å (or more preferably not more than 1.0 Å, or most preferably, not more than 0.5 Å), and more specifically may comprise the relative structural coordinates of residues according to FIGS. 1 and 1A-1 to 1A-107 from ACPS1 and ACPS2, respectively; from ACPS2 and ACPS3, respectively; from ACPS1 and ACPS3, respectively; from ACPS4 and ACPS5, respectively; from ACPS5 and ACPS6, respectively; and from ACPS4 and ACPS6, respectively.

Further, the ACPS used to generate the crystals and/or crystal complexes of the present invention may comprise the entire 121 amino acid residues of FIG. 8, and the structural coordinates of these residues according to FIGS. 1 and 1A-1 to 1A-107 or FIGS. 2 and 2A-1 to 2A-19, ± a root mean square deviation from the backbone atoms of said amino acid residues of not more than 1.5 Å, or more preferably not more than 1.0 Å, or most preferably, not more than 0.5 Å.

The crystals of the present invention may take a wide variety of forms, all of which are included in the present invention. However, in a preferred embodiment of the present invention, the crystallized ACPS enzyme is characterized as being in plate form with space group $P2_1$, and having unit cell parameters of a=76.26 Å, b=76.16 Å, c=85.69 Å, and beta=93.3°, and further consists of six molecules of ACPS in the asymmetric unit. Similarly, in a preferred embodiment of the present invention, the crystallized ACPS-CoA complex is characterized as being in pyramidal form with space group R3, and having unit cell parameters of a=b=55.82 Å and c=92.28 Å, and further consists of one molecule of ACPS and one molecule of CoA in the asymmetric unit.

Once a crystal or crystal complex of the present invention is grown, X-ray diffraction data can be collected by a variety of means in order to obtain the atomic coordinates of the crystallized molecule or molecular complex. With the aid of specifically designed computer software, such crystallographic data can be used to generate a three dimensional structure of the molecule or molecular complex. Various methods used to generate and refine the three dimensional structure of a crystallized molecule or molecular structure are well known to those skilled in the art, and include, without limitation, multiwavelength anomalous dispersion (MAD), multiple isomorphous replacement, reciprocal space solvent flattening, molecular replacement, and single isomorphous replacement with anomalous scattering (SIRAS).

The three dimensional structure of the preferred ACPS enzyme of the present invention exists in its active state as a trimer, wherein each copy of the ACPS molecule comprises amino acid residues 1–118 as shown in FIG. 8. The core of the enzyme is an α helix (α4) composed of residues 43 to 64, which runs the entire length of the protein. One side of this helix is covered by an antiparallel β sheet (the A-sheet), with topology β1, β5 and β4. A β ribbon composed of strands β3 and β2, combine with α3 to cover another side of helix α4. The encasement of α4 is completed by α1, α2 and a loop consisting of residues 66–75.

Molecular modeling methods known in the art may be used to identify an active site of the ACPS molecule or ACPS molecular complex. The identification of putative active sites of a molecule or molecular complex is of great importance, as most often the biological activity of a molecule or molecular complex results from the interaction between an agent and one or more active sites of the molecule or molecular complex. Accordingly, the active sites of a molecule or molecular complex are the best targets to use in the design or selection of activators or inhibitors that affect the activity of the molecule or molecular complex.

As used herein, an "active site" refers to a region of a molecule or molecular complex that, as a result of its shape and charge potential, interacts with another agent (including, without limitation, a protein, polypeptide, peptide, nucleic acid, including DNA or RNA, molecule, compound, antibiotic or drug). The agent may be an activator or inhibitor of the molecular or molecular complex activity. The present invention is directed to a CoA active site of an ACPS-like P-pant transferase, including the active site of an acyl carrier protein synthase, comprising the relative structural coordinates according to FIGS. 1 and 1A-1 to 1A-107 of residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, or more preferably, not more than 1.0 Å, or most preferably, not more than 0.5 Å. More specifically, the active site of ACPS in its native (i.e., unbound) state may comprise the relative structural coordinates of the residues according to FIGS. 1 and 1A-1 to 1A-107 from ACPS1 and ACPS2, respectively; from ACPS2 and ACPS3, respectively; from ACPS1 and ACPS3, respectively; from ACPS4 and ACPS5, respectively; from ACPS5 and ACPS6, respectively; and from ACPS4 and ACPS6, respectively.

In an alternate embodiment, the GoA active site of the present invention comprises the relative structural coordinates according to FIGS. 1 and 1A-1 to 1A-107 of residues ARG53, ASN84, GLY85, LYS86, PRO87, ILE103, THR104, and HIS 105 from one monomer of ACPS and of residues ASP8, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, or more preferably not more than 1.0 Å, or most preferably, not more than 0.5 Å. The active site may comprise the relative structural coordinates of the residues according to FIGS. 1 and 1A-1 to 1A-107 from ACPS1 and ACPS2, respectively; from ACPS2 and ACPS3, respectively; from ACPS1 and ACPS3, respectively; from ACPS4 and ACPS5, respectively; from ACPS5 and ACPS6, respectively; and from ACPS4 and ACPS6, respectively.

In a yet further embodiment, the CoA active site of the present invention comprises the relative structural coordinates according to FIGS. 1 and 1A-1 to 1A-107 of residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and of residues ILES, GLY6, LEU7, ILE9, THR10, ARG14, ILE 15, MET18, GLN22, ALA55, LYS57, ALA59, PHE60, ALA63, PHE64, GLY69, ARG70, GLN71 and LEU72 from a second monomer of ACPS, in each case ± a root mean square deviation from the backbone atoms of said amino acids of not more than 1.5 Å, or more preferably, not more than 1.0 Å, and most preferably, not more than 0.5 Å. The active site may comprise the relative structural coordinates of the residues according to FIGS. 1 and 1A-1 to 1A-107 from ACPS1 and ACPS2, respectively; from ACPS2 and ACPS3, respectively; from ACPS1 and ACPS3, respectively; from ACPS4 and ACPS5, respectively; from ACPSS and ACPS6, respectively; and from ACPS4 and ACPS6, respectively.

Further still, an alternate embodiment of the CoA active site of the present invention comprises the relative structural coordinates according to FIGS. 1 and 1A-1 to 1A-107 of GLY6, ASP8, ALA51, ARGS3, LYS57, GLU58, ALA59, LYS62 and ALA63, ± a root mean square deviation from the backbone atoms of said amino acids of not more than 1.5 Å, or more preferably, not more than 1.0 Å, and most preferably, not more than 0.5 Å.

The invention is further directed to a CoA active site of an ACPS-like P-pant transferase, including an acyl carrier protein synthase, in its "bound state", i.e., configured in a state of association or interaction with an agent, wherein the agent may be a protein, polypeptide, peptide, nucleic acid, including DNA or RNA, molecule, compound, antibiotic or drug. In one preferred embodiment of the invention, the active site of the present invention is configured in a state of association or interaction with CoA.

In a preferred embodiment of the invention, the CoA active site in its bound state comprises the relative structural coordinates according to FIGS. 2 and 2A-1 to 2A-19 of residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, or more preferably not more than 1.0 Å, or most preferably, not more than 0.5 Å.

In an alternate embodiment, the active site comprises the relative structural coordinates according to FIGS. 2 and 2A-1 to 2A-19 of residues ARG53, ASN84, GLY85, LYS86, PRO87, ILE103, THR104, and HIS105 from one monomer of ACPS and of residues ASP8, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, or more preferably not more than 1.0 Å, or most preferably, not more than 0.5 Å.

In a yet further embodiment, the active site comprises the relative structural coordinates according to FIGS. 2 and 2A-1 to 2A-19 of residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and of residues ILE5, GLY6, LEU7, ILE9, THR10, ARG14, ILE15, MET18, GLN22, ALA55, LYS57, ALA59, PHE60, ALA63, PHE64, ALA69, ARG70, GLN71 and LEU72 from a second monomer of ACPS, in each case ± a root mean square deviation from the backbone atoms of said amino acids of not more than 1.5 Å, or more preferably, not more than 1.0 Å, and most preferably, not more than 0.5 Å.

Finally, a CoA active site of the present invention comprises the relative structural coordinates according to FIGS. 2 and 2A-1 to 2A-19 of GLY6, ASP8, ALA51, ARG53, LYS57, GLU58, ALA59, LYS62 and ALA63, ± a root mean square deviation from the backbone atoms of said amino acids of not more than 1.5 Å, or more preferably, not more than 1.0 Å, and most preferably, not more than 0.5 Å.

Another aspect of the present invention is directed to a method for identifying an agent that interacts with an active site of ACPS, including a CoA active site in either its native or bound state, comprising the steps of determining an active site of ACPS from a three dimensional model of the ACPS enzyme and performing computer fitting analyses to identify an agent which interacts with said active site. Computer fitting analyses utilize various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. Three dimensional models of the putative active site may be generated using any one of a number of methods known in the art, and include, but are not limited to, homology modeling as well as computer analysis of raw data generated using crystallographic or spectroscopy data. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. Mo.) and LEAPFROG (TRIPOS, Inc., St. Louis, Mo.).

The effect of such an agent identified by computer fitting analyses on ACPS activity may be further evaluated by contacting the identified agent with ACPS and measuring the effect of the agent on ACPS activity. Depending upon the action of the agent on the active site of ACPS, the agent may act either as an inhibitor or activator of ACPS activity. Standard enzymatic assays may be performed and the results analyzed to determine whether the agent is an inhibitor of ACPS activity (i.e., the agent may reduce or prevent binding affinity between ACPS and the relevant substrate, such as ACP or CoA, and thereby reduce the level or rate of ACPS activity compared to baseline), or an activator of ACPS activity (i.e., the agent may increase binding affinity between ACPS and the relevant substrate molecule, such as ACP or CoA, and thereby increase the level or rate of ACPS activity compared to baseline). Further tests may be performed to evaluate the effect of the identified agent on bacterial or eukaryotic cell populations, wherein an inhibitor of ACPS activity inhibits cell viability or reproduction.

A similar method may be used in order to identify an agent that interacts with an active site of ACPS-CoA complex, including an ACP active site, comprising the steps of determining an active site of the ACPS-CoA complex from a three dimensional model of the ACPS-CoA complex, and performing computer fitting analyses to identify an agent which interacts with said active site. Again, the effect of the agent on ACPS-CoA complex activity may be further evaluated by contacting the identified agent with ACPS-CoA complex and measuring the effect of the agent on ACPS-CoA complex activity using standard enzymatic assays. Depending upon the action of the agent on the active site of the ACPS-CoA complex, the agent may act either as an inhibitor (by reducing or preventing binding affinity between ACPS-CoA and the relevant substrate, such as ACP, and thereby reducing the level or rate of ACPS-CoA activity compared to baseline) or activator (by increasing or enhancing binding affinity between ACPS-COA and the relevant substrate, such as ACP, and thereby increasing the level or rate of ACPS-CoA activity compared to baseline). Further tests may be performed to evaluate the effect of the identified agent on bacterial or eukaryotic cell populations, wherein an inhibitor of ACPS-CoA activity inhibits cell viability or reproduction.

The present invention is not limited to identifying agents which interact with an active site of ACPS or ACPS-CoA complex, but also is directed to a method for identifying an activator or inhibitor of any molecule or molecular complex comprising a CoA binding site, comprising the first step of generating a three dimensional model of said molecule or molecular complex comprising a CoA binding site using the relative structural coordinates according to FIGS. 1 and 1A-1 to 1A-107 or FIGS. 2 and 2A-1 to 2A-19 of residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, in each case ± a root mean square deviation from the backbone atoms of said amino acids of not more than 1.5 Å, or more preferably not more than 1.0 Å, or most preferably, not more than 0.5 Å. In alternate embodiments, the relative structural coordinates according to FIGS. 1 and 1A-1 to 1A-107 are from ACPS1 and ACPS2, respectively; from ACPS2 and ACPS3, respectively; from ACPS1 and ACPS3, respectively; from ACPS4 and ACPS5, respectively; from ACPSS and ACPS6, respectively; and from ACPS4 and ACPS6, respectively. Then, a candidate activator or inhibitor is selected or designed by performing computer fitting analyses of said candidate agent with the three dimensional model of the molecule or molecular complex comprising a CoA active site. Once the candidate activator or inhibitor is obtained, it may be contacted with the molecule or molecular complex in order to measure the effect the candidate activator or inhibitor has on said molecule or molecular complex.

Alternatively, the three dimensional structure of the molecule or molecular complex comprising a CoA binding site may be determined using (a) the relative structural coordinates according to FIGS. 1 and 1A-1 to 1A-107 or FIGS. 2 and 2A-1 to 2A-19 of residues ARG53, ASN84, GLY85, LYS86, PRO87, ILE103, THR104, and HIS105 from one monomer of ACPS and of residues ASP8, PHE25, ARG28, ILE29, PHE54, GLU58, SER61, LYS62, GLY65, THR66, GLY67, ILE68 and PHE74 from a second monomer of ACPS, or (b) of LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and of residues ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, in each case ± a root mean square deviation from the backbone atoms of said amino acids of not more than 1.5 Å, or more preferably not more than 1.0 Å, or most preferably, nor more than 0.5 Å. Again, in alternate embodiments, the relative structural coordinates according to FIGS. 1 and 1A-1 to 1A-107 are from ACPS1 and ACPS2, respectively; from ACPS2 and ACPS3, respectively; from ACPS1 and ACPS3, respectively; from ACPS4 and ACPS5, respectively; from ACPS5 and ACPS6, respectively; and from ACPS4 and ACPS6, respectively.

The present invention is also directed to the activators or inhibitors identified using the foregoing methods.

Finally, the present invention is further directed to a method for determining the three dimensional structure of a molecule or molecular complex whose structure is unknown, comprising the steps of obtaining crystals of the molecule or molecular complex whose structure is unknown and generating X-ray diffraction data from the crystallized molecule or molecular complex. The X-ray diffraction data from the molecule or molecular complex is then compared with the known three dimensional structure determined from the ACPS and/or ACPS-CoA crystals of the present invention. Then, the known three dimensional structure determined from the crystals of the present invention is "conformed" using molecular replacement analysis to the X-ray diffraction data from the crystallized molecule or molecular complex. Alternatively, spectroscopic data or homology modeling may be used to generate a putative three dimensional structure for the molecule or molecular complex, and the putative structure is refined by conformation to the known three dimensional structure determined from the ACPS and/or ACPS-CoA crystals of the present invention.

The present invention may be better understood by reference to the following non-limiting Examples. The following Examples are presented in order to more fully illustrate the preferred embodiments of the invention, and should in no way be construed as limiting the scope of the present invention.

EXAMPLE 1
(i) Material and Methods
Expression and Purification of ACPS and SeMet-ACPS: ACPS, cloned into pBAD/HIS, was expressed in DH10B *Escherichia coli* at 37° C. Cells were grown in a Biostat C-10 (10L) vessel (B. Braun Biotech) using rich media and induced four hours with 0.2% final arabinose. SeMet labeled expression of ACPS.pBAD/His was carried out in LeMaster media in BL21DE3 *Escherichia coli* at 37° C. These cultures were also induced for 4 hours with 0.2% final arabinose at log phase.

20 grams of wet *E. coli* BL21 (DE3)/pML-7 cells expressing ACPS were resuspended in 200 ml basic buffer A (50 mM Hepes Cl, pH 7.4, 250 mM NaCl, 10 mM $MgCl_2$, 10 mM DTT) and lysed by two passages through a Microfluidizer (Microfluidics Corporation, Newton, Mass.). Cellular debris was removed by centrifugation at 15,000 g for 30 min. The soluble extract was then loaded onto a 2×20-cm Poros PI (PerSeptive Biosystems, Framingham, Mass.) column pre-equilibrated with basic buffer A. The flow-through material was applied onto a 2×20-cm Poros HS (PerSeptive Biosystems, Framingham, Mass.) column pre-equilibrated with the same buffer. The column was washed with a large amount of basic buffer A until no protein was present in the flow-through as judged by Bradford protein assay. ACPS was then eluted with a linear 0.25–1.0 M NaCl gradient.

ACPS containing fractions were pooled and dialyzed against acidic buffer A (50 mM NaAc, pH 4.6, 50 mM NaCl, 10 mM $MgCl_2$, 10 mM DTT) overnight, and applied onto a 0.46×10 cm Poros HS column pre-equilibrated with the same acidic buffer A. Greater than 95% pure ACPS was eluted with a linear 0.05–2.0 M NaCl gradient. The fractions were subjected to SDS-PAGE analysis and good fractions were combined and concentrated before loading onto an TSK G2000 (TosoHaas, Montgomeryville, Pa.) equilibrated with buffer containing 50 mM NaAc, pH 4.6, 0.5 M NaCl, 10 mM $MgCl_2$, 10 mM DTT. ACPS containing fractions were concentrated and used for crystallization. SeMet-ACPS was purified using the same procedure.

Crystallization of ACPS: Prior to crystallization, the protein was dialyzed against a solution containing 10 mM Sodium Acetate pH 4.4, 2 mM $MgCl_2$, 100 mM NaCl, 5 mM DTT and then concentrated to ~10 mg/mL according to the Bradford method [17]. Crystallization conditions for ACPS were determined using the sparse matrix screens available from both Hampton Research and Emerald Biostructures. All screening was done using hanging-drop vapor diffusion by mixing 1 µL well plus 1 mL protein at both 18° C. and 4° C. Diffraction quality plate-like crystals were obtained from 2.5 M NaCl, 0.1 M Tris pH 7.0, 0.2 M $MgCl_2$. These crystals belonged to space group $P2_1$ with cell dimensions of a=76.26 Å, b=76.16 Å, c=85.69 Å, beta=93.3° and contained six molecules of ACPS in the asymmetric unit. The SeMet ACPS also crystallized using these conditions with the exception that the concentration of DTT was increased to 10 mM to help protect against oxidation of the Selenium atoms.

Crystallization of ACPS with Coenzyme A: The protein solution was prepared as above but 24 hours prior to setting up the screening trays, 1 mM Coenzyme A (di-sodium salt, Fluka) was added. The sparse matrix screens from Hampton Research and Emerald Biostructures were again utilized at 18 and 4° C. with 2 µL hanging drops. Diffraction quality CoA-ACPS co-crystals were obtained from 0.2 M $CaCl_2$ and 20% PEG. These crystals belonged to space group R3 with cell dimensions a=b=55.82 Å, c=92.28 Å and contained one molecule of ACPS and one molecule of CoA in the asymmetric unit. The selenomethionine ACPS-CoA crystallized under the same conditions with the exception that the concentration of DTT was increased to 10 mM to help protect against oxidation of the Selenium atoms.

Native Data Collection: Single-wavelength (1.2 Å) data for the native protein crystals were collected on beamline 5.O.2 at the ALS, Berkley. A single crystal, cooled to −180° C., was used for each data set. In preparation for cryo-cooling, the $P2_1$ form of ACPS was slowly equilibrated to 30% glycerol. Crystals of the ACPS-CoA complex did not tolerate slow equilibration so they were dipped quickly through synthetic mother liquor, which had the PEG concentration increased to 30%, and then cooled quickly to −180° C. Using the ADSC Quantum-4 CCD detector, the data to 1.4 Å were collected for the ACPS-CoA complex crystal and data to 1.8 Å were collected for the ACPS crystal using one-degree oscillations. The data were processed using DENZO and Scalepack [18] and the statistics from refinement are given in Table 1.

MAD Data Collection: MAD data were collected on beamline X12-C at the NSLS (Brookhaven National Laboratory, Upton, N.Y.) from a single crystal of SeMet-ACPS, $P2_1$ form and from a single crystal of the SeMet-ACPS/CoA complex, R3 form. Each crystal was cooled to −180° C. for data collection as described above. Prior to each data collection the wavelength necessary for the experiment was determined by examining an X-ray fluorescence spectrum in the vicinity of the K-absorbance edge of the Selenium atom. Diffraction data were then collected at the inflection point of the spectrum, the peak and at a wavelength remote from the peak for each crystal. The wavelengths used can be found in Table 1. The data to 1.9 Å were collected for the ACPS-CoA complex crystal and the data to 2.4 Å were collected for the ACPS crystal using one degree oscillations with the single-module Brandeis CCD detector. These data were then used as input to the program SOLVE [19] for local scaling of the data sets and determination of the Selenium atom positions. SOLVE was able to determine the position of each of the six Selenium atoms in the asymmetric unit of the ACPS crystal and the single site for the Selenium in the ACPS-CoA crystal. Heavy atom parameters for each were refined with SHARP [20].

Model Building and Refinement: The structure of the ACPS monoclinic form was built into the original 2.5 Å resolution solvent flattened symmetry-averaged MAD map using the X-AUTOFIT features within QUANTA (Molecular Simulations, Inc.). For symmetry averaging, a section of the protein, which corresponded to the 3-member beta sheet, was rotated and translated onto the density corresponding to the other five protein molecules in the asymmetric unit. The NCS operators were then determined using program LSQKAB and refined further with DM (both programs from the CCP4 suite). The resulting map was of sufficiently high quality that only residues 1, 18–25, and 118–121 were not fit initially. The phases were then extended from 2.5 Å to 2.2 Å in 1000 cycles using a separate run of DM. Investigation of the resolution-extended electron density maps for monomers 2 through 6 showed that residues 18–25 were now traceable and that their positions differed between the structures. Alternate tracings of residues 80–99 were also visible between monomers.

This model was then used as the initial model for refinement using the program CNS [21] against the native data, which extended to 1.8 Å, rather than the Se-Met MAD data. Following seven cycles of refining and rebuilding, the refinement converged with a model which contained 6 molecules of ACPS and 505 solvent molecules at a Rcryst of 19.6% and a Rfree of 21.9%. The refinement statistics are given in Table 1.

The structure of Monomer 1 of the monoclinic ACPS structure was placed into the solvent averaged MAD map calculated from the ACPS-COA data and rebuilt. During this rebuilding, extra electron density was observed in the vicinity of HIS105. This density was compared with the structure of CoA and it was quite clear that it did indeed correspond to CoA. The initial model, which did not contain the CoA, was refined using CNS against the 1.5 Å native data. After two cycles of rebuilding and refining, the CoA was placed into density. Refinement converged after four additional rebuilding cycles with a $R_{cryst}$ of 18.5% and a $R_{free}$ of 20.1%. The final model consisted of residues 1–118, CoA, 99 waters, two $Ca^{2+}$ and one $Cl^-$. The refinement statistics are given in Table 1.

TABLE 1

Statistics for Data Collection, Phase Determination, and Refinement

| | ACPS MAD | | | ACPS-CoA MAD | | | ACPS | ACPS-CoA |
|---|---|---|---|---|---|---|---|---|
| | Remote | Peak | Inflection | Remote | Peak | Inflection | Native | Native |
| Data Collection | | | | | | | | |
| Wavelength(Å) | λ3 = 0.93 | λ1 = 0.97853 | λ2 = 0.97860 | λ3 = 0.93 | λ1 = 0.97836 | λ2 = 0.97858 | λ = 1.2 | λ = 1.2 |
| resolution range(Å) | 15–2.4 | 15–2.5 | 15–2.4 | 15–1.9 | 15–1.9 | 15–1.9 | 20–1.8 | 100–1.5 |
| $R_{merge}$[a] | 8.0%(25.8) | 6.8%(15.5) | 7.8%(29.4) | 6.0%(36.1) | 5.9%(21.4) | 5.7%(20.5) | 7.6%(46.8) | 6.4%(30.7) |
| % complete | 100(100) | 100(100) | 100(100) | 99.9(100) | 99.9(100) | 99.6(100) | 96.4(68.6) | 99.9(98.9) |
| total reflections | 432961 | 390215 | 432248 | 121119 | 118498 | 110614 | 614385 | 121535 |
| unique reflections | 38299 | 33941 | 38335 | 8174 | 6982 | 7031 | 87902 | 17170 |
| I/σ(L) | 26.1(7.03) | 31.9(12.7) | 28.4(8.1) | 33.2(13.1) | 36.9(16.9) | 35.8(16.7) | 15.1(1.9) | 18.1(4.0) |
| f'(e−) | −2.18 | −7.35 | −9.5 | −2.18 | −7.35 | −9.52 | | |
| f"(e−) | 3.46 | 5.92 | 3.15 | 3.46 | 5.92 | 3.15 | | |
| MAD Phasing | ACPS | | | | | | | |
| Resolution Limits(Å) Phasing Power[c] | 6.46 | 4.8 | 3.99 | 3.49 | 3.13 | 2.87 | 2.67 | 2.5 | Overall |
| λ3 anomalous | 2.88 | 2.01 | 1.39 | 1.03 | 0.8 | 0.59 | 0.46 | 0.35 | 0.93 |
| λ1 isomorphous | 0.003 | 0.003 | 0.003 | 0.003 | 0.003 | 1.86 | 1.48 | 1.2 | 0.003 |
| λ1 anomalous | 3.85 | 3.10 | 2.09 | 1.59 | 1.29 | 1.01 | 0.80 | 0.64 | 1.45 |
| λ2 isomorphous | 6.96 | 5.15 | 3.34 | 2.54 | 2.03 | 1.64 | 1.25 | 0.03 | 2.19 |
| λ2 anomalous | 2.37 | 1.81 | 1.28 | 1.00 | 0.77 | 0.60 | 0.46 | 0.01 | 0.80 |
| Mean FOM[d] | 0.77 | 0.71 | 0.58 | 0.48 | 0.39 | 0.29 | 0.21 | 0.15 | 0.38 |
| MAD Phasing | ACPS-CoA | | | | | | | |
| Resolution Limits(Å) Phasing Power | 6.73 | 4.41 | 3.50 | 2.99 | 2.64 | 2.40 | 2.21 | 2.06 | Overall |
| λ3 anomalous | 3.50 | 2.50 | 1.99 | 1.83 | 1.42 | 1.14 | 0.83 | 0.66 | 1.42 |
| λ1 isomorphous | 1.57 | 1.22 | 1.11 | 1.16 | 1.12 | 1.11 | 1.01 | 0.92 | 1.10 |
| λ1 anomalous | 4.54 | 3.42 | 2.87 | 2.64 | 2.11 | 1.61 | 1.22 | 0.97 | 2.04 |
| λ2 isomorphous | 1.53 | 1.00 | 0.67 | 0.53 | 0.45 | 0.36 | 0.37 | 0.24 | 0.51 |
| λ2 anomalous | 2.81 | 2.29 | 1.98 | 1.70 | 1.40 | 1.14 | 0.85 | 0.68 | 1.37 |
| Mean FOM | 0.62 | 0.51 | 0.51 | 0.50 | 0.44 | 0.38 | 0.28 | 0.12 | 0.38 |

TABLE 1-continued

Statistics for Data Collection, Phase Determination, and Refinement

| Model Refinement | ACPS | ACPS-CoA |
|---|---|---|
| Maximum Resolution(Å) | 1.8 | 1.5 |
| $R_{work}^{c}$(%) | 19.6 | 18.6 |
| $R_{free}$(%) | 21.9 | 20.1 |
| <B value>(Å$^3$) | 30.6 | 17.5 |
| R.m.s. Deviations from ideal geometry for | | |
| Bonds(Å) | 0.007 | 0.008 |
| Angles(°) | 1.34 | 1.31 |
| 13 values (Å$^2$) | 2.185 | 2.189 |
| Non-hydrogen Protein Atoms | 6972 | 1147 |
| Water Molecules | 471 | 99 |
| Ions | 8 sodium, 19 chlorine | 2 Calcium |
| Other Molecules | 5 DTT, 2 Glycerol | 1 CoA |

[a] $R_{merge} = |I_h - <I_h>|/I_h$, where $<I_h>$ is the average intensity over symmetry equivalents. Number in parentheses reflect statistics for the last shell
[b] f' and f'' reported values were refined by SHARP.
[c] Phasing power = $|F_H|/|||F_{P\ Hobs}| - |F_{PHcalc}||$, where $F_H$ is the calculated heavy atom structure factor amplitude.
[d] Figure of merit = $<P(\alpha)e^{i\alpha}/P(\alpha)|>$, where $\alpha$ is the phase and $P(\alpha)$ is the phase probability distribution.
[e] $R_{work} = ||F_{obs}| - |F_{calc}|/|F_{obs}|$, $R_{free}$ is equivalent to $R_{work}$, but calculated for a randomly chosen 5% (or 10%) of reflections omitted from the refinement process.

(ii) Results
Structure Determination:

Large plate-like crystals (0.5×0.5×0.15 mm) of ACPS were grown in hanging drops using 2.5 M NaCl, 0.2 M MgCl$_2$, 0.1 M Tris pH 7.0. These crystals belong to space group P2$_1$ with unit cell parameters a=76.26 Å, b=76.16 Å, c=85.69 Å, beta=93.3° and diffract to 2.2 Å in-house using a R-Axis IV mounted on a Rigaku RUH2R rotating anode operating at 5 kW or beyond 1.8 Å using synchrotron radiation. Assuming a molecular weight of 14.8 kDa, a protein density of 1.34 g/mL, and six molecules in the asymmetric unit, the Matthew's coefficient is 2.8 Å$^3$/Dalton for a solvent content of 55.7%.

The selenomethionine ACPS protein was expressed in *E. coli* so that the structure could be solved using multi-wavelength anomalous dispersion (MAD) phasing [16]. The selenomethionine ACPS crystallized under identical conditions as the wild-type protein. Data at three different wavelengths around the Se K edge (see Table 1) were collected from a single crystal of the Se-Met ACPS, P2$_1$ form on beamline X12-C of the National Synchrotron Light Source at Brookhaven Laboratory. Experimental phases were determined at 2.5 Å, modified by solvent flattening, non-crystallographic symmetry averaging and extended to 2.2 Å. This resulted in an experimental map that was of exceptionally high quality.

When the protein is incubated with 1 mM CoA di-sodium salt for 24 hours prior to crystallization, crystals are no longer obtained using the conditions optimized for the ACPS alone. Instead, screening found that this material crystallized from 0.2 M CaCl$_2$ and 20% PEG3350. Similar to the crystals obtained without CoA these crystals showed strong diffraction in-house (to 1.9 Å) and using synchrotron radiation, diffraction was seen beyond 1.4 Å. These crystals are small pyramids (0.1×0.1×0.1 mm) which grow in space group R3 with cell dimensions a=b=55.82 Å and c=92.28 Å. Once again, assuming a molecular weight of 14.8 kDa, a protein density of 1.34 g/mL, and one molecule in the asymmetric unit, the Matthew's coefficient is 1.87 Å$^3$/Dalton for a solvent content of 33.7%. Data from a Selenomethionine ACPS-CoA crystal were also collected at three different wavelengths around the Se K edge (Table 1) on beamline X12-C of the National Synchrotron Light Source. Experimental phases were determined at 1.9 Å and modified by solvent flattening. This also resulted in an experimental map that was of exceptionally high quality and using the P2$_1$ ACPS structure as a starting point, the protein was rebuilt according to the experimental density.

Structural Analysis of the Protein: The final model of ACPS (FIG. 3) contains six copies of the protein arranged as two trimers. Each copy consists of residues 1–118 and the asymmetric unit also contains 471 solvent molecules, 8 sodium atoms and 19 chloride ions. The core of the protein is an α-helix (α4) composed of residues 43 to 64, which runs the entire length of the protein. One side of this helix is covered by an antiparallel β-sheet (A-Sheet) with topology β1, β5 and β4. A β-ribbon composed of strands β3 and β2, along with α3 combine to cover another side of helix α4. The encasement of α4 is completed by α1, α2 and a loop consisting of residues 66–75. This fold results in a majority of the surface of this protein being composed of β-strands. The superimposition of the Cα trace of each monomer is depicted in FIG. 4 and shows that the six molecules of ACPS in the asymmetric unit have slightly different tracing of three loops (15–24, 80–88, 91–99) due to symmetry contacts. These molecules overlap with an average RMS delta of 0.497 Å but since the beta sheets and helices are almost identical, the RMS delta improves to 0.168 Å when the loops are omitted. There are no breaks in the electron density for any of the six monomers and only a few residues are not clearly defined. As a result of poor density beyond Cβ, the following residues were modeled as alanine: in monomer 1, LYS13, ARG70, and LYS107; in monomer 2, LYS13 and ARG70; in monomer 3, LYS13, GLU43, ARG70, and LYS107; in monomer 4, LYS13 and ARG70; and in monomer 6, LYS13 and ARG70. In monomers 2 and 4, the first glycine of the histidine tag, which was used as a purification tool, is visible but no density is observed for the remainder of the his-tag. The electron density for Monomers 2, 3, 4 and 5 ends at residue 118. The electron density in Monomer 1 extends until residue 119 while it is traceable to residue 120 in monomer 6. The sequence of ACPS, SWISS-PROT accession number P96618, has a glutamine at position 96. The structure describe herein is of a mutant that has a proline instead of a glutamine at residue 96. This mutation is located in a flexible loop and is over 18 Å from the CoA binding site. The mobility of this loop coupled with the fact that this protein retains its enzymatic activity suggests that this mutation is on a portion of the structure which is not associated with binding of ACP or CoA.

The crystal structure reveals that ACPS is a trimer. A predominant force behind the formation of the trimer appears to be burying of the 527 Å$^3$ surface of the A-Sheet. This sheet is composed of twenty seven amino acids and of the fifteen that are exposed, six are hydrophobic. The exposed ends of strand β1 are hydrophilic (TYR3 and GLU11) but the residues exposed on the interior are hydrophobic (ILE2, ILE5, LEU7 and ILE9). Likewise, the exposed ends of strand β5 are hydrophilic (TYR109 and GLU117) and in addition, the residue in the center of the strand, GLN113, is also a polar residue. The two remaining exposed residues of strand β5, ALA111 and VAL115, are hydrophobic. Unlike either β1 or β5, all the exposed residues of strand β4 are hydrophilic (HIS100, SER102, THR104, and THR106).

In this trimer, the A-sheet of each molecule comes together to form an arrangement similar to a three-faced beta barrel (FIG. 4). This packing results in strand β1 from the first A-sheet packing against strands β4 and β5 of the second A-sheet. Strand β1 of the second sheet then packs against strands β4 and β5 of the third sheet while strand β1 of the third sheet packs against strands β4 and β5 of the first A-sheet. This results in the formation of an elongated three-faced β-sandwich. The packing at the junction between monomers forces the main chain of strand β1 to point in the same direction as the polar side chains of strand β4. The interface where the β-sheets meet between two of the molecules of the trimer is therefore exceptionally polar. The area above this intersection is open to solvent and is at the bottom of a bowl-shaped depression in the surface of the protein assembly. This depression measures approximately 14 Å in width, 20 Å in length, and 8 Å in depth and is where CoA binds to this protein. Examination of an electrostatic representation of this depression shows that the bottom of the cavity is anionic in nature while the sides are either cationic or hydrophilic. In this structure, the cavity is filled with numerous water molecules as well as three chloride ions and one sodium ion. The sodium ion is located at the intersection of two A-sheets and has as ligands residue HIS105 from one monomer and residue ILE9 from another monomer. There is a sodium ion in each of the six cavities present in the asymmetric unit of the P2$_1$ form and in each case, the ligand architecture is identical. Aside from the packing of the β-sheets, the only other interactions (both VDW and ionic) between the molecules of the trimer occur between residues of two loops containing residues 65–67 from one monomer and residues 84–86 from another monomer.

The final model of ACPS-CoA in the rhombohedral crystal contains residues 1–118, one molecule of coenzyme A, 99 solvent molecules, two calcium atoms, and one chloride ion. Similar to the ACPS structure alone, the electron density extends to residue 118 and there are no breaks in the density between residues 1 to 118. The side chains for residues LYS23, ARG70, ARG118 were not visible past Cβ and have been modeled as ALA. The binding of CoA has not resulted in any changes in the secondary structure of the protein since the same trimeric arrangement of the protein molecules described in the P2$_1$ space group above is also present in this structure. The monomer of ACPS in this structure of the ACPS-CoA complex is positioned such that the molecular three-fold axis is coincident with a crystallographic three-fold axis. The trimer in this structure is generated by symmetry operators (–Y, X–Y, Z) and (–X+Y, –X, Z) In this structure, the metal binding site described in the monoclinic structure is not present. Instead, there are two six-coordinate metal binding sites that are both occupied by calcium ions. The first calcium is found at one end of the 3-sided β-sandwich and sits on a special position (z=0). Only two of its ligands come from the molecule in the asymmetric unit of this structure, GLU108 and HOH21. Two symmetry-related copies of GLU108 and HOH21 finish out the coordination shell for this calcium. The site in which the sodium ion is found in the monoclinic ACPS structure is now occupied by the side chain of LYS62. As a consequence of this rearrangement, a second metal binding site is formed in the cavity just 5 Å above that location. GLU58 and ASP8 occupy two equatorial sites and the α2 phosphate from the Coenzyme A pyrophosphate occupies an axial coordination site on the calcium. It is this metal binding site which is the location of the magnesium ion required for the enzymatic activity of this protein.

CoA Binding Site: The depression described in the monoclinic ACPS structure is the location of the active site of this protein. The rearrangement associated with moving LYS62 into the sodium-binding pocket allows two residues, ASP8 and GLU58, to define a binding pocket along the anionic ridge between the A-sheets into which a divalent cation fits. The calcium occupying this binding site serves to anchor the CoA in the pocket by coordinating to the α2 phosphate of the CoA pyrophosphate. The adenosine ring of CoA fits snugly into a pocket formed by a loop consisting of residues 80–88 and the C-terminal end of the α4 helix along with the loop immediately following (residues 62–70) of a symmetry related molecule. The 3'-phosphate of CoA is held in place by the protein through hydrogen bonds provided by the side chains of ARG53 and HIS105. The interactions between the pantetheinyl group and the protein are predominately van der Waals interactions. The sulfhydryl group rests in a hydrophobic pocket formed by the aliphatic portion of the side chains of ARG28, MET18, PHE25, ILE29, PHE54 and PHE74. These interactions are detailed in FIG. 5.

Superimposition of ACPS Dimer and Sfp: The molecular coordinates for Sfp were obtained from the protein data bank, code 1QR0. All solvent molecules were ignored during the alignment calculations. The ACPS dimer and Sfp molecules were manually aligned using QUANTA (Molecular Simulations, Inc.) and the resulting overlapped coordinates written to disk. These coordinates were then read into 6D_LSQMAN and the alignment refined in an iterative process. When the alignment process converged, the ACPS dimer and Sfp superimposed with a RMS of 2.19 Å.

When examining the coordinates of Sfp within QUANTA, it was evident that a loop corresponding to residues 83 to 94 had adopted an extended conformation in the C-terminal side of the molecule. The corresponding loop on the N-terminal side of Sfp clings to the protein body in an identical fashion to that found in ACPS. Therefore the superimposition was repeated with this C-terminal loop excised from both structures. The superimposition of the structures then improved to a RMS of 1.81 Å. When the coordinate set used in the alignment was limited to those residues within 8 Å of the CoA, the RMS remained at 1.81 Å. However, when the coordinate set was limited to those atoms within 4 Å of the CoA binding site, the RMS improved to 1.66Å.

Differences between Sfp and ACPS: Sfp is a monomer consisting of 228 residues. ACPS is a monomer consisting of 121 residues. The sequence identity between Sfp and an ACPS dimer is quite low, as only 55 of the 226 residues in Sfp have an identical counterpart in ACPS (24%). A further 56 residues of Sfp have a counterpart in the ACPS dimer which have similar properties.

Sfp contains two domains. Both of these domains are similar to an ACPS monomer. Where the third monomer would bind in the ACPS triad, Sfp contains a twenty residue C-terminal extension.

Three molecules of ACPS combine to form a trimer with three active sites. Sfp does not aggregate and the active site is contained within the monomer.

In ACPS, residues 83 to 94 comprise a loop that packs tightly against the main protein body. In Sfp, the corresponding loop on the N-terminal domain (residues 67–83) packs in the same fashion. However, the same loop on the C-terminal domain protrudes out from the protein body.

The adenine, ribose and pyrophosphate from the CoA moiety are similar in the active site of both proteins. However, the pantetheinyl group is modeled closer to the adenine in the Sfp structure while in the ACPS structure it adopts an extended conformation.

Figure 5:
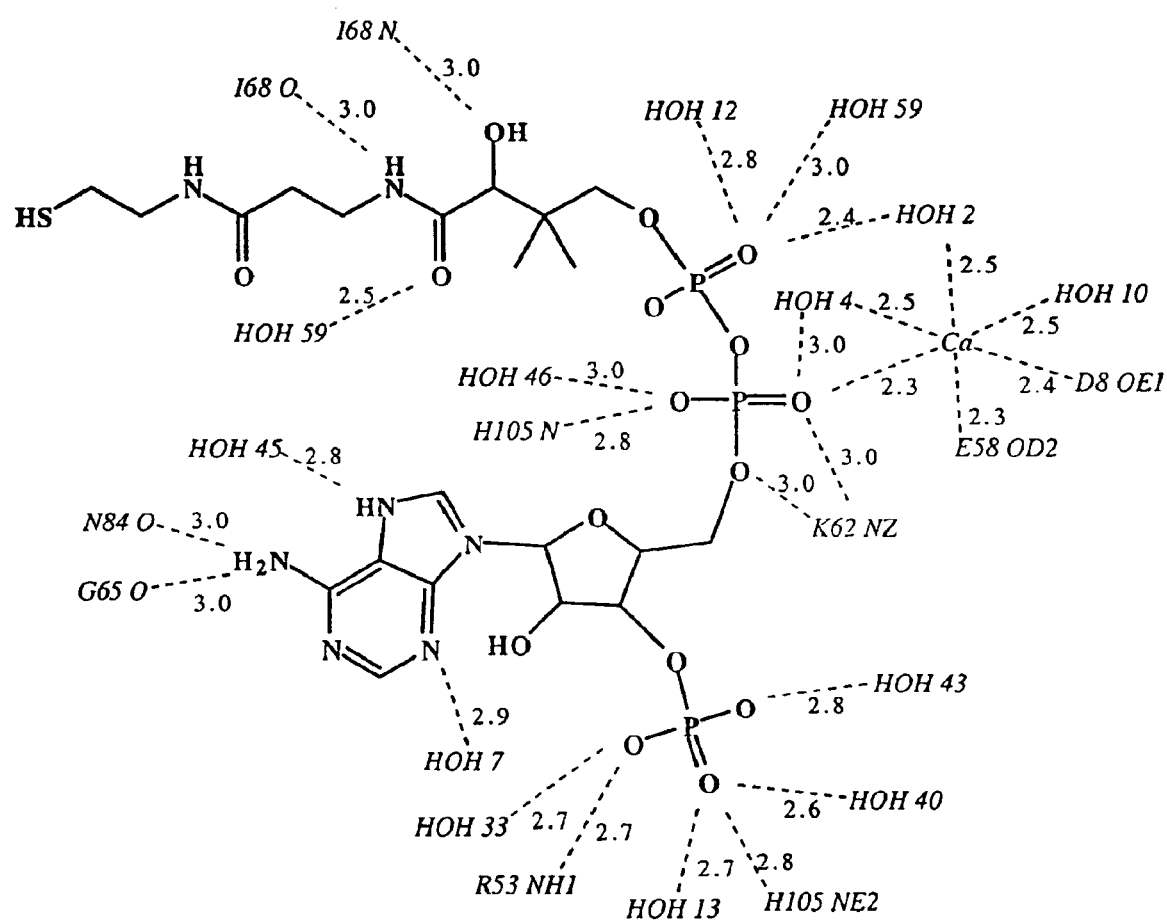
Figure 6B:
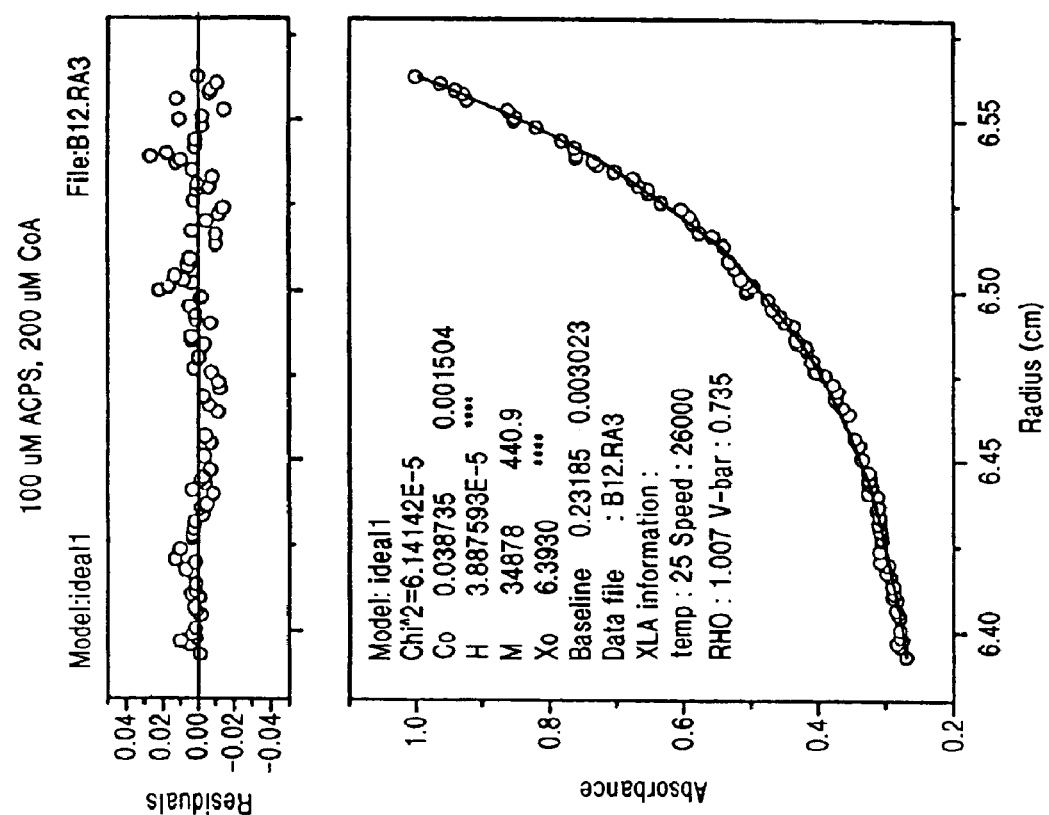
FIGS. 6A and 6B illustrate results from equilibrium ultracentrifugation experiments using 100 μM and 100 μM ACPS/200 μM CoA, at pH 6.4 and 25° C.
Figure 6A:
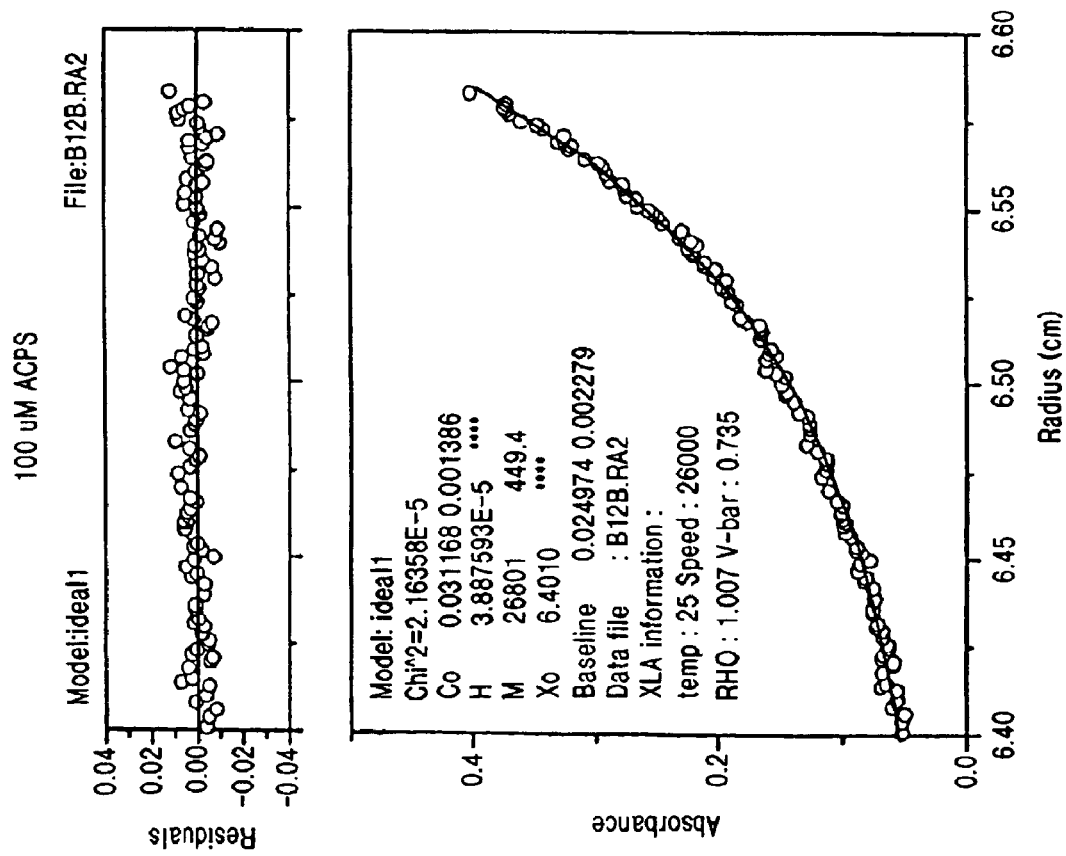

Differences between Sfp and ACPS Active Sites: As shown in FIG. 5, extensive interactions exist between CoA and ACPS. When compared with Sfp, some residues in the active site are in essentially the same location while others have moved dramatically. Six of the nine residues that have significant interactions with this part of the CoA are identical between the two proteins (ASP8, GLU58, LYS62, HIS105, GLY65). The residues that are not identical are ASN84, ARG53, and PHE49.

Those residues that are almost identically placed include ASN84 and GLY65 (TYR73 and GLY158 in Sfp). These residues move by only 0.2 Å. ASP8 (ASP107 in Sfp) moves by only 0.4 Å, while LYS62 (LYS155 in Sfp) moves by 1.3 Å. The positions of the other residues in the active site are dramatically different. For example, GLU58 (GLU151 in Sfp) moves 2.4 Å. In Sfp, this residue is hydrogen bonded to the pyrophosphate group of CoA as well as to the metal ion. In ACPS, it is only bonded to the metal ion.

Proline 87 (PRO76 in Sfp) assists in defining the cavity into which the adenine group is wedged. This residue moves 1.9 Å. PHE49 is replaced by THR44 in Sfp. In the ACPS structure, this residue is not significantly interacting with the CoA. In Sfp, THR44 is hydrogen bonded to the phosphate directly attached to the ribose. This residue has moved 4.2 Å. ARG53 is replaced by ASP48 in Sfp. In ACPS, ARG53 is hydrogen bonded to the phosphate that is directly attached to the ribose. The positioning of this residue differs 4.5 Å between the two structures.

EXAMPLE 2

(i) Materials and Methods

Equilibrium analytical ultracentrifugation experiments were performed on a Beckman XLI/XLA Analytical Ultracentrifuge operating at three rotor speeds of 20K, 26K, and 30K rpm. Equilibrium was judged to be achieved when no deviations in a plot of the difference between successive scans taken 3 hrs apart was observed, usually within 20 hours. Scans were recorded at 10° C. and 25° C., and signal was detected using absorbance optics (285 nM) and interference optics. Samples were then loaded into six-channel cells at 3 different protein concentrations under argon. The self-association of ACPS as a function of pH (pH 5.2, 6.4, and 7.5) and the effect of the substrates CoA and ACP upon the molecular mass at pH 6.4 were characterized by sedimentation equilibrium measurements. After the experiments, 15% non-reducing denaturing gels were run to determine if irreversible aggregation of ACPS occurred during the equilibrium experiments which were performed typically over 4 days. The partial specific volumes of ACPS and ACP were calculated based on the amino acid composition, and the density of the solvent was calculated from the chemical composition of the buffer using the computer program SEDNTERP.

Isothermal titration calorimetry (ITC) was used to monitor the heat of binding observed upon addition of 8 μL aliquots of 269 μM ACPS in 100 mM Bis-Tris buffer (pH 6.4), to 1.38 ml of 10 μM ACP in 100 mM Bis-Tris, pH 6.4.

Equations: The molecular weight of the protein in the presence and absence of ligand was obtained from sedimentation equilibrium experiments using the following equation:

$$a_r = a_{r0} \exp[(\omega^2 M/2RT)(1-\nu\rho)(r^2-r_0^2)] + E$$

where:

$a_r$ = concentration at radius r $a_{r0}$ = absorbance at reference radius x0

$\nu$ = partial specific volume of the macromolecule (mL/g)

$\rho$ = density of the solvent $\omega$ = angular velocity of the rotor (radians/sec)

E = baseline offset

M = gram MW of the macromolecule

R = gas constant

T = temperature (ii) Results

Analytical ultracentrifugation is a classical biochemical method used to characterize the solution behavior of solutes. The technique relies on the principal property of mass and the fundamentals of gravitation, and can be used to obtain information about the solution molar mass, association constants, and stoichiometries by performing sedimentation equilibrium experiments. The monomer molecular weight of 15 kDa was obtained using a sample of ACPS in a solution containing 6 M of the denaturant guanidine hydrochloride (Table 2). Results from the equilibrium experiments with 100 μM ACPS and 100 μM ACPS/200 μM CoA at 6.4 pH and 25 deg. are presented in FIGS. 6A and B. The concentration gradient of ACPS across the cell readily fit the equation for the presence of a single species as evidenced by the random distribution of the residuals, with a molecular weight of 22.5 kDa and 39.7 kDa, respectively. These molecular weights corresponded to a dimeric ACPS in the absence of CoA which then increases to a trimeric species in the presence of CoA. At 100 μM ACPS pH 5.2 and 6.4, the molecular weights are 22K and 25.8K, respectively (Table 2). When assuming the presence of monomer or trimer, the fits of the curves yielded greater than 90% dimer at pH 5.2 and 6.4.

15% nonreducing denaturing gels indicate the association is not due to covalent crosslinking of the subunits but self association, as greater than 95% of ACPS is monomeric before and after the centrifugation experiments (FIG. 7).

The observation of a trimeric ACPS in the presence of CoA is in good agreement with the X-ray derived crystal structure of the CoA complex and supports the use of the trimeric structure for future drug screening assays, but also indicates the solution association interactions of ACPS with the two substrates CoA and ACP is a complex mixture of multiple species which may impact enzyme assay design and development.

TABLE 2

Apparent Molecular Weights of ACPS

| Sample | pH | Temperature (° C.) | MW |
|---|---|---|---|
| 100 μM ACPS | 5.2 | 10 | 22,000 ± 600 |
| 100 μM ACP | 6.4 | 10 | 9,160 ± 300 |
| 100 μM ACPS | 6.4 | 25 | 25,800 ± 900 |
| 300 μM ACPS/ 6 μM GuHCl | 5.2 | 25 | 15,000 ± 400 |
| 100 μM ACPS/ 200 μM CoA | 6.4 | 25 | 39,700 ± 700 |

MW based on amino acid composition
ACPS: 13.7 kDa
ACP: 8.8 kDa

References (1) Lynen, F. (1980) Eur. J. Biochem. 112, 431–442.
(2) Wakil, S. J., Stoops, J. K. and Joshi, V. C. (1983) Annu. Rev. Biochem. 52, 537–579.
(3) B. Shen, B., Summers, R. G., Gramajo, H., Bibb, M. J. and Hutchinson, C. R. (1992) J. Bacteriol. 174, 3818.
(4) Hopwood, D. A., and Sherman, D. H. (1990) Annu. Rev. Genet. 24, 37–66.
(5) Kleinkauf, H., and Von Dohren, H. (1996) Eur. J. Biochem. 236, 335–351.
(6) Marahiel, M. A. (1992) FEBS Lett. 307, 40.
(7) White, R. H. (1980) Biochemistry 19, 9–15.
(8) Sanyal, I., Lee, S. -L. and Flint, D. H. (1994) J. Am. Chem. Soc. 116, 2637–2638.
(9) Furukawa, H., Tsay, J. T., Jackowski, S., Takamura, Y. and Rock, C. O. (1993) J. Bacteriol. 175, 3723–3729.
(10) Bergler, H., Wallner, P., Ebeling, A., Leitinger, B., Fuchsbichler, S., Aschauer, H., Kollenz, G., Högenauer, G. and Turnowsky, F. (1994) J. Biol. Chem. 269, 5493–5496.
(11) Dessen, A., Quémard, A., Blanchard, J. S., Jacobs, W. R., Jr. and Sacchettini, J. C. (1995) Science 267, 1638–1641.
(12) Quémard, A., Sacchettini, J. C, Dessen, A., Vilcheze, C., Bittman, R., Jacobs, W. R., Jr. and Blanchard, J. S. (1995) Biochemistry 34, 8235–8241.
(13) Lambalot, R. H., Gehring, A. M., Flugel, R. S. Zuber, P., LaCelle, M., Marahiel, M. A., Reid, R., Khosla, C., and Walsh, C. T. (1996) Chemisty & Biology 3, 923–936.
(14) Elovson, J. and Vagelos, P. R. (1968) J. Biol. Chem. 243, 3603.
(15) Lambalot, R. H. and Walsh, C. T. (1995) J. Biol. Chem. 270, 24658–24661.
(16) Hendrickson, W. A. (1991) Science 254, 51–58.
(17) Bradford, M. (1976) Anal. Biochem. 72, 248–254.
(18) Otwinowski, Z; and Minor, W. (1997) "Processing of X-ray diffraction data collected in oscillation mode." Methods Enzymol. 276, 307–326.
(19) Terwilliger, T. C. and J. Berendzen. (1999) "Automated structure solution for MIR and MAD". Acta Crystallographica D55, 849–861.
(20) La Fortelle, E. de & Bricogne, G. (1997) Methods in Enzymology, Macromolecular Crystallography, volume 276, pp. 472–494, edited by R. M. Sweet and C. W. Carter, Jr. New York: Academic Press. "Maximum-Likelihood Heavy-Atom Parameter Refinement in the MIR and MAD Methods".
(21) Brunger, A. T., Adams, P. D., Clore, G. M., Delano, W. L., Gros, P., Grosse-Kuntsleve, R. W., Jiang, J-S., Kuszewski, J., Nilges, N., Pannu, N. S., Read, R. J., Rice, L. M., Simonson, T., and Warren, G. L. (1998) Acta Crystallographica D54, 905–921.
(22) Reuter, K., Mofid, M. R., Marahiel, M. A. and Ficner, R. (1999) EMBO 18(23), 6823–6831.

All publications mentioned herein above, whether to issued patents, pending applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

We claim:

1. A method for identifying an agent that interacts with an active site of acyl carrier protein synthase (ACPS), comprising the steps of:
   (a) obtaining a crystallized ACPS, wherein the crystallized ACPS is characterized as being in plate form with space group P2$_1$, and having unit cell parameters of a=76.26 Å, b=76.16 Å, c=85.69 Å, and beta=93.3°, and wherein ACPS is cloned and isolated from *B. subtilis*;
   (b) obtaining the structural coordinates of the crystallized ACPS of step (a), wherein the structural coordinates are set forth in FIG. 1 and 1A-1 to 1A-107;
   (c) generating a three dimensional model of ACPS using the structural coordinates of the amino acids of ACPS obtained in step (b), and ± a root mean square deviation from the backbone atoms of not more than 1.5 Å;
   (d) determining an active site of ACPS from said three dimensional model; and
   (e) performing computer fitting analysis to identify an agent which interacts with said active site.

2. The method of claim 1, further comprising contacting the identified agent with ACPS in order to determine the effect the agent has on ACPS activity.

3. The method of claim 2, wherein the agent is an inhibitor of ACPS activity.

4. A method for identifying an agent that interacts with an active site of an acyl carrier protein synthase-coenzyme A (ACPS-CoA) complex, comprising the steps of:
   (a) obtaining a crystallized complex comprising acyl carrier protein synthase (ACPS) and coenzyme A (CoA), wherein the crystallized complex is characterized as being in pyramidal form with space group R3, and having unit cell parameters of a=b=55.82 Å and c=92.28 Å, and wherein ACPS is cloned and isolated from *B. subtilis*;
   (b) obtaining the structural coordinates of the amino acids of the crystallized complex of step (a), wherein the structural coordinates are set forth in FIG. 2 and 2A-1 to 2A-19;
   (c) generating a three dimensional model of ACPS-CoA using the structural coordinates of the amino acids obtained in step (b) and ± a root mean square deviation from the backbone atoms of not more than 1.5 Å;
   (d) determining an active site of the ACPS-CoA complex from said three dimensional model; and
   (e) performing computer fitting analysis to identify an agent which interacts with said active site.

5. The method of claim 4, further comprising contacting the identified agent with ACPS-CoA complex in order to determine the effect the agent has on ACPS-CoA complex activity.

6. The method of claim 5, wherein the agent is an inhibitor of ACPS-CoA complex activity.

7. A method for identifying an agent that interacts with an active site of acyl carrier protein synthase (ACPS), comprising the steps of:
   (a) obtaining a crystallized complex comprising acyl carrier protein synthase (ACPS) and coenzyme A (CoA), wherein the crystallized complex is characterized as being in pyramidal form with space group R3, and having unit cell parameters of a=b=55.82 Å and c=92.28 Å, and wherein ACPS is cloned and isolated from *B. subtilis*;
   (b) obtaining the structural coordinates of the amino acids of the crystallized complex of step (a), wherein the structural coordinates are set forth in FIG. 2 and 2A-1 to 2A-19;
   (c) generating a three dimensional model of ACPS using the structural coordinates of the amino acids obtained in step (b) and ± a root mean square deviation from the backbone atoms of not more than 1.5 Å;
   (d) determining an active site of ACPS from said three dimensional model; and
   (e) performing computer fitting analysis to identify an agent which interacts with said active site.

8. The method of claim 7, further comprising contacting the identified agent with ACPS in order to determine the effect the agent has on ACPS activity.

9. The method of claim 8, wherein the agent is an inhibitor of ACPS activity.

10. The method of claim 1, wherein the active site of ACPS determined in step (d) comprises the structural coordinates according to FIG. 1 and 1A-1 to 1A-107 of amino acid residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

11. The method of claim 1, wherein the active site of ACPS determined in step (d) comprises the structural coordinates according to FIG. 1 and 1A-1 to 1A-107 of amino acid residues ARG53, ASN84, GLY85, LYS86, PRO87, ILE103, THR104, and HIS105 from one monomer of ACPS and of amino acid residues ASP8, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

12. The method of claim 1, wherein the active site of ACPS determined in step (d) comprises the structural coordinates according to FIG. 1 and 1A-1 to 1A-107 of amino acid residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and of amino acid residues ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, ± a root mean square deviation from the backbone atoms of said amino acids of not more than 1.5 Å.

13. The method of claim 1, wherein the active site of ACPS determined in step (d) comprises the structural coordinates of amino acid residues GLY6, ASP8, ALA51, ARG53, LYS57, GLU58, ALA59, LYS62, and ALA63 according to FIG. 1 and 1A-1 to 1A-107, ± a root mean square deviation from the backbone atoms of said amino acids of not more than 1.5 Å.

14. The method of claim 7, wherein the active site of ACPS determined in step (d) comprises the structural coordinates according to FIG. 2 and 2A-1 to 2A-19 of amino acid residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

15. The method of claim 7, wherein the active site of ACPS determined in step (d) comprises the structural coordinates according to FIG. 2 and 2A-1 to 2A-19 of amino acid residues ARG53, ASN84, GLY85, LYS86, PRO87, ILE103, THR104, and HIS105 from one monomer of ACPS and of amino acid residues ASP8, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

16. The method of claim 7, wherein the active site of ACPS determined in step (d) comprises the structural coordinates according to FIG. 2 and 2A-1 to 2A-19 of amino acid residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and of amino acid residues ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, ± a root mean square deviation from the backbone atoms of said amino acids of not more than 1.5 Å.

17. The method of claim 7, wherein the active site of ACPS determined in step (d) comprises the structural coordinates of amino acid residues GLY6, ASP8, ALA51, ARG53, LYS57, GLU58, ALA59, LYS62, and ALA63 according to FIG. 2 and 2A-1 to 2A-19, ± a root mean square deviation from the backbone atoms of said amino acids of not more than 1.5 Å.

18. The method of claim 1, wherein the ± root mean square deviation from the backbone atoms is not more than 1.0 Å.

19. The method of claim 18, wherein the ± root mean square deviation from the backbone atoms is not more than 0.5 Å.

20. The method of claim 4, wherein the ± root mean square deviation from the backbone atoms is not more than 1.0 Å.

21. The method of claim 20, wherein the ± root mean square deviation from the backbone atoms is not more than 0.5 Å.

22. The method of claim 7, wherein the ± root mean square deviation from the backbone atoms of said amino acids is not more than 1.0 Å.

23. The method of claim 22, wherein the ± root mean square deviation from the backbone atoms of said amino acids is not more than 0.5 Å.

24. The method of claim 10, wherein the ± root mean square deviation from the backbone atoms of said amino acids is not more than 1.0 Å.

25. The method of claim 24, wherein the ± root mean square deviation from the backbone atoms of said amino acids is not more than 0.5 Å.

26. The method of claim 11, wherein the ± root mean square deviation from the backbone atoms of said amino acids is not more than 1.0 Å.

27. The method of claim 26, wherein the ± root mean square deviation from the backbone atoms of said amino acids is not more than 0.5 Å.

28. The method of claim 12, wherein the ± root mean square deviation from the backbone atoms of said amino acids is not more than 1.0 Å.

29. The method of claim 28, wherein the ± root mean square deviation from the backbone atoms of said amino acids is not more than 0.5 Å.

30. The method of claim 13, wherein the ± root mean square deviation from the backbone atoms of said amino acids is not more than 1.0 Å.

31. The method of claim 30, wherein the ± root mean square deviation from the backbone atoms of said amino acids is not more than 0.5 Å.

32. The method of claim 14, wherein the ± root mean square deviation from the backbone atoms of said amino acids is not more than 1.0 Å.

33. The method of claim 32, wherein the ± root mean square deviation from the backbone atoms of said amino acids is not more than 0.5 Å.

34. The method of claim 15, wherein the ± root mean square deviation from the backbone atoms of said amino acids is not more than 1.0 Å.

35. The method of claim 34, wherein the ± root mean square deviation from the backbone atoms of said amino acids is not more than 0.5 Å.

36. The method of claim 16, wherein the ± root mean square deviation from the backbone atoms of said amino acids is not more than 1.0 Å.

37. The method of claim 36, wherein the ± root mean square deviation from the backbone atoms of said amino acids is not more than 0.5 Å.

38. The method of claim 17, wherein the ± root mean square deviation from the backbone atoms of said amino acids is not more than 1.0 Å.

39. The method of claim 38, wherein the ± root mean square deviation from the backbone atoms of said amino acids is not more than 0.5 Å.

40. A method for identifying an agent that interacts with an active site of acyl carrier protein synthase (ACPS), comprising the steps of:
  (a) obtaining a crystallized ACPS, wherein the crystallized ACPS is characterized as being in plate form with space group $P2_1$, and having unit cell parameters of a=76.26 Å, b=76.16 Å, c=85.69 Å, and beta=93.3°, and wherein ACPS is cloned and isolated from *B. subtilis*;
  (b) obtaining the structural coordinates of the crystallized ACPS of step (a);
  (c) generating a three dimensional model of ACPS using the structural coordinates of the amino acids of ACPS obtained in step (b), and ± a root mean square deviation from the backbone atoms of not more than 1.5 Å;
  (d) determining an active site of ACPS from said three dimensional model; and
  (e) performing computer fitting analysis to identify an agent which interacts with said active site.

41. The method of claim 40, further comprising contacting the identified agent with ACPS in order to determine the effect the agent has on ACPS activity.

42. The method of claim 41, wherein the agent is an inhibitor of ACPS activity.

43. A method for identifying an agent that interacts with an active site of an acyl carrier protein synthase-coenzyme A (ACPS-CoA) complex, comprising the steps of:
    (a) obtaining a crystallized complex comprising acyl carrier protein synthase (ACPS) and coenzyme A (CoA), wherein the crystallized complex is characterized as being in pyramidal form with space group R3, and having unit cell parameters of a=b=55.82 Å and c=92.28 Å, and wherein ACPS is cloned and isolated from *B. subtilis*;
    (b) obtaining the structural coordinates of the amino acids of the crystallized complex of step (a);
    (c) generating a three dimensional model of ACPS-CoA using the structural coordinates of the amino acids obtained in step (b), and ± a root mean square deviation from the backbone atoms of not more than 1.5 Å;
    (d) determining an active site of the ACPS-CoA complex from said three dimensional model; and
    (e) performing computer fitting analysis to identify an agent which interacts with said active site.

44. The method of claim 43, further comprising contacting the identified agent with ACPS-CoA complex in order to determine the effect the agent has on ACPS-CoA complex activity.

45. The method of claim 44, wherein the agent is an inhibitor of ACPS-CoA complex activity.

46. A method for identifying an agent that interacts with an active site of acyl carrier protein synthase (ACPS), comprising the steps of:
    (a) obtaining a crystallized complex comprising acyl carrier protein synthase (ACPS) and coenzyme A (CoA), wherein the crystallized complex is characterized as being in pyramidal form with space group R3, and having unit cell parameters of a=b=55.82 Å and c=92.28 Å, and wherein ACPS is cloned and isolated from *B. subtilis*;
    (b) obtaining the structural coordinates of the amino acids of the crystallized complex of step (a);
    (c) generating a three dimensional model of ACPS using the structural coordinates of the amino acids obtained in step (b), and ± a root mean square deviation from the backbone atoms of not more than 1.5 Å;
    (d) determining an active site of ACPS from said three dimensional model; and
    (e) performing computer fitting analysis to identify an agent which interacts with said active site.

47. The method of claim 46, further comprising contacting the identified agent with ACPS in order to determine the effect the agent has on ACPS activity.

48. The method of claim 47, wherein the agent is an inhibitor of ACPS activity.

49. The method of claim 40, wherein the active site of ACPS determined in step (d) comprises the structural coordinates of amino acid residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

50. The method of claim 40, wherein the active site of ACPS determined in step (d) comprises the structural coordinates of amino acid residues ARG53, ASN84, GLY85, LYS86, PRO87, ILE103, THR104, and HIS105 from one monomer of ACPS and of amino acid residues ASP8, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

51. The method of claim 40, wherein the active site of ACPS determined in step (d) comprises the structural coordinates of amino acid residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and of amino acid residues ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, ± a root mean square deviation from the backbone atoms of said amino acids of not more than 1.5 Å.

52. The method of claim 40, wherein the active site of ACPS determined in step (d) comprises the structural coordinates of amino acid residues GLY6, ASP8, ALA51, ARG53, LYS57, GLU58, ALA59, LYS62, and ALA63, ± a root mean square deviation from the backbone atoms of said amino acids of not more than 1.5 Å.

53. The method of claim 46, wherein the active site of ACPS determined in step (d) comprises the structural coordinates according of amino acid residues ARG45, PHE49, ARG53, LYS81, ASN84, GLY85, LYS86, PRO87, ILE103, THR104 and HIS105 from one monomer of ACPS, and of ASP8, GLU11, ARG14, MET18, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

54. The method of claim 46, wherein the active site of ACPS determined in step (d) comprises the structural coordinates of amino acid residues ARG53, ASN84, GLY85, LYS86, PRO87, ILE103, THR104, and HIS 105 from one monomer of ACPS and of amino acid residues ASP8, PHE25, ARG28, ILE29, PHE54, GLU58, SER61, LYS62, GLY65, THR66, GLY67, ILE68 and PHE74 from a second monomer of ACPS, ± a root mean square deviation from the backbone atoms of said amino acids of not more than 1.5 Å.

55. The method of claim 46, wherein the active site of ACPS determined in step (d) comprises the structural coordinates of amino acid residues LEU41, ARG45, GLU48, PHE49, LEU50, ALA51, GLY52, ILE79, ARG80, LYS81, ASP82, GLN83, TYR88, VAL101, SER102, THR106, TYR109, ALA110, and ALA111 from one monomer of ACPS and of amino acid residues ILE5, GLY6, LEU7, ILE9, THR10, ARG14, ILE15, MET18, GLN22, ALA55, LYS57, ALA59, PHE60, ALA63, PHE64, GLY69, ARG70, GLN71 and LEU72 from a second monomer of ACPS, ± a root mean square deviation from the backbone atoms of said amino acids of not more than 1.5 Å.

56. The method of claim 46, wherein the active site of ACPS determined in step (d) comprises the structural coordinates of amino acid residues GLY6, ASP8, ALA51, ARG53, LYS57, GLU58, ALA59, LYS62, and ALA63, ± a root mean square deviation from the backbone atoms of said amino acids of not more than 1.5 Å.

* * * * *

UNITED STATES PATENT AND TRADEMARK OFFICE
CERTIFICATE OF CORRECTION

PATENT NO. : 6,957,150 B2  Page 1 of 1
APPLICATION NO. : 09/771383
DATED : October 18, 2005
INVENTOR(S) : Parris et al.

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by (232) days Delete the phrase "by 232" and insert -- by 246 days--

Signed and Sealed this

Fifth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 6,957,150 B2  Page 1 of 1
APPLICATION NO. : 09/771383
DATED : October 18, 2005
INVENTOR(S) : Parris et al.

It is certified that error appears in the above-identified patent and that said Letters Patent is hereby corrected as shown below:

<u>Title Page</u>
Under the section item 56 titled OTHER PUBLICATIONS, and in the first column, in the Jan Drenth citation, replace "p. 16).*" with --p. 16.*--.

Col. 35, Line 55, replace "step (b) and" with --step (b), and--.

Col. 36, Line 31, replace "step (b) and" with --step (b), and--.

Col. 40, Lines 28-29, replace "structural coordinates according of" with --structural coordinates of--.

Signed and Sealed this

Seventeenth Day of April, 2007

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 121
<212> TYPE: PRT
<213> ORGANISM: B. subtilis

<400> SEQUENCE: 1

Met Ile Tyr Gly Ile Gly Leu Asp Ile Thr Glu Leu Lys Arg Ile Ala
1               5                   10                  15

Ser Met Ala Gly Arg Gln Lys Arg Phe Ala Glu Arg Ile Leu Thr Arg
            20                  25                  30

Ser Glu Leu Asp Gln Tyr Tyr Glu Leu Ser Glu Lys Arg Lys Asn Glu
        35                  40                  45

Phe Leu Ala Gly Arg Phe Ala Ala Lys Glu Ala Phe Ser Lys Ala Phe
    50                  55                  60

Gly Thr Gly Ile Gly Arg Gln Leu Ser Phe Gln Asp Ile Glu Ile Arg
65                  70                  75                  80

Lys Asp Gln Asn Gly Lys Pro Tyr Ile Ile Cys Thr Lys Leu Ser Gln
```

```
                         85                  90                  95
Ala Ala Val His Val Ser Ile Thr His Thr Lys Glu Tyr Ala Ala Ala
            100                 105                 110

Gln Val Val Ile Glu Arg Leu Ser Ser
        115                 120

<210> SEQ ID NO 2
<211> LENGTH: 122
<212> TYPE: PRT
<213> ORGANISM: Aquifex

<400> SEQUENCE: 2

Met Ile Gly Val Asp Ile Val Lys Asn Glu Arg Ile Lys Asp Ala Leu
1               5                   10                  15

Glu Arg Phe Gly Asp Lys Phe Leu Asp Arg Ile Tyr Thr Lys Arg Glu
            20                  25                  30

Leu Glu Tyr Cys Tyr Ala His Cys Asp Phe Leu Pro Cys Leu Ala Ala
        35                  40                  45

Arg Trp Ala Gly Lys Glu Ala Val Leu Lys Ala Phe Tyr Thr Glu Phe
    50                  55                  60

Lys Ile Phe Leu Arg Phe Lys Glu Ile Glu Ile Leu Gly Asn Arg Gly
65                  70                  75                  80

Arg Pro Pro Thr Val Val Ile Asn Arg Glu Gly Val Glu Glu Ile Leu
                85                  90                  95

Lys Asn Tyr Glu Val Ile Val Ser Leu Ser His Glu Arg Asp Tyr Ser
            100                 105                 110

Val Ala Val Ala Tyr Ile Lys Lys Lys Ser
        115                 120

<210> SEQ ID NO 3
<211> LENGTH: 122
<212> TYPE: PRT
<213> ORGANISM: Chlamydophila

<400> SEQUENCE: 3

Met Glu Ile Ile His Ile Gly Thr Asp Ile Ile Glu Ile Ser Arg Ile
1               5                   10                  15

Arg Glu Ala Ile Ala Thr His Gly Asn Arg Leu Leu Asn Arg Ile Phe
            20                  25                  30

Thr Glu Ala Glu Gln Lys Tyr Cys Leu Glu Lys Thr Asp Pro Ile Pro
        35                  40                  45

Ser Phe Ala Gly Arg Phe Ala Gly Lys Glu Ala Val Ala Lys Ala Leu
    50                  55                  60

Gly Thr Gly Ile Gly Ser Val Val Ala Trp Lys Asp Ile Glu Val Phe
65                  70                  75                  80

Lys Val Ser His Gly Pro Glu Val Leu Leu Pro Ser His Val Tyr Ala
                85                  90                  95

Lys Ile Gly Ile Ser Lys Val Ile Leu Ser Ile Ser His Cys Lys Glu
            100                 105                 110

Tyr Ala Thr Ala Thr Ala Ile Ala Leu Ala
        115                 120

<210> SEQ ID NO 4
<211> LENGTH: 119
<212> TYPE: PRT
<213> ORGANISM: Helicobacter

<400> SEQUENCE: 4
```

```
Met Ile Gly Ile Asp Ile Val Ser Ile Ala Arg Ile Glu Lys Cys Val
1               5                   10                  15

Lys Arg Phe Lys Met Lys Phe Leu Glu Arg Phe Leu Ser Pro Ser Glu
            20                  25                  30

Ile Val Leu Cys Lys Asp Lys Ser Ser Ile Ala Gly Phe Phe Ala
        35                  40                  45

Leu Lys Glu Ala Cys Ser Lys Ala Leu Gln Val Gly Ile Gly Lys Glu
    50                  55                  60

Leu Ser Phe Leu Asp Ile Lys Ile Ser Lys Ser Pro Lys Asn Ala Pro
65                  70                  75                  80

Leu Ile Thr Leu Ser Lys Glu Lys Met Asp Tyr Phe Asn Ile Gln Ser
                85                  90                  95

Leu Ser Ala Ser Ile Ser His Asp Ala Gly Phe Ala Ile Ala Val Val
                100                 105                 110

Val Val Ser Ser Ser Asn Glu
        115
```

<210> SEQ ID NO 5
<211> LENGTH: 119
<212> TYPE: PRT
<213> ORGANISM: Staphylococcus

<400> SEQUENCE: 5

```
Met Ile His Gly Ile Gly Val Asp Leu Ile Glu Ile Asp Arg Ile Gln
1               5                   10                  15

Ala Leu Tyr Ser Lys Gln Pro Lys Leu Val Glu Arg Ile Leu Thr Lys
            20                  25                  30

Asn Glu Gln His Lys Phe Asn Asn Phe Thr His Glu Gln Arg Lys Ile
            35                  40                  45

Glu Phe Leu Ala Gly Arg Phe Ala Thr Lys Glu Ala Phe Ser Lys Ala
    50                  55                  60

Leu Gly Thr Gly Leu Gly Lys His Val Ala Phe Asn Asp Ile Asp Cys
65                  70                  75                  80

Tyr Asn Asp Glu Leu Gly Lys Pro Lys Ile Asp Tyr Glu Gly Phe Ile
                85                  90                  95

Val His Val Ser Ile Ser His Thr Glu His Tyr Ala Met Ser Gln Val
                100                 105                 110

Val Leu Glu Lys Ser Ala Phe
        115
```

<210> SEQ ID NO 6
<211> LENGTH: 169
<212> TYPE: PRT
<213> ORGANISM: Thermotoga

<400> SEQUENCE: 6

```
Met Ile Val Gly Val Gly Ile Asp Val Leu Glu Val Glu Arg Val Pro
1               5                   10                  15

Glu Lys Phe Ala Glu Arg Ile Leu Gly Glu Ser Glu Lys Arg Leu Phe
            20                  25                  30

Leu Thr Arg Lys Arg Arg Arg Glu Phe Ile Ala Gly Arg Phe Ala Leu
            35                  40                  45

Lys Glu Ala Phe Phe Lys Ala Leu Gly Thr Gly Leu Asn Gly His Ser
    50                  55                  60

Phe Thr Asp Val Glu Phe Leu Glu Ser Asn Gly Lys Pro Val Leu Cys
65                  70                  75                  80
```

```
Val His Lys Asp Phe Gly Phe Asn Tyr Ala His Val Ser Leu Ser
            85                  90                  95

His Asp Arg Phe Ala Val Ala Leu Val Val Leu Glu Lys Arg Lys Gly
            100                 105                 110

Asp Ile Ile Val Glu Gly Asp Glu Ser Phe Leu Arg Lys Arg Phe Glu
            115                 120                 125

Val Leu Glu Arg Ser Val Glu Gly Trp Glu Ile Glu Thr Ser Leu Pro
        130                 135                 140

Pro Phe Thr Leu Lys Lys Leu Leu Glu Ser Ser Gly Cys Arg Leu Val
145                 150                 155                 160

Arg Tyr Gly Asn Ile Leu Ile Gly Glu
                165
```

```
<210> SEQ ID NO 7
<211> LENGTH: 126
<212> TYPE: PRT
<213> ORGANISM: Escherichia

<400> SEQUENCE: 7
```

```
Met Ala Ile Leu Gly Leu Gly Thr Asp Ile Val Glu Ile Ala Arg Ile
1               5                   10                  15

Glu Ala Val Ile Ala Arg Ser Gly Asp Arg Leu Ala Arg Arg Val Leu
            20                  25                  30

Ser Asp Asn Glu Trp Ala Ile Trp Lys Thr His His Gln Pro Val Arg
        35                  40                  45

Phe Leu Ala Lys Arg Phe Ala Val Lys Glu Ala Ala Ala Lys Ala Phe
    50                  55                  60

Gly Thr Gly Ile Arg Asn Gly Leu Ala Phe Asn Gln Phe Glu Val Phe
65                  70                  75                  80

Asn Asp Glu Leu Gly Lys Pro Arg Leu Arg Leu Trp Gly Glu Ala Leu
                85                  90                  95

Lys Leu Ala Glu Lys Leu Gly Val Ala Asn Met His Val Thr Leu Ala
            100                 105                 110

Asp Glu Arg His Tyr Ala Cys Ala Thr Val Ile Ile Glu Ser
            115                 120                 125
```

```
<210> SEQ ID NO 8
<211> LENGTH: 126
<212> TYPE: PRT
<213> ORGANISM: Rickettsia

<400> SEQUENCE: 8
```

```
Met Leu Ile Gly Val Gly Thr Asp Ile Val Gln Ile Pro Arg Ile Glu
1               5                   10                  15

Lys Ile Leu Asn Ile Tyr Gln Glu Leu Phe Ala Lys Lys Ile Leu Ala
            20                  25                  30

Leu Lys Glu Leu Lys Gln Phe Thr Leu Leu Asn Lys Thr Asn His Ala
        35                  40                  45

Thr Phe Leu Ala Lys Arg Phe Ser Ala Lys Glu Ala Val Ser Lys Ala
    50                  55                  60

Phe Gly Val Gly Ile Gly Arg Gly Ile Asn Phe Lys Asp Ile Thr Ile
65                  70                  75                  80

Leu Asn Asp Asn Leu Gly Lys Pro Thr Val Glu Ile Ser Ser His Tyr
                85                  90                  95

Thr Asn Lys Leu Ala Pro Phe Asn Ile His Leu Ser Leu Ser Asp Asp
            100                 105                 110
```

```
Tyr Pro Ile Cys Ile Ala Phe Ala Ile Ile Glu Ser Asn Cys
        115                 120                 125

<210> SEQ ID NO 9
<211> LENGTH: 123
<212> TYPE: PRT
<213> ORGANISM: Streptomyces

<400> SEQUENCE: 9

Met Ser Ile Ile Gly Val Gly Ile Asp Val Ala Glu Val Glu Arg Phe
1               5                   10                  15

Gly Ala Ala Leu Glu Arg Thr Pro Ala Leu Ala Gly Arg Leu Phe Leu
            20                  25                  30

Glu Ser Glu Leu Leu Pro Gly Gly Glu Arg Arg Gly Val Ala Ser
        35                  40                  45

Leu Ala Ala Arg Phe Ala Ala Lys Glu Ala Leu Ala Lys Ala Leu Gly
    50                  55                  60

Ala Pro Ala Gly Leu Leu Trp Thr Asp Ala Glu Val Trp Val Glu Ala
65                  70                  75                  80

Gly Gly Arg Pro Arg Leu Arg Val Thr Gly Thr Val Ala Ala Arg Ala
                85                  90                  95

Ala Glu Leu Gly Val Ala Ser Trp His Val Ser Leu Ser His Asp Ala
            100                 105                 110

Gly Ile Ala Ser Ala Val Val Ile Ala Glu Gly
        115                 120

<210> SEQ ID NO 10
<211> LENGTH: 125
<212> TYPE: PRT
<213> ORGANISM: Treponema

<400> SEQUENCE: 10

Met Ile Ile Gly Val Gly Ile Asp Ile Val Glu Ile Glu Arg Phe Val
1               5                   10                  15

Ser Trp Thr His Asn Val Arg Leu Leu Arg Arg Phe Phe His Gln Glu
            20                  25                  30

Glu Ile Val Asp Phe Phe Lys Asn His Met Arg Ala Gln Phe Leu Ala
        35                  40                  45

Thr Arg Phe Ala Ala Lys Glu Ala Phe Gly Lys Ala Leu Gly Thr Gly
    50                  55                  60

Leu Arg Asn Met Glu Leu Arg Asn Ile Arg Val Cys Gln Asn Gly Trp
65                  70                  75                  80

Gly Lys Pro Arg Leu Glu Val Tyr Gly Ala Ala Gln Ala Met Leu Ala
                85                  90                  95

Ala Thr Gly Gly Thr His Ile Gln Val Ser Leu Thr His Glu Arg Glu
            100                 105                 110

Val Ala Ser Ala Ile Val Ile Glu Gly Glu Pro Leu
        115                 120                 125

<210> SEQ ID NO 11
<211> LENGTH: 121
<212> TYPE: PRT
<213> ORGANISM: Bacillus

<400> SEQUENCE: 11

Met Ile Tyr Gly Ile Gly Leu Asp Ile Thr Glu Leu Lys Arg Ile Ala
1               5                   10                  15
```

```
Ser Met Ala Gly Arg Gln Lys Arg Phe Ala Glu Arg Ile Leu Thr Arg
            20                  25                  30

Ser Glu Leu Asp Gln Tyr Tyr Glu Leu Ser Glu Lys Arg Lys Asn Glu
        35                  40                  45

Phe Leu Ala Gly Arg Phe Ala Ala Lys Glu Ala Phe Ser Lys Ala Phe
    50                  55                  60

Gly Thr Gly Ile Gly Arg Gln Leu Ser Phe Gln Asp Ile Glu Ile Arg
65                  70                  75                  80

Lys Asp Gln Asn Gly Lys Pro Tyr Ile Ile Cys Thr Lys Leu Ser Gln
                85                  90                  95

Ala Ala Val His Val Ser Ile Thr His Thr Lys Glu Tyr Ala Ala Ala
            100                 105                 110

Gln Val Val Ile Glu Arg Leu Ser Ser
        115                 120
```

<210> SEQ ID NO 12
<211> LENGTH: 139
<212> TYPE: PRT
<213> ORGANISM: Bradyrhizobium

<400> SEQUENCE: 12

```
Met Ile Ile Gly Ile Gly Ser Asp Leu Ile Asp Ile Thr Arg Val Gly
1               5                   10                  15

Lys Val Ile Glu Arg His Gly Glu Arg Phe Leu Asp Arg Ile Phe Thr
            20                  25                  30

Ala Ala Glu Arg Ala Lys Ala Glu Arg Arg Ala Lys Asn Glu Lys Met
        35                  40                  45

Val Val Ala Thr Tyr Ala Lys Arg Phe Ala Ala Lys Glu Ala Cys Ser
    50                  55                  60

Lys Ala Leu Gly Thr Gly Ile Arg Arg Gly Val Trp Trp Arg Asp Met
65                  70                  75                  80

Gly Val Val Asn Leu Pro Gly Gly Arg Pro Thr Met Gln Leu Thr Gly
                85                  90                  95

Gly Ala Leu Ala Arg Leu Gln Ala Leu Thr Pro Asp Gly Phe Glu Ala
            100                 105                 110

Arg Ile Asp Val Ser Ile Thr Asp Asp Trp Pro Leu Ala Gln Ala Phe
        115                 120                 125

Val Ile Ile Ser Ala Val Pro Leu Ala Lys Ser
    130                 135
```

<210> SEQ ID NO 13
<211> LENGTH: 130
<212> TYPE: PRT
<213> ORGANISM: Mycobacterium

<400> SEQUENCE: 13

```
Met Gly Ile Val Gly Val Gly Ile Asp Leu Val Ser Ile Pro Asp Phe
1               5                   10                  15

Ala Glu Gln Val Ser Gln Pro Gly Thr Val Phe Met Thr Ile Phe Thr
            20                  25                  30

Pro Gly Glu Arg Arg Asp Ala Ser Val Lys Ser Ser Ser Ala Val Cys
        35                  40                  45

His Leu Ala Ala Arg Trp Ala Val Lys Glu Ala Val Ile Lys Ala Trp
    50                  55                  60

Ser Gly Ser Arg Phe Ala Gln Arg Pro Met Leu Pro Glu Asn Ile His
65                  70                  75                  80
```

```
-continued

Arg Asp Ile Glu Val Val Asn Asp Met Trp Gly Arg Pro Arg Val Arg
            85              90              95

Leu Thr Gly Ala Ile Ala Lys His Leu Thr Asp Val Thr Ile His Val
            100             105                 110

Ser Leu Thr His Glu Gly Asp Ile Ala Ala Ala Val Val Ile Leu Glu
        115             120             125

Val Leu
    130
```